(12) United States Patent
Semler et al.

(10) Patent No.: US 10,130,736 B1
(45) Date of Patent: *Nov. 20, 2018

(54) TISSUE-DERIVED TISSUEGENIC IMPLANTS, AND METHODS OF FABRICATING AND USING SAME

(71) Applicant: MUSCULOSKELETAL TRANSPLANT FOUNDATION, Edison, NJ (US)

(72) Inventors: Eric Semler, Piscataway, NJ (US); Alex Callahan, Edison, NJ (US); Joed Canales, Harrison, NJ (US); Katrina Carroll, Jacobstown, NJ (US); Anouska Dasgupta, North Brunswick, NJ (US); Roman Shikhanovich, Edison, NJ (US)

(73) Assignee: Musculoskeletal Transplant Foundation, Edison, NJ (US)

( * ) Notice: Subject to any disclaimer, the term of this patent is extended or adjusted under 35 U.S.C. 154(b) by 0 days.

This patent is subject to a terminal disclaimer.

(21) Appl. No.: 14/933,176

(22) Filed: Nov. 5, 2015

Related U.S. Application Data

(63) Continuation-in-part of application No. 13/690,542, filed on Nov. 30, 2012, now Pat. No. 9,352,003, which is a continuation-in-part of application No. 13/108,856, filed on May 16, 2011, now Pat. No. 8,883,210.

(60) Provisional application No. 61/345,057, filed on May 14, 2010, provisional application No. 62/071,946, filed on Nov. 7, 2014.

(51) Int. Cl.
| | | |
|---|---|---|
| *A61L 27/56* | (2006.01) |
| *A61L 27/58* | (2006.01) |
| *A61L 27/36* | (2006.01) |
| *A61L 27/54* | (2006.01) |
| *A61L 27/40* | (2006.01) |
| *A61L 27/38* | (2006.01) |

(52) U.S. Cl.
CPC ......... *A61L 27/3608* (2013.01); *A61L 27/365* (2013.01); *A61L 27/3687* (2013.01); *A61L 27/3691* (2013.01); *A61L 27/3834* (2013.01); *A61L 27/3847* (2013.01); *A61L 27/40* (2013.01); *A61L 27/54* (2013.01); *A61L 27/58* (2013.01); *A61L 2300/414* (2013.01); *A61L 2300/604* (2013.01); *A61L 2300/64* (2013.01); *A61L 2430/02* (2013.01); *A61L 2430/38* (2013.01)

(58) Field of Classification Search
CPC .. A61L 27/3608; A61L 27/3691; A61L 27/58; A61L 27/54; A61L 27/40; A61L 27/365; A61L 27/3687; A61L 27/3834; A61L 27/3847; A61L 2300/414; A61L 2430/02; A61L 2300/64; A61L 2300/604; A61L 2430/38

See application file for complete search history.

(56) References Cited

U.S. PATENT DOCUMENTS

| | | |
|---|---|---|
| 4,065,816 A | 1/1978 | Sawyer |
| 4,108,161 A | 8/1978 | Samuels et al. |
| 4,294,753 A | 10/1981 | Urist |
| 4,361,552 A | 11/1982 | Baur, Jr. |
| 4,434,094 A | 2/1984 | Seyedin et al. |
| 4,627,853 A | 12/1986 | Campbell et al. |
| 4,802,853 A | 2/1989 | Krasner |
| 4,820,626 A | 4/1989 | Williams et al. |
| 5,002,071 A | 3/1991 | Harrell |
| 5,035,708 A | 7/1991 | Alchas et al. |
| 5,073,373 A | 12/1991 | O'Leary et al. |
| 5,079,160 A | 1/1992 | Lacy et al. |
| 5,112,354 A | 5/1992 | Sires |
| 5,131,907 A | 7/1992 | Williams et al. |
| 5,204,319 A | 4/1993 | Enomoto et al. |
| 5,219,576 A | 6/1993 | Chu et al. |
| 5,230,693 A | 7/1993 | Williams et al. |
| 5,236,456 A | 8/1993 | O'Leary et al. |
| 5,284,655 A | 2/1994 | Bogdansky et al. |
| 5,290,558 A | 3/1994 | O'Leary et al. |
| 5,298,254 A | 3/1994 | Prewett et al. |
| 5,314,476 A | 5/1994 | Prewett et al. |

(Continued)

FOREIGN PATENT DOCUMENTS

| | | |
|---|---|---|
| CA | 2177017 | 6/1995 |
| CA | 2446573 A1 | 3/1998 |

(Continued)

OTHER PUBLICATIONS

Gray's Anatomy of the Human Body, "Tendons, Aponeuroses, and Fasciae", http://education.yahoo.com/reference/gray/subjects/subject/104, printed May 16, 2011, 2 pages.

Gregoire et al., "Understanding Adipocyte Differentiation", Physiological Reviews, vol. 78, No. 3, Jul. 1998, pp. 783-809.

Grogan et al., "Mesenchymal progenitor cell markers in human articular cartilage: normal distribution and changes in osteoarthritis", Arthritis Research & Therapy, vol. 11, No. 3, Jun. 5, 2009, pp. 1-13.

Gronthos et al., "Surface Protein Characterization of Human Adipose Tissue-Derived Stromal Cells", Journal of Cellular Physiology, vol. 189, (2001), pp. 54-63.

Guilak et al., "The Pericellular Matrix as a Transducer of Biomechanical and Biochemical Signals in Articular Cartilage", Ann. N.Y. Acad. Sci., vol. 1068, (2006), pp. 498-512.

(Continued)

*Primary Examiner* — Valarie E Bertoglio
(74) *Attorney, Agent, or Firm* — Cole Schotz, P.C.

(57) ABSTRACT

The disclosure provides implants containing a plurality of particles containing at least one population of viable osteogenic cells adherent to and resident in an osteoconductive matrix or at least one viable population of osteogenic cells caused to be in contact with the osteoconductive matrix; methods of fabricating the implants; and use of the implants in bone repair. The implant further contains an osteoinductive component. An example of an osteoinductive component is a demineralized bone matrix in the form of particles or fibers.

11 Claims, 4 Drawing Sheets

(56) References Cited

U.S. PATENT DOCUMENTS

| | | |
|---|---|---|
| 5,333,626 A | 8/1994 | Morse et al. |
| 5,345,746 A | 9/1994 | Franchi |
| 5,385,229 A | 1/1995 | Bittmann et al. |
| 5,439,684 A | 8/1995 | Prewett et al. |
| 5,480,424 A | 1/1996 | Cox |
| 5,486,359 A | 1/1996 | Caplan et al. |
| 5,507,813 A | 4/1996 | Dowd et al. |
| 5,513,662 A | 5/1996 | Morse et al. |
| 5,531,791 A | 7/1996 | Wolfinbarger, Jr. |
| 5,556,379 A | 9/1996 | Wolfinbarger |
| 5,612,028 A | 3/1997 | Sackier et al. |
| 5,628,781 A | 5/1997 | Williams et al. |
| 5,676,146 A | 10/1997 | Scarborough |
| 5,697,383 A | 12/1997 | Manders et al. |
| 5,700,289 A | 12/1997 | Breitbart et al. |
| 5,744,360 A | 4/1998 | Hu et al. |
| 5,788,941 A | 8/1998 | Dalmasso et al. |
| 5,797,871 A | 8/1998 | Wolfinbarger, Jr. |
| 5,804,366 A | 9/1998 | Hu et al. |
| 5,807,275 A | 9/1998 | Jamshidi |
| 5,824,078 A | 10/1998 | Nelson et al. |
| 5,824,084 A | 10/1998 | Muschler |
| 5,837,235 A | 11/1998 | Mueller et al. |
| 5,842,477 A | 12/1998 | Naughton et al. |
| 5,869,037 A | 2/1999 | Crystal et al. |
| 5,899,939 A | 5/1999 | Boyce et al. |
| 5,910,315 A | 6/1999 | Stevenson et al. |
| 5,989,498 A | 11/1999 | Odland |
| 6,020,196 A | 2/2000 | Hu et al. |
| 6,024,735 A | 2/2000 | Wolfinbarger, Jr. |
| 6,030,635 A | 2/2000 | Gertzman et al. |
| 6,051,750 A | 4/2000 | Bell |
| 6,077,987 A | 6/2000 | Breitbart et al. |
| 6,083,690 A | 7/2000 | Harris et al. |
| 6,123,731 A | 9/2000 | Boyce et al. |
| 6,149,906 A | 11/2000 | Mosca |
| 6,152,142 A | 11/2000 | Tseng |
| 6,187,053 B1 | 2/2001 | Minuth |
| 6,189,537 B1 | 2/2001 | Wolfinbarger, Jr. |
| 6,203,755 B1 | 3/2001 | Odland |
| 6,254,635 B1 | 7/2001 | Schroeder et al. |
| 6,284,284 B1 | 9/2001 | Naughton |
| 6,293,970 B1 | 9/2001 | Wolfinbarger, Jr. et al. |
| 6,294,187 B1 | 9/2001 | Boyce et al. |
| 6,305,379 B1 | 10/2001 | Wolfinbarger, Jr. |
| 6,311,690 B1 | 11/2001 | Jefferies |
| 6,312,952 B1 | 11/2001 | Hicks, Jr. |
| 6,316,247 B1 | 11/2001 | Katz et al. |
| 6,326,019 B1 | 12/2001 | Tseng |
| 6,332,779 B1 | 12/2001 | Boyce et al. |
| 6,340,477 B1 | 1/2002 | Anderson |
| 6,348,069 B1 | 2/2002 | Vacanti et al. |
| 6,355,239 B1 | 3/2002 | Bruder et al. |
| 6,375,663 B1 | 4/2002 | Ebner et al. |
| 6,376,244 B1 | 4/2002 | Atala |
| 6,379,371 B1 | 4/2002 | Novak et al. |
| 6,387,693 B2 | 5/2002 | Rieser et al. |
| 6,391,297 B1 | 5/2002 | Halvorsen |
| 6,398,819 B1 | 6/2002 | Bell |
| 6,429,013 B1 | 8/2002 | Halvorsen et al. |
| 6,432,436 B1 | 8/2002 | Gertzman et al. |
| 6,436,138 B1 | 8/2002 | Dowd et al. |
| 6,437,018 B1 | 8/2002 | Gertzman et al. |
| 6,440,444 B2 | 8/2002 | Boyce et al. |
| 6,458,375 B1 | 10/2002 | Gertzman et al. |
| 6,465,208 B1 | 10/2002 | Hicks, Jr. |
| 6,478,825 B1 | 11/2002 | Winterbottom et al. |
| 6,534,095 B1 | 3/2003 | Moore-Smith et al. |
| 6,596,274 B1 | 7/2003 | Abatangelo et al. |
| 6,599,520 B2 | 7/2003 | Scarborough et al. |
| 6,616,698 B2 | 9/2003 | Scarborough |
| 6,652,593 B2 | 11/2003 | Boyer, II et al. |
| 6,652,818 B1 | 11/2003 | Mills et al. |
| 6,652,872 B2 | 11/2003 | Nevo et al. |
| 6,696,073 B2 | 2/2004 | Boyce et al. |
| 6,706,067 B2 | 3/2004 | Shimp et al. |
| 6,723,131 B2 | 4/2004 | Muschler |
| 6,739,112 B1 | 5/2004 | Marino |
| 6,752,831 B2 | 6/2004 | Sybert et al. |
| 6,777,231 B1 | 8/2004 | Katz et al. |
| 6,808,585 B2 | 10/2004 | Boyce et al. |
| 6,830,763 B2 | 12/2004 | O'Leary et al. |
| 6,841,150 B2 | 1/2005 | Halvorsen et al. |
| 6,863,694 B1 | 3/2005 | Boyce et al. |
| 6,899,107 B2 | 5/2005 | Lewandrowski et al. |
| 6,911,212 B2 | 6/2005 | Gertzman et al. |
| 6,979,307 B2 | 12/2005 | Beretta et al. |
| 6,991,652 B2 | 1/2006 | Burg |
| 7,004,977 B2 | 2/2006 | Ashman |
| 7,008,591 B2 | 3/2006 | Kafesjian et al. |
| 7,008,763 B2 | 3/2006 | Cheung |
| 7,019,192 B2 | 3/2006 | Gertzman et al. |
| 7,029,666 B2 | 4/2006 | Bruder et al. |
| 7,029,689 B2 | 4/2006 | Berglund et al. |
| 7,029,838 B2 | 4/2006 | Williams et al. |
| 7,033,587 B2 | 4/2006 | Halvorsen et al. |
| 7,045,141 B2 | 5/2006 | Merboth et al. |
| 7,052,829 B2 | 5/2006 | Williams et al. |
| 7,052,907 B2 | 5/2006 | Shi et al. |
| 7,078,230 B2 | 7/2006 | Wilkison et al. |
| 7,078,232 B2 | 7/2006 | Konkle et al. |
| 7,148,036 B2 | 12/2006 | Luyten et al. |
| 7,162,850 B2 | 1/2007 | Marino et al. |
| 7,163,691 B2 | 1/2007 | Knaack et al. |
| 7,166,133 B2 | 1/2007 | Evans et al. |
| 7,179,299 B2 | 2/2007 | Edwards et al. |
| 7,186,557 B2 | 3/2007 | Marko |
| 7,201,917 B2 | 4/2007 | Malaviya et al. |
| 7,241,316 B2 | 7/2007 | Evans et al. |
| 7,244,444 B2 | 7/2007 | Bates |
| 7,255,879 B2 | 8/2007 | Hariri |
| 7,273,756 B2 | 9/2007 | Adkisson et al. |
| 7,294,509 B2 | 11/2007 | Darimont et al. |
| 7,297,540 B2 | 11/2007 | Mitrani |
| 7,311,904 B2 | 12/2007 | Hariri |
| 7,311,905 B2 | 12/2007 | Hariri |
| 7,323,190 B2 | 1/2008 | Chu et al. |
| 7,323,193 B2 | 1/2008 | Morris et al. |
| 7,335,381 B2 | 2/2008 | Malinin |
| 7,347,876 B2 | 3/2008 | Tsai |
| 7,390,484 B2 | 6/2008 | Fraser et al. |
| 7,413,576 B2 | 8/2008 | Sybert et al. |
| 7,413,734 B2 | 8/2008 | Mistry et al. |
| 7,416,889 B2 | 8/2008 | Ciombor et al. |
| 7,429,488 B2 | 9/2008 | Fraser et al. |
| 7,445,793 B2 | 11/2008 | Niwa et al. |
| 7,459,307 B2 | 12/2008 | Ha et al. |
| 7,468,242 B2 | 12/2008 | Bellomo et al. |
| 7,468,276 B2 | 12/2008 | Hariri |
| 7,470,537 B2 | 12/2008 | Hedrick et al. |
| 7,473,420 B2 | 1/2009 | Fraser et al. |
| 7,473,678 B2 | 1/2009 | Lynch |
| 7,476,257 B2 | 1/2009 | Sah et al. |
| 7,494,802 B2 | 2/2009 | Tseng et al. |
| 7,498,040 B2 | 3/2009 | Masinaei et al. |
| 7,498,041 B2 | 3/2009 | Masinaei |
| 7,498,171 B2 | 3/2009 | Hariri et al. |
| 7,501,115 B2 | 3/2009 | Fraser et al. |
| 7,514,075 B2 | 4/2009 | Hedrick et al. |
| 7,524,489 B2 | 4/2009 | Messina et al. |
| 7,531,355 B2 | 5/2009 | Rodriguez et al. |
| 7,560,276 B2 | 7/2009 | Harmon et al. |
| 7,575,743 B2 | 8/2009 | Hunziker |
| 7,582,292 B2 | 9/2009 | Wilkison et al. |
| 7,582,309 B2 | 9/2009 | Rosenberg et al. |
| 7,585,670 B2 | 9/2009 | Hedrick et al. |
| 7,592,174 B2 | 9/2009 | Sylvester et al. |
| 7,595,043 B2 | 9/2009 | Hedrick et al. |
| 7,595,062 B2 | 9/2009 | Pedrozo et al. |
| 7,608,113 B2 | 10/2009 | Boyer, II et al. |
| 7,621,963 B2 | 11/2009 | Simon et al. |
| 7,637,872 B1 | 12/2009 | Fox |
| 7,651,684 B2 | 1/2010 | Hedrick et al. |
| 7,662,184 B2 | 2/2010 | Edwards et al. |

(56) References Cited

U.S. PATENT DOCUMENTS

| | | |
|---|---|---|
| 7,670,384 B2 | 3/2010 | Kumar et al. |
| 7,678,385 B2 | 3/2010 | Reddi |
| 7,682,803 B2 | 3/2010 | Paludan et al. |
| 7,687,059 B2 | 3/2010 | Fraser et al. |
| 7,726,319 B1 | 6/2010 | Boyce, II et al. |
| 7,732,126 B2 | 6/2010 | Zhang et al. |
| 7,744,597 B2 | 6/2010 | Gaskins et al. |
| 7,745,106 B2 | 6/2010 | Beretta et al. |
| 7,753,963 B2 | 7/2010 | Boyce |
| 7,767,452 B2 | 8/2010 | Kleinsek |
| 7,771,716 B2 | 8/2010 | Hedrick et al. |
| 7,775,965 B2 | 8/2010 | McFetridge |
| 7,776,596 B2 | 8/2010 | Badylak |
| 7,785,582 B2 | 8/2010 | Johnson |
| 7,785,634 B2 | 8/2010 | Borden |
| 7,795,022 B2 | 9/2010 | Badylak |
| 7,795,027 B2 | 9/2010 | Hiles |
| 7,799,076 B2 | 9/2010 | Sybert et al. |
| 7,807,461 B2 | 10/2010 | Kang et al. |
| 7,815,686 B2 | 10/2010 | Badylak |
| 7,824,671 B2 | 11/2010 | Binder et al. |
| 7,833,278 B2 | 11/2010 | Evans et al. |
| 7,837,708 B2 | 11/2010 | Schmieding et al. |
| 7,846,728 B2 | 12/2010 | Brooks et al. |
| 7,858,296 B2 | 12/2010 | Sowemimo-Coker et al. |
| 7,871,646 B2 | 1/2011 | Ghinelli |
| 7,875,272 B2 | 1/2011 | Messina et al. |
| 7,875,273 B2 | 1/2011 | Messina et al. |
| 7,875,296 B2 | 1/2011 | Binette et al. |
| 7,887,795 B2 | 2/2011 | Fraser et al. |
| 7,888,119 B2 | 2/2011 | Sugaya et al. |
| 7,892,577 B2 | 2/2011 | Borden |
| 7,901,461 B2 | 3/2011 | Harmon et al. |
| 7,901,672 B2 | 3/2011 | Fraser et al. |
| 7,906,110 B2 | 3/2011 | Chancellor et al. |
| 7,914,779 B2 | 3/2011 | Hariri |
| 7,915,039 B2 | 3/2011 | Teplyashin |
| 7,923,246 B2 | 4/2011 | Sasai et al. |
| 7,931,687 B2 | 4/2011 | Masuda et al. |
| 7,932,084 B2 | 4/2011 | Katz et al. |
| 7,939,108 B2 | 5/2011 | Morris et al. |
| 7,947,266 B2 | 5/2011 | Gronthos et al. |
| 7,968,329 B2 | 6/2011 | Dancu |
| 7,977,094 B2 | 7/2011 | Masinaei et al. |
| 7,998,472 B2 | 8/2011 | Huss et al. |
| 7,998,735 B2 | 8/2011 | Morrison et al. |
| 8,002,813 B2 | 8/2011 | Scarborough et al. |
| 8,039,016 B2 | 10/2011 | Drapeau et al. |
| 8,133,421 B2 | 3/2012 | Boyce et al. |
| 8,137,408 B2 | 3/2012 | Kadiyala et al. |
| 8,177,738 B2 | 5/2012 | Schmieding et al. |
| 8,197,474 B2 | 6/2012 | Scarborough et al. |
| 8,292,968 B2 | 10/2012 | Truncale et al. |
| 8,309,106 B2 | 11/2012 | Masinaei et al. |
| 8,313,742 B2 | 11/2012 | Kadiyala et al. |
| 8,357,384 B2 | 1/2013 | Behnam et al. |
| 8,419,802 B2 | 4/2013 | Evans et al. |
| 8,460,860 B2 * | 6/2013 | Williams ............ A61L 27/3608 424/549 |
| 8,475,824 B2 | 7/2013 | McKay |
| 8,496,970 B2 | 7/2013 | Binette et al. |
| 8,524,253 B2 | 9/2013 | Kinnane et al. |
| 8,529,862 B2 | 9/2013 | Tennent et al. |
| 8,658,217 B2 | 2/2014 | McKay et al. |
| 8,663,672 B2 | 3/2014 | Manrique et al. |
| 8,734,525 B2 | 5/2014 | Behnam |
| 8,834,928 B1 | 9/2014 | Truncale et al. |
| 8,883,210 B1 | 11/2014 | Truncale et al. |
| 9,138,509 B2 | 9/2015 | Sunwoo et al. |
| 9,211,359 B2 | 12/2015 | McKay et al. |
| 9,320,708 B2 | 4/2016 | Scifert et al. |
| 9,352,003 B1 | 5/2016 | Semler et al. |
| 9,364,583 B2 | 6/2016 | McKay |
| 9,387,094 B2 | 7/2016 | Manrique et al. |
| 9,393,116 B2 | 7/2016 | Betz et al. |
| 9,398,948 B2 | 7/2016 | Mills et al. |
| 9,486,483 B2 | 11/2016 | Bhat et al. |
| 9,539,286 B2 | 1/2017 | Bhat et al. |
| 2001/0014831 A1 | 8/2001 | Scarborough |
| 2001/0033834 A1 | 10/2001 | Wilkison et al. |
| 2001/0039458 A1 | 11/2001 | Boyer, II et al. |
| 2001/0041792 A1 | 11/2001 | Donda et al. |
| 2002/0018796 A1 | 2/2002 | Wironen |
| 2002/0076395 A1 | 6/2002 | Crystal et al. |
| 2002/0076400 A1 | 6/2002 | Katz et al. |
| 2002/0110544 A1 | 8/2002 | Goldberg et al. |
| 2002/0122790 A1 | 9/2002 | Hunziker |
| 2002/0159982 A1 | 10/2002 | Bonassar et al. |
| 2003/0054331 A1 | 3/2003 | Fraser et al. |
| 2003/0077825 A1 | 4/2003 | Bhatnagar et al. |
| 2003/0082152 A1 | 5/2003 | Hedrick et al. |
| 2003/0091543 A1 | 5/2003 | Klein et al. |
| 2003/0113813 A1 | 6/2003 | Heidaran et al. |
| 2003/0148510 A1 | 8/2003 | Mitrani |
| 2003/0152558 A1 | 8/2003 | Luft et al. |
| 2003/0161816 A1 | 8/2003 | Fraser et al. |
| 2003/0162707 A1 | 8/2003 | Fraser et al. |
| 2003/0180269 A1 | 9/2003 | Hariri |
| 2003/0181978 A1 | 9/2003 | Brown et al. |
| 2003/0187515 A1 | 10/2003 | Hariri et al. |
| 2003/0206937 A1 | 11/2003 | Gertzman et al. |
| 2003/0224518 A1 | 12/2003 | Adkisson, IV |
| 2003/0235580 A1 | 12/2003 | Zhang |
| 2004/0010320 A1 | 1/2004 | Huckle et al. |
| 2004/0028660 A1 | 2/2004 | Hariri et al. |
| 2004/0030406 A1 | 2/2004 | Ochi et al. |
| 2004/0048375 A1 | 3/2004 | Alt |
| 2004/0048796 A1 | 3/2004 | Hariri et al. |
| 2004/0052768 A1 | 3/2004 | Morrison et al. |
| 2004/0057938 A1 | 3/2004 | Ghinelli |
| 2004/0059364 A1 | 3/2004 | Gaskins et al. |
| 2004/0067218 A1 | 4/2004 | Casteilla et al. |
| 2004/0077079 A1 | 4/2004 | Storgaard et al. |
| 2004/0078077 A1 | 4/2004 | Binette et al. |
| 2004/0078090 A1 | 4/2004 | Binette et al. |
| 2004/0082063 A1 | 4/2004 | Deshpande et al. |
| 2004/0091462 A1 | 5/2004 | Lin et al. |
| 2004/0092011 A1 | 5/2004 | Wilkison et al. |
| 2004/0096430 A1 | 5/2004 | Bauer |
| 2004/0096431 A1 | 5/2004 | Fraser et al. |
| 2004/0097867 A1 | 5/2004 | Fraser et al. |
| 2004/0106196 A1 | 6/2004 | Fraser et al. |
| 2004/0115172 A1 | 6/2004 | Bianchi et al. |
| 2004/0126878 A1 | 7/2004 | Ramos et al. |
| 2004/0166096 A1 | 8/2004 | Kolkin et al. |
| 2004/0171146 A1 | 9/2004 | Katz et al. |
| 2004/0181240 A1 | 9/2004 | Tseng et al. |
| 2004/0191226 A1 | 9/2004 | Badylak |
| 2004/0197367 A1 | 10/2004 | Rezania et al. |
| 2004/0229351 A1 | 11/2004 | Rodriguez et al. |
| 2004/0230309 A1 | 11/2004 | DiMauro et al. |
| 2004/0241146 A1 | 12/2004 | Biscup |
| 2004/0265971 A1 | 12/2004 | Sato et al. |
| 2004/0267362 A1 | 12/2004 | Hwang et al. |
| 2005/0002910 A1 | 1/2005 | Wolfinbarger, Jr. et al. |
| 2005/0003532 A1 | 1/2005 | Nakamura et al. |
| 2005/0008626 A1 | 1/2005 | Fraser et al. |
| 2005/0009000 A1 | 1/2005 | Wilhelm et al. |
| 2005/0019908 A1 | 1/2005 | Hariri |
| 2005/0025755 A1 | 2/2005 | Hedrick et al. |
| 2005/0026279 A1 | 2/2005 | Tseng et al. |
| 2005/0033449 A1 | 2/2005 | Ashman |
| 2005/0048033 A1 | 3/2005 | Fraser et al. |
| 2005/0048034 A1 | 3/2005 | Fraser et al. |
| 2005/0048035 A1 | 3/2005 | Fraser et al. |
| 2005/0048036 A1 | 3/2005 | Hedrick et al. |
| 2005/0048644 A1 | 3/2005 | Hedrick et al. |
| 2005/0058629 A1 | 3/2005 | Harmon et al. |
| 2005/0058630 A1 | 3/2005 | Harris et al. |
| 2005/0058631 A1 | 3/2005 | Kihm et al. |
| 2005/0058632 A1 | 3/2005 | Hedrick et al. |
| 2005/0064041 A1 | 3/2005 | O'Leary et al. |
| 2005/0074436 A1 | 4/2005 | Fraser et al. |
| 2005/0076396 A1 | 4/2005 | Katz et al. |

(56) References Cited

U.S. PATENT DOCUMENTS

| | | |
|---|---|---|
| 2005/0084961 A1 | 4/2005 | Hedrick et al. |
| 2005/0095228 A1 | 5/2005 | Fraser et al. |
| 2005/0100555 A1 | 5/2005 | Pitzalis et al. |
| 2005/0112761 A1 | 5/2005 | Halvorsen et al. |
| 2005/0118228 A1 | 6/2005 | Trieu |
| 2005/0125077 A1 | 6/2005 | Harmon et al. |
| 2005/0136042 A1 | 6/2005 | Betz et al. |
| 2005/0147642 A1 | 7/2005 | Laredo et al. |
| 2005/0147959 A1 | 7/2005 | Frondoza et al. |
| 2005/0152941 A1 | 7/2005 | Hunter et al. |
| 2005/0152944 A1 | 7/2005 | Hunter et al. |
| 2005/0152945 A1 | 7/2005 | Hunter et al. |
| 2005/0152947 A1 | 7/2005 | Hunter et al. |
| 2005/0152948 A1 | 7/2005 | Hunter et al. |
| 2005/0153441 A1 | 7/2005 | Hedrick et al. |
| 2005/0153442 A1 | 7/2005 | Katz et al. |
| 2005/0181973 A1 | 8/2005 | Genove et al. |
| 2005/0182463 A1 | 8/2005 | Hunter et al. |
| 2005/0182496 A1 | 8/2005 | Hunter et al. |
| 2005/0187639 A1 | 8/2005 | Hunter et al. |
| 2005/0203635 A1 | 9/2005 | Hunter et al. |
| 2005/0209705 A1 | 9/2005 | Niederauer et al. |
| 2005/0214259 A1 | 9/2005 | Sano et al. |
| 2005/0250202 A1 | 11/2005 | March et al. |
| 2005/0255588 A1 | 11/2005 | Young et al. |
| 2005/0260174 A1 | 11/2005 | Fraser et al. |
| 2005/0260175 A1 | 11/2005 | Hedrick et al. |
| 2005/0260748 A1 | 11/2005 | Chang et al. |
| 2005/0281788 A1 | 12/2005 | De Bari et al. |
| 2005/0282275 A1 | 12/2005 | Katz et al. |
| 2005/0288796 A1 | 12/2005 | Awad et al. |
| 2006/0002900 A1 | 1/2006 | Binder et al. |
| 2006/0018887 A1 | 1/2006 | Kadiyala et al. |
| 2006/0045872 A1 | 3/2006 | Miguel et al. |
| 2006/0051327 A1 | 3/2006 | Johnson |
| 2006/0051865 A1 | 3/2006 | Higgins et al. |
| 2006/0073124 A1 | 4/2006 | Garcia Castro et al. |
| 2006/0078993 A1 | 4/2006 | Phan et al. |
| 2006/0083720 A1 | 4/2006 | Fraser et al. |
| 2006/0083769 A1 | 4/2006 | Kumar et al. |
| 2006/0084602 A1 | 4/2006 | Lynch |
| 2006/0121004 A1 | 6/2006 | Echelard et al. |
| 2006/0136068 A1 | 6/2006 | de Bruijn et al. |
| 2006/0147424 A1 | 7/2006 | Sakuragawa et al. |
| 2006/0147430 A1 | 7/2006 | Sayre et al. |
| 2006/0147433 A1 | 7/2006 | Hiles |
| 2006/0153815 A1 | 7/2006 | Seyda et al. |
| 2006/0153816 A1 | 7/2006 | Brown et al. |
| 2006/0153817 A1 | 7/2006 | Kihm et al. |
| 2006/0153818 A1 | 7/2006 | Dhanaraj et al. |
| 2006/0153928 A1 | 7/2006 | Kinoshita et al. |
| 2006/0171930 A1 | 8/2006 | Seyda et al. |
| 2006/0171932 A1 | 8/2006 | Hendricks et al. |
| 2006/0204556 A1 | 9/2006 | Daniels et al. |
| 2006/0222634 A1 | 10/2006 | Clarke et al. |
| 2006/0228339 A1 | 10/2006 | Wang |
| 2006/0228796 A1 | 10/2006 | Kolkin et al. |
| 2006/0240064 A9 | 10/2006 | Hunter et al. |
| 2006/0240555 A1 | 10/2006 | Ronfard |
| 2006/0263335 A1 | 11/2006 | France et al. |
| 2007/0003593 A1 | 1/2007 | Wironen et al. |
| 2007/0025973 A1 | 2/2007 | Fitzsimmons et al. |
| 2007/0026518 A1 | 2/2007 | Healy et al. |
| 2007/0027543 A1 | 2/2007 | Gimble et al. |
| 2007/0036768 A1 | 2/2007 | Fraser et al. |
| 2007/0048292 A1 | 3/2007 | Morita et al. |
| 2007/0056597 A1 | 3/2007 | Fitzsimmons et al. |
| 2007/0065938 A1 | 3/2007 | Gronthos et al. |
| 2007/0071740 A1 | 3/2007 | Tseng et al. |
| 2007/0071828 A1 | 3/2007 | Tseng et al. |
| 2007/0077649 A1 | 4/2007 | Sammak et al. |
| 2007/0082057 A1 | 4/2007 | Masinaei et al. |
| 2007/0082058 A1 | 4/2007 | Masinaei et al. |
| 2007/0092492 A1 | 4/2007 | Matsuda et al. |
| 2007/0098756 A1 | 5/2007 | Behnam |
| 2007/0104692 A1 | 5/2007 | Quijano et al. |
| 2007/0104693 A1 | 5/2007 | Quijano et al. |
| 2007/0110732 A1 | 5/2007 | Johnson |
| 2007/0110820 A1 | 5/2007 | Behnam |
| 2007/0128171 A1 | 6/2007 | Tranquillo et al. |
| 2007/0128173 A1 | 6/2007 | Verbruggen et al. |
| 2007/0134210 A1 | 6/2007 | Heidaran |
| 2007/0134211 A1 | 6/2007 | Halvorsen |
| 2007/0148766 A1 | 6/2007 | Yoshimura et al. |
| 2007/0154515 A1 | 7/2007 | Johnson et al. |
| 2007/0154563 A1 | 7/2007 | Behnam et al. |
| 2007/0172812 A1 | 7/2007 | Ochi et al. |
| 2007/0185585 A1 | 8/2007 | Bracy et al. |
| 2007/0190034 A1 | 8/2007 | Paludan et al. |
| 2007/0196421 A1 | 8/2007 | Hunter et al. |
| 2007/0202592 A1 | 8/2007 | Kitagawa et al. |
| 2007/0207127 A1 | 9/2007 | Kato et al. |
| 2007/0212336 A1 | 9/2007 | Fulkerson et al. |
| 2007/0212396 A1 | 9/2007 | Zheng et al. |
| 2007/0212676 A1 | 9/2007 | Takakura et al. |
| 2007/0213822 A1 | 9/2007 | Trieu |
| 2007/0213823 A1 | 9/2007 | Trieu |
| 2007/0213824 A1 | 9/2007 | Trieu |
| 2007/0218039 A1 | 9/2007 | Devi et al. |
| 2007/0231297 A1 | 10/2007 | Smith et al. |
| 2007/0231305 A1 | 10/2007 | Noll et al. |
| 2007/0231401 A1 | 10/2007 | Tseng et al. |
| 2007/0233272 A1 | 10/2007 | Boyce et al. |
| 2007/0243172 A1 | 10/2007 | Ra et al. |
| 2007/0248580 A1 | 10/2007 | Garcia Castro et al. |
| 2007/0248998 A1 | 10/2007 | Zhang |
| 2007/0249044 A1 | 10/2007 | Desai et al. |
| 2007/0249045 A1 | 10/2007 | Gimble et al. |
| 2007/0258956 A1 | 11/2007 | Higgins et al. |
| 2007/0260326 A1 | 11/2007 | Williams et al. |
| 2007/0264239 A1 | 11/2007 | Huard et al. |
| 2007/0264240 A1 | 11/2007 | Slavin et al. |
| 2007/0275362 A1 | 11/2007 | Edinger et al. |
| 2007/0276489 A1 | 11/2007 | Bindseil et al. |
| 2007/0282456 A1 | 12/2007 | Geng et al. |
| 2007/0292401 A1 | 12/2007 | Harmon et al. |
| 2007/0292872 A1 | 12/2007 | Sylvester et al. |
| 2007/0299508 A1 | 12/2007 | Morrison et al. |
| 2008/0004713 A1 | 1/2008 | Nakamura et al. |
| 2008/0014179 A1 | 1/2008 | Ferree |
| 2008/0025957 A1 | 1/2008 | Lapidot et al. |
| 2008/0026461 A1 | 1/2008 | Deshpande et al. |
| 2008/0027546 A1 | 1/2008 | Semler et al. |
| 2008/0031858 A1 | 2/2008 | Chan et al. |
| 2008/0033572 A1 | 2/2008 | D'Antonio et al. |
| 2008/0038314 A1 | 2/2008 | Hunziker |
| 2008/0039940 A1 | 2/2008 | Hashimoto et al. |
| 2008/0039955 A1 | 2/2008 | Hunziker |
| 2008/0046095 A1 | 2/2008 | Daniel |
| 2008/0050814 A1 | 2/2008 | Allickson |
| 2008/0057578 A1 | 3/2008 | Kuwabara et al. |
| 2008/0058953 A1 | 3/2008 | Scarborough |
| 2008/0071385 A1 | 3/2008 | Binette et al. |
| 2008/0075699 A1 | 3/2008 | Buhring et al. |
| 2008/0077251 A1 | 3/2008 | Chen et al. |
| 2008/0081369 A1 | 4/2008 | Adkisson, IV et al. |
| 2008/0089871 A1 | 4/2008 | Hunziker |
| 2008/0091270 A1 | 4/2008 | Miller et al. |
| 2008/0095748 A1 | 4/2008 | Kharazi et al. |
| 2008/0108045 A1 | 5/2008 | Ghinelli |
| 2008/0112837 A1 | 5/2008 | Yoshizawa et al. |
| 2008/0113007 A1 | 5/2008 | Kurihara et al. |
| 2008/0131522 A1 | 6/2008 | Liu et al. |
| 2008/0152624 A1 | 6/2008 | Paludan et al. |
| 2008/0152629 A1 | 6/2008 | Edinger et al. |
| 2008/0153157 A1 | 6/2008 | Yao et al. |
| 2008/0160085 A1 | 7/2008 | Boland et al. |
| 2008/0161410 A1 | 7/2008 | Kusters et al. |
| 2008/0175824 A1 | 7/2008 | Heidaran et al. |
| 2008/0181967 A1 | 7/2008 | Liu et al. |
| 2008/0187518 A1 | 8/2008 | Ogle et al. |
| 2008/0188945 A1 | 8/2008 | Boyce et al. |
| 2008/0193554 A1 | 8/2008 | Dua et al. |
| 2008/0199443 A1 | 8/2008 | Moos et al. |

(56) References Cited

U.S. PATENT DOCUMENTS

| | | |
|---|---|---|
| 2008/0206208 A1 | 8/2008 | Casteilla et al. |
| 2008/0206343 A1 | 8/2008 | Edinger et al. |
| 2008/0213228 A1 | 9/2008 | Edinger et al. |
| 2008/0213230 A1 | 9/2008 | Phillips et al. |
| 2008/0213235 A1 | 9/2008 | Katz et al. |
| 2008/0221527 A1 | 9/2008 | Bradley et al. |
| 2008/0226595 A1 | 9/2008 | Edinger et al. |
| 2008/0226612 A1 | 9/2008 | Treves et al. |
| 2008/0226692 A1 | 9/2008 | Sato et al. |
| 2008/0233088 A1 | 9/2008 | Guha et al. |
| 2008/0233203 A1 | 9/2008 | Woodell-May et al. |
| 2008/0248003 A1 | 10/2008 | Katz et al. |
| 2008/0248005 A1 | 10/2008 | Phan |
| 2008/0248481 A1 | 10/2008 | Rapko et al. |
| 2008/0254092 A1 | 10/2008 | McDevitt et al. |
| 2008/0260703 A1 | 10/2008 | Riordan et al. |
| 2008/0262633 A1 | 10/2008 | Williams et al. |
| 2008/0269762 A1 | 10/2008 | Simon et al. |
| 2008/0274185 A1 | 11/2008 | Mao |
| 2008/0286241 A1 | 11/2008 | Lee et al. |
| 2008/0286267 A1 | 11/2008 | Sing et al. |
| 2008/0286324 A1 | 11/2008 | Stolen et al. |
| 2008/0288085 A1 | 11/2008 | Mao |
| 2008/0175825 A1 | 12/2008 | Shelby et al. |
| 2008/0299087 A1 | 12/2008 | Tseng et al. |
| 2008/0317718 A1 | 12/2008 | Yoshimura |
| 2008/0318317 A1 | 12/2008 | Roche et al. |
| 2009/0004161 A1 | 1/2009 | Palladino et al. |
| 2009/0010899 A1 | 1/2009 | Palladino et al. |
| 2009/0012629 A1 | 1/2009 | Yao et al. |
| 2009/0017438 A1 | 1/2009 | Roy et al. |
| 2009/0017439 A1 | 1/2009 | Shimko et al. |
| 2009/0022698 A1 | 1/2009 | Ha et al. |
| 2009/0024223 A1 | 1/2009 | Chen et al. |
| 2009/0024224 A1 | 1/2009 | Chen et al. |
| 2009/0024229 A1 | 1/2009 | Chen et al. |
| 2009/0028834 A1 | 1/2009 | Siegel et al. |
| 2009/0028919 A1 | 1/2009 | Dancu |
| 2009/0035282 A1 | 2/2009 | Schierholz et al. |
| 2009/0041825 A1 | 2/2009 | Kotov et al. |
| 2009/0053277 A1 | 2/2009 | Nagaya et al. |
| 2009/0054983 A1 | 2/2009 | Wuisman et al. |
| 2009/0060974 A1 | 3/2009 | Schmieding et al. |
| 2009/0062870 A1 | 3/2009 | Milano et al. |
| 2009/0068154 A1 | 3/2009 | Ueda |
| 2009/0074728 A1 | 3/2009 | Gronthos et al. |
| 2009/0074753 A1 | 3/2009 | Lynch |
| 2009/0074871 A1 | 3/2009 | Sunwoo et al. |
| 2009/0075381 A1 | 3/2009 | Clarke et al. |
| 2009/0075863 A1 | 3/2009 | O'Driscoll et al. |
| 2009/0082717 A1 | 3/2009 | Bellomo et al. |
| 2009/0093056 A1 | 4/2009 | Iskovitz-Eldor et al. |
| 2009/0104164 A1 | 4/2009 | Zhang et al. |
| 2009/0130067 A1 | 5/2009 | Buscher et al. |
| 2009/0130756 A1 | 5/2009 | Klann et al. |
| 2009/0136457 A1 | 5/2009 | Sing et al. |
| 2009/0136471 A1 | 5/2009 | Heidaran et al. |
| 2009/0136988 A1 | 5/2009 | Reschiglian et al. |
| 2009/0142311 A1 | 6/2009 | Masuda et al. |
| 2009/0142835 A1 | 6/2009 | Kobayashi et al. |
| 2009/0155340 A1 | 6/2009 | Chu et al. |
| 2009/0162445 A1 | 6/2009 | Masinaei et al. |
| 2009/0163990 A1 | 6/2009 | Yang et al. |
| 2009/0169642 A1 | 7/2009 | Fradette et al. |
| 2009/0170059 A1 | 7/2009 | Klingemann |
| 2009/0175954 A1 | 7/2009 | Kinoshita et al. |
| 2009/0181104 A1 | 7/2009 | Rigotti et al. |
| 2009/0181456 A1 | 7/2009 | Hedrick et al. |
| 2009/0185978 A1 | 7/2009 | Lundgren-Akerlund |
| 2009/0191160 A1 | 7/2009 | Hong |
| 2009/0196901 A1 | 8/2009 | Guilak et al. |
| 2009/0202977 A1 | 8/2009 | Ott et al. |
| 2009/0203613 A1 | 8/2009 | Beretta et al. |
| 2009/0209020 A1 | 8/2009 | Park et al. |
| 2009/0214649 A1 | 8/2009 | Gazit et al. |
| 2009/0220569 A1 | 9/2009 | Williams et al. |
| 2009/0220605 A1 | 9/2009 | Wei et al. |
| 2009/0221075 A1 | 9/2009 | Dorian et al. |
| 2009/0222086 A1 | 9/2009 | Lui et al. |
| 2009/0227704 A1 | 9/2009 | Troxel et al. |
| 2009/0228105 A1 | 9/2009 | Son et al. |
| 2009/0232772 A1 | 9/2009 | Amano et al. |
| 2009/0238801 A1 | 9/2009 | Woodbury et al. |
| 2009/0239299 A1 | 9/2009 | Buss |
| 2009/0246182 A1 | 10/2009 | Casteilla et al. |
| 2009/0252710 A1 | 10/2009 | Zhang et al. |
| 2009/0252711 A1 | 10/2009 | Boquest et al. |
| 2009/0258082 A1 | 10/2009 | Nikaido et al. |
| 2009/0258337 A1 | 10/2009 | Yagi |
| 2009/0269315 A1 | 10/2009 | Fraser et al. |
| 2009/0274665 A1 | 11/2009 | Akabutu et al. |
| 2009/0275011 A1 | 11/2009 | Eibl et al. |
| 2009/0292311 A1 | 11/2009 | Garcia Olmo et al. |
| 2009/0297488 A1 | 12/2009 | Fraser et al. |
| 2009/0304643 A1 | 12/2009 | Khurgel et al. |
| 2009/0304644 A1 | 12/2009 | Hadrick et al. |
| 2009/0304646 A1 | 12/2009 | Sakurada et al. |
| 2009/0304654 A1 | 12/2009 | Lue et al. |
| 2009/0311223 A1 | 12/2009 | Ichim |
| 2010/0003299 A1 | 1/2010 | Tseng et al. |
| 2010/0008967 A1 | 1/2010 | Grande et al. |
| 2010/0015104 A1 | 1/2010 | Fraser et al. |
| 2010/0015204 A1 | 1/2010 | Hedrick et al. |
| 2010/0015712 A1 | 1/2010 | Sakuragawa et al. |
| 2010/0022005 A1 | 1/2010 | March et al. |
| 2010/0028306 A1 | 2/2010 | Clarke et al. |
| 2010/0028308 A1 | 2/2010 | Knipper et al. |
| 2010/0028407 A1 | 2/2010 | Del Priore et al. |
| 2010/0036503 A1 | 2/2010 | Chen et al. |
| 2010/0047213 A1 | 2/2010 | Zeitlin et al. |
| 2010/0047214 A1 | 2/2010 | Abramson et al. |
| 2010/0047351 A1 | 2/2010 | Zeitlin et al. |
| 2010/0055757 A1 | 3/2010 | Lin et al. |
| 2010/0068180 A1 | 3/2010 | Marshall et al. |
| 2010/0080779 A1 | 4/2010 | Smith et al. |
| 2010/0082113 A1 | 4/2010 | Gingras et al. |
| 2010/0098669 A1 | 4/2010 | Fernandez Miguel et al. |
| 2010/0098673 A1 | 4/2010 | D'Antonio et al. |
| 2010/0098739 A1 | 4/2010 | Katz et al. |
| 2010/0098743 A1 | 4/2010 | Nikaido et al. |
| 2010/0104539 A1 | 4/2010 | Daniel et al. |
| 2010/0104542 A1 | 4/2010 | Austen, Jr. |
| 2010/0105100 A1 | 4/2010 | Sakurada et al. |
| 2010/0106233 A1 | 4/2010 | Grant et al. |
| 2010/0111897 A1 | 5/2010 | Katz et al. |
| 2010/0112031 A1 | 5/2010 | Katz |
| 2010/0112084 A1 | 5/2010 | Wu et al. |
| 2010/0112543 A1 | 5/2010 | Ngo et al. |
| 2010/0112695 A1 | 5/2010 | Min |
| 2010/0112696 A1 | 5/2010 | Min |
| 2010/0114013 A1 | 5/2010 | Boyden et al. |
| 2010/0119492 A1 | 5/2010 | Hans et al. |
| 2010/0119496 A1 | 5/2010 | Wilkison et al. |
| 2010/0120069 A1 | 5/2010 | Sakurada et al. |
| 2010/0124563 A1 | 5/2010 | Coleman et al. |
| 2010/0124569 A1 | 5/2010 | Abbot et al. |
| 2010/0124776 A1 | 5/2010 | Shi |
| 2010/0129328 A1 | 5/2010 | Sing et al. |
| 2010/0129330 A1 | 5/2010 | Wilkison et al. |
| 2010/0136114 A1 | 6/2010 | Mao |
| 2010/0136668 A1 | 6/2010 | Hedrick et al. |
| 2010/0143312 A1 | 6/2010 | Hariri et al. |
| 2010/0143477 A1 | 6/2010 | Siegel et al. |
| 2010/0145473 A1 | 6/2010 | Yannas et al. |
| 2010/0150878 A1 | 6/2010 | Bellomo et al. |
| 2010/0151435 A1 | 6/2010 | Thatte et al. |
| 2010/0151574 A1 | 6/2010 | Matsuyama et al. |
| 2010/0158876 A1 | 6/2010 | Alessandri et al. |
| 2010/0158975 A1 | 6/2010 | Naughton et al. |
| 2010/0166716 A1 | 7/2010 | Serikov et al. |
| 2010/0166824 A1 | 7/2010 | Naughton et al. |
| 2010/0166879 A1 | 7/2010 | Shim et al. |
| 2010/0168022 A1 | 7/2010 | Centeno |
| 2010/0173352 A1 | 7/2010 | Blanc-Brude |

(56) References Cited

U.S. PATENT DOCUMENTS

| | | |
|---|---|---|
| 2010/0173411 A1 | 7/2010 | Katz et al. |
| 2010/0178274 A1 | 7/2010 | Sekiya et al. |
| 2010/0178681 A1 | 7/2010 | Lee et al. |
| 2010/0183568 A1 | 7/2010 | Matuyama et al. |
| 2010/0183571 A1 | 7/2010 | Paludan et al. |
| 2010/0196333 A1 | 8/2010 | Gaskins et al. |
| 2010/0196439 A1 | 8/2010 | Beck et al. |
| 2010/0196480 A1 | 8/2010 | Hiles et al. |
| 2010/0209387 A1 | 8/2010 | Wasielewski |
| 2010/0209408 A1 | 8/2010 | Stephen A. et al. |
| 2010/0209470 A1 | 8/2010 | Mohan et al. |
| 2010/0215714 A1 | 8/2010 | Messina et al. |
| 2010/0215717 A1 | 8/2010 | Soker et al. |
| 2010/0221231 A1 | 9/2010 | Smith |
| 2010/0221268 A1 | 9/2010 | Parolini |
| 2010/0227399 A1 | 9/2010 | Funaki et al. |
| 2010/0233131 A1 | 9/2010 | Kang et al. |
| 2010/0233139 A1 | 9/2010 | Hedrick et al. |
| 2010/0239539 A1 | 9/2010 | Sing et al. |
| 2010/0239540 A1 | 9/2010 | Brinchmann et al. |
| 2010/0239542 A1 | 9/2010 | Young et al. |
| 2010/0239543 A1 | 9/2010 | Young et al. |
| 2010/0249758 A1 | 9/2010 | Sengun et al. |
| 2010/0254954 A1 | 10/2010 | Sakuragawa et al. |
| 2010/0255115 A1 | 10/2010 | Mohan et al. |
| 2010/0256774 A1 | 10/2010 | Wang et al. |
| 2010/0260843 A1 | 10/2010 | Messina et al. |
| 2010/0261276 A1 | 10/2010 | Park et al. |
| 2010/0266553 A1 | 10/2010 | Ra et al. |
| 2010/0267107 A1 | 10/2010 | Zuba-Surma et al. |
| 2010/0272694 A1 | 10/2010 | Yang et al. |
| 2010/0272803 A1 | 10/2010 | Mistry et al. |
| 2010/0278783 A1 | 11/2010 | Rouy et al. |
| 2010/0279405 A1 | 11/2010 | Peterson et al. |
| 2010/0285521 A1 | 11/2010 | Vossman et al. |
| 2010/0285580 A1 | 11/2010 | Evans et al. |
| 2010/0285582 A1 | 11/2010 | Choung |
| 2010/0285588 A1 | 11/2010 | Stubbers et al. |
| 2010/0291042 A1 | 11/2010 | Crawford et al. |
| 2010/0291219 A1 | 11/2010 | Karp et al. |
| 2010/0291679 A1 | 11/2010 | Edinger et al. |
| 2010/0292791 A1 | 11/2010 | Lu et al. |
| 2010/0297089 A1 | 11/2010 | Oh |
| 2010/0297689 A1 | 11/2010 | Edinger et al. |
| 2010/0303766 A1 | 12/2010 | Miyaji et al. |
| 2010/0303773 A1 | 12/2010 | Yang et al. |
| 2010/0303774 A1 | 12/2010 | Hedrick et al. |
| 2010/0304477 A1 | 12/2010 | Buscher et al. |
| 2010/0305696 A1 | 12/2010 | Mao et al. |
| 2010/0310527 A1 | 12/2010 | Alt et al. |
| 2010/0330047 A1 | 12/2010 | Valorani |
| 2010/0330182 A1 | 12/2010 | Young et al. |
| 2010/0330672 A1 | 12/2010 | Sakuragawa et al. |
| 2010/0330673 A1 | 12/2010 | Fraser et al. |
| 2011/0002904 A1 | 1/2011 | Johnson |
| 2011/0003387 A1 | 1/2011 | Abbot et al. |
| 2011/0003388 A1 | 1/2011 | Fraser et al. |
| 2011/0008300 A1 | 1/2011 | Wouters et al. |
| 2011/0008397 A1 | 1/2011 | Cohen |
| 2011/0008763 A1 | 1/2011 | Lee |
| 2011/0009963 A1 | 1/2011 | Binnette et al. |
| 2011/0014701 A1 | 1/2011 | Ghosh |
| 2011/0020196 A1 | 1/2011 | Grippi et al. |
| 2011/0020293 A1 | 1/2011 | Woda et al. |
| 2011/0027871 A1 | 2/2011 | Gaskins et al. |
| 2011/0027879 A1 | 2/2011 | Katz et al. |
| 2011/0028903 A1 | 2/2011 | Schmieding et al. |
| 2011/0038903 A1 | 2/2011 | Singh |
| 2011/0039332 A1 | 2/2011 | Sakurada et al. |
| 2011/0040388 A1 | 2/2011 | Alini et al. |
| 2011/0045044 A1 | 2/2011 | Masinaei et al. |
| 2011/0045588 A1 | 2/2011 | Kawase et al. |
| 2011/0045949 A1 | 2/2011 | Kurihara et al. |
| 2011/0046628 A1 | 2/2011 | Jamali |
| 2011/0064701 A1 | 3/2011 | Young et al. |
| 2011/0064705 A1 | 3/2011 | Lanza et al. |
| 2011/0064810 A1 | 3/2011 | Ghanavi |
| 2011/0065083 A1 | 3/2011 | Shimko et al. |
| 2011/0070205 A1 | 3/2011 | Crawford et al. |
| 2011/0070647 A1 | 3/2011 | Dezawa et al. |
| 2011/0077679 A1 | 3/2011 | Moran et al. |
| 2011/0081326 A1 | 4/2011 | Hantash |
| 2011/0086008 A1 | 4/2011 | Hoemann et al. |
| 2011/0086068 A1 | 4/2011 | Gourdie et al. |
| 2011/0086426 A1 | 4/2011 | Freund |
| 2011/0087338 A1 | 4/2011 | Siemionow et al. |
| 2011/0091517 A1 | 4/2011 | Binette et al. |
| 2011/0097381 A1 | 4/2011 | Binette et al. |
| 2011/0098826 A1 | 4/2011 | Mauck et al. |
| 2011/0104133 A1 | 5/2011 | Tseng et al. |
| 2011/0104735 A1 | 5/2011 | Buehrer et al. |
| 2011/0110898 A1 | 5/2011 | Kleinsek et al. |
| 2011/0111497 A1 | 5/2011 | Tamai et al. |
| 2011/0111499 A1 | 5/2011 | Torihashi et al. |
| 2011/0117167 A1 | 5/2011 | Sanford et al. |
| 2011/0117171 A1 | 5/2011 | Melican et al. |
| 2011/0117650 A1 | 5/2011 | Riordan |
| 2011/0124105 A1 | 5/2011 | Hampson et al. |
| 2011/0129447 A1 | 6/2011 | Meretzki et al. |
| 2011/0143331 A1 | 6/2011 | Roy et al. |
| 2011/0143429 A1 | 6/2011 | Chun et al. |
| 2011/0150845 A1 | 6/2011 | Parekkadan et al. |
| 2011/0150846 A1 | 6/2011 | Van Epps |
| 2011/0151005 A1 | 6/2011 | Ylikomi et al. |
| 2011/0151011 A1 | 6/2011 | Flynn |
| 2011/0158959 A1 | 6/2011 | McIntosh et al. |
| 2011/0158966 A1 | 6/2011 | Seligman |
| 2011/0158968 A1 | 6/2011 | Fraser et al. |
| 2011/0171726 A1 | 7/2011 | Kang et al. |
| 2011/0177132 A1 | 7/2011 | Allon et al. |
| 2011/0177134 A1 | 7/2011 | Harmon et al. |
| 2011/0177593 A1 | 7/2011 | Funaki et al. |
| 2011/0182962 A1 | 7/2011 | McKay |
| 2011/0182963 A1 | 7/2011 | McKay |
| 2011/0183001 A1 | 7/2011 | Rosson et al. |
| 2011/0184381 A1 | 7/2011 | Shintani |
| 2011/0189140 A1 | 8/2011 | Christman et al. |
| 2011/0189254 A1 | 8/2011 | Liu et al. |
| 2011/0189696 A1 | 8/2011 | Gronthos et al. |
| 2011/0195052 A1 | 8/2011 | Behnam et al. |
| 2011/0274668 A1 | 11/2011 | Scarborough et al. |
| 2012/0009230 A1 | 1/2012 | Drapeau et al. |
| 2012/0046758 A1 | 2/2012 | Evans et al. |
| 2012/0093895 A1 | 4/2012 | Song et al. |
| 2012/0100225 A1 | 4/2012 | McKay |
| 2012/0116515 A1 | 5/2012 | Semler et al. |
| 2012/0143334 A1 | 6/2012 | Boyce et al. |
| 2012/0156265 A1 | 6/2012 | Binette et al. |
| 2012/0195952 A1 | 8/2012 | King |
| 2012/0213859 A1 | 8/2012 | Shelby et al. |
| 2012/0251609 A1 | 10/2012 | Huang et al. |
| 2012/0269892 A1 | 10/2012 | Mussand |
| 2012/0330423 A1 | 12/2012 | Lin et al. |
| 2013/0073041 A1 | 3/2013 | Scifert et al. |
| 2013/0115255 A1 | 5/2013 | Bosley, Jr. et al. |
| 2013/0136777 A1 | 5/2013 | Behnam et al. |
| 2013/0149356 A1 | 6/2013 | Mills et al. |
| 2013/0158676 A1 | 6/2013 | Hayzlett et al. |
| 2013/0189338 A1 | 7/2013 | Drapeau et al. |
| 2013/0190893 A1 | 7/2013 | Roock et al. |
| 2013/0195805 A1 | 8/2013 | Wei et al. |
| 2013/0261634 A1 | 10/2013 | McKay |
| 2013/0273121 A1 | 10/2013 | Mizuno et al. |
| 2013/0287741 A1 | 10/2013 | Stilwell et al. |
| 2013/0287753 A1 | 10/2013 | Centeno |
| 2013/0297038 A1 | 11/2013 | McKay |
| 2014/0065238 A1 | 3/2014 | Wolfinbarger, Jr. et al. |
| 2014/0212499 A1 | 7/2014 | Cooper et al. |
| 2014/0314822 A1 | 10/2014 | Carter et al. |
| 2014/0341870 A1 | 11/2014 | Isaev et al. |
| 2015/0010642 A1 | 1/2015 | Anderson et al. |
| 2015/0093429 A1 | 4/2015 | Carter et al. |
| 2015/0110747 A1 | 4/2015 | Bhat et al. |
| 2015/0110748 A1 | 4/2015 | Bhat et al. |

(56) References Cited

U.S. PATENT DOCUMENTS

| | | | |
|---|---|---|---|
| 2015/0140096 | A1 | 5/2015 | Malinin |
| 2015/0224227 | A1 | 8/2015 | Bhat et al. |
| 2015/0251361 | A1 | 9/2015 | Meyer et al. |
| 2015/0258243 | A1 | 9/2015 | Malinin |
| 2015/0283292 | A1 | 10/2015 | Voor et al. |
| 2015/0297793 | A1 | 10/2015 | McKay |
| 2015/0306278 | A1 | 10/2015 | McKay |
| 2015/0343114 | A1 | 12/2015 | Drapeau et al. |
| 2016/0000062 | A1 | 1/2016 | Chen et al. |
| 2016/0017112 | A1 | 1/2016 | Naruse et al. |
| 2016/0038639 | A1 | 2/2016 | Carter et al. |
| 2016/0081803 | A1 | 3/2016 | McKay |
| 2016/0082155 | A1 | 3/2016 | Uveges et al. |
| 2016/0136329 | A1 | 5/2016 | Schlachter et al. |
| 2016/0144075 | A1 | 5/2016 | Behnam et al. |
| 2016/0151537 | A1 | 6/2016 | Govil |
| 2016/0166729 | A1 | 6/2016 | Mossaad et al. |
| 2016/0206782 | A1 | 7/2016 | Pedrozo |
| 2016/0206784 | A1 | 7/2016 | Jessop et al. |
| 2016/0256607 | A1 | 9/2016 | Francis et al. |
| 2016/0361171 | A1 | 12/2016 | Wang et al. |
| 2017/0014550 | A1 | 1/2017 | Elazizi et al. |

FOREIGN PATENT DOCUMENTS

| | | | |
|---|---|---|---|
| CA | 2505737 A1 | 6/2004 | |
| CA | 2415061 A1 | 11/2010 | |
| EP | 0333328 A2 | 9/1989 | |
| EP | 0518389 A2 | 12/1992 | |
| EP | 0669138 A2 | 8/1995 | |
| EP | 1847277 A1 | 10/2007 | |
| JP | 2004210713 | 7/2004 | |
| JP | 2006230749 | 9/2006 | |
| JP | 2007054015 | 3/2007 | |
| KR | 20040020413 A | 3/2004 | |
| WO | WO 89/04646 | 6/1989 | |
| WO | 1989/07425 A2 | 8/1989 | |
| WO | 1998/37903 A1 | 9/1998 | |
| WO | 2000/73421 A2 | 12/2000 | |
| WO | 2001/23532 A1 | 4/2001 | |
| WO | WO 02/02156 A2 | 1/2002 | |
| WO | 0232474 | 4/2002 | |
| WO | WO 0236049 A2 | 8/2002 | |
| WO | 2003/077794 A2 | 9/2003 | |
| WO | 2004/000164 A2 | 12/2003 | |
| WO | 2004/026244 A2 | 4/2004 | |
| WO | 2004/033635 A2 | 4/2004 | |
| WO | WO 2004/045372 A2 | 6/2004 | |
| WO | 2004/078225 A1 | 9/2004 | |
| WO | 2006/094247 A2 | 9/2006 | |
| WO | 2007/037572 A1 | 4/2007 | |
| WO | 2007/038686 A2 | 4/2007 | |
| WO | 2007133451 | 11/2007 | |
| WO | 2008/003042 A2 | 1/2008 | |
| WO | 2009036279 | 3/2009 | |
| WO | 2009/102452 A2 | 8/2009 | |
| WO | 2009134815 | 11/2009 | |
| WO | 2012061024 | 5/2012 | |
| WO | 2012135205 | 10/2012 | |

OTHER PUBLICATIONS

Guimberteau, et al., "The Microvacuolar System: How Connective Tissue Sliding Works", The Journal of Hand Surgery (European Volume), vol. 35E, No. 8, (2010), pp. 614-622.
Halberg et al., "The Adipocyte as an Endocrine Cell", Endocrinol Metab. Clin. North Amer., vol. 37, No. 3, Sep. 2008, pp. 753-767.
Hardingham, "Extracellular Matrix and Pathogenic Mechanisms in Osteoarthritis", Current Rheumatology Reports, vol. 10, (2008), pp. 30-36.
Heinegard et al., "The role of the cartilage matrix in osteoarthritis", www.nature.com/nrrheum, Nat. Rev. Rheumatot., vol. 7, Jan. 2011, pp. 50-56.
Heller, "Soft Tissue, Fascia and the Adjustment", http://chiroweb.com/mpacms/dc/article.php?t=39&id=18250&no_paginate=true&p_friendly=true&no_b=true, printed Jun. 28, 2011.
Henriksson et al., "Identification of Cell Proliferation Zones, Progenitor Cells and a Potential Stem Cell Niche in the Intervertebral Disc Region", SPINE, vol. 34, No. 21, (2009), pp. 2278-2287.
Hidaka et al., "Regulatory Mechanisms of Chondrogenesis and Implications for Understanding Articular Cartilage Homeostasis", Current Rheumatology Reviews, vol. 4, No. 3, (2008), pp. 1-12.
Hiraoka et al., "Mesenchymal progenitor cells in adult human articular cartilage", Biorheology, vol. 43, (2006), pp. 447-454.
Hirschi et al., "Smooth Muscle Stem Cells", The Anatomical Record Part A, vol. 276A, (2004), pp. 22-33.
Hodde et al. "Extracellular Matrix as a Strategy for Treating Chronic Wounds" Am J. Clin Dermatol, vol. 8, No. 2, (2007), pp. 61-66.
Hoell, et al.; "Auto fluorescence of intervertebral disc tissue: a new diagnostic tool", Eur Spine J, vol. 15 (Suppl. 3), (2006), pp. S345-353.
Hollander et al., "Stem Cells and Cartilage Development: Complexities of a Simple Tissue", Stem Cells, vol. 28, (2010), pp. 1992-1996.
Honda et al., "Dental follicle stem cells and tissue engineering", Journal of Oral Science, vol. 52, No. 4, (2010), pp. 541-552.
Hsieh et al., "Cellular Mechanobiology of the Intervertebral Disc: New Directions and Approaches", J. Biomech., vol. 43, No. 1, Jan. 5, 2010, 20 pages.
Huang et al., "Mesenchymal Stem Cells Derived from Dental Tissues vs. Those from Other Sources: Their Biology and Role in Regenerative Medicine", J. Dent. Res., vol. 88, No. 9, Sep. 2009, pp. 792-806.
Ingram et al., "Vessel wall-derived endothelial cells rapidly proliferate because they contain a complete hierarchy of endothelial progenitor cells", Blood, vol. 105, No. 7, Apr. 1, 2005, pp. 2783-2786.
Jones et al., "No place like home: anatomy and function of the stem cell niche", Nature Reviews/Molecular Cell Biology, vol. 9, Jan. 2008, pp. 11-13.
Kajstura et al., "Evidence for Human Lung Stem Cells", The New England Journal of Medicine, vol. 364, No. 19, May 12, 2011, pp. 1795-1806.
Karlsson et al., "Articular cartilage stem cell signalling", Arthritis Research & Therapy, vol. 11, No. 4, Jul. 24, 2009, pp. 1-2.
Kilroy et al., "Cytokine Profile of Human Adiopose-Derived Stem Cells: Expression of Angiogenic, Hematopoietic, and Pro-Inflammatory Factors", Journal of Cellular Physiology, vol. 212, (2007), pp. 702-709.
Koga et al., "Comparison of mesenchymal tissues-derived stem cells for in vivo chondrogenesis: suitable conditions for cell therapy of cartilage defects in rabbit", Cell Tissue Res., vol. 333, (2008), pp. 207-215.
Kondo, et al. "Intervertebral Disc Development is Regulated by Wnt/β-catenin Signaling", SPINE, vol. 36, No. 8, (2011), pp. E513-E518.
Kuhbier et al., "Stem cells from fatty tissue. A new resource for regenerative medicine?", Chirug , vol. 81, (2010), pp. 826-832.
Kurth et al., "Functional Mesenchymal Stem Cell Niches in Adult Mouse Knee Joint Synovium In Vivo", Arthritis & Rheumatism, vol. 63, No. 5, May 2011, pp. 1289-1300.
LaBarge et al., "Of Microenvironments and Mammary Stem Cells", Stem Cell Reviews, vol. 3, No. 2, (2007) pp. 137-146.
Lahm et al., "Unraveling the hidden catalytic activity of vertebrate class lla histone deacetylases", PNAS, vol. 104, No. 44, Oct. 30, 2007, pp. 17335-17340.
Lee, et al., "Mesenchymal Progenitor Cells Derived from Synovium and Infrapatellar Fat Pad as a Source for Superficial Zone Cartilage Tissue Engineering: Analysis of Superficial Zone Protein/Lubricin Expression", Tissue Engineering: Part A, vol. 16, No. 1, (2010), pp. 317-325.
Li et al., "Human treated dentin matrix as a natural scaffold for complete human dentin tissue regeneration", Biomaterials (2011), pp. 1-14.

(56) References Cited

OTHER PUBLICATIONS

Lin et al., "The Chondrocyte: Biology and Clinical Application", Tissue Engineering, vol. 12, No. 7, (2006), pp. 1971-1984.
Lozito et al., "Mesenchymal Stem Cell Modification of Endothelial Matrix Regulates Their Vascular Differentiation", Journal of Cellular Biochemistry, vol. 107, (2009), pp. 706-713.
Lyngstadaas et al., "Enamel matrix proteins; old molecules for new applications", Orthod Craniofac Res., vol. 12, No. 3, Aug. 2009, pp. 243-253.
Lynn, et al., "Antigenicity and Immunogenicity of Collagen", published online Jul. 16, 2004 in Wiley InterScience (www.interscience.wiley.com), pp. 343-354.
Mariman et al., "Adipocyte extracellular matrix composition, dynamics and role in obesity", Cell. Mol. Life Sci., vol. 67, (2010), pp. 1277-1292.
Massirer et al., "Maintenance and differentiation of neural stem cells", WIREs Systems Biology and Medicine, vol. 3, Jan./Feb. 2011, pp. 107-114.
Masuda, "Biological repair of the degenerated intervertabral disc by the injection of growth factors", Eur. Spine J., vol. 17 (Suppl. 4), (2008), pp. S441-S451.
McNally et al., "Plantar Fascia: Imaging Diagnosis and Guided Treatment", Seminars in Musculoskeletal Radiology, vol. 14, No. 3, (2010), pp. 334-343.
Meisel et al.; "Clinical experience in cell-based therapeutics: Disc chondrocyte transplantation A treatment for degenerated or damaged intervertebral disc", Biomolecular Engineering, vol. 24, (2007), pp. 5-21.
Melero-Martin et al., "Concise Review: Vascular Stem Cells and Tumor Angiogeneses", Stem Cells, vol. 29, (2011) pp. 163-168.
Mercuri, et al., "Novel tissue-derived biomimetic scaffold for regenerating the human nucleus pulposus", J. Biomed. Mater. Res. A, vol. 96, No. 2, Feb. 2011, p. 35.
Metcalf, "Stem Cells, Pre-Progenitor Cells and Lineage-Committed Cells: Are Our Dogmas Correct?", Annals New York Academy of Sciences, Feb. 6, 2006, pp. 289-.
Miki et al., "Stem Cell Characteristics of Amniotic Epithelial Cells", Stem Cells, vol. 23, (2005), pp. 1549-1559.
Minguell et al., "Mesenchymal Stem Cells", Exp. Biol. Med., vol. 226, No. 6, (2001), pp. 507-520.
Miyamoto et al., "Intradiscal transplantation of synovial mesenchymal stem cells prevents intervertebral disc degeneration through suppression of matrix metalloproteinase-related genes in nucleus pulposus cells in rabbits", Arthritis Research & Therapy, vol. 12, (2010), pp. 1-13.
Mizuno, "Adipose-derived Stem Cells for Tissue Repair and Regeneration: Ten Years of Research and a Literature Review", Journal of Nippon Medical School, vol. 76, No. 2, (2009), pp. 56-66.
Murakami et al., "Quantitative differences in intervertebral disc-matrix composition with age-related degeneration", Med. Biol. Eng. Comput., vol. 48, (2010), pp. 469-474.
Murtuza et al., "Micro- and Nanoscale Control of the Cardiac Stem Cell Niche for Tissue Fabrication", Tissue Engineering: Part B; vol. 15, No. 4, (2009), pp. 443-454.
OPTP, "The Anatomy of Fascia-Revealed! a discovery of 3-D continuity for MFR therapists", Feb. 2006, 2 pages.
Osathanon et al., "Basic fibroblast growth inhibits mineralization but induces neuronal differentiation by human dental pulp stem cells through a FGFR and PLCy signaling pathway", Journal of Cellular Biochemistry, Mar. 4, 2011, pp. 1807-1816.
Pacifici et al., Mechanisms of Synovial Joint and Articular Cartilage Formation: Recent Advances, But Many Lingering Mysteries, Birth Defects Research (Part C), vol. 75, (2005), pp. 237-248.
Pacilli, "Vascular wall resident progenitor cells, A review", Experimental Cell Research, vol. 315, (2009) pp. 901-914.
Paterson et al., "Dental tissue engineering products in the U.S. market to double by 2015", Dental Tribune, Dec. 2009, p. 5A.
Peng et al., "Comparative Analysis of Mesenchymal Stem Cells from Bone Marrow, Cartilage, and Adipose Tissue", Stem Cells and Development, vol. 17, (2008), pp. 761-774.
Peng et al., "Mesenchymal Stem Cells and Tooth Engineering", Int J Oral Sci, vol. 1, No. 1, (2009), pp. 6-12.
Peroni et al., "Stem molecular signature of adipose-derived stromal cells", Experimental Cell Research, vol. 314, (2008), pp. 603-615.
Piekarz et al., "Phase II Multi-Institutional Trial of the Histone Deacetylase Inhibitor Romidepsin as Monotherapy for Patients with Cutaneous T-Cell Tymphoma", American Society of Clinical Oncology, vol. 27, No. 32, Nov. 10, 2009, pp. 5410-5412.
Potten et al., "Stem Cells: attributes, cycles, spirals, pitfalls and uncertainties—Lessons for and from the Crypt", Development, vol. 110, (1990), pp. 1001-1020.
Pretzel et al., "Relative percentage and zonal distribution of mesenchymal progenitor cells in human osteoarthritic and normal cartilage", Arthritis Research & Therapy, vol. 13, R64, (2011), 37 pages, http://arthritis-research.com/content/13/2/R65.
Puetzer et al., "Comparative Review of Growth Factors for Induction of Three-Dimensional In Vitro Chondrogenesis in Human Mesenchymal Stem Cells Isolated from Bone Marrow and Adipose Tissue", Tissue Engineering: Part B, vol. 16, No. 4, (2010), pp. 435-444.
Risau et al., "Vasculogenesis", Annual Review of Cell and Developmental Biology, vol. 11, (1995), pp. 73-91.
Sandberg, "Matrix in Cartilage and Bone Development: Current Views on the Function and Regulation of Major Organic Components", Annals of Medicine, vol. 23, (1991), pp. 207-217.
Sandjeu et al., " Desmosealin and other Components of the Epidermal Extracellular Matrix", Journal of Physiology and Pharmacology, vol. 60, Suppl. 4, (2009), pp. 23-30.
Shamji et al., "Proinflammatory Cytokine Expression Profile in Degenerated and Herniated Human Intervertebral Disc Tissues", Arthritis & Rheumatism, vol. 62, No. 7, Jul. 2010, pp. 1974-1982.
Sheikh et al., "Cell-Cell Connection to Cardiac Disease", TCM, vol. 19, No. 6, (2009), pp. 182-190.
Shoulders et al, "Collagen Structure and Stability", Annu Rev Biochem., vol. 78, (2009), pp. 927-958.
Smith et al., "Degeneration and regeneration of the intervertebral disc: lessons from development", Dis. Model Mech., vol. 4, No. 1, Jan. 2011, pp. 31-41.
Som et al., "Fascia and Spaces of the Neck", Head and Neck Imaging, 4th Ed., Chapter 34, Mosby, Inc., (2003), pp. 1805-1827.
Somerman et al., "Human Dentin Matrix Induces Cartilage Formation in vitro Mesenchymal Cells Derived from Embryonic Muscle", J Den Res, vol. 66, No. 10, Oct. 1987, pp. 1551-1558.
Steiner et al., "Mesenchymal Stem Cell Characteristics of Human Anterior Cruciate Ligament Outgrowth cells", Tissue Eng., Part A, vol. 17, No. 9 and 10, pp. 1375-1388, 2011.
Thesleff et al., "Cell-matrix interactions in tooth development", Int. J. Dev. Biol., vol. 33, (1989), pp. 91-97.
Tilki et al., "Emerging biology of vascular wall progenitor cells in health and disease", Trends in Molecular Medicine, vol. 15, No. 11, (2009), pp. 501-509.
Trujillo et al., "Adipose Tissue-Derived Factors: Impact on Health and Disease", Endocrine Reviews, vol. 27, No. 7, (2006), pp. 762-778.
Ulmer et al., "Stem Cells—Prospects in Dentistry", Schweiz Monatsschr Zahnmed, vol. 120, Oct. 2010, pp. 860-872.
Umlauf et al., "Cartilage biology, pathology, and repair", Cell. Mol. Life Sci., vol. 67, (2010), pp. 4197-4211.
Uriel et al., "The role of adipose protein derived hydrogels in adipogenesis", Biomaterials, vol. 29, (2008), pp. 3712-3719.
Voskerician et al., "Human Peritoneal Membrane Reduces the Formation of Intra-Abdominal Adhesions in Ventral Hernia Repair: Experimental Study in a Chronic Hernia Rat Model", J. Surg. Res., vol. 157, pp. 108-114, 2011.
Wilson et al., "Adipose-derived stem cells for clinical applications: a review", Cell Proliferation, vol. 44, (2011), pp. 86-98.
Wilson et al., "Proteomic analysis of cartilage proteins", Methods, vol. 45, (2008), pp. 22-31.
Wu et al., "Muscle-derived stem cells: isolation, characterization, differentiation, and application in cell and gene therapy", Cell Tissue Res., vol. 340, (2010), pp. 549-567.

(56) References Cited

OTHER PUBLICATIONS

Xiao et al., "Clonal Characterization of Bone Marrow Derived Stem Cells and Their Application for Bone Regeneration", Int. J. Oral Sci., vol. 2, No. 3, (2010), pp. 127-135.
Xu, et al., "Umbilical Cord-Derived Mesenchymal Stem Cells Isolated by a Novel Explantation Technique Can Differentiate into Functional Endothelial Cells and Promote Revascularization", Stem Cells and Development, vol. 19, No. 10, Oct. 2010, pp. 1511-1523.
Yoder et al., "Redefining endothelial progenitor cells via clonal analysis and hematopoetic stem/progenitor cell principals", Blood, vol. 109, No. 5, Mar. 1, 2007, pp. 1801-1809.
Young et al., "Bone matrix proteins: their function, regulation, and relationship to osteoporosis", Osteoporos Int., vol. 14 (Suppl 3), (2003), pp. S35-S42.
Young et al., "Injectable hydrogel scaffold from decellularized human lipoaspirate", Acta Biomaterialia, vol. 7, (2011), pp. 1040-1049.
Yun et al., "Transcriptional Regulatory Networks Associated with Self-Renewal and Differentiation of Neural Stem Cells", Journal of Cellular Physiology, vol. 225, published online in Wiley Online Library (wileyonlinelibrary.com) Jul. 6, 2010, pp. 337-347.
Zengin et al., "Vascular wall resident progenitor cells: a source for postnatal vasculogenesis", Development, vol. 133, No. 8, (2006), pp. 1543-1551.
Zhang et al., "A nerve graft constructed with xenogeneic acellular nerve matrix and autologous adipose-derived mesenchymal stem cells", Biomaterials, vol. 31, (2010), pp. 5312-5324.
Zouboulis et al., "Human skin stem cells and the ageing process", Experimental Gerontology, vol. 43, (2008), pp. 986-997.
Office Action for U.S. Appl. No. 13/108,856, dated Dec. 31, 2012.
Bigham et al., "Xengogenic Demineralized bone matrix and fresh autogenous cortical bone effects on experimental bone healing: radiological, histopathological and biomechanical evaluation", Journal of Orthopaed Traumatol, vol. 9, (2008), pp. 73-80.
Nilsen et al., "Cytokine profiles of cultured microvascular endothelial cells from the human intestine", downloaded from gut.bmj.com on Dec. 18, 2012, pp. 635-642.
Rabie et al., "The Effect of Demineralized Bone Matrix on the Healing of Intramembranous Bone Grafts in Rabbit Skull Defects", J. Dent. Res, vol. 75, No. 4, (Apr. 1996), pp. 1045-1051.
"Adipose Tissue", http://users.rcn.com/jkimball.ma.ultranet/BiologyPages/A/AdiposeTissue.html, dated Dec. 1, 2009, printed Apr. 15, 2011, 1 page.
"Brachium to Hand Musculature", http://www.ptcentral.com/muscles/musclearms.html, printed Apr. 15, 2011, 12 pages.
"Fascia", Wikipedia, http://en.wikipedia.org/wiki/Fascia, printed May 16, 2011, 3 pages.
"Isolation of Stromal Stem Cells from Human Adipose Tissue", http://www.collaslab.com/UserFiles/File/Adipose%20stem%20cell%20isolation.pdf; article not dated, printed Jul. 20, 2011.
"Stem Cell Basics", U.S. Department of Health and Human Services, National Institutes of Health, http://stemcells.hih/gov/info/basics/, last updated: Apr. 28, 2009, 26 pages.
"The Hosford Muscle Tables: Skeletal Muscles of the Human Body", http://www.ptcentral.com/muscles/, printed Apr. 15, 2011, 3 pages.
Alsalameh et al., "Identification of Mesenchymal Progenitor Cells in Normal and Osteoarthritic Human Articular cartilage", Arthritis & Rheumatism, vol. 50, No. 5, May 2004, pp. 1522-1532.
Alvarez-Buylla et al., "For the Long Run: Maintaining Germinal Niches in the Adult Brain", Neuron, vol. 41, Mar. 4, 2004, pp. 683-686.
Amir et al., "Harvesting Large Fascia Lata Sheaths: A Rational Approach", Skull Base Surgery, vol. 10, No. 1, (2000), pp. 29-34.
Anderson et al., "The performance of human mesenchymal stem cells encapsulated in cell-degradable polymer-peptide hydrogels", Biomaterials, vol. 32, (2011), pp. 3564-3574.
Antuna-Puente et al., "Adipokines: The missing link between insulin resistance and obesity", Diabetes & Metabolism, vol. 34, (2008), pp. 2-11.

Badylak et al., "The extracellular matrix as a biologic scaffold material", Biomaterials, vol. 28, (2007), pp. 3587-3593.
Bakopoulou et al., "Comparative Analysis of in vitro osteo/odontogenic differentiation potential of human dental pulp stem cells (DPSCs) and stem cells from the apical papilla (SCAP)", Archives of Oral Biology, vol. 56, Jan. 10, 2011, pp. 709-721.
Bakopoulou et al., "Effects of HEMA and TEDGMA on the in vitro odontogenic differentiation potential of human pulp stem/progenitor cells derived from decidous teeth", Dental Materials, vol. 27, Apr. 11, 2011, pp. 608-617.
Barker et al., "Leucine-rich repeat-containing G-protein-coupled receptors as markers of adult stem cells", Gastroenterology, vol. 138, No. 5, May 2010, pp. 1681-1696.
Becher et al., "Regeneration of the vascular compartment", Herz, vol. 35, (2010), pp. 342-351.
Benjamin, "The Fascia of the limbs and back—a review", Journal of Anatomy, vol. 214, (2009), pp. 1-18.
Bi et al., "Identification of tendon stem/progenitor cells and the role of the extracellular matrix in their niche", Nature Medicine, vol. 13, No. 10, Oct. 2007, pp. 1219-1227.
Bieliauskas et al.; "Isoform-selective histone deacetylas inhibitors", Chemical Society Reviews, vol. 37, (2008), pp. 1402-1412.
Blanpain et al., "Epidermal homeostasis: a balancing act of stem cells in the skin", Nat. Rev. Mol. Cell Biol., vol. 10, No. 3, Mar. 2009, pp. 207-217.
Blanpain, "Skin regeneration and repair", Nature, vol. 464, Apr. 1, 2010, pp. 686-687.
Boonen et al., "The Muscle Stem Cell Niche: Regulation of Satellite Cells During Regeneration", Tissue Engineering: Part B, vol. 14, No. 4, (2008) pp. 419-431.
Bradner et al., "Chemical phylogenetics of histone deacetylases", Nature Chemical Biology, vol. 6, Mar. 2010, pp. 238-240.
Breitling et al., "Robust signaling networks of the adipose secretome", Trends in Endocrinology and Metabolism, vol. 20, No. 1, (2008), pp. 1-7.
Brochhausen et al., "Signalling molecules and growth factors for tissue engineering of cartilage—what can we learn from the growth plate?", Journal of Tissue Engineering and Regenerative Medicine, vol. 3, (2009), pp. 416-429.
Brown et al., "Basic Science Review on Adipose Tissue for Clinicians", Plastic and Reconstructive Surgery, vol. 126, No. 6, Dec. 2010, pp. 1936-1946.
Brown et al., "Comparison of Three Methods for the Derivation of a Biologic Scaffold Composed of Adipose Tissue Extracellular Matrix", Tissue Engineering: Part C, vol. 17, No. 4 (2011), pp. 411-421.
Butler et al., "Dentin Extracellular Matrix (ECM) Proteins: Comparison to Bone ECM and Contribution to Dynamics of Dentinogenesis", Connective Tissue Research, vol. 44 (Suppl. 1), (2003), pp. 171-178.
Butler et al., "Extracellular Matrix Proteins and the Dynamics of Dentin Formation", Connective Tissue Research, vol. 43, (2002), pp. 301-307.
Chapman, "Toward Lung Regeneration", The New England Journal of Medicine, vol. 364, No. 19, May 12, 2011, pp. 1867-1868.
Chen, "Extracellular Matrix Provides an Optimal Niche for the Maintenance and Propagation of Mesenchymal Stem Cells", Birth Defects Research (Part C), vol. 90, (2010), pp. 45-54.
Cheng, et al., "Chondrogenic Differentiation of Adipose-Derived Adult Stem Cells by a Porous Scaffold Derived from Native Articular Cartilage Extracellular Matrix", Tissue Engineering: Part A, vol. 15, No. 2, (2009), pp. 231-241.
Cheng, et al., "Comparison of Potentials Between Stem Cells Isolated from Human Anterior Cruciate Ligament and Bone Marrow for Ligament Tissue Engineering", Tissue Engineering: Part A, vol. 16, No. 7, (2010), pp. 2237-2253.
Choi et al., "Decellularized extracellular matrix derived from human adipose tissue as a potential scaffold for allograft tissue engineering", J Biomed Mater Res A., Mar. 29, 2011, 1 page http://www.ncbi.nlm.hih.gov/pubmed printed Apr. 15, 2011 (abstract only).
Choi et al., "Fabrication of Porous Extracellular Matrix Scaffolds from Human Adipose Tissue", Tissue Engineering: Part C, vol. 16, No. 3, (2010), pp. 387-396.

(56) References Cited

OTHER PUBLICATIONS

Chun et al., "Analysis of the Soluble Human Tooth Proteome and Its Ability to Induce Dentin/Tooth Regeneration", Tissue Engineering: Part A, vol. 17, Nos. 1 & 2, (2011), pp. 181-191.
Cinti, "The Adipose Organ", Prostaglandins Leukotrienes Essential Fatty Acids, vol. 73, No. 1, Jul. 2005, pp. 9-15.
Cosgrove et al., "A home away from home: Challenges and opportunities in engineering in vitro muscle satellite cell niches", Differentiation, vol. 78, (2009), pp. 184-194.
Diaz-Prado et al., "Isolation and Characterization of Mesenchymal Stem Cells from Human Amniotic Membrane", Tissue Engineering: Part C, vol. 17, No. 1, (2011), pp. 49-59.
Discher et al., "Growth factors, matrices, and forces combine and control stem cells", Science, vol. 324, No. 5935, Jun. 26, 2009, pp. 1673-1677.
Feng et al., "Extracellular Matrix in Disc Degeneration", The Journal of Bone & Joint Surgery, vol. 88, (2006), pp. 25-29.
Fernandez-Tresguerres Hernandez-Gil, et al., "Physiological bases of bone regeneration I. Histology and physiology of bone tissue", Med. Oral Patol Oral Cir. Bucal, vol. 11, (2006), pp. E47-E51.
Finnin et al., "Structures of a histone deacetylase homologue bound to the TSA and SAHA inhibitors", Nature, vol. 401, Sep. 9, 1999, pp. 188-190.
Flynn et al., "Adipose tissue engineering with cells in engineered matrices", Organogenesis, vol. 4, No. 4, (2008), pp. 228-235.
Flynn, "The use of decellularized adipose tissue to provide an inductive microenvironment for the adipogenic differentiation of human adipose-derived stem cells", Biomaterials, vol. 31, (2010) pp. 4715-4724.
Fong et al., "The Crowning Achievement: Getting to the Root of the Problem", Journal of Dental Education, vol. 69, No. 5, May 2005, pp. 555-570.
Fraser et al., "Fat tissue: an underappreciated source of stem cells for biotechnology", Trends in Biotechnology, vol. 24, No. 4, Apr. 2006, pp. 150-154.
Fuchs et al., "Building Epithelial Tissues from Skin Stem Cells", Cold Spring Harb Symp Quant Biol., vol. 73, (2008), pp. 333-350.
Gaissmaier et al., "Growth and differentiation factors for cartilage healing and repair", Injury, Int. J. Care Injured, vol. 3951, (2008), pp. 588-596.
Gopinath et al., "Stem Cell Review Series: Aging of the skeletal muscle stem cell niche", Aging Cell, vol. 7, (2008), pp. 590-598.
Jin et al., Human Amniotic Membrane as a Delivery Matrix for Articular Cartilage Repair, Tissue Engineering, vol. 13, No. 4, 2007, pp. 693-702.
Schwam et al., Human Amniotic Membrane Transplantation for the Treatment of Ocular Surface Disease, DCMS Northeast Florida Medicine Journal, http://www.dmcsonline.org/jax-medicine/2002journals/augsept2002/amniotic.htm, Aug.-Sep. 2002 (printed Aug. 30, 2010), 6 pages.
Non-Final Office Action for U.S. Appl. No. 13/690,542, dated Nov. 24, 2014.
Non-Final Office Action for U.S. Appl. No. 13/828,525, dated Dec. 19, 2014.
Final Office Action for U.S. Appl. No. 13/108,856, dated May 14, 2013.
Van der Donk, "Rinsing Morselized Allographs Improves Bone and Tissue Ingrowth", Clinical Orthopaedics and Related Research, 2003, 408:302-310.
Cowin, ed., "Bone Mechanics", CRC Press, Inc., 1989, pp. 1-13.
Non-Final Office Action for U.S. Appl. No. 13/108,856, dated Feb. 27, 2014.
Non-Final Office Action for U.S. Appl. No. 13/948,798, dated Mar. 14, 2014.
Non-Final Office Action for U.S. Appl. No. 13/690,542, dated Jul. 2, 2015.
Oh et al., "A new bone banking technique to maintain osteoblast viability in frozen human iliac cancellous bone"; Cryobiology, vol. 44, (2002), pp. 279-287.

Mulliken, "Use of Demineralized Allogenic Bone Implants for the Correction of Maxillocraniofacial Deformalities", Ann. Surg., vol. 194, No. 3 (1981), pp. 366-372.
Non-Final Office Action for U.S. Appl. No. 13/828,525, dated Jan. 7, 2016.
U.S. Appl. No. 14/933,176, filed Nov. 5, 2015.
Non-Final Office Action for U.S. Appl. No. 14/537,253, dated Nov. 25, 2015.
Alberts et al., Chapter 23 Specialized Tissues, Stem Cells and Tissue Renewal, Molecular Biology of the Cell, 5th Edition, 2008, p. 1457, Garland Science, New York, New York.
An et al., "Comparison Between Allograft Plus Demineralized Bone Matrix Versus Autograft in Anterior Cervical Fusion", Spine, 1995, 20(20):2211-2216.
Bacterin International, Inc.: OsteoSponge®, dated Mar. 2006, from http://odev.com/health_professional/pdfs/spine/Osteosponge%20Brochure.pdf. 5 pages.
Caplan, A., "What's in a Name?", Tissue Engineering, 2010, 16(8):2415-2417.
Cook et al., "In Vivo Evaluation of Demineralized Bone Matrix as a Bone Graft Substitute in Posterior Spinal Fusion", Spine, 1995, 20(8):877-886.
Davisson et al., "Novel Allograft Sponge Supports Fill of Osteochondral Defects in Caprine Model," 55th Annual Meeting of the Orthopaedic Research Society (Feb. 2009), Paper No. 57, 1 page.
DiBella et al., "Injection of Demineralized Bone Matrix with Bone Marrow Concentrate Improves Healing in Unicameral Bone Cyst," Clinical Orthopaedics and Related Research, Symposium: Highlights of the ISOLS/MSTS, 2009 Meeting, (2009), 9 pages.
Final Office Action for U.S. Appl. No. 13/690,542, dated Jul. 2, 2015.
Final Office Action for U.S. Appl. No. 13/828,525, dated May 12, 2017.
Final Office Action for U.S. Appl. No. 13/828,525, dated Jul. 1, 2016.
Final Office Action for U.S. Appl. No. 13/828,525, dated Jul. 24, 2015.
Final Office Action for U.S. Appl. No. 13/948,798, dated Mar. 14, 2014.
Gazdag et al., "Alternatives to Autogenous Bone Graft: Efficacy and Indications", J Am Arad Orthop Surg, 1995, 3(1):1-8.
Han et al., "The Effect of Thrombin Activation of Platelet-Rich Plasma on Demineralized Bone Matrix Osteoinductivity," The Journal of Bone and Joint Surgery, vol. 91, (2009), pp. 1459-1470.
International Search Report and Written Opinion for PCT/US2016/033246, dated Sep. 5, 2016.
Lambrecht et al., "Human Osteoclast—like Cells in Primary Cultures" Clinical Anatomy, 1996, 9:41-45.
Laursen et al., "Optimal handling of fresh cancellous bone graft. Different peroperative storing techniques evaluated by in vitro osteo-blast-like cell metabolism", Acta Orthop Scand, 2003, 74(4):490-496.
Mauney et al., "In vitro and in vivo evaluation of differentially demineralized cancellous bone scaffolds combined with human bone marrow stromal cells for tissue engineering", Biomaterials, 26, 2005, pp. 3173-3185., 13 pages.
Meinel et al., "Bone Tissue Engineering Using Human Mesenchymal Stem Cells: Effects of Scaffold Material and Medium Flow," Annals of Biomedical Engineering, vol. 32, No. 1, (Jan. 2004) pp. 112-122.
Meinel et al., "Engineering bone-like tissue in vitro using human bone marrow stem cells and silk scaffolds," Journal of Biomedical Materials Research; 71A, pp. 25-34, (2004).
Meinel et al., "Engineering Cartilage-Like Tissue Using Human Mesenchymal Stem Cells and Silk Protein Scaffolds," Biotechnology and Bioengineering, vol. 88, No. 3, (2004) pp. 379-391.
Mayer, H. "Properties of Human Trabecular Bone Cells from Elderly Women: Implications for Cell-Based Bone Engraftment". Cells Tissues Organs, vol. 177, No. 2 (2004) 57-67.
Non-Final Office Action for U.S. Appl. No. 13/828,525, dated Oct. 7, 2016.
Non-Final Office Action for U.S. Appl. No. 13/948,798, dated Nov. 27, 2013.

(56) References Cited

OTHER PUBLICATIONS

Non-Final Office Action for U.S. Appl. No. 14/942,292, dated Nov. 2, 2016.
Non-Final Office Action for U.S. Appl. No. 15/288,539, dated Jun. 5, 2017.
Non-Final Office Action for U.S. Appl. No. 15/159,406, dated Aug. 7, 2017.
Osteotech, Inc.: Xpanse® R Bone Insert—Introduction, web page printed Jun. 23, 2011, from http://osteotech.com/prodxpanseR.shtm, 1 page.
Pantou et al., "The effect of platelet-rich plasma (PRP) combined with a bone allograft on human periodontal ligament (PDL) cells," Cell Tissue Bank, vol. 13, (2012), pp. 81-88.
PCT Patent Application No. PCT/US2016/033246, Modified Demineralized Cortal Bone Fibers, filed May 19, 2016.
Robey et al., "Human Bone Cells in Vitro", Calcif Tissue Int, 1985, 37:453-460.
Sakaguchi et al., "Suspended cells from trabecular bone by collagenase digestion become virtually identical to mesenchymal stem cells obtained from marrow aspirates", Blood, 2004, 104(9):2728-2735.
Trombi et al., "Human Autologous Plasma-Derived Clot as a Biological Scaffold for Mesenchymal Stem Cells in Treatment of Orthopedic Healing," Journal of Orthopaedic Research (Feb. 2009), pp. 176-183.
U.S. Appl. No. 13/828,525, filed Mar. 14, 2013.
U.S. Appl. No. 14/537,253, filed Nov. 10, 2014.
U.S. Appl. No. 14/942,292, filed Nov. 16, 2015.
U.S. Appl. No. 15/159,174, filed May 19, 2016.
U.S. Appl. No. 15/288,539, filed Oct. 7, 2016.
Blackstone Medical, Inc., Trinity™ Multipotential Cellular Bone Matrix Technical Monograph, 2006.
Identification of MSCs in Trinity® Evolution™ Explant Cultures using FACS Analysis, Mar. 21, 2011.
Musculoskeletal Transplant Foundation, Multipotential Differentiation of Cells Derived from Trinity® Evolution™, Mar. 21, 2011.
Gertzman, A. et al., A Pilot Study Evaluating Sodium Hyaluronate as a Carrier for Freeze-Dried Demineralized Bone Powder, Cell and Tissue Banking, 2:87-94, 2001.
Gertzman, A. et al., DBX®: A New Bone Defect Filler Utilizing Hyaluronan as a Carrier, Pittsburgh Bone Symposium, Aug. 23, 2003.
Musculoskeletal Transplant Foundation, Quality Must Be First Priority, Apr. 1996.
Musculoskeletal Transplant Foundation, Safety Profile of Trinity® Evolution™ Viable Cryopreserved Cellular Bone Matrix, Jun. 2009.
Musculoskeletal Transplant Foundation, Trinity Elite—Allograft With Viable Cells—Technical Monograph—A Fully Moldable Allograft with Viable Cells, Aug. 2013.
Musculoskeletal Transplant Foundation, Trinity Elite—Allograft With Viable Cells—A Fully Moldable Allograft with Viable Cells—Shape the Possibilities, Oct. 2013.
Musculoskeletal Transplant Foundation, Trinity® Evolution—An Allograft With Viable Cells, Apr. 2010.
Musculoskeletal Transplant Foundation, Trinity® Evolution™—An Allograft With Viable Cells, Nov. 2011.
Orthofix International, N.V., Orthofix International Announces Limited Market Release of Trinity® Evolution™ and Completion of First Surgical Procedure Using New Stem Cell-Based Allograft, http://files.shareholder.com/downloads/OFIX/3724257842x0x292362/A99F10B9-5487-482C-9191-8C3340FFECF3/OFIX_News_2009_5_5_General_Releases.pdf, May 5, 2009.
Musculoskeletal Transplant Foundation, "Allografts With Viable Cells: Redefining your bone grafting options through stem cell technology", Trinity Evolution Tech Brief, Dec. 2012 (12 pages).

* cited by examiner

TISSUE-DERIVED TISSUEGENIC IMPLANTS, AND METHODS OF FABRICATING AND USING SAME

CROSS-REFERENCE TO RELATED APPLICATIONS

This application claims the benefit of U.S. Provisional Patent Application No. 62/071,946, filed on Nov. 7, 2014, and is a continuation-in-part of U.S. patent application Ser. No. 13/690,542, filed on Nov. 30, 2012, (now U.S. Pat. No. 9,352,003) which is a continuation-in-part of U.S. patent application Ser. No. 13/108,856, filed on May 16, 2011, now U.S. Pat. No. 8,883,210) which claims priority from U.S. Provisional Patent Application Ser. No. 61/345,057, filed May 14, 2010, and the disclosures of the aforesaid earlier applications are incorporated herein by reference in their entireties.

FIELD OF THE INVENTION

The described invention relates to surgical implants that contain cells, growth factors, and a physical matrix, and methods of fabrication thereof, in particular, to implantable compositions for bone repair containing an osteoconductive matrix, endogenous cells, and an osteoinductive matrix.

BACKGROUND OF THE INVENTION

1. Tissue Compartments

In multicellular organisms, cells that are specialized to perform common functions are usually organized into cooperative assemblies embedded in a complex network of secreted extracellular macromolecules, the extracellular matrix (ECM), to form specialized tissue compartments. Individual cells in such tissue compartments are in contact with ECM macromolecules. The ECM helps hold the cells and compartments together and provides an organized lattice or scaffold within which cells can migrate and interact with one another. In many cases, cells in a compartment can be held in place by direct cell-cell adhesions. In vertebrates, such compartments may be of four major types, a connective tissue (CT) compartment, an epithelial tissue (ET) compartment, a muscle tissue (MT) compartment and a nervous tissue (NT) compartment, which are derived from three embryonic germ layers: ectoderm, mesoderm and endoderm. The NT and portions of the ET compartments are differentiated from the ectoderm; the CT, MT and certain portions of the ET compartments are derived from the mesoderm; and further portions of the ET compartment are derived from the endoderm.

1.1. Extracellular Matrix

The ECM is an intricate network of secreted extracellular macromolecules that largely fills the extracellular space in the tissue compartments and comprises large polymeric complexes of glycosaminoglycans (GAGs) and proteoglycans. GAGs are negatively charged unbranched polysaccharide chains comprising repeating disaccharide units. Each repeating disaccharide unit of a GAG chain contains an amino sugar (N-acetylglucosamine or N-acetyl glucosamine), which in most cases is sulfated, and an -uronic acid (glucuronic or iduronic acid). Four main types of GAG molecules are distinguished based on sugar residues, type of linkage, number and location of sulfate groups: (1) hyaluronan; (2) chondroitan sulfate and dermatan sulfate; (3) heparan sulfate and heparin; and (4) keratin sulfate.

GAG chains are inflexible and tend to adopt extended conformations occupying a huge volume relative to their mass, forming gels even at low concentrations. Their high density of negative charges attracts cations, such as $Na^+$, that are effective in osmotic absorption of large amounts of water into the matrix. This creates high turgor enabling the ECM to withstand compressive forces.

Hyaluronan (also termed hyaluronic acid or hyaluronate) (HA), which comprises a regular repeating sequence of up to 25,000 nonsulfated disaccharide units, serves many functions, many of which depend on the binding of HA-binding proteins and proteoglycans, which are either themselves constituents of the ECM or are integral constituents of cell surfaces. For example, HA resists compressive forces in joints as a major constituent of joint fluid serving as a lubricant; serves as a space filler during embryonic development; creates a cell-free space in epithelial compartment to allow cell migration during the formation of heart, cornea and other organs; and plays a role in wound repair. Excess HA is usually degraded by hyaluronidase.

All GAGs, except for HA, are covalently linked to proteins in the form of proteoglycans. During their synthesis, the polypeptide chain of proteoglycans is synthesized on membrane-bound ribosomes and threaded into the lumen of endoplasmic reticulum, from which they are sorted in the Golgi apparatus, and assembled with polysaccharide chains. While still in the Golgi, proteoglycans undergo a series of sequential and coordinated sulfation and epimerization reactions to produce sulfated proteoglycans. Sulfated and nonsulfated proteoglycans then travel through the Golgi network and are ultimately secreted into the ECM by exocytosis with the help of secretory vesicles.

Proteoglycans are heterogenous molecules, with core proteins ranging in molecular weight from 10 kD to about 600 kD and with attached GAG chains varying in number and type, further modified by a complex variable pattern of sulfate groups. At least one of the proteoglycan sugar side chains is a GAG; the core protein is usually a glycoprotein, but may comprise up to 95% carbohydrate by weight, mostly as long unbranched GAG chains up to at least 80 sugar residues long.

Proteoglycans along with their attached GAG chains regulate the activities of secreted macromolecules. They can serve as selective molecular sieves regulating a size-based trafficking of molecules and cells, and play a role in cell-cell signaling. Proteoglycans modulate the activities of secreted factors, such as growth factors and cytokines, by binding to them. For example, binding of fibroblast growth factor (FGF) to heparan sulfate chains of proteoglycans is required for FGF activation of its cell surface receptors. On the other hand, for example, binding of a ubiquitous growth regulatory factor, such as transforming growth factor 0 (TGF-β) to core proteins of several ECM proteoglycans, such as decorin, results in inhibition of TGF-β activity. Proteoglycans also bind and regulate the activities of other types of secreted proteins, such as proteases and protease inhibitors. Cell-surface proteoglycans also may act as co-receptors: for example, syndecan binds to FGF and presents it to the FGF-receptor. Similarly, betaglycan binds to TGF-β and presents it to TGF-β receptors.

Collagens and elastin are the major fibrous proteins of the ECM. Collagens comprise a family of highly characteristic fibrous proteins and are a major component of skin and bone. Collagen fibers consist of globular units of the collagen subunit tropocollagen. Each tropocollagen subunit molecule comprises three polypeptide chains, called a chains, each exhibiting a left-handed helical conformation, that are wrapped around each other in a right-handed coiled coil structure, also called a triple helix or super helix. A characteristic feature of collagen is a repeating tripeptide unit comprising Glycine-Proline-X or Glycine-X-Hydroxyproline, where X may be any amino acid. The presence of Glycine at every third position in a collagen unit is critical for maintaining the coiled coil structure, since each repeating glycine residue sits on the interior axis of the helix, which sterically hinders bulkier sidechains. Prolines and hydroxyprolines help stabilize the triple helix. Collagen is secreted as procollagen molecules, which undergo proteolytic processing and subsequent assembly to form collagenous fibrils. Collagens are highly glycosylated during protein trafficking through intracellular secretory pathways.

Collagens are classified into various types depending on the nature of their a chains. Table 1 lists types of collagen, composition, class and distribution. (Reproduced from Shoulders and Raines, Annu. Rev. Biochem. 2009, 78: 929-958 and Bailey's Textbook of Microscopic Anatomy, Kelly et al., Williams and Wilkins, 18$^{th}$ edition, 1984).

ylysine. Elastin molecules are secreted into the ECM and assemble into elastic fibers close to the plasma membrane. Upon secretion, elastin molecules become highly cross-linked to form an extensive network of fibers and sheets.

The ECM also comprises many non-collagen adhesive proteins, usually with multiple domains containing binding sites of other macromolecules and for cell-surface receptors. One such adhesive protein, fibronectin, is a large glycoprotein comprising two subunits joined by a pair of disulfide bonds near the carboxy termini. Each subunit is folded into a series of rod-like domains interspersed by regions of flexible polypeptide chains. Each domain further comprises repeating modules of various types. One major type of fibronectin repeating module, called type III fibronectin repeat, is about 90 amino acids in length and occurs at least 15 times in each subunit. Fibronectin type III repeats have characteristic Arg-Gly-Asp (RGD) tripeptide repeats that function as binding sites for other proteins such as collagen, heparin or cell surface receptors. Fibronectin not only plays an important role in cell adhesion to the ECM, but also in guiding cell migration in vertebrate embryos.

TABLE 1

Collagen Type, Class and Distribution

| Collagen Type | Composition | Class | Distribution |
|---|---|---|---|
| I | $\alpha_1[I]_2\alpha_2[I]$ | Fibrillar | Dermis, tendon, ligament, bone, cornea |
| II | $\alpha_1[II]_3$ | Fibrillar | Cartilage, intervertebral disc, vitreous body |
| III | $\alpha_1[III]_3$ | Fibrillar | Fetal skin, cardiovascular system, basal lamina, intestine. |
| IV | $\alpha_1[IV]_2\alpha_2[IV]$; $\alpha_3[IV]\alpha_4[IV]\alpha_5[IV]$; $\alpha_5[IV]_2\alpha_6[IV]$ | Network | Basal lamina, external lamina |
| V | $\alpha_1[V]_3$; $\alpha_1[V]_2\alpha_2[V]$; $A_1[V]\alpha_2[V]\alpha_3[V]$ | Fibrillar | Bone, dermis, cornea, placenta |
| VI | $\alpha_1[VI]\alpha_2[VI]\alpha_3[VI]$; $\alpha_1[VI]\alpha_2[VI]\alpha_4[VI]$ | Network | Bone, cartilage, cornea, dermis |
| VII | $\alpha_1[VII]_2\alpha_2[VII]$ | Anchoring fibril | Dermis, bladder |
| VIII | $\alpha_1[VIII]_3$; $\alpha_2[VIII]_3$; $\alpha_1[VIII]_2\alpha_2[VIII]$ | Network | Dermis, brain, heart, kidney |
| IX | $\alpha_1[IX]\alpha_2[IX]\alpha_3[IX]$ | FACIT[a] | Cartilage, cornea, vitreous |
| X | $\alpha_1[X]_3$ | Network | Cartilage |
| XI | $\alpha_1[XI]\alpha_2[XI]\alpha_3[XI]$ | Fibrillar | Cartilage, intervertebral disc |
| XII | $\alpha_1[XII]_3$ | FACIT | Dermis, tendon |
| XIII | $\alpha_1[XIII]_3$ | MACIT[a] | Endothelial cells, dermis, eye, heart |
| XIV | $\alpha_1[XIV]_3$ | FACIT | Bone, dermis, cartilage |
| XV | | MULTIPLEXIN[a] | Capillaries, testis, kidney, heart, bone |
| XVI | | FACIT | Dermis, kidney |
| XVII | $\alpha_1[XVII]_3$ | MACIT | Hemidesmosomes in epithelia |
| XVIII | | MULTIPLEXIN | Basal lamina, liver |
| XIX | | FACIT | Basal lamina |
| XX | | FACIT | Cornea |
| XXI | | FACIT | Stomach, kidney |
| XXII | | FACIT | Tissue junctions |
| XXIII | | MACIT | Heart, retina |
| XXIV | | Fibrillar | Bone, cornea |
| XXV | | MACIT | Brain, heart, testis |
| XXVI | | FACIT | Testis, ovary |
| XXVII | | | Dermis, sciatic nerve |
| XXIX | | | Dermis |

[a]Abbreviations: FACIT, fibril-associated collagen with interrupted triple helices; MACIT, membrane-associated collagen with interrupted triple helices; MULTIPLEXIN, multiple triple helix domains.

A network of elastic fibers in the ECM offers resilience and elasticity so that organs are able to recoil following transient stretch. Elastic fibers primarily comprise the fibrous protein elastin, a highly hydrophobic protein about 750 amino acids in length that is rich in proline and glycine, is not glycosylated and is low in hydroxyproline and hyrox- Laminin, another adhesive glycoprotein of the ECM, is a major constituent (along with type IV collagen and another glycoprotein, entactin) of the basal lamina, a tough sheet of ECM formed at the base of epithelial cells. Laminin is a large flexible complex, about 850 kD in molecular weight, with three very long polypeptide chains arranged in the form of an asymmetric cross held together with disulfide bonds. Laminin contains numerous functional domains, e.g., one binds to type IV collagen, one to heparan sulfate, one to entactin and two or more to laminin receptor proteins on the cell surface.

1.2. Stem Cells

The term "stem cells" as used herein refers to undifferentiated cells having high proliferative potential with the ability to self-renew that can generate daughter cells that can undergo terminal differentiation into more than one distinct cell phenotype. Stem cells are distinguished from other cell types by two characteristics. First, they are unspecialized cells capable of renewing themselves through cell division, sometimes after long periods of inactivity. Second, under certain physiologic or experimental conditions, they can be induced to become tissue- or organ-specific cells with special functions. In some organs, such as the gut and bone marrow, stem cells regularly divide to repair and replace worn out or damaged tissues. In other organs, however, such as the pancreas and the heart, stem cells only divide under special conditions.

Embryonic stem cells (EmSC) are stem cells derived from an embryo that are pluripotent, i.e., they are able to differentiate in vitro into endodermal, mesodermal and ectodermal cell types.

Adult (somatic) stem cells are undifferentiated cells found among differentiated cells in a tissue or organ. Their primary role in vivo is to maintain and repair the tissue in which they are found. Adult stem cells have been identified in many organs and tissues, including brain, bone marrow, peripheral blood, blood vessels, skeletal muscles, skin, teeth, gastrointestinal tract, liver, ovarian epithelium, and testis. Adult stem cells are thought to reside in a specific area of each tissue, known as a stem cell niche, where they may remain quiescent (non-dividing) for long periods of time until they are activated by a normal need for more cells to maintain tissue, or by disease or tissue injury. Examples of adult stem cells include, but not limited to, hematopoietic stem cells, mesenchymal stem cells, neural stem cells, epithelial stem cells, and skin stem cells.

Hematopoietic Stem Cells (HSCs)

Hematopoietic stem cells (also known as the colony-forming unit of the myeloid and lymphoid cells (CFU-M,L), or CD34+ cells) are rare pluripotential cells within the blood-forming organs that are responsible for the continued production of blood cells during life. While there is no single cell surface marker exclusively expressed by hematopoietic stem cells, it generally has been accepted that human HSCs have the following antigenic profile: CD 34+, CD59+, Thy1+(CD90), CD38low/−, C-kit-/low and, lin−. CD45 is also a common marker of HSCs, except platelets and red blood cells. HSCs can generate a variety of cell types, including erythrocytes, neutrophils, basophils, eosinophils, platelets, mast cells, monocytes, tissue macrophages, osteoclasts, and the T and B lymphocytes. The regulation of hematopoietic stem cells is a complex process involving self-renewal, survival and proliferation, lineage commitment and differentiation and is coordinated by diverse mechanisms including intrinsic cellular programming and external stimuli, such as adhesive interactions with the micro-environmental stroma and the actions of cytokines.

Different paracrine factors are important in causing hematopoietic stem cells to differentiate along particular pathways. Paracrine factors involved in blood cell and lymphocyte formation are called cytokines. Cytokines can be made by several cell types, but they are collected and concentrated by the extracellular matrix of the stromal (mesenchymal) cells at the sites of hematopoiesis. For example, granulocyte-macrophage colony-stimulating factor (GM-CSF) and the multilineage growth factor IL-3 both bind to the heparan sulfate glycosaminoglycan of the bone marrow stroma. The extracellular matrix then presents these factors to the stem cells in concentrations high enough to bind to their receptors.

Mesenchymal Stem Cells (MSCs)

Mesenchymal stem cells (MSCs) (also known as bone marrow stromal stem cells or skeletal stem cells) are non-blood adult stem cells found in a variety of tissues. They are characterized by their spindle-shape morphologically; by the expression of specific markers on their cell surface; and by their ability, under appropriate conditions, to differentiates along a minimum of three lineages (osteogenic, chondrogenic, and adipogenic).

No single marker that definitely delineates MSCs in vivo has been identified due to the lack of consensus regarding the MSC phenotype, but it generally is considered that MSCs are positive for cell surface markers CD105, CD166, CD90, and CD44 and that MSCs are negative for typical hematopoietic antigens, such as CD45, CD34, and CD14. As for the differentiation potential of MSCs, studies have reported that populations of bone marrow-derived MSCs have the capacity to develop into terminally differentiated mesenchymal phenotypes both in vitro and in vivo, including bone, cartilage, tendon, muscle, adipose tissue, and hematopoietic-supporting stroma. Studies using transgenic and knockout mice and human musculoskeletal disorders have reported that MSC differentiate into multiple lineages during embryonic development and adult homeostasis.

Analyses of the in vitro differentiation of MSCs under appropriate conditions that recapitulate the in vivo process have led to the identification of various factors essential for stem cell commitment. Among them, secreted molecules and their receptors (e.g., transforming growth factor-β), extracellular matrix molecules (e.g., collagens and proteoglycans), the actin cytoskeleton, and intracellular transcription factors (e.g., Cbfa1/Runx2, PPARγ, Sox9, and MEF2) have been shown to play important roles in driving the commitment of multipotent MSCs into specific lineages, and maintaining their differentiated phenotypes.

For example, it has been shown that osteogenesis of MSCs, both in vitro and in vivo, involves multiple steps and the expression of various regulatory factors. During osteogenesis, multipotent MSCs undergo asymmetric division and generate osteoprecursors, which then progress to form osteoprogenitors, preosteoblasts, functional osteoblasts, and eventually osteocytes. This progression from one differentiation stage to the next is accompanied by the activation and subsequent inactivation of transcription factors, i.e., Cbfa1/Runx2, Msx2, Dlx5, Osx, and expression of bone-related marker genes, i.e., osteopontin, collagen type I, alkaline phosphatase, bone sialoprotein, and osteocalcin.

Members of the Wnt family also have been shown to impact MSC osteogenesis. Wnts are a family of secreted cysteine-rich glycoproteins that have been implicated in the regulation of stem cell maintenance, proliferation, and differentiation during embryonic development. Canonical Wnt signaling increases the stability of cytoplasmic β-catenin by receptor-mediated inactivation of GSK-3 kinase activity and promotes β-catenin translocation into the nucleus. The active β-catenin/TCF/LEF complex then regulates the transcription of genes involved in cell proliferation. In humans, mutations in the Wnt co-receptor, LRP5, lead to defective bone formation. "Gain of function" mutation results in high bone mass, whereas "loss of function" causes an overall loss of bone mass and strength, indicating that Wnt signaling is positively involved in embryonic osteogenesis. Canonical Wnt signaling pathway also functions as a stem cell mitogen via stabilization of intracellular β-catenin and activation of the β-catenin/TCF/LEF transcription complex, resulting in activated expression of cell cycle regulatory genes, such as Myc, cyclin D1, and Msx1. When MSCs are exposed to Wnt3a, a prototypic canonical Wnt signal, under standard growth medium conditions, they show markedly increased cell proliferation and a decrease in apoptosis, consistent with the mitogenic role of Wnts in hematopoietic stem cells. However, exposure of MSCs to Wnt3a conditioned medium or overexpression of ectopic Wnt3a during osteogenic differentiation inhibits osteogenesis in vitro through β-catenin mediated down-regulation of TCF activity. The expression of several osteoblast specific genes, e.g., alkaline phosphatase, bone sialoprotein, and osteocalcin, is dramatically reduced, while the expression of Cbfa1/Runx2, an early osteo-inductive transcription factor is not altered, implying that Wnt3a-mediated canonical signaling pathway is necessary, but not sufficient, to completely block MSC osteogenesis. On the other hand, Wnt5a, a typical non-canonical Wnt member, has been shown to promote osteogenesis in vitro. Since Wnt3a promotes MSC proliferation during early osteogenesis, it is thought likely that canonical Wnt signaling functions in the initiation of early osteogenic commitment by increasing the number of osteoprecursors in the stem cell compartment, while non-canonical Wnt drives the progression of osteoprecursors to mature functional osteoblasts.

Epithelial Stem Cells.

An epithelial membrane is a continuous multicellular sheet composed of an epithelium adhered to underlying connective tissue. Epithelial membranes can be cutaneous (e.g. skin), mucous (e.g., gastrointestinal lining) and serous (e.g. pleural lining, pericardial lining and peritoneal lining).

Epithelial stem cells line the gastrointestinal tract in deep crypts and give rise to absorptive cells, goblet cells, paneth cells, and enteroendocrine cells.

Components of the Human Gastrointestinal Tract

The gastrointestinal tract is a continuous tube that extends from the mouth to the anus. On a gross level, the gastrointestinal tract is composed of the following organs: the mouth, most of the pharynx, the esophagus, the stomach, the small intestine (duodenum, jejunum and ileum), and the large intestine. Each segment of the gastrointestinal tract participates in the absorptive processes essential to digestion by producing chemical substances that facilitate digestion of orally taken foods, liquids, and other substances such as therapeutic agents.

Within the gastrointestinal tract, the small intestine, the site of most digestion and absorption, is structured specifically for these important functions. The small intestine is divided into three segments: the duodenum, the jejunum, and the ileum. The absorptive cells of the small intestine produce several digestive enzymes called the 'brush-border' enzymes. Together with pancreatic and intestinal juices, these enzymes facilitate the absorption of substances from the chime in the small intestine. The large intestine, the terminal portion of the gastrointestinal tract, contributes to the completion of absorption, the production of certain vitamins, and the formation and expulsion of feces.

At the cellular level, the epithelium is a purely cellular avascular tissue layer that covers all free surfaces (cutaneous, mucous, and serous) of the body including the glands and other structures derived from it. It lines both the exterior of the body, as skin, and the interior cavities and lumen of the body. While the outermost layer of human skin is composed of dead stratified squamous, keratinized epithelial cells, mucous membranes lining the inside of the mouth, the esophagus, and parts of the rectum are themselves lined by nonkeratinized stratified squamous epithelium. Epithelial cell lines are present inside of the lungs, the gastrointestinal tract, and the reproductive and urinary tracts, and form the exocrine and endocrine glands.

Epithelial cells are involved in secretion, absorption, protection, transcellular transport, sensation detection and selective permeability. There are variations in the cellular structures and functions in the epithelium throughout the gastrointestinal tract. The epithelium in the mouth, pharynx, esophagus and anal canal is mainly a protective, nonkeratinized, squamous epithelium. The epithelium of the stomach is composed of (i) simple columnar cells that participate in nutrient and fluid absorption and secretion, (ii) mucus producing goblet cells that participate in protective and mechanical functions, and (iii) enteroendocrine cells that participate in the secretion of gastrointestinal hormones. Additionally, within the intestine, the epithelial lining provides an important defense barrier against microbial pathogens.

The development of intestinal epithelium involves three major phases: 1) an early phase of epithelial proliferation and morphogenesis; 2) an intermediate period of cellular differentiation in which the distinctive cell types characteristic of intestinal epithelium appear; and 3) a final phase of biochemical and functional maturation. Intestinal crypts, located at the base of villi, contain stem cells which supply the entire epithelial cell surface with a variety of epithelial cell subtypes. These specialized cells provide for an external environment-internal environment interface, ion and fluid secretion and reabsorption, antigen recognition, hormone secretion, and surface protection. The exposure of epithelial cells on the surfaces of the intestinal lumen subjects them to a wide range of assaults, including microbial, chemical, and physical forces; thus they also may contribute to pathophysiologic impairment in diseases. Additionally, these cells are targets for inflammation, infection, and malignant transformation.

Within the intestinal tract, the epithelium forms upon stem cell differentiation.

Molecular Markers of Gastrointestinal Epithelial Stem Cells

As disclosed in U.S. Published Application No. 2009/0269769, which is incorporated herein by reference in its entirety, there are no universally accepted molecular markers that identify gastrointestinal stem cells. However, several markers have been used to identify stem cells in small and large intestinal tissues. These include: β-1-integrin, mushashi-1, CD45, and cytokeratin.

CD45, also called the common leukocyte antigen, T220 and B220 in mice, is a transmembrane protein with cytoplasmic protein tyrosine phosphatase (PTP) activity. CD45 is found in hematopoietic cells except erythrocytes and platelets. CD45 has several isoforms that can be seen in the various stages of differentiation of normal hematopoietic cells.

Mushashi-1 is an early developmental antigenic marker of stem cells and glial/neuronal cell precursor cells.

β-1-integrin (CD29, fibronectin receptor), is a β-subunit of a heterodimer protein member of the integrin family of proteins; integrins are membrane receptors involved in cell adhesion and recognition.

Cytokeratins are intermediate filament proteins found in the intracytoplasmic cystoskeleton of the cells that comprise epithelial tissue.

There are four main epithelial cell lineages: (i) columnar epithelial cells, (ii) goblet cells, (iii) enteroendocrine chromaffin cells, and (iv) Paneth cells. Several molecular markers have been used to identify each of these lineages.

The markers used to identify columnar epithelial cells include: intestinal alkaline phosphatase (ALP1), sucrase isomaltase (SI), sodium/glucose cotransporter (SLGT1), dipeptidyl-peptidase 4 (DPP4), and CD26. Intestinal alkaline phosphatase (E.C. 3.1.3.1) is a membrane-bound enzyme localized in the brush border of enterocytes in the human intestinal epithelium. Sucrase-isomaltase (SI, EC 3.2.1.48) is an enterocyte-specific small intestine brush-border membrane disaccharidase. Dipeptidyl-peptidase 4 (E.C. 3.4.14.5) is a membrane bound serine-type peptidase. Sodium/glucose transporter (SGLT) mediates transport of glucose into epithelial cells. SGLT belongs to the sodium/glucose cotransporter family SLCA5. Two different SGLT isoforms, SGLT1 and SGLT2, mediate renal tubular glucose reabsorption in humans. Both of them are characterized by their different substrate affinity. SGLT1 transports glucose as well as galactose, and is expressed both in the kidney and in the intestine. SGLT2 transports glucose and is believed to be responsible for 98% of glucose reabsorption; SGLT2 is generally found in the 51 and S2 segments of the proximal tubule of the nephron. CD26 is a multifunctional protein of 110 KDa strongly expressed on epithelial cells (kidney proximal tubules, intestine, and bile duct) and on several types of endothelial cells and fibroblasts and on leukocyte subsets.

The markers used to identify goblet cells include mucin 2 (MUC2) and trefoil factor 3 (TFF3). Mucin-2, a secreted gel-forming mucin, is the major gel-forming mucin secreted by goblet cells of the small and large intestines and is the main structural component of the mucus gel. Intestinal trefoil factor 3 is a nonmucin protein and a product of fully differentiated goblet cells.

The markers used to identify enteroendocrine chromaffin cells include chromogranin A (CHGA) and synaptophysin (SYP). Chromogranin A (CHGA) and its derived peptides, which are stored and released from dense-core secretory granules of neuroendocrine cells, have been implicated as playing multiple roles in the endocrine, cardiovascular, and nervous systems. Synaptophysin I (SYP) is a synaptic vesicle membrane protein that is ubiquitously expressed throughout the brain without a definite synaptic function.

The markers used to identify Paneth cells include lysozyme (LYZ), defensin (DEFA1), and matrix metallopeptidase 7 (MMPI). Lysozyme (LYZ or muramidase) (E.C. 3.2.1.17) catalyzes the hydrolysis of 1,4-beta-linkages between N-acetylmuramic acid and N-acetyl-D-glucosamine residues in a peptidoglycan and between N-acetyl-D-glucosamine residues in chitodextrins. Defensins (DEFA1) are small peptides that are produced by leukocytes and epithelial cells. Human defensin α-1 is a 3.5-kDa, 30-amino-acid peptide that has shown effector functions in host innate immunity against some microorganisms. Matrix metalloproteinases (MMPs) are a family of metal-dependant enzymes that are responsible for the degradation of extracellular matrix components. MMPs are involved in various physiologic processes, such as embryogenesis and tissue remodeling and also play a role in invasion and metastasis of tumor cells, which require proteolysis of basal membranes and extracellular matrix.

Neural Stem Cells

The adult mammalian brain contains multipotent neural stem cells (NSCs) that have the capacity to self-renew and are responsible for neurogenesis and maintenance of specific regions of the adult brain. Neural stem cells can generate astrocytes, oligodendrocytes, and neurons. Self-renewal and differentiation of neural stem cells are directed by interactions within a complex network of intrinsic regulators and extrinsic factors. Recent proteomic analyses have identified a horde of transcription factors belonging to the Wnt/β-catenin, Notch and Sonic Hedgehog (shh) pathways, in addition to epigenetic modifications, microRNA networks and extrinsic growth factor networks, including but not limited to the FGFs and BMPs. (Yun ey al., 2010, J. Cell. Physiol. 225: 337-347).

With the advent of high throughput microarray and proteomic technologies, a number of different molecular signatures of neural stem cells have been identified, including but not limited to CD133/promini, nestin, NCAM, the HMG-box transcription factor, Sox2 and the bHLH protein, Olig2. (Holmberg et al., 2011, PLoS One., 6(3): e18454; Hombach-Klonisch et al., 2008, J. Mol. Med. 86(12): 1301-1314).

Skin Stem Cells.

Several different adult stem cell populations with distinct molecular signatures are responsible for maintaining skin homeostasis. These include, but are not limited to, epidermal stem cells of the interfollicular region, epidermal stem cells of the hair follicle (also known as the bulge stem cells), dermal stem cells, dermal papilla stem cells, and sebaceous gland stems. The epidermal stem cells are ectodermal in origin while the dermal stem cells originate from the mesoderm and are mesenchymal in nature. (Zouboulis et al., 2008, Exp. Gerontol., 43: 986-997).

The interfollicular epidermal stem cells reside in the basal layer of the epidermis and give rise to keratinocytes, which migrate to the surface of the skin and form a protective layer. A diverse range of molecular signatures has been described for such epidermal stem cells including but not limited to high a6-integrin, low CD71, high Delta 1 (Notch signaling ligand) and high CD200 expression levels. The follicular stem cells located at the base of hair follicles give rise to both hair follicle and to the epidermis. These are characterized by Cytokeratin 15 (K15) immunostaining and high levels of β1-integrin. Dermal stem cell marker proteins include but are not limited to nestin, fibronectin and vimentin, the surface markers for dermal papilla stem cells include mesenchymal stem cell markers such as for example CD44, CD73 and CD90 and sebaceous stem cells express keratin 14. (Zouboulis et al., 2008, Exp. Gerontol., 43: 986-997).

In addition, adult somatic cells can be reprogrammed to enter an embryonic stem cell-like state by being forced to express a set of transcription factors, for example, Oct-3/4 (or Pou5f1, the Octamer transcription factor-3/4), the Sox family of transcription factors (e.g., Sox-1, Sox-2, Sox-3, and Sox-15), the Klf family transcription factors (Klf-1, Klf-2, Klf-4, and Klf-5), and the Myc family of transcription factors (e.g., c-Myc, N-Myc, and L-Myc). For example, human inducible Pluripotent Stem cells (iPSCs) are cells reprogrammed to express transcription factors that express stem cell markers and are capable of generating cells characteristic of all three germ layers (i.e., ectoderm, mesoderm, and endoderm).

1.3. Stem Cell Niches

Adult tissue compartments contain endogenous niches of adult stem cells that are capable of differentiating into diverse cell lineages of determined endodermal, mesodermal or ectodermal fate depending on their location in the body. For example, in the presence of an appropriate set of internal and external signals, bone marrow-derived adult hematopoietic stem cells (HSCs) have the potential to differentiate into blood, endothelial, hepatic and muscle cells; brain-derived neural stem cells (NSCs) have the potential to differentiate into neurons, astrocytes, oligodendrocytes and blood cells; gut- and epidermis-derived adult epithelial stem cells (EpSCs) have the potential to give rise to cells of the epithelial crypts and epidermal layers; adipose-derived stem cells (ASCs) have the potential to give rise to fat, muscle, cartilage, endothelial cells, neuron-like cells and osteoblasts; and bone-marrow-derived adult mesenchymal stem cells (MSCs) have the potential to give rise to bone, cartilage, tendon, adipose, muscle, marrow stroma and neural cells.

Endogenous adult stem cells are embedded within the ECM component of a given tissue compartment, which, along with support cells, form the cellular niche. Such cellular niches within the ECM scaffold together with the surrounding microenvironment contribute important biochemical and physical signals, including growth factors and transcription factors required to initiate stem cell differentiation into committed precursors cells and subsequent precursor cell maturation to form adult tissue cells with specialized phenotypic and functional characteristics.

1.4. Growth Factors

Growth factors are extracellular polypeptide molecules that bind to a cell-surface receptor triggering an intracellular signaling pathway, leading to proliferation, differentiation, or other cellular response. These pathways stimulate the accumulation of proteins and other macromolecules, and they do so by both increasing their rate of synthesis and decreasing their rate of degradation. One intracellular signaling pathway activated by growth factor receptors involves the enzyme PI 3-kinase, which adds a phosphate from ATP to the 3 position of inositol phospholipids in the plasma membrane. The activation of PI 3-kinase leads to the activation of several protein kinases, including S6 kinase. The S6 kinase phosphorylates ribosomal protein S6, increasing the ability of ribosomes to translate a subset of mRNAs, most of which encode ribosomal components, as a result of which, protein synthesis increases. When the gene encoding S6 kinase is inactivated in *Drosophila*, cell numbers are normal, but cell size is abnormally small, and the mutant flies are small. Growth factors also activate a translation initiation factor called eIF4E, further increasing protein synthesis and cell growth.

Growth factor stimulation also leads to increased production of the gene regulatory protein Myc, which plays a part in signaling by mitogens. Myc increases the transcription of a number of genes that encode proteins involved in cell metabolism and macromolecular synthesis. In this way, it stimulates both cell metabolism and cell growth.

Some extracellular signal proteins, including platelet-derived growth factor (PDGF), can act as both growth factors and mitogens, stimulating both cell growth and cell-cycle progression. This functional overlap is achieved in part by overlaps in the intracellular signaling pathways that control these two processes. The signaling protein Ras, for example, is activated by both growth factors and mitogens. It can stimulate the PI3-kinase pathway to promote cell growth and the MAP-kinase pathway to trigger cell-cycle progression. Similarly, Myc stimulates both cell growth and cell-cycle progression. Extracellular factors that act as both growth factors and mitogens help ensure that cells maintain their appropriate size as they proliferate.

Since many mitogens, growth factors, and survival factors are positive regulators of cell-cycle progression, cell growth, and cell survival, they tend to increase the size of organs and organisms. In some tissues, however, cell and tissue size also is influenced by inhibitory extracellular signal proteins that oppose the positive regulators and thereby inhibit organ growth. The best-understood inhibitory signal proteins are TGF-β and its relatives. TGF-β inhibits the proliferation of several cell types, either by blocking cell-cycle progression in G1 or by stimulating apoptosis. TGF-β binds to cell-surface receptors and initiates an intracellular signaling pathway that leads to changes in the activities of gene regulatory proteins called Smads. This results in complex changes in the transcription of genes encoding regulators of cell division and cell death.

Bone morphogenetic protein (BMP), a TGF-β family member, helps trigger the apoptosis that removes the tissue between the developing digits in the mouse paw. Like TGF-β, BMP stimulates changes in the transcription of genes that regulate cell death.

Fibroblast Growth Factor (FGF)

The fibroblast growth factor (FGF) family currently has over a dozen structurally related members. FGF1 is also known as acidic FGF; FGF2 is sometimes called basic FGF (bFGF); and FGF7 sometimes goes by the name keratinocyte growth factor. Over a dozen distinct FGF genes are known in vertebrates; they can generate hundreds of protein isoforms by varying their RNA splicing or initiation codons in different tissues. FGFs can activate a set of receptor tyrosine kinases called the fibroblast growth factor receptors (FGFRs). Receptor tyrosine kinases are proteins that extend through the cell membrane. The portion of the protein that binds the paracrine factor is on the extracellular side, while a dormant tyrosine kinase (i.e., a protein that can phosphorylate another protein by splitting ATP) is on the intracellular side. When the FGF receptor binds an FGF (and only when it binds an FGF), the dormant kinase is activated, and phosphorylates certain proteins within the responding cell, activating those proteins.

FGFs are associated with several developmental functions, including angiogenesis (blood vessel formation), mesoderm formation, and axon extension. While FGFs often can substitute for one another, their expression patterns give them separate functions. FGF2 is especially important in angiogenesis, whereas FGF8 is involved in the development of the midbrain and limbs.

The expression levels of angiogenic factors, such as VEGF, IGF, PDGF, HGF, FGF, TGFm Angiopoeitin-1, and stem cell factor (SCF) have been found to differ amongst bone-derived-, cartilage-derived-, and adipose-derived MSCs. (Peng et al., 2008, Stems Cells and Development, 17: 761-774).

Insulin-Like Growth Factor (IGF-1)

IGF-1, a hormone similar in molecular structure to insulin, has growth-promoting effects on almost every cell in the body, especially skeletal muscle, cartilage, bone, liver, kidney, nerves, skin, hematopoietic cell, and lungs. It plays an important role in childhood growth and continues to have anabolic effects in adults. IGF-1 is produced primarily by the liver as an endocrine hormone as well as in target tissues in a paracrine/autocrine fashion. Production is stimulated by growth hormone (GH) and can be retarded by undernutrition, growth hormone insensitivity, lack of growth hormone receptors, or failures of the downstream signaling molecules, including SHP2 and STAT5B. Its primary action is mediated by binding to its specific receptor, the Insulin-like growth factor 1 receptor (IGF1R), present on many cell types in many tissues. Binding to the IGF1R, a receptor tyrosine kinase, initiates intracellular signaling; IGF-1 is one of the most potent natural activators of the AKT signaling pathway, a stimulator of cell growth and proliferation, and a potent inhibitor of programmed cell death. IGF-1 is a primary mediator of the effects of growth hormone (GH). Growth hormone is made in the pituitary gland, released into the blood stream, and then stimulates the liver to produce IGF-1. IGF-1 then stimulates systemic body growth. In addition to its insulin-like effects, IGF-1 also can regulate cell growth and development, especially in nerve cells, as well as cellular DNA synthesis.

Transforming Growth Factor Beta (TGF-β)

There are over 30 structurally related members of the TGF-β superfamily, and they regulate some of the most important interactions in development. The proteins encoded by TGF-β superfamily genes are processed such that the carboxy-terminal region contains the mature peptide. These peptides are dimerized into homodimers (with themselves) or heterodimers (with other TGF-β peptides) and are secreted from the cell. The TGF-β superfamily includes the TGF-β family, the activin family, the bone morphogenetic proteins (BMPs), the Vg-1 family, and other proteins, including glial-derived neurotrophic factor (GDNF, necessary for kidney and enteric neuron differentiation) and Müllerian inhibitory factor, which is involved in mammalian sex determination. TGF-β family members TGF-β1, 2, 3, and 5 are important in regulating the formation of the extracellular matrix between cells and for regulating cell division (both positively and negatively). TGF-β1 increases the amount of extracellular matrix epithelial cells make both by stimulating collagen and fibronectin synthesis and by inhibiting matrix degradation. TGF-βs may be critical in controlling where and when epithelia can branch to form the ducts of kidneys, lungs, and salivary glands.

The members of the BMP family were originally discovered by their ability to induce bone formation. Bone formation, however, is only one of their many functions, and they have been found to regulate cell division, apoptosis (programmed cell death), cell migration, and differentiation. BMPs can be distinguished from other members of the TGF-β superfamily by their having seven, rather than nine, conserved cysteines in the mature polypeptide. The BMPs include proteins such as Nodal (responsible for left-right axis formation) and BMP4 (important in neural tube polarity, eye development, and cell death).

Neural Epidermal Growth-Factor-Like 1 (NELL1)

Neural epidermal growth-factor-like 1 (NEL-like 1, NELL1) is a gene that encodes an 810-amino acid polypeptide, which trimerizes to form a mature protein involved in the regulation of cell growth and differentiation. The neural epidermal growth-factor-like (nel) gene first was detected in neural tissue from an embryonic chicken cDNA library, and its human orthologue NELL1 was discovered later in B-cells. Studies have reported the presence of NELL in various fetal and adult organs, including, but not limited to, the brain, kidneys, colon, thymus, lung, and small intestine.

NELL1—General Structure

Generally, the arrangement of the functional domains of the 810 amino acid NELL1 protein bears resemblance to thrombospondin-1 ("THBS1") and consists of a thrombospondin N-terminal domain ("TSPN") and several von Willebrand factor, type C ("VWC"), and epidermal growth-factor ("EGF") domains.

Additional studies have shown that there are two transcript variants encoding different isoforms. The nel-like 1 isoform 1 precursor transcript variant represents the longer transcript and encodes the longer isoform 1.

The conserved domains of the nel-like 1 isoform 1 precursor transcript reside in seven regions of the isoform 1 peptide and include: (1) a TSPN domain/Laminin G superfamily domain; (2) a VWC domain; (3) an EGF-like domain; (4) an EGF-like domain; (5) an EGF-like domain; (6) an EGF-like domain and (7) a VWC domain.

The first conserved domain region comprises amino acids (amino acids 29 to 213) that are most similar to a thrombospondin N-terminal-like domain. Thrombospondins are a family of related, adhesive glycoproteins, which are synthesized, secreted and incorporated into the extracellular matrix of a variety of cells, including alpha granules of platelets following thrombin activation and endothelial cells. They interact with a number of blood coagulation factors and anticoagulant factors, and are involved in cell adhesion, platelet aggregation, cell proliferation, angiogenesis, tumor metastasis, vascular smooth muscle growth and tissue repair. The first conserved domain also comprises amino acids (amino acids 82 to 206; amino acids 98 to 209) that are similar to a Laminin G-like domain. Laminin G-like (LamG) domains usually are $Ca^{2+}$ mediated receptors that can have binding sites for steroids, β1-integrins, heparin, sulfatides, fibulin-1, and α-dystroglycans. Proteins that contain LamG domains serve a variety of purposes, including signal transduction via cell-surface steroid receptors, adhesion, migration and differentiation through mediation of cell adhesion molecules.

Much of what is known about NELL1 concerns its role in bone development. See, e.g., U.S. Pat. No. 7,884,066, U.S. Pat. No. 7,833,968, U.S. Pat. No. 7,807,787, U.S. Pat. No. 7,776,361, U.S. Pat. No. 7,691,607, U.S. Pat. No. 7,687,462, U.S. Pat. No. 7,544,486, and U.S. Pat. No. 7,052,856, the entire contents of which are incorporated herein by reference. It generally is believed that during osteogenic differentiation, NELL1 signaling may involve an integrin-related molecule and tyrosine kinases that are triggered by NELL1 binding to a NELL1 specific receptor and a subsequent formation of an extracellular complex. As thus far understood, in human NELL1 (hNELL1), the laminin G domain comprises about 128 amino acid residues that show a high degree of similarity to the laminin G domain of extracellular matrix ("ECM") proteins, such as human laminin α3 chain (hLAMA3), mouse laminin α3 chain (mLAMA3), human collagen 11 α3 chain (hCOLA1), and human thrombospondin-1 (hTSP1). This complex facilitates either activation of Tyr-kinases, inactivation of Tyr phosphatases, or intracellular recruitment of Tyr-phosphorylated proteins. The ligand bound integrin (cell surface receptors that interact with ECM proteins such as, for example, laminin 5, fibronectin, vitronectin, TSP1/2) transduces the signals through activation of the focal adhesion kinase (FAK) followed by indirect activation of the Ras-MAPK cascade, and then leads to osteogenic differentiation through Runx2; the laminin G domain is believed to play a role in the interaction between integrins and a 67 kDa laminin receptor.

The second conserved domain (amino acids 273 to 331) and seventh conserved domain (amino acids 701 to 749; amino acids 703 to 749) are similar to von Willebrand factor type C (VWC) domains, also known as chordin-like repeats. VWC domains occur in numerous proteins of diverse functions. It is thought that these domains may be involved in protein oligomerization.

The third conserved domain (amino acids 434 to 471; amino acids 434 to 466), fourth conserved domain (amino acids 478 to 512), fifth conserved domain (amino acids 549 to 586; amino acids 549 to 582), and sixth conserved domain (amino acids 596 to 627; amino acids 596 to 634) are similar to a calcium-binding EGF-like domain. Calcium-binding EGF-like domains are present in a large number of membrane-bound and extracellular (mostly animal) proteins. Many of these proteins require calcium for their biological function. Calcium-binding sites have been found to be located at the N-terminus of particular EGF-like domains, suggesting that calcium-binding may be crucial for numerous protein-protein interactions. Six conserved core cysteines form three disulfide bridges as in non-calcium-binding EGF domains whose structures are very similar.

The nel-like 1 isoform 2 precursor transcript variant lacks an alternate in-frame exon compared to variant 1. The resulting isoform 2, which has the same N- and C-termini as isoform 1 but is shorter compared to isoform 1, has six conserved regions including a TSPN domain/LamG superfamily domain (amino acids 29 to 313); VWC domains (amino acids 273 to 331; amino acids 654 to 702); and calcium-binding EGF-like domains (amino acids 478 to 512; amino acids 434 to 471; amino acids 549 to 580).

NELL1 and its orthologs are found across several species including *Homo sapiens* (man), *Mus musculus* (mouse), *Rattus norvegicus* (rat), Pan troglodytes (chimpanzee), *Xenopus* (Silurana) *tropicalis* (frog), *Canis lupus familiaris* (dog), *Culex quinquefasciatus* (mosquito) *Pediculus humanus corporis* (head louse), *Aedes aegypti* (mosquito), *Ixodes scapularis* (tick), Strongylocentrotus purpuratus (purple sea urchin), and *Acyrthosiphon pisum* (pea aphid).

NELL1 is Variable

NELL1 comprises several regions susceptible to increased recombination. Studies have indicated that susceptibilities to certain diseases may be associated with genetic variations within these regions, suggesting the existence of more than one causal variant in the NELL1 gene. For example, in patients suffering irritable bowel syndrome ("IBS"), six different single nucleotide polymorphisms (SNPs) within NELL1 have been identified, with most of these SNPs near the 5' end of the gene and fewer at the 3' end. These include R136S and A153T (which reside in the TSPN) and R354W (which resides in a VWC domain). Additional studies have identified at least 26 variants comprising some of at least 263 SNPs within the NELL1 region.

NELL1-Function

The NELL1 protein is a secreted cytoplasmic heterotrimeric protein. The complete role NELL1 plays in vivo remains unknown.

Several studies have indicated that NELL1 may play a role in bone formation, inflammatory bowel disease, and esophageal adenocarcinoma, among others.

NELL1 in Osteogenesis

It generally is believed that NELL1 induces osteogenic differentiation and bone formation of osteoblastic cells during development. Studies have shown that the NELL1 protein (1) transiently activates the mitogen-activated protein kinase ("MAPK") signaling cascade (which is involved in various cellular activities such as gene expression, mitosis, differentiation, proliferation and apotosis); and (2) induces phosphorylation of Runx2 (a transcription factor associated with osteoblast differentiation). Consequently, it generally is believed that upon binding to a specific receptor, NELL1 transduces an osteogenic signal through activation of certain Tyr-kinases associated with the Ras-MAPK cascade, which ultimately leads to osteogenic differentiation. Studies have shown that bone development is severely disturbed in transgenic mice where over-expression of NELL1 has been shown to lead to craniosynotosis (premature ossification of the skull and closure of the sutures) and NELL1 deficiency manifests in skeletal defects due to reduced chondrogenesis and osteogenesis.

Additional studies have supported a role for NELL-1 as a craniosynostosis-related gene. For example, three regions within the NELL-1 promoter have been identified that are directly bound and transactivated by Runx2. Further, studies in rat skullcaps have indicated that forced expression of Runx2 induces NELL-1 expression (which is suggestive that Nell-1 is a downstream target of Runx2).

2. Cells of the Connective Tissue Compartment

The connective tissue compartment contains cells that primarily function to elaborate and maintain ECM structure. The character of the extracellular matrix is region-specific and is determined by the amount of the extracellular materials.

Common cell types of connective tissue compartments include: fibroblasts, macrophages, mast cells, and plasma cells. Specialized connective tissue compartments, such as cartilage, bone, and the vasculature, and those with special properties, such as adipose, tendons, ligaments, etc., have specialized cells to perform specialized functions.

2.1. Adipose Tissue Compartment

Adipose tissue compartments are dynamic, multifunctional, ubiquitous and loose connective tissue compartments. Adipose comprises fibroblasts, smooth muscle cells, endothelial cells, leukocytes, macrophages, and closely packed mature lipid-filled fat cells, termed adipocytes, with characteristic nuclei pushed to one side, embedded within an areolar matrix that are located in subcutaneous layers of skin and muscle (panniculus adiposus), in the kidney region, cornea, breasts, mesenteries, mediastinium, and in the cervical, axillary and inguinal regions. Adipocytes play a primary role in energy storage and in providing insulation and protection. As sites of energy storage, adipocytes regulate the accumulation or mobilization of triacylglycerol in response to the body's energy requirements and store energy in the form of a single fat droplet of triglycerides.

Adipocyte Matrix

Each adipocyte is surrounded by a thick ECM called the basal lamina. The strong adipocyte ECM scaffold lowers mechanical stress by spreading forces over a large surface area of the adipose tissue compartments. The ECM composition of adipocytes is similar to that of other cell types, but it is the relative quantity of individual components that impart cell specificity. Adipocyte ECM is particularly enriched in collagen VI, a coiled coil comprising α1(VI), α2(VI) and α3(VI) subunits. Collagen VI binds to collagen IV and also to other matrix proteins such as proteoglycans and fibronectin. Table 2 lists core proteins that have been annotated to the adipocyte ECM with current proteomic techniques. (Mariman et al., 2010, *Cell. Mol. Life Sci.*, 67:1277-1292).

TABLE 2

Core Proteins of Human Adipocyte ECM

| Protein | Symbol |
|---|---|
| Basement membrane-specific heparan sulfate proteoglycan core protein (HSPG) (perlecan) | HSPG2 |
| Calreticulin | CALR |
| Chitinase-3-like protein 1 | CHI3l1 |
| Coiled coil domain containing protein 80 | CCDC80 |
| Collagen α 1(I) chain | COL1A1 |
| Collagen α 2(I) chain | COL1A2 |
| Collagen α 1(III) chain | COL2A1 |

TABLE 2-continued

Core Proteins of Human Adipocyte ECM

| Protein | Symbol |
|---|---|
| Collagen α 2(IV) chain | COL4A2 |
| Collagen α 1(V) chain | COL5A1 |
| Collagen α 1(VI) chain | COL6A1 |
| Collagen α 2(VI) chain | COL6A2 |
| Collagen α 3(VI) chain | COL6A3 |
| Collagen α 1(XII) chain | COL12A1 |
| Collagen α 1(XIV) chain (undulin) | COL14A1 |
| Collagen α 1(XV) chain | COL15A1 |
| Collagen α 1(XVIII) chain | COL18A1 |
| Decorin (bone proteoglycan II) | DCN |
| Dermatopontin (tyrosine-rich acidic matrix protein; early quiescence protein 1) | DPT |
| Elastin microfibril interface-located protein 1 | EMILIN1 |
| Fibronectin (FN) (cold-insoluble globulin) | FN1 |
| Fibulin-1 | FBLN1 |
| Fibulin-3 (EGF-containing fibulin-like extracellular matrix protein 1) | FBLN3 |
| Fibulin-5 (developmental arteries and neural crest EGF-like protein | FBLN5 |
| Galectin-1 | LGALS1 |
| Galectin-3-binding protein (lectin galactoside-binding soluble 3-binding protein) | LGALS3BP |
| Glypican 1 | GPC1 |
| Laminin α-4 chain | LAMA4 |
| Laminin β-1 chain | LAMB1 |
| Laminin β-2 chain | LAMB2 |
| Laminin γ-1 chain | LAMC1 |
| Lumican (keratan sulfate proteoglycan lumican) | LUM |
| Matrilin-2 | MATN2 |
| Microfibril-associated glycoprotein 4 | MFAP4 |
| Mimecan (osteoglycin) | OGN |
| Nidogen 1 (entactin) | NID1 |
| Nidogen 2 (osteonidogen)) | NID2 |
| Periostin | POSTN |
| Proteoglycan 4 | PRG4 |
| SPARC (osteonectin) | SPARC |
| Spondin-1 (F-spondin) (vascular smooth muscle cell growth-promoting factor) | SPON1 |
| Spondin-2 (mindin) | SPON2 |
| Tenascin-C (TN) (hexabrachion) (cytotactin) (neuronectin) (GMEM) | TNC |
| Tenascin-X | TNXB |
| Thrombospondin-1 | THBS1 |
| Thrombospondin-2 | THBS2 |
| Transforming growth factor-b-induced protein IG-H3 (bIG-H3) | TGFB1 |
| Versican core protein (large fibroblast proteoglycan) | CSPG2 |
| Versican V3 isoform | VCAN |

Adipocyte ECM undergoes biphasic development during adipogenesis, the process of formation of mature adipose tissue compartments. There is an initial decrease in collagen I and III, whereas their levels come back to pre differentiation state at later stages. Mature adipocyte ECM is maintained in a dynamic state with constant turnover of ECM components by a balance of activities of ECM constructive enzymes and ECM degradation enzymes. In early stages of differentiation, the balance is shifted towards the constructive factors. (Mariman et al., 2010, *Cell. Mol. Life Sci.,* 67:1277-1292). Maturation of newly synthesized ECM components is initiated in the ER lumen where ECM proteins undergo biochemical modifications and proteolytic processing prior to assembly. For collagen, such modifications include proline- and lysine-hydroxylation and glycosylation and clipping of N- and C-terminal peptides by respective procollagen-N- and -C-collagenase. Processed proteins are then assembled and secreted into the extracellular environment where they undergo further processing by secreted extracellular modification and processing enzymes. As the preadipocytes differentiate and begin to store fat, ECM assumes a basal laminar structure.

Adipose-Derived Stem Cells

Adipose also comprises a population of pluripotent stem cells that have the potential to give rise to cells of all three embryonic lineages: ectodermal, mesodermal and endodermal. Adipogenesis, which comprises the steps of differentiation of such pluripotent cells to mature adipocytes, is initiated by differentiation of these pluripotent cells to give rise to a population of mesenchymal precursor cells or mesenchymal stem cells (MSCs), which have the potential to differentiate into a variety of mesodermal cell lineages such as for example, myoblasts, chondroblasts, osteoblasts and adipocytes. In the presence of appropriate environmental and gene expression signals, the MSCs go through growth arrest and differentiate into precursors with a determined fate that undergo clonal expansion, become committed and terminally differentiate to give rise to mature cells. The population of MSCs and more committed adipose progenitors that are found along with the stroma of adipose tissue collectively are termed adipose-derived stem cells (ASCs). These cells have a characteristic $CD45^-CD31^-CD34^+CD105^+$ surface phenotype. In the case of adipocyte differentiation, ASCs differentiate to proadipocytes that undergo final differentiation to give rise to mature adipocytes. Mesenchymal progenitor cells with chondrogenic potential have also been identified in the infrapatellar fat pad in joints. (Lee et al., Tissue Engg. 2010, 16(1): 317-325).

Table 3 lists cell lineages and respective inductive factors that can be derived from ASC lines. (Brown et. al., 2010, Plast. Reconstr. Surg., 126(6): 1936-1946; Gregoire et al., 1998, Physiol. Rev. 78(3): 783-809).

TABLE 3

Inductive Factors and Cell Lineages from Adipose-derived Stem Cells

| Cell Lineage | Inductive Factors |
|---|---|
| Adipocyte | Dexamethasone; isobutyl methylxanthine,; indoxanthine; insulin; thiazolidinedione; nuclear hormone glucocorticoids ,e.g., 3,3',5-triiodothyronine ($T_3$) and retinoic acid (RA); IGF-1; $PGE_2$ |
| Cardiomyocyte | Transferrin; IL-3; IL-6; VEGF |
| Chondrocyte | Ascorbic acid; bone morphogenetic protein 6; dexamethasone; insulin; transforming growth factor-β (TGF-β) |
| Endothelial | EGM-2-MV medium (Cambrex, Walkersville, Md) containing ascorbate, epidermal growth factor, basic fibroblast growth factor, and hydrocortisone |
| Myocyte | Dexamethasone horse serum |
| Neuronal-like | Butylated hydroxianisole; valproic acid; insulin |
| Osteoblast | Ascorbic acid; bone morphogenetic protein-2; dexamethasone; 1,25-dihydroxyvitamin D |

Adipose Secreted Factors

Adipose is considered a secretory organ. The adipose secretome not only includes structural and soluble factors contributing to the formation of the adipose matrix, but also a horde of soluble factors with endocrine function, such as growth factors, hormones, chemokines and lipids, collectively termed adipokines. Exemplary adipokines include, without limitation, leptin, adiponectin, resistin, interleukin 6 (IL-6), monocyte chemoattractant protein 1 (MCP-1), tumor necrosis factor alpha (TNF-α); fibroblast growth factor (FGF), and vascular endothelial growth factor (VEGF). Exemplary immunogical adipokines, particularly involved in inflammatory pathways include, without limitation, serum amyloid A3 (SAA3), IL-6, adiponectin, TNF-α and haptoglobin. Exemplary adipokines involved in the production of new blood vessels include, without limitation, angiopoietin- 1, angiopoietin-2, VEGF, transforming growth factor beta (TGF-β), hepatic growth factor (HGF), stromal derived growth factor 1 (SDF-1), TNF-α, resistin, leptin, tissue factor, placental growth factor (PGF), insulin like growth factor (IGF), and monobutyrin.

Adiponectin, a key metabolic factor secreted from adipocytes, is a 30-KDa protein that may exist as a trimer, low molecular weight hexamers or high molecular weight 18mers. Adiponectin circulates throughout the plasma and has a variety of metabolic effects including, but not limited to, glucose lowering and cardioprotection stimulation of smooth muscle proliferation. Adiponectin has been implicated in a number of pathological conditions including, but not limited to diabetes, obesity, metabolic syndrome, cardiovascular disease and wound healing.

Resistin, a member of the resistin-like (RELM) hormone family, is secreted by stromal vascular cells of adipose. Resistin is secreted in two multimeric isoforms and functions to counterbalance the insulin sensitizing effects of adiponectin. (Truillo, M. E. and Scherer P. E., Endocrine Rev. 2006, 27(7): 762-778).

Secretions from resident adipocytes, macrophages and ASCs collectively contribute to the adipose secretome. Table 4 provides a reported adipokine profile of ASCs. (Kilroy et. al., 2007, J. Cell. Physiol. 212: 702-709.)

TABLE 4

Reported Adipokine Profile of Human ASCs

| Function | Adipokine |
| --- | --- |
| Angiogenic | HGF |
|  | VEGF |
| Hematopoietic | Flt-3 ligand |
|  | G-CSF |
|  | GM-CSF |
|  | IL-7 |
|  | IL-12 |
|  | M-CSF |
|  | SCF |
| Proinflammatory | IL-1alpha |
|  | IL-6 |
|  | IL-8 |
|  | IL-11 |
|  | LIF |
|  | TNF-alpha |

Transcription Factors Responsible for Adipogenesis

Adipocyte differentiation involves the crosstalk between external signals in the ECM environment with internal signals generated from the nucleus. The peroxisome proliferator-activated receptors (PPAR) and CCAAT-enhancer-binding proteins (C/EBP) family of transcription factors play an important role in adipogenesis. The PPARs, members of type II nuclear hormone receptor family, form heterodimers with the retinoid X receptor (RXR). They regulate transcription by binding of PPAR-RXR heterodimers to a response element characterized by a direct repeat of the nuclear receptor hexameric DNA recognition motif, PuGG-TCA. PPAR-γ is most adipose-specific of all PPARs and is activated prior to transcriptional up-regulation of most other adipocyte genes. The C/EBP family of transcription factors are also induced prior to activation of other adipocyte genes and plays a major role in adipocyte differentiation. Members of the basic helix-loop-helix (bHLH) family of transcription factors have also been implicated in adipogenesis. (Gregoire et al., 1998, Physiol. Rev. 78(3): 783-809).

2.2. Bone (Osseous) Tissue Compartment

Osseous tissue is a rigid form of connective tissue normally organized into definite structures, the bones. These form the skeleton, serve for the attachment and protection of the soft parts, and, by their attachment to the muscles, act as levers that bring about body motion. Bone is also a storage place for calcium that can be withdrawn when needed to maintain a normal level of calcium in the blood.

Bones can be classified according to their shape. Examples of bone types include: long bones whose length is greater than their widths (e.g., femur (thigh bone), humerus (long bone of the upper limb), tibia (shin bone), fibula (calf bone), radius (the outer of the two bones of the forearm), and ulna (inner of two bones of the forearm)), short bones whose length and width is approximately equal (e.g., carpals bones (wrist bones in the hand)), flat bones (e.g., cranium (skull bones surrounding the brain), scapula (shoulder blade), and ilia (the uppermost and largest bone of the pelvis)), irregular bones (e.g., vertebra), and Sesamoid bones, small bones present in the joints to protect tendons (fibrous connective tissues that connect muscles to the bones, e.g., patella bones (knee cap)).

Grossly, two types of bone may be distinguished: cancellous, trabecular or spongy bone, and cortical, compact, or dense bone.

Cortical bone, also referred to as compact bone or dense bone, is the tissue of the hard outer layer of bones, so-called due to its minimal gaps and spaces. This tissue gives bones their smooth, white, and solid appearance. Cortical bone consists of haversian sites (the canals through which blood vessels and connective tissue pass in bone) and osteons (the basic units of structure of cortical bone comprising a haversian canal and its concentrically arranged lamellae), so that in cortical bone, bone surrounds the blood supply. Cortical bone has a porosity of about 5% to about 30%, and accounts for about 80% of the total bone mass of an adult skeleton.

Cancellous Bone (Trabecular or Spongy Bone)

Cancellous bone tissue, an open, cell-porous network also called trabecular or spongy bone, fills the interior of bone and is composed of a network of rod- and plate-like elements that make the overall structure lighter and allows room for blood vessels and marrow so that the blood supply surrounds bone. Cancellous bone accounts for the remaining 20% of total bone mass but has nearly ten times the surface area of cortical bone. It does not contain haversian sites and osteons and has a porosity of about 30% to about 90%.

The head of a bone, termed the epiphysis, has a spongy appearance and consists of slender irregular bone trabeculae, or bars, which anastomose to form a lattice work, the interstices of which contain the marrow, while the thin outer shell appears dense. The irregular marrow spaces of the epiphysis become continuous with the central medullary cavity of the bone shaft, termed the diaphysis, whose wall is formed by a thin plate of cortical bone.

Both cancellous and cortical bone have the same types of cells and intercellular substance, but they differ from each other in the arrangement of their components and in the ratio of marrow space to bone substance. In cancellous bone, the marrow spaces are relatively large and irregularly arranged, and the bone substance is in the form of slender anastomosing trabeculae and pointed spicules. In cortical bone, the spaces or channels are narrow and the bone substance is densely packed.

With very few exceptions, the cortical and cancellous forms are both present in every bone, but the amount and distribution of each type vary considerably. The diaphyses of the long bones consist mainly of cortical tissue; only the innermost layer immediately surrounding the medullary cavity is cancellous bone. The tabular bones of the head are composed of two plates of cortical bone enclosing marrow space bridged by irregular bars of cancellous bone. The epiphyses of the long bones and most of the short bones consist of cancellous bone covered by a thin outer shell of cortical bone.

Each bone, except at its articular end, is surrounded by a vascular fibroelastic coat, the periosteum. The so-called endosteum, or inner periosteum of the marrow cavity and marrow spaces, is not a well-demarcated layer; it consists of a variable concentration of medullary reticular connective tissue that contains osteogenic cells that are in immediate contact with the bone tissue.

Components of Bone

Bone is composed of cells and an intercellular matrix of organic and inorganic substances.

The organic fraction consists of collagen, glycosaminoglycans, proteoglycans, and glycoproteins. The protein matrix of bone largely is composed of collagen, a family of fibrous proteins that have the ability to form insoluble and rigid fibers. The main collagen in bone is type I collagen.

The inorganic component of bone, which is responsible for its rigidity and may constitute up to two-thirds of its fat-free dry weight, is composed chiefly of calcium phosphate and calcium carbonate, in the form of calcium hydroxyapatite, with small amounts of magnesium hydroxide, fluoride, and sulfate. The composition varies with age and with a number of dietary factors. The bone minerals form long fine crystals that add strength and rigidity to the collagen fibers; the process by which it is laid down is termed mineralization.

Bone Cells

Four cell types in bone are involved in its formation and maintenance. These are 1) osteoprogenitor cells, 2) osteoblasts, 3) osteocytes, and 4) osteoclasts.

Osteoprogenitor Cells

Osteoprogenitor cells arise from mesenchymal cells, and occur in the inner portion of the periosteum and in the endosteum of mature bone. They are found in regions of the embryonic mesenchymal compartment where bone formation is beginning and in areas near the surfaces of growing bones. Structurally, osteoprogenitor cells differ from the mesenchymal cells from which they have arisen. They are irregularly shaped and elongated cells having pale-staining cytoplasm and pale-staining nuclei. Osteoprogenitor cells, which multiply by mitosis, are identified chiefly by their location and by their association with osteoblasts. Some osteoprogenitor cells differentiate into osteocytes. While osteoblasts and osteocytes are no longer mitotic, it has been shown that a population of osteoprogenitor cells persists throughout life.

Osteoblasts

Osteoblasts, which are located on the surface of osteoid seams (the narrow region on the surface of a bone of newly formed organic matrix not yet mineralized), are derived from osteoprogenitor cells. They are immature, mononucleate, bone-forming cells that synthesize collagen and control mineralization. Osteoblasts can be distinguished from osteoprogenitor cells morphologically; generally they are larger than osteoprogenitor cells, and have a more rounded nucleus, a more prominent nucleolus, and cytoplasm that is much more basophilic. Osteoblasts make a protein mixture known as osteoid, primarily composed of type I collagen, which mineralizes to become bone. Osteoblasts also manufacture hormones, such as prostaglandins, alkaline phosphatase, an enzyme that has a role in the mineralization of bone, and matrix proteins.

Osteocytes

Osteocytes, star-shaped mature bone cells derived from ostoblasts and the most abundant cell found in compact bone, maintain the structure of bone. Osteocytes, like osteoblasts, are not capable of mitotic division. They are actively involved in the routine turnover of bony matrix and reside in small spaces, cavities, gaps or depressions in the bone matrix called lacuna. Osteocytes maintain the bone matrix, regulate calcium homeostasis, and are thought to be part of the cellular feedback mechanism that directs bone to form in places where it is most needed. Bone adapts to applied forces by growing stronger in order to withstand them; osteocytes may detect mechanical deformation and mediate bone-formation by osteoblasts.

Osteoclasts

Osteoclasts, which are derived from a monocyte stem cell lineage and possess phagocytic-like mechanisms similar to macrophages, often are found in depressions in the bone referred to as Howship's lacunae. They are large multinucleated cells specialized in bone resorption. During resorption, osteoclasts seal off an area of bone surface; then, when activated, they pump out hydrogen ions to produce a very acid environment, which dissolves the hydroxyapatite component. The number and activity of osteoclasts increase when calcium resorption is stimulated by injection of parathyroid hormone (PTH), while osteoclastic activity is suppressed by injection of calcitonin, a hormone produced by thyroid parafollicular cells.

Bone Matrix

The bone matrix accounts for about 90% of the total weight of compact bone and is composed of microcrystalline calcium phosphate resembling hydroxyapatite (60%) and fibrillar type I collagen (27%). The remaining 3% consists of minor collagen types and other proteins including osteocalcin, osteonectin, osteopontin, bone sialoprotein, as well as proteoglycans, glycosaminoglycans, and lipids.

Bone matrix is also a major source of biological information that skeletal cells can receive and act upon. For example, extracellular matrix glycoproteins and proteoglycans in bone bind a variety of growth factors and cytokines, and serve as a repository of stored signals that act on osteoblasts and osteoclasts. Examples of growth factors and cytokines found in bone matrix include, but are not limited to, Bone Morphogenic Proteins (BMPs), Epidermal Growth Factors (EGFs), Fibroblast Growth Factors (FGFs), Platelet-Derived Growth Factors (PDGFs), Insulin-like Growth Factor-1 (IGF-1), Transforming Growth Factors (TGFs), Bone-Derived Growth Factors (BDGFs), Cartilage-Derived Growth Factor (CDGF), Skeletal Growth Factor (hSGF), Interleukin-1 (IL-1), and macrophage-derived factors.

There is an emerging understanding that extracellular matrix molecules themselves can serve regulatory roles, providing both direct biological effects on cells as well as key spatial and contextual information.

The Periosteum and Endosteum

The periosteum is a fibrous connective tissue investment of bone, except at the bone's articular surface. Its adherence to the bone varies by location and age. In young bone, the periosteum is stripped off easily. In adult bone, it is more firmly adherent, especially so at the insertion of tendons and ligaments, where more periosteal fibers penetrate into the bone as the perforating fibers of Sharpey (bundles of collagenous fibers that pass into the outer circumferential lamellae of bone). The periosteum consists of two layers, the outer of which is composed of coarse, fibrous connective tissue containing few cells but numerous blood vessels and nerves. The inner layer, which is less vascular but more cellular, contains many elastic fibers. During growth, an osteogenic layer of primitive connective tissue forms the inner layer of the periosteum. In the adult, this is represented only by a row of scattered, flattened cells closely applied to the bone. The periosteum serves as a supporting bed for the blood vessels and nerves going to the bone and for the anchorage of tendons and ligaments. The osteogenic layer, which is considered a part of the periosteum, is known to furnish osteoblasts for growth and repair, and acts as an important limiting layer controlling and restricting the extend of bone formation. Because both the periosteum and its contained bone are regions of the connective tissue compartment, they are not separated from each other or from other connective tissues by basal laminar material or basement membranes. Perosteal stem cells have been shown to be important in bone regeneration and repair. (Zhang et al., 2005, J. Musculoskelet. Neuronal. Interact. 5(4): 360-362).

The endosteum lines the surface of cavities within a bone (marrow cavity and central canals) and also the surface of trabeculae in the marrow cavity. In growing bone, it consists of a delicate striatum of myelogenous reticular connective tissue, beneath which is a layer of osteoblasts. In the adult, the osteogenic cells become flattened and are indistinguishable as a separate layer. They are capable of transforming into osteogenic cells when there is a stimulus to bone formation, as after a fracture.

Marrow

The marrow is a soft connective tissue that occupies the medullary cavity of the long bones, the larger central canals, and all of the spaces between the trabeculae of spongy bone. It consists of a delicate reticular connective tissue, in the meshes of which lie various kinds of cells. Two varieties of marrow are recognized: red and yellow. Red marrow is the only type found in fetal and young bones, but in the adult it is restricted to the vertebrae, sternum, ribs, cranial bones, and epiphyses of long bones. It is the chief site for the genesis of blood cells in the adult body. Yellow marrow consists primarily of fat cells that gradually have replaced the other marrow elements. Under certain conditions, the yellow marrow of old or emaciated persons loses most of its fat and assumes a reddish color and gelatinous consistency, known as gelatinous marrow. With adequate stimulus, yellow marrow may resume the character of red marrow and play an active part in the process of blood development.

Osteogenesis or Ossification

Osteogenesis or ossification is a process by which the bones are formed. There are three distinct lineages that generate the skeleton. The somites generate the axial skeleton, the lateral plate mesoderm generates the limb skeleton, and the cranial neural crest gives rise to the branchial arch, craniofacial bones, and cartilage. There are two major modes of bone formation, or osteogenesis, and both involve the transformation of a preexisting mesenchymal tissue into bone tissue. The direct conversion of mesenchymal tissue into bone is called intramembranous ossification. This process occurs primarily in the bones of the skull. In other cases, mesenchymal cells differentiate into cartilage, which is later replaced by bone. The process by which a cartilage intermediate is formed and replaced by bone cells is called endochondral ossification.

Intramembranous Ossification

Intramembraneous ossification is the characteristic way in which the flat bones of the scapula, the skull and the turtle shell are formed. In intramembraneous ossification, bones develop sheets of fibrous connective tissue. During intramembranous ossification in the skull, neural crest-derived mesenchymal cells proliferate and condense into compact nodules. Some of these cells develop into capillaries; others change their shape to become osteoblasts, committed bone precursor cells. The osteoblasts secrete a collagen-proteoglycan matrix that is able to bind calcium salts. Through this binding, the prebone (osteoid) matrix becomes calcified. In most cases, osteoblasts are separated from the region of calcification by a layer of the osteoid matrix they secrete. Occasionally, osteoblasts become trapped in the calcified matrix and become osteocytes. As calcification proceeds, bony spicules radiate out from the region where ossification began, the entire region of calcified spicules becomes surrounded by compact mesenchymal cells that form the periosteum, and the cells on the inner surface of the periosteum also become osteoblasts and deposit osteoid matrix parallel to that of the existing spicules. In this manner, many layers of bone are formed.

Intramembraneous ossification is characterized by invasion of capillaries into the mesenchymal zone, and the emergence and differentiation of mesenchymal cells into mature osteoblasts, which constitutively deposit bone matrix leading to the formation of bone spicules, which grow and develop, eventually fusing with other spicules to form trabeculae. As the trabeculae increase in size and number they become interconnected forming woven bone (a disorganized weak structure with a high proportion of osteocytes), which eventually is replaced by more organized, stronger, lamellar bone.

The molecular mechanism of intramembranoaus ossification involves bone morphogenetic proteins (BMPs) and the activation of a transcription factor called CBFA1. Bone morphogenetic proteins, for example, BMP2, BMP4, and BMP7, from the head epidermis are thought to instruct the neural crest-derived mesenchymal cells to become bone cells directly. BMPs activate the Cbfa1 gene in mesenchymal cells. The CBFA1 transcription factor is known to transform mesenchymal cells into osteoblasts. Studies have shown that the mRNA for mouse CBFA1 is largely restricted to the mesenchymal condensations that form bone, and is limited to the osteoblast lineage. CBFA1 is known to activate the genes for osteocalcin, osteopontin, and other bone-specific extracellular matrix proteins.

Endochondral Ossification (Intracartilaginous Ossification)

Endochondral ossification, which involves the in vivo formation of cartilage tissue from aggregated mesenchymal cells, and the subsequent replacement of cartilage tissue by bone, can be divided into five stages. The skeletal components of the vertebral column, the pelvis, and the limbs are first formed of cartilage and later become bone.

First, the mesenchymal cells are committed to become cartilage cells. This commitment is caused by paracrine factors that induce the nearby mesodermal cells to express two transcription factors, Pax1 and Scleraxis. These transcription factors are known to activate cartilage-specific genes. For example, Scleraxis is expressed in the mesenchyme from the sclerotome, in the facial mesenchyme that forms cartilaginous precursors to bone, and in the limb mesenchyme.

During the second phase of endochondral ossification, the committed mesenchyme cells condense into compact nodules and differentiate into chondrocytes (cartilage cells that produce and maintain the cartilaginous matrix, which consists mainly of collagen and proteoglycans). Studies have shown that N-cadherin is important in the initiation of these condensations, and N-CAM is important for maintaining them. In humans, the SOX9 gene, which encodes a DNA-binding protein, is expressed in the precartilaginous condensations.

During the third phase of endochondral ossification, the chondrocytes proliferate rapidly to form the model for bone. As they divide, the chondrocytes secrete a cartilage-specific extracellular matrix.

In the fourth phase, the chondrocytes stop dividing and increase their volume dramatically, becoming hypertrophic chondrocytes. These large chondrocytes alter the matrix they produce (by adding collagen X and more fibronectin) to enable it to become mineralized by calcium carbonate.

The fifth phase involves the invasion of the cartilage model by blood vessels. The hypertrophic chondrocytes die by apoptosis, and this space becomes bone marrow. As the cartilage cells die, a group of cells that have surrounded the cartilage model differentiate into osteoblasts, which begin forming bone matrix on the partially degraded cartilage. Eventually, all the cartilage is replaced by bone. Thus, the cartilage tissue serves as a model for the bone that follows.

The replacement of chondrocytes by bone cells is dependent on the mineralization of the extracellular matrix. A number of events lead to the hypertrophy and mineralization of the chondrocytes, including an initial switch from aerobic to anaerobic respiration, which alters their cell metabolism and mitochondrial energy potential. Hypertrophic chondrocytes secrete numerous small membrane-bound vesicles into the extracellular matrix. These vesicles contain enzymes that are active in the generation of calcium and phosphate ions and initiate the mineralization process within the cartilaginous matrix. The hypertrophic chondrocytes, their metabolism and mitochondrial membranes altered, then die by apoptosis.

In the long bones of many mammals (including humans), endochondral ossification spreads outward in both directions from the center of the bone. As the ossification front nears the ends of the cartilage model, the chondrocytes near the ossification front proliferate prior to undergoing hypertrophy, pushing out the cartilaginous ends of the bone. The cartilaginous areas at the ends of the long bones are called epiphyseal growth plates. These plates contain three regions: a region of chondrocyte proliferation, a region of mature chondrocytes, and a region of hypertrophic chondrocytes. As the inner cartilage hypertrophies and the ossification front extends farther outward, the remaining cartilage in the epiphyseal growth plate proliferates. As long as the epiphyseal growth plates are able to produce chondrocytes, the bone continues to grow.

Bone Remodeling

Bone constantly is broken down by osteoclasts and re-formed by osteoblasts in the adult. It has been reported that as much as 18% of bone is recycled each year through the process of renewal, known as bone remodeling, which maintains bone's rigidity. The balance in this dynamic process shifts as people grow older: in youth, it favors the formation of bone, but in old age, it favors resorption.

As new bone material is added peripherally from the internal surface of the periosteum, there is a hollowing out of the internal region to form the bone marrow cavity. This destruction of bone tissue is due to osteoclasts that enter the bone through the blood vessels. Osteoclasts dissolve both the inorganic and the protein portions of the bone matrix. Each osteoclast extends numerous cellular processes into the matrix and pumps out hydrogen ions onto the surrounding material, thereby acidifying and solubilizing it. The blood vessels also import the blood-forming cells that will reside in the marrow for the duration of the organism's life.

The number and activity of osteoclasts must be tightly regulated. If there are too many active osteoclasts, too much bone will be dissolved, and osteoporosis will result. Conversely, if not enough osteoclasts are produced, the bones are not hollowed out for the marrow, and osteopetrosis (known as stone bone disease, a disorder whereby the bones harden and become denser) will result.

Bone Regeneration and Fracture Repair

A fracture, like any traumatic injury, causes hemorrhage and tissue destruction. The first reparative changes thus are characteristic of those occurring in any injury of soft tissue. Proliferating fibroblasts and capillary sprouts grow into the blood clot and injured area, thus forming granulation tissue. The area also is invaded by poly morphonuclear leukocytes and later by macrophages that phagocytize the tissue debris. The granulation tissue gradually becomes denser, and in parts of it, cartilage is formed. This newly formed connective tissue and cartilage is designated as a callus. It serves temporarily in stabilizing and binding together the fracture bone. As this process is taking place, the dormant osteogenic cells of the periosteum enlarge and become active osteoblasts. On the outside of the fractured bone, at first at some distance from the fracture, osseous tissue is deposited. This formation of new bone continues toward the fractured ends of the bone and finally forms a sheath-like layer of bone over the fibrocartilaginous callus. As the amount of bone increases, osteogenic buds invade the fibrous and cartilaginous callus and replace it with a bony one. The cartilage undergoes calcification and absorption in the replacement of the fibrocartilaginous callus and intramembraneous bone formation also takes place. The newly formed bone is at first a spongy and not a compact type, and the callus becomes reduced in diameter. At the time when this subperiosteal bone formation is taking place, bone also forms in the marrow cavity. The medullary bone growing centripetally from each side of the fracture unites, thus aiding the bony union.

The process of repair is, in general, an orderly process, but it varies greatly with the displacement of the fractured ends of the bone and the degree of trauma inflicted. Uneven or protruding surfaces gradually are removed, and the healed bone, especially, in young individuals, assumes its original contour.

Osteogenesis and Angiogenesis

Skeletal development and fracture repair includes the coordination of multiple events such as migration, differentiation, and activation of multiple cell types and tissues. The development of a microvasculature and microcirculation is important for the homeostasis and regeneration of living bone, without which the tissue would degenerate and die. Recent developments using in vitro and in vivo models of osteogenesis and fracture repair have provided a better understanding of the recruitment nature of the vasculature in skeletal development and repair.

The vasculature transports oxygen, nutrients, soluble factors and numerous cell types to all tissues in the body. The growth and development of a mature vascular structure is one of the earliest events in organogenesis. In mammalian embryonic development, the nascent vascular networks develop by aggregation of de novo forming angioblasts into a primitive vascular plexus (vasculogenesis). This undergoes a complex remodeling process in which sprouting, bridging and growth from existing vessels (angiogenesis) leads to the onset of a functional circulatory system.

The factors and events that lead to the normal development of the embryonic vasculature are recapitulated during situations of neoangiogenesis in the adult. There are a number of factors involved in neoangiogenesis; these include, but are not limited to, Vascular Endothelial Growth Factor (VEGF), basic Fibroblast Growth Factor (bFGF), various members of the Transforming Growth factor beta (TGFβ) family and Hypoxia-Inducible Transcription Factor (HIF). Other factors that have angiogenic properties include the Angiopoietins, (Ang-1); Hepatocyte Growth Factor (HGF); Platelet-Derived Growth Factor (PDGF); Insulin-like Growth Factor family (IGF-1, IGF-2) and the Neurotrophins (NGF).

The VEGFs and their corresponding receptors are key regulators in a cascade of molecular and cellular events that ultimately lead to the development of the vascular system, either by vasculogenesis, angiogenesis or in the formation of the lymphatic vascular system. Although VEGF is a critical regulator in physiological angiogenesis, it also plays a significant role in skeletal growth and repair.

In the mature established vasculature, the endothelium plays an important role in the maintenance of homeostasis of the surrounding tissue by providing the communicative network to neighboring tissues to respond to requirements as needed. Furthermore, the vasculature provides growth factors, hormones, cytokines, chemokines and metabolites, and the like, needed by the surrounding tissue and acts as a barrier to limit the movement of molecules and cells. Signals and attractant factors expressed on the bone endothelium help recruit circulating cells, particularly hematopoietic cells, to the bone marrow and coordinate with metastatic cells to target them to skeletal regions. Thus, any alteration in the vascular supply to bone tissue can lead to skeletal pathologies, such as osteonecrosis (bone death caused by reduced blood flow to bones), osteomyelitis (infection of the bone or bone marrow by microorganism), and osteoporosis (loss of bone density). A number of factors have been found to have a prominent effect on the pathology of the vasculature and skeleton, including Osteoprotegerin (OPG), which inhibits Receptor Activator of NF-κB Ligand (RANKL)-induced osteoclastogenic bone resorption.

Both intramembraneous and endochondral bone ossification occur in close proximity to vascular ingrowth. In endochondral ossification, the coupling of chondrogenesis and osteogenesis to determine the rate of bone ossification is dependent on the level of vascularization of the growth plate. For example, vascular endothelial growth (VEGF) factor isoforms are essential in coordinating metaphyseal and epiphyseal vascularization, cartilage formation, and ossification during endochondral bone development. HIF-1 stimulates transcription of the VEGF gene (and of other genes whose products are needed when oxygen is in short supply). The VEGF protein is secreted, diffuses through the tissue, and acts on nearby endothelial cells.

The response of the endothelial cells includes at least four components. First, the cells produce proteases to digest their way through the basal lamina of the parent capillary or venule. Second, the endothelial cells migrate toward the source of the signal. Third, the cells proliferate. Fourth, the cells form tubes and differentiate. VEGF acts on endothelial cells selectively to stimulate this entire set of effects. Other growth factors, including some members of the fibroblast growth factor family, also can stimulate angiogenesis, but they influence other cell types besides endothelial cells. As the new vessels form, bringing blood to the tissue, the oxygen concentration rises, HIF-1 activity declines, VEGF production is shut off, and angiogenesis ceases.

The vascularization of cartilage regions in long bones occurs at different stages of development. In early embryonic development, blood vessels that originate from the perichondrium invaginate into the cartilage structures. During elevated postnatal growth, capillaries invade the growth plate of long bones. In adulthood, angiogenesis periodically can be switched on during bone remodeling in response to bone trauma or pathophysiological conditions such as rheumatoid arthritis (RA) and osteoarthritis (OA).

Bone has the unique capacity to regenerate without the development of a fibrous scar, which is symptomatic of soft tissue healing of wounds. This is achieved through the complex interdependent stages of the healing process, which mimic the tightly regulated development of the skeleton. Following trauma with damage to the musculoskeletal system, disruption of the vasculature leads to acute necrosis and hypoxia of the surrounding tissue. This disruption of the circulation leads to the activation of thrombotic factors in a coagulation cascade leading to the formation of a hematoma. The inflammatory response and tissue breakdown activate factors such as cytokines and growth factors that recruit osteoprogenitor and mesenchymal cells to the fracture site. The stimulation of the endosteal circulation in the fractured bone allows mesenchymal cells associated with growing capillaries to invade the wound region from the endosteum and bone marrow. At the edge of a bone fracture, the transiently formed granulation tissue is replaced by fibrocartilage. Concomitantly, the periosteum directly undergoes intramembranous bone formation leading to the formation of an external callus; while internally, the tissue is being mineralized to form woven bone. After stabilization of the bone tissue and vasculature in the bone fracture, the cell mediated remodeling cascade is activated where osteoclastic removal of necrotic bone is followed by the replacement of the large fracture callus by lamellar bone, the callus size is reduced and the normal vascular supply is restored.

A plurality of mediators associated with fetal and postnatal bone development plays a prominent role in the cascade response in bone fracture repair. These include but are not limited to BMP-2 and 4, VEGF, bFGF, TGF-β, and PDGF. VEGF expression is detected on chondroblasts, chondrocytes, osteoprogenitor cells and osteoblasts in the fracture callus where it is highly expressed in angioblasts, osteoprogenitor and osteoblast cells during the first seven days of healing but decreases after eleven days. Additionally, osteoclasts release heparinase that induces the release of the active form of VEGF from heparin, activating not only angiogenesis but also osteoclast recruitment, differentiation and activity leading to the remodeling of the fracture callus during endochondral ossification. Fractures in some cases fail to repair or unite resulting in fibrous filled pseudarthrosis. A number of contributing factors can lead to non-union or delayed union of bone fractures, such as, but not limited to, anti-inflammatory drugs, steroids, Vitamin C, Vitamin D and calcium deficiencies, tobacco smoking, diabetes, and other physiological disorders.

The absence of a functional vascular network is also an important factor in the lack of bone healing in non-union fractures. Studies have reported that angiogenic factors released from biomimetic scaffolds can enhance bone regeneration and that combination strategies that release both angiogenic and osteogenic factors can enhance the regenerative capacity of bone.

The critical sequential timing of osteoclast differentiation and activation, angiogenesis, recruitment of osteoprogenitor cells and the release of growth factors such as BMP-2 in osteogenesis and fracture repair may be enhanced by the synchronized endogenous production of angiogenic and osteogenic mediators. Studies in rat femoral drill-hole injury have shown differential expression of VEGF splicing isoforms along with its receptors, indicating an important role in the bone healing process. Other studies have demonstrated that angiogenesis occurs predominantly before the onset of osteogenesis in bone lengthening in an osteodistraction model.

Another angiogenic inducing growth factor, FGF-2, can accelerate fracture repair when added exogenously to the early healing stage of a bone. Although the mechanism has not been fully elucidated, it has the ability to stimulate angiogenesis and the proliferation and differentiation of osteoblasts to possibly aid the repair of bone fractures.

2.3. Cartilaginous Tissue Compartments

Cartilaginous tissue compartments are specialized connective tissue compartments comprising cartilage cells, known as chondrocytes, cartilage fibers and ground substance constituting the cartilage matrix, that collectively contribute to characteristic elastic firmness rendering cartilage capable of withstanding high levels of pressure or sheer. Cartilage is histologically classified into three types depending on its molecular composition: hyaline cartilage; fibrocartilage and elastic cartlage.

Hyaline cartilage is the predominant form of cartilage comprising an amorphous matrix surrounding chondrocytes embedded within spaces, known as lacunae. Hyaline cartilage, which is commonly associated with the skeletal system and found in the nose, trachea, bronchi and larynx, predominantly functions to provide support. Hyaline cartilage associated with the articular portions of bone, forming the major component of synovial joints, is termed articular cartilage. Hyaline cartilage is usually avascular except where vessels may pass through to supply other tissues and in ossification centers involved in intracartilaginous bone development.

Fibrocartilage, which is commonly found in intervertebral discs and pubic symphysis and functions to provide tensile strength and in shock absorption, is less firm than hyaline cartilage. It comprises a combination of dense collagenous fibers with cartilage cells and a scant cartilage matrix. Fibrocartilage is not usually circumscribed by a perichondrium. Proportions of cells, fibers and ECM components in fribrocartilage are variable.

Elastic cartilage, which is found in the external ear, the Eustachian tube, epiglottis and some of the lanryngeal cartilages, is characterized by a large number of elastic fibers that branch and course in all directions to form a dense network of anastomising and interlacing fibers.

Articular Cartilage Matrix

The chondrocytes in articular cartilage are surrounded by a narrow region of connective tissue ECM, termed the pericellular matrix (PCM), which together with the chondrocyte, is termed chondron. The PCM, which is very rich in fibronectin, proteoglycans (e.g., aggrecan, hyaluron and decorin) and collagen (types II, VI and IX), is particularly characterized by a high concentration of type VI collagen as compared to the surrounding ECM. In normal articular cartilage, type VI collagen is restricted to the chondrons, but in osteoarthritic cartilage, it is upregulated and found throughout the ECM. A proteomic analysis of articular cartilage revealed the presence of collagen α1(II) C-propeptide, collagen α1(XI) C-propeptide, collagen α2(XI) C-propeptide, collagen α1(VI), collagen α2(VI), link protein, biglycan, decorin, osteonectin, matrillin-1, annexin-V, lactadherin, and binding immunoglobulin protein (BiP), in addition to metabolic proteins. (Wilson et. al., 2008, Methods, 48: 22-31).

Chondrocyte Differentiation

The specific structure of articular cartilage, with endogenous chondrocytes forming adult joints, is the result of endochondral ossification, as described above under the Heading, Osseous Tissue Compartments Formation.

Chondrocyte differentiation and maintenance in articular cartilage is governed by interaction of multiple factors. Key players include, but are not limited to, ions (e.g., calcium); steroids (e.g., estrogens); terpenoids (e.g., retinoic acid); peptides (e.g., Parathyroid hormone (PTH), parathyroid hormone-related peptide (PTHrP)), insulin growth factors (e.g., TGFβ hormones, including, without limitation, BMPs, IGF-1, VEGF, PDGF, FGF); transcription factors (e.g., Wnt, SOX-9); eicosanoids (e.g., prostaglandins); catabolic interleukins (e.g., IL-1); and anabolic interleukins (e.g., IL-6, IL-4 and IL-10). (Gaissmaier et al., 2008, Int. J. Care Injured, 3951: S88-S96).

Growth Plate

The epiphyseal plates or growth plates are a hyaline cartilage plate located in the metaphysis at the end of long bones. Whereas endochondral ossification is responsible for the formation of cartilage in utero and in infants, the growth plates are responsible for the longitudinal growth of long bones via a cartilage template. The ongoing developmental processes of proliferation and differentiation within the growth plates are mediated by a number of hormonal and paracrine factors secreted by the growth plate chondrocytes. The growth plate is a highly organized structure comprising a large number of chondrocytes in various stages of differentiation and proliferation embedded in a scaffold of ECM components.

The growth plate can be subdivided into four zones depending on the stage of differentiation and spatial distribution of collagen types. The resting zone is the smallest zone close to the epiphyseal cartilage comprising small monomorphic chondrocytes with a narrow rim of cytoplasm. The chondrocytes of the resting zone secrete growth plate orienting factor (GPOF) that aligns proliferating cells parallel to the long axis of the developing bone. Stem cell-like cells of the resting zone have a limited proliferative capacity, which eventually leads to fusion of the growth plate (epiphyseal fusion). The proliferative zone of the growth plate comprises chondrocytes that are arranged in characteristic columns parallel to the longitudinal axis of the bone and are separated by ECM with high type II collagen. The chondrocytes of the proliferative zone are mitotically active, have high oxygen and glycogen content, and exhibit increased mitochondrial ATP production. The hypertrophic zone refers to the zone farthest from the resting zone where prehypertrophic chondrocytes stop dividing and terminally differentiate into elongated hypertrophic chondrocytes embedded in ECM high in type X collagen. Hypertrophic chondrocytes have a high intracellular calcium concentration required for the production of release vesicles containing $Ca^{2+}$-binding annexins, that secrete calcium phosphate, hydroxyapatite, phosphatases (such as alkaline phosphatase), metalloproteinases, all instrumental in proteolytic remodeling and mineralization of the surrounding matrix. The hypertrophic chondrocytes produce factors, such as VEGF, that initiate vascularization of the mineralized matrix that is then degraded by invading phagocytic chondroclasts and osteoclasts constituting the invading zone.

The developmental processes involving chondrogenesis are regulated by an interplay of a large number of systemic hormones and paracrine factors, including growth factors, cytokines and transcription factors. Table 5 lists key factors involved in chondrocyte proliferation and differentiation in the growth plate. (Brochhausen et al., J. Tissue Eng. Regen. Med. 2009, 3: 416-429).

TABLE 5

Summary of Key Factors involved in Chondrocyte Proliferation and Differentiation in the Growth Plate

| Name | Class | Expression | Effect |
| --- | --- | --- | --- |
| ATF-2 | Transcription factor | Resting chondrocytes; proliferative chondrocytes | Apoptosis |
| Bcl-2 | Inner mitochondrial membrane protein | Proliferative chondrocytes; prehypertrophic chondrocytes | Apoptosis |
| Ihh | Signaling molecule | Prehypertrophic chondrocytes | Proliferation |
| PTHrP | Peptide hormone | Perichondrium perarticular chondrocytes | Proliferation |
| BMP | TGF-β superfamily growth factors | Prehypertrophic chondrocytes | Cartilage formation; proliferation |
| PGE$_2$ | Lipid mediator | All zones of growth plate | Proliferation matrix synthesis |
| MMP | Metalloproteinase | Hypertrophic chondrocytes; chondroclasts | Apoptosis; vascularization matrix degradation |
| Sox | Transcription factor | Resting and proliferative chondrocytes; hypertrophic chondrocytes | Differentiation; proliferation; |
| Runx 2 (Cbfa 1) | Transcription factor | Hypertrophic chondrocytes | Terminal differentiation; matrix mineralization |
| NOTCH | Single pass transmembrane protein | Prehypertrophic and hypertrophic chondrocytes | Inhibits terminal differentiation |
| HOX | Homeobox transcription factors | Hypertrophic chondrocytes | Activates osteogenic genes |
| FGF | Fibroblast growth factor | Proliferative chondrocytes | Antiproliferation |

Stem Cells of Cartilaginous Tissue Compartments

Multipotent mesenchymal progenitor cells with adipogenic, osteogenic and chondrogenic potential, and that are CD105+/CD166+(corresponding to TGF-β type III receptor (endoglin) and ALCAM, respectively), have been identified in articular cartilage. (Asalameh et al., Arthritis & Rheumatism, 2004, 50(5): 1522-1532). The presence of CD34−/CD45−/CD44+/CD73+/CD90+ mesenchymal stem cells with adipogenic, chondrogenic and osteogenic potential also has been shown. (Peng et al., Stem Cells and Development (2008), 17: 761-774). Similar to bone-derived MSCs, articular-derived MSCs are positive for surface expression of Notch-1. (Hiraoka et al., Biorheology, 2006, 43: 447-454). A potential MSC niche positive for Stro-1, Jagged-1 and BMPr1a has also been identified in the perichondrial zone of Ranvier on the growth plate. (Karlsson et al., 2009, J. Anat. 215(3): 355-63).

Differential expression of Notch-1, Stro-1 and VCAM-1/CD106 markers has been observed in normal articular cartilage versus osteoarthritic (OA) cartilage. In normal cartilage, expression of these markers is higher in the superficial zone (SZ) as compared to the middle zone (MZ) and deep zone (DZ). On the other hand, OA cartilage SZ has reduced Notch-1 and Sox-9 while MZ has increased Notch-1, Stro-1 and VCAM-1 positive cells. (Grogan et al., Arthritis Res. Ther. 2009, 11(3): R85-R97).

Intervertebral Disc Fibrocartilage Tissue Compartments

The intervertebral discs (IVD) predominantly are comprised of fibrocartilage. The IVD fibrocartilage is continuous both with and below the articular cartilage of adjacent vertebrae as well as peripherally with spinal ligaments. The IVD is a unique structure containing annulus fibrosus (AF) and nucleus pulposus (NP), a gelatinous ellipsoidal remnant of the embryonic notochord, and is sandwiched between two adjacent cartilaginous endplates (EP). IVD rupture and herniation of the nucleus pulposus into the spinal cord may cause severe pain and other neurological symptoms. The NP and AF synergistically function to achieve the primary role of IVD in transferring load, dissipating energy and facilitating in joint mobility.

The adult IVD is essentially avascular; hence, endogenous cells survive in a low-nutrient and low-oxygen microenvironment. The major ECM components of IVD include but are not limited to aggrecan, collagen (e.g., types I, II and IX), leucine rich repeat (LRR) proteins and proteoglycans (e.g., fibromodulin, decorin, lumican), cartilage oligomatrix protein, and collagen VI beaded filament network. (Feng et al., 2006, J. Bone Joint Surg. Am. 88: 25-29). The water content, GAG content, aggrecan levels and levels of type II collagen are significantly lower in older discs demonstrating the effects of IVD degeneration with age. (Murakami et al., 2010, Med. Biol. Eng. Comput. 48: 469-474).

The central nucleus pulposus (NP) is rich in aggrecan and hyaluron. The developing NP is characterized by the presence of highly vacuolated chondrocytes and small chondroblasts inherited from the notochord. Primarily functioning as a primitive axial support, the integrity of the notochord is maintained by a proteoglycan (PG-) and laminin-rich sheath. As NP matures, the cellular composition becomes predominantly chondrocytic. Mature NP cells are small and have an aggrecan rich matrix, which is essential in maintaining requisite hydration levels for mechanical function. Their gene expression profile and metabolic activity are distinct from the chondrocytes of articular cartilage. The ECM of immature NP has high aggrecan levels and primarily contains type II collagen, with the type IIA isoform expressed by progenitor cells during chondrogenesis, not by mature chondrocytes. (Hsieh A. H. and Tworney J. D., J. Biomech., 2010, 43(1): 137-156).

The AF surrounds the NP with layers of unidirectional sheets of collagen parallel to the circumference of a disc to form collagen lamellae. Alternating bidirectional collagen fibers intersperse the AF collagen lamellae. AF can be subdivided into three regions: inner AF, middle AF and outer AF. The inner AF arises along with endochondral formation of the vertebrae. The outer AF arises as a separate cell condensation with slower matrix formation. Lamellae of inner AF comprises predominantly of type II collagen and fibrochondrocytes, while those of outer AF are comprised of type I collagen and fibroblasts. A population of pancake shaped interlamellar cells as well as elastin fibers are also found within the lamellae, in vertebral attachments, and at the NP-AF interface. Large proteoglycans (PGs; for example aggrecan and versican) and type I and VI collagen permeate interlamellar and translamellar ECM. (Hsieh A. H. and Tworney J. D., J. Biomech., 2010, 43(1): 137-156).

A large number of coordinated signals originating from the cells of the notochord and floor plate of the embryonal neural tube are instrumental in disc embryogenesis. Key signals include, but are not limited to, sonic hedgehog (Shh), Wnt, noggin, Pax family of transcription factors (e.g., Pax 1 and Pax 9), Sox family of transcription factors (Sox5, Sox6 and Sox) and TGF-β. (Smith et al., 2011, Dis Model Mech. 4(1): 31-41). Herniation and IVD degeneration are associated with changes in inflammatory and immune cytokine profiles, including, but not limited to, the activation of Th1-related cytokines (e.g. IFNγ) as well as Th17-related cytokines (e.g., IL-4, IL-6, IL-12 and IL-17). (Shamji et al., 2010, Arthritis & Rheumatism, 62(7): 1974-1982).

A potential stem cell niche comprised of progenitor cells that are positive for Notch1, Delta4, Jagged1, CD117, Stro-1 and Ki67 has been identified in intervertebral discs of a number of animals, including humans. It has been reported that the IVD tissue compartments comprise a slow growing zone in the AF as well as the NP regions. (Henriksson et al., 2009, SPINE, 34(21): 2278-2287).

2.4. Dental Tissue Compartments

A tooth has three anatomical divisions (crown, root and neck), and four structural components (enamel, dentin, cementum and pulp).

Enamel is the hardest, most mineralized biological tissue in the human body. It is composed of elongated hydroxyapatite crystallites bundled into rods or prisms, interspersed with crystalline interrods filling the interstitial space. Enamel cells, known as ameloblasts, are responsible for enamel development. Ameloblastin, TRAP and enamelin are key proteins found in enamel tissue whereas the enamel matrix is devoid of collagen, composed primarily of amelogenin. An intricate orchestration of signaling factors, such as BMPs (e.g., BMP-2, BMP-4, BMP-7), FGFs (e.g., FGF-3, -4, -9, -20), Wnt-3, 10a, 10b and transcription factors, such as, p21, Msx2 and Lef1 is responsible for morphogenesis of enamel. Self-assembly of amelogens to form amelogenin nanospheres play a role in nucleation of hydroxyapatite crystallization and enamel mineralization. Matrix processing enzymes, such as MMP-20, kallikrein-4 (KLK4), also known as enamel matrix serine protease-1 (EMSP-1), are involved in the complete elimination of the protein matrix and replacement with a mineralized matrix. (Fong et al., 2005, J. Dent. Educ., 69(5): 555-570). Ameloblasts arise from epithelial stem cells of ectodermal origin. They are lost after tooth eruption leaving no adult human ectodermal stem cells in the mature enamel. In contrast, rodent enamel retain a niche of epithelial stem cells, known as apical bud cells, for continuous enamel production. (Ulmer et al., 2010, Schweiz Monatsschr Zahnmed, 120:860-872).

Dentin is a hard, yellowish and elastic living connective tissue compartment with biomechanical properties similar to bone. The formation of dentin is driven by mesenchymally derived mature odontoblasts that are fully differentiated and nondividing and that form a single layer underneath the dentin in a mature tooth. A series of epithelial-mesenchymal interactions regulates odontoblast differentiation from neural crest cells in the first branchial arch and frontonasal processes. Mature dentin is comprised of a mantle, composed of intertubular and peritubular dentin made of a collagen fibril matrix, with odontoblast cell processes extending into dentin tubules. During dentinogenesis, odontoblasts secrete predentin, a mineralized tissue composed of type I collagen. Unlike osteogenesis, in dentinogenesis, as the predentin layer is formed, the odontoblasts recede instead of becoming embedded within the dentin matrix, leaving behind cells processes within dentinal tubules. Subsequently, the unmineralized predentin is converted to dentin by gradual mineralization of collagen. Dentinogenesis is directed by a series of highly controlled biochemical events that control the rates of collagen secretion, its maturation into thick fibrils, loss of proteoglycans, mineral formation including hydroxy apatite crystallization, and growth. The dentin matrix is primarily composed of collagens (e.g., types I, III and V) as well as other matrix proteins, including, but not limited to, phosphorylated and nonphosphorylated matrix proteins, proteoglycans, growth factors, metalloproteinases, alkaline phosphatase serum derived proteins, and phospholipids. (Fong et al., 2005, J. Dent. Educ., 69(5): 555-570). No stem cells have been identified in mature dentin.

The dental pulp is the tooth's living tissue that respond to pain and damage and initiates tissue repair. An odontoblast cell layer forms the outer boundary of the pulp and is associated with an underlying network of dendritic cells. A cell-free zone underlying the odontoblast layer is rich in nerve fibers and blood vessels. Similar to dentin, dental pulp also differentiates from neural crest-derived ectomesenchyme during tooth development.

Several sources of stem cells have been identified associated with pulp tissue. In immature teeth, apical papilla, the embryonal organ responsible for pulp differentiation, is the source for stem cells of apical papilla (SCAP). Mature dental pulp is the source of dental pulp stem cells (DPSC) whereas stem cells are also extracted from exfoliated deciduous teeth (SHED). Additional cells of the dental pulp core that functionin pulpal defense, include, but are not limited to, macrophages, lymphocytes and mast cells. Pulp matrix is composed of collagens (e.g., types I, III V and VI), but lacks mineralization. Other noncollagenous proteins of the pulp matrix are similar in composition to dentin. The dental pulp is capable of responding to dentin tissue damage by secreting new dentin from old odontoblast populations or generation and secretion of dentin from new secondary odontoblast populations. (Fong et al., 2005, J. Dent. Educ., 69(5): 555-570).

The periodontium consists of tissues supporting the tooth crown, including a nonmineralized periodontal ligament (PDL) sandwiched between layers of mineralized tissues, including the cementum, alveolar bone and dentin. Cementum is a thin mineralized layer covering the dentin. Cementoblasts are cells responsible for cementum matrix secretion and subsequent mineralization. When cementoblasts become entrapped within cementum matrix, they are termed cementocytes. Cementoblasts are ectomesenchymal, being derived from neural crest cells, similar to PDL and alveolar bone. Like bone and dentin, cementum is a collagenous mineralized tissue that hardens upon formation of carbonated hydroxyapatite. (Fong et al., 2005, J. Dent. Educ., 69(5): 555-570).

PDL is a space between cementum and alveolar bone. It represents a replacement of the dental follicle region in immature developing teeth. Mature PDL contains mostly periodontal fibroblasts as well as stem cells, known as the periodontal ligament stem cells (PDLSCs). The immature dental follicle is also a source of mesenchymal stem cells, known as dental follicle stem cells (DFSCs). (Fong et al., 2005, J. Dent. Educ., 69(5): 555-570).

Table 6 shows the differentiation potential of dental mesenchymal cells. (Ulmer et al., 2010, Schweiz Monatsschr Zahnmed, 120:860-872).

TABLE 6

Differentiation Potential Dental Mesenchymal Stem Cells

| | DPSC | SHED | PDLSC | DFSC | SCAP |
|---|---|---|---|---|---|
| Adipocytes | X | X | X | X | |
| Cementoblasts | | | X | X | |
| Chondrocytes | X | | X | | |
| Dental pulp | X | | | | |
| Dentin | X | | | | |
| Endothelocytes | X | X | | | |
| Musculature | X | | | | |
| Neuroblasts | | | | X | |
| Neurons | X | X | | | |
| Odontoblasts | X | X | X | | X |
| Osteoblasts | X | X | X | X | X |
| PDL Progenitors | | | | X | |
| Periodontium | | | X | | |

Several dental stem cell markers have been identified. Stro-1 and Stro-4 are commonly used dental stem cell markers for all dental mesenchymal stem cells. Dental stem cells originating from the neural crest have the neural marker, nestin. An osteoblast marker, osteocalcin, is also used as a stem cell marker for DPSCs. Similarly, SCAPs express Oct-4, Nanog, SSEA-3, SSEA-4, TRA-1-60 and TRA-1-81. (Ulmer et al., 2010, Schweiz Monatsschr Zahnmed, 120:860-872).

2.5. Fascial Tissue Compartment

Fascial tissue compartments form a layer of fibrous tissue found throughout the body surrounding softer and more delicate organs, including but not limited to muscles, groups of muscles, blood vessels, nerves, etc. Fascial tissue originates from the embryonic mesenchyme. Fasciae form during the development of bones, muscles and vessels from the mesodermal layer of the embryo. Fascial tissue can be categorized into three types depending on location: (1) superficial fascial tissue, which is found beneath the integument throughout the body, usually blending with the reticular layer of the dermis; (2) deep fascial tissue comprising dense fibroareolar connective tissue surrounding muscles, bones, nerves and blood vessels; and (3) visceral or subserous fascia, which suspends organs within their cavities and wraps them in layers of connective tissue membranes. (Chaper IV. Myology, Section 3. Tendons, Aponeuroses, and Fasciae, Gray's Anatomy of the Human Body, 20$^{th}$ Edition, Re-edited by Lewis, W. H., Lea & Febiger, Philadelphia, 1918, Bartleby.com, New York, 2000).

The fibroareolar connective tissue of fascia comprises four kinds of cells: (1) flattened lamellar cells, which may be branched or unbranched (branched lamellar cells contain clear cytoplasm and oval nuclei and project multidirectional processes that may unite to form an open network, such as in the cornea; unbranched lamellar cells are joined end to end. (2) Clasmatocytes, which are large irregular vacuolated or granulated cells with oval nuclei. (3) Granule cells, which are ovoid or spherical in shape. (4) Plasma cells of Waldeyer, usually spheroidal, characterized by vacuolated protoplasm.

2.5. Ligament Tissue Compartment

The term "ligaments" as used herein refers to dense regular connective tissue comprising attenuated collagenous fibers that connect bones at joints. Ligament ECM is composed of type I and type III collagens together with other proteoglycans and glycoproteins. Mesenchymal stem cells have been found in the human anterior cruciate ligament that exhibit multilineage differentiation potential, like bone-derived mesenchymal stem cells. (Cheng et al., 2010, Tissue Engg. A, 16(7):2237-2253).

2.6. Synovial Tissue Compartment

The synovial membrane is composed of fibrous connective tissue and lines the joint cavity of synovial joints. It is made up of a layer of macrophage (type A) and fibroblast-like (type B) synoviocytes and a loose sublining tissue. Synovial fluid is secreted by synovial cells lining the synovial membrane in the joint capsule. It is a viscid, mucoalbuminous fluid, rich in hyaluronic acid. It acts as a lubricating fluid, facilitating the smooth gliding of the articular surface. Functional mesenchymal stem cell niches have been identified as resident to synovial lining and subsynovial tissue. These cells are positive for the artificial nucleoside, iododeoxyuridine (IdU) as well as MSC markers such as PDGFRα, p75 and CD44 and have chondrogenic potential. (Kurth et al., Arthritis Rheum., 2011, 63(5): 1289-1300). Synovial fluid-derived MSCs have also been identified, and these have higher chondrogenic potential as compared to bone marrow-derived and adipogenic MSCs. (Koga et al., 2008, Cell Tissue Res., 333: 207-215). Synovial MSCs and MPCs have been shown to prevent degeneration due to intervertebral disc disease (IVD) and to be useful for cartilage tissue engineering. (Miyamoto et al., 2010, Arthritis Res. Ther., 12: R206-218; Lee et al., 2010, Tissue Engg. A, 16(1): 317-325).

2.7. Tendon Tissue Compartment

Tendons are specialized connective tissue compartments that connect bone to muscle. Tendon cells are embedded amongst a parallel group of collagenous fibers that secrete a unique ECM containing collagens, large proteoglycans, and small leucine rich proteoglycans that function as lubricators and organizers of collagen fibril assembly. A unique tendon stem/progenitor cell (TSPC) niche has been identified amongst the parallel collagen fibrils surrounded by ECM. The TSPCs exhibit osteogenic and adipogenic potential. Biglycan and fibromodulin are key tendon ECM components that direct TSPC fate through BMP signaling. These TSPCs are positive for bone marrow derived stem cell markers such as Stro-1, CD146, CD90 and CD44 but not for CD18. TSPCs do not express hematopoietic markers, such as CD34, CD45 and CD117, or the endothelial marker CD106. (Bi et al., 2007, Nat. Med., 13(10): 1219-1227).

2.8. Vasculature Tissue Compartment

The vascular wall is made of three concentric zones with distinct cellular composition, all mesodermal in origin: the tunica intima, containing predominantly mature differentiated endothelial cells (EC), the tunica media, containing mature and differentiated smooth muscle cells, and the tunica adventitia, containing mature fibroblasts. (Tilki et al., 2009, Trends Mol. Med. 15(11): 501-509). Endothelial progenitor cells (EPCs), meaning cells that exhibit clonal expression, stemness characteristics, adherence to matrix molecules and an ability to differentiate into endothelial cells (ECs) have been implicated in the formation of new blood vessels through angiogenesis and postnatal vasculogenesis. EPCs have many characteristic cell surface markers, including, but not limited to, CD34, AC133, KDR (VEGFR-2), Tie-2 and ligand for UEA-1 lectin. (Tilki et al., 2009, Trends Mol. Med. 15(11): 501-509; Melero-Martin and Dudley, 2011, Stem Cells, 29: 163-168; Pascilli et al., 2008, Exp. Cell Res., 315: 901-914).

EPC niches have been identified in the bone-marrow, peripheral cord blood and vascular wall matrix. Bone-marrow derived and cord blood EPCs essentially may be proangiogenic hematopoietic progenitor cells (HPCs), circulating in the blood and committed to myeloid lineage. (Tilki et al., 2009, Trends Mol. Med. 15(11): 501-509). The vascular wall stem and progenitor cells (VW-EPCs) reside in distinct zones of the vessel wall within subendothelial space, known as avasculogenic zone, within the vascular adventitia, forming vascular wall-specific niches. Fetal and adult arterial and venous blood vessel walls have also been found to harbor resident niches for a variety of stem and progenitor cells, such as EPCs, smooth muscle progenitors, HSCs, MSCs, mesangial cells coexpressing myogenic and endothelial markers, neural stem cells (NSCs), etc. (Tilki et al., 2009, Trends Mol. Med. 15(11): 501-509). The VW-EPCs are CD34(+)VEGFR-2(+)Tie-2(+)CD31(−)CD144(−). Proliferating and differentiating VW-EPCs become CD144(+).

During embryogenesis, there is evidence of the existence of a hemangioblast (giving rise to endothelial and hematopoietic cells) and hemogenic endothelium, originating from precursors resident in the vascular wall. However, whether adult VW also contains ancestral progenitor hemangioblasts giving rise to both VW-EPCs as well as VW-HSCs is not known. Vascular wall also contains resident pericyte-like cells in the subendothelial spaces. These pericyte-like cells serve as a cellular reservoir for VW-MSCs, which can differentiate into colonies with adipogenic, osteogenic and chondrgenic markers. (Tilki et al., 2009, Trends Mol. Med. 15(11): 501-509).

3. Cells of the Epithelial Tissue Compartment 3.1. Placental Tissue Matrix

The placenta is considered one of the most important sources of stem cells, and has been studied extensively. It fulfills two main *desiderata* of cell therapy: a source of a high as possible number of cells and the use of non-invasive methods for their harvesting. Their high immunological tolerance supports their use as an adequate source in cell therapy (Mihu, C. et al., 2008, Romanian Journal of Morphology and Embryology, 2008, 49(4):441-446).

The fetal adnexa is composed of the placenta, fetal membranes, and umbilical cord. The term placenta is discoid in shape with a diameter of 15-20 cm and a thickness of 2-3 cm. The fetal membranes, amnion and chorion, which enclose the fetus in the amniotic cavity, and the endometrial decidua extend from the margins of the chorionic disc. The chorionic plate is a multilayered structure that faces the amniotic cavity. It consists of two different structures: the amniotic membrane (composed of epithelium, compact layer, amniotic mesoderm, and spongy layer) and the chorion (composed of mesenchyme and a region of extravillous proliferating trophoblast cells interposed in varying amounts of Langhans fibrinoid, either covered or not by syncytiotrophoblast).

Villi originate from the chorionic plate and anchor the placenta through the trophoblast of the basal plate and maternal endometrium. From the maternal side, protrusions of the basal plate within the chorionic villi produce the placental septa, which divide the parenchyma into irregular cotyledons (Parolini, O. et al., 2008, Stem Cell, 2008, 26:300-311).

Some villi anchor the placenta to the basal plate, whereas others terminate freely in the intervillous space. Chorionic villi present with different functions and structure. In the term placenta, the stem villi show an inner core of fetal vessels with a distinct muscular wall and connective tissue consisting of fibroblasts, myofibroblasts, and dispersed tissue macrophages (Hofbauer cells). Mature intermediate villi and term villi are composed of capillary vessels and thin mesenchyme. A basement membrane separates the stromal core from an uninterrupted multinucleated layer, called the syncytiotrophoblast. Between the syncytiotrophoblast and its basement membrane are single or aggregated Langhans cytotrophoblastic cells, commonly called cytotrophoblast cells (Parolini, O. et al., 2008, Stem Cell, 2008, 26:300-311).

Four regions of fetal placenta can be distinguished: an amniotic epithelial region, an amniotic mesenchymal region, a chorionic mesenchymal region, and a chorionic trophoblastic region.

Amniotic Membrane

Fetal membranes continue from the edge of the placenta and enclose the amniotic fluid and the fetus. The amnion is a thin, avascular membrane composed of an inner epithelial layer and an outer layer of connective tissue that, and is contiguous, over the umbilical cord, with the fetal skin. The amniotic epithelium (AE) is an uninterrupted, single layer of flat, cuboidal and columnar epithelial cells in contact with amniotic fluid. It is attached to a distinct basal lamina that is, in turn, connected to the amniotic mesoderm (AM). In the amniotic mesoderm closest to the epithelium, an acellular compact layer is distinguishable, composed of collagens I and III and fibronectin. Deeper in the AM, a network of dispersed fibroblast-like mesenchymal cells and rare macrophages are observed. It has been reported that the mesenchymal layer of amnion indeed contains two subfractions, one having a mesenchymal phenotype, also known as amniotic mesenchymal stromal cells, and the second containing monocyte-like cells.

Chorionic Membrane

A spongy layer of loosely arranged collagen fibers separates the amniotic and chorionic mesoderm. The chorionic membrane (chorion leave) consists of mesodermal and trophoblastic regions. Chorionic and amniotic mesoderm are similar in composition. A large and incomplete basal lamina separates the chorionic mesoderm from the extravillous trophoblast cells. The latter, similar to trophoblast cells present in the basal plate, are dispersed within the fibrinoid layer and express immunohistochemical markers of proliferation. The Langhans fibrinoid layer usually increases during pregnancy and is composed of two different types of fibrinoid: a matrix type on the inner side (more compact) and a fibrin type on the outer side (more reticulate). At the edge of the placenta and in the basal plate, the trophoblast interdigitates extensively with the decidua (Cunningham, F. et al., The placenta and fetal membranes, Williams Obstetrics, 20th ed. Appleton and Lange, 1997, 95-125; Benirschke, K. and Kaufmann, P. Pathology of the human placenta. New York, Springer-Verlag, 2000, 42-46, 116, 281-297).

Amnion-Derived Stem Cells

The amniotic membrane itself contains multipotent cells that are able to differentiate in the various layers. Studies have reported their potential in neural and glial cells, cardiac repair and also hepatocyte cells. Studies have shown that human amniotic epithelial cells express stem cell markers and have the ability to differentiate toward all three germ layers. These properties, the ease of isolation of the cells, and the availability of placenta, make amnionic membrane a useful and noncontroversial source of cells for transplantation and regenerative medicine.

Amniotic epithelial cells can be isolated from the amniotic membrane by several methods that are known in the art. According to one such method, the aminiotic membrane is stripped from the underlying chorion and digested with trypsin or other digestive enzymes. The isolated cells readily attach to plastic or basement membrane-coated culture dishes. Culture is established commonly in a simple medium such as Dulbecco's Modified Eagle's Medium (DMEM) supplemented with 5%-10% serum and epidermal growth factor (EGF), in which the cells proliferate robustly and display typical cuboidal epithelial morphology. Normally, 2-6 passages are possible before proliferation ceases. Amniotic epithelial cells do not proliferate well at low densities.

Amniotic membrane contains epithelial cells with different surface markers, suggesting some heterogeneity of phenotype. Immediately after isolation, human amniotic epithelial cells express very low levels of human leukocyte antigen (HLA)-A, B, C; however, by passage 2, significant levels are observed. Additional cell surface antigens on human amniotic epithelial cells include, but are not limited to, ATP-binding cassette transporter G2 (ABCG2/BCRP), CD9, CD24, E-cadherin, integrins α6 and β1, c-met (hepatocyte growth factor receptor), stage-specific embryonic antigens (SSEAs) 3 and 4, and tumor rejection antigens 1-60 and 1-81. Surface markers thought to be absent on human amniotic epithelial cells include SSEA-1, CD34, and CD133, whereas other markers, such as CD117 (c-kit) and CCR4 (CC chemokine receptor), are either negative or may be expressed on some cells at very low levels. Although initial cell isolates express very low levels of CD90 (Thy-1), the expression of this antigen increases rapidly in culture (Miki, T. et al., Stem Cells, 2005, 23: 1549-1559; Miki, T. et al., Stem Cells, 2006, 2: 133-142).

In addition to surface markers, human amniotic epithelial cells express molecular markers of pluripotent stem cells, including octamer-binding protein 4 (OCT-4) SRY-related HMG-box gene 2 (SOX-2), and Nanog (Miki, T. et al., Stem Cells, 2005, 23: 1549-1559). Previous studies also have shown that human amnion cells in xenogeneic, chimeric aggregates, which contain mouse embryonic stem cells, can differentiate into all three germ layers and that cultured human amniotic epithelial cells express neural and glial markers, and can synthesize and release acetylcholine, cateholamines, and dopamine. Hepatic differentiation of human amniotic epithelial cells also has been reported. Studies have reported that cultured human amniotic epithelial cells produce albumin and α-fetroprotein and that albumin and α-fetroprotein-positive hepatocyte-like cells could be identified integrated into hepatic parenchyma following transplantation of human amniotic epithelial cells into the livers of severe combined inmmunodeficiency (SCID) mice. The hepatic potential of human amniotic epithelial cells was confirmed and extended, whereby in addition to albumin and α-fetroprotein production, other hepatic functions, such as glycogen storage and expression of liver-enriched transcription factors, such as hepatocyte nuclear factor (HNF) 3γ and HNF4α, CCAAT/enhancer-binding protein (CEBP α and β), and several of the drug metabolizing genes (cytochrome P450) were demonstrated. The wide range of hepatic genes and functions identified in human amniotic epithelial cells has suggested that these cells may be useful for liver-directed cell therapy (Parolini, O. et al., 2008, Stem Cell, 2008, 26:300-311).

Differentiation of human amniotic epithelial cells to another endodermal tissue, pancreas, also has been reported. For example, it was shown that human amniotic epithelial cells cultured for 2-4 weeks in the presence of nicotinamide to induce pancreatic differentiation, expressed insulin. Subsequent transplantation of the insulin-expressing human amniotic epithelial cells corrected the hyperglycemia of streptozotocin-induced diabetic mice. In the same setting, human amniotic mesenchymal stromal cells were ineffective, suggesting that human amniotic epithelial cells, but not human amniotic mesenchymal stromal cells, were capable of acquiring β-cell fate (Parolini, O. et al., 2008, Stem Cell, 2008, 26:300-311).

Mesenchymal Stromal Cells from Amnion and Chorion: hAMSC and hCMSC

Human amniotic mesenchymal cells (hAMSC) and human chorionic mesenchymal cells (hCMSC) are thought to be derived from extraembryonic mesoderm. hAMSC and hCMSC can be isolated from first-, second-, and third-trimester mesoderm of amnion and chorion, respectively. For hAMSC, isolations are usually performed with term amnion dissected from the deflected part of the fetal membranes to minimize the presence of maternal cells. For example, homogenous hAMSC populations can be obtained by a two-step procedure, whereby: minced amnion tissue is treated with trypsin to remove hAEC and the remaining mesenchymal cells are then released by digestion (e.g., with collagenase or collagenase and DNase). The yield from term amnion is about 1 million hAMSC and 10-fold more hAEC per gram of tissue (Casey, M. and MacDonald P., Biol Reprod, 1996, 55: 1253-1260).

hCMSCs are isolated from both first- and third-trimaster chorion after mechanical and enzymatic removal of the trophoblastic layer with dispase. Chorionic mesodermal tissue is then digested (e.g., with collagenase or collagenase plus DNase). Mesenchymal cells also have been isolated from chorionic fetal villi through explant culture, although maternal contamination is more likely (Zhang, X., et al., Biochem Biophys Res Commun, 2006, 340: 944-952; Soncini, M. et al., J Tissue Eng Regen Med, 2007, 1:296-305; Zhang et al., Biochem Biophys Res Commun, 2006, 351: 853-859).

The surface marker profile of cultured hAMSC and hCMSC, and mesenchymal stromal cells (MSC) from adult bone marrow are similar. All express typical mesenchymal markers (Table 7) but are negative for hematopoietic (CD34 and CD45) and monocytic markers (CD14). Surface expression of SSEA-3 and SSEA-4 and RNA for OCT-4 has been reported (Wei J. et al., Cell Transplant, 2003, 12: 545-552; Wolbank, S. et al., Tissue Eng, 2007, 13: 1173-1183; Alviano, F. et al., BMC Dev Biol, 2007, 7: 11; Zhao, P. et al, Transplantation, 2005, 79: 528-535). Both first- and third trimester hAMSC and hCMSC express low levels of HLA-A, B, C but not HLA-DR, indicating an immunoprivileged status (Portmann-Lanz, C. et al, Am J Obstet Gynecol, 2006, 194: 664-673; Wolbank, S. et al., Tissue Eng, 2007, 13: 1173-1183).

Table 7 provides surface antigen expression profile at passages 2-4 for amniotic mesencymal stromal and human chorionic mesenchymal stromal stem cells.

TABLE 7

Specific surface antigen expression for aminiotic mesenchymal stromal cells and human chorionic mesenchymal stromal cells

| Positive (≥95%) | Negative (≤2%) |
|---|---|
| CD90 | CD45 |
| CD73 | CD34 |
| CD105 | HLA-DR |

Both hAMSCs and hCMSCs differentiate toward "classic" mesodermal lineages (osteogenic, chondrogenic, and adipogenic) and differentiation of hAMSC to all three germ layers-ectoderm (neural), mesoderm (skeletal muscle, cardiomyocytic and endothelial), and endoderm (pancreatic) was reported (Int'Anker, P. et al., Stem Cells, 2004, 22: 1338-1345; Portmann-Lanz, C. et al, Am J Obstet Gynecol, 2006, 194: 664-673; Wolbank, S. et al., Tissue Eng, 2007, 13: 1173-1183; Soncini, M. et al., J Tissue Eng Regen Med, 2007, 1:296-305; Alviano, F., BMC Dev Biol, 2007, 7: 11).

Human amniotic and chorionic cells successfully and persistently engraft in multiple organs and tissues in vivo. Human chimerism detection in brain, lung, bone marrow, thymus, spleen, kidney, and liver after either intraperitoneal or intravenous transplantation of human amnion and chorion cells into neonatal swine and rats was indeed indicative of an active migration consistent with the expression of adhesion and migration molecules (L-selectin, VLA-5, CD29, and P-selectin ligand 1), as well as cellular matrix proteinase (MMP-2 and MMP-9) (Bailo, M. et al., Transplantation, 2004, 78:1439-1448).

Umbilical Cord

Two types of umbilical stem cells can be found, namely hematopoietic stem cells (UC-HS) and mesenchymal stem cells, which in turn can be found in umbilical cord blood (UC-MS) or in Wharton's jelly (UC-MM). The blood of the umbilical cord has long been in the focus of attention of researchers as an important source of stem cells for transplantation, for several reasons: (1) it contains a higher number of primitive hematopoietic stem cells (HSC) per volume unit, which proliferate more rapidly, than bone marrow; (2) there is a lower risk of rejection after transplantation; (3) transplantation does not require a perfect HLA antigen match (unlike in the case of bone marrow); (4) UC blood has already been successfully used in the treatment of inborn metabolic errors; and (5) there is no need for a new technology for collection and storage of the mononuclear cells from UC blood, since such methods are long established.

Umbilical cord (UC) vessels and the surrounding mesenchyma (including the connective tissue known as Wharton's jelly) derive from the embryonic and/or extraembryonic mesodermis. Thus, these tissues, as well as the primitive germ cells, are differentiated from the proximal epiblast, at the time of formation of the primitive line of the embryo, containing MSC and even some cells with pluripotent potential. The UC matrix material is speculated to be derived from a primitive mesenchyma, which is in a transition state towards the adult bone marrow mesenchyma (Mihu, C. et al., 2008, Romanian Journal of Morphology and Embryology, 2008, 49(4):441-446).

The blood from the placenta and the umbilical cord is relatively easy to collect in usual blood donation bags, which contain anticoagulant substances. Mononuclear cells are separated by centrifugation on Ficoll gradient, from which the two stem cell populations will be separated: (1) hematopoietic stem cells (HSC), which express certain characteristic markers (CD34, CD133); and (2) mesenchymal stem cells (MSC) that adhere to the culture surface under certain conditions (e.g., modified McCoy medium and lining of vessels with Fetal Bovine Serum (FBS) or Fetal Calf Serum (FCS)). (Munn, D. et al., Science, 1998, 281: 1191-1193; Munn, D. et al., J Exp Med, 1999, 189: 1363-1372). Umbilical cord blood MSCs (UC-MS) can produce cytokines, which facilitate grafting in the donor and in vitro HSC survival compared to bone marrow MSC. (Zhang, X et al., Biochem Biophys Res Commun, 2006, 351: 853-859).

MSCs from the umbilical cord matrix (UC-MM) are obtained by different culture methods depending on the source of cells, e.g., MSCs from the connective matrix, from subendothelial cells from the umbilical vein or even from whole umbilical cord explant. They are generally well cultured in DMEM medium, supplemented with various nutritional and growth factors; in certain cases prior treatment of vessels with hyaluronic acid has proved beneficial (Baban, B. et al., J Reprod Immunol, 2004, 61: 67-77).

3.2. Lung

The lungs, which are paired organs that fill up the thoracic cavity, constitute an efficient air-blood gaseous exchange mechanism, accomplished by the passage of air from the mouth or nose, sequentially through an oropharynx, nasopharynx, a larynx, a trachea and finally through a progressively subdividing system of bronchi and bronchioles until it finally reaches alveoli where the air-blood gaseous exchange takes place. A resident niche with characteristic multipotent stem cells with c-kit positive surface profiles recently has been identified localized in small bronchioles alveoli. These stem cells express the transcription factors, Nanog, Oct3/4, Sox2 and Klf4, that govern pluripotency in embryonic stem cells. (Kajstura, J. et al., 2011, New Engl. J. Med., 364(19): 1795-1806)).

3.2. Mammary

The mammary gland is a hormone sensitive bilayered epithelial organ comprising an inner luminal epithelial layer and an outer myoepithelial layer surrounded by a basement membrane in a stromal fat pad. Mammary stem cells with myoepithelial potential have been identified in their niches in the terminal ducts of mammary gland. (LaBarge, 2007, Stem Cell Rev., 3(2): 137-146).

3.3. Skin

The skin functions as the primary barrier imparting protection from environmental insults. Skin is composed of an outer epidermis and inner dermis separated by a basement membrane (BM), rich in ECM and growth factors. The BM of the epidermal-dermal junction is composed of collagens (e.g., type IV and XVII), laminins, nidogen, fibronectin and proteoglycans that provide storage sites for growth factors and nutrients supporting the proliferation and adhesion of epidermal keratinocytes.

The epidermis is a solid epithelial tissue comprising keratinocytes that are linked to each other via cellular junctions, such as desmosomes. Keratinocytes are organized into distinct layers, comprising the stratum corneum, stratum granulosum, stratum spinosum and stratum basale. The epidermal matrix is made up of hyaluronan and other proteoglycans, including but not limited to, desmosealin, glycipans, versican, perlecan, and syndecans. (Sandjeu and Haftek, 2009, J. Physiol. Pharmacol. 60 (S4): 23-30). Epidermal desmosomes are multimeric complexes of transmembrance glycoprotein and cytosolic proteins with the keratin cytoskeleton. Desmosal proteins of the epidermis predominantly belong to the cadherin, *Armadillo* and plakin superfamilies.

The underlying dermis is connective tissue comprised primarily of fibroblasts with occasional inflammatory cells. Embedded within the dermis are also epidermal appendages, such as hair follicles and sebaceous glands, as well as nerves and cutaneous vasculature. The dermal ECM is essentially made of type I, III and V collagens and elastin together with noncollagenous components such as glycoproteins, proteoglycans, GAGs, cytokines and growth factors. Dermal collagens help mediate fibroblast-matrix interactions through a number of cell surface receptors and proteoglycans, such as β1-integrins. (Hodde and Johnson, 2007, Am. J. Clin. Dermatol. 8(2): 61-66).

During embryonic development, the epidermis originates from the ectoderm, while the dermis differentiates from the mesoderm. Following gastrulation, as mesenchymal stem cells of mesodermal origin populate the skin, they send signals to the single epidermal layer for initiation of epidermal stratification and direct the positioning of outgrowths of epidermal appendages, such as the hair follicles and sebaceous glands. Along with the mesenchyme, the basal layer of the epidermis organizes into a basement membrane that is rich in ECM proteins and growth factors. A number of different signaling pathways have been implicated in skin morphogenesis, including but not limited to Notch, Wnt, mitogen activated protein kinase (MAPK), nuclear factor-κB (NF-κB), transcriptional regulator, p63, the AP2 family of transcription factors, CCAAT/enhancer binding protein (C/EBP) transcriptional regulators, interferon regulatory 6 (URF6), grainyhead-like 3 (GRHL3) and Kruppel-like factor (KLF4). (Blanpain and Fuchs, 2009, Nat. Rev. Mol. Cell. Biol., 10(3): 207-217).

Adult skin undergoes constant cellular turnover whereby dead skin cells are shed and new cells are regenerated and replaced, by a process known as skin homeostasis. Several stem cell niches with distinct surface marker profiles and differentiation potentials have been identified. These include, but are not limited to, epidermal stem cells of interfollicular epidermis; bulge stem cells and epithelial stem cells of the hair follicle, dermal stem cells (e.g., multipotent dermal cells, skin-derived progenitor cells, dermis-derived multipotent stem cells and fibrocytes), dermal papilla stem cells, and sebaceous gland stem cells. Collectively, these skin stem cell niches partake in maintaining skin homeostasis with the help of growth factors and cytokines. (Zouboulis et al., 2008, Exp. Gerontol. 43: 986-997; Blanpain, 2010, Nature, 464: 686-687).

4. Cells of the Muscular Tissue Compartment

The muscular tissue compartments are comprised of contractile muscle tissue. These can be of three kinds: skeletal muscle associated with the skeletal system; cardiac muscle associated with the heart; and smooth muscle associated with the vasculature and gastrointestinal tract. Skeletal muscle tissue fibers are striated and are voluntary in function. Cardiac muscle fibers have characteristic intercalated discs and are involuntary in function. Smooth muscle tissue is comprised of spindle shaped cells and is involuntary in function.

Skeletal muscles are composed of a population of quiescent myogenic precursor cells known as satellite cells with muscle regenerating and self-renewal properties, as well as a population of multipotent muscle-derived stem cells (MDSC) with multilineage differentiation potential, such as mesodermal lineages including, but not limited to, myogenic lineages, adipogenic lineages, osteogenic lineages, chondrogenic lineages, endothelial and hematopoetic lineages, and ectodermal lineages, including not limited to neuron-like cells. (Xu et al., 2010, Cell Tissue Res., 340: 549-567).

Skeletal muscle satellite cells are quiescent mononucleated cells that are resident in the muscle fiber membrane, beneath the basal lamina forming distinct stem cell niches. Similar to other stem cell niches, the skeletal muscle satellite cell niche is a dynamic structure, capable of altering between inactive (quiescent) and activated states in response to external signals. Once activated, satellite cells have the potential to proliferate, expand and differentiate along the myogenic lineage. The basal lamina, which serves to separate individual skeletal muscle fibers, known as myofibers, and their associated satellite cell and stem cell niches, from the cells of the interstitium, is rich in collagen type IV, perlecan, laminin, entactin, fibronectin and several other glycoproteins and proteoglycans, that may function as receptors to growth factors effectuating their activation by extracellular processing and modifications. In addition to these interactions provided by the ECM, neighboring cells, such as endothelial cells and multipotent stem cells derived from blood vessels, such as pericytes and mesoangioblasts, or neural components, all have the potential of affecting the niche microenvironment. (Gopinath et al., 2008, Aging Cell, 7: 590-598).

Endogenous cardiac stem cells have also been identified in cardiac stem cell niches. (Mazhari and Hare, 2007, Nat. Clin. Pract. Cardiovasc. Med., 4(S1): S21-S26).

Vascular smooth muscle cells are derived from embryonic cardiac neural crest stem cells, as well as proepicardial cells and endothelial progenitor cells. Smooth muscle differentiation is dependent on a combination of factors, including but not limited to Pax3, Tbx1, FoxC1 and serum response factor, interacting with microenvironment components of the ECM, such as BMPs, Wnts, endothelin (ET)-1, and FGF8. In the adult, vascular smooth muscle cells undergo constant degeneration, repair and regeneration by the concerted efforts of both multipotent bone-derived mesenchymal cells as well as smooth muscle stem cells resident within vascular smooth muscle tissue. (Hirschi and Majesky, 2004, The Anatomical Record, Part A, 276A: 22-33).

5. Cells of the Neural Tissue Compartment

The neural tissue compartments are comprised of neurons and the neuroglia, embedded with the neural matrix. Neural tissue is ectodermal in origin, derived from the embryonic neural plate. Neural tissue is primarily located within the brain, spinal cord and nerves.

Resident neural stem cell niches have been identified in the adult mammalian brain, restricted to the subventricular zone as well as to the lateral ventricle and dentate gyrus subgranular zone of the hippocampus. Astrocytes, which are star-shaped nerve cells, serve as both neural stem cells as well as supporting niche cells secreting essential growth factors that provide support for neurogenesis and vasculogenesis. The basal lamina and associated vasculogenesis are essential components of the niche. Embryonic molecular factors and signals persist within the neural stem cell niches and play critical role in neurogenesis. Neural stem cells have VEGFR2, doublecortin and Lex (CD15) markers. Major signaling pathways implicated in neurogenesis include but are not limited to Notch, Eph/ephrins, Shh, and BMPs. (Alvarez-Buylla and Lim, 2004, Neuron, 41: 683-686).

6. Grafts—Grafts and Graft Rejection

A graft is a tissue or organ used for transplantation to a patient. A common strategy employed in tissue engineering involves the seeding of decellularized natural ECM or synthetic scaffolds with a variety of different stem or progenitor cells that are capable of regeneration (see, for example, Flynn and Woodhouse, 2008, Organogenesis, 4(4): 228-235; Uriel et al., 2008, Biomaterials, 29: 3712-3719; Flynn, 2010, Biomaterials, 31: 4715-4724; Choi et al., Tissue Engg. C., 16(3): 387-396; Brown et al., 2011, Tissue Engg. C., 17(4): 411-421; Cheng et al., 2009, Tissue Engg. A, 15(2): 231-241; Li et al., 2011, Biomaterials, doi:10: 1016/j.biomaterials.2011.03.008; Butler et al., 2003, Connective Tissue Research, 44(S1): 171-178); Mercuri et al., J. Biomed. Mater. Res. A., 96(2): 422-435); Olson et al., 2011, Chonnam. Med. J. 47:1-13).

Transplanted grafts may be rejected by the recipient host via an orchestrated immune response against the histocompatibility antigens expressed by the grafted tissue, which the recipient host may see as foreign. Effectors primarily responsible for such rejections include type 1 helper CD4+ cells, cytotoxic CD8+ cells and antibodies. Alternative mechanisms of rejection include the involvement of type 2 helper CD4+ cells, memory CD8+ cells, and cells that belong to the innate immune system, such as natural killer cells, eosinophils, and neutrophils. In addition, local inflammation associated with rejection is tightly regulated at the graft level by regulatory T cells and mast cells.

Implants

Patients suffering from affected or injured organs may be treated with organ transplantation. However, current methods of organ transplantation are faced with challenges due, in part to the need to suppress immune rejection of the transplanted organ. Most methods rely on the use of immunesuppressive drugs that are associated with unwanted side effects.

It is estimated that more than one million patients need to be treated surgically for skeletal afflictions every year due to bony defects created during tumor surgery or caused by trauma, congenital skeletal abnormalities, fracture, scoliosis, spinal arthrodesis, or joint and tooth replacement. Surgical treatments, however, are not always effective to address these problems because of inadequate local bone conditions and impaired bone healing. For example, complicated fractures may fail to heal, resulting in delayed unions (a bone fracture that is taking an exceptionally long amount of time to heal) or non-unions (absence of healing in a fracture). In addition, the treatment of bone tumors or congenital syndromes often requires the artificial creation of large bony defects, which need to be filled, demanding suitable and biocompatible substitutes for bone grafts.

Bone healing around implants involves the activation of a sequence of osteogenic, vascular, and immunological events that are similar to those occurring during bone healing. Various cell types, growth factors and cytokines are involved and interact throughout the stages of osteointegration, including inflammation, vascularization, bone formation, and ultimately bone remodeling.

Bone Grafts

Fresh autologous bone grafts for the treatment of an osseous defect or fracture in a patient are derived from bone marrow freshly harvested from the iliac crest (the thick curved upper border of the ilium, the most prominent bone on the pelvis) and combined with other materials including osteoconductive substrates. Complications associated with autologous harvest include donor site morbidity as high as 25%, infection, malformation, pain, and loss of function.

Bone Matrix with Mesenchymal Stem Cells

Attempts have been made to repair osseous defects by implanting a bone matrix comprising autologous or allogeneic mesenchymal stem cells (MSCs). MSCs are considered immunologically neutral, meaning that the mesenchymal stem cells from the donor need not be tissue-matched to the recipient, thus allowing MSCs to be used effectively in allogeneic grafts. In addition, culture-expanded allogeneic MSCs have been implanted either directly or combined with a matrix, such as a gelatin-based or collagen-based matrix, or a bone matrix, in order to support differentiation of the MSCs in vivo.

In other instances, MSCs have been combined with a bone matrix from which bone marrow has been removed in order to remove undesirable cells, and the matrix then seeded with culture-expanded MSCs. Such compositions then are cryopreserved under standard cryopreservation procedures for later use. However, this method is not ideal for several reasons. First, because the MSCs have been removed from the original stem cell niche and seeded onto a new bone matrix, the MSCs in such a composition are not well-attached to the bone matrix and become merely suspended in the cryopreservation solution. As a result, many active cells can be lost during the process of removing the cryopreservation solution before transplantation into a subject. Secondly, since the cells are not attached to the stem cell niche or lacunae to which they were originally attached and in which they were nurtured, the expandability and osteogenic potential of the cells may be affected negatively by the separation and seeding procedures.

Tissue-derived implant materials replicate the biological and mechanical function of naturally occurring extracellular matrix found in body tissues. Such tissue-derived matrices provide the necessary support on which cells can adhere to, migrate and expand and allow the influx and efflux of cells, such as stem cells and progenitor cells, and other factors, such as growth factors and cytokines, capable of inducing and supporting growth and tissue repair.

A new approach to prepare and transplant an allograft is presented herein in which biological contents of a matrix are preserved such that factors and biologically active cells with the potential to differentiate into adult tissue cells are attached in situ, and undesirable cells are removed. An alternative approach, in which biologically active cells with the potential to differentiate into adult tissue cells, growth-inductive and growth-conductive factors are added back to a tissue derived matrix also is presented. Such approaches would allow faster regeneration of tissue in transplanted individuals.

SUMMARY OF THE INVENTION

According to one aspect, the described invention provides a tissue-derived implant comprising: (a) at least one tissue-derived growth conductive matrix from which unwanted cells have been removed; and (b) at least one viable population of nonexpanded tissuegenic cells adherent to and resident in an endogenous milieu of the growth conductive matrix.

According to one embodiment, the implant comprises a plurality of pieces of the growth conductive matrix comprising a circular shape, a square shape, a polygonal shape, a rectangular shape, a triangular shape, an octagonal shape, an irregular shape, an elongated shape (e.g., as a fiber), an amorphous shape, or a combination thereof. According to another embodiment, the growth conductive matrix exists in a plurality of pieces ranging from about 10 μm to about 20 cm in length. According to another embodiment, the plurality of pieces of the growth conductive matrix comprises a block form, a dowel form, a powder form, a slurry form, a paste form, a three-dimensional form, a sheet form, or a combination thereof. According to another embodiment, the growth conductive matrix is derived from a mammalian tissue. According to another embodiment, the growth conductive matrix is derived from a tissue selected from the group consisting of an adipose tissue, an amnion tissue, an artery tissue, a bone tissue, a cartilage tissue, a chorion tissue, a colon tissue, a dental tissue, a dermal tissue, a duodenal tissue, an endothelial tissue, an epithelial tissue, a fascial tissue, a gastrointestinal tissue, a growth plate tissue, an intervertebral disc tissue, an intestinal mucosal tissue, an intestinal serosal tissue, a ligament tissue, a liver tissue, a lung tissue, a mammary tissue, a meniscal tissue, a muscle tissue, a nerve tissue, an ovarian tissue, a parenchymal organ tissue, a pericardial tissue, a periosteal tissue, a peritoneal tissue, a placental tissue, a skin tissue, a spleen tissue, a stomach tissue, a synovial tissue, a tendon tissue, a testes tissue, an umbilical cord tissue, a urological tissue, a vascular tissue, a vein tissue, and a combination thereof. According to another embodiment, the tissue is derived from a human donor. According to another embodiment, the human donor is a cadaveric donor. According to another embodiment, the human donor is a living donor. According to another embodiment, the tissuegenic cells are present in the growth conductive matrix at a relative frequency substantially similar to the relative frequency of the tissuegenic cells found in vivo. According to another embodiment, the implant further comprises at least one growth-inductive component. According to another embodiment, the growth-inductive component is tissue-derived. According to another embodiment, the growth-inductive component comprises demineralized bone matrix, which may have any of the shapes or dimensions recited herein for growth-conductive matrix, and which may be derived from cortical bone. According to another embodiment, the tissue-derived growth-inductive component originates from a component of the tissue-derived growth-inductive component other than cells. According to another embodiment, the growth-conductive component comprises a growth medium derived from expanded tissuegenic cells. According to another embodiment, the tissuegenic cells adherent to and resident in an endogenous milieu of the growth conductive matrix secrete the at least one growth-inductive component. According to another embodiment, the at least one growth-inductive component comprises at least one cytokine. According to another embodiment, the at least one growth-inductive component comprises at least one growth factor. According to another embodiment, the least one growth factor is selected from the group consisting of fibroblast growth factor-2 (FGF-2), fibroblast growth factor-5 (FGF-5), insulin-like growth factor 1 (IGF-1), neural epidermal growth-factor-like 1 (Nel-like 1, NELL1), transforming growth factor beta (TGF-β), a bone morphogenic protein, bone morphogenic protein-2 (BMP-2), bone morphogenic protein-7 (BMP-7), platelet-derived growth factor (PDGF), vascular endothelial growth factor (VEGF), and a combination thereof. According to another embodiment, the growth-conductive matrix and the tissuegenic cells are derived from a bone tissue. According to another embodiment, the bone tissue comprises a cancellous bone, a cortical bone, or a combination thereof. According to another embodiment, the bone tissue comprises a cancellous bone. According to another embodiment, the cancellous bone is selected from the group consisting of a calcaneus, a distal femur bone, a proximal femur, a proximal humerus, an ilium, a patella, a distal tibia, a proximal tibia, a scapula, a cancellous bone from a sternum, a talus, at least one vertebral body, and a combination thereof. According to another embodiment, the bone tissue comprises a cortical bone. According to another embodiment, the bone tissue comprises periosteal tissue. According to another embodiment, the at least one viable population of tissuegenic cells is derived from a tissue selected from the group consisting of an adipose tissue, an amnion tissue, an artery tissue, a bone tissue, a cartilage tissue, a chorion tissue, a colon tissue, a dental tissue, a dermal tissue, a duodenal tissue, an endothelial tissue, an epithelial tissue, a fascia, a gastrointestinal tissue, a growth plate tissue, an intervertebral disc tissue, an intestinal mucosal tissue, an intestinal serosal tissue, a ligament tissue, a liver tissue, a lung tissue, a mammary tissue, a meniscal tissue, a muscle tissue, a nerve tissue, an ovarian tissue, a parenchymal organ tissue, a pericardial tissue, a periosteal tissue, a peritoneal tissue, a placental tissue, a skin tissue, a spleen tissue, a stomach tissue, a synovial tissue, a tendon tissue, a testes tissue, an umbilical cord tissue, a urological tissue, a vascular tissue, a vein tissue, and a combination thereof. According to another embodiment, the at least one viable population of tissuegenic cells adherent to and resident in an endogenous milieu of the growth conductive matrix comprises at least one viable population selected from the group consisting of a viable stem cell population and a viable progenitor cell population. According to another embodiment, the at least one viable population of tissuegenic cells comprises a population of viable multipotent stem cells. According to another embodiment, the at least one viable population of tissuegenic cells comprises a population of viable pluripotent stem cells. According to another embodiment, the at least one viable population of tissuegenic cells comprises a population of viable bone-derived osteoprogenitor cells. According to another embodiment, the at least one tissue-derived growth-conductive matrix is derived from an autologous tissue. According to another embodiment, the at least one growth-conductive matrix is derived from an allogeneic tissue. According to another embodiment, the endogenous niche of the growth conductive matrix comprises a tissuegenic cell niche.

According to another embodiment, the implant is an implantable composition comprising a growth-conductive matrix (e.g., an osteoconductive matrix including bone), a viable population of tissuegenic cells (e.g., osteogenic cells), and a growth-inductive matrix (e.g., demineralized bone matrix). In an embodiment, a second growth-inductive matrix (e.g., a second demineralized bone matrix) is provided separately from the aforesaid implantable composition for addition to the implantable composition at a later time.

According to another aspect, the described invention provides a method of fabricating a tissue-derived implant, the method comprising steps: (a) isolating a tissue comprising at least tissue-derived one growth-conductive matrix from which unwanted cells have been removed, wherein the growth-conductive matrix comprises at least one viable nonexpanded population of endogenous tissuegenic cells, and wherein the tissuegenic cells are adherent to and resident in an endogenous milieu of the growth-conductive matrix; (b) separating the at least one growth-conductive matrix from the tissue of (a) to generate a plurality of separated matrix pieces comprising the at least one viable population of tissuegenic cells adherent to and resident in the endogenous milieu of the growth-conductive matrix, wherein the tissuegenic cells in the separated matrix pieces is of a relative frequency substantially similar to that found in the growth matrix of step (a); (c) rinsing the plurality of the separated matrix pieces of (b) to form a plurality of rinsed separated matrix pieces comprising the at least one viable population of tissuegenic cells adherent to and resident in the endogenous milieu of the growth-conductive matrix of (b), wherein the tissuegenic cells in the rinsed separated matrix pieces of step (c) is of a relative frequency substantially similar to that found in the growth-conductive matrix of step (a); (d) collecting the plurality of the rinsed separated matrix pieces of (c) comprising the at least one viable population of tissuegenic cells adherent to and resident in the endogenous milieu of the growth-conductive matrix of (c), wherein the at least one viable tissuegenic cell population in the collected rinsed separated matrix pieces is of a relative frequency substantially similar to that found in the growth-conductive matrix of step (a); (e) packaging the plurality of the collected rinsed separated matrix pieces of (d) comprising at least one viable population of tissuegenic cells adherent to and resident in the endogenous milieu of the growth-conductive matrix, wherein the at least one viable tissuegenic cell population is of a relative frequency substantially similar to that found in the growth-conductive matrix of step (a), to form the implant.

According to one embodiment of the method, steps (a)-(d) are carried out at a temperature of about 4° C. to about 10° C. According to another embodiment, the at least one tissue-derived growth-conductive matrix is derived from a tissue selected from the group consisting of an adipose tissue, an amnion tissue, an artery tissue, a bone tissue, a cartilage tissue, a chorion tissue, a colon tissue, a dental tissue, a dermal tissue, a duodenal tissue, an endothelial tissue, an epithelial tissue, a fascial tissue, a gastrointestinal tissue, a growth plate tissue, an intervertebral disc tissue, an intestinal mucosal tissue, an intestinal serosal tissue, a ligament tissue, a liver tissue, a lung tissue, a mammary tissue, a meniscal tissue, a muscle tissue, a nerve tissue, an ovarian tissue, a parenchymal organ tissue, a pericardial tissue, a periosteal tissue, a peritoneal tissue, a placental tissue, a skin tissue, a spleen tissue, a stomach tissue, a synovial tissue, a tendon tissue, a testes tissue, an umbilical cord tissue, a urological tissue, a vascular tissue, a vein tissue, and a combination thereof. According to another embodiment, the growth-conductive matrix and the tissuegenic cells are derived from a bone tissue. According to another embodiment, the bone tissue comprises a cancellous bone, a cortical bone, or a combination thereof. According to another embodiment, the bone tissue comprises a cancellous bone. According to another embodiment, the cancellous bone is selected from the group consisting of a calcaneus, a distal femur bone, a proximal femur, a proximal humerus, an ilium, a patella, a distal tibia, a proximal tibia, a scapula, a cancellous bone from a sternum, a talus, at least one vertebral body, and a combination thereof. According to another embodiment, the bone tissue comprises a cortical bone. According to another embodiment, the bone tissue comprises periosteal tissue. According to another embodiment, the method further comprises step (f) supplementing the growth-conductive matrix of step (a) with at least one growth-inductive component. According to another embodiment, the growth-inductive component is tissue-derived. According to another embodiment, the growth-inductive component comprises demineralized bone matrix, which may be derived from cortical bone. According to another embodiment, the growth-inductive component originates from a component of the growth-inductive component other than cells. According to another embodiment, the growth-conductive component comprises a growth medium derived from expanded tissuegenic cells. According to another embodiment, the at least one growth-inductive component comprises at least one cytokine. According to another embodiment, the at least one growth-inductive component comprises at least one growth factor. According to another embodiment, the least one growth factor is selected from the group consisting of fibroblast growth factor-2 (FGF-2), fibroblast growth factor-5 (FGF-5), insulin-like growth factor 1 (IGF-1), neural epidermal growth-factor-like 1 (Nel-like 1, NELL1), transforming growth factor beta (TGF-β), a bone morphogenic protein, bone morphogenic protein-2 (BMP-2), bone morphogenic protein-7 (BMP-7), platelet-derived growth factor (PDGF), vascular endothelial growth factor (VEGF), and a combination thereof. According to another embodiment, the tissue-derived growth-conductive matrix is derived from a cadaveric donor. According to another embodiment, the tissue-derived growth conductive matrix is derived from a living donor. According to another embodiment, the tissue-derived growth-conductive matrix is derived from an autologous tissue. According to another embodiment, the at least one growth-conductive matrix is derived from an allogeneic tissue. According to another embodiment, the endogenous niche of the growth conductive matrix comprises a tissuegenic cell niche. According to another embodiment, the at least one viable population of tissuegenic cells adherent to and resident in an endogenous milieu of the growth conductive matrix comprises at least one viable population selected from the group consisting of a viable stem cell population and a viable progenitor cell population. According to another embodiment, the at least one viable population of tissuegenic cells comprises at least one viable pluripotent stem cell population. According to another embodiment, the at least one viable population of tissuegenic cells comprises at least one viable multipotent stem cell population. According to another embodiment, the at least one viable population of tissuegenic cells is derived from a tissue selected from the group consisting of an adipose tissue, an amnion tissue, an artery tissue, a bone tissue, a cartilage tissue, a chorion tissue, a colon tissue, a dental tissue, a dermal tissue, a duodenal tissue, an endothelial tissue, an epithelial tissue, a fascial tissue, a gastrointestinal tissue, a growth plate tissue, an intervertebral disc tissue, an intestinal mucosal tissue, an intestinal serosal tissue, a ligament tissue, a liver tissue, a lung tissue, a mammary tissue, a meniscal tissue, a muscle tissue, a nerve tissue, an ovarian tissue, a parenchymal organ tissue, a pericardial tissue, a periosteal tissue, a peritoneal tissue, a placental tissue, a skin tissue, a spleen tissue, a stomach tissue, a synovial tissue, a tendon tissue, a testes tissue, an umbilical cord tissue, a urological tissue, a vascular tissue, a vein tissue, and a combination thereof. According to another embodiment, separating step (b) comprises mincing the tissue to yield a plurality of growth-conductive matrix pieces. According to another embodiment, separating step (b) comprises cutting the tissue to yield a plurality of growth-conductive matrix pieces. According to another embodiment, separating step (b) comprises milling the tissue to yield a plurality of growth-conductive matrix pieces. According to another embodiment, rinsing step (c) comprises admixing the plurality of separated growth-conductive matrix pieces of (b) comprising the at least one viable population of tissuegenic cells adherent to and resident in the endogenous milieu of the growth-conductive matrix with a liquid. According to another embodiment, the plurality of the separated matrix pieces of (b) is rinsed with a buffered isotonic solution.

According to another aspect, the described invention provides a method of treating a bony defect at a defect site in a subject (e.g., a patient) in need thereof, comprising steps: (a) providing a tissue-derived orthopedic implant comprising (i) a plurality of pieces comprising at least one tissue-derived growth conductive matrix; and (ii) at least one viable population of tissuegenic cells adherent to and resident in an endogenous milieu of the growth conductive matrix, wherein the at least one population of tissuegenic cells is present in the growth conductive matrix at a relative frequency substantially similar to the relative frequency of the tissuegenic cells found in vivo; (b) implanting the orthopedic implant at the defect site; and (c) filling the bony defect.

According to one embodiment of the method, the bony defect resulted from tumor surgery. According to another embodiment, the bony defect resulted from a traumatic injury. According to another embodiment, the bony defect resulted from a congenital skeletal abnormality. According to another embodiment, the bony defect resulted from a fracture. According to another embodiment, the bony defect resulted from a spinal arthrodesis. According to another embodiment, the bony defect resulted from scoliosis. According to another embodiment, the tissue-derived growth conductive matrix is derived from a mammalian tissue. According to another embodiment, the at least one tissue-derived growth conductive matrix is derived from a tissue selected from the group consisting of an adipose tissue, an amnion tissue, an artery tissue, a bone tissue, a cartilage tissue, a chorion tissue, a colon tissue, a dental tissue, a dermal tissue, a duodenal tissue, an endothelial tissue, an epithelial tissue, a fascial tissue, a gastrointestinal tissue, a growth plate tissue, an intervertebral disc tissue, an intestinal mucosal tissue, an intestinal serosal tissue, a ligament tissue, a liver tissue, a lung tissue, a mammary tissue, a meniscal tissue, a muscle tissue, a nerve tissue, an ovarian tissue, a parenchymal organ tissue, a pericardial tissue, a periosteal tissue, a peritoneal tissue, a placental tissue, a skin tissue, a spleen tissue, a stomach tissue, a synovial tissue, a tendon tissue, a testes tissue, an umbilical cord tissue, a urological tissue, a vascular tissue, a vein tissue, and a combination thereof. According to another embodiment, the tissue-derived growth conductive matrix is derived from a human donor. According to another embodiment, the tissue-derived growth conductive matrix is derived from a cadaveric donor. According to another embodiment, the tissue-derived growth conductive matrix is derived from a living donor. According to another embodiment, the at least one tissue-derived growth conductive matrix is derived from an autologous tissue. According to another embodiment, the at least one growth conductive matrix is derived from an allogeneic tissue. According to another embodiment, the endogenous milieu of the growth conductive matrix comprises a tissuegenic cell niche. According to another embodiment, the at least one viable population of tissuegenic cells adherent to and resident in an endogenous milieu of the growth conductive matrix comprises at least one viable population selected from the group consisting of a viable stem cell population and a viable progenitor cell population. According to another embodiment, the at least one viable population of tissuegenic cells comprises at least one viable pluripotent stem cell population. According to another embodiment, the viable population of tissuegenic cells comprises at least one viable multipotent stem cell population. According to another embodiment, the at least one viable population of tissuegenic cells comprises a population of viable bone-derived osteoprogenitor cells. According to another embodiment, the at least one viable population of tissuegenic cells is derived from a tissue selected from the group consisting of an adipose tissue, an amnion tissue, a bone tissue, a cartilage tissue, a chorion tissue, a dental tissue, a dermal tissue, a gastrointestinal tissue, an intervertebral disc tissue, an epithelial tissue, a fascial tissue, a growth plate tissue, a ligament tissue, a lung tissue, a liver tissue, a mammary tissue, a meniscal tissue, a muscle tissue, a nerve tissue, a periosteal tissue, a placental tissue, a skin tissue, a synovial tissue, a tendon tissue, an umbilical cord tissue, a urological tissue, a vascular tissue, and a combination thereof. According to another embodiment, the implant further comprises at least one growth-inductive component. According to another embodiment, the growth-inductive component is tissue-derived. According to another embodiment, the growth-inductive component comprises demineralized bone matrix, which may be derived from cortical bone. According to another embodiment, the tissue-derived growth-inductive component originates from a component of the tissue-derived growth-inductive component other than cells. According to another embodiment, the growth-conductive component comprises a growth medium derived from expanded tissuegenic cells. According to another embodiment, the tissuegenic cells adherent to and resident in the endogenous milieu of the growth conductive matrix secrete the at least one growth-inductive component. According to another embodiment, the at least one growth-inductive component comprises at least one cytokine. According to another embodiment, the at least one growth-inductive factor comprises at least one growth factor. According to another embodiment, the at least one growth factor is selected from the group consisting of fibroblast growth factor-2 (FGF-2), fibroblast growth factor-5 (FGF-5), insulin-like growth factor 1 (IGF-1), neural epidermal growth-factor-like 1 (Nel-like 1, NELL1), transforming growth factor beta (TGF-β), a bone morphogenic protein, bone morphogenic protein-2 (BMP-2), bone morphogenic protein-7 (BMP-7), platelet-derived growth factor (PDGF), vascular endothelial growth factor (VEGF), and a combination thereof. According to another embodiment, the growth conductive matrix and the tissuegenic cells are derived from a bone tissue. According to another embodiment, the bone tissue comprises as cancellous bone, a cortical bone, or a combination thereof. According to another embodiment, the bone tissue comprises a cancellous bone. According to another embodiment, the cancellous bone is selected from the group consisting of a calcaneus, a distal femur bone, a proximal femur, a proximal humerus, an ilium, a patella, a distal tibia, a proximal tibia, a scapula, a cancellous bone from a sternum, a talus, at least one vertebral body, and a combination thereof. According to another embodiment, the bone tissue comprises a cortical bone. According to another embodiment, the bone tissue comprises periosteal tissue.

BRIEF DESCRIPTION OF THE DRAWINGS

For a more complete understanding of the present invention, reference is made to the following detailed description of exemplary embodiments considered in conjunction with the accompanying drawings, in which.

DETAILED DESCRIPTION

Glossary

Figure 1:
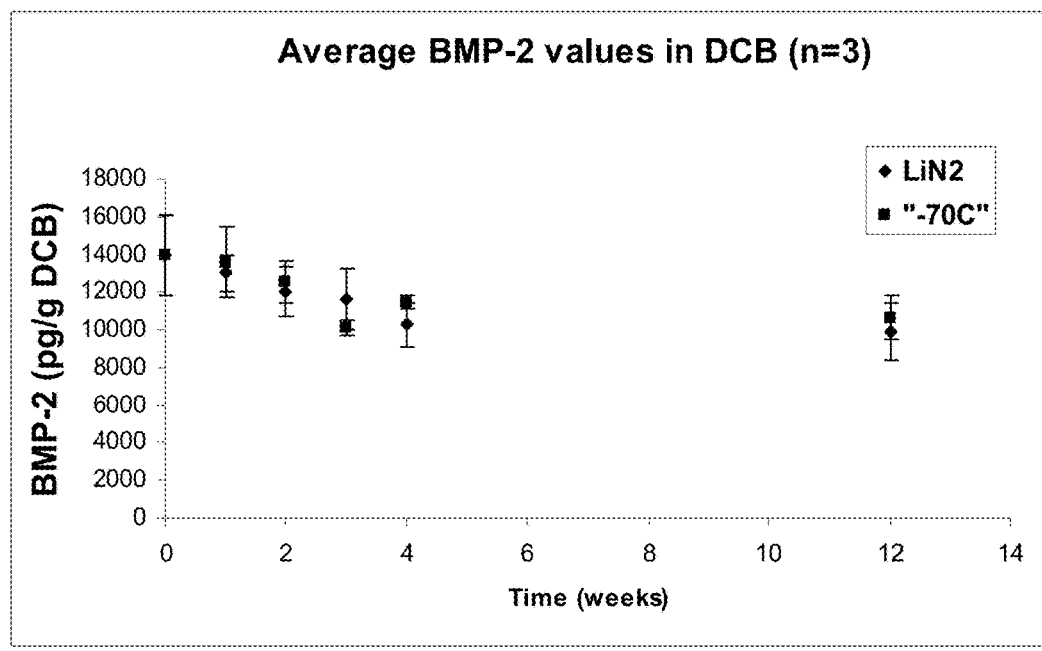
FIG. 1 shows a plot of BMP-2 (pg/g DCB) versus time (weeks). The levels of BMP-2 remain about or above 10,000 pg/g DCB after 12 weeks post-thaw.

The term "ambient temperature" as used herein refers to the temperature of the immediate, unaltered surroundings. Ambient temperature is between about 18° C. and about 28° C. According to some embodiments, ambient temperature is room temperature.

The term "adherent" as used herein refers to the act of sticking to, clinging, or staying attached.

The term "adipokine" as used herein refers to a factor secreted by adipose tissue.

The term "adipocyte" as used herein refers to the functional cell type of fat, or adipose tissue, that is found throughout the body, particularly under the skin. Adipocytes store and synthesize fat for energy, thermal regulation and cushioning against mechanical shock. Although the lineage of adipocytes is still unclear, it appears that MSCs can differentiate into two types of lipoblasts, one that give rise to white adipocytes and the other to brown adipocytes. Both types of adipocytes store fat.

The term "adipogenic" as used herein refers to a potential of undifferentiated precursor cells to differentiate into fat forming or adipocompetent cells.

The term "adipose stem cell" (ASC) as used herein refers to pluripotent stem cells, MSCs and more committed adipose progenitors and stroma obtained from adipose tissue.

The term "administer" as used herein means to give or to apply.

The term "allogeneic" as used herein refers to being genetically different although belonging to or obtained from the same species.

The term "amniotic stem cells" as used herein refers to pluripotent stem cells, multipotent stem cells and progenitor cells derived from amniotic membrane, which can give rise to a limited number of cell types in vitro and/or in vivo under an appropriate condition, and expressly includes both amniotic epithelial cells and amniotic stromal cells.

The term "attached" as used herein refers to being fastened, fixed, joined, connected, bound, adhered to or assembled with.

The term "autologous" as used herein means derived from the same organism.

The term "autologous graft" or "autograft" as used herein refers to a tissue that is grafted into a new position in or on the body of the same individual.

The term "basic fibroblast growth factor" (bFGF) as used herein refers to a multifunctional effector for many cells of mesenchymal and neuroectodermal origin that is a potent inducer of neovascularization and angiogenesis.

The term "biocompatible" as used herein refers to causing no clinically relevant tissue irritation, injury, toxic reaction, or immunological reaction to living tissue.

The term "biomarkers" (or "biosignatures") as used herein refers to peptides, proteins, nucleic acids, antibodies, genes, metabolites, or any other substances used as indicators of a biologic state. It is a characteristic that is measured objectively and evaluated as a cellular or molecular indicator of normal biologic processes, pathogenic processes, or pharmacologic responses to a therapeutic intervention.

The term "bone" as used herein refers to a hard connective tissue consisting of cells embedded in a matrix of mineralized ground substance and collagen fibers. The fibers are impregnated with a form of calcium phosphate similar to hydroxyapatite as well as with substantial quantities of carbonate, citrate and magnesium. Bone consists of a dense outer layer of compact substance or cortical substance covered by the periosteum and an inner loose, spongy substance; the central portion of a long bone is filled with marrow.

The terms "cancellous bone" or "trabecular bone" as used herein refer to the spongy bone found in the inner parts of compact bone in which the matrix forms a lattice of large plates and rods known as the trabeculae, which anastomose to form a latticework. This latticework partially encloses many intercommunicating spaces filled with bone marrow. The marrow spaces are relatively large and irregularly arranged, and the bone substance is in the form of slender anastomosing trabeculae and pointed spicules.

The terms "cortical bone" or "compact bone" as used herein refer to the dense outer layer of bone that consists largely of concentric lamellar osteons and interstitial lamellae. The spaces or channels are narrow and the bone substance is densely packed.

The term "bone morphogenetic protein (BMP) as used herein refers to a group of cytokines that are part of the transforming growth factor-β (TGF-β) superfamily. BMP ligands bind to a complex of the BMP receptor type II and a BMP receptor type I (Ia or Ib). This leads to the phosphorylation of the type I receptor that subsequently phosphorylates the BMP-specific Smads (Smad1, Smad5, and Smad8), allowing these receptor-associated Smads to form a complex with Smad4 and move into the nucleus where the Smad complex binds a DNA binding protein and acts as a transcriptional enhancer. BMPs have a significant role in bone and cartilage formation in vivo. It has been reported that most BMPs are able to stimulate osteogenesis in mature osteoblasts, while BMP-2, 6, and 9 may play an important role in inducing osteoblast differentiation of mesenchymal stem cells. Cheng, H. et al., J. Bone & Joint Surgery 85: 1544-52 (2003).

The term "bound" or any of its grammatical forms as used herein refers to the capacity to hold onto, attract, interact with or combine with.

The term "buffer" or "buffer solution" as used herein refers to a compound, usually a salt, which, when dissolved in an aqueous medium, serves to maintain the free hydrogen ion concentration of the solution within a certain pH range when hydrogen ions are added or removed from the solution. A salt or solution is said to have a "buffering capacity" or to buffer the solution over such a range, when it provides this function. Generally a buffer will have adequate buffering capacity over a range that is within .±.1 pH unit of its pK.

The term "buffered isotonic solution" as used herein refers to any buffer that is commonly used in biological research. Exemplary buffered isotonic solutions include but are not limited to balanced salt solution (BSS), Hank's Balanced Salt Solution, Gey's Balanced Salt Solution, Hank's Buffered Salt Solution, Phosphate Buffered Saline, Tris-Buffered Saline, etc. The term "isotonic solution" as used herein refers to a solution whose osmolarity and ion concentrations closely match those within normal cells of the body and the blood.

The term "carrier" as used herein refer to a pharmaceutically acceptable inert agent or vehicle for delivering one or more active agents to a subject, and often is referred to as "excipient." The carrier must be of sufficiently high purity and of sufficiently low toxicity to render it suitable for administration to the subject being treated. The carrier further should maintain the stability and bioavailability of an active agent Stem Cell Markers Coating the surface of every cell in the body are specialized proteins ("receptors") capable of selectively binding or adhering to other "signaling" molecules. Normally, cells use these receptors and the molecules that bind to them as a way of communicating with other cells and to carry out their proper functions in the body. These cell surface receptors are the stem cell markers. Each cell type has a certain combination of receptors on their surface that makes them distinguishable from other kinds of cells.

The cluster of differentiation (CD) system is a protocol used for the identification of cell surface molecules. CD molecules can act in numerous ways, often acting as receptors or ligands; by which a signal cascade is initiated, altering the behavior of the cell. Some CD proteins do not play a role in cell signaling, but have other functions, such as cell adhesion. Generally, a proposed surface molecule is assigned a CD number once two specific monoclonal antibodies (mAb) are shown to bind to the molecule. If the molecule has not been well-characterized, or has only one mAb, the molecule usually is given the provisional indicator "w."

The CD system nomenclature commonly used to identify cell markers thus allows cells to be defined based on what molecules are present on their surface. These markers often are used to associate cells with certain functions. While using one CD molecule to define populations is uncommon, combining markers has allowed for cell types with very specific definitions. More than 350 CD molecules have been identified for humans.

CD molecules are utilized in cell sorting using various methods, including flow cytometry. Cell populations usually are defined using a "+" or a "−" symbol to indicate whether a certain cell fraction expresses or lacks a particular CD molecule.

Table 8 identifies markers commonly used to identify stem cells and to characterize differentiated cell types:

TABLE 8

Commonly-Used Stem Cell Surface Surface Markers and Corresponding Differentiated Cell Types

| Marker Name | Cell Type | Significance |
| --- | --- | --- |
| Blood Vessel | | |
| Fetal liver kinase-1 (Flk1) | Endothelial | Cell-surface receptor protein that identifies endothelial cell progenitor; marker of cell-cell contacts |
| Smooth muscle cell-specific myosin heavy chain | Smooth muscle | Identifies smooth muscle cells in the wall of blood vessels |
| Vascular endothelial cell cadherin | Smooth muscle | Identifies smooth muscle cells in the wall of blood vessels |
| Bone | | |
| Bone-specific alkaline phosphatase (BAP) | Osteoblast | Enzyme expressed in osteoblast; activity indicates bone formation |
| Hydroxyapatite | Osteoblast | Mineralized bone matrix that provides structural integrity; marker of bone formation |
| Osteocalcin (OC) | Osteoblast | Mineral-binding protein synthesized by osteoblast; marker of bone formation |
| Bone Marrow and Blood | | |
| Bone morphogenetic protein receptor (BMPR) | Mesenchymal stem and progenitor cells | Important for the differentiation of committed mesenchymal cell types from mesenchymal stem and progenitor cells; BMPR identifies early mesenchymal lineages (stem and progenitor cells) |
| CD4 and CD8 | White blood cell (WBC) | Cell-surface protein markers specific for mature T lymphocyte (WBC subtype) |
| CD34 | Hematopoietic stem cell (HSC), satellite, endothelial progenitor | Cell-surface protein on bone marrow cell, indicative of a HSC and endothelial progenitor; CD34 also identifies muscle satellite, a muscle stem cell |
| CD34+Sea1+ Lin− profile | Mesenchymal stem cell (MSC) | Identifies MSCs, which can differentiate into adipocyte, osteocyte, chondrocyte, and myocyte |

TABLE 8-continued

Commonly-Used Stem Cell Surface Surface Markers and Corresponding Differentiated Cell Types

| Marker Name | Cell Type | Significance |
| --- | --- | --- |
| CD38 | Absent on HSC Present on WBC lineages | Cell-surface molecule that identifies WBC lineages. Selection of CD34+/CD38− cells allows for purification of HSC populations |
| CD44 | Mesenchymal | A type of cell-adhesion molecule used to identify specific types of mesenchymal cells |
| c-Kit | HSC, MSC | Cell-surface receptor on BM cell types that identifies HSC and MSC; binding by fetal calf serum (FCS) enhances proliferation of ES cells, HSCs, MSCs, and hematopoietic progenitor cells |
| Colony-forming unit (CFU) | HSC, MSC progenitor | CFU assay detects the ability of a single stem cell or progenitor cell to give rise to one or more cell lineages, such as red blood cell (RBC) and/or white blood cell (WBC) lineages |
| Fibroblast colony-forming unit (CFU-F) | Bone marrow fibroblast | An individual bone marrow cell that has given rise to a colony of multipotent fibroblastic cells; such identified cells are precursors of differentiated mesenchymal lineages |
| Hoechst dye | Absent on HSC | Fluorescent dye that binds DNA; HSC extrudes the dye and stains lightly compared with other cell types |
| Leukocyte common antigen (CD45) | WBC | Cell-surface protein on WBC progenitor |
| Lineage surface antigen (Lin) | HSC, MSC Differentiated RBC and WBC lineages | Thirteen to 14 different cell-surface proteins that are markers of mature blood cell lineages; detection of Lin-negative cells assists in the purification of HSC and hematopoietic progenitor populations |
| Mac-1 | WBC | Cell-surface protein specific for mature granulocyte and macrophage (WBC subtypes) |
| Muc-18 (CD146) | Bone marrow fibroblasts, endothelial | Cell-surface protein (immunoglobulin superfamily) found on bone marrow fibroblasts, which may be important in hematopoiesis; a subpopulation of Muc-18+ cells are mesenchymal precursors |
| Stem cell antigen (Sca-1) | HSC, MSC | Cell-surface protein on bone marrow (BM) cell, indicative of HSC and MSC Bone Marrow and Blood cont. |
| Stro-1 antigen | Stromal (mesenchymal) precursor cells, hematopoietic cells | Cell-surface glycoprotein on subsets of bone marrow stromal (mesenchymal) cells; selection of Stro-1+ cells assists in isolating mesenchymal precursor cells, which are multipotent cells that give rise to adipocytes, osteocytes, smooth myocytes, fibroblasts, chondrocytes, and blood cells |
| Thy-1 | HSC, MSC | Cell-surface protein; negative or low detection is suggestive of HSC |
| Cartilage | | |
| Collagen types II and IV | Chondrocyte | Structural proteins produced specifically by chondrocyte |

TABLE 8-continued

Commonly-Used Stem Cell Surface Surface Markers and Corresponding Differentiated Cell Types

| Marker Name | Cell Type | Significance |
|---|---|---|
| Keratin | Keratinocyte | Principal protein of skin; identifies differentiated keratinocyte |
| Sulfated proteoglycan | Chondrocyte | Molecule found in connective tissues; synthesized by chondrocyte |

Fat

| Marker Name | Cell Type | Significance |
|---|---|---|
| Adipocyte lipid-binding protein (ALBP) | Adipocyte | Lipid-binding protein located specifically in adipocyte |
| Fatty acid transporter (FAT) | Adipocyte | Transport molecule located specifically in adipocyte |
| Adipocyte lipid-binding protein (ALBP) | Adipocyte | Lipid-binding protein located specifically in adipocyte |

Liver

| Marker Name | Cell Type | Significance |
|---|---|---|
| Albumin | Hepatocyte | Principal protein produced by the liver; indicates functioning of maturing and fully differentiated hepatocytes |
| B-1 integrin | Hepatocyte | Cell-adhesion molecule important in cell-cell interactions; marker expressed during development of liver |

Nervous System

| Marker Name | Cell Type | Significance |
|---|---|---|
| CD133 | Neural stem cell, HSC | Cell-surface protein that identifies neural stem cells, which give rise to neurons and glial cells |
| Glial fibrillary acidic protein (GFAP) | Astrocyte | Protein specifically produced by astrocyte |
| Microtubule-associated protein-2 (MAP-2) | Neuron | Dendrite-specific MAP; protein found specifically in dendritic branching of neuron |
| Myelin basic protein (MPB) | Oligo-dendrocyte | Protein produced by mature oligodendrocytes; located in the myelin sheath surrounding neuronal structures |
| Nestin | Neural progenitor | Intermediate filament structural protein expressed in primitive neural tissue |
| Neural tubulin | Neuron | Important structural protein for neuron; identifies differentiated neuron |
| Neurofilament (NF) | Neuron | Important structural protein for neuron; identifies differentiated neuron |
| Neurosphere | Embryoid body (EB), ES | Cluster of primitive neural cells in culture of differentiating ES cells; indicates presence of early neurons and glia |
| Noggin | Neuron | A neuron-specific gene expressed during the development of neurons |
| O4 | Oligo-dendrocyte | Cell-surface marker on immature, developing oligodendrocyte |
| O1 | Oligo-dendrocyte | Cell-surface marker that characterizes mature oligodendrocyte |
| Synaptophysin | Neuron | Neuronal protein located in synapses; indicates connections between neurons |
| Tau | Neuron | Type of MAP; helps maintain structure of the axon |

Pancreas

| Marker Name | Cell Type | Significance |
|---|---|---|
| Cytokeratin 19 (CK19) | Pancreatic epithelium | CK19 identifies specific pancreatic epithelial cells that are progenitors for islet cells and ductal cells |
| Glucagon | Pancreatic islet | Expressed by alpha-islet cell of pancreas |
| Insulin | Pancreatic islet | Expressed by beta-islet cell of pancreas |
| Insulin-promoting factor-1 (PDX-1) | Pancreatic islet | Transcription factor expressed by beta-islet cell of pancreas |
| Nestin | Pancreatic progenitor | Structural filament protein indicative of progenitor cell lines including pancreatic |
| Pancreatic polypeptide | Pancreatic islet | Expressed by gamma-islet cell of pancreas |
| Somatostatin | Pancreatic islet | Expressed by delta-islet cell of pancreas |

Pluripotent Stem Cells

| Marker Name | Cell Type | Significance |
|---|---|---|
| Alkaline phosphatase | Embryonic stem (ES), embryonal carcinoma (EC) | Elevated expression of this enzyme is associated with undifferentiated pluripotent stem cell (PSC) |
| Alpha-fetoprotein (AFP) | Endoderm | Protein expressed during development of primitive endoderm; reflects endodermal differentiation |

Pluripotent Stem Cells

| Marker Name | Cell Type | Significance |
|---|---|---|
| Bone morphogenetic protein-4 | Mesoderm | Growth and differentiation factor expressed during early mesoderm formation and differentiation |
| Brachyury | Mesoderm | Transcription factor important in the earliest phases of mesoderm formation and differentiation; used as the earliest indicator of mesoderm formation |
| Cluster designation 30 (CD30) | ES, EC | Surface receptor molecule found specifically on PSC |
| Cripto (TDGF-1) | ES, cardiomyocyte | Gene for growth factor expressed by ES cells, primitive ectoderm, and developing cardiomyocyte |
| GATA-4 gene | Endoderm | Expression increases as ES differentiates into endoderm |
| GCTM-2 | ES, EC | Antibody to a specific extracellular-matrix molecule that is synthesized by undifferentiated PSCs |
| Genesis | ES, EC | Transcription factor uniquely expressed by ES cells either in or during the undifferentiated state of PSCs |
| Germ cell nuclear factor | ES, EC | Transcription factor expressed by PSCs |
| Hepatocyte nuclear factor-4 (HNF-4) | Endoderm | Transcription factor expressed early in endoderm formation |
| Nestin | Ectoderm, neural and pancreatic progenitor | Intermediate filaments within cells; characteristic of primitive neuroectoderm formation |
| Neuronal cell-adhesion molecule (N-CAM) | Ectoderm | Cell-surface molecule that promotes cell-cell interaction; indicates primitive neuroectoderm formation |
| OCT4/ POU5F1 | ES, EC | Transcription factor unique to PSCs; essential for establishment and maintenance of undifferentiated PSCs |

TABLE 8-continued

Commonly-Used Stem Cell Surface Surface Markers and Corresponding Differentiated Cell Types

| Marker Name | Cell Type | Significance |
|---|---|---|
| Pax6 | Ectoderm | Transcription factor expressed as ES cell differentiates into neuroepithelium |
| Stage-specific embryonic antigen-3 (SSEA-3) | ES, EC | Glycoprotein specifically expressed in early embryonic development and by undifferentiated PSCs |
| Stage-specific embryonic antigen-4 (SSEA-4) | ES, EC | Glycoprotein specifically expressed in early embryonic development and by undifferentiated PSCs |
| Stem cell factor (SCF or c-Kit ligand) | ES, EC, HSC, MSC | Membrane protein that enhances proliferation of ES and EC cells, hematopoietic stem cell (HSCs), and mesenchymal stem cells (MSCs); binds the receptor c-Kit |
| Telomerase | ES, EC | An enzyme uniquely associated with immortal cell lines; useful for identifying undifferentiated PSCs |
| TRA-1-60 | ES, EC | Antibody to a specific extracellular matrix molecule is synthesized by undifferentiated PSCs |
| TRA-1-81 | ES, EC | Antibody to a specific extra-cellular matrix molecule normally synthesized by undifferentiated PSCs |
| Vimentin | Ectoderm, neural and pancreatic progenitor | Intermediate filaments within cells; characteristic of primitive neuroectoderm formation |
| Skeletal Muscle/Cardiac/Smooth Muscle | | |
| MyoD and Pax7 | Myoblast, myocyte | Transcription factors that direct differentiation of myoblasts into mature myocytes |
| Myogenin and MR4 | Skeletal myocyte | Secondary transcription factors required for differentiation of myoblasts from muscle stem cells |
| Myosin heavy chain | Cardiomyocyte | A component of structural and contractile protein found in cardiomyocyte |
| Myosin light chain | Skeletal myocyte | A component of structural and contractile protein found in skeletal myocyte |

Table 9 shows commonly used markers employed by skilled artisans to identify and characterize differentiated white blood cell types:

TABLE 9

List of Surface Markers on White Blood Cell Types

| Type of Cell | CD Markers |
|---|---|
| Stem cells | CD34+, CD31− |
| All leukocyte groups | CD45+ |
| Granulocyte | CD45+, CD15+ |
| Monocyte | CD45+, CD14+ |
| T lymphocyte | CD45+, CD3+ |
| T helper cell | CD45+, CD3+, CD4+ |
| Cytotoxic T cell | CD45+, CD3+, CD8+ |
| B lymphocyte | CD45+, CD19+ or CD45+, CD20+ |
| Thrombocyte | CD45+, CD61+ |
| Natural killer cell | CD16+, CD56+, CD3− |

Table 10 correlates the exemplary protein expression profile of adipose derived stem cells (ASCs) with the corresponding surface markers (Flynn et. al., 2208 Organogenesis, 4(4): 228-235; Gronthos et. al., 2011, J. Cell. Physiol., 189: 54-63).

TABLE 10

Adipose-derived Stem Cell Protein Expression and Surface Marker Profile

| Class | Protein | Marker |
|---|---|---|
| Cell Adhesion | Integrin $\beta_1$ | CD29 |
| | Integrin $\alpha_4$ | $CD49_d$ |
| | Integrin $a_a$ | $CD49_e$ |
| | Vascular Cell Adhesion Molecule | VCAM; CD106 |
| | Intracellular Adhesion Molecule −1 | ICAM; CD54 |
| | Activated Leukocyte Cell Adhesion Molecule | ALCAM; CD166 |
| | Tetraspan | CD9 |
| | Endoglin | CD105 |
| | Muc18 | CD146 |
| Receptors | Hyaluronate receptor | CD44 |
| | Transferrin receptor | CD71 |
| | Insulin receptor | |
| | Glucocorticoid receptor | |
| | Triiodothyronine (T3) receptor | |
| | Retinoic acid receptor | |
| ECM | Collagen type I | |
| | Collagen type III | |
| | Collagen type IV | |
| | Collagen type VI | CD68 |
| | Osteopontin | |
| | Osteonectin | |
| Cytoskeletal | A-smooth muscle actin | |
| | Vimentin | |
| Other | HLA-ABC | Major histocompatibility complex class I antigen |
| | DAF | CD55 |
| | Complement protectin | CD59 |

CD3 (TCR complex) is a protein complex composed of four distinct chains. In mammals, the complex contains a CD3γ chain, a CD3δ chain, and two CD3ε chains, which associate with the T cell receptor (TCR) and the ζ-chain to generate an activation signal in T lymphocytes. Together, the TCR, the ζ-chain and CD3 molecules comprise the TCR complex. The intracellular tails of CD3 molecules contain a conserved motif known as the immunoreceptor tyrosine-based activation motif (ITAM), which is essential for the signaling capacity of the TCR. Upon phosphorylation of the ITAM, the CD3 chain can bind ZAP70 (zeta associated protein), a kinase involved in the signaling cascade of the T cell.

Integrins are receptors that mediate attachment between a cell and the tissues surrounding it and are involved in cell-cell and cell-matrix interactions. In mammals, 18 α and 8 β subunits have been characterized. Both α and β subunits contain two separate tails, both of which penetrate the plasma membrane and possess small cytoplasmic domains.

Integrin αM (ITGAM; CD11b; macrophage-1 antigen (Mac-1); complement receptor 3 (CR3)) is a protein subunit of the heterodimeric integrin αMβ2 molecule. The second chain of αMβ2 is the common integrin β2 subunit (CD18). αMβ2 is expressed on the surface of many leukocytes including monocytes, granulocytes, macrophages and natural killer cells. It generally is believed that αMβ2 mediates inflammation by regulating leukocyte adhesion and migration. Further, αMβ2 is thought to have a role in phagocytosis, cell-mediated cytotoxicity, chemotaxis and cellular activation, as well as being involved in the complement system due to its capacity to bind inactivated complement component 3b (iC3b). The ITGAM subunit of integrin αMβ2 is involved directly in causing the adhesion and spreading of cells, but cannot mediate cellular migration without the presence of the β2 (CD18) subunit.

CD14 is a cell surface protein expressed mainly by macrophages and, to a lesser extent, neutrophil granulocytes. CD14+ cells are monocytes that can differentiate into a host of different cells; for example, differentiation to dendritic cells is promoted by cytokines such as GM-CSF and IL-4. CD14 acts as a co-receptor (along with toll-like receptor (TLR) 4 and lymphocyte antigen 96 (MD-2)) for the detection of bacterial lipopolysaccharide (LPS). CD14 only can bind LPS in the presence of lipopolysaccharide binding protein (LBP).

CD15 (3-fucosyl-N-acetyl-lactosamine; stage specific embryonic antigen 1 (SSEA-1)) is a carbohydrate adhesion molecule that can be expressed on glycoproteins, glycolipids and proteoglycans. CD15 commonly is found on neutrophils and mediates phagocytosis and chemotaxis.

CD16 is an Fc receptor (FcγRIIIa and FcγRIIIb) found on the surface of natural killer cells, neutrophil polymorphonuclear leukocytes, monocytes and macrophages. Fc receptors bind to the Fc portion of IgG antibodies.

CD19 is a human protein expressed on follicular dendritic cells and B cells. This cell surface molecule assembles with the antigen receptor of B lymphocytes in order to decrease the threshold for antigen receptor-dependent stimulation. It generally is believed that, upon activation, the cytoplasmic tail of CD19 becomes phosphorylated, which allows binding by Src-family kinases and recruitment of phosphoinositide 3 (PI-3) kinases.

CD20 is a non-glycosylated phosphoprotein expressed on the surface of all mature B-cells. Studies suggest that CD20 plays a role in the development and differentiation of B-cells into plasma cells. CD20 is encoded by a member of the membrane-spanning 4A gene family (MS4A). Members of this protein family are characterized by common structural features and display unique expression patterns among hematopoietic cells and nonlymphoid tissues.

CD31 (platelet/endothelial cell adhesion molecule; PECAM1) normally is found on endothelial cells, platelets, macrophages and Kupffer cells, granulocytes, T cells, natural killer cells, lymphocytes, megakaryocytes, osteoclasts and neutrophils. CD31 has a key role in tissue regeneration and in safely removing neutrophils from the body. Upon contact, the CD31 molecules of macrophages and neutrophils are used to communicate the health status of the neutrophil to the macrophage.

CD34 is a monomeric cell surface glycoprotein normally found on hematopoietic cells, endothelial progenitor cells, endothelial cells of blood vessels, and mast cells. The CD34 protein is a member of a family of single-pass transmembrane sialomucin proteins and functions as a cell-cell adhesion factor. Studies suggest that CD34 also may mediate the attachment of stem cells to bone marrow extracellular matrix or directly to stromal cells.

CD44 (the "hyaluronan receptor"), a cell-surface glycoprotein involved in cell-cell interactions, cell adhesion and migration, is used to identify specific types of mesenchymal cells.

CD45 (protein tyrosine phosphatase, receptor type, C; PTPRC) cell surface molecule is expressed specifically in hematopoietic cells. CD45 is a protein tyrosine phosphatase (PTP) with an extracellular domain, a single transmembrane segment, and two tandem intracytoplasmic catalytic domains, and thus belongs to receptor type PTP. Studies suggest it is an essential regulator of T-cell and B-cell antigen receptor signaling that functions by direct interaction with components of the antigen receptor complexes, or by activating various Src family kinases required for antigen receptor signaling. CD45 also suppresses JAK kinases, and thus functions as a regulator of cytokine receptor signaling. The CD45 family consists of multiple members that are all products of a single complex gene. Various known isoforms of CD45 include: CD45RA, CD45RB, CD45RC, CD45RAB, CD45RAC, CD45RBC, CD45RO, and CD45R (ABC). Different isoforms may be found on different cells. For example, CD45RA is found on naïve T cells and CD45RO is found on memory T cells.

CD56 (neural cell adhesion molecule, NCAM) is a homophilic binding glycoprotein expressed on the surface of neurons, glia, skeletal muscle and natural killer cells. It generally is believed that NCAM has a role in cell-cell adhesion, neurite outgrowth, and synaptic plasticity. There are three known main isoforms of NCAM, each varying only in their cytoplasmic domains: NCAM-120 kDA (glycosyl-phopharidylinositol (GPI) anchored); NCAM-140 kDa (short cytoplasmic domain); and NCAM (long cytoplasmic domain). The different domains of NCAM have different roles, with the Ig domains being involved in homophilic binding to NCAM, and the fibronectin type III (FNIII) domains being involved in signaling leading to neurite outgrowth.

CD59 refers to a glycosylphosphatidylinositol (GPI)-linked membrane glycoprotein which protects human cells from complement-mediated lysis.

The CD66 antigen family identifies a neutrophil-specific epitope within the hematopoietic system that is expressed by members of the carcinoembryonic antigen family of adhesion molecules, which belong within the immunoglobulin gene superfamily. The extracellular portions of all CD66 (a-f) molecules possess a N-terminal V-set IgSF domain which, lacks the canonical inter-b-sheet disulfide of the CD-2 family. CD66a is heavily glycosylated type 1 glycoprotein with more than 60% of the mass contributed by N-linked glycans, which bear sialylated Lex (sLe x, CD15s) structures. In CD66a they are spaced further apart, VxYxxLx21IxYxxV, and resemble motifs which bind tyrosine phosphatases such as SHIP-1 and -2. Activation of neutrophils leads to phosphorylation of tyrosine residues in the CD66a cytoplasmic domain. CD66a is expressed on granulocytes and epithelial cells. Products of 4 of the 7 functional carcinoembryonic antigen (CEA) family genes, CD66a-d, are known to be expressed on hematopoietic cells. The expression of these molecules on hematopoietic cells is generally restricted to the myeloid lineage. These molecules are present at low levels on resting mature granulocytes but expression increases rapidly following activation with inflammatory agonists, probably as a result of exocytosis from storage granules. CD66a is detected on some macrophages in tissue sections and has been reported on T cells and a subpopulation of activated NK cells.

CD66b ((CGM1); CD67, CGM6, NCA-95) is a glycosylphosphatidylinositol (GPI)-linked protein that is a member of the immunoglobulin superfamily and carcinoembryonic antigen (CEA)-like subfamily. CD66b, expressed on granulocytes, generally is believed to be involved in regulating adhesion and activation of human eosinophils.

CD90 or Thy-1 is a 25-37 kDa heavily N-glycosylated, glycophosphatidylinositol (GPI) anchored conserved cell surface protein with a single V-like immunoglobulin domain, originally discovered as a thymocyte antigen. It belongs to the immunoglobulin gene superfamily. The complex carbohydrate side chains vary in composition between tissues and species. Generally, CD90 is expressed on hematopoietic stem cells and neurons. CD90 is highly expressed in connective tissue, on various fibroblast and stromal cell lines and is expressed on all thymocytes and peripheral T cells in mice. In humans, CD90 is expressed only on a small number of fetal thymocytes, 10%-40% of blood CD34+ cells in bone marrow, and <1% of CD3+CD4+ lymphocytes in peripheral circulation. CD90 also is expressed in the human lymph node HEV endothelium but not on other endothelia and lastly, is expressed on a limited number of lymphoblastoid and leukemic cell lines.

CD105 (endoglin) is a homodimeric integral membrane glycoprotein composed of disulfide-linked subunits of 90-95 kDa. In humans, it is expressed at high levels on vascular endothelial cells and on syncytiotrophoblast of term placenta. During human heart development, it is expressed at high levels on endocardial cushion tissue mesenchyme during heart septation and valve formation; subsequently expression drops as the valves mature. It also is expressed by a population of pre-erythroblasts, leukemic cells of lymphoid and myeloid lineages, and bone marrow stromal fibroblasts. Endoglin is an accessory protein of multiple kinase receptor complexes of the TGF-β superfamily. The TGF-β1 superfamily of structurally related peptides includes the TGF-β isoforms, β1, β2, β3, and β5, the activins and the bone morphogenetic proteins (BMPs). TGF-β-like factors are a multifunctional set of conserved growth and differentiation factors that control biological processes such as embryogenesis, organogenesis, morphogenesis of tissues like bone and cartilage, vasculogenesis, wound repair and angiogenesis, hematopoiesis, and immune regulation. Signaling by ligands of the TGF-β superfamily is mediated by a high affinity, ligand-induced, heteromeric complex consisting of related Ser/Thr kinase receptors divided into two subfamilies, type I and type II. The type II receptor transphosphorylates and activates the type I receptor in a Gly/Ser-rich region. The type I receptor in turn phosphorylates and transduces signals to a novel family of recently identified downstream targets, termed Smads. Endoglin binds transforming growth factor (TGF) TGF-β1 and -β3 by associating with the TGF-β type II receptor, interacts with activin-A, interacts with bone morphogenic protein (BMP)-7 via activin type II receptors, ActRII and ActRIIB, and binds BMP-2 by interacting with the ligand binding type I receptors ALK3 and ALK6.

CD166 antigen (ALCAM), a 556 amino acid glycoprotein belonging to the immunoglobulin gene superfamily, is encoded by the activated leukocyte-cell adhesion molecule (ALCAM) gene in humans. It contains a secretory signal sequence, an extracellular domain which contains 3 Ig-like C2-type domains, 2 Ig-like V-type domains and 9 potential N-linked glycosylation sites, a hydrophobic transmembrane spanning domain and a 32 amino acid cytoplasmic domain with no known motifs. The N-terminal Ig domain is the binding site for both homophilic and CD166-CD6 interactions. CD166 is anchored to the actin cytoskeleton via the cytoplasmic domain but the receptors involved in this interaction are unknown. The soluble CD166 is produced by proteolytic cleavage of extracellular domains or by alternative splicing. It is expressed on mesenchymal stem cells and progenitor cells and on cortical thymic epithelial cells and medullary thymic epithelial cells, neurons, activated T cells, B cells, monocytes, fibroblasts, endothelium, epithelium, primitive subsets of hematopoietic cells including pluripotent stem cells, blastocysts and endometrium.

The term "CXCR-4" as used herein refers to a G-protein-linked chemokine receptor. Stromal-derived factor-1 (SDF-1), an alpha-chemokine that binds to G-protein-coupled CXCR4, plays an important role in the regulation of stem/progenitor cell trafficking.

The term "cell" is used herein to refer to the structural and functional unit of living organisms and is the smallest unit of an organism classified as living.

The term "chemokine" as used herein refers to a class of chemotactic cytokines that signal leukocytes to move in a specific direction.

The terms "chemotaxis" or "chemotactic" refer to the directed motion of a motile cell or part along a chemical concentration gradient towards environmental conditions it deems attractive and/or away from surroundings it finds repellent.

The term "chondrocytes" as used herein refers to cells found in cartilage that produce and maintain the cartilaginous matrix for, for example, joints, ear canals, trachea, epiglottis, larynx, the discs between vertebrae and the ends of ribs. From least to terminally differentiated, the chondrocytic lineage is (i) Colony-forming unit-fibroblast (CFU-F); (ii) mesenchymal stem cell/marrow stromal cell (MSC); (iii) chondrocyte.

The term "chondrogenesis" as used herein refers to the formation of new cartilage from cartilage forming or chondrocompetent cells.

The term "chondrogenic" as used herein refers to a potential of undifferentiated precursor cells to differentiate into cartilage forming or chondrocompetent cells cells.

The term "compatible" as used herein means that the components of a composition are capable of being combined with each other in a manner such that there is no interaction that would substantially reduce the efficacy of the composition under ordinary use conditions.

The term "component" as used herein refers to a constituent part, element or ingredient.

The term "condition", as used herein, refers to a variety of health states and is meant to include disorders or diseases caused by any underlying mechanism or disorder, injury, and the promotion of healthy tissues and organs.

The term "contact" and its various grammatical forms as used herein refers to a state or condition of touching or of immediate or local proximity. Contacting a composition to a target destination may occur by any means of administration known to the skilled artisan.

The term "cut section thickness" as used herein refers to thickness of a section as measured directly from the sectioning device (cryostat, microtome, etc.) prior to histological processing, which may cause shrinkage in the z-axis. Also known as the block advance of the microtome.

The term "cytokine" as used herein refers to small soluble protein substances secreted by cells which have a variety of effects on other cells. Cytokines mediate many important physiological functions including growth, development, wound healing, and the immune response. They act by binding to their cell-specific receptors located in the cell membrane, which allows a distinct signal transduction cascade to start in the cell, which eventually will lead to biochemical and phenotypic changes in target cells. Generally, cytokines act locally. They include type I cytokines, which encompass many of the interleukins, as well as several hematopoietic growth factors; type II cytokines, including the interferons and interleukin-10; tumor necrosis factor ("TNF")-related molecules, including TNFα and lymphotoxin; immunoglobulin super-family members, including interleukin 1 ("IL-1"); and the chemokines, a family of molecules that play a critical role in a wide variety of immune and inflammatory functions. The same cytokine can have different effects on a cell depending on the state of the cell. Cytokines often regulate the expression of, and trigger cascades of other cytokines. Nonlimiting examples of cytokines include e.g., IL-1.alpha., IL-.beta., IL-2, IL-3, IL-4, IL-5, IL-6, IL-7, IL-8, IL-9, IL-10, IL-11, IL-12/IL-23 P40, IL13, IL-17, IL-18, TGF-beta., IFN-gamma., GM-CSF, Gro.alpha., MCP-1 and TNF-alpha.

The term "cytometry" as used herein refers to a process in which physical and/or chemical characteristics of single cells, or by extension, of other biological or nonbiological particles in roughly the same size or stage, are measured. In flow cytometry, the measurements are made as the cells or particles pass through the measuring apparatus (a flow cytometer) in a fluid stream. A cell sorter, or flow sorter, is a flow cytometer that uses electrical and/or mechanical means to divert and collect cells (or other small particles) with measured characteristics that fall within a user-selected range of values.

"Demineralized bone matrix" (DBM) refers to a bone-derived material that has osteoconductive and osteoinductive activity. DBM may be prepared by acid extraction of allograft bone, resulting in loss of most of the mineralized component but retention of collagen and noncollagenous proteins, including growth factors. Methods for preparing demineralized bone matrix from bone are known in the art, as disclosed, for example, in U.S. Pat. Nos. 5,073,373; 5,484,601; and 5,284,655, which are incorporated herein by reference. DBM may be prepared from autologous bone, allogeneic (or "allograft") bone, or xenogeneic bone. DBM may be prepared from cancellous bone, cortical bone, or combinations of cancellous and cortical bone. For the purpose of the present disclosure, demineralized bone includes bone matrix having a residual mineral content of 5% or less (w/w), 2% or less (w/w), 1% or less (w/w), 0.5% or less (w/w), or consisting essentially of collagen, non-collagen proteins such as growth factors, and other nonmineral substances found in the original bone, although not necessarily in their original quantities. The term "demineralized cortical bone" (DCB) as used herein refers to a demineralized allograft cortical bone The term "derivative" as used herein means a compound that may be produced from another compound of similar structure in one or more steps. A "derivative" or "derivatives" of a peptide or a compound retains at least a degree of the desired function of the peptide or compound. Accordingly, an alternate term for "derivative" may be "functional derivative." Derivatives can include chemical modifications of the peptide, such as akylation, acylation, carbamylation, iodination or any modification that derivatizes the peptide. Such derivatized molecules include, for example, those molecules in which free amino groups have been derivatized to form amine hydrochlorides, p-toluene sulfonyl groups, carbobenzoxy groups, t-butyloxycarbonyl groups, chloroacetyl groups or formal groups. Free carboxyl groups can be derivatized to form salts, esters, amides, or hydrazides. Free hydroxyl groups can be derivatized to form O-acyl or O-alkyl derivatives. The imidazole nitrogen of histidine can be derivatized to form N-im-benzylhistidine. Also included as derivatives or analogues are those peptides that contain one or more naturally occurring amino acid derivative of the twenty standard amino acids, for example, 4-hydroxyproline, 5-hydroxylysine, 3-methylhistidine, homoserine, ornithine or carboxyglutamate, and can include amino acids that are not linked by peptide bonds. Such peptide derivatives can be incorporated during synthesis of a peptide, or a peptide can be modified by well-known chemical modification methods (see, e.g., Glazer et al., Chemical Modification of Proteins, Selected Methods and Analytical Procedures, Elsevier Biomedical Press, New York (1975)).

The term "detectable marker" encompasses both selectable markers and assay markers. The term "selectable markers" refers to a variety of gene products to which cells transformed with an expression construct can be selected or screened, including drug-resistance markers, antigenic markers useful in fluorescence-activated cell sorting, adherence markers such as receptors for adherence ligands allowing selective adherence, and the like.

The term "detectable response" refers to any signal or response that may be detected in an assay, which may be performed with or without a detection reagent. Detectable responses include, but are not limited to, radioactive decay and energy (e.g., fluorescent, ultraviolet, infrared, visible) emission, absorption, polarization, fluorescence, phosphorescence, transmission, reflection or resonance transfer. Detectable responses also include chromatographic mobility, turbidity, electrophoretic mobility, mass spectrum, ultraviolet spectrum, infrared spectrum, nuclear magnetic resonance spectrum and x-ray diffraction. Alternatively, a detectable response may be the result of an assay to measure one or more properties of a biologic material, such as melting point, density, conductivity, surface acoustic waves, catalytic activity or elemental composition. A "detection reagent" is any molecule that generates a detectable response indicative of the presence or absence of a substance of interest. Detection reagents include any of a variety of molecules, such as antibodies, nucleic acid sequences and enzymes. To facilitate detection, a detection reagent may comprise a marker.

The term "differential label" as used herein generally refers to a stain, dye, marker, or antibody used to characterize or contrast structures, components or proteins of a single cell or organism.

The term "differentiation" as used herein refers to the process of development with an increase in the level of organization or complexity of a cell or tissue, accompanied with a more specialized function.

The terms "disease" or "disorder" as used herein refer to an impairment of health or a condition of abnormal functioning.

The term "dye" (also referred to as "fluorochrome" or "fluorophore") as used herein refers to a component of a molecule which causes the molecule to be fluorescent. The component is a functional group in the molecule that absorbs energy of a specific wavelength and re-emits energy at a different (but equally specific) wavelength. The amount and wavelength of the emitted energy depend on both the dye and the chemical environment of the dye. Many dyes are known, including, but not limited to, FITC, R-phycoerythrin (PE), PE-Texas Red Tandem, PE-Cy5 Tandem, propidium iodem, EGFP, EYGP, ECF, DsRed, allophycocyanin (APC), PerCp, SYTOX Green, courmarin, Alexa Fluors (350, 430, 488, 532, 546, 555, 568, 594, 633, 647, 660, 680, 700, 750), Cy2, Cy3, Cy3.5, Cy5, Cy5.5, Cy7, Hoechst 33342, DAPI, Hoechst 33258, SYTOX Blue, chromomycin A3, mithramycin, YOYO-1, SYTOX Orange, ethidium bromide, 7-AAD, acridine orange, TOTO-1, TO-PRO-1, thiazole orange, TOTO-3, TO-PRO-3, thiazole orange, propidium iodide (PI), LDS 751, Indo-1, Fluo-3, DCFH, DHR, SNARF, Y66F, Y66H, EBFP, GFPuv, ECFP, GFP, AmCyan1, Y77W, S65A, S65C, S65L, S65T, ZsGreen1, ZsYellow1, DsRed2, DsRed monomer, AsRed2, mRFP1, HcRed1, monochlorobimane, calcein, the DyLight Fluors, cyanine, hydroxycoumarin, aminocoumarin, methoxycoumarin, Cascade Blue, Lucifer Yellow, NBD, PE-Cy5 conjugates, PE-Cy7 conjugates, APC-Cy7 conjugates, Red 613, fluorescein, FluorX, BODIDY-FL, TRITC, X-rhodamine, Lissamine Rhodamine B, Texas Red, TruRed, and derivatives thereof.

The term "nonexpanded" as used herein refers to a cell population that has not been grown in culture (in vitro) to increase the number of cells in the cell population.

The term "endogenous" as used herein refers to that which is naturally occurring, incorporated within, housed within, adherent to, attached to or resident in.

The term "extracellular matrix" as used herein refers to a scaffold in a cell's external environment with which the cell interacts via specific cell surface receptors. The extracellular matrix serves many functions, including, but not limited to, providing support and anchorage for cells, segregating one tissue from another tissue, and regulating intracellular communication. The extracellular matrix is composed of an interlocking mesh of fibrous proteins and glycosaminoglycans (GAGs). Examples of fibrous proteins found in the extracellular matrix include collagen, elastin, fibronectin, and laminin. Examples of GAGs found in the extracellular matrix include proteoglycans (e.g., heparin sulfate), chondroitin sulfate, keratin sulfate, and non-proteoglycan polysaccharide (e.g., hyaluronic acid). The term "proteoglycan" refers to a group of glycoproteins that contain a core protein to which is attached one or more glycosaminoglycans.

The term "factors" as used herein refers to nonliving components that have a chemical or physical effect. For example, a "paracrine factor" is a diffusible signaling molecule that is secreted from one cell type that acts on another cell type in a tissue. A "transcription factor" is a protein that binds to specific DNA sequences and thereby controls the transfer of genetic information from DNA to mRNA.

The term "fluorescence" as used herein refers to the result of a three-state process that occurs in certain molecules, generally referred to as "fluorophores" or "fluorescent dyes," when a molecule or nanostructure relaxes to its ground state after being electrically excited. Stage 1 involves the excitation of a fluorophore through the absorption of light energy; Stage 2 involves a transient excited lifetime with some loss of energy; and Stage 3 involves the return of the fluorophore to its ground state accompanied by the emission of light.

The term "fluorescent-activated cell sorting" (also referred to as "FACS") as used herein refers to a method for sorting a heterogeneous mixture of biological cells into one or more containers, one cell at a time, based upon the specific light scattering and fluorescent characteristics of each cell.

The term "fossa" as used herein means a small cavity or depression, as in a bone.

The term "fragment" as used herein refers to a small part, which may be, without exclusion, a particle, chip, or fiber, derived from, cut off, or broken from a larger unit which retains the desired biological activity of the larger unit.

The term "functional equivalent" or "functionally equivalent" are used interchangeably herein to refer to substances, molecules, polynucleotides, proteins, peptides, or polypeptides having similar or identical effects or use.

The term "graft" as used herein refers to a tissue or organ transplanted from a donor to a recipient. It includes, but is not limited to, a self tissue transferred from one body site to another in the same individual ("autologous graft"), a tissue transferred between genetically identical individuals or sufficiently immunologically compatible to allow tissue transplant ("syngeneic graft"), a tissue transferred between genetically different members of the same species ("allogeneic graft" or "allograft"), and a tissue transferred between different species ("xenograft").

The term "growth" as used herein refers to a process of becoming larger, longer or more numerous, or an increase in size, number, or volume.

The term "growth conduction" as used herein refers to a process by which a tissue is directed to regenerate or grow so as to conform to a material's surface. A growth-conductive surface is one that permits tissue growth on its surface or down into pores, channels or pipes. Growth-conductive material facilitates the spontaneous formation of a tissue by furnishing a microenvironment that supports deposition or adhesion of tissuegenic cells and optionally, vascularization. Examples of growth-conductive materials, include, but are not limited to, processed human bone (e.g., allograft bone, which may be an osteoconductive material), purified collagen, calcium phosphate ceramics, synthetic polymers, tissue-derived matrices, BMP-2 and 4, VEGF, bFGF, TGF-β, and PDGF.

The term "growth-conductive matrix" as used herein refers to a matrix that may be inert in and of itself but which supports three-dimensional tissue formation. For example, allograft bone tissue may be an osteoconductive matrix.

The term "growth factor" as used herein refers to extracellular polypeptide molecules that bind to a cell-surface receptor triggering an intracellular signaling pathway, leading to proliferation, differentiation, or other cellular response. Growth factors include, but are not limited to, cytokines and hormones.

The term "growth induction" as used herein refers to a process by which primitive, undifferentiated and tissuegenic cells are stimulated to develop into an ensemble of cells, not necessarily identical, that together carry out a specific function. This ensemble of cells is termed a tissue.

The term "growth-inductive matrix" as used herein refers to a matrix containing a substance or substances capable of recruiting or stimulating local tissuegenic cells so that the cells are induced (meaning to cause, bring about, bring about, or trigger) to differentiate and/or produce a tissue.

The terms "growth-inductive components" or "growth-inductive factors" or "tissuegenic factors" are used interchangeably to refer to the plethora of mediators associated with tissue development and repair.

For example, Table 11 lists exemplary growth-inductive factors secreted by adipose tissue classified according to metabolic, immunological or other function. (Halberg et. al., 2008, Endocrinol. Metab. Clin. North Am., 37(3): 753-767). The subcutaneous adipose secretome includes adiponectin, leptin, IL-6, IL-7, IL-8, MCP-1, GRO, angiogenin, HGF, VEGF, TIMP-1, TIMP-2, etc. (Klimkakova et. al., 2007, Biochem. Biophys. Res. Commun., 358: 897-902).

TABLE 11

Secreted Soluble non-ECM Factors of Adipose Secretome

| Metabolic Factors | Immunological Factors | Other Factors |
|---|---|---|
| Adipsin | Alpha 1 acid glycoprotein | Angiogenin |
| Adiponectin | Colony stimulating factor-1 | Angiopoietin 1 |
| Apelin | Complement component inhibitor C1 | Angiopoietin 2 |
| ApoE | Complement C1 | Angiotensinogen |
| Cortisol | Complement C2 | Calcitonin |
| Insulin-like growth factor 1 (IGF-1) | Complement C3 | Chemerin |

TABLE 11-continued

Secreted Soluble non-ECM Factors of Adipose Secretome

| Metabolic Factors | Immunological Factors | Other Factors |
|---|---|---|
| Insulin-like growth factor (IGF) | Complement C4 | Cyclophilin A |
| Binding protein 7 (Bp 7) | Complement C7 | Extracellular SOD |
| Lipoprotein lipase | Complement factor B | Galectin 1 |
| Leptin | Complement factor C | Growth related oncogene (GRO) |
| Fasting induced adipose factor | Complement factor D | Fibroblast growth factor (FGF) |
| Plasminogen activated inhibitor-1 | C reactive protein | Hepatic growth factor (GF) |
| Resistin | Haptoglobin | Mineralcorticoid releasing factor (MRF) |
| Retinol binding protein 4 | Interleukin 1 beta (IL-1β) | Monocyte chemoattractant protein 1 (MCP-1) |
| Vaspin | Interleukin 4 (IL-4) | Nerve growth factor (NGF) |
| Vistafin | Interleukin 6 (IL-6) | Pigment epithelium derived factor (PEDF) |
|  | Interleukin 7 (IL-7) | Prostaglandin E2 |
|  | Interleukin 8 (IL-8) | Prostaglandin I2 |
|  | Interleukin 10 (IL-10) | Prostaglandin 2alpha |
|  | Interleukin 12 (IL-12) | Serum transferring |
|  | Interleukin 18 (IL-18) | Stromal derived factor 1 |
|  | Lipocalin 24p3 | TGF beta |
|  | Macrophage migration inhibitory factor 1 | TIMP-1 |
|  | Serum amyloid A3 (SAA3) | TIMP-2 |
|  | Tumor necrosis factor alpha (TNF-α) | Tissue factor |
|  |  | Vascular endothelial growth factor (VEGF) |

The term "hematopoietic stem cell" refers to a cell isolated from the blood or from the bone marrow that can renew itself, differentiate to a variety of specialized cells, mobilize out of the bone marrow into the circulating blood, and undergo programmed cell death (apoptosis). In some embodiments of the described invention, hematopoietic stem cells derived from human subjects express at least one type of cell surface marker, including, but not limited to, CD34, CD38, HLA-DR, c-kit, CD59, Sca-1, Thy-1, and/or CXCR-4, or a combination thereof.

"HLA-DR" refers to a human class II histocompatibility antigen present on several cell types, including antigen-presenting cells, B cells, monocytes, macrophages, and activated T cells.

The term "interleukin" as used herein refers to a cytokine secreted by white blood cells as a means of communication with other white blood cells.

The term "implant" refers to any device or material inserted or placed, permanently or temporarily, into or onto a subject as well as those used for the administration or delivery of a therapeutic agent(s) or substance.

The term "improve" (or improving) as used herein refers to bring into a more desirable or excellent condition.

The terms "in the body", "void volume", "resection pocket", "excavation", "injection site", "deposition site" or "implant site" as used herein are meant to include all tissues of the body without limit, and may refer to spaces formed therein from injections, surgical incisions, tumor or tissue removal, tissue injuries, abscess formation, or any other similar cavity, space, or pocket formed thus by action of clinical assessment, treatment or physiologic response to disease or pathology as non-limiting examples thereof.

The term "indicator" as used herein refers to any substance, number or ratio derived from a series of observed facts that may reveal relative changes as a function of time; or a signal, sign, mark, note or symptom that is visible or evidence of the existence or presence thereof.

The term "inflammation" as used herein refers to the physiologic process by which vascularized tissues respond to injury. See, e.g., FUNDAMENTAL IMMUNOLOGY, 4th Ed., William E. Paul, ed. Lippincott-Raven Publishers, Philadelphia (1999) at 1051-1053, incorporated herein by reference. During the inflammatory process, cells involved in detoxification and repair are mobilized to the compromised site by inflammatory mediators. Inflammation is often characterized by a strong infiltration of leukocytes at the site of inflammation, particularly neutrophils (polymorphonuclear cells). These cells promote tissue damage by releasing toxic substances at the vascular wall or in uninjured tissue. Traditionally, inflammation has been divided into acute and chronic responses.

The term "acute inflammation" as used herein refers to the rapid, short-lived (minutes to days), relatively uniform response to acute injury characterized by accumulations of fluid, plasma proteins, and neutrophilic leukocytes. Examples of injurious agents that cause acute inflammation include, but are not limited to, pathogens (e.g., bacteria, viruses, parasites), foreign bodies from exogenous (e.g. asbestos) or endogenous (e.g., urate crystals, immune complexes), sources, and physical (e.g., burns) or chemical (e.g., caustics) agents.

The term "chronic inflammation" as used herein refers to inflammation that is of longer duration and which has a vague and indefinite termination. Chronic inflammation takes over when acute inflammation persists, either through incomplete clearance of the initial inflammatory agent or as a result of multiple acute events occurring in the same location. Chronic inflammation, which includes the influx of lymphocytes and macrophages and fibroblast growth, may result in tissue scarring at sites of prolonged or repeated inflammatory activity.

The term "injury," as used herein, refers to damage or harm to a structure or function of the body caused by an outside agent or force, which may be physical or chemical.

The term "isolate" and its various grammatical forms as used herein refers to placing, setting apart, or obtaining a protein, molecule, substance, nucleic acid, peptide, cell or particle, in a form essentially free from contaminants or other materials with which it is commonly associated, separate from its natural environment.

The term "labeling" as used herein refers to a process of distinguishing a compound, structure, protein, peptide, antibody, cell or cell component by introducing a traceable constituent. Common traceable constituents include, but are not limited to, a fluorescent antibody, a fluorophore, a dye or a fluorescent dye, a stain or a fluorescent stain, a marker, a fluorescent marker, a chemical stain, a differential stain, a differential label, and a radioisotope.

The term "labile" as used herein refers to subject to increased degradation.

The terms "marker" or "cell surface marker" are used interchangeably herein to refer to an antigenic determinant or epitope found on the surface of a specific type of cell. Cell surface markers can facilitate the characterization of a cell type, its identification, and eventually its isolation. Cell sorting techniques are based on cellular biomarkers where a cell surface marker(s) may be used for either positive selection or negative selection, i.e., for inclusion or exclusion, from a cell population.

The term "matrix" refers to a surrounding substance within which something is contained or embedded.

The term "mechanical agitation" as used herein refers to a process whereby tissue is physically shaken or churned via mechanical means. Such mechanical means include, but are not limited to, a mixer or other mechanical device.

The term "mesenchymal stem cells (MSCs)" as used herein refers to non-blood adult stem cells found in a variety of tissues. They are characterized by their spindle-shape morphologically; by the expression of specific markers on their cell surface; and by their ability under appropriate conditions, to differentiates along a minimum of three lineages (osteogenic, chondrogenic and adipogenic). When referring to bone or cartilage, MSCs commonly are known as osteochondrogenic, osteogenic, or chondrogenic, since a single MSC has shown the ability to differentiate into chondrocytes or osteoblasts, depending on the medium.

MSCs secrete many biologically important molecules, including interleukins 6, 7, 8, 11, 12, 14, and 15, M-CSF, Flt-3 ligand, SCF, LIF, bFGF, VEGF, P1GF and MCP1 (Majumdar, et al., J. Cell Physiol. 176: 57-66 (1998), Kinnaird et al, Circulation 109: 1543-49 (2004)). In 2004, it was reported that no single marker that definitively identifies MSCs in vivo had yet been identified, due to the lack of consensus from diverse documentations of the MSC phenotype. Baksh, et al., J. Cell. Mol. Med. 8(3): 301-16, 305 (2004). There is general agreement that MSCs lack typical hematopoietic antigens, namely CD14, CD34, and CD45. (Id.; citing Pittenger, M. F. et al., Science 284: 143-47 (1999)).

The term "mill," and its various grammatical forms, as used herein refers to grind, to cut, to shred, to chip, or to pulverize a substance.

The term "mounted section thickness" as used herein, refers to the thickness of tissue sections after histological processing.

The term "multipotent" as used herein refers to a cell capable of giving rise to a limited number of cell types of a particular cell line.

The term "myogenic" refers to a potential of undifferentiated precursor cells to differentiate into a muscle forming or myocompetent cells.

The term "Optical Disector" refers to a stereological probe for counting or selecting objects in a tissue section. This is an extension to the basic Disector method, which is applied to a thick section using a series, or stack, of Disectors. Rather than using pairs of physical sections (the basic Disector method), optical sectioning is used by creating focal planes with a thin depth-of-field through the section. The Optical Disector begins with a lookup section at the top of the optical disector and ends with a reference section at the bottom of the optical disector. The focal plane is the current reference section. The lookup section is immediately above the focal plane. A particle in focus at the top of the optical disector is therefore seen in the lookup section and not counted. A particle in focus at the bottom of the optical disector is in the reference section and therefore not in the lookup section, is counted. Counting frame rules are applied when the particle first comes into focus.

The term "osteoblasts" as used herein refers to cells that arise when osteoprogenitor cells or mesenchymal cells, which are located near all bony surfaces and within the bone marrow, differentiate under the influence of growth factors. Osteoblasts, which are responsible for bone matrix synthesis, secrete a collagen rich ground substance essential for later mineralization of hydroxyapatite and other crystals. The collagen strands to form osteoids (spiral fibers of bone matrix). Osteoblasts cause calcium salts and phosphorus to precipitate from the blood, which bond with the newly formed osteoid to mineralize the bone tissue. Once osteoblasts become trapped in the matrix they secrete, they become osteocytes. From least to terminally differentiated, the osteocyte lineage is (i) Colony-forming unit-fibroblast (CFU-F); (ii) mesenchymal stem cell/marrow stromal cell (MSC); (iii) osteoblast; and (iv) osteocyte.

The term "osteocalcin" as used herein refers to a protein constituent of bone; circulating levels are used as a marker of increased bone turnover.

The term "osteoclast" as used herein refers to large multinucleate cells associated with areas of bone resorption (breakdown).

The term "osteoconduction" as used herein refers to a process by which bone is directed so as to conform to a material's surface. An osteoconductive surface is one that permits bone growth on its surface or down into pores, channels or pipes. Osteoconductive material facilitates the spontaneous formation of bone by furnishing a microenvironment that supports the ingrowth of blood vessels, perivascular tissue and osteoprogenitor cells into the site where it is deposited. Examples of osteoconductive materials, include, but not limited to, processed human bone (allograft bone), purified collagen, calcium phosphate ceramics, synthetic polymers, BMP-2 and 4, VEGF, bFGF, TGF-β, and PDGF.

The term "osteoconductive matrix" as used herein refers to a matrix that is inert in and of itself but on which cells can climb and grow bone.

The term "osteogenic" refers to a potential of undifferentiated precursor cells to differentiate into bone forming or osteocompetent cells.

The term "osteogenesis" as used herein refers to the development or formation of new bone by bone forming or osteocompetent cells.

The term "osteoinduction" as used herein refers to a process by which primitive, undifferentiated and pluripotent cells are stimulated to develop into a bone forming cell lineage thereby inducing osteogenesis. For example, the majority of bone healing in a fracture is dependent on osteoinduction. Osteoinductive materials can be generated by combining a porous scaffold with osteogenic cells and/or osteoinductive components, including, but not limited to, growth factors such as BMP-2 and 4, VEGF, bFGF, TGF-β, and PDGF.

The term "osteoinductive matrix" as used herein refers to a matrix containing a substance or substances that recruit local cells to induce (meaning to cause, bring about, bring about, or trigger) local cells to produce bone.

The terms "osteoinductive components" or "osteogenic factors" are used interchangeably to refer to the plethora of mediators associated with bone development and repair, including, but not limited to, bone morphogenic proteins (BMPs), vascular endothelial growth factor (VEGF), basic fibroblast growth factor (bFGF), transforming growth factor beta (TGFβ), and platelet-derived growth factor (PDGF).

The term "osteointegration" refers to an anchorage mechanism whereby nonvital components can be incorporated reliably into living bone and that persist under all normal conditions of loading.

The term "particle" as used herein refers to a chip, fragment, slice, fiber or other small constituent of a larger body (e.g., picoparticles, nanoparticles, microparticles, milliparticle, centiparticle, deciparticle; fractions thereof, or, in some instances, a larger segment or piece).

The term "piece" as used herein refers to a particle, section, strip, chip, fragment, slice, fiber or other part, derived from, cut off, or broken from a larger unit.

The term "peptide" is used herein to refer to two or more amino acids joined by a peptide bond.

The term "periosteum" as used herein refers to the normal investment of bone, consisting of a dense, fibrous outer layer, to which muscles attach, and a more delicate, inner layer capable of forming bone.

The term "Platelet Derived Growth Factor" (PDGF) as used herein refers to a major mitogen for connective tissue cells and certain other cell types. It is a dimeric molecule consisting of disulfide-bonded, structurally similar A and B-polypeptide chains, which combine to homo- and heterodimers. The PDGF isoforms exert their cellular effects by binding to and activating two structurally related protein tyrosine kinase receptors, the α-receptor and the β-receptor. Activation of PDGF receptors leads to stimulation of cell growth, but also to changes in cell shape and motility; PDGF induces reorganization of the actin filament system and stimulates chemotaxis, i.e., a directed cell movement toward a gradient of PDGF. In vivo, PDGF plays a role in embryonic development and during wound healing.

The term "pluripotent" as used herein refers to the ability to develop into multiple cells types, including all three embryonic lineages, forming the body organs, nervous system, skin, muscle and skeleton.

The term "progenitor cell" as used herein refers to an early descendant of a stem cell that can only differentiate, but can no longer renew itself. Progenitor cells mature into precursor cells that mature into mature phenotypes. Hematopoietic progenitor cells are referred to as colony-forming units (CFU) or colony-forming cells (CFC). The specific lineage of a progenitor cell is indicated by a suffix, such as, but not limited to, CFU-E (erythrocytic), CFU-F (fibroblastic), CFU-GM (granulocytic/macrophage), and CFU-GEMM (pluripotent hematopoietic progenitor). Osteoclasts arise from hematopoietic cells of the monocyte/neutrophil lineage (CFU-GM). Osteoprogenitor cells arise from mesenchymal stem cells and are committed to an osteocyte lineage.

The term "propagate" as used herein refers to reproduce, multiply, or to increase in number, amount or extent by any process.

The term "purification" as used herein refers to the process of isolating or freeing from foreign, extraneous, or objectionable elements.

The term "random" as used herein refers to unpredictable. There is some element of chance. This is the opposite of deterministic, in which the next number or event is knowable.

The term "reduced" or "to reduce" as used herein refers to a diminishing, a decrease in, an attenuation or abatement of the degree, intensity, extent, size, amount, density or number of.

The term "regeneration" or "regenerate" as used herein refers to a process of recreation, reconstitution, renewal, revival, restoration, differentiation and growth to form a tissue with characteristics that conform with a natural counterpart of the tissue.

The term "relative" as used herein refers to something having, or standing in, some significant association to something else. The term "relative frequency" as used herein refer to the rate of occurrence of something having or standing in some significant association to the rate of occurrence of something else. For example, two cell types, X cells and Y cells occupy a given location. There are 5x cells and 5 Y cells in that location. The relative frequency of cell type X is 5/10; the relative frequency of cell type Y is 5/10 in that location. Following processing, there are 5x cells, but only 1 Y cell in that location. The relative frequency of cell type X following processing is 5/6, and the relative frequency of cell type Y following processing is 1/6 in that location.

The term "repair" as used herein as a noun refers to any correction, reinforcement, reconditioning, remedy, making up for, making sound, renewal, mending, patching, or the like that restores function. When used as a verb, it means to correct, to reinforce, to recondition, to remedy, to make up for, to make sound, to renew, to mend, to patch or to otherwise restore function. In some embodiments "repair" includes full repair and partial repair.

The term "resident," and its various grammatical forms, as used herein refers to being present habitually, existing in or intrinsic to or incorporated therein.

The term "rinse," and its various grammatical forms, as used herein refers to wash, to douse with a liquid or liquids or to flow a liquid or liquids over the material being rinsed.

The term "scaffold" as used herein refers to a structure capable of supporting a three-dimensional tissue formation. A three-dimensional scaffold is believed to be critical to replicate the in vivo milieu and to allow the cells to influence their own microenvironment. Scaffolds may serve to promote cell attachment and migration, to deliver and retain cells and biochemical factors, to enable diffusion of vital cell nutrients and expressed products, and to exert certain mechanical and biological influences to modify the behavior of the cell phase. A scaffold utilized for tissue reconstruction has several requisites. Such a scaffold should have a high porosity and an adequate pore size to facilitate cell seeding and diffusion of both cells and nutrients throughout the whole structure. Biodegradability of the scaffold is also an essential requisite. The scaffold should be absorbed by the surrounding tissues without the necessity of a surgical removal, such that the rate at which degradation occurs coincides as closely as possible with the rate of tissue formation. As cells are fabricating their own natural matrix structure around themselves, the scaffold provides structural integrity within the body and eventually degrades leaving the neotissue (newly formed tissue) to assume the mechanical load.

The term "section" when used in the context of stereology refers to a cut through material that has effectively zero thickness compared to the size of the particles being studied. Biologists refer to sections as thick slices through tissue. The actual thickness of sections can leads to the Holmes effect.

The term "side-effect" as used herein refers to a result of a therapy in addition to, or in extension of, the desired therapeutic effect.

The term "similar" is used interchangeably with the terms analogous, comparable, or resembling, meaning having traits or characteristics in common.

A "solution" generally is considered as a homogeneous mixture of two or more substances. It is frequently, though not necessarily, a liquid. In a solution, the molecules of the solute (or dissolved substance) are uniformly distributed among those of the solvent. The term "solvent" as used herein refers to a substance capable of dissolving another substance (termed a "solute") to form a uniformly dispersed mixture (solution).

The term "stain" as used herein refers to a composition of a dye(s) or pigment(s) used to make a structure, a material, a cell, a cell component, a membrane, a granule, a nucleus, a cell surface receptor, a peptide, a microorganism, a nucleic acid, a protein or a tissue differentiable.

The term "Sca-1" or "stem cell antigen-1" refers to a surface protein component in a signaling pathway that affects the self-renewal ability of mesenchymal stem cells.

The term "stem cells" refers to undifferentiated cells having high proliferative potential with the ability to self-renew (make more stem cells by cell division) that can generate daughter cells that can undergo terminal differentiation into more than one distinct cell phenotype.

The term "stereology" as used herein refers to a method of quantifying 2D and 3D structures using estimation methods.

The term "stimulate" as used herein refers to activate, provoke, or spur. The term "stimulating agent" as used herein refers to a substance that exerts some force or effect.

The phrase "subject in need thereof" as used herein refers to a patient that (i) will be administered at least one allograft, (ii) is receiving at least one allograft; or (iii) has received at least one allograft, unless the context and usage of the phrase indicates otherwise.

The term "substantially similar" as used herein means that a first value, aspect, trait, feature, number, or amount is of at least 70%, at least 75%, at least 80%, at least 85%, at least 90%, or at least 95% of a second value, aspect, trait, feature, number, or amount.

The term "surfactant", as used herein, refers to a surface-active agent that acts to reduce surface tension, which is the elastic like force existing in the surface of a body, e.g., a liquid, at an interface between two liquids, or that between a liquid and a solid, tending to minimize the area of the surface, caused by asymmetries in the intermolecular forces between surface molecules. Surfactants usually are organic comounds that contain both hydrophobic groups and hydrophilic groups, i.e., are amphiphilic. Surfactants can be anionic, cationic, nonionic, and zwitterionic. Exemplary surfactants include, but are not limited to, Triton®, Tween® 80, egg lecithin, vitamin E-t d-α-tocopheryl polyethylene glycol 1000 succinate (TPGS). Exemplary surfactants suitable for use in this invention are described in, for example, Becher, Emulsions Theory and Practice; Robert E. Krieger Publishing, Malabar, Fla. (1965), which is incorporated herein by reference.

The term "symptom" as used herein refers to a sign or an indication of disorder or disease, especially when experienced by an individual as a change from normal function, sensation, or appearance.

The term "therapeutic effect" as used herein refers to a consequence of treatment, the results of which are judged to be desirable and beneficial. A therapeutic effect may include, directly or indirectly, the arrest, reduction, or elimination of a disease manifestation. A therapeutic effect also may include, directly or indirectly, the arrest reduction or elimination of the progression of a disease manifestation.

The term "tissuegenic" as used herein refers to a potential of an undifferentiated precursor cell to differentiate into a mature cell type and to regenerate a tissue. Exemplary tissuegenic cells include but are not limited to a stem cell, a progenitor cell or a combination thereof. The term "osteogenic" refers more specifically to cell differentiation and tissue regeneration with regard to bone.

The term "transforming growth factor beta (TGFβ) signaling pathway" is used herein to refer to the signaling pathway is involved in many cellular processes in both the adult organism and the developing embryo including cell growth, cell differentiation, apoptosis, cellular homeostasis and other cellular functions. TGFβ superfamily ligands bind to a type II receptor, which recruits and phosphorylates a type I receptor. The type I receptor then phosphorylates receptor-regulated SMADs (R-SMADs) which can now bind the coSMAD SMAD4. R-SMAD/coSMAD complexes accumulate in the nucleus where they act as transcription factors and participate in the regulation of target gene expression.

The term "treat" or "treating" includes abrogating, substantially inhibiting, slowing or reversing the progression of a disease, condition or disorder, substantially ameliorating clinical or esthetical symptoms of a condition, substantially preventing the appearance of clinical or esthetical symptoms of a disease, condition, or disorder, and protecting from harmful or annoying symptoms. Treating further refers to accomplishing one or more of the following: (a) reducing the severity of the disorder; (b) limiting development of symptoms characteristic of the disorder(s) being treated; (c) limiting worsening of symptoms characteristic of the disorder(s) being treated; (d) limiting recurrence of the disorder (s) in patients that have previously had the disorder(s); and (e) limiting recurrence of symptoms in patients that were previously asymptomatic for the disorder(s).

The term "vascularization" as used herein refers to a process of ingrowth of blood vessels and perivascular tissue within a growth-conductive matrix to support the deposition and adhesion of tissuegenic cells to effect tissue regeneration.

The terms "VEGF", "VEGF-1" or "vascular endothelial growth factor-1" are used interchangeably herein to refer to a cytokine that mediates numerous functions of endothelial cells including proliferation, migration, invasion, survival, and permeability. The term "VEGF-2" refers to a regulator for growth of vascular endothelial and smooth muscle cells. VEGF-2 stimulates the growth of human vascular endothelial cells but inhibits growth of human aortic smooth muscle cells induced by platelet-derived growth factor.

The term "viable" as used herein refers to having the ability to grow, expand, or develop; capable of living.

The term "xenogeneic" as used herein refers to cells or tissues derived from individuals of different species, including, but not limited to, porcine, bovine, caprine, equine, canine, lapine, feline, and/or non-human mammals, such as, but not limited to, whale, and porpoise.

1. Implant

According to one aspect, the described invention provides an implant comprising (a) a plurality of pieces comprising at least one tissue-derived growth-conductive matrix; and (b) at least one viable population of tissuegenic cells.

According to one embodiment, the at least one viable population of tissuegenic cells is adherent to and resident in an endogenous milieu of the growth-conductive matrix. According to another embodiment, the at least one viable population of tissuegenic cells is caused to be in contact with the growth-conductive matrix.

According to one embodiment, the implant is an allogeneic implant. According to another embodiment, the implant is an autologous implant. According to another embodiment, the implant is a xenogeneic implant.

A Tissue Comprising a Matrix and Tissuegenic Cells

According to one embodiment, a tissue that comprises a growth-conductive matrix and at least one viable population of tissuegenic cells is selected from the group consisting of an adipose tissue, an amnion tissue, an artery tissue, a bone tissue, a cartilage tissue, a chorion tissue, a colon tissue, a dental tissue, a dermal tissue, a duodenum tissue, an epithelial tissue, a fascial tissue, a gastrointestinal tissue, a growth plate tissue, an intestinal mucosal tissue, an intestinal serosal tissue, an intervertebral disc tissue, a kidney tissue, a ligament tissue, a liver tissue, a lung tissue, a mammary tissue, a meniscal tissue, a muscle tissue, a nerve tissue, an ovary tissue, a pancreas tissue, a parenchymal organ tissue, a pericardial tissue, a periosteal tissue, a peritoneal tissue, a placental tissue, a reproductive epithelial tissue, a respiratory epithelial tissue, a skin tissue, a spleen tissue, a stomach tissue, a synovial tissue, a tendon tissue, a testes tissue, an umbilical cord tissue, a urological tissue, a vascular tissue, a vein tissue, and, a combination thereof.

According to one embodiment, the tissue comprises an adipose tissue. According to one embodiment, the tissue comprises an amnion tissue. According to one embodiment, the tissue comprises an artery tissue. According to one embodiment, the tissue comprises a bone tissue. According to one embodiment, the tissue comprises a cartilage tissue. According to one embodiment, the tissue comprises a chorion tissue. According to one embodiment, the tissue comprises a colon tissue. According to one embodiment, the tissue comprises a dental tissue. According to one embodiment, the tissue comprises a dermal tissue. According to one embodiment, the tissue comprises a duodenal tissue. According to one embodiment, the tissue comprises an epithelial tissue. According to one embodiment, the tissue comprises a fascial tissue. According to one embodiment, the tissue comprises a gastrointestinal tissue. According to one embodiment, the tissue comprises a growth plate tissue. According to one embodiment, the tissue comprises an intervertebral disc tissue. According to one embodiment, the tissue comprises an intestinal mucosal tissue. According to one embodiment, the tissue comprises an intestinal serosal tissue. According to one embodiment, the tissue comprises a kidney tissue. According to one embodiment, the tissue comprises a ligament tissue. According to one embodiment, the tissue comprises a liver tissue. According to one embodiment, the tissue comprises a lung tissue. According to one embodiment, the tissue comprises a mammary tissue. According to one embodiment, the tissue comprises a meniscal tissue. According to one embodiment, the tissue comprises a muscle tissue. According to one embodiment, the tissue comprises a nerve tissue. According to one embodiment, the tissue comprises an ovarian tissue. According to one embodiment, the tissue comprises a pancreatic tissue. According to one embodiment, the tissue comprises a parenchymal organ tissue. According to one embodiment, the tissue comprises a pericardial tissue tissue. According to one embodiment, the tissue for fabricating the at implant comprises a periosteal tissue. According to one embodiment, the tissue comprises a peritoneal tissue. According to one embodiment, the tissue for fabricating the at implant comprises a placental tissue. According to one embodiment, the tissue for fabricating the at implant comprises a reproductive epithelial tissue. According to one embodiment, the tissue for fabricating the at implant comprises a respiratory epithelial tissue. According to one embodiment, the tissue comprises a skin tissue. According to one embodiment, the tissue comprises a spleen tissue. According to one embodiment, the tissue comprises a stomach tissue. According to one embodiment, the tissue comprises a synovial tissue. According to one embodiment, the implant comprises a tendon tissue. According to one embodiment, the tissue comprises a testes tissue. According to one embodiment, the tissue comprises an umbilical cord tissue. According to one embodiment, the implant comprises a tendon tissue. According to one embodiment, the tissue comprises a urological tissue. According to one embodiment, the tissue comprises a vascular tissue. According to one embodiment, the tissue comprises a vein tissue.

According to one embodiment, the tissue is derived from a parenchymal organ. The term "parenchymal organ" as used herein refers to an organ in which a specialized cell type carries out a specialized physiological function of the organ. According to one embodiment, the parenchymal organ is selected from the group consisting of an artery, a brain, a colon, a duodenum, an intestinal mucosa, an intestinal serosa, a kidney, a liver, a lung, an ovary, a pancreas, a pericardium, a periotoneum, a spleen, a stomach, a testis, a vein, and a combination thereof. According to some embodiments, the parenchymal organ comprises an artery. According to some embodiments, the parenchymal organ comprises a brain. According to some embodiments, the parenchymal organ comprises a colon. According to some embodiments, the parenchymal organ comprises a duodenum. According to some embodiments, the parenchymal organ comprises an intestinal mucosa. According to some embodiments, the parenchymal organ comprises an intestinal serosa. According to some embodiments, the parenchymal organ comprises a kidney. According to some embodiments, the parenchymal organ comprises a liver. According to some embodiments, the parenchymal organ comprises a lung. According to some embodiments, the parenchymal organ comprises an ovary. According to some embodiments, the parenchymal organ comprises a pancreas. According to some embodiments, the parenchymal organ comprises a pericardium. According to some embodiments, the parenchymal organ comprises a periotoneum. According to some embodiments, the parenchymal organ comprises a spleen. According to some embodiments, the parenchymal organ comprises a stomach. According to some embodiments, the parenchymal organ comprises a testis. According to some embodiments, the parenchymal organ comprises a vein.

According to one embodiment, the tissue comprises an autologous tissue. According to another embodiment, the tissue comprises an allogeneic tissue. According to another embodiment, the tissue comprises a xenogeneic tissue.

According to one embodiment, the source of the tissue is a mammalian donor. According to one embodiment, the source of the tissue is a human donor. According to one embodiment, the human donor is a living donor. According to another embodiment, is the human donor is a cadeveric donor.

Adipose Tissue

According to some embodiments, the tissue comprises an adipose tissue derived from an adipose-rich body region.

According to some embodiments, the adipose rich body region is selected from the group consisting of an abdomen, a hip, a hypodermal region of skin, an infrapatellar fat pad, a knee, a mammary organ, a thigh, and, a combination thereof. According to some embodiments, the adipose rich body region is an abdomen. According to some embodiments, the adipose rich body region is a hip. According to some embodiments, the adipose rich body region is a hypodermal region of skin. According to some embodiments, the adipose rich body region is an infrapatellar fat pad. According to some embodiments, the adipose rich body region is a knee. According to some embodiments, the adipose rich body region is a mammary organ. According to some embodiments, the adipose rich body region is a thigh.

According to some embodiments, the tissue is an adipose tissue selected from the group consisting of a visceral adipose tissue, a subcutaneous adipose tissue and, a combination thereof. According to some embodiments, the tissue is an adipose tissue comprising a visceral adipose tissue. According to some embodiments, the tissue is an adipose tissue comprising a subcutaneous adipose tissue.

According to one embodiment, the source of the tissue is a mammalian donor. According to some embodiments, the tissue is an adipose tissue derived from an adipose-rich body region of a human donor. According to some embodiments, the human donor is a cadaveric donor. According to some embodiments, the human donor is of a living donor.

According to one embodiment, the tissue is an adipose tissue derived from an autologous adipose tissue. According to one embodiment, the tissue is an adipose tissue comprising an adipose tissue derived from an allogeneic adipose tissue. According to one embodiment, the tissue is an adipose tissue comprising an adipose tissue derived from a xenogeneic adipose tissue.

Bone Tissue

According to some embodiments, the tissue comprises a bone tissue or at least one fragment thereof.

According to another embodiment, the bone tissue comprises a cancellous bone. According to some such embodiments, the cancellous bone is selected from the group consisting of a calcaneus, a distal femur bone, a proximal femur, a proximal humerus, an ilium, a patella, a distal tibia, a proximal tibia, a scapula, a cancellous bone from a sternum, a talus, at least one vertebral body and, a combination thereof. According to some embodiments, the bone tissue comprises a periosteum.

According to some such embodiments, the cancellous bone comprises cancellous bone from a calcaneus. According to some such embodiments, the cancellous bone comprises cancellous bone from a distal femur. According to some such embodiments, the cancellous bone comprises cancellous bone from a proximal femur. According to some such embodiments, the cancellous bone comprises cancellous bone from a proximal humerus. According to some such embodiments, the cancellous bone comprises cancellous bone from an ilium. According to some such embodiments, the cancellous bone comprises cancellous bone from a patella. According to some such embodiments, the cancellous bone comprises cancellous bone from a distal tibia. According to some such embodiments, the cancellous bone comprises cancellous bone from a proximal tibia. According to some such embodiments, the cancellous bone comprises cancellous bone from a scapula. According to some such embodiments, the cancellous bone comprises cancellous bone from a sternum. According to some such embodiments, the cancellous bone comprises cancellous bone from a talus. According to some embodiments, the cancellous bone comprises cancellous bone from at least one vertebral body. A vertebral body refers to the largest portion of a vertebral unit of a vertebral column.

According to another embodiment, the bone tissue comprises a cortical bone. According to some such embodiments, the cortical bone is selected from the group consisting of a calcaneus, a distal femur bone, a proximal femur, a proximal humerus, an ilium, a patella, a distal tibia, a proximal tibia, a scapula, a cancellous bone from a sternum, a talus, at least one vertebral body and, a combination thereof.

According to some such embodiments, the cortical bone comprises cortical bone from a calcaneus. According to some such embodiments, the cortical bone comprises cortical bone from a distal femur. According to some such embodiments, the cortical bone comprises cortical bone from a proximal femur. According to some such embodiments, the cortical bone comprises cortical bone from a proximal humerus. According to some such embodiments, the cortical bone comprises cortical bone from an ilium. According to some such embodiments, the cortical bone comprises cortical bone from a patella. According to some such embodiments, the cortical bone comprises cortical bone from a distal tibia. According to some such embodiments, the cortical bone comprises cortical bone from a proximal tibia. According to some such embodiments, the cortical bone comprises cortical bone from a scapula. According to some such embodiments, the cortical bone comprises cortical bone from a sternum. According to some such embodiments, the cortical bone comprises cortical bone from a talus. According to some embodiments, the cortical bone comprises cortical bone from at least one vertebral body.

According to some such embodiments, the bone is at least one fragment of an ilium. According to some such embodiments, the bone is at least one fragment of a long bone. According to some such embodiments, the long bone is selected from the group consisting of a femur, a fibula, a humerus, a metacarpal, a metatarsal, a phalange, a radius, a tibia, an ulna and, a combination thereof. According to some such embodiments, the long bone is a femur. According to some such embodiments, the long bone is a fibula. According to some such embodiments, the long bone is a humerus. According to some such embodiments, the long bone is a metacarpal. According to some such embodiments, the long bone is a metatarsal. According to some such embodiments, the long bone is a phalange. According to some such embodiments, the long bone is a radii. According to some such embodiments, the long bone is a tibia. According to some such embodiments, the long bone is an ulna.

According to one embodiment, the source of the tissue is a mammalian donor. According to some embodiments, the tissue is a bone tissue derived from a human donor. According to some embodimentshuman donor is a cadaveric donor. According to some embodiments, the human donor is a living donor.

According to one embodiment, the tissue is a bone tissue derived from an autologous bone tissue. According to one embodiment, the tissue is a bone tissue derived from an allogeneic bone tissue. According to one embodiment, the tissue is a bone tissue derived from a xenogeneic bone tissue.

According to some embodiments, the synovial tissue comprises a synovial membrane tissue. According to some embodiments, the synovial tissue is derived from a synovial joint. According to some such embodiments, the synovial joint is at least one selected from the group consisting of a knee, an elbow, a shoulder, a hip, a condyloid joint, a pivot joint, and, a combination thereof. According to some such embodiments, the synovial joint comprises a synovial joint of a knee. According to some such embodiments, the synovial joint comprises a synovial joint of an elbow. According to some such embodiments, the synovial joint comprises a synovial joint of a shoulder. According to some such embodiments, the synovial joint comprises a synovial joint of a hip. According to some such embodiments, the synovial joint comprises a condyloid joint. According to some such embodiments, the synovial joint comprises a pivot joint.

According to some embodiments, the tissue comprises a tendon. As used herein the term "tendon" refer to a nondistensible fibrous court or band of variable length that is the part of the muscle that connects the fleshy/contractile part of muscle with its bony attachment or other structure. It consists of fascicles of very densely arranged, almost parallel collagenous fibers, rows of elongated fibrocytes, and a minimum of ground substance.

According to some embodiments, the tendon is derived from a cadaveric donor. According to some embodiments, the tendon is derived from a living donor. According to one embodiment, the tissue is an autologous tendon. According to one embodiment, the tissue is an allogeneic tendon. According to one embodiment, the tissue is a xenogeneic tendon.

Cartilage Tissue

According to some embodiments, the tissue comprises a cartilage tissue selected from the group consisting of a hyaline cartilage tissue, a fibrocartilage tissue, an elastic cartilage tissue and, a combination thereof. According to some embodiments, the tissue comprises a hyaline cartilage tissue. According to some embodiments, the tissue comprises a a fibrocartilage cartilage tissue. According to some embodiments, the tissue comprises an elastic cartilage tissue.

According to some embodiments, the tissue comprises a cartilage tissue derived from a cartilaginous organ or at least one fragment thereof.

According to some embodiments, the cartilaginous organ is selected from the group consisting of an articular cartilage organ, a bronchus, a growth plate, an intervertebral disc, a larynx, a meniscus, a nose, a trachea and, a combination thereof. According to some embodiments, the cartilaginous organ is an articular cartilage organ. According to some embodiments, the cartilaginous organ is a bronchus. According to some embodiments, the cartilaginous organ is a growth plate. According to some embodiments, the cartilaginous organ is an intervertebral disc. According to some embodiments, the cartilaginous organ is a larynx. According to some embodiments, the cartilaginous organ is a meniscus. According to some embodiments, the cartilaginous organ is a nose. According to some embodiments, the cartilaginous organ is a trachea.

According to one embodiment, the source of the tissue is a mammalian donor. According to some embodiments, the tissue comprises a cartilage tissue derived from a human donor. According to some embodiments, the human donor is a cadaveric donor. According to some embodiments, from the human donor is a living donor.

According to one embodiment, the tissue is a cartilage tissue derived from an autologous cartilage tissue. According to one embodiment, the tissue is a cartilage tissue derived from an allogeneic cartilage tissue. According to one embodiment, the tissue is a cartilage tissue derived from a xenogeneic cartilage tissue.

Dental Tissue

According to some embodiments, the tissue comprises a dental tissue. According to some such embodiments, the tissue comprises a dental tissue selected from the group consisting of a tooth, a cementum tissue, a dental pulp tissue, a dentin tissue, and an enamel tissue and, a combination thereof. According to some embodiments, the tissue comprises a dental tissue comprising a cementum tissue. According to some embodiments, the tissue comprises a dental tissue comprising a dental pulp tissue. According to some embodiments, the tissue comprises a dental tissue comprising a dentin tissue. According to some embodiments, the tissue comprises a dental tissue comprising an enamel tissue.

According to some embodiments, the tissue comprises a dental tissue derived from at least one tooth or at least one fragment thereof. According to some embodiments, the tissue comprises a dental tissue derived from a plurality of teeth.

According to some embodiments, the tissue comprises a dental tissue derived from a tooth crown. According to some embodiments, the tissue comprises a dental tissue derived from at least one fragment of a tooth crown. According to some embodiments, the tissue comprises a dental tissue derived from a tooth root. According to some embodiments, the tissue comprises a dental tissue derived from at least one fragment of a tooth root. According to some embodiments, the tissue comprises a dental tissue derived from a tooth neck. According to some embodiments, the tissue is a dental tissue comprises adental tissue derived from at least one fragment of a tooth neck.

According to some embodiments, the tooth is selected from the group consisting of a deciduous tooth, a permanent tooth, and, a combination thereof. According to some embodiments, the tooth is a deciduous tooth. According to some embodiments, the tooth is a permanent tooth.

According to one embodiment, the source of the tissue is a mammalian donor. According to some embodiments, the tissue is a dental tissue derived from a human donor. According to some embodiments, the human donor is a cadaveric donor. According to some embodiments, the human donor is a living donor.

According to one embodiment, the tissue is an autologous dental tissue. According to one embodiment, the tissue is an allogeneic dental tissue. According to one embodiment, the tissue is a xenogeneic dental tissue.

Epithelial Tissue

According to some embodiments, the tissue comprises an epithelial tissue selected from the group consisting of a cutaneous epithelial tissue, a mucuous epithelial tissue, a serous epithelial tissue and, a combination thereof. According to some embodiments, the tissue comprises a cutaneous epithelial tissue. According to some embodiments, the tissue comprises a mucuous epithelial tissue. According to some embodiments, the tissue comprises a serous epithelial tissue. According to some embodiments, the tissue comprises a basement membrane tissue.

According to some embodiments, the tissue comprises an epithelial tissue derived from an epithelial organ or at least one fragment thereof.

According to some embodiments, the epithelial tissue is selected from the group consisting of a gastrointestinal lining, a pericardial lining, a peritoneal lining, a pleural lining, a reproductive, a respiratory lining, a urinary lining and, a combination thereof. According to some embodiments, the epithelial tissue is derived from a gastrointestinal lining. According to one embodiment, the epithelial tissue is derived from an intestinal mucosal lining. According to one embodiment, the epithelial tissue is derived from an intestinal serosal lining. According to some embodiments, the epithelial tissue is derived from a pericardial lining. According to some embodiments, the epithelial tissue is derived from a peritoneal lining. According to some embodiments, the epithelial tissue is derived from a pleural lining. According to some embodiments, the epithelial tissue is derived from a reproductive lining. According to some embodiments, the epithelial tissue is derived from a respiratory lining. According to some embodiments, the epithelial tissue is derived from a urinary lining.

According to some embodiments, the gastrointestinal lining is selected from the group consisting of a duodenum lining, an esophagus lining, an ileum lining, a jejunum lining, a large intestine lining, a mouth lining, a pharynx lining, a small intestine lining, a stomach lining and, a combination thereof. According to some embodiments, the gastrointestinal lining is a duodenum lining. According to some embodiments, the gastrointestinal lining is an esophagus lining. According to some embodiments, the gastrointestinal lining is an ileum lining. According to some embodiments, the gastrointestinal lining is a jejunum lining. According to some embodiments, the gastrointestinal lining is a large intestine lining. According to some embodiments, the gastrointestinal lining is a pharynx lining. According to some embodiments, the gastrointestinal lining is a small intestine lining. According to some embodiments, the gastrointestinal lining is a stomach lining.

According to some embodiments, the epithelial organ is selected from the group consisting of a gastrointestinal organ, a respiratory organ, a urological organ and, a combination thereof. According to some embodiments, the epithelial organ comprises a gastrointestinal organ. According to some embodiments, the epithelial organ comprises a respiratory organ. According to some embodiments, the epithelial organ comprises a urological organ.

According to some embodiments, the gastrointestinal organ is selected from the group consisting of a duodenum, an esophagus, an ileum, a jejunum, a large intestine, a mouth, a small intestine, a stomach and a combination thereof. According to some embodiments, the gastrointestinal organ comprises a duodenum. According to some embodiments, the gastrointestinal organ comprises an esophagus. According to some embodiments, the gastrointestinal organ comprises an ileum. According to some embodiments, the gastrointestinal organ comprises a jejunum. According to some embodiments, the gastrointestinal organ comprises a large intestine. According to some embodiments, the gastrointestinal organ comprises a small intestine. According to some embodiments, the gastrointestinal organ comprises a stomach.

According to some embodiments, the respiratory organ is selected from the group consisting of a bronchii, a diaphragm, a heart, a larynx, a lung, a mouth, a nose, a pharynx, a trachea and a combination thereof. According to some embodiments, the respiratory organ comprises a bronchii. According to some embodiments, the respiratory organ comprises a diaphragm. According to some embodiments, the respiratory organ comprises a heart. According to some embodiments, the respiratory organ comprises a larynx. According to some embodiments, the respiratory organ a lung. According to some embodiments, the respiratory organ comprises a mouth. According to some embodiments, the respiratory organ comprises a nose. According to some embodiments, the respiratory organ comprises a pharynx. According to some embodiments, the respiratory organ comprises a trachea.

According to some embodiments, the urological organ is selected from the group consisting of an adrenal gland, an epididymis, a kidney, an ovary, a penis, a prostate gland, a seminal vesicle, a testis, a ureter, a urethra, a urinary bladder, a vas deferens and a combination thereof. According to some embodiments, the urological organ comprises an adrenal gland. According to some embodiments, the urological organ comprises an epididymis. According to some embodiments, the urological organ comprises a kidney. According to some embodiments, the urological organ comprises an ovary. According to some embodiments, the urological organ comprises a penis. According to some embodiments, the urological organ comprises a prostate gland. According to some embodiments, the urological organ comprises a seminal vesicle. According to some embodiments, the urological organ comprises a testis. According to some embodiments, the urological organ comprises a ureter. According to some embodiments, the urological organ comprises a urethra. According to some embodiments, the urological organ comprises a urinary bladder. According to some embodiments, the urological organ comprises a vas deferens.

According to some embodiments, the epithelial organ is selected from the group consisting of a duodenum, an esophagus, a heart, an ileum, a jejunum, a large intestine, a lung, a mouth, a pharynx, a small intestine, a skin, a stomach, and, a combination thereof. According to some embodiments, the epithelial organ comprises a duodenum. According to some embodiments, the epithelial organ comprises an esophagus. According to some embodiments, the epithelial organ comprises a heart. According to some embodiments, the epithelial organ comprises an ileum. According to some embodiments, the epithelial organ comprises a jejunum. According to some embodiments, the epithelial organ comprises a large intestine. According to some embodiments, the epithelial organ comprises a lung. According to some embodiments, the epithelial organ comprises a mouth. According to some embodiments, the epithelial organ comprises a pharynx. According to some embodiments, the epithelial organ comprises a small intestine. According to some embodiments, the epithelial organ is comprises a skin. According to some embodiments, the epithelial organ comprises a stomach.

According to one embodiment, the source of the tissue is a mammalian donor. According to some embodiments, the tissue is an epithelial tissue derived from a human donor. According to some embodiments, the human donor is a cadaveric donor. According to some embodiments, human donor is a living donor.

According to one embodiment, the tissue is an epithelial tissue derived from an autologous epithelial tissue. According to one embodiment, the tissue is an epithelial tissue derived from an allogeneic epithelial tissue. According to one embodiment, the tissue is an epithelial tissue derived from a xenogeneic epithelial tissue.

Fascial Tissue

According to some embodiments, the tissue comprises a fascial tissue selected from the group consisting of a superficial fascia, a deep fascia, a visceral fascia, and, a combination thereof. The term "fascia" as used herein refers to a fibroareolar connective tissue lamellae distributed throughout the body surrounding delicate organs. According to some embodiments, the tissue comprises a fascial tissue derived from a superficial fascia. According to some embodiments, the tissue comprises a fascial tissue derived from a deep fascia. According to some embodiments, the tissue comprises a fascial tissue derived from a visceral fascia ligament.

According to some embodiments, the tissue comprises a fascial tissue derived from a fascia-rich body part or at least one fragment thereof. According to some embodiments, the fascia-rich body part is selected from the group consisting of an arm, a back, an elbow, a foot, a hand, a head, a knee, a leg, a muscle, a neck, a skin, a thigh, a toe, a wrist, and, a combination thereof. According to some embodiments, the fascia-rich body part comprises an arm. According to some embodiments, the fascia-rich body part comprises a back. According to some embodiments, the fascia-rich body part comprises an elbow. According to some embodiments, the fascia-rich body part comprises a foot. According to some embodiments, the fascia-rich body part comprises a hand. According to some embodiments, the fascia-rich body part comprises a head. According to some embodiments, the fascia-rich body part comprises a knee. According to some embodiments, the fascia-rich body part comprises a leg. According to some embodiments, the fascia-rich body part comprises a muscle. According to some embodiments, the fascia-rich body part comprises a neck. According to some embodiments, the fascia-rich body part comprises a skin. According to some embodiments, the fascia-rich body part comprises a thigh. According to some embodiments, the fascia-rich body part comprises a toe. According to some embodiments, the fascia-rich body part comprises a wrist.

According to some embodiments, the tissue comprises fascial tissue selected from the group consisting of a myofascia associated with a muscle, palmar fascia associated with a palm of a hand, plantar fascia associated with a sole of a foot, thoracolumbar fascia associated with a back, fascii lata associated with a thigh, tensor fascia lata associated with tendon tissue, and a combination thereof. According to some embodiments, the tissue comprises a fascial tissue derived from myofascia associated with a muscle. According to some embodiments, the tissue comprises a fascial tissue derived from palmar fascia associated with a palm of a hand. According to some embodiments, the tissue comprises a fascial tissue derived from plantar fascia associated with a sole of a foot. According to some embodiments, the tissue comprises a fascial tissue derived from thoracolumbar fascia associated with a back. According to some embodiments, the tissue comprises a fascial tissue derived from fascii lata associated with a thigh. According to some embodiments, the tissue comprises a fascial tissue derived from tensor fascia lata associated with tendon tissue.

According to one embodiment, the source of the tissue is a mammalian donor. According to some embodiments, the tissue comprises a fascia tissue derived from a human donor. According to some embodiments, the human donor is a cadaveric donor. According to some embodiments, human donor is a living donor.

According to one embodiment, the tissue is a fascial tissue derived from an autologous fascia. According to one embodiment, the tissue is a fascial tissue derived from an allogeneic fascia. According to one embodiment, the tissue is a fascial tissue derived from a xenogeneic fascia.

Ligament Tissue

According to some embodiments, the tissue comprises a ligament tissue selected from the group consisting of a capsular ligament, an extra-capsular ligament, an intracapsular ligament, a cruciate ligament, and, a combination thereof. The term "ligament" as used herein refers to a band or sheet of fibrous tissue connecting two or more bones, cartilages, or other structures, or serving as support for fasciae or muscles and a fold of peritoneum supporting any of the abdominal viscera. According to some embodiments, the tissue comprises a ligament tissue derived from a capsular ligament. According to some embodiments, the tissue comprises a ligament tissue derived from an extra-capsular ligament. According to some embodiments, the tissue comprises a ligament tissue derived from an intracapsular ligament. According to some embodiments, the tissue comprises a ligament tissue derived from a cruciate ligament.

According to some embodiments, the tissue comprises a ligament tissue derived from a ligament-rich body part or at least one fragment thereof. According to some embodiments, the ligament-rich body part is selected from the group consisting of an arm, an elbow, a foot, a hand, a head, a knee, a leg, a neck, a pelvis, a phalange, a thorax, a toe, a wrist, and, a combination thereof. According to some embodiments, the ligament-rich body part comprises an arm. According to some embodiments, the ligament-rich body part comprises an elbow. According to some embodiments, the ligament-rich body part comprises a foot. According to some embodiments, the ligament-rich body part comprises a hand. According to some embodiments, the ligament-rich body part comprises a head. According to some embodiments, the ligament-rich body part comprises a knee. According to some embodiments, the ligament-rich body part comprises a leg. According to some embodiments, the ligament-rich body part comprises a neck. According to some embodiments, the ligament-rich body part comprises a pelvis. According to some embodiments, the ligament-rich body part comprises a phalange. According to some embodiments, the ligament-rich body part comprises a thorax. According to some embodiments, the ligament-rich body part comprises a toe. According to some embodiments, the ligament-rich body part comprises a wrist.

According to some embodiments, the tissue comprises a ligament tissue derived from a ligament organ or a fragment thereof. According to some embodiments, the ligament organ is selected from the group consisting of a joint, a mouth, a patella, and, a combination thereof. According to some embodiments, the ligament organ comprises a joint. According to some embodiments, the ligament organ comprises a mouth. According to some embodiments, the ligament organ comprises a patella.

According to one embodiment, the source of the tissue is a mammalian donor. According to some embodiments, the tissue comprises a ligament tissue derived from a human donor. According to some embodiments, the human donor is a cadaveric donor. According to some embodiments, human donor is a living donor.

According to one embodiment, the tissue is a ligament tissue derived from an autologous ligament. According to one embodiment, the tissue is a ligament tissue derived from an allogeneic ligament tissue. According to one embodiment, the tissue is a ligament tissue derived from a xenogeneic ligament tissue.

Mammary Tissue

According to some embodiments, the tissue comprises a mammary tissue derived from a mammary organ or at least one fragment thereof.

According to one embodiment, the source of the tissue is a mammalian donor. According to some embodiments, the tissue is a mammary organ from a human donor. According to some embodiments, the human donor is a cadaveric donor. According to some embodiments, the human donor is a living donor.

According to one embodiment, the tissue is a mammary tissue derived from an autologous mammary organ. According to one embodiment, the tissue is a mammary tissue derived from an allogeneic mammary organ. According to one embodiment, the tissue is a mammary tissue derived from a xenogeneic mammary organ.

Muscle Tissue

According to some embodiments, the tissue comprises a muscle tissue selected from the group consisting of a cardiac muscle tissue, a skeletal muscle tissue, a smooth muscle tissue, and, a combination thereof. According to some embodiments, the tissue comprises a cardiac muscle tissue. According to some embodiments, the tissue comprises a skeletal muscle tissue. According to some embodiments, the tissue comprises a smooth muscle tissue.

According to some embodiments, the tissue is a muscle tissue derived from a muscle tissue-rich organ or at least one fragment thereof.

According to some embodiments, the muscle tissue-rich organ is selected from the group consisting of a gastrointestinal organ, a skeletal organ, a heart, and, a combination thereof. According to some embodiments, the muscle tissue-rich organ comprises a gastrointestinal organ. According to some embodiments, the muscle tissue-rich organ comprises a skeletal organ. According to some embodiments, the muscle tissue-rich organ comprises a heart.

According to one embodiment, the source of the tissue is a mammalian donor. According to some embodiments, the tissue comprises a muscle tissue derived from a human donor. According to some embodiments, the human donor is a cadaveric donor. According to some embodiments, human donor is a living donor.

According to one embodiment, the tissue comprises a muscle tissue derived from an autologous muscle tissue. According to one embodiment, the tissue comprises a muscle tissue derived from an allogeneic muscle tissue. According to one embodiment, the tissue comprises a muscle tissue derived from a xenogeneic muscle tissue.

Nerve Tissue

According to some embodiments, the tissue comprises a nerve tissue comprising a nerve tissue derived from a nerve tissue-rich organ or at least one fragment thereof.

According to some embodiments, the nerve tissue-rich organ is selected from the group consisting of a brain, a spinal cord, and, a combination thereof. According to some embodiments, the nerve tissue-rich organ is a brain. According to some embodiments, the nerve tissue-rich organ is a spinal cord.

According to one embodiment, the source of the tissue is a mammalian donor. According to some embodiments, the tissue is a nerve tissue derived from a human donor. According to some embodiments, the human donor is a cadaveric donor.

According to one embodiment, the tissue comprises a nerve tissue derived from an autologous nerve tissue. According to one embodiment, the tissue comprises a nerve tissue derived from an allogeneic nerve tissue. According to one embodiment, the tissue comprises a nerve tissue derived from a xenogeneic nerve tissue.

Placental Tissue

According to some embodiments, the tissue comprises a placental tissue selected from the group consisting of an amnion tissue, a chorion tissue, an umbilical cord tissue, and, a combination thereof. According to some embodiments, the tissue comprises an amnion tissue. According to some embodiments, the tissue comprises a chorion tissue. According to some embodiments, the tissue comprises an umbilical cord tissue.

According to some embodiments, the tissue comprises a placental tissue derived from an isolated placental organ or at least one fragment thereof. According to some embodiments, the placental organ is selected from the group consisting of an amnion, a chorion, an umbilical cord, a placenta, and, a combination thereof. According to some embodiments, the placental organ is an amnion. According to some embodiments, the placental organ is a chorion. According to some embodiments, the placental organ is a placenta. According to some embodiments, the placental organ is an umbilical cord. According to some embodiments, the tissue comprises an umbilical cord tissue selected from the group consisting of an umbilical cord membrane tissue, umbilical cord blood, and, a combination thereof.

According to one embodiment, the tissue comprises a placental tissue derived from an autologous placental tissue. According to one embodiment, the tissue comprises a placental tissue derived from an allogeneic placental tissue. According to one embodiment, the tissue comprises a placental tissue derived from a xenogeneic placental tissue.

According to one embodiment, the tissue is an umbilical cord derived from an autologous umbilical cord. According to one embodiment, the tissue is an umbilical cord tissue derived from an allogeneic umbilical cord. According to one embodiment, the tissue is an umbilical cord tissue derived from a xenogeneic umbilical cord.

Skin Tissue

According to some embodiments, the tissue comprises a skin tissue selected from the group consisting of an epidermal tissue, a dermal tissue, a basement membrane tissue, and a combination thereof. According to some embodiments, the skin tissue is an epidermal tissue. According to some embodiments, the skin tissue is a dermal tissue. According to some embodiments, the skin tissue is a basement membrane tissue.

According to one embodiment, the source of the tissue is a mammalian donor. According to some embodiments, the skin tissue is derived from a human donor. According to some embodiments, the human donor is a cadaveric donor. According to some embodiments, the human donor is a living donor.

According to one embodiment, the tissue comprises a skin tissue derived from an autologous skin tissue. According to one embodiment, the tissue comprises a skin tissue derived from an allogeneic skin tissue. According to one embodiment, the tissue comprises a skin tissue derived from a xenogeneic skin tissue.

Vascular Tissue

The term "vasculature" or "vascular tissue" as used herein refers to the vascular network of a part of the body and its arrangement. The vascular network comprises blood vessels, i.e. any vessel conveying blood: arteries, arterioles, capillaries, venules, and veins. An artery is a relatively thick-walled, musclular pulsating vessel conveying blood away from the heart. A vein is a blood essel carrying blood toward the heart. Both arteries and veins comprises three layers: the tunica intima, the tunica media and the tunica adventitia. Veins contain valves that prevent blood backflow. The tunica intima, a single layer of simple squamous endothelial cells glued by a polysaccharide intercellular matrix, surrounded by a thin layer of subendothelial connective tissue interlaced with a number of circularly arranged elastic bands called the internal elastic lamina; a tunica media, comprising circularly arranged elastic fiber, connective tissue, polysaccharide substances, and a thick elastic band called the external elastic lamina, and the tunica adventitia, entirely made of conenctive tissue. Capillaries comprise a layer of endothelium and connective tissue. According to some embodiments, the tissue comprises vascular tissue.

According to some embodiments, the vascular tissue is derived from a cadaveric donor. According to some embodiments, the vascular tissue is derived from a living donor.

According to one embodiment, the tissue is a vascular tissue derived from an autologous vascular tissue. According to one embodiment, the tissue is a vascular tissue derived from an allogeneic vascular tissue. According to one embodiment, the tissue is a vascular tissue derived from a xenogeneic vascular tissue.

Matrix

According to one embodiment, the at least one growth-conductive matrix derived from a tissue is selected from the group consisting of an adipose tissue matrix, an amnion tissue matrix, an artery tissue matrix, a bone tissue matrix, a cartilage tissue matrix, a chorion tissue matrix, a colon tissue matrix, a dental tissue matrix, a dermal tissue matrix, a duodenum tissue matrix, an epithelial tissue matrix, a fascial tissue matrix, a gastrointestinal tissue matrix, a growth plate tissue matrix, an intervertebral disc tissue matrix, an intestinal mucosal tissue matrix, an s intestinal serosal tissue matrix, a kidney tissue matrix, a ligament tissue matrix, a liver tissue matrix, a lung tissue matrix, a mammary tissue matrix, a meniscal tissue matrix, a muscle tissue matrix, a nerve tissue matrix, an ovary tissue, a pancreatic tissue matrix, a parenchymal organ tissue matrix, a pericardial tissue matrix, a periosteal tissue matrix, a peritoneal tissue matrix, a placental tissue matrix, a reproductive epithelial tissue matrix, a respiratory epithelial tissue matrix, a skin tissue matrix, a spleen tissue matrix, a stomach tissue matrix, a synovial tissue matrix, a tendon tissue matrix, a testes tissue matrix, an umbilical cord tissue matrix, a urological tissue matrix, a vascular tissue matrix, a vein tissue matrix, and, a combination thereof.

According to one embodiment, the at least one growth-conductive matrix comprises an adipose tissue matrix. According to one embodiment, the at least one growth-conductive matrix comprises an amnion tissue matrix. According to one embodiment, the at least one growth-conductive matrix comprises an artery tissue matrix. According to one embodiment, the at least one growth-conductive matrix comprises a bone tissue matrix. According to one embodiment, the at least one growth-conductive matrix comprises a cartilage tissue matrix. According to one embodiment, the at least one growth-conductive matrix comprises a chorion tissue matrix. According to one embodiment, the at least one growth-conductive matrix comprises a colon tissue matrix. According to one embodiment, the at least one growth-conductive matrix comprises a dental tissue matrix. According to one embodiment, the at least one growth-conductive matrix comprises a dermal tissue matrix. According to one embodiment, the at least one growth-conductive matrix comprises a duodenal tissue matrix. According to one embodiment, the at least one growth-conductive matrix comprises an epithelial tissue matrix. According to one embodiment, the at least one growth-conductive matrix comprises a fascial tissue matrix. According to one embodiment, the at least one growth-conductive matrix comprises a gastrointestinal tissue matrix. According to one embodiment, the at least one growth-conductive matrix comprises a growth plate tissue matrix. According to one embodiment, the at least one growth-conductive matrix comprises an intervertebral disc tissue matrix. According to one embodiment, the at least one growth-conductive matrix comprises an intestinal mucosal tissue matrix. According to one embodiment, the at least one growth-conductive matrix comprises an intestinal serosal tissue matrix. According to one embodiment, the at least one growth-conductive matrix comprises a kidney tissue matrix. According to one embodiment, the at least one growth-conductive matrix comprises a ligament tissue matrix. According to one embodiment, the at least one growth-conductive matrix comprises a liver tissue matrix. According to one embodiment, the at least one growth-conductive matrix comprises a lung tissue matrix. According to one embodiment, the at least one growth-conductive matrix comprises a mammary tissue matrix. According to one embodiment, the at least one growth-conductive matrix comprises a meniscal tissue matrix. According to one embodiment, the at least one growth-conductive matrix comprises a muscle tissue matrix. According to one embodiment, the at least one growth-conductive matrix comprises a nerve tissue matrix. According to one embodiment, the at least one growth-conductive matrix comprises an ovarian tissue matrix. According to one embodiment, the at least one growth-conductive matrix comprises a pancreatic tissue matrix. According to one embodiment, the at least one growth-conductive matrix comprises a parenchymal organ tissue matrix. According to one embodiment, the at least one growth-conductive matrix comprises a pericardial tissue matrix. According to one embodiment, the at least one growth-conductive matrix comprises a periosteal tissue matrix. According to one embodiment, the at least one growth-conductive matrix comprises a peritoneal tissue matrix. According to one embodiment, the at least one growth-conductive matrix comprises a placental tissue matrix. According to one embodiment, the at least one growth-conductive matrix comprises a reproductive epithelial tissue matrix. According to one embodiment, the at least one growth-conductive matrix comprises a respiratory epithelial tissue matrix. According to one embodiment, the at least one growth-conductive matrix comprises a skin tissue matrix. According to one embodiment, the at least one growth-conductive matrix comprises a spleen tissue matrix. According to one embodiment, the at least one growth-conductive matrix comprises a stomach tissue matrix. According to one embodiment, the at least one growth-conductive matrix comprises a synovial tissue matrix. According to one embodiment, the at least one growth-conductive matrix comprises a tendon tissue matrix. According to one embodiment, the at least one growth-conductive matrix comprises a testes tissue matrix. According to one embodiment, the at least one growth-conductive matrix comprises an umbilical cord tissue matrix. According to one embodiment, the at least one growth-conductive matrix comprises a urological tissue matrix. According to one embodiment, the at least one growth-conductive matrix comprises a vascular tissue matrix. According to one embodiment, the at least one growth-conductive matrix comprises a vein tissue matrix.

According to one embodiment, the at least one growth-conductive matrix comprises a purified collagen matrix. According to one embodiment, the at least one growth-conductive matrix comprises a calcium phosphate ceramic matrix. According to one embodiment, the at least one growth-conductive matrix comprises a calcium phosphate ceramic matrix.

According to one embodiment, the at least one growth-conductive matrix is derived from an autologous tissue. According to one embodiment, the at least one growth-conductive matrix is derived from an allogeneic tissue. According to one embodiment, the at least one growth-conductive matrix is derived from a xenogeneic tissue.

According to one embodiment, the source of the tissue is a mammalian donor. According to one embodiment, the at least one growth-conductive matrix is derived from a human donor. According to one embodiment, the at least one growth-conductive matrix is derived from a living donor. According to one embodiment, the at least one growth-conductive matrix is derived from a cadeveric donor.

According to one embodiment, the at least one tissue derived growth-conductive matrix comprises a tissuegenic cell niche endogenous to the at least one tissue-derived growth-conductive matrix.

According to one embodiment, the at least one tissue derived growth-conductive matrix comprises a tissue-derived growth conductive matrix from which unwanted cells have been removed.

Adipose Tissue Matrix

According to one embodiment, the at least one growth-conductive matrix comprises an adipose tissue matrix. According to one embodiment, the at least one growth-conductive matrix comprises an adipose tissue matrix derived from an adipose-rich body region.

According to some embodiments, the adipose rich body region is selected from the group consisting of an abdomen, a hip, a hypodermal region of skin, an infrapatellar fat pad, a knee, a mammary organ, a thigh and, a combination thereof. According to some embodiments, the adipose rich body region is an abdomen. According to some embodiments, the adipose rich body region is a hip. According to some embodiments, the adipose rich body region is a hypodermal region of skin. According to some embodiments, the adipose rich body region is an infrapatellar fat pad. According to some embodiments, the adipose rich body region is a knee. According to some embodiments, the adipose rich body region is a mammary organ. According to some embodiments, the adipose rich body region is a thigh.

According to some embodiments, the adipose tissue matrix comprises tissue matrix derived from an adipose tissue selected from the group consisting of a visceral adipose tissue, a subcutaneous adipose tissue and, a combination thereof. According to some embodiments, the adipose tissue matrix comprises tissue matrix derived from a visceral adipose tissue. According to some embodiments, the adipose tissue matrix comprises tissue matrix derived from a subcutaneous adipose tissue.

According to some embodiments, the adipose tissue matrix comprises tissue matrix derived from an adipose-rich body region of a human donor. According to some embodiments, the human donor is a cadaveric donor. According to some embodiments, the human donor is a living donor.

According to one embodiment, the adipose tissue matrix comprises tissue matrix derived from an autologous adipose tissue matrix. According to one embodiment, the adipose tissue matrix comprises tissue matrix derived from an allogeneic adipose tissue matrix. According to one embodiment, the adipose tissue matrix comprises tissue matrix derived from a xenogeneic adipose tissue matrix.

According to one embodiment, the at least one adipose tissue derived growth-conductive matrix comprises a tissue-genic cell niche endogenous to the at least one adipose tissue-derived growth-conductive matrix.

According to one embodiment, the at least one tissue derived growth-conductive matrix comprises an adipose tissue-derived growth conductive matrix from which unwanted cells have been removed.

Bone Tissue Matrix

According to one embodiment, the at least one growth-conductive matrix comprises a bone tissue matrix. According to some embodiments, the bone tissue matrix is derived from a bone or at least one fragment thereof.

According to another embodiment, the bone comprises a cancellous bone. According to some such embodiments, the cancellous bone is selected from the group consisting of a cancellous bone from a calcaneus, a cancellous bone from a distal femur, a cancellous bone from a proximal femur, a cancellous bone from a proximal humerus, a cancellous bone from a ilium, a cancellous bone from a patella, a cancellous bone from a distal tibia, a cancellous bone from a proximal tibia, a cancellous bone from a scapula, a cancellous bone from a sternum, a cancellous bone from a talus, a cancellous bone from at least one vertebral body and, a combination thereof. According to some embodiments, the bone tissue comprises a periosteum.

According to some such embodiments, the cancellous bone comprises cancellous bone from a calcaneus. According to some such embodiments, the cancellous bone comprises cancellous bone from a distal femur. According to some such embodiments, the cancellous bone comprises cancellous bone from a proximal femur. According to some such embodiments, the cancellous bone comprises cancellous bone from a proximal humerus. According to some such embodiments, the cancellous bone comprises cancellous bone from an ilium. According to some such embodiments, the cancellous bone comprises cancellous bone from a patella. According to some such embodiments, the cancellous bone comprises cancellous bone from a distal tibia. According to some such embodiments, the cancellous bone comprises cancellous bone from a proximal tibia. According to some such embodiments, the cancellous bone comprises cancellous bone from a scapula. According to some such embodiments, the cancellous bone comprises cancellous bone from a sternum. According to some such embodiments, the cancellous bone comprises cancellous bone from a talus. According to some embodiments, the cancellous bone comprises cancellous bone from at least one vertebral body.

According to another embodiment, the bone comprises cortical bone. According to some such embodiments, the cortical bone is selected from the group consisting of a calcaneus, a distal femur bone, a proximal femur, a proximal humerus, an ilium, a patella, a distal tibia, a proximal tibia, a scapula, a cancellous bone from a sternum, a talus, at least one vertebral body and, a combination thereof.

According to some such embodiments, the cortical bone comprises cortical bone from a calcaneus. According to some such embodiments, the cortical bone comprises cortical bone from a distal femur. According to some such embodiments, the cortical bone comprises cortical bone from a proximal femur. According to some such embodiments, the cortical bone comprises cortical bone from a proximal humerus. According to some such embodiments, the cortical bone comprises cortical bone from an ilium. According to some such embodiments, the cortical bone comprises cortical bone from a patella. According to some such embodiments, the cortical bone comprises cortical bone from a distal tibia. According to some such embodiments, the cortical bone comprises cortical bone from a proximal tibia. According to some such embodiments, the cortical bone comprises cortical bone from a scapula. According to some such embodiments, the cortical bone comprises cortical bone from a sternum. According to some such embodiments, the cortical bone comprises cortical bone from a talus. According to some embodiments, the cortical bone comprises cortical bone from at least one vertebral body.

According to some such embodiments, the bone is at least one fragment of an ilium. According to some such embodiments, the bone is at least one fragment of a long bone. According to some such embodiments, the long bone is selected from the group consisting of a femur, a fibula, a humerus, a metacarpal, a metatarsal, a phalange, a radii, a tibia, an ulna and, a combination thereof. According to some such embodiments, the long bone is a femur. According to some such embodiments, the long bone is a fibula. According to some such embodiments, the long bone is a humerus. According to some such embodiments, the long bone is a metacarpal. According to some such embodiments, the long bone is a metatarsal. According to some such embodiments, the long bone is a phalange. According to some such embodiments, the long bone is a radii. According to some such embodiments, the long bone is a tibia. According to some such embodiments, the long bone is an ulna.

According to another embodiment, the at least one growth-conductive matrix comprises cancellous bone and cortical bone. According to some embodiments, the at least one growth-conductive matrix comprises cancellous bone and cortical bone in a ratio of about 60:40 w/w. According to some embodiments, the at least one growth-conductive matrix comprises cancellous bone and cortical bone in a ratio of about 65:35 w/w. According to some embodiments, the at least one growth-conductive matrix comprises cancellous bone and cortical bone in a ratio of about 66:34 w/w. According to some embodiments, the at least one growth-conductive matrix comprises cancellous bone and cortical bone in a ratio of about 67:33 w/w. According to some embodiments, the at least one growth-conductive matrix comprises cancellous bone and cortical bone in a ratio of about 68:32 w/w. According to some embodiments, the at least one growth-conductive matrix comprises cancellous bone and cortical bone in a ratio of about 69:31 w/w. According to some embodiments, the at least one growth-conductive matrix comprises cancellous bone and cortical bone in a ratio of about 70:30 w/w. According to some embodiments, the at least one growth-conductive matrix comprises cancellous bone and cortical bone in a ratio of about 75:25 w/w. According to some embodiments, the at least one growth-conductive matrix comprises cancellous bone and cortical bone in a ratio of about 80:20 w/w. According to some embodiments, the at least one growth-conductive matrix comprises cancellous bone and cortical bone in a ratio of about 85:15 w/w. According to some embodiments, the at least one growth-conductive matrix comprises cancellous bone and cortical bone in a ratio of about 90:10 w/w. According to some embodiments, the at least one growth-conductive matrix comprises cancellous bone and cortical bone in a ratio of about 95:5 w/w. According to some embodiments, the at least one growth-conductive matrix comprises cancellous bone and cortical bone in a ratio of about 96:4 w/w. According to some embodiments, the at least one growth-conductive matrix comprises cancellous bone and cortical bone in a ratio of about 97:3 w/w. According to some embodiments, the at least one growth-conductive matrix comprises cancellous bone and cortical bone in a ratio of about 98:2 w/w. According to some embodiments, the at least one growth-conductive matrix comprises cancellous bone and cortical bone in a ratio of about 99:1 w/w.

According to one embodiment, the at least one growth-conductive matrix derived from a bone tissue matrix comprises an osteoconductive matrix. According to one embodiment, the at least one osteoconductive matrix is bone. According to another embodiment, the at least one osteoconductive matrix is at least one fragment of bone.

According to another embodiment, the at least one osteoconductive matrix comprises cancellous bone. According to some such embodiments, the cancellous bone is cancellous bone from a proximal femur. According to some such embodiments, the cancellous bone is cancellous bone from a distal femur. According to some such embodiments, the cancellous bone is cancellous bone from a proximal tibia. According to some such embodiments, the cancellous bone is cancellous bone from a distal tibia. According to some such embodiments, the cancellous bone is cancellous bone from a patella. According to some such embodiments, the cancellous bone is cancellous bone from a calcaneus. According to some such embodiments, the cancellous bone is cancellous bone from a talus. According to some such embodiments, the cancellous bone is cancellous bone from a proximal humerus. According to some such embodiments, the cancellous bone is cancellous bone from a scapula. According to some such embodiments, the cancellous bone is cancellous bone from a sternum. According to some such embodiments, the cancellous bone is cancellous bone from an ilium. According to some embodiments, the at least one osteoconductive comprises cancellous bone from at least one vertebral body.

According to another embodiment, the at least one osteoconductive matrix comprises cortical bone. According to some such embodiments, the cortical bone is cortical bone from a proximal femur. According to some such embodiments, the cortical bone is cortical bone from a distal femur. According to some such embodiments, the cortical bone is cortical bone from a proximal tibia. According to some such embodiments, the cortical bone is cortical bone from a distal tibia. According to some such embodiments, the cortical bone is cortical bone from a patella. According to some such embodiments, the cortical bone is cortical bone from a calcaneus. According to some such embodiments, the cortical bone is cortical bone from a talus. According to some such embodiments, the cortical bone is cortical bone from a proximal humerus. According to some such embodiments, the cortical bone is cortical bone from a scapula. According to some such embodiments, the cortical bone is cortical bone from a sternum. According to some such embodiments, the cortical bone is cortical bone from an ilium. According to some embodiments, the at least one osteoconductive matrix comprises cortical bone from at least one vertebral body.

According to another embodiment, the at least one osteoconductive matrix comprises cancellous bone and cortical bone. According to some embodiments, the at least one osteoconductive matrix comprises cancellous bone and cortical bone in a ratio of about 60:40 w/w. According to some embodiments, the at least one osteoconductive matrix comprises cancellous bone and cortical bone in a ratio of about 65:35 w/w. According to some embodiments, the at least one growth-conductive matrix comprises cancellous bone and cortical bone in a ratio of about 66:34 w/w. According to some embodiments, the at least one growth-conductive matrix comprises cancellous bone and cortical bone in a ratio of about 67:33 w/w. According to some embodiments, the at least one growth-conductive matrix comprises cancellous bone and cortical bone in a ratio of about 68:32 w/w. According to some embodiments, the at least one growth-conductive matrix comprises cancellous bone and cortical bone in a ratio of about 69:31 w/w. According to some embodiments, the at least one osteoconductive matrix comprises cancellous bone and cortical bone in a ratio of about 70:30 w/w. According to some embodiments, the at least one osteoconductive matrix comprises cancellous bone and cortical bone in a ratio of about 75:25 w/w. According to some embodiments, the at least one osteoconductive matrix comprises cancellous bone and cortical bone in a ratio of about 80:20 w/w. According to some embodiments, the at least one osteoconductive matrix comprises cancellous bone and cortical bone in a ratio of about 85:15 w/w. According to some embodiments, the at least one osteoconductive matrix comprises cancellous bone and cortical bone in a ratio of about 90:10 w/w. According to some embodiments, the at least one osteoconductive matrix comprises cancellous bone and cortical bone in a ratio of about 95:5 w/w. According to some embodiments, the at least one osteoconductive matrix comprises cancellous bone and cortical bone in a ratio of about 96:4 w/w. According to some embodiments, the at least one osteoconductive matrix comprises cancellous bone and cortical bone in a ratio of about 97:3 w/w. According to some embodiments, the at least one osteoconductive matrix comprises cancellous bone and cortical bone in a ratio of about 98:2 w/w. According to some embodiments, the at least one osteoconductive matrix comprises cancellous bone and cortical bone in a ratio of about 99:1 w/w.

According to some embodiments, the bone tissue matrix comprises tissue matrix derived from a bone matrix from a human donor. According to some embodiments, the human donor is a cadaveric donor. According to some embodiments, the human donor is a living donor.

According to some embodiments, the bone tissue matrix is derived from an autologous bone tissue. According to some embodiments, the bone tissue matrix is derived from an allogeneic bone tissue. According to some embodiments, the bone tissue matrix is derived from a xenogeneic bone tissue.

According to one embodiment, the at least one bone tissue-derived growth-conductive matrix comprises a tissue-genic cell niche endogenous to the at least one growth-conductive matrix.

According to one embodiment, the at least one growth-conductive matrix comprises a synovial tissue matrix. According to some embodiments, the synovial tissue comprises a synovial membrane. According to some embodiments, the synovial tissue is derived from a synovial joint. According to some such embodiments, the synovial joint is at least one selected from the group consisting of a knee, an elbow, a shoulder, a hip, a condyloid joint, a pivot joint, and, a combination thereof. According to some such embodiments, the synovial joint comprises a synovial joint of a knee. According to some such embodiments, the synovial joint comprises a synovial joint of an elbow. According to some such embodiments, the synovial joint comprises a synovial joint of a shoulder. According to some such embodiments, the synovial joint comprises a synovial joint of a hip. According to some such embodiments, the synovial joint comprises a condyloid joint. According to some such embodiments, the synovial joint comprises a pivot joint.

According to one embodiment, the at least one growth-conductive matrix comprises a tendon tissue matrix. According to some embodiments, the tendon tissue matrix comprises tissue matrix derived from a tendon. As used herein the term "tendon" refer to a nondistensible fibrous court or band of variable length that is the part of the muscle that connects the fleshy/contractile part of muscle with its bony attachment or other structure. It consists of fascicles of very densely arranged, almost parallel collagenous fibers, rows of elongated fibrocytes, and a minimum of ground substance.

According to one embodiment, the at least one tissue derived growth-conductive matrix comprises a bone tissue-derived growth conductive matrix from which unwanted cells have been removed. According to one embodiment, the at least one tissue derived growth-conductive matrix comprises a periosteal tissue-derived growth conductive matrix from which unwanted cells have been removed. According to one embodiment, the at least one tissue derived growth-conductive matrix comprises a synovial tissue-derived growth conductive matrix from which unwanted cells have been removed.

Cartilage Tissue Matrix

According to one embodiment, the at least one growth-conductive matrix derived from a tissue comprises a cartilage tissue matrix. According to some embodiments, the cartilage tissue matrix is derived from a cartilage tissue selected from the group consisting of a hyaline cartilage, a fibrocartilage tissue, an elastic cartilage tissue and, a combination thereof. According to some embodiments, the cartilage tissue matrix is derived from a hyaline cartilage tissue. According to some embodiments, the cartilage tissue matrix is derived from a fibrocartilage cartilage tissue. According to some embodiments, the cartilage tissue matrix is derived from an elastic cartilage tissue.

According to some embodiments, the cartilage tissue matrix is derived from a cartilaginous organ or at least one fragment thereof.

According to some embodiments, the cartilaginous organ is selected from the group consisting of an articular cartilage organ, a bronchus, a growth plate, an intervertebral disc, a larynx, a meniscus, a nose, a trachea and, a combination thereof. According to some embodiments, the cartilaginous organ comprises an articular cartilage organ. According to some embodiments, the cartilaginous organ comprises a bronchus. According to some embodiments, the cartilaginous organ comprises a growth plate. According to some embodiments, the cartilaginous organ comprises an intervertebral disc. According to some embodiments, the cartilaginous organ comprises a larynx. According to some embodiments, the cartilaginous organ comprises a meniscus. According to some embodiments, the cartilaginous organ comprises a nose. According to some embodiments, the cartilaginous organ comprises a trachea.

According to some embodiments, the cartilage tissue matrix is derived from a cartilage tissue from a human donor. According to some embodiments, the human donor is a cadaveric donor. According to some embodiments, the human donor is a living donor.

According to one embodiment, the cartilage tissue matrix is derived from an autologous cartilage tissue. According to one embodiment, the cartilage tissue matrix is derived from an allogeneic cartilage tissue. According to one embodiment, the cartilage tissue matrix is derived from a xenogeneic cartilage tissue.

According to one embodiment, the at least one cartilage tissue derived growth-conductive matrix comprises a tissue-genic cell niche endogenous to the at least one cartilage tissue-derived growth-conductive matrix.

According to one embodiment, the at least one tissue derived growth-conductive matrix comprises a cartilage tissue-derived growth conductive matrix from which unwanted cells have been removed. According to one embodiment, the at least one tissue derived growth-conductive matrix comprises a bronchial tissue-derived growth conductive matrix from which unwanted cells have been removed. According to one embodiment, the at least one tissue derived growth-conductive matrix comprises a growth plate tissue-derived growth conductive matrix from which unwanted cells have been removed. According to one embodiment, the at least one tissue derived growth-conductive matrix comprises an invertebral plate tissue-derived growth conductive matrix from which unwanted cells have been removed. According to one embodiment, the at least one tissue derived growth-conductive matrix comprises a larynx tissue-derived growth conductive matrix from which unwanted cells have been removed. According to one embodiment, the at least one tissue derived growth-conductive matrix comprises a meniscal tissue-derived growth conductive matrix from which unwanted cells have been removed. According to one embodiment, the at least one tissue derived growth-conductive matrix comprises a tracheal tissue-derived growth conductive matrix from which unwanted cells have been removed.

Dental Tissue Matrix

According to one embodiment, the at least one growth-conductive matrix derived from a tissue comprises a dental tissue matrix. According to some embodiments, the dental tissue matrix is derived from a dental tissue selected from the group consisting of a cementum tissue, a dental pulp tissue, a dentin tissue, an enamel tissue and, a combination thereof. According to some embodiments, the at least one growth-conductive matrix is derived from a cementum tissue. According to some embodimentsthe at least one growth-conductive matrix is derived from a dental pulp tissue. According to some embodiments, the at least one growth-conductive matrix is derived from a dentin tissue. According to some embodiments, the at least one growth-conductive matrix is derived from an enamel tissue.

According to some embodiments, the dental tissue matrix comprises tissue matrix derived from at least one tooth or at least one fragment thereof.

According to some embodiments, the dental tissue matrix is derived from a tooth crown or at least one fragment therefrom. According to some embodiments, the dental tissue matrix is derived from a tooth root or at least one fragment therefrom. According to some embodiments, the dental tissue matrix is derived from a tooth neck or at least one fragment therefrom.

According to some embodiments, the tooth is selected from the group consisting of a deciduous tooth, a permanent tooth and a combination therefrom. According to some embodiments, the tooth is a deciduous tooth. According to some embodiments, tooth is a permanent tooth.

According to some embodiments, the dental tissue matrix is derived from a dental tissue from a human donor. According to some embodiments, the human donor is a cadaveric donor. According to some embodiments, the human donor is a living donor.

According to one embodiment, the dental tissue matrix is derived from an autologous dental tissue. According to one embodiment, the dental tissue matrix is derived from an allogeneic dental tissue. According to one embodiment, the dental tissue matrix is derived from a xenogeneic dental tissue.

According to one embodiment, the at least one dental tissue derived growth-conductive matrix comprises a tissue-genic cell niche endogenous to the at least one dental tissue-derived growth-conductive matrix.

According to one embodiment, the at least one tissue derived growth-conductive matrix comprises a dental tissue-derived growth conductive matrix from which unwanted cells have been removed.

Epithelial Tissue Matrix

According to one embodiment, the at least one growth-conductive matrix derived from a tissue comprises an epithelial tissue matrix. According to some embodiments, the epithelial tissue matrix is derived from an epithelial tissue selected from the group consisting of a cutaneous epithelial tissue, a mucuous epithelial tissue, a serous epithelial tissue and, a combination thereof. According to some embodiments, the epithelial tissue matrix is derived from a cutaneous epithelial tissue. According to some embodiments, the epithelial tissue matrix is derived from a mucuous epithelial tissue. According to some embodiments, the epithelial tissue matrix is derived from a serous epithelial tissue. According to some embodiments, the epithelial tissue matrix is derived from a basement membrane tissue. According to one embodiment, the epithelial tissue matrix is derived from an intestinal mucosal lining. According to one embodiment, the epithelial tissue matrix is derived from an intestinal serosal lining.

According to some embodiments, the epithelial tissue is selected from the group consisting of a gastrointestinal lining, a pericardial lining, a peritoneal lining, a pleural lining, a reproductive lining, a respiratory lining, a urinary lining and, a combination thereof. According to some embodiments, the epithelial tissue is derived from a gastrointestinal lining. According to some embodiments, the epithelial tissue is derived from a pericardial lining. According to some embodiments, the epithelial tissue is derived from a peritoneal lining. According to some embodiments, the epithelial tissue is derived from a pleural lining. According to some embodiments, the epithelial tissue is derived from a reproductive lining. According to some embodiments, the epithelial tissue is derived from a respiratory lining. According to some embodiments, the epithelial tissue is derived from a urinary lining.

According to some embodiments, the gastrointestinal lining is selected from the group consisting of a duodenum lining, an esophagus lining, an ileum lining, a jejunum lining, a large intestine lining, a mouth lining, a pharynx lining, a small intestine lining, a stomach lining and, a combination thereof. According to some embodiments, the gastrointestinal lining is a duodenum lining. According to some embodiments, the gastrointestinal lining is an esophagus lining. According to some embodiments, the gastrointestinal lining is an ileum lining. According to some embodiments, the gastrointestinal lining is a jejunum lining. According to some embodiments, the gastrointestinal lining is a large intestine lining. According to some embodiments, the gastrointestinal lining is a pharynx lining. According to some embodiments, the gastrointestinal lining is a small intestine lining. According to some embodiments, the gastrointestinal lining is a stomach lining.

According to some embodiments, the epithelial tissue matrix is derived from an epithelial organ or at least one fragment thereof.

According to some embodiments, the epithelial organ is selected from the group consisting of a gastrointestinal organ, a respiratory organ, a urological organ and, a combination thereof. According to some embodiments, the epithelial organ comprises a gastrointestinal organ. According to some embodiments, the epithelial organ comprises a respiratory organ. According to some embodiments, the epithelial organ comprises a urological organ.

According to some embodiments, the gastrointestinal organ is selected from the group consisting of a duodenum, an esophagus, an ileum, a jejunum, a large intestine, a mouth, a small intestine, a stomach and a combination thereof. According to some embodiments, the gastrointestinal organ comprises a duodenum. According to some embodiments, the gastrointestinal organ comprises an esophagus. According to some embodiments, the gastrointestinal organ comprises an ileum. According to some embodiments, the gastrointestinal organ comprises a jejunum. According to some embodiments, the gastrointestinal organ comprises a large intestine. According to some embodiments, the gastrointestinal organ comprises a small intestine. According to some embodiments, the gastrointestinal organ comprises a stomach.

According to some embodiments, the respiratory organ is selected from the group consisting of a bronchii, a diaphragm, a heart, a larynx, a lung, a mouth, a nose, a pharynx, a trachea and a combination thereof. According to some embodiments, the respiratory organ comprises a bronchii. According to some embodiments, the respiratory organ comprises a diaphragm. According to some embodiments, the respiratory organ comprises a heart. According to some embodiments, the respiratory organ comprises a larynx. According to some embodiments, the respiratory organ a lung. According to some embodiments, the respiratory organ comprises a mouth. According to some embodiments, the respiratory organ comprises a nose. According to some embodiments, the respiratory organ comprises a pharynx. According to some embodiments, the respiratory organ comprises a trachea.

According to some embodiments, the urological organ is selected from the group consisting of an adrenal gland, an epididymis, a kidney, an ovary, a penis, a prostate, a seminal vesicle, a testis, a ureter, a urethra, a urinary bladder, a vas deferens and a combination thereof. According to some embodiments, the urological organ comprises an adrenal gland. According to some embodiments, the urological organ comprises an epididymis. According to some embodiments, the urological organ comprises a kidney. According to some embodiments, the urological organ comprises an ovary. According to some embodiments, the urological organ comprises a penis. According to some embodiments, the urological organ comprises a prostate. According to some embodiments, the urological organ comprises a seminal vesicle. According to some embodiments, the urological organ comprises a testis. According to some embodiments, the urological organ comprises a ureter. According to some embodiments, the urological organ comprises a urethra. According to some embodiments, the urological organ comprises a urinary bladder. According to some embodiments, the urological organ comprises a vas deferens.

According to some embodiments, the epithelial organ is selected from the group consisting of a duodenum, an esophagus, a heart, an ileum, a jejunum, a large intestine, a lung, a mouth, a pharynx, a small intestine, a skin, a stomach and, a combination thereof. According to some embodiments, the epithelial organ comprises a duodenum. According to some embodiments, the epithelial organ comprises an esophagus. According to some embodiments, the epithelial organ comprises a heart. According to some embodiments, the epithelial organ comprises an ileum. According to some embodiments, the epithelial organ comprises a jejunum. According to some embodiments, the epithelial organ comprises a large intestine. According to some embodiments, the epithelial organ comprises a lung. According to some embodiments, the epithelial organ comprises a mouth. According to some embodiments, the epithelial organ comprises a pharynx. According to some embodiments, the epithelial organ comprises a small intestine. According to some embodiments, the epithelial organ comprises a skin. According to some embodiments, the epithelial organ comprises a stomach.

According to some embodiments, the epithelial tissue matrix is derived from an epithelial tissue from a human donor. According to some embodiments, the human donor is a cadaveric donor. According to some embodiments, the human donor is a living donor.

According to one embodiment, the epithelial tissue matrix is derived from an autologous epithelial tissue. According to one embodiment, the epithelial tissue matrix is derived from an allogeneic epithelial tissue. According to one embodiment, the epithelial tissue matrix is derived from a xenogeneic epithelial tissue.

According to one embodiment, the at least one epithelial tissue derived growth-conductive matrix comprises a tissuegenic cell niche endogenous to the at least one epithelial tissue-derived growth-conductive matrix.

According to one embodiment, the at least one tissue derived growth-conductive matrix comprises an epithelial tissue-derived growth conductive matrix from which unwanted cells have been removed. According to one embodiment, the at least one tissue derived growth-conductive matrix comprises a gastrointestinal tissue-derived growth conductive matrix from which unwanted cells have been removed. According to one embodiment, the at least one tissue derived growth-conductive matrix comprises a liver tissue-derived growth conductive matrix from which unwanted cells have been removed. According to one embodiment, the at least one tissue derived growth-conductive matrix comprises a lung tissue-derived growth conductive matrix from which unwanted cells have been removed. According to one embodiment, the at least one tissue derived growth-conductive matrix comprises a urological tissue-derived growth conductive matrix from which unwanted cells have been removed.

Fascial Tissue Matrix

According to one embodiment, the at least one growth-conductive matrix derived from a tissue comprises a fascial tissue matrix. According to some embodiments, the fascial tissue matrix is derived from a fascial tissue selected from the group consisting of a superficial fascia, a deep fascia, a visceral fascia, and, a combination thereof. The term "fascia" as used herein refers to a fibroareolar connective tissue lamellae distributed throughout the body surrounding delicate organs. According to some embodiments, the fascial tissue matrix is derived from a superficial fascia. According to some embodiments, tthe fascial tissue matrix is derived from a deep fascia. According to some embodiments, the fascial tissue matrix is a visceral fascia.

According to some embodiments, the fascial tissue matrix is derived from a fascia-rich body part or at least one fragment thereof. According to some embodiments, the fascia-rich body part is selected from the group consisting of an arm, a back, an elbow, a foot, a hand, a head, a knee, a leg, a muscle, a neck, a skin, a thigh, a toe, a wrist, and, a combination thereof. According to some embodiments, the fascia-rich body part comprises an arm. According to some embodiments, the fascia-rich body part comprises a back. According to some embodiments, the fascia-rich body part comprises an elbow. According to some embodiments, the fascia-rich body part comprises a foot. According to some embodiments, the fascia-rich body part comprises a hand. According to some embodiments, the fascia-rich body part comprises a head. According to some embodiments, the fascia-rich body part comprises a knee. According to some embodiments, the fascia-rich body part comprises a leg. According to some embodiments, the fascia-rich body part comprises a muscle. According to some embodiments, the fascia-rich body part comprises a neck. According to some embodiments, the fascia-rich body part comprises a skin. According to some embodiments, the fascia-rich body part comprises a thigh. According to some embodiments, the fascia-rich body part comprises a toe. According to some embodiments, the fascia-rich body part comprises a wrist.

According to some embodiments, the fascial tissue matrix is derived from a fascial tissue selected from the group consisting of a myofascia associated with a muscle, palmar fascia associated with a palm of a hand, plantar fascia associated with a sole of a foot, thoracolumbar fascia associated with a back, fascii lata associated with a thigh, tensor fascia lata associated with tendon tissue, and a combination thereof. According to some embodiments, the fascial tissue matrix is derived from myofascia associated with a muscle. According to some embodiments, fascial tissue matrix is derived from palmar fascia associated with a palm of a hand. According to some embodiments, fascial tissue matrix is derived from plantar fascia associated with a sole of a foot. According to some embodiments, tfascial tissue matrix is derived from thoracolumbar fascia associated with a back. According to some embodiments, fascial tissue matrix is derived from fascii lata associated with a thigh. According to some embodiments, fascial tissue matrix is derived from tensor fascia lata associated with tendon tissue.

According to some embodiments, the fascial tissue matrix is derived from a fascial tissue from a mammalian donor. According to some embodiments, the fascial tissue matrix is derived from a fascial tissue from a human donor. According to some embodiments, the human donor is a cadaveric donor. According to some embodiments, the human donor is a living donor.

According to one embodiment, the fascial tissue matrix is derived from an autologous fascial tissue. According to one embodiment, the fascial tissue matrix is derived from an allogeneic fascial tissue. According to one embodiment, the fascial tissue matrix is derived from a xenogeneic fascial tissue.

According to one embodiment, the at least one fascial tissue derived growth-conductive matrix comprises a tissue-genic cell niche endogenous to the at least one fascial tissue-derived growth-conductive matrix.

According to one embodiment, the at least one tissue derived growth-conductive matrix comprises a fascial tissue-derived growth conductive matrix from which unwanted cells have been removed.

Ligament Tissue Matrix

According to one embodiment, the at least one growth-conductive matrix derived from a tissue comprises a ligament tissue matrix. According to some embodiments, the ligament tissue matrix is derived from a ligament tissue selected from the group consisting of a capsular ligament, an extra-capsular ligament, an intracapsular ligament, a cruciate ligament and, a combination thereof. The term "ligament" as used herein refers to a band or sheet of fibrous tissue connecting two or more bones, cartilages, or other structures, or serving as support for fasciae or muslces and a fold of peritoneum supporting any of the abdominal viscera.

According to some embodiments, the ligament tissue matrix is derived from a capsular ligament. According to some embodiments, the ligament tissue matrix is derived from an extra-capsular ligament. According to some embodiments, the ligament tissue matrix is derived from an intracapsular ligament. According to some embodiments, the ligament tissue matrix is derived from a cruciate ligament.

According to some embodiments, the ligament tissue matrix is derived from a ligament-rich body part or at least one fragment thereof. According to some embodiments, the ligament-rich body part is selected from the group consisting of an arm, an elbow, a foot, a hand, a head, a knee, a leg, a neck, a pelvis, a phalange, a thorax, a toe, a wrist and, a combination thereof. According to some embodiments, the ligament-rich body part comprises an arm. According to some embodiments, the ligament-rich body part comprises an elbow. According to some embodiments, the ligament-rich body part comprises a foot. According to some embodiments, the ligament-rich body part comprises a hand. According to some embodiments, the ligament-rich body part comprises a head. According to some embodiments, the ligament-rich body part comprises a knee. According to some embodiments, the ligament-rich body part comprises a leg. According to some embodiments, the ligament-rich body part comprises a neck. According to some embodiments, the ligament-rich body part comprises a pelvis. According to some embodiments, the ligament-rich body part comprises a phalange. According to some embodiments, the ligament-rich body part comprises a thorax. According to some embodiments, the ligament-rich body part comprises a toe. According to some embodiments, the ligament-rich body part comprises a wrist.

According to some embodiments, the ligament tissue matrix is derived from a ligament organ or at least one fragment thereof. According to some embodiments, the ligament organ is selected from the group consisting of a joint, a mouth, a patella and, a combination thereof. According to some embodiments, the ligament organ comprises a joint. According to some embodiments, the ligament organ comprises a mouth. According to some embodiments, the ligament organ comprises a patella.

According to some embodiments, the ligament tissue matrix is derived from a ligament tissue from a human donor. According to some embodiments, the human donor is a cadaveric donor. According to some embodiments, the human donor is a living donor.

According to one embodiment, the ligament tissue matrix is derived from an autologous ligament tissue. According to one embodiment, the ligament tissue matrix is derived from an allogeneic ligament tissue. According to one embodiment, the ligament tissue matrix is derived from a xenogeneic ligament tissue.

According to one embodiment, the at least one ligament tissue derived growth-conductive matrix comprises a tissue-genic cell niche endogenous to the at least one ligament tissue-derived growth-conductive matrix.

According to one embodiment, the at least one tissue derived growth-conductive matrix comprises a ligament tissue-derived growth conductive matrix from which unwanted cells have been removed.

Mammary Tissue Matrix

According to one embodiment, the at least one growth-conductive matrix derived from a tissue comprises a mammary tissue matrix. According to some embodiments, the mammary tissue matrix is derived from a mammary organ.

According to some embodiments, the mammary tissue matrix is derived from a mammary tissue of a human donor. According to some embodiments, the human donor is a cadaveric donor. According to some embodiments, the human donor is a living donor.

According to one embodiment, the mammary tissue matrix is derived from an autologous mammary tissue. According to one embodiment, the mammary tissue matrix is derived from an allogeneic mammary tissue. According to one embodiment, the mammary tissue matrix is derived from a xenogeneic mammary tissue.

According to one embodiment, the at least one mammary tissue derived growth-conductive matrix comprises a tissue-genic cell niche endogenous to the at least one mammary tissue-derived growth-conductive matrix.

According to one embodiment, the at least one tissue derived growth-conductive matrix comprises a mammary tissue-derived growth conductive matrix from which unwanted cells have been removed.

Muscle Tissue Matrix

According to one embodiment, the at least one growth-conductive matrix derived from a tissue comprises a muscle tissue matrix. According to some embodiments, the muscle tissue matrix is derived from a muscle tissue selected from the group consisting of a cardiac muscle tissue, a skeletal muscle tissue, a smooth muscle tissue and, a combination thereof. According to some embodiments, the muscle tissue matrix is derived from a cardiac muscle tissue. According to some embodiments, the muscle tissue matrix is derived from a muscle tissue comprising a skeletal muscle tissue. According to some embodiments, the muscle tissue matrix is derived from a smooth muscle tissue.

According to some embodiments, the muscle tissue matrix is derived from a muscle tissue-rich organ or at least one fragment thereof.

According to some embodiments, the muscle tissue-rich organ is selected from the group consisting of a gastrointestinal organ, a skeletal organ, a heart and, a combination thereof. According to some embodiments, the muscle tissue-rich organ comprises a gastrointestinal organ. According to some embodiments, the muscle tissue-rich organ comprises a skeletal organ. According to some embodiments, the muscle tissue-rich organ comprises a heart.

According to some embodiments, the muscle tissue matrix is derived from a muscle tissue from a human donor. According to some embodiments, the human donor is a cadaveric donor. According to some embodiments, the human donor is a living donor.

According to one embodiment, the muscle tissue matrix is derived from an autologous muscle tissue. According to one embodiment, the muscle tissue matrix is derived from an allogeneic muscle tissue. According to one embodiment, the muscle tissue matrix is derived from a xenogeneic muscle tissue.

According to one embodiment, the at least one muscle tissue derived growth-conductive matrix comprises a tissue-genic cell niche endogenous to the at least one muscle tissue-derived growth-conductive matrix.

According to one embodiment, the at least one tissue derived growth-conductive matrix comprises a muscle tissue-derived growth conductive matrix from which unwanted cells have been removed.

Nerve Tissue Matrix

According to one embodiment, the at least one growth-conductive matrix derived from a tissue comprises a nerve tissue matrix. According to some embodiments, the nerve tissue matrix is derived from a nerve tissue from a nerve tissue-rich organ or at least one fragment thereof.

According to some embodiments, the nerve tissue-rich organ is selected from the group consisting of a brain, a spinal cord, and, a combination thereof. According to some embodiments, the nerve tissue-rich organ is a brain. According to some embodiments, the nerve tissue-rich organ is a spinal cord.

According to some embodiments, the nerve tissue matrix is derived from a nerve tissue derived from a human donor. According to some embodiments, the human donor is a cadaveric donor.

According to one embodiment, the nerve tissue matrix is derived from an autologous nerve tissue. According to one embodiment, the nerve tissue matrix is derived from an allogeneic nerve tissue. According to one embodiment, the nerve tissue matrix is derived from from a xenogeneic nerve tissue.

According to one embodiment, the at least one nerve tissue derived growth-conductive matrix comprises a tissue-genic cell niche endogenous to the at least one nerve tissue-derived growth-conductive matrix.

According to one embodiment, the at least one tissue derived growth-conductive matrix comprises a nerve tissue-derived growth conductive matrix from which unwanted cells have been removed.

Placental Tissue Matrix

According to one embodiment, the at least one growth-conductive matrix derived from a tissue comprises a placental tissue matrix. According to some embodiments, the placental tissue matrix is derived from a placental tissue selected from the group consisting of an amnion tissue, a chorion tissue, an umbilical cord tissue, and a combination thereof. According to some embodiments, the placental tissue matrix is derived from an amnion tissue. According to some embodiments, the placental tissue matrix is derived from a chorion tissue. According to some embodiments, the placental tissue matrix is derived from a combination of amnion tissue and chorion tissue. According to some embodiments, the placental tissue matrix is derived from a combination of amnion tissue, chorion tissue and umbilical cord tissue. According to some embodiments, the placental tissue matrix is derived from an umbilical cord tissue. According to some embodiments, the umbilical cord tissue is selected from the group consisting of an umbilical cord membrane, umbilical cord blood, and a combination thereof.

According to some embodiments, the placental tissue matrix is derived from an isolated placental organ. According to some embodiments, the placental organ is selected from the group consisting of an amnion, a chorion, an umbilical cord, a placenta, and a combination thereof. According to some embodiments, the placental organ is an amnion. According to some embodiments, the placental organ is a chorion. According to some embodiments, the placental organ is a placenta. According to some embodiments, the placental organ is an umbilical cord.

According to some embodiments, the placental tissue matrix is derived from an autologous placental tissue. According to some embodiments, the placental tissue matrix is derived from an allogeneic placental tissue. According to some embodiments, the placental tissue matrix is derived from a xenogeneic placental tissue.

According to one embodiment, the at least one placental tissue derived growth-conductive matrix comprises a tissue-genic cell niche endogenous to the at least one placental tissue-derived growth-conductive matrix.

According to one embodiment, the at least one tissue derived growth-conductive matrix comprises a placental tissue-derived growth conductive matrix from which unwanted cells have been removed. According to one embodiment, the at least one tissue derived growth-conductive matrix comprises an amnion tissue-derived growth conductive matrix from which unwanted cells have been removed. According to one embodiment, the at least one tissue derived growth-conductive matrix comprises a chorion tissue-derived growth conductive matrix from which unwanted cells have been removed. According to one embodiment, the at least one tissue derived growth-conductive matrix comprises an umbilical cord tissue-derived growth conductive matrix from which unwanted cells have been removed.

Skin Tissue Matrix

According to one embodiment, the at least one growth-conductive matrix derived from a tissue comprises a skin tissue matrix. According to some embodiments, the skin tissue matrix is derived from a skin tissue selected from the group consisting of an epidermal tissue, a dermal tissue, a basement membrane tissue, and a combination thereof. According to some embodiments, the skin tissue matrix is derived from an epidermal tissue. According to some embodiments, the skin tissue matrix is derived from a dermal tissue. According to some embodiments, the skin tissue matrix is derived from a basement membrane tissue.

According to some embodiments, the skin tissue comprises a tissue matrix derived from a human donor. According to some embodiments, the human donor is a living donor. According to some embodiments, human donor is a cadaveric donor.

According to some embodiments, the skin tissue matrix is derived from an autologous skin tissue. According to some embodiments, the skin tissue matrix is derived from from an allogeneic skin tissue. According to some embodiments, the skin tissue matrix is derived from a xenogeneic skin tissue.

According to one embodiment, the at least one skin tissue derived growth-conductive matrix comprises a tissuegenic cell niche endogenous to the at least one skin tissue-derived growth-conductive matrix.

According to one embodiment, the at least one tissue derived growth-conductive matrix comprises a skin tissue-derived growth conductive matrix from which unwanted cells have been removed. According to one embodiment, the at least one tissue derived growth-conductive matrix comprises a dermal tissue-derived growth conductive matrix from which unwanted cells have been removed.

Vascular Tissue Matrix

The term "vasculature" as used herein refers to the vascular network of a part of the body and its arrangement. The vascular tissue refers to the tissue comprising the vascular network. The vascular network comprises blood vessels, i.e. any vessel conveying blood: arteries, arterioles, capillaries, venules, and veins. An artery is a relatively thick-walled, musclular pulsating vessel conveying blood away from the heart. A vein is a blood essel carrying blood toward the heart. Both arteries and veins comprises three layers: the tunica intima, the tunica media and the tunica adventitia. Veins contain valves that prevent blood backflow. The tunica intima, a single layer of simple squamous endothelial cells glued by a polysaccharide intercellular matrix, surrounded by a thin layer of subendothelial connective tissue interlaced with a number of circularly arranged elastic bands called the internal elastic lamina; a tunica media, comprising circularly arranged elastic fiber, connective tissue, polysaccharide substances, and a thick elastic band called the external elastic lamina, and the tunica adventitia, entirely made of connective tissue. Capillaries comprise a layer of endothelium and connective tissue. According to some embodiments, the tissue comprises vascular tissue.

According to one embodiment, the at least one growth-conductive matrix derived from a tissue comprises an vascular tissue matrix.

According to some embodiments, the vascular tissue matrix is derived from a human donor. According to some embodiments, the human donor is a cadaveric donor. According to some embodiments, the human donor is a living donor.

According to one embodiment, the vascular tissue matrix is derived from an autologous vascular tissue. According to one embodiment, the vascular tissue matrix is derived from an allogeneic vascular tissue. According to one embodiment, the vascular tissue matrix is derived from a xenogeneic vascular tissue.

According to one embodiment, the at least one vascular tissue derived growth-conductive matrix comprises a tissuegenic cell niche endogenous to the at least one vascular tissue-derived growth-conductive matrix.

According to one embodiment, the at least one tissue derived growth-conductive matrix comprises a vascular tissue-derived growth conductive matrix from which unwanted cells have been removed. According to one embodiment, the at least one tissue derived growth-conductive matrix comprises an endothelial tissue-derived growth conductive matrix from which unwanted cells have been removed.

Tissuegenic Cells

According to one embodiment, the at least one viable population of tissuegenic cells of the implant is adherent to and resident in an endogenous milieu of the growth-conductive matrix. According to one embodiment, the at least one viable population of tissuegenic cells adherent to and resident in an endogenous milieu of the growth-conductive matrix comprises at least one viable population of tissuegenic cells selected from the group consisting of a viable stem cell population and a viable progenitor cell population. According to one embodiment, the at least one viable population of tissuegenic cells adherent to and resident in the endogenous milieu of the growth-conductive matrix comprises at least one viable stem cell population. According to one embodiment, the at least one viable population of tissuegenic cells adherent to and resident in the endogenous milieu of the growth-conductive matrix comprises at least one viable progenitor cell population.

According to one embodiment, the at least one viable stem cell population is selected from the group consisting of a viable embryonic stem cell population, a viable pluripotent stem cell population and a viable somatic stem cell population. According to one embodiment, the at least one viable stem cell population comprises at least one viable embryonic stem cell population. According to one embodiment, the at least one viable stem cell population comprises at least one viable pluripotent stem cell population. According to one embodiment, the at least one viable stem cell population comprises at least one viable somatic stem cell population. According to one embodiment, the at least one viable pluripotent stem cell population comrpises at least one viable induced pluripotent stem cell (iPSC) population. According to one embodiment, the at least one viable tissuegenic cell population can be reprogrammed to form at least one viable induced pluripotent stem cell (iPSC) population.

According to one embodiment, the at least one viable somatic stem cell population is selected from the group consisting of a viable hematopoetic stem cell population, a viable mesenchymal stem cell population, a viable neural stem cell population, a viable epithelial stem cell population, a viable lung stem cell, a viable skin stem cell population, and a combination thereof. According to one embodiment, the at least one viable somatic stem cell population comprises at least one viable hematopoetic stem cell population. According to one embodiment, the at least one viable somatic stem cell population comprises at least one viable mesenchymal stem cell population. According to one embodiment, the at least one viable somatic stem cell population comprises at least one viable neural stem cell population. According to one embodiment, the at least one viable somatic stem cell population comprises at least one viable epithelial stem cell population. According to one embodiment, the at least one viable somatic stem cell population comprises at least one viable lung stem cell population. According to one embodiment, the at least one viable somatic stem cell population comprises at least one viable skin stem cell population.

According to one embodiment, the at least one viable pluripotent stem cell population is selected from the group consisting of a viable pluripotent stem cell population derived from an adipose tissue, a viable pluripotent stem cell population derived from an amnion tissue, a viable pluripotent stem cell population derived from an artery tissue, a viable pluripotent stem cell population derived from a bone tissue, a viable pluripotent stem cell population derived from a cartilage tissue, a viable pluripotent stem cell population derived from a chorion tissue, a viable pluripotent stem cell population derived from a colon tissue, a viable pluripotent stem cell population derived from a dental tissue, a viable pluripotent stem cell population derived from a dermal tissue, a viable pluripotent stem cell population derived from a duodenal tissue, a viable pluripotent stem cell population derived from an epithelial tissue, a viable pluripotent stem cell population derived from a fascial tissue, a viable pluripotent stem cell population derived from a gastrointestinal tissue, a viable pluripotent stem cell population derived from a growth plate tissue, a viable pluripotent stem cell population derived from an intervertebral disc tissue, a viable pluripotent stem cell population derived from an intestinal mucosal disc tissue, a viable pluripotent stem cell population derived from an intestinal serosal tissue, a viable pluripotent stem cell population derived from a kidney tissue, a viable pluripotent stem cell population derived from a ligament tissue, a viable pluripotent stem cell population derived from a liver tissue, a viable pluripotent stem cell population derived from a lung tissue, a viable pluripotent stem cell population derived from a mammary tissue, a viable pluripotent stem cell population derived from a meniscal tissue, a viable pluripotent stem cell population derived from a muscle tissue, a viable pluripotent stem cell population derived from a nerve tissue, a viable pluripotent stem cell population derived from an ovarian tissue, a viable pluripotent stem cell population derived from a pancreatic tissue, a viable pluripotent stem cell population derived from a parenchymal organ tissue, a viable pluripotent stem cell population derived from a pericardial tissue, a viable pluripotent stem cell population derived from a periosteal tissue, a viable pluripotent stem cell population derived from a peritoneal tissue, a viable pluripotent stem cell population derived from a placental tissue, a viable pluripotent stem cell population derived from a reproductive epithelial tissue, a viable pluripotent stem cell population derived from a respiratory epithelial tissue, a viable pluripotent stem cell population derived from a skin tissue, a viable pluripotent stem cell population derived from a spleen tissue, a viable pluripotent stem cell population derived from a stomach tissue, a viable pluripotent stem cell population derived from a synovial tissue, a viable pluripotent stem cell population derived from a tendon tissue, a viable pluripotent stem cell population derived from a testes tissue, a viable pluripotent stem cell population derived from an umbilical cord tissue, a viable pluripotent stem cell population derived from a urological tissue, a viable pluripotent stem cell population derived from a vascular tissue, a viable pluripotent stem cell population derived from a vein tissue, and a combination thereof. According to one embodiment, the at least one viable pluripotent stem cell population comprises a viable pluripotent stem cell population derived from an adipose tissue. According to one embodiment, the at least one viable pluripotent stem cell population comprises a viable pluripotent stem cell population derived from an amnion tissue. According to one embodiment, the at least one viable pluripotent stem cell population comprises a viable pluripotent stem cell population derived from an artery tissue. According to one embodiment, the at least one viable pluripotent stem cell population comprises a viable pluripotent stem cell population derived from a bone tissue. According to one embodiment, the at least one viable pluripotent stem cell population comprises a viable pluripotent stem cell population derived from a cartilage tissue. According to one embodiment, the at least one viable pluripotent stem cell population comprises a viable pluripotent stem cell population derived from a chorion tissue.

According to one embodiment, the at least one viable pluripotent stem cell population comprises a viable pluripotent stem cell population derived from a colon tissue. According to one embodiment, the at least one viable pluripotent stem cell population comprises a viable pluripotent stem cell population derived from a dental tissue. According to one embodiment, the at least one viable pluripotent stem cell population comprises a viable pluripotent stem cell population derived from a dermal tissue. According to one embodiment, the at least one viable pluripotent stem cell population comprises a viable pluripotent stem cell population derived from a duodenal tissue. According to one embodiment, the at least one viable pluripotent stem cell population comprises a viable pluripotent stem cell population derived from an epithelial tissue. According to one embodiment, the at least one viable pluripotent stem cell population comprises a viable pluripotent stem cell population derived from a fascial tissue. According to one embodiment, the at least one viable pluripotent stem cell population comprises a viable pluripotent stem cell population derived from a gastrointestinal tissue. According to one embodiment, the at least one viable pluripotent stem cell population comprises a viable pluripotent stem cell population derived from a growth plate tissue. According to one embodiment, the at least one viable pluripotent stem cell population comprises a viable pluripotent stem cell population derived from an intervertebral disc tissue. According to one embodiment, the at least one viable pluripotent stem cell population comprises a viable pluripotent stem cell population derived from an intestinal mucosal tissue. According to one embodiment, the at least one viable pluripotent stem cell population comprises a viable pluripotent stem cell population derived from an intestinal serosal tissue. According to one embodiment, the at least one viable pluripotent stem cell population comprises a viable pluripotent stem cell population derived from a kidney tissue. According to one embodiment, the at least one viable pluripotent stem cell population comprises a viable pluripotent stem cell population derived from a ligament tissue. According to one embodiment, the at least one viable pluripotent stem cell population comprises a viable pluripotent stem cell population derived from a liver tissue. According to one embodiment, the at least one viable pluripotent stem cell population comprises a viable pluripotent stem cell population derived from a lung tissue. According to one embodiment, the at least one viable pluripotent stem cell population comprises a viable pluripotent stem cell population derived from a mammary tissue. According to one embodiment, the at least one viable pluripotent stem cell population comprises a viable pluripotent stem cell population derived from a meniscal tissue. According to one embodiment, the at least one viable pluripotent stem cell population comprises a viable pluripotent stem cell population derived from a muscle tissue. According to one embodiment, the at least one viable pluripotent stem cell population comprises a viable pluripotent stem cell population derived from a nerve tissue. According to one embodiment, the at least one viable pluripotent stem cell population comprises a viable pluripotent stem cell population derived from an ovarian tissue. According to one embodiment, the at least one viable pluripotent stem cell population comprises a viable pluripotent stem cell population derived from a pancreatic tissue. According to one embodiment, the at least one viable pluripotent stem cell population comprises a viable pluripotent stem cell population derived from a parenchymal organ tissue. According to one embodiment, the at least one viable pluripotent stem cell population comprises a viable pluripotent stem cell population derived from a pericardial tissue. According to one embodiment, the at least one viable pluripotent stem cell population comprises a viable pluripotent stem cell population derived from a periosteal tissue. According to one embodiment, the at least one viable pluripotent stem cell population comprises a viable pluripotent stem cell population derived from a peritoneal tissue. According to one embodiment, the at least one viable pluripotent stem cell population comprises a viable pluripotent stem cell population derived from a placental tissue. According to one embodiment, the at least one viable pluripotent stem cell population comprises a viable pluripotent stem cell population derived from a reproductive epithelial tissue. According to one embodiment, the at least one viable pluripotent stem cell population comprises a viable pluripotent stem cell population derived from a respiratory epithelial tissue. According to one embodiment, the at least one viable pluripotent stem cell population comprises a viable pluripotent stem cell population derived from a skin tissue. According to one embodiment, the at least one viable pluripotent stem cell population comprises a viable pluripotent stem cell population derived from a spleen tissue. According to one embodiment, the at least one viable pluripotent stem cell population comprises a viable pluripotent stem cell population derived from a stomach tissue. According to one embodiment, the at least one viable pluripotent stem cell population comprises a viable pluripotent stem cell population derived from a synovial tissue. According to one embodiment, the at least one viable pluripotent stem cell population comprises a viable pluripotent stem cell population derived from a tendon tissue. According to one embodiment, the at least one viable pluripotent stem cell population comprises a viable pluripotent stem cell population derived from a testes tissue. According to one embodiment, the at least one viable pluripotent stem cell population comprises a viable pluripotent stem cell population derived from an umbilical cord tissue. According to one embodiment, the at least one viable pluripotent stem cell population comprises a viable pluripotent stem cell population derived from a urological tissue. According to one embodiment, the at least one viable pluripotent stem cell population comprises a viable pluripotent stem cell population derived from a vascular tissue. According to one embodiment, the at least one viable pluripotent stem cell population comprises a viable pluripotent stem cell population derived from a vein tissue. According to one embodiment, the at least one viable somatic stem cell population is selected from the group consisting of a viable somatic stem cell population derived from an adipose tissue, a viable somatic stem cell population derived from an amnion tissue, a viable somatic stem cell population derived from an artery tissue, a viable somatic stem cell population derived from a bone tissue, a viable somatic stem cell population derived from a cartilage tissue, a viable somatic stem cell population derived from a chorion tissue, a viable somatic stem cell population derived from a colon tissue, a viable somatic stem cell population derived from a dental tissue, a viable somatic stem cell population derived from a dermal tissue, a viable somatic stem cell population derived from a duodenal tissue, a viable somatic stem cell population derived from an epithelial tissue, a viable somatic stem cell population derived from a fascial tissue, a viable somatic stem cell population derived from a gastrointestinal tissue, a viable somatic stem cell population derived from a growth plate tissue, a viable somatic stem cell population derived from an intervertebral disc tissue, a viable somatic stem cell population derived from an intestinal mucosal disc tissue, a viable somatic stem cell population derived from an intestinal serosal tissue, a viable somatic stem cell population derived from a kidney tissue, a viable somatic stem cell population derived from a ligament tissue, a viable somatic stem cell population derived from a liver tissue, a viable somatic stem cell population derived from a lung tissue, a viable somatic stem cell population derived from a mammary tissue, a viable somatic stem cell population derived from a meniscal tissue, a viable somatic stem cell population derived from a muscle tissue, a viable somatic stem cell population derived from a nerve tissue, a viable somatic stem cell population derived from an ovarian tissue, a viable somatic stem cell population derived from a pancreatic tissue, a viable somatic stem cell population derived from a parenchymal organ tissue, a viable somatic stem cell population derived from a pericardial tissue, a viable somatic stem cell population derived from a periosteal tissue, a viable somatic stem cell population derived from a peritoneal tissue, a viable somatic stem cell population derived from a placental tissue, a viable somatic stem cell population derived from a reproductive epithelial tissue, a viable somatic stem cell population derived from a respiratory epithelial tissue, a viable somatic stem cell population derived from a skin tissue, a viable somatic stem cell population derived from a spleen tissue, a viable somatic stem cell population derived from a stomach tissue, a viable somatic stem cell population derived from a synovial tissue, a viable somatic stem cell population derived from a tendon tissue, a viable somatic stem cell population derived from a testes tissue, a viable somatic stem cell population derived from an umbilical cord tissue, a viable somatic stem cell population derived from a urological tissue, a viable somatic stem cell population derived from a vascular tissue, a viable somatic stem cell population derived from a vein tissue, and a combination thereof. According to one embodiment, the at least one viable somatic stem cell population comprises a viable somatic stem cell population derived from an adipose tissue. According to one embodiment, the at least one viable somatic stem cell population comprises a viable somatic stem cell population derived from an amnion tissue. According to one embodiment, the at least one viable somatic stem cell population comprises a viable somatic stem cell population derived from an artery tissue. According to one embodiment, the at least one viable somatic stem cell population comprises a viable somatic stem cell population derived from a bone tissue. According to one embodiment, the at least one viable somatic stem cell population comprises a viable somatic stem cell population derived from a cartilage tissue. According to one embodiment, the at least one viable somatic stem cell population comprises a viable somatic stem cell population derived from a chorion tissue. According to one embodiment, the at least one viable somatic stem cell population comprises a viable somatic stem cell population derived from a colon tissue. According to one embodiment, the at least one viable somatic stem cell population comprises a viable somatic stem cell population derived from a dental tissue. According to one embodiment, the at least one viable somatic stem cell population comprises a viable somatic stem cell population derived from a dermal tissue. According to one embodiment, the at least one viable somatic stem cell population comprises a viable somatic stem cell population derived from a duodenal tissue. According to one embodiment, the at least one viable somatic stem cell population comprises a viable somatic stem cell population derived from an epithelial tissue. According to one embodiment, the at least one viable somatic stem cell population comprises a viable somatic stem cell population derived from a fascial tissue. According to one embodiment, the at least one viable somatic stem cell population comprises a viable somatic stem cell population derived from a gastrointestinal tissue. According to one embodiment, the at least one viable somatic stem cell population comprises a viable somatic stem cell population derived from a growth plate tissue. According to one embodiment, the at least one viable somatic stem cell population comprises a viable somatic stem cell population derived from an intervertebral disc tissue. According to one embodiment, the at least one viable somatic stem cell population comprises a viable somatic stem cell population derived from an intestinal mucosal tissue. According to one embodiment, the at least one viable somatic stem cell population comprises a viable somatic stem cell population derived from an intestinal serosal tissue. According to one embodiment, the at least one viable somatic stem cell population comprises a viable somatic stem cell population derived from a kidney tissue. According to one embodiment, the at least one viable somatic stem cell population comprises a viable somatic stem cell population derived from a ligament tissue. According to one embodiment, the at least one viable somatic stem cell population comprises a viable somatic stem cell population derived from a liver tissue. According to one embodiment, the at least one viable somatic stem cell population comprises a viable somatic stem cell population derived from a lung tissue. According to one embodiment, the at least one viable somatic stem cell population comprises a viable somatic stem cell population derived from a mammary tissue. According to one embodiment, the at least one viable somatic stem cell population comprises a viable somatic stem cell population derived from a meniscal tissue. According to one embodiment, the at least one viable somatic stem cell population comprises a viable somatic stem cell population derived from a muscle tissue. According to one embodiment, the at least one viable somatic stem cell population comprises a viable somatic stem cell population derived from a nerve tissue. According to one embodiment, the at least one viable somatic stem cell population comprises a viable somatic stem cell population derived from an ovarian tissue. According to one embodiment, the at least one viable somatic stem cell population comprises a viable somatic stem cell population derived from a pancreatic tissue. According to one embodiment, the at least one viable somatic stem cell population comprises a viable somatic stem cell population derived from a parenchymal organ tissue. According to one embodiment, the at least one viable somatic stem cell population comprises a viable somatic stem cell population derived from a pericardial tissue. According to one embodiment, the at least one viable somatic stem cell population comprises a viable somatic stem cell population derived from a periosteal tissue. According to one embodiment, the at least one viable somatic stem cell population comprises a viable somatic stem cell population derived from a peritoneal tissue. According to one embodiment, the at least one viable somatic stem cell population comprises a viable somatic stem cell population derived from a placental tissue. According to one embodiment, the at least one viable somatic stem cell population comprises a viable somatic stem cell population derived from a reproductive epithelial tissue. According to one embodiment, the at least one viable somatic stem cell population comprises a viable somatic stem cell population derived from a respiratory epithelial tissue. According to one embodiment, the at least one viable somatic stem cell population comprises a viable somatic stem cell population derived from a skin tissue. According to one embodiment, the at least one viable somatic stem cell population comprises a viable somatic stem cell population derived from a spleen tissue. According to one embodiment, the at least one viable somatic stem cell population comprises a viable somatic stem cell population derived from a stomach tissue. According to one embodiment, the at least one viable somatic stem cell population comprises a viable somatic stem cell population derived from a synovial tissue. According to one embodiment, the at least one viable somatic stem cell population comprises a viable somatic stem cell population derived from a tendon tissue. According to one embodiment, the at least one viable somatic stem cell population comprises a viable somatic stem cell population derived from a testes tissue. According to one embodiment, the at least one viable somatic stem cell population comprises a viable somatic stem cell population derived from an umbilical cord tissue. According to one embodiment, the at least one viable somatic stem cell population comprises a viable somatic stem cell population derived from a urological tissue. According to one embodiment, the at least one viable somatic stem cell population comprises a viable somatic stem cell population derived from a vascular tissue. According to one embodiment, the at least one viable somatic stem cell population comprises a viable somatic stem cell population derived from a vein tissue.

According to one embodiment, the at least one viable progenitor stem cell population is selected from the group consisting of a viable progenitor stem cell population derived from an adipose tissue, a viable progenitor stem cell population derived from an amnion tissue, a viable progenitor stem cell population derived from an artery tissue, a viable progenitor stem cell population derived from a bone tissue, a viable progenitor stem cell population derived from a cartilage tissue, a viable progenitor stem cell population derived from a chorion tissue, a viable progenitor stem cell population derived from a colon tissue, a viable progenitor stem cell population derived from a dental tissue, a viable progenitor stem cell population derived from a dermal tissue, a viable progenitor stem cell population derived from a duodenal tissue, a viable progenitor stem cell population derived from an epithelial tissue, a viable progenitor stem cell population derived from a fascial tissue, a viable progenitor stem cell population derived from a gastrointestinal tissue, a viable progenitor stem cell population derived from a growth plate tissue, a viable progenitor stem cell population derived from an intervertebral disc tissue, a viable progenitor stem cell population derived from an intestinal mucosal disc tissue, a viable progenitor stem cell population derived from an intestinal serosal tissue, a viable progenitor stem cell population derived from a kidney tissue, a viable progenitor stem cell population derived from a ligament tissue, a viable progenitor stem cell population derived from a liver tissue, a viable progenitor stem cell population derived from a lung tissue, a viable progenitor stem cell population derived from a mammary tissue, a viable progenitor stem cell population derived from a meniscal tissue, a viable progenitor stem cell population derived from a muscle tissue, a viable progenitor stem cell population derived from a nerve tissue, a viable progenitor stem cell population derived from an ovarian tissue, a viable progenitor stem cell population derived from a pancreatic tissue, a viable progenitor stem cell population derived from a parenchymal organ tissue, a viable progenitor stem cell population derived from a pericardial tissue, a viable progenitor stem cell population derived from a periosteal tissue, a viable progenitor stem cell population derived from a peritoneal tissue, a viable progenitor stem cell population derived from a placental tissue, a viable progenitor stem cell population derived from a reproductive epithelial tissue, a viable progenitor stem cell population derived from a respiratory epithelial tissue, a viable progenitor stem cell population derived from a skin tissue, a viable progenitor stem cell population derived from a spleen tissue, a viable progenitor stem cell population derived from a stomach tissue, a viable progenitor stem cell population derived from a synovial tissue, a viable progenitor stem cell population derived from a tendon tissue, a viable progenitor stem cell population derived from a testes tissue, a viable progenitor stem cell population derived from an umbilical cord tissue, a viable progenitor stem cell population derived from a urological tissue, a viable progenitor stem cell population derived from a vascular tissue, a viable progenitor stem cell population derived from a vein tissue, and a combination thereof.

According to one embodiment, the at least one viable progenitor stem cell population comprises a viable progenitor stem cell population derived from an adipose tissue. According to one embodiment, the at least one viable progenitor stem cell population comprises a viable progenitor stem cell population derived from an amnion tissue. According to one embodiment, the at least one viable progenitor stem cell population comprises a viable progenitor stem cell population derived from an artery tissue. According to one embodiment, the at least one viable progenitor stem cell population comprises a viable progenitor stem cell population derived from a bone tissue. According to one embodiment, the at least one viable progenitor stem cell population comprises a viable progenitor stem cell population derived from a cartilage tissue. According to one embodiment, the at least one viable progenitor stem cell population comprises a viable progenitor stem cell population derived from a chorion tissue. According to one embodiment, the at least one viable progenitor stem cell population comprises a viable progenitor stem cell population derived from a colon tissue. According to one embodiment, the at least one viable progenitor stem cell population comprises a viable progenitor stem cell population derived from a dental tissue. According to one embodiment, the at least one viable progenitor stem cell population comprises a viable progenitor stem cell population derived from a dermal tissue. According to one embodiment, the at least one viable progenitor stem cell population comprises a viable progenitor stem cell population derived from a duodenal tissue. According to one embodiment, the at least one viable progenitor stem cell population comprises a viable progenitor stem cell population derived from an epithelial tissue. According to one embodiment, the at least one viable progenitor stem cell population comprises a viable progenitor stem cell population derived from a fascial tissue. According to one embodiment, the at least one viable progenitor stem cell population comprises a viable progenitor stem cell population derived from a gastrointestinal tissue. According to one embodiment, the at least one viable progenitor stem cell population comprises a viable progenitor stem cell population derived from a growth plate tissue. According to one embodiment, the at least one viable progenitor stem cell population comprises a viable progenitor stem cell population derived from an intervertebral disc tissue. According to one embodiment, the at least one viable progenitor stem cell population comprises a viable progenitor stem cell population derived from an intestinal mucosal tissue. According to one embodiment, the at least one viable progenitor stem cell population comprises a viable progenitor stem cell population derived from an intestinal serosal tissue. According to one embodiment, the at least one viable progenitor stem cell population comprises a viable progenitor stem cell population derived from a kidney tissue. According to one embodiment, the at least one viable progenitor stem cell population comprises a viable progenitor stem cell population derived from a ligament tissue. According to one embodiment, the at least one viable progenitor stem cell population comprises a viable progenitor stem cell population derived from a liver tissue. According to one embodiment, the at least one viable progenitor stem cell population comprises a viable progenitor stem cell population derived from a lung tissue. According to one embodiment, the at least one viable progenitor stem cell population comprises a viable progenitor stem cell population derived from a mammary tissue. According to one embodiment, the at least one viable progenitor stem cell population comprises a viable progenitor stem cell population derived from a meniscal tissue. According to one embodiment, the at least one viable progenitor stem cell population comprises a viable progenitor stem cell population derived from a muscle tissue. According to one embodiment, the at least one viable progenitor stem cell population comprises a viable progenitor stem cell population derived from a nerve tissue. According to one embodiment, the at least one viable progenitor stem cell population comprises a viable progenitor stem cell population derived from an ovarian tissue. According to one embodiment, the at least one viable progenitor stem cell population comprises a viable progenitor stem cell population derived from a pancreatic tissue. According to one embodiment, the at least one viable progenitor stem cell population comprises a viable progenitor stem cell population derived from a parenchymal organ tissue. According to one embodiment, the at least one viable progenitor stem cell population comprises a viable progenitor stem cell population derived from a pericardial tissue. According to one embodiment, the at least one viable progenitor stem cell population comprises a viable progenitor stem cell population derived from a periosteal tissue. According to one embodiment, the at least one viable progenitor stem cell population comprises a viable progenitor stem cell population derived from a peritoneal tissue. According to one embodiment, the at least one viable progenitor stem cell population comprises a viable progenitor stem cell population derived from a placental tissue. According to one embodiment, the at least one viable progenitor stem cell population comprises a viable progenitor stem cell population derived from a reproductive epithelial tissue. According to one embodiment, the at least one viable progenitor stem cell population comprises a viable progenitor stem cell population derived from a respiratory epithelial tissue. According to one embodiment, the at least one viable progenitor stem cell population comprises a viable progenitor stem cell population derived from a skin tissue. According to one embodiment, the at least one viable progenitor stem cell population comprises a viable progenitor stem cell population derived from a spleen tissue. According to one embodiment, the at least one viable progenitor stem cell population comprises a viable progenitor stem cell population derived from a stomach tissue. According to one embodiment, the at least one viable progenitor stem cell population comprises a viable progenitor stem cell population derived from a synovial tissue. According to one embodiment, the at least one viable progenitor stem cell population comprises a viable progenitor stem cell population derived from a tendon tissue. According to one embodiment, the at least one viable progenitor stem cell population comprises a viable progenitor stem cell population derived from a testes tissue. According to one embodiment, the at least one viable progenitor stem cell population comprises a viable progenitor stem cell population derived from an umbilical cord tissue. According to one embodiment, the at least one viable progenitor stem cell population comprises a viable progenitor stem cell population derived from a urological tissue. According to one embodiment, the at least one viable progenitor stem cell population comprises a viable progenitor stem cell population derived from a vascular tissue. According to one embodiment, the at least one viable progenitor stem cell population comprises a viable progenitor stem cell population derived from a vein tissue.

According to one embodiment, the at least one viable population of tissuegenic cells is capable of migrating from or to the at least one growth-conductive matrix.

According to some embodiments, the at least one viable population of tissuegenic cells adherent to and resident in the endogenous milieu of the growth conductive matrix is immune privileged. The term "immune privileged" as used herein refers to a characteristic of tissuegenic cells by which there is no induction of an immune response upon transplantation of such cells of such cells into an allogeneic host.

Growth-Inductive Factors

Evidence supports the notion that stem cells can adjust their properties according to their surroundings and select specific lineages according to cues they receive from their niche. It follows that in order for a tissuegenic cell therapy to be successful in the repair of a specific tissue type, the microenvironment of the tissuegenic cells should be designed to relay the appropriate chemical and physical signals to them.

According to one embodiment, the implant further comprises at least one growth-inductive component. According to one embodiment, the at least one growth-inductive component is tissue-derived. According to one embodiment, the at least one growth-inductive component comprises inducible pluripotent stem cells (iPSCs). According to one embodiment, the at least one growth-inductive component originates from a component of the tissue-derived growth-inductive component other than cells. According to one embodiment, the at least one growth-inductive factor is endogenous to the at least one growth-conductive matrix. According to one embodiment, the tissuegenic cells adherent to and resident in the endogenous milieu of the growth conductive matrix secrete the at least one growth-inductive component. According to one embodiment, the at least one growth-inductive component is exogenous to the at least one growth-conductive matrix. According to one embodiment, the growth-inductive component comprises a growth medium derived from expanded tissuegenic cells. According to another embodiment, a growth-inductive matrix (e.g., an osteoinductive matrix) includes a demineralized bone matrix, which may be prepared from one or more of the bone tissue matrix types and sources of bone tissue matrix described above with regard to growth-conductive matrices that include bone tissue matrices. According to one embodiment, the at least one growth-inductive component is a growth-inductivefactor. According to some such embodiments, the at least one growth-inductivefactor is selected from the group consisting of a bone morphogenic protein (BMP), a fibroblast growth factor (FGF), an insulin-like growth factor (IGF), a platelet-derived growth factor (PDGF), a transforming growth factor-β (TGF-β), a neural epidermal growth-factor-like 1 (NELL-1), and a combination thereof. According to one embodiment, the at least one viable population of tissuegenic cells secretes the at least one growth-inductivefactor. According to some such embodiments, the at least one growth-inductivefactor comprises a bone morphogenic protein. According to some such embodiments, the at least one growth-inductivefactor comprises a fibroblast growth factor. According to some such embodiments, the at least one growth-inductivefactor comprises an insulin-like growth factor. According to some such embodiments, the at least one growth-inductive factor comprises a platelet-derived growth factor. According to some such embodiments, the at least one growth-inductivefactor comprises a transforming growth factor-β. According to some such embodiments, the at least one growth-inductivefactor comprises a neural epidermal growth-factor-like 1.

Target Lineage of Tissuegenic Cells

According to one embodiment, the at least one viable population of tissuegenic cells is capable of differentiating into cells of at least one embryonic lineage. According to one embodiment, the embryonic lineage is selected from the group consisting of an ectodermal lineage, a mesodermal lineage and an endodermal lineage. According to one embodiment, the at least one viable population of tissuegenic cells is capable of differentiating into cells of an ectodermal lineage. According to one embodiment, the at least one viable population of tissuegenic cells is capable of differentiating into cells of a mesodermal lineage. According to one embodiment, the at least one viable population of tissuegenic cells is capable of differentiating into cells of an endodermal lineage.

According to one embodiment, the at least one viable population of tissuegenic cells is capable of regenerating a target tissue. According to one embodiment, the target tissue is selected from the group consisting of an adipose tissue, an amnion tissue, an artery tissue, a bone tissue, a cartilage tissue, a chorion tissue, a colon tissue, a dental tissue, a dermal tissue, a duodenal tissue, an endothelial tissue, an epithelial tissue, a fascial tissue, a gastrointestinal tissue, a growth plate tissue, an intervertebral disc tissue, an intestinal mucosal tissue, an intestinal serosal tissue, a kidney tissue, a ligament tissue, a liver tissue, a lung tissue, a meniscal tissue, a muscle tissue, a nerve tissue, an ovarian tissue, a pancreatic tissue, a parenchymal organ tissue, a pericardial tissue, a periosteal tissue, a peritoneal tissue, a skin tissue, a spleen tissue, a synovial tissue, a tendon tissue, a testes tissue, a urological tissue, a vascular tissue, a vein tissue, and a combination thereof.

According to one embodiment, the at least one viable population of tissuegenic cells is capable of regenerating an adipose tissue. According to one embodiment, the at least one viable population of tissuegenic cells is capable of regenerating an amnion tissue. According to one embodiment, the at least one viable population of tissuegenic cells is capable of regenerating an artery tissue. According to one embodiment, the at least one viable population of tissuegenic cells is capable of regenerating a bone tissue. According to one embodiment, the at least one viable population of tissuegenic cells is capable of regenerating a cartilage tissue. According to one embodiment, the at least one viable population of tissuegenic cells is capable of regenerating a chorion tissue. According to one embodiment, the at least one viable population of tissuegenic cells is capable of regenerating a colon tissue. According to one embodiment, the at least one viable population of tissuegenic cells is capable of regenerating a dental tissue. According to one embodiment, the at least one viable population of tissuegenic cells is capable of regenerating a dermal tissue. According to one embodiment, the at least one viable population of tissuegenic cells is capable of regenerating a duodenal tissue. According to one embodiment, the at least one viable population of tissuegenic cells is capable of regenerating an endothelial tissue. According to one embodiment, the at least one viable population of tissuegenic cells is capable of regenerating a fascial tissue. According to one embodiment, the at least one viable population of tissuegenic cells is capable of regenerating a gastrointestinal tissue. According to one embodiment, the at least one viable population of tissuegenic cells is capable of regenerating a growth plate tissue. According to one embodiment, the at least one viable population of tissuegenic cells is capable of regenerating an intervertebral disc tissue. According to one embodiment, the at least one viable population of tissuegenic cells is capable of regenerating an intestinal mucosal tissue. According to one embodiment, the at least one viable population of tissuegenic cells is capable of regenerating an intestinal serosal tissue. According to one embodiment, the at least one viable population of tissuegenic cells is capable of regenerating a kidney tissue. According to one embodiment, the at least one viable population of tissuegenic cells is capable of regenerating a ligament tissue. According to one embodiment, the at least one viable population of tissuegenic cells is capable of regenerating a liver tissue. According to one embodiment, the at least one viable population of tissuegenic cells is capable of regenerating a lung tissue. According to one embodiment, the at least one viable population of tissuegenic cells is capable of regenerating a meniscal tissue. According to one embodiment, the at least one viable population of tissuegenic cells is capable of regenerating a muscle tissue. According to one embodiment, the at least one viable population of tissuegenic cells is capable of regenerating a nerve tissue. According to one embodiment, the at least one viable population of tissuegenic cells is capable of regenerating an ovarian tissue. According to one embodiment, the at least one viable population of tissuegenic cells is capable of regenerating a pancreatic tissue. According to one embodiment, the at least one viable population of tissuegenic cells is capable of regenerating a parenchymal organ tissue. According to one embodiment, the at least one viable population of tissuegenic cells is capable of regenerating a pericardial tissue. According to one embodiment, the at least one viable population of tissuegenic cells is capable of regenerating a periosteal tissue. According to one embodiment, the at least one viable population of tissuegenic cells is capable of regenerating a peritoneal tissue. According to one embodiment, the at least one viable population of tissuegenic cells is capable of regenerating a skin tissue. According to one embodiment, the at least one viable population of tissuegenic cells is capable of regenerating a spleen tissue. According to one embodiment, the at least one viable population of tissuegenic cells is capable of regenerating a synovial tissue. According to one embodiment, the at least one viable population of tissuegenic cells is capable of regenerating a tendon tissue. According to one embodiment, the at least one viable population of tissuegenic cells is capable of regenerating a testes tissue. According to one embodiment, the at least one viable population of tissuegenic cells is capable of regenerating a urological tissue. According to one embodiment, the at least one viable population of tissuegenic cells is capable of regenerating a vascular tissue. According to one embodiment, the at least one viable population of tissuegenic cells is capable of regenerating a vein tissue.

According to one embodiment, the at least one viable population of tissuegenic cells is capable of differentiating into a target tissue cell lineage. According to one embodiment, the target tissue cell lineage is selected from the group consisting of an adipose cell lineage, an amnion cell lineage, an artery cell lineage, a bone cell lineage, a cartilage cell lineage, a dental cell lineage, a dermal cell lineage, a duodenal cell lineage, an endothelial lineage, an epithelial cell lineage, a fascial cell lineage, a gastrointestinal cell lineage, a growth plate cell lineage, an intervertebral disc cell lineage, an intestinal mucosal cell lineage, an intestinal serosal cell lineage, a kidney cell lineage, a ligament cell lineage, a liver cell lineage, a lung cell lineage, a meniscal cell lineage, a muscle cell lineage, a nerve cell lineage, an ovarian cell lineage, a pancreatic cell lineage, a parenchymal organ cell lineage, a pericardial cell lineage, a periosteal cell lineage, a peritoneal cell lineage, a skin cell lineage, a spleen cell lineage, a synovial cell lineage, a tendon cell lineage, a testes cell lineage, a urological cell lineage, a vascular cell lineage, a vein cell lineage, and a combination thereof.

According to one embodiment, the at least one viable population of tissuegenic cells is capable of differentiating into an adipose cell lineage. According to one embodiment, the at least one viable population of tissuegenic cells is capable of differentiating into an amnion cell lineage. According to one embodiment, the at least one viable population of tissuegenic cells is capable of differentiating into an artery cell lineage. According to one embodiment, the at least one viable population of tissuegenic cells is capable of differentiating into a bone cell lineage. According to one embodiment, the at least one viable population of tissuegenic cells is capable of differentiating into a cartilage cell lineage. According to one embodiment, the at least one viable population of tissuegenic cells is capable of differentiating into a chorion cell lineage. According to one embodiment, the at least one viable population of tissuegenic cells is capable of differentiating into a colon cell lineage. According to one embodiment, the at least one viable population of tissuegenic cells is capable of differentiating into a dental cell lineage. According to one embodiment, the at least one viable population of tissuegenic cells is capable of differentiating into a dermal cell lineage. According to one embodiment, the at least one viable population of tissuegenic cells is capable of differentiating into a duodenal cell lineage. According to one embodiment, the at least one viable population of tissuegenic cells is capable of differentiating into an endothelial cell lineage. According to one embodiment, the at least one viable population of tissuegenic cells is capable of differentiating into an epithelial cell lineage. According to one embodiment, the at least one viable population of tissuegenic cells is capable of differentiating into a fascial cell lineage. According to one embodiment, the at least one viable population of tissuegenic cells is capable of differentiating into a gastrointestinal cell lineage. According to one embodiment, the at least one viable population of tissuegenic cells is capable of differentiating into a growth plate cell lineage. According to one embodiment, the at least one viable population of tissuegenic cells is capable of differentiating into an intervertebral disc cell lineage. According to one embodiment, the at least one viable population of tissuegenic cells is capable of differentiating into an intestinal mucosal cell lineage. According to one embodiment, the at least one viable population of tissuegenic cells is capable of differentiating into an intestinal serosal cell lineage. According to one embodiment, the at least one viable population of tissuegenic cells is capable of differentiating into a kidney cell lineage. According to one embodiment, the at least one viable population of tissuegenic cells is capable of differentiating into a ligament cell lineage. According to one embodiment, the at least one viable population of tissuegenic cells is capable of differentiating into a liver cell lineage. According to one embodiment, the at least one viable population of tissuegenic cells is capable of differentiating into a lung cell lineage. According to one embodiment, the at least one viable population of tissuegenic cells is capable of differentiating into a meniscal cell lineage. According to one embodiment, the at least one viable population of tissuegenic cells is capable of differentiating into a muscle cell lineage. According to one embodiment, the at least one viable population of tissuegenic cells is capable of differentiating into a nerve cell lineage. According to one embodiment, the at least one viable population of tissuegenic cells is capable of differentiating into an ovarian cell lineage. According to one embodiment, the at least one viable population of tissuegenic cells is capable of differentiating into a pancreatic cell lineage. According to one embodiment, the at least one viable population of tissuegenic cells is capable of differentiating into a parenchymal organ cell lineage. According to one embodiment, the at least one viable population of tissuegenic cells is capable of differentiating into a pericardial cell lineage. According to one embodiment, the at least one viable population of tissuegenic cells is capable of differentiating into a periosteal cell lineage. According to one embodiment, the at least one viable population of tissuegenic cells is capable of differentiating into a peritoneal cell lineage. According to one embodiment, the at least one viable population of tissuegenic cells is capable of differentiating into a skin cell lineage. According to one embodiment, the at least one viable population of tissuegenic cells is capable of differentiating into a spleen cell lineage. According to one embodiment, the at least one viable population of tissuegenic cells is capable of differentiating into a synovial cell lineage. According to one embodiment, the at least one viable population of tissuegenic cells is capable of differentiating into a tendon cell lineage. According to one embodiment, the at least one viable population of tissuegenic cells is capable of differentiating into a testes cell lineage. According to one embodiment, the at least one viable population of tissuegenic cells is capable of differentiating into a urological cell lineage. According to one embodiment, the at least one viable population of tissuegenic cells is capable of differentiating into a vascular cell lineage. According to one embodiment, the at least one viable population of tissuegenic cells is capable of differentiating into a vein cell lineage.

According to one embodiment, the at least one viable population of tissuegenic cells comprises a viable nonexpanded population of tissuegenic cells. According to one embodiment, the at least one viable population of tissuegenic cells comprises a viable expanded population of tissuegenic cells. According to one embodiment, the at least one viable population of tissuegenic cells is capable of migrating from or to the at least one growth-conductive matrix. According to some embodiments, the at least one viable population of tissuegenic cells adherent to and resident in the endogenous milieu of the growth conductive matrix is immune privileged. The term "immune privileged" as used herein refers to the characteristic of tissuegenic cells by which there is no induction of an immune response upon transplantation of such cells.

According to one embodiment, the bone cell lineage is selected from the group consisting of an osteoprogenitor cell lineage, an osteoblast lineage, an osteocyte lineage, and an osteoclast lineage. According to one embodiment, the bone cell lineage comprises an osteoprogenitor cell lineage. According to one embodiment, the bone cell lineage comprises an osteoblast lineage. According to one embodiment, the bone cell lineage comprises an osteocyte lineage.

According to one embodiment, the cartilage cell lineage is selected from the group consisting of a chondrocyte lineage, a chondroblast lineage and a chondroclast lineage. According to one embodiment, the cartilage cell lineage comprises a chondrocyte lineage. According to one embodiment, the cartilage cell lineage comprises a chondroblast lineage. According to one embodiment, the cartilage cell lineage comprises a chondroclast lineage.

According to one embodiment, the dental cell lineage is selected from the group consisting of an ameloblast lineage, an odontoblast lineage, a cementoblast and a nerve cell lineage. According to one embodiment, the dental cell lineage comprises an ameloblast lineage. According to one embodiment, the dental cell lineage comprises an odontoblast lineage. According to one embodiment, the dental cell lineage comprises a cementoblast lineage. According to one embodiment, the dental cell lineage comprises a nerve cell lineage.

According to one embodiment, the intervertebral disc cell lineage comprises a cartilage cell lineage. According to one embodiment, the intervertebral disc cell lineage is selected from the group consisting of an annulus fibrosus lineage, a nucleus pulposus lineage and an endplate lineage. According to one embodiment, the intervertebral disc cell lineage comprises an annulus fibrosus cell lineage. According to one embodiment, the intervertebral disc cell lineage comprises a nucleus pulposus cell lineage. According to one embodiment, the inetrvertebral disc cell embodiment comprises an endplate lineage.

According to one embodiment, the gastrointestinal cell lineage comprises a gastrointestinal epithelial cell lineage. According to one embodiment, the gastrointestinal epithelial cell lineage is selected from the group consisting of a columnar epithelial cell lineage, a goblet cell lineage, an enteroendocrine chromaffin cell lineage and a Paneth cell lineage. According to one embodiment, the gastrointestinal epithelial cell lineage comprises a columnar epithelial cell lineage. According to one embodiment, the gastrointestinal epithelial cell lineage comprises a goblet cell lineage. According to one embodiment, the gastrointestinal epithelial cell lineage comprises an enteroendocrine chromaffin cell lineage. According to one embodiment, the gastrointestinal epithelial cell lineage comprises a Paneth cell lineage.

According to one embodiment, the growth plate cell lineage comprises a cartilage cell lineage.

According to one embodiment, the ligament cell lineage comprises a fibroblast lineage. According to one embodiment, the connective tissue cell lineage is selected from the group consisting of a fibroblast lineage, a macrophage lineage, and a mast cell lineage. According to one embodiment, the connective tissue cell lineage comprises a fibroblast lineage. According to one embodiment, the connective tissue cell lineage comprises a macrophage lineage. According to one embodiment, the connective tissue cell lineage comprises a mast cell lineage.

According to one embodiment, the liver cell lineage comprises a hepatocyte lineage.

According to one embodiment, the meniscal cell lineage comprises a cartilage cell lineage.

According to one embodiment, the lung cell lineage comprises an epithelial cell lineage. According to one embodiment, the lung cell lineage comprises a vascular cell lineage.

According to one embodiment, the muscle cell lineage is selected from the group consisting of a smooth muscle cell lineage, a skeletal muscle cell lineage and a cardiomyocyte lineage. According to one embodiment, the muscle cell lineage comprises a smooth muscle cell lineage. According to one embodiment, the muscle cell lineage comprises a skeletal muscle cell lineage. According to one embodiment, the muscle cell lineage comprises a cardiomyocyte lineage.

According to one embodiment, the nerve cell lineage is selected from the group consisting of an astrocyte lineage, a dendritic cell lineage, a neuroglial cell lineage, and a neuron lineage. According to one embodiment, the nerve cell lineage comprises an astrocyte lineage. According to one embodiment, the nerve cell lineage comprises a dendritic cell lineage. According to one embodiment, the nerve cell lineage comprises a neuroglial cell lineage. According to one embodiment, the nerve cell lineage comprises a neuron lineage.

According to one embodiment, the periosteal cell lineage comprises a connective tissue cell lineage.

According to one embodiment, the skin cell lineage is selected from a group consisting of an epidermal cell lineage and a dermal cell lineage. According to one embodiment, the skin cell lineage comprises an epidermal cell lineage. According to one embodiment, the skin cell lineage comprises a dermal cell lineage. According to one embodiment, the skin cell lineage is selected from a group consisting of a fibroblast lineage, a keratinocyte lineage, a macrophage lineage and a mast cell lineage. According to one embodiment, the skin cell lineage comprises a fibroblast lineage. According to one embodiment, the skin cell lineage comprises a keratinocyte lineage. According to one embodiment, the skin cell lineage comprises a macrophage lineage. According to one embodiment, the skin cell lineage comprises a mast cell lineage.

According to one embodiment, the synovial cell lineage comprises a connective tissue cell lineage. According to one embodiment, the connective tissue cell lineage is selected from the group consisting of a fibroblast lineage, a macrophage lineage, and a mast cell lineage. According to one embodiment, the connective tissue cell lineage comprises a fibroblast lineage. According to one embodiment, the connective tissue cell lineage comprises a macrophage lineage. According to one embodiment, the connective tissue cell lineage comprises a mast cell lineage.

According to one embodiment, the tendon cell lineage comprises a connective tissue cell lineage. According to one embodiment, the connective tissue cell lineage is selected from the group consisting of a fibroblast lineage, a macrophage lineage, and a mast cell lineage. According to one embodiment, the connective tissue cell lineage comprises a fibroblast lineage. According to one embodiment, the connective tissue cell lineage comprises a macrophage lineage. According to one embodiment, the connective tissue cell lineage comprises a mast cell lineage. According to one embodiment, the tendon cell lineage comprises a tenocyte lineage. According to one embodiment, the connective tissue cell lineage comprises a mast cell lineage.

According to one embodiment, the vascular cell lineage comprises a connective tissue cell lineage. According to one embodiment, the connective tissue cell lineage is selected from the group consisting of a fibroblast lineage, a macrophage lineage, and a mast cell lineage. According to one embodiment, the connective tissue cell lineage comprises a fibroblast lineage. According to one embodiment, the connective tissue cell lineage comprises a macrophage lineage. According to one embodiment, the connective tissue cell lineage comprises a mast cell lineage. According to one embodiment, the tendon cell lineage comprises an endothelial lineage.

Tissuegenic Cells Derived from Adipose Tissue

According to one embodiment, the at least one viable population of tissuegenic cells derived from adipose tissue is selected from the group consisting of a viable population of pluripotent stem cells, a viable population of mesenchymal stem cells, a viable population of adipose-derived stem cells, and a viable population of adipose-derived progenitor cells. According to one embodiment, the at least one viable population of tissuegenic cells derived from adipose tissue is a viable pluripotent stem cell population. According to one embodiment, the at least one viable population of tissuegenic cells derived from adipose tissue is a viable mesenchymal stem cell population. According to one embodiment, the at least one viable population of tissuegenic cells derived from adipose tissue is a viable adipose-derived stem cell population. According to one embodiment, the at least one viable population of tissuegenic cells derived from adipose tissue is a viable adipose-derived progenitor cell population.

According to one embodiment, the at least one viable population of tissuegenic cells from adipose tissue secretes at least one growth-inductive factor. According to one embodiment, the at least one viable population of tissuegenic cells derived from adipose tissue secretes at least one growth-inductive factor such as an adipokine. According to one embodiment, the adipokine is selected from the group consisting of HGF, VEGF, Flt-3 ligand, G-CSF, GM-CSF, IL-7, IL-12, M-CSF, SCF, IL-1alpha, IL-6, IL-8, IL-11, LIF, and TNF-alpha. Other exemplary adipokinesare listed in Kilroy et. al. (2007), J. Cell. Physiol. 212: 702-709, the entire contents of which are incorporated by reference herein. According to one embodiment, the adipokine is an adiponectin. According to one embodiment, the adipokine is a leptin. According to one embodiment, the adipokine is an IL-6. According to one embodiment, the adipokine is an IL-7. According to one embodiment, the adipokine is an IL-8. According to one embodiment, the adipokine is a MCP-1. According to one embodiment, the adipokine is a GRO. According to one embodiment, the adipokine is an angiogenin. According to one embodiment, the adipokine is a HGF. According to one embodiment, the adipokine is a VEGF. According to one embodiment, the adipokine is a TIMP-1. According to one embodiment, the adipokine is a TIMP-2. Other exemplary adipokines, as used in this invention, are listed in Halberg et al. (2008), Endocrinol. Metab. Clin. North Am., 37(3): 753-767 and in Klimkakova et al. (2007), Biochem. Biophys. Res. Commun., 358: 897-902, which are incorporated herein by reference.

According to one embodiment, the at least one viable population of tissuegenic cells derived from adipose tissue is capable of differentiating into cells of at least one embryonic lineage. According to one embodiment, the embryonic lineage is selected from the group consisting of an ectodermal lineage, a mesodermal lineage and an endodermal lineage. According to one embodiment, the at least one viable population of tissuegenic cells derived from adipose tissue is capable of differentiating into cells of an ectodermal lineage. According to one embodiment, the at least one viable population of tissuegenic cells derived from adipose tissue is capable of differentiating into cells of a mesodermal lineage. According to one embodiment, the at least one viable population of tissuegenic cells derived from adipose tissue is capable of differentiating into cells of an endodermal lineage.

According to one embodiment, the at least one viable population of tissuegenic cells derived from adipose tissue is capable of regenerating a target tissue. According to one embodiment, the target tissue is selected from the group consisting of an adipose tissue, an amnion tissue, an artery tissue, a bone tissue, a cartilage tissue, a chorion tissue, a colon tissue, a dental tissue, a dermal tissue, a duodenal tissue, an endothelial tissue, an epithelial tissue, a gastrointestinal tissue, a growth plate tissue, an intervertebral disc tissue, an intestinal mucosal tissue, an intestinal serosal tissue, a kidney tissue, a ligament tissue, a liver tissue, a lung tissue, a meniscal tissue, a muscle tissue, a nerve tissue, an ovarian tissue, a pancreatic tissue, a parenchymal organ tissue, a pericardial tissue, a periosteal tissue, a peritoneal tissue, a skin tissue, a spleen tissue, a synovial tissue, a tendon tissue, a testes tissue, a urological tissue, a vascular tissue, a vein tissue, and a combination thereof.

According to one embodiment, the at least one viable population of tissuegenic cells derived from adipose tissue is capable of regenerating an adipose tissue. According to one embodiment, the at least one viable population of tissuegenic cells derived from adipose tissue is capable of regenerating an amnion tissue. According to one embodiment, the at least one viable population of tissuegenic cells derived from adipose tissue is capable of regenerating an artery tissue. According to one embodiment, the at least one viable population of tissuegenic cells derived from adipose tissue is capable of regenerating a bone tissue. According to one embodiment, the at least one viable population of tissuegenic cells derived from adipose tissue is capable of regenerating a cartilage tissue. According to one embodiment, the at least one viable population of tissuegenic cells derived from adipose tissue is capable of regenerating a chorion tissue. According to one embodiment, the at least one viable population of tissuegenic cells derived from adipose tissue is capable of regenerating a colon tissue. According to one embodiment, the at least one viable population of tissuegenic cells derived from adipose tissue is capable of regenerating a dental tissue. According to one embodiment, the at least one viable population of tissuegenic cells derived from adipose tissue is capable of regenerating a dermal tissue. According to one embodiment, the at least one viable population of tissuegenic cells derived from adipose tissue is capable of regenerating a duodenal tissue. According to one embodiment, the at least one viable population of tissuegenic cells derived from adipose tissue is capable of regenerating an endothelial tissue. According to one embodiment, the at least one viable population of tissuegenic cells derived from adipose tissue is capable of regenerating a gastrointestinal tissue. According to one embodiment, the at least one viable population of tissuegenic cells derived from adipose tissue is capable of regenerating a growth plate tissue. According to one embodiment, the at least one viable population of tissuegenic cells derived from adipose tissue is is capable of regenerating an intervertebral disc tissue. According to one embodiment, the at least one viable population of tissuegenic cells derived from adipose tissue is is capable of regenerating an intestinal mucosal tissue. According to one embodiment, the at least one viable population of tissuegenic cells derived from adipose tissue is is capable of regenerating an intestinal serosal tissue. According to one embodiment, the at least one viable population of tissuegenic cells derived from adipose tissue is is capable of regenerating a kidney tissue. According to one embodiment, the at least one viable population of tissuegenic cells derived from adipose tissue is capable of regenerating a ligament tissue. According to one embodiment, the at least one viable population of tissuegenic cells derived from adipose tissue is capable of regenerating a liver tissue. According to one embodiment, the at least one viable population of tissuegenic cells derived from adipose tissue is capable of regenerating a lung tissue. According to one embodiment, the at least one viable population of tissuegenic cells derived from adipose tissue is capable of regenerating a meniscal tissue. According to one embodiment, the at least one viable population of tissuegenic cells derived from adipose tissue is capable of regenerating a muscle tissue. According to one embodiment, the at least one viable population of tissuegenic cells derived from adipose tissue is capable of regenerating a nerve tissue. According to one embodiment, the at least one viable population of tissuegenic cells derived from adipose tissue is capable of regenerating an ovarian tissue. According to one embodiment, the at least one viable population of tissuegenic cells derived from adipose tissue is capable of regenerating a pancreatic tissue. According to one embodiment, the at least one viable population of tissuegenic cells derived from adipose tissue is capable of regenerating a parenchymal organ tissue. According to one embodiment, the at least one viable population of tissuegenic cells derived from adipose tissue is capable of regenerating a pericardial tissue. According to one embodiment, the at least one viable population of tissuegenic cells derived from adipose tissue is capable of regenerating a periosteal tissue. According to one embodiment, the at least one viable population of tissuegenic cells derived from adipose tissue is capable of regenerating a peritoneal tissue. According to one embodiment, the at least one viable population of tissuegenic cells derived from adipose tissue is capable of regenerating a skin tissue. According to one embodiment, the at least one viable population of tissuegenic cells derived from adipose tissue is capable of regenerating a spleen tissue. According to one embodiment, the at least one viable population of tissuegenic cells derived from adipose tissue is capable of regenerating a synovial tissue. According to one embodiment, the at least one viable population of tissuegenic cells derived from adipose tissue is capable of regenerating a tendon tissue. According to one embodiment, the at least one viable population of tissuegenic cells derived from adipose tissue is capable of regenerating a testes tissue. According to one embodiment, the at least one viable population of tissuegenic cells derived from adipose tissue is capable of regenerating a urological tissue. According to one embodiment, the at least one viable population of tissuegenic cells derived from adipose tissue is capable of regenerating a vascular tissue. According to one embodiment, the at least one viable population of tissuegenic cells derived from adipose tissue is capable of regenerating a vein tissue.

According to one embodiment, the at least one viable population of tissuegenic cells derived from adipose tissue is capable of differentiating into a target tissue cell lineage. According to one embodiment, the target tissue cell lineage is selected from the group consisting of an adipose cell lineage, an amnion cell lineage, an artery cell lineage, a bone cell lineage, a cartilage cell lineage, a dental cell lineage, a dermal cell lineage, a duodenal cell lineage, an endothelial lineage, an epithelial cell lineage, a gastrointestinal cell lineage, a growth plate cell lineage, an intervertebral disc cell lineage, an intestinal mucosal cell lineage, an intestinal serosal cell lineage, a kidney cell lineage, a ligament cell lineage, a liver cell lineage, a lung cell lineage, a meniscal cell lineage, a muscle cell lineage, a nerve cell lineage, an ovarian cell lineage, a pancreatic cell lineage, a parenchymal organ cell lineage, a pericardial cell lineage, a periosteal cell lineage, a peritoneal cell lineage, a skin cell lineage, a spleen cell lineage, a synovial cell lineage, a tendon cell lineage, a testes cell lineage, a urological cell lineage, a vascular cell lineage, a vein cell lineage, and a combination thereof.

According to one embodiment, the at least one viable population of tissuegenic cells derived from adipose tissue is capable of differentiating into an adipose cell lineage. According to one embodiment, the at least one viable population of tissuegenic cells derived from adipose tissue is capable of differentiating into an amnion cell lineage. According to one embodiment, the at least one viable population of tissuegenic cells derived from adipose tissue is capable of differentiating into an artery cell lineage. According to one embodiment, the at least one viable population of tissuegenic cells derived from adipose tissue is capable of differentiating into a bone cell lineage. According to one embodiment, the at least one viable population of tissuegenic cells derived from adipose tissue is capable of differentiating into a cartilage cell lineage. According to one embodiment, the at least one viable population of tissuegenic cells derived from adipose tissue is capable of differentiating into a chorion cell lineage. According to one embodiment, the at least one viable population of tissuegenic cells derived from adipose tissue is capable of differentiating into a colon cell lineage. According to one embodiment, the at least one viable population of tissuegenic cells derived from adipose tissue is capable of differentiating into a dental cell lineage. According to one embodiment, the at least one viable population of tissuegenic cells derived from adipose tissue is capable of differentiating into a dermal cell lineage. According to one embodiment, the at least one viable population of tissuegenic cells derived from adipose tissue is capable of differentiating into a duodenal cell lineage. According to one embodiment, the at least one viable population of tissuegenic cells derived from adipose tissue is capable of differentiating into an endothelial cell lineage. According to one embodiment, the at least one viable population of tissuegenic cells derived from adipose tissue is capable of differentiating into an epithelial cell lineage. According to one embodiment, the at least one viable population of tissuegenic cells derived from adipose tissue is capable of differentiating into a gastrointestinal cell lineage. According to one embodiment, the at least one viable population of tissuegenic cells derived from adipose tissue is capable of differentiating into a growth plate cell lineage. According to one embodiment, the at least one viable population of tissuegenic cells derived from adipose tissue is capable of differentiating into an intervertebral disc cell lineage. According to one embodiment, the at least one viable population of tissuegenic cells derived from adipose tissue is capable of differentiating into an intestinal mucosal cell lineage. According to one embodiment, the at least one viable population of tissuegenic cells derived from adipose tissue is capable of differentiating into an intestinal serosal cell lineage. According to one embodiment, the at least one viable population of tissuegenic cells derived from adipose tissue is capable of differentiating into a kidney cell lineage. According to one embodiment, the at least one viable population of tissuegenic cells derived from adipose tissue is capable of differentiating into a ligament cell lineage. According to one embodiment, the at least one viable population of tissuegenic cells derived from adipose tissue is capable of differentiating into a liver cell lineage. According to one embodiment, the at least one viable population of tissuegenic cells derived from adipose tissue is capable of differentiating into a lung cell lineage. According to one embodiment, the at least one viable population of tissuegenic cells derived from adipose tissue is capable of differentiating into a meniscal cell lineage. According to one embodiment, the at least one viable population of tissuegenic cells derived from adipose tissue is capable of differentiating into a muscle cell lineage. According to one embodiment, the at least one viable population of tissuegenic cells derived from adipose tissue is capable of differentiating into a nerve cell lineage. According to one embodiment, the at least one viable population of tissuegenic cells derived from adipose tissue is capable of differentiating into an ovarian cell lineage. According to one embodiment, the at least one viable population of tissuegenic cells derived from adipose tissue is capable of differentiating into a pancreatic cell lineage. According to one embodiment, the at least one viable population of tissuegenic cells derived from adipose tissue is capable of differentiating into a parenchymal organ cell lineage. According to one embodiment, the at least one viable population of tissuegenic cells derived from adipose tissue is capable of differentiating into a pericardial cell lineage. According to one embodiment, the at least one viable population of tissuegenic cells derived from adipose tissue is capable of differentiating into a periosteal cell lineage. According to one embodiment, the at least one viable population of tissuegenic cells is capable of differentiating into a peritoneal cell lineage. According to one embodiment, the at least one viable population of tissuegenic cells derived from adipose tissue is capable of differentiating into a skin cell lineage. According to one embodiment, the at least one viable population of tissuegenic cells derived from adipose tissue is capable of differentiating into a spleen cell lineage. According to one embodiment, the at least one viable population of tissuegenic cells derived from adipose tissue is capable of differentiating into a synovial cell lineage. According to one embodiment, the at least one viable population of tissuegenic cells derived from adipose tissue is capable of differentiating into a tendon cell lineage. According to one embodiment, the at least one viable population of tissuegenic cells derived from adipose tissue is capable of differentiating into a testes cell lineage. According to one embodiment, the at least one viable population of tissuegenic cells derived from adipose tissue is capable of differentiating into a urological cell lineage. According to one embodiment, the at least one viable population of tissuegenic cells derived from adipose tissue is capable of differentiating into a vascular cell lineage. According to one embodiment, the at least one viable population of tissuegenic cells derived from adipose tissue is capable of differentiating into a vein cell lineage. According to one embodiment, the at least one viable population of tissuegenic cells derived from adipose tissue can be reprogrammed to form at least one viable induced pluripotent stem cell (iPSC) population.

According to one embodiment, the at least one viable population of tissuegenic cells derived from adipose tissue differentiates along an osteogenic lineage. According to one embodiment, the at least one viable population of tissuegenic cells derived from adipose tissue differentiates along an adipogenic lineage. According to one embodiment, the at least one viable population of tissuegenic cells derived from adipose tissue differentiates along a chondrogenic lineage. According to one embodiment, the at least one viable population of tissuegenic cells derived from adipose tissue differentiates along a neurogenic lineage.

According to one embodiment, the at least one viable population of tissuegenic cells derived from adipose tissue is capable of migrating from or to the at least one growth-conductive matrix. According to one embodiment, the at least one viable population of tissuegenic cells derived from adipose tissue comprises a viable nonexpanded population of tissuegenic cells. According to one embodiment, the at least one viable population of tissuegenic cells derived from adipose tissue comprises a viable expanded population of tissuegenic cells. According to some embodiments, the at least one viable population of tissuegenic cells derived from adipose tissue adherent to and resident in the endogenous milieu of the growth conductive matrix is immune privileged. The term "immune privileged" as used herein refers to the characteristic of tissuegenic cells by which there is no induction of an immune response upon transplantation of such cells of such cells.

Tissuegenic Cells Derived from Bone Tissue

According to one embodiment, the at least one viable population of tissuegenic cells derived from bone tissue is selected from the group consisting of a viable population of bone-derived mesenchymal stem cells, a viable population of osteoprogenitor cells, or a combination thereof. According to one embodiment, the at least one viable population of tissuegenic cells derived from bone tissue is a viable mesenchymal stem cell population. According to one embodiment, the at least one viable population of tissuegenic cells derived from bone tissue is a viable osteoprogenitor cell population.

According to one embodiment, the at least one viable population of tissuegenic cells from bone tissue secretes at least one growth-inductive factor. Examples of growth-inductive factors secreted by bone tissue include, but are not limited to, Bone Morphogenic Proteins (BMPs), Epidermal Growth Factors (EGFs), Fibroblast Growth Factors (FGFs), Platelet-Derived Growth Factors (PDGFs), Insulin-like Growth Factor-1 (IGF-1), Transforming Growth Factors (TGFs), Bone-Derived Growth Factors (BDGFs), Cartilage-Derived Growth Factor (CDGF), Skeletal Growth Factor (hSGF), Interleukin-1 (IL-1), and macrophage-derived factors.

According to one embodiment, the at least one viable population of tissuegenic cells derived from bone tissue is capable of differentiating into cells of at least one embryonic lineage. According to one embodiment, the embryonic lineage is selected from the group consisting of an ectodermal lineage, a mesodermal lineage and an endodermal lineage. According to one embodiment, the at least one viable population of tissuegenic cells derived from bone tissue is capable of differentiating into cells of an ectodermal lineage. According to one embodiment, the at least one viable population of tissuegenic cells derived from bone tissue is capable of differentiating into cells of a mesodermal lineage. According to one embodiment, the at least one viable population of tissuegenic cells derived from bone tissue is capable of differentiating into cells of an endodermal lineage.

According to one embodiment, the at least one viable population of tissuegenic cells derived from bone tissue is capable of regenerating a target tissue. According to one embodiment, the target tissue is selected from the group consisting of an adipose tissue, an amnion tissue, an artery tissue, a bone tissue, a cartilage tissue, a chorion tissue, a colon tissue, a dental tissue, a dermal tissue, a duodenal tissue, an endothelial tissue, an epithelial tissue, a gastrointestinal tissue, a growth plate tissue, an intervertebral disc tissue, an intestinal mucosal tissue, an intestinal serosal tissue, a kidney tissue, a ligament tissue, a liver tissue, a lung tissue, a meniscal tissue, a muscle tissue, a nerve tissue, an ovarian tissue, a pancreatic tissue, a parenchymal organ tissue, a pericardial tissue, a periosteal tissue, a peritoneal tissue, a skin tissue, a spleen tissue, a synovial tissue, a tendon tissue, a testes tissue, a urological tissue, a vascular tissue, a vein tissue, and a combination thereof.

According to one embodiment, the at least one viable population of tissuegenic cells derived from bone tissue is capable of regenerating an adipose tissue. According to one embodiment, the at least one viable population of tissuegenic cells derived from bone tissue is capable of regenerating an amnion tissue. According to one embodiment, the at least one viable population of tissuegenic cells derived from bone tissue is capable of regenerating an artery tissue. According to one embodiment, the at least one viable population of tissuegenic cells derived from bone tissue is capable of regenerating a bone tissue. According to one embodiment, the at least one viable population of tissuegenic cells derived from bone tissue is capable of regenerating a cartilage tissue. According to one embodiment, the at least one viable population of tissuegenic cells derived from bone tissue is capable of regenerating a chorion tissue. According to one embodiment, the at least one viable population of tissuegenic cells derived from bone tissue is capable of regenerating a colon tissue. According to one embodiment, the at least one viable population of tissuegenic cells derived from bone tissue is capable of regenerating a dental tissue. According to one embodiment, the at least one viable population of tissuegenic cells derived from bone tissue is capable of regenerating a dermal tissue. According to one embodiment, the at least one viable population of tissuegenic cells derived from bone tissue is capable of regenerating a duodenal tissue. According to one embodiment, the at least one viable population of tissuegenic cells derived from bone tissue is capable of regenerating an endothelial tissue. According to one embodiment, the at least one viable population of tissuegenic cells derived from bone tissue is capable of regenerating a gastrointestinal tissue. According to one embodiment, the at least one viable population of tissuegenic cells derived from bone tissue is capable of regenerating a growth plate tissue. According to one embodiment, the at least one viable population of tissuegenic cells derived from bone tissue is is capable of regenerating an intervertebral disc tissue. According to one embodiment, the at least one viable population of tissuegenic cells derived from bone tissue is is capable of regenerating an intestinal mucosal tissue. According to one embodiment, the at least one viable population of tissuegenic cells derived from bone tissue is is capable of regenerating an intestinal serosal tissue. According to one embodiment, the at least one viable population of tissuegenic cells derived from bone tissue is is capable of regenerating a kidney tissue. According to one embodiment, the at least one viable population of tissuegenic cells derived from bone tissue is capable of regenerating a ligament tissue. According to one embodiment, the at least one viable population of tissuegenic cells derived from bone tissue is capable of regenerating a liver tissue. According to one embodiment, the at least one viable population of tissuegenic cells derived from bone tissue is capable of regenerating a lung tissue. According to one embodiment, the at least one viable population of tissuegenic cells derived from adipose tissue is capable of regenerating a meniscal tissue. According to one embodiment, the at least one viable population of tissuegenic cells derived from bone tissue is capable of regenerating a muscle tissue. According to one embodiment, the at least one viable population of tissuegenic cells derived from bone tissue is capable of regenerating a nerve tissue. According to one embodiment, the at least one viable population of tissuegenic cells derived from bone tissue is capable of regenerating an ovarian tissue. According to one embodiment, the at least one viable population of tissuegenic cells derived from bone tissue is capable of regenerating a pancreatic tissue. According to one embodiment, the at least one viable population of tissuegenic cells derived from bone tissue is capable of regenerating a parenchymal organ tissue. According to one embodiment, the at least one viable population of tissuegenic cells derived from bone tissue is capable of regenerating a pericardial tissue. According to one embodiment, the at least one viable population of tissuegenic cells derived from bone tissue is capable of regenerating a periosteal tissue. According to one embodiment, the at least one viable population of tissuegenic cells derived from bone tissue is capable of regenerating a peritoneal tissue. According to one embodiment, the at least one viable population of tissuegenic cells derived from bone tissue is capable of regenerating a skin tissue. According to one embodiment, the at least one viable population of tissuegenic cells derived from bone tissue is capable of regenerating a spleen tissue. According to one embodiment, the at least one viable population of tissuegenic cells derived from bone tissue is capable of regenerating a synovial tissue. According to one embodiment, the at least one viable population of tissuegenic cells derived from bone tissue is capable of regenerating a tendon tissue. According to one embodiment, the at least one viable population of tissuegenic cells derived from bone tissue is capable of regenerating a testes tissue. According to one embodiment, the at least one viable population of tissuegenic cells derived from bone tissue is capable of regenerating a urological tissue. According to one embodiment, the at least one viable population of tissuegenic cells derived from bone tissue is capable of regenerating a vascular tissue. According to one embodiment, the at least one viable population of tissuegenic cells derived from bone tissue is capable of regenerating a vein tissue.

According to one embodiment, the at least one viable population of tissuegenic cells derived from bone tissue is capable of differentiating into a target tissue cell lineage. According to one embodiment, the target tissue cell lineage is selected from the group consisting of an adipose cell lineage, an amnion cell lineage, an artery cell lineage, a bone cell lineage, a cartilage cell lineage, a dental cell lineage, a dermal cell lineage, a duodenal cell lineage, an endothelial lineage, an epithelial cell lineage, a gastrointestinal cell lineage, a growth plate cell lineage, an intervertebral disc cell lineage, an intestinal mucosal cell lineage, an intestinal serosal cell lineage, a kidney cell lineage, a ligament cell lineage, a liver cell lineage, a lung cell lineage, a meniscal cell lineage. a muscle cell lineage, a nerve cell lineage, an ovarian cell lineage, a pancreatic cell lineage, a parenchymal organ cell lineage, a pericardial cell lineage, a periosteal cell lineage, a peritoneal cell lineage, a skin cell lineage, a spleen cell lineage, a synovial cell lineage, a tendon cell lineage, a testes cell lineage, a urological cell lineage, a vascular cell lineage, a vein cell lineage, and a combination thereof.

According to one embodiment, the at least one viable population of tissuegenic cells derived from bone tissue is capable of differentiating into an adipose cell lineage. According to one embodiment, the at least one viable population of tissuegenic cells derived from bone tissue is capable of differentiating into an amnion cell lineage. According to one embodiment, the at least one viable population of tissuegenic cells derived from bone tissue is capable of differentiating into an artery cell lineage. According to one embodiment, the at least one viable population of tissuegenic cells derived from bone tissue is capable of differentiating into a bone cell lineage. According to one embodiment, the at least one viable population of tissuegenic cells derived from bone tissue is capable of differentiating into a cartilage cell lineage. According to one embodiment, the at least one viable population of tissuegenic cells derived from bone tissue is capable of differentiating into a chorion cell lineage. According to one embodiment, the at least one viable population of tissuegenic cells derived from bone tissue is capable of differentiating into a colon cell lineage. According to one embodiment, the at least one viable population of tissuegenic cells derived from bone tissue is capable of differentiating into a dental cell lineage. According to one embodiment, the at least one viable population of tissuegenic cells derived from bone tissue is capable of differentiating into a dermal cell lineage. According to one embodiment, the at least one viable population of tissuegenic cells derived from bone tissue is capable of differentiating into a duodenal cell lineage. According to one embodiment, the at least one viable population of tissuegenic cells derived from bone tissue is capable of differentiating into an endothelial cell lineage. According to one embodiment, the at least one viable population of tissuegenic cells derived from bone tissue is capable of differentiating into an epithelial cell lineage. According to one embodiment, the at least one viable population of tissuegenic cells derived from bone tissue is capable of differentiating into a gastrointestinal cell lineage. According to one embodiment, the at least one viable population of tissuegenic cells derived from bone tissue is capable of differentiating into a growth plate cell lineage. According to one embodiment, the at least one viable population of tissuegenic cells derived from bone tissue is capable of differentiating into an intervertebral disc cell lineage. According to one embodiment, the at least one viable population of tissuegenic cells derived from bone tissue is capable of differentiating into an intestinal mucosal cell lineage. According to one embodiment, the at least one viable population of tissuegenic cells derived from bone tissue is capable of differentiating into an intestinal serosal cell lineage. According to one embodiment, the at least one viable population of tissuegenic cells derived from bone tissue is capable of differentiating into a kidney cell lineage. According to one embodiment, the at least one viable population of tissuegenic cells derived from bone tissue is capable of differentiating into a ligament cell lineage. According to one embodiment, the at least one viable population of tissuegenic cells derived from bone tissue is capable of differentiating into a liver cell lineage. According to one embodiment, the at least one viable population of tissuegenic cells derived from bone tissue is capable of differentiating into a lung cell lineage. According to one embodiment, the at least one viable population of tissuegenic cells derived from bone tissue is capable of differentiating into a meniscal cell lineage. According to one embodiment, the at least one viable population of tissuegenic cells derived from bone tissue is capable of differentiating into a muscle cell lineage. According to one embodiment, the at least one viable population of tissuegenic cells derived from bone tissue is capable of differentiating into a nerve cell lineage. According to one embodiment, the at least one viable population of tissuegenic cells derived from bone tissue is capable of differentiating into an ovarian cell lineage. According to one embodiment, the at least one viable population of tissuegenic cells derived from bone tissue is capable of differentiating into a pancreatic cell lineage. According to one embodiment, the at least one viable population of tissuegenic cells derived from bone tissue is capable of differentiating into a parenchymal organ cell lineage. According to one embodiment, the at least one viable population of tissuegenic cells derived from bone tissue is capable of differentiating into a pericardial cell lineage. According to one embodiment, the at least one viable population of tissuegenic cells derived from bone tissue is capable of differentiating into a periosteal cell lineage. According to one embodiment, the at least one viable population of tissuegenic cells is capable of differentiating into a peritoneal cell lineage. According to one embodiment, the at least one viable population of tissuegenic cells derived from bone tissue is capable of differentiating into a skin cell lineage. According to one embodiment, the at least one viable population of tissuegenic cells derived from bone tissue is capable of differentiating into a spleen cell lineage. According to one embodiment, the at least one viable population of tissuegenic cells derived from bone tissue is capable of differentiating into a synovial cell lineage. According to one embodiment, the at least one viable population of tissuegenic cells derived from bone tissue is capable of differentiating into a tendon cell lineage. According to one embodiment, the at least one viable population of tissuegenic cells derived from bone tissue is capable of differentiating into a testes cell lineage. According to one embodiment, the at least one viable population of tissuegenic cells derived from bone tissue is capable of differentiating into a urological cell lineage. According to one embodiment, the at least one viable population of tissuegenic cells derived from bone tissue is capable of differentiating into a vascular cell lineage. According to one embodiment, the at least one viable population of tissuegenic cells derived from bone tissue is capable of differentiating into a vein cell lineage.

According to one embodiment, the at least one viable population of tissuegenic cells derived from bone tissue can be reprogrammedreprogrammed to at least one viable induced pluripotent stem cell (iPSC) population.

According to one embodiment, the at least one viable population of tissuegenic cells derived from bone tissue differentiates along an osteogenic lineage. According to one embodiment, the at least one viable population of tissuegenic cells derived from bone tissue differentiates along an adipogenic lineage. According to one embodiment, the at least one viable population of tissuegenic cells derived from bone tissue differentiates along a chondrogenic lineage. According to one embodiment, the at least one viable population of tissuegenic cells derived from bone tissue differentiates along a neurogenic lineage.

According to one embodiment, the at least one viable population of tissuegenic cells derived from bone tissue is capable of migrating from or to the at least one growth-conductive matrix. According to one embodiment, the at least one viable population of tissuegenic cells derived from bone tissue comprises a viable nonexpanded population of tissuegenic cells. According to one embodiment, the at least one viable population of tissuegenic cells derived from bone tissue comprises a viable expanded population of tissuegenic cells. According to some embodiments, the at least one viable population of tissuegenic cells derived from bone tissue adherent to and resident in the endogenous milieu of the growth conductive matrix is immune privileged. The term "immune privileged" as used herein refers to the characteristic of tissuegenic cells by which there is no induction of an immune response upon transplantation of such cells of such cells.

Tissuegenic Cells Derived from Cartilage Tissue

According to one embodiment, the at least one viable population of tissuegenic cells derived from cartilage tissue is selected from the group consisting of a viable population of cartilage-derived mesenchymal stem cells and a viable population of cartilage derived progenitor cells. According to one embodiment, the at least one viable population of tissuegenic cells derived from cartilage tissue is a viable cartilage-derived mesenchymal stem cell population. According to one embodiment, the at least one viable population of tissuegenic cells derived from cartilage tissue is a viable cartilage-derived progenitor cell population. Exemplary tissuegenic cells derived from cartilage tissue are listed in Asalameh et al., Arthritis & Rheumatism (2004), 50(5): 1522-1532, Peng et al., Stem Cells and Development (2008), 17: 761-774, Hiraoka et al., Biorheology (2006), 43: 447-454, Karlsson et al., 2009, J. Anat. 215(3): 355-63 and Grogan et al., Arthritis Res. Ther. (2009), 11(3): R85-R97, the entire contents of which are incorporated herein by reference. Exemplary tissuegenic cells derived from cartilage tissue of intervertebral discs are listed in Henriksson et al. (2009), SPINE, 34(21): 2278-2287, the entire contents of which are incorporated herein by reference.

According to one embodiment, the at least one viable population of tissuegenic cells from cartilage tissue secretes at least one growth-inductive factor. Exemplary growth-inductive components include, but are not limited to, ions (e.g., calcium); steroids (e.g., estrogens); terpenoids (e.g., retinoic acid); peptides (e.g., parathyroid hormone (PTH), parathyroid hormone-related peptide (PTHrP), insulin growth factors (e.g., TGFβ hormones, including, without limitation, BMPs, IGF-1, VEGF, PDGF, FGF); transcription factors (e.g., Wnt, SOX-9); eicosanoids (e.g., prostaglandins); catabolic interleukins (e.g., IL-1); and anabolic interleukins (e.g., IL-6, IL-4 and IL-10). Other growth-inductive components are listed in Gaissmaier et al. (2008), Int. J. Care Injured, 39S1: S88-S96, the entire contents of which are incorporated by reference herein. According to one embodiment, the at least one viable population of tissuegenic cells derived from cartilage tissue is capable of differentiating into cells of at least one embryonic lineage. According to one embodiment, the embryonic lineage is selected from the group consisting of an ectodermal lineage, a mesodermal lineage and an endodermal lineage. According to one embodiment, the at least one viable population of tissuegenic cells derived from cartilage tissue is capable of differentiating into cells of an ectodermal lineage. According to one embodiment, the at least one viable population of tissuegenic cells derived from cartilage t tissue is capable of differentiating into cells of a mesodermal lineage. According to one embodiment, the at least one viable population of tissuegenic cells derived from cartilage tissue is capable of differentiating into cells of an endodermal lineage.

According to one embodiment, the at least one viable population of tissuegenic cells derived from cartilage tissue is capable of regenerating a target tissue. According to one embodiment, the target tissue is selected from the group consisting of an adipose tissue, an amnion tissue, an artery tissue, a bone tissue, a cartilage tissue, a chorion tissue, a colon tissue, a dental tissue, a dermal tissue, a duodenal tissue, an endothelial tissue, an epithelial tissue, a gastrointestinal tissue, a growth plate tissue, an intervertebral disc tissue, an intestinal mucosal tissue, an intestinal serosal tissue, a kidney tissue, a ligament tissue, a liver tissue, a lung tissue, a meniscal tissue, a muscle tissue, a nerve tissue, an ovarian tissue, a pancreatic tissue, a parenchymal organ tissue, a pericardial tissue, a periosteal tissue, a peritoneal tissue, a skin tissue, a spleen tissue, a synovial tissue, a tendon tissue, a testes tissue, a urological tissue, a vascular tissue, a vein tissue, and a combination thereof.

According to one embodiment, the at least one viable population of tissuegenic cells derived from cartilage tissue is capable of regenerating an adipose tissue. According to one embodiment, the at least one viable population of tissuegenic cells derived from cartilage tissue is capable of regenerating an amnion tissue. According to one embodiment, the at least one viable population of tissuegenic cells derived from cartilage tissue is capable of regenerating an artery tissue. According to one embodiment, the at least one viable population of tissuegenic cells derived from cartilage tissue is capable of regenerating a bone tissue. According to one embodiment, the at least one viable population of tissuegenic cells derived from cartilage tissue is capable of regenerating a cartilage tissue. According to one embodiment, the at least one viable population of tissuegenic cells derived from cartilage tissue is capable of regenerating a chorion tissue. According to one embodiment, the at least one viable population of tissuegenic cells derived from cartilage tissue is capable of regenerating a colon tissue. According to one embodiment, the at least one viable population of tissuegenic cells derived from cartilage tissue is capable of regenerating a dental tissue. According to one embodiment, the at least one viable population of tissuegenic cells derived from cartilage tissue is capable of regenerating a dermal tissue. According to one embodiment, the at least one viable population of tissuegenic cells derived from cartilage tissue is capable of regenerating a duodenal tissue. According to one embodiment, the at least one viable population of tissuegenic cells derived from cartilage tissue is capable of regenerating an endothelial tissue. According to one embodiment, the at least one viable population of tissuegenic cells derived from cartilage tissue is capable of regenerating a gastrointestinal tissue. According to one embodiment, the at least one viable population of tissuegenic cells derived from cartilage tissue is capable of regenerating a growth plate tissue. According to one embodiment, the at least one viable population of tissuegenic cells derived from cartilage tissue is is capable of regenerating an intervertebral disc tissue. According to one embodiment, the at least one viable population of tissuegenic cells derived from cartilage tissue is is capable of regenerating an intestinal mucosal tissue. According to one embodiment, the at least one viable population of tissuegenic cells derived from cartilage tissue is is capable of regenerating an intestinal serosal tissue. According to one embodiment, the at least one viable population of tissuegenic cells derived from cartilage tissue is is capable of regenerating a kidney tissue. According to one embodiment, the at least one viable population of tissuegenic cells derived from cartilage tissue is capable of regenerating a ligament tissue. According to one embodiment, the at least one viable population of tissuegenic cells derived from cartilage tissue is capable of regenerating a liver tissue. According to one embodiment, the at least one viable population of tissuegenic cells derived from cartilage tissue is capable of regenerating a lung tissue. According to one embodiment, the at least one viable population of tissuegenic cells derived from cartilage tissue is capable of regenerating a meniscal tissue. According to one embodiment, the at least one viable population of tissuegenic cells derived from cartilage tissue is capable of regenerating a muscle tissue. According to one embodiment, the at least one viable population of tissuegenic cells derived from cartilage tissue is capable of regenerating a nerve tissue. According to one embodiment, the at least one viable population of tissuegenic cells derived from cartilage tissue is capable of regenerating an ovarian tissue. According to one embodiment, the at least one viable population of tissuegenic cells derived from cartilage tissue is capable of regenerating a pancreatic tissue. According to one embodiment, the at least one viable population of tissuegenic cells derived from cartilage tissue is capable of regenerating a parenchymal organ tissue. According to one embodiment, the at least one viable population of tissuegenic cells derived from cartilage tissue is capable of regenerating a pericardial tissue. According to one embodiment, the at least one viable population of tissuegenic cells derived from cartilage tissue is capable of regenerating a periosteal tissue. According to one embodiment, the at least one viable population of tissuegenic cells derived from cartilage tissue is capable of regenerating a peritoneal tissue. According to one embodiment, the at least one viable population of tissuegenic cells derived from cartilage tissue is capable of regenerating a skin tissue. According to one embodiment, the at least one viable population of tissuegenic cells derived from cartilage tissue is capable of regenerating a spleen tissue. According to one embodiment, the at least one viable population of tissuegenic cells derived from cartilage tissue is capable of regenerating a synovial tissue. According to one embodiment, the at least one viable population of tissuegenic cells derived from cartilage tissue is capable of regenerating a tendon tissue. According to one embodiment, the at least one viable population of tissuegenic cells derived from cartilage tissue is capable of regenerating a testes tissue. According to one embodiment, the at least one viable population of tissuegenic cells derived from cartilage tissue is capable of regenerating a urological tissue. According to one embodiment, the at least one viable population of tissuegenic cells derived from cartilage tissue is capable of regenerating a vascular tissue. According to one embodiment, the at least one viable population of tissuegenic cells derived from cartilage tissue is capable of regenerating a vein tissue.

According to one embodiment, the at least one viable population of tissuegenic cells derived from cartilage tissue is capable of differentiating into a target tissue cell lineage. According to one embodiment, the target tissue cell lineage is selected from the group consisting of an adipose cell lineage, an amnion cell lineage, an artery cell lineage, a bone cell lineage, a cartilage cell lineage, a dental cell lineage, a dermal cell lineage, a duodenal cell lineage, an endothelial lineage, an epithelial cell lineage, a gastrointestinal cell lineage, a growth plate cell lineage, an intervertebral disc cell lineage, an intestinal mucosal cell lineage, an intestinal serosal cell lineage, a kidney cell lineage, a ligament cell lineage, a liver cell lineage, a lung cell lineage, a meniscal cell lineage, a muscle cell lineage, a nerve cell lineage, an ovarian cell lineage, a pancreatic cell lineage, a parenchymal organ cell lineage, a pericardial cell lineage, a periosteal cell lineage, a peritoneal cell lineage, a skin cell lineage, a spleen cell lineage, a synovial cell lineage, a tendon cell lineage, a testes cell lineage, a urological cell lineage, a vascular cell lineage, a vein cell lineage, and a combination thereof.

According to one embodiment, the at least one viable population of tissuegenic cells derived from cartilage tissue is capable of differentiating into an adipose cell lineage. According to one embodiment, the at least one viable population of tissuegenic cells derived from cartilage tissue is capable of differentiating into an amnion cell lineage. According to one embodiment, the at least one viable population of tissuegenic cells derived from cartilage tissue is capable of differentiating into an artery cell lineage. According to one embodiment, the at least one viable population of tissuegenic cells derived from cartilage tissue is capable of differentiating into a bone cell lineage. According to one embodiment, the at least one viable population of tissuegenic cells derived from cartilage tissue is capable of differentiating into a cartilage cell lineage. According to one embodiment, the at least one viable population of tissuegenic cells derived from cartilage tissue is capable of differentiating into a chorion cell lineage. According to one embodiment, the at least one viable population of tissuegenic cells derived from cartilage tissue is capable of differentiating into a colon cell lineage. According to one embodiment, the at least one viable population of tissuegenic cells derived from cartilage tissue is capable of differentiating into a dental cell lineage. According to one embodiment, the at least one viable population of tissuegenic cells derived from cartilage tissue is capable of differentiating into a dermal cell lineage. According to one embodiment, the at least one viable population of tissuegenic cells derived from cartilage tissue is capable of differentiating into a duodenal cell lineage. According to one embodiment, the at least one viable population of tissuegenic cells derived from cartilage tissue is capable of differentiating into an endothelial cell lineage. According to one embodiment, the at least one viable population of tissuegenic cells derived from cartilage tissue is capable of differentiating into an epithelial cell lineage. According to one embodiment, the at least one viable population of tissuegenic cells derived from cartilage tissue is capable of differentiating into a gastrointestinal cell lineage. According to one embodiment, the at least one viable population of tissuegenic cells derived from cartilage tissue is capable of differentiating into a growth plate cell lineage. According to one embodiment, the at least one viable population of tissuegenic cells derived from cartilage tissue is capable of differentiating into an intervertebral disc cell lineage. According to one embodiment, the at least one viable population of tissuegenic cells derived from cartilage tissue is capable of differentiating into an intestinal mucosal cell lineage. According to one embodiment, the at least one viable population of tissuegenic cells derived from cartilage tissue is capable of differentiating into an intestinal serosal cell lineage. According to one embodiment, the at least one viable population of tissuegenic cells derived from cartilage tissue is capable of differentiating into a kidney cell lineage. According to one embodiment, the at least one viable population of tissuegenic cells derived from cartilage tissue is capable of differentiating into a ligament cell lineage. According to one embodiment, the at least one viable population of tissuegenic cells derived from cartilage tissue is capable of differentiating into a liver cell lineage. According to one embodiment, the at least one viable population of tissuegenic cells derived from cartilage tissue is capable of differentiating into a lung cell lineage. According to one embodiment, the at least one viable population of tissuegenic cells derived from cartilage tissue is capable of differentiating into a meniscal cell lineage. According to one embodiment, the at least one viable population of tissuegenic cells derived from cartilage tissue is capable of differentiating into a muscle cell lineage. According to one embodiment, the at least one viable population of tissuegenic cells derived from cartilage tissue is capable of differentiating into a nerve cell lineage. According to one embodiment, the at least one viable population of tissuegenic cells derived from cartilage tissue is capable of differentiating into an ovarian cell lineage. According to one embodiment, the at least one viable population of tissuegenic cells derived from cartilage tissue is capable of differentiating into a pancreatic cell lineage. According to one embodiment, the at least one viable population of tissuegenic cells derived from cartilage tissue is capable of differentiating into a parenchymal organ cell lineage. According to one embodiment, the at least one viable population of tissuegenic cells derived from cartilage tissue is capable of differentiating into a pericardial cell lineage. According to one embodiment, the at least one viable population of tissuegenic cells derived from cartilage tissue is capable of differentiating into a periosteal cell lineage. According to one embodiment, the at least one viable population of tissuegenic cells is capable of differentiating into a peritoneal cell lineage. According to one embodiment, the at least one viable population of tissuegenic cells derived from cartilage tissue is capable of differentiating into a skin cell lineage. According to one embodiment, the at least one viable population of tissuegenic cells derived from cartilage tissue is capable of differentiating into a spleen cell lineage. According to one embodiment, the at least one viable population of tissuegenic cells derived from cartilage tissue is capable of differentiating into a synovial cell lineage. According to one embodiment, the at least one viable population of tissuegenic cells derived from cartilage tissue is capable of differentiating into a tendon cell lineage. According to one embodiment, the at least one viable population of tissuegenic cells derived from cartilage tissue is capable of differentiating into a testes cell lineage. According to one embodiment, the at least one viable population of tissuegenic cells derived from cartilage tissue is capable of differentiating into a urological cell lineage. According to one embodiment, the at least one viable population of tissuegenic cells derived from cartilage tissue is capable of differentiating into a vascular cell lineage. According to one embodiment, the at least one viable population of tissuegenic cells derived from cartilage tissue is capable of differentiating into a vein cell lineage.

According to one embodiment, the at least one viable population of tissuegenic cells derived from cartilage tissue can be reprogrammedreprogrammed to at least one viable induced pluripotent stem cell (iPSC) population.

According to one embodiment, the at least one viable population of tissuegenic cells derived from cartilage tissue differentiates along an osteogenic lineage. According to one embodiment, the at least one viable population of tissuegenic cells derived from cartilage tissue differentiates along an adipogenic lineage. According to one embodiment, the at least one viable population of tissuegenic cells derived from cartilage tissue differentiates along a chondrogenic lineage. According to one embodiment, the at least one viable population of tissuegenic cells derived from cartilage tissue differentiates along a neurogenic lineage.

According to one embodiment, the at least one viable population of tissuegenic cells derived from cartilage tissue is capable of migrating from or to the at least one growth-conductive matrix. According to one embodiment, the at least one viable population of tissuegenic cells derived from cartilage tissue comprises a viable nonexpanded population of tissuegenic cells. According to one embodiment, the at least one viable population of tissuegenic cells derived from cartilage tissue comprises a viable expanded population of tissuegenic cells. According to some embodiments, the at least one viable population of tissuegenic cells derived from cartilage tissue adherent to and resident in the endogenous milieu of the growth conductive matrix is immune privileged. The term "immune privileged" as used herein refers to the characteristic of tissuegenic cells by which there is no induction of an immune response upon transplantation of such cells.

Tissuegenic Cells Derived from Dental Tissue

According to one embodiment, the at least one viable population of tissuegenic cells derived from dental tissue is selected from the group consisting of a viable population of stem cells of apical papilla (SCAP), a viable population of dental pulp stem cells (DPSCs), a viable population of stem cells from exfoliated deciduous teeth (SHED), a viable population of periodontal ligament stem cells (PDLSCs), and a viable population of dental follicle stem cells (DFSCs). According to one embodiment, the at least one viable population of tissuegenic cells derived from dental tissue is a viable population of stem cells of apical papilla. According to one embodiment, the at least one viable population of tissuegenic cells derived from dental tissue is a viable population of stem cells of apical papilla. According to one embodiment, the at least one viable population of tissuegenic cells derived from dental tissue is a viable population of dental pulp stem cells. According to one embodiment, the at least one viable population of tissuegenic cells derived from dental tissue is a viable population of stem cells from exfoliated deciduous teeth. According to one embodiment, the at least one viable population of tissuegenic cells derived from dental tissue is a viable population of periodontal ligament stem cells. According to one embodiment, the at least one viable population of tissuegenic cells derived from dental tissue is a viable population of dental follicle stem cells. Exemplary tissuegenic cells derived from dental tissue are listed in Fong et al. (2005), J. Dent. Educ., 69(5): 555-570, and Ulmer et al. (2010), Schweiz Monatsschr Zahnmed, 120:860-872, the entire contents of which are incorporated herein by reference.

According to one embodiment, the at least one viable population of tissuegenic cells from dental tissue secretes at least one growth-inductive factor.

According to one embodiment, the at least one viable population of tissuegenic cells derived from dental tissue is capable of differentiating into cells of at least one embryonic lineage. According to one embodiment, the embryonic lineage is selected from the group consisting of an ectodermal lineage, a mesodermal lineage and an endodermal lineage. According to one embodiment, the at least one viable population of tissuegenic cells derived from dental tissue is capable of differentiating into cells of an ectodermal lineage. According to one embodiment, the at least one viable population of tissuegenic cells derived from dental tissue is capable of differentiating into cells of a mesodermal lineage. According to one embodiment, the at least one viable population of tissuegenic cells derived from dental tissue is capable of differentiating into cells of an endodermal lineage. Exemplary target lineages of tissuegenic cells derived from dental tissue are listed in Ulmer et al. (2010), Schweiz Monatsschr Zahnmed, 120:860-872, the entire contents of which are incorporated herein by reference.

According to one embodiment, the at least one viable population of tissuegenic cells derived from dental tissue is capable of regenerating a target tissue. According to one embodiment, the target tissue is selected from the group consisting of an adipose tissue, an amnion tissue, an artery tissue, a bone tissue, a cartilage tissue, a chorion tissue, a colon tissue, a dental tissue, a dermal tissue, a duodenal tissue, an endothelial tissue, an epithelial tissue, a gastrointestinal tissue, a growth plate tissue, an intervertebral disc tissue, an intestinal mucosal tissue, an intestinal serosal tissue, a kidney tissue, a ligament tissue, a liver tissue, a lung tissue, a meniscal tissue, a muscle tissue, a nerve tissue, an ovarian tissue, a pancreatic tissue, a parenchymal organ tissue, a pericardial tissue, a periosteal tissue, a peritoneal tissue, a skin tissue, a spleen tissue, a synovial tissue, a tendon tissue, a testes tissue, a urological tissue, a vascular tissue, a vein tissue, and a combination thereof.

According to one embodiment, the at least one viable population of tissuegenic cells derived from dental tissue is capable of regenerating an adipose tissue. According to one embodiment, the at least one viable population of tissuegenic cells derived from dental tissue is capable of regenerating an amnion tissue. According to one embodiment, the at least one viable population of tissuegenic cells derived from dental tissue is capable of regenerating an artery tissue. According to one embodiment, the at least one viable population of tissuegenic cells derived from dental tissue is capable of regenerating a bone tissue. According to one embodiment, the at least one viable population of tissuegenic cells derived from dental tissue is capable of regenerating a cartilage tissue. According to one embodiment, the at least one viable population of tissuegenic cells derived from dental tissue is capable of regenerating a chorion tissue. According to one embodiment, the at least one viable population of tissuegenic cells derived from dental tissue is capable of regenerating a colon tissue. According to one embodiment, the at least one viable population of tissuegenic cells derived from dental tissue is capable of regenerating a dental tissue. According to one embodiment, the at least one viable population of tissuegenic cells derived from dental tissue is capable of regenerating a dermal tissue. According to one embodiment, the at least one viable population of tissuegenic cells derived from dental tissue is capable of regenerating a duodenal tissue. According to one embodiment, the at least one viable population of tissuegenic cells derived from dental tissue is capable of regenerating an endothelial tissue. According to one embodiment, the at least one viable population of tissuegenic cells derived from dental tissue is capable of regenerating a gastrointestinal tissue. According to one embodiment, the at least one viable population of tissuegenic cells derived from dental tissue is capable of regenerating a growth plate tissue. According to one embodiment, the at least one viable population of tissuegenic cells derived from dental tissue is is capable of regenerating an intervertebral disc tissue. According to one embodiment, the at least one viable population of tissuegenic cells derived from dental tissue is is capable of regenerating an intestinal mucosal tissue. According to one embodiment, the at least one viable population of tissuegenic cells derived from dental tissue is is capable of regenerating an intestinal serosal tissue. According to one embodiment, the at least one viable population of tissuegenic cells derived from dental tissue is is capable of regenerating a kidney tissue. According to one embodiment, the at least one viable population of tissuegenic cells derived from dental tissue is capable of regenerating a ligament tissue. According to one embodiment, the at least one viable population of tissuegenic cells derived from dental tissue is capable of regenerating a liver tissue. According to one embodiment, the at least one viable population of tissuegenic cells derived from dental tissue is capable of regenerating a lung tissue. According to one embodiment, the at least one viable population of tissuegenic cells derived from dental tissue is capable of regenerating a meniscal tissue. According to one embodiment, the at least one viable population of tissuegenic cells derived from dental tissue is capable of regenerating a muscle tissue. According to one embodiment, the at least one viable population of tissuegenic cells derived from dental tissue is capable of regenerating a nerve tissue. According to one embodiment, the at least one viable population of tissuegenic cells derived from dental tissue is capable of regenerating an ovarian tissue. According to one embodiment, the at least one viable population of tissuegenic cells derived from dental tissue is capable of regenerating a pancreatic tissue. According to one embodiment, the at least one viable population of tissuegenic cells derived from dental tissue is capable of regenerating a parenchymal organ tissue. According to one embodiment, the at least one viable population of tissuegenic cells derived from dental tissue is capable of regenerating a pericardial tissue. According to one embodiment, the at least one viable population of tissuegenic cells derived from dental tissue is capable of regenerating a periosteal tissue. According to one embodiment, the at least one viable population of tissuegenic cells derived from dental tissue is capable of regenerating a peritoneal tissue. According to one embodiment, the at least one viable population of tissuegenic cells derived from dental tissue is capable of regenerating a skin tissue. According to one embodiment, the at least one viable population of tissuegenic cells derived from dental tissue is capable of regenerating a spleen tissue. According to one embodiment, the at least one viable population of tissuegenic cells derived from dental tissue is capable of regenerating a synovial tissue. According to one embodiment, the at least one viable population of tissuegenic cells derived from dental tissue is capable of regenerating a tendon tissue. According to one embodiment, the at least one viable population of tissuegenic cells derived from dental tissue is capable of regenerating a testes tissue. According to one embodiment, the at least one viable population of tissuegenic cells derived from dental tissue is capable of regenerating a urological tissue. According to one embodiment, the at least one viable population of tissuegenic cells derived from dental tissue is capable of regenerating a vascular tissue. According to one embodiment, the at least one viable population of tissuegenic cells derived from dental tissue is capable of regenerating a vein tissue.

According to one embodiment, the at least one viable population of tissuegenic cells derived from dental tissue is capable of differentiating into a target tissue cell lineage. According to one embodiment, the target tissue cell lineage is selected from the group consisting of an adipose cell lineage, an amnion cell lineage, an artery cell lineage, a bone cell lineage, a cartilage cell lineage, a dental cell lineage, a dermal cell lineage, a duodenal cell lineage, an endothelial lineage, an epithelial cell lineage, a gastrointestinal cell lineage, a growth plate cell lineage, an intervertebral disc cell lineage, an intestinal mucosal cell lineage, an intestinal serosal cell lineage, a kidney cell lineage, a ligament cell lineage, a liver cell lineage, a lung cell lineage, a meniscal cell lineage, a muscle cell lineage, a nerve cell lineage, an ovarian cell lineage, a pancreatic cell lineage, a parenchymal organ cell lineage, a pericardial cell lineage, a periosteal cell lineage, a peritoneal cell lineage, a skin cell lineage, a spleen cell lineage, a synovial cell lineage, a tendon cell lineage, a testes cell lineage, a urological cell lineage, a vascular cell lineage, a vein cell lineage, and a combination thereof.

According to one embodiment, the at least one viable population of tissuegenic cells derived from dental tissue is capable of differentiating into an adipose cell lineage. According to one embodiment, the at least one viable population of tissuegenic cells derived from dental tissue is capable of differentiating into an amnion cell lineage. According to one embodiment, the at least one viable population of tissuegenic cells derived from dental tissue is capable of differentiating into an artery cell lineage. According to one embodiment, the at least one viable population of tissuegenic cells derived from dental tissue is capable of differentiating into a bone cell lineage. According to one embodiment, the at least one viable population of tissuegenic cells derived from dental tissue is capable of differentiating into a cartilage cell lineage. According to one embodiment, the at least one viable population of tissuegenic cells derived from dental tissue is capable of differentiating into a chorion cell lineage. According to one embodiment, the at least one viable population of tissuegenic cells derived from dental tissue is capable of differentiating into a colon cell lineage. According to one embodiment, the at least one viable population of tissuegenic cells derived from dental tissue is capable of differentiating into a dental cell lineage. According to one embodiment, the at least one viable population of tissuegenic cells derived from dental tissue is capable of differentiating into a dermal cell lineage. According to one embodiment, the at least one viable population of tissuegenic cells derived from dental tissue is capable of differentiating into a duodenal cell lineage. According to one embodiment, the at least one viable population of tissuegenic cells derived from dental tissue is capable of differentiating into an endothelial cell lineage. According to one embodiment, the at least one viable population of tissuegenic cells derived from dental tissue is capable of differentiating into an epithelial cell lineage. According to one embodiment, the at least one viable population of tissuegenic cells derived from dental tissue is capable of differentiating into a gastrointestinal cell lineage. According to one embodiment, the at least one viable population of tissuegenic cells derived from dental tissue is capable of differentiating into a growth plate cell lineage. According to one embodiment, the at least one viable population of tissuegenic cells derived from dental tissue is capable of differentiating into an intervertebral disc cell lineage. According to one embodiment, the at least one viable population of tissuegenic cells derived from dental tissue is capable of differentiating into an intestinal mucosal cell lineage. According to one embodiment, the at least one viable population of tissuegenic cells derived from dental tissue is capable of differentiating into an intestinal serosal cell lineage. According to one embodiment, the at least one viable population of tissuegenic cells derived from dental tissue is capable of differentiating into a kidney cell lineage. According to one embodiment, the at least one viable population of tissuegenic cells derived from dental tissue is capable of differentiating into a ligament cell lineage. According to one embodiment, the at least one viable population of tissuegenic cells derived from dental tissue is capable of differentiating into a liver cell lineage. According to one embodiment, the at least one viable population of tissuegenic cells derived from dental tissue is capable of differentiating into a lung cell lineage. According to one embodiment, the at least one viable population of tissuegenic cells derived from dental tissue is capable of differentiating into a meniscal cell lineage. According to one embodiment, the at least one viable population of tissuegenic cells derived from dental tissue is capable of differentiating into a muscle cell lineage. According to one embodiment, the at least one viable population of tissuegenic cells derived from dental tissue is capable of differentiating into a nerve cell lineage. According to one embodiment, the at least one viable population of tissuegenic cells derived from dental tissue is capable of differentiating into an ovarian cell lineage. According to one embodiment, the at least one viable population of tissuegenic cells derived from dental tissue is capable of differentiating into a pancreatic cell lineage. According to one embodiment, the at least one viable population of tissuegenic cells derived from dental tissue is capable of differentiating into a parenchymal organ cell lineage. According to one embodiment, the at least one viable population of tissuegenic cells derived from dental tissue is capable of differentiating into a pericardial cell lineage. According to one embodiment, the at least one viable population of tissuegenic cells derived from dental tissue is capable of differentiating into a periosteal cell lineage. According to one embodiment, the at least one viable population of tissuegenic cells is capable of differentiating into a peritoneal cell lineage. According to one embodiment, the at least one viable population of tissuegenic cells derived from dental tissue is capable of differentiating into a skin cell lineage. According to one embodiment, the at least one viable population of tissuegenic cells derived from dental tissue is capable of differentiating into a spleen cell lineage. According to one embodiment, the at least one viable population of tissuegenic cells derived from dental tissue is capable of differentiating into a synovial cell lineage. According to one embodiment, the at least one viable population of tissuegenic cells derived from dental tissue is capable of differentiating into a tendon cell lineage. According to one embodiment, the at least one viable population of tissuegenic cells derived from dental tissue is capable of differentiating into a testes cell lineage. According to one embodiment, the at least one viable population of tissuegenic cells derived from dental tissue is capable of differentiating into a urological cell lineage. According to one embodiment, the at least one viable population of tissuegenic cells derived from dental tissue is capable of differentiating into a vascular cell lineage. According to one embodiment, the at least one viable population of tissuegenic cells derived from dental tissue is capable of differentiating into a vein cell lineage.

According to one embodiment, the at least one viable population of tissuegenic cells derived from dental tissue can be reprogrammedreprogrammed to at least one viable induced pluripotent stem cell (iPSC) population.

According to one embodiment, the at least one viable population of tissuegenic cells derived from dental tissue differentiates along an osteogenic lineage. According to one embodiment, the at least one viable population of tissuegenic cells derived from dental tissue differentiates along an adipogenic lineage. According to one embodiment, the at least one viable population of tissuegenic cells derived from dental tissue differentiates along a chondrogenic lineage. According to one embodiment, the at least one viable population of tissuegenic cells derived from dental tissue differentiates along a neurogenic lineage.

According to one embodiment, the at least one viable population of tissuegenic cells derived from dental tissue is capable of migrating from or to the at least one growth-conductive matrix. According to one embodiment, the at least one viable population of tissuegenic cells derived from dental tissue comprises a viable nonexpanded population of tissuegenic cells. According to one embodiment, the at least one viable population of tissuegenic cells derived from dental tissue comprises a viable expanded population of tissuegenic cells. According to some embodiments, the at least one viable population of tissuegenic cells derived from dental tissue adherent to and resident in the endogenous milieu of the growth conductive matrix is immune privileged. The term "immune privileged" as used herein refers to the characteristic of tissuegenic cells by which there is no induction of an immune response upon transplantation of such cells.

Tissuegenic Cells Derived from Epithelial Tissue

According to one embodiment, the at least one viable population of tissuegenic cells derived from epithelial tissue comprises a viable gastrointestinal-derived stem cell population. Exemplary tissuegenic cells derived from gastrointestinal tissue are listed in U.S. Published Application No. 2009/0269769, the entire contents of which are incorporated herein by reference.

According to one embodiment, the at least one viable population of tissuegenic cells from epithelial tissue secretes at least one growth-inductive factor.

According to one embodiment, the at least one viable population of tissuegenic cells derived from epithelial tissue is capable of differentiating into cells of at least one embryonic lineage. According to one embodiment, the embryonic lineage is selected from the group consisting of an ectodermal lineage, a mesodermal lineage and an endodermal lineage. According to one embodiment, the at least one viable population of tissuegenic cells derived from epithelial tissue is capable of differentiating into cells of an ectodermal lineage. According to one embodiment, the at least one viable population of tissuegenic cells derived from epithelial tissue is capable of differentiating into cells of a mesodermal lineage. According to one embodiment, the at least one viable population of tissuegenic cells derived from epithelial tissue is capable of differentiating into cells of an endodermal lineage. Exemplary target lineages of tissuegenic cells derived from epithelial tissue are listed in Ulmer et al. (2010), Schweiz Monatsschr Zahnmed, 120:860-872, the entire contents of which are incorporated herein by reference.

According to one embodiment, the at least one viable population of tissuegenic cells derived from epithelial tissue is capable of regenerating a target tissue. According to one embodiment, the target tissue is selected from the group consisting of an adipose tissue, an amnion tissue, an artery tissue, a bone tissue, a cartilage tissue, a chorion tissue, a colon tissue, a dental tissue, a dermal tissue, a duodenal tissue, an endothelial tissue, an epithelial tissue, a gastrointestinal tissue, a growth plate tissue, an intervertebral disc tissue, an intestinal mucosal tissue, an intestinal serosal tissue, a kidney tissue, a ligament tissue, a liver tissue, a lung tissue, a meniscal tissue, a muscle tissue, a nerve tissue, an ovarian tissue, a pancreatic tissue, a parenchymal organ tissue, a pericardial tissue, a periosteal tissue, a peritoneal tissue, a skin tissue, a spleen tissue, a synovial tissue, a tendon tissue, a testes tissue, a urological tissue, a vascular tissue, a vein tissue, and a combination thereof.

According to one embodiment, the at least one viable population of tissuegenic cells derived from epithelial tissue is capable of regenerating an adipose tissue. According to one embodiment, the at least one viable population of tissuegenic cells derived from epithelial tissue is capable of regenerating an amnion tissue. According to one embodiment, the at least one viable population of tissuegenic cells derived from epithelial tissue is capable of regenerating an artery tissue. According to one embodiment, the at least one viable population of tissuegenic cells derived from epithelial tissue is capable of regenerating a bone tissue. According to one embodiment, the at least one viable population of tissuegenic cells derived from epithelial tissue is capable of regenerating a cartilage tissue. According to one embodiment, the at least one viable population of tissuegenic cells derived from epithelial tissue is capable of regenerating a chorion tissue. According to one embodiment, the at least one viable population of tissuegenic cells derived from epithelial tissue is capable of regenerating a colon tissue. According to one embodiment, the at least one viable population of tissuegenic cells derived from epithelial tissue is capable of regenerating a dental tissue. According to one embodiment, the at least one viable population of tissuegenic cells derived from epithelial tissue is capable of regenerating a dermal tissue. According to one embodiment, the at least one viable population of tissuegenic cells derived from epithelial tissue is capable of regenerating a duodenal tissue. According to one embodiment, the at least one viable population of tissuegenic cells derived from epithelial tissue is capable of regenerating an endothelial tissue. According to one embodiment, the at least one viable population of tissuegenic cells derived from epithelial tissue is capable of regenerating a gastrointestinal tissue. According to one embodiment, the at least one viable population of tissuegenic cells derived from epithelial tissue is capable of regenerating a growth plate tissue. According to one embodiment, the at least one viable population of tissuegenic cells derived from epithelial tissue is is capable of regenerating an intervertebral disc tissue. According to one embodiment, the at least one viable population of tissuegenic cells derived from epithelial tissue is is capable of regenerating an intestinal mucosal tissue. According to one embodiment, the at least one viable population of tissuegenic cells derived from epithelial tissue is is capable of regenerating an intestinal serosal tissue. According to one embodiment, the at least one viable population of tissuegenic cells derived from epithelial tissue is is capable of regenerating a kidney tissue. According to one embodiment, the at least one viable population of tissuegenic cells derived from epithelial tissue is capable of regenerating a ligament tissue. According to one embodiment, the at least one viable population of tissuegenic cells derived from epithelial tissue is capable of regenerating a liver tissue. According to one embodiment, the at least one viable population of tissuegenic cells derived from epithelial tissue is capable of regenerating a lung tissue. According to one embodiment, the at least one viable population of tissuegenic cells derived from epithelial tissue is capable of regenerating a meniscal tissue. According to one embodiment, the at least one viable population of tissuegenic cells derived from epithelial tissue is capable of regenerating a muscle tissue. According to one embodiment, the at least one viable population of tissuegenic cells derived from epithelial tissue is capable of regenerating a nerve tissue. According to one embodiment, the at least one viable population of tissuegenic cells derived from epithelial tissue is capable of regenerating an ovarian tissue. According to one embodiment, the at least one viable population of tissuegenic cells derived from epithelial tissue is capable of regenerating a pancreatic tissue. According to one embodiment, the at least one viable population of tissuegenic cells derived from epithelial tissue is capable of regenerating a parenchymal organ tissue. According to one embodiment, the at least one viable population of tissuegenic cells derived from epithelial tissue is capable of regenerating a pericardial tissue. According to one embodiment, the at least one viable population of tissuegenic cells derived from epithelial tissue is capable of regenerating a periosteal tissue. According to one embodiment, the at least one viable population of tissuegenic cells derived from epithelial tissue is capable of regenerating a peritoneal tissue. According to one embodiment, the at least one viable population of tissuegenic cells derived from epithelial tissue is capable of regenerating a skin tissue. According to one embodiment, the at least one viable population of tissuegenic cells derived from epithelial tissue is capable of regenerating a spleen tissue. According to one embodiment, the at least one viable population of tissuegenic cells derived from epithelial tissue is capable of regenerating a synovial tissue. According to one embodiment, the at least one viable population of tissuegenic cells derived from epithelial tissue is capable of regenerating a tendon tissue. According to one embodiment, the at least one viable population of tissuegenic cells derived from epithelial tissue is capable of regenerating a testes tissue. According to one embodiment, the at least one viable population of tissuegenic cells derived from epithelial tissue is capable of regenerating a urological tissue. According to one embodiment, the at least one viable population of tissuegenic cells derived from epithelial tissue is capable of regenerating a vascular tissue. According to one embodiment, the at least one viable population of tissuegenic cells derived from epithelial tissue is capable of regenerating a vein tissue.

According to one embodiment, the at least one viable population of tissuegenic cells derived from epithelial tissue is capable of differentiating into a target tissue cell lineage. According to one embodiment, the target tissue cell lineage is selected from the group consisting of an adipose cell lineage, an amnion cell lineage, an artery cell lineage, a bone cell lineage, a cartilage cell lineage, a dental cell lineage, a dermal cell lineage, a duodenal cell lineage, an endothelial lineage, an epithelial cell lineage, a gastrointestinal cell lineage, a growth plate cell lineage, an intervertebral disc cell lineage, an intestinal mucosal cell lineage, an intestinal serosal cell lineage, a kidney cell lineage, a ligament cell lineage, a liver cell lineage, a lung cell lineage, a meniscal cell lineage, a muscle cell lineage, a nerve cell lineage, an ovarian cell lineage, a pancreatic cell lineage, a parenchymal organ cell lineage, a pericardial cell lineage, a periosteal cell lineage, a peritoneal cell lineage, a skin cell lineage, a spleen cell lineage, a synovial cell lineage, a tendon cell lineage, a testes cell lineage, a urological cell lineage, a vascular cell lineage, a vein cell lineage, and a combination thereof.

According to one embodiment, the at least one viable population of tissuegenic cells derived from epithelial tissue is capable of differentiating into an adipose cell lineage. According to one embodiment, the at least one viable population of tissuegenic cells derived from epithelial tissue is capable of differentiating into an amnion cell lineage. According to one embodiment, the at least one viable population of tissuegenic cells derived from epithelial tissue is capable of differentiating into an artery cell lineage. According to one embodiment, the at least one viable population of tissuegenic cells derived from epithelial tissue is capable of differentiating into a bone cell lineage. According to one embodiment, the at least one viable population of tissuegenic cells derived from epithelial tissue is capable of differentiating into a cartilage cell lineage. According to one embodiment, the at least one viable population of tissuegenic cells derived from epithelial tissue is capable of differentiating into a chorion cell lineage. According to one embodiment, the at least one viable population of tissuegenic cells derived from epithelial tissue is capable of differentiating into a colon cell lineage. According to one embodiment, the at least one viable population of tissuegenic cells derived from epithelial tissue is capable of differentiating into a dental cell lineage. According to one embodiment, the at least one viable population of tissuegenic cells derived from epithelial tissue is capable of differentiating into a dermal cell lineage. According to one embodiment, the at least one viable population of tissuegenic cells derived from epithelial tissue is capable of differentiating into a duodenal cell lineage. According to one embodiment, the at least one viable population of tissuegenic cells derived from epithelial tissue is capable of differentiating into an endothelial cell lineage. According to one embodiment, the at least one viable population of tissuegenic cells derived from epithelial tissue is capable of differentiating into an epithelial cell lineage. According to one embodiment, the at least one viable population of tissuegenic cells derived from epithelial tissue is capable of differentiating into a gastrointestinal cell lineage. According to one embodiment, the at least one viable population of tissuegenic cells derived from epithelial tissue is capable of differentiating into a growth plate cell lineage. According to one embodiment, the at least one viable population of tissuegenic cells derived from epithelial tissue is capable of differentiating into an intervertebral disc cell lineage. According to one embodiment, the at least one viable population of tissuegenic cells derived from epithelial tissue is capable of differentiating into an intestinal mucosal cell lineage. According to one embodiment, the at least one viable population of tissuegenic cells derived from epithelial tissue is capable of differentiating into an intestinal serosal cell lineage. According to one embodiment, the at least one viable population of tissuegenic cells derived from epithelial tissue is capable of differentiating into a kidney cell lineage. According to one embodiment, the at least one viable population of tissuegenic cells derived from epithelial tissue is capable of differentiating into a ligament cell lineage. According to one embodiment, the at least one viable population of tissuegenic cells derived from epithelial tissue is capable of differentiating into a liver cell lineage. According to one embodiment, the at least one viable population of tissuegenic cells derived from epithelial tissue is capable of differentiating into a lung cell lineage. According to one embodiment, the at least one viable population of tissuegenic cells derived from epithelial tissue is capable of differentiating into a meniscal cell lineage. According to one embodiment, the at least one viable population of tissuegenic cells derived from epithelial tissue is capable of differentiating into a muscle cell lineage. According to one embodiment, the at least one viable population of tissuegenic cells derived from epithelial tissue is capable of differentiating into a nerve cell lineage. According to one embodiment, the at least one viable population of tissuegenic cells derived from epithelial tissue is capable of differentiating into an ovarian cell lineage. According to one embodiment, the at least one viable population of tissuegenic cells derived from epithelial tissue is capable of differentiating into a pancreatic cell lineage. According to one embodiment, the at least one viable population of tissuegenic cells derived from epithelial tissue is capable of differentiating into a parenchymal organ cell lineage. According to one embodiment, the at least one viable population of tissuegenic cells derived from epithelial tissue is capable of differentiating into a pericardial cell lineage. According to one embodiment, the at least one viable population of tissuegenic cells derived from epithelial tissue is capable of differentiating into a periosteal cell lineage. According to one embodiment, the at least one viable population of tissuegenic cells is capable of differentiating into a peritoneal cell lineage. According to one embodiment, the at least one viable population of tissuegenic cells derived from epithelial tissue is capable of differentiating into a skin cell lineage. According to one embodiment, the at least one viable population of tissuegenic cells derived from epithelial tissue is capable of differentiating into a spleen cell lineage. According to one embodiment, the at least one viable population of tissuegenic cells derived from epithelial tissue is capable of differentiating into a synovial cell lineage. According to one embodiment, the at least one viable population of tissuegenic cells derived from epithelial tissue is capable of differentiating into a tendon cell lineage. According to one embodiment, the at least one viable population of tissuegenic cells derived from epithelial tissue is capable of differentiating into a testes cell lineage. According to one embodiment, the at least one viable population of tissuegenic cells derived from epithelial tissue is capable of differentiating into a urological cell lineage. According to one embodiment, the at least one viable population of tissuegenic cells derived from epithelial tissue is capable of differentiating into a vascular cell lineage. According to one embodiment, the at least one viable population of tissuegenic cells derived from epithelial tissue is capable of differentiating into a vein cell lineage.

According to one embodiment, the at least one viable population of tissuegenic cells derived from epithelial tissue can be reprogrammedreprogrammed to at least one viable induced pluripotent stem cell (iPSC) population.

According to one embodiment, the at least one viable population of tissuegenic cells derived from gastrointestinal tissue differentiates along an osteogenic lineage. According to one embodiment, the at least one viable population of tissuegenic cells derived from gastrointestinal tissue differentiates along an adipogenic lineage. According to one embodiment, the at least one viable population of tissuegenic cells derived from gastrointestinal tissue differentiates along a chondrogenic lineage. According to one embodiment, the at least one viable population of tissuegenic cells derived from gastrointestinal tissue differentiates along a neurogenic lineage.

According to one embodiment, the at least one viable population of tissuegenic cells derived from epithelial tissue differentiates along an osteogenic lineage. According to one embodiment, the at least one viable population of tissuegenic cells derived from epithelial tissue differentiates along an adipogenic lineage. According to one embodiment, the at least one viable population of tissuegenic cells derived from epithelial tissue differentiates along a chondrogenic lineage. According to one embodiment, the at least one viable population of tissuegenic cells derived from epithelial tissue differentiates along a neurogenic lineage.

According to one embodiment, the at least one viable population of tissuegenic cells derived from epithelial tissue is capable of migrating from or to the at least one growth-conductive matrix. According to one embodiment, the at least one viable population of tissuegenic cells derived from epithelial tissue comprises a viable nonexpanded population of tissuegenic cells. According to one embodiment, the at least one viable population of tissuegenic cells derived from epithelial tissue comprises a viable expanded population of tissuegenic cells. According to some embodiments, the at least one viable population of tissuegenic cells derived from epithelial tissue adherent to and resident in the endogenous milieu of the growth conductive matrix is immune privileged. The term "immune privileged" as used herein refers to the characteristic of tissuegenic cells by which there is no induction of an immune response upon transplantation of such cells.

Tissuegenic Cells Derived from Fascial Tissue

According to one embodiment, the at least one viable population of tissuegenic cells derived from fascial tissue is selected from the group consisting of a viable pluripotent stem cell population, a viable multipotent stem cell population, a viable progenitor cell population, and a combination thereof.

According to one embodiment, the at least one viable population of tissuegenic cells from fascial tissue secretes at least one growth inductive factor.

According to one embodiment, the at least one viable population of tissuegenic cells derived from fascial tissue is capable of differentiating into cells of at least one embryonic lineage. According to one embodiment, the embryonic lineage is selected from the group consisting of an ectodermal lineage, a mesodermal lineage and an endodermal lineage. According to one embodiment, the at least one viable population of tissuegenic cells derived from fascial tissue is capable of differentiating into cells of an ectodermal lineage. According to one embodiment, the at least one viable population of tissuegenic cells derived from fascial tissue is capable of differentiating into cells of a mesodermal lineage. According to one embodiment, the at least one viable population of tissuegenic cells derived from fascial tissue is capable of differentiating into cells of an endodermal lineage.

According to one embodiment, the at least one viable population of tissuegenic cells derived from fascial tissue is capable of regenerating a target tissue. According to one embodiment, the target tissue is selected from the group consisting of an adipose tissue, an amnion tissue, an artery tissue, a bone tissue, a cartilage tissue, a chorion tissue, a colon tissue, a dental tissue, a dermal tissue, a duodenal tissue, an endothelial tissue, an epithelial tissue, a fascial tissue, a gastrointestinal tissue, a growth plate tissue, an intervertebral disc tissue, an intestinal mucosal tissue, an intestinal serosal tissue, a kidney tissue, a ligament tissue, a liver tissue, a lung tissue, a meniscal tissue, a muscle tissue, a nerve tissue, an ovarian tissue, a pancreatic tissue, a parenchymal organ tissue, a pericardial tissue, a periosteal tissue, a peritoneal tissue, a skin tissue, a spleen tissue, a synovial tissue, a tendon tissue, a testes tissue, a urological tissue, a vascular tissue, a vein tissue, and a combination thereof.

According to one embodiment, the at least one viable population of tissuegenic cells derived from fascial tissue is capable of regenerating an adipose tissue. According to one embodiment, the at least one viable population of tissuegenic cells derived from fascial tissue is capable of regenerating an amnion tissue. According to one embodiment, the at least one viable population of tissuegenic cells derived from fascial tissue is capable of regenerating an artery tissue. According to one embodiment, the at least one viable population of tissuegenic cells derived from fascial tissue is capable of regenerating a bone tissue. According to one embodiment, the at least one viable population of tissuegenic cells derived from fascial tissue is capable of regenerating a cartilage tissue. According to one embodiment, the at least one viable population of tissuegenic cells derived from fascial tissue is capable of regenerating a chorion tissue. According to one embodiment, the at least one viable population of tissuegenic cells derived from fascial tissue is capable of regenerating a colon tissue. According to one embodiment, the at least one viable population of tissuegenic cells derived from fascial tissue is capable of regenerating a dental tissue. According to one embodiment, the at least one viable population of tissuegenic cells derived from fascial tissue is capable of regenerating a dermal tissue. According to one embodiment, the at least one viable population of tissuegenic cells derived from fascial tissue is capable of regenerating a duodenal tissue. According to one embodiment, the at least one viable population of tissuegenic cells derived from fascial tissue is capable of regenerating an endothelial tissue. According to one embodiment, the at least one viable population of tissuegenic cells derived from fascial tissue is capable of regenerating an epithelial tissue. According to one embodiment, the at least one viable population of tissuegenic cells derived from fascial tissue is capable of regenerating a gastrointestinal tissue. According to one embodiment, the at least one viable population of tissuegenic cells derived from fascial tissue is capable of regenerating a growth plate tissue. According to one embodiment, the at least one viable population of tissuegenic cells derived from fascial tissue is capable of regenerating an intervertebral disc tissue. According to one embodiment, the at least one viable population of tissuegenic cells derived from fascial tissue is capable of regenerating an intestinal mucosal tissue. According to one embodiment, the at least one viable population of tissuegenic cells derived from fascial tissue is capable of regenerating an intestinal serosal tissue. According to one embodiment, the at least one viable population of tissuegenic cells derived from fascial tissue is capable of regenerating a kidney tissue. According to one embodiment, the at least one viable population of tissuegenic cells derived from fascial tissue is capable of regenerating a ligament tissue. According to one embodiment, the at least one viable population of tissuegenic cells derived from fascial tissue is capable of regenerating a liver tissue. According to one embodiment, the at least one viable population of tissuegenic cells derived from fascial tissue is capable of regenerating a lung tissue. According to one embodiment, the at least one viable population of tissuegenic cells derived from fascial tissue is capable of regenerating a meniscal tissue. According to one embodiment, the at least one viable population of tissuegenic cells derived from fascial tissue is capable of regenerating a muscle tissue. According to one embodiment, the at least one viable population of tissuegenic cells derived from fascial tissue is capable of regenerating a nerve tissue. According to one embodiment, the at least one viable population of tissuegenic cells derived from fascial tissue is capable of regenerating an ovarian tissue. According to one embodiment, the at least one viable population of tissuegenic cells derived from fascial tissue is capable of regenerating a pancreatic tissue. According to one embodiment, the at least one viable population of tissuegenic cells derived from fascial tissue is capable of regenerating a parenchymal organ tissue. According to one embodiment, the at least one viable population of tissuegenic cells derived from fascial tissue is capable of regenerating a pericardial tissue. According to one embodiment, the at least one viable population of tissuegenic cells derived from fascial tissue is capable of regenerating a periosteal tissue. According to one embodiment, the at least one viable population of tissuegenic cells derived from fascial tissue is capable of regenerating a peritoneal tissue. According to one embodiment, the at least one viable population of tissuegenic cells derived from fascial tissue is capable of regenerating a skin tissue. According to one embodiment, the at least one viable population of tissuegenic cells derived from fascial tissue is capable of regenerating a spleen tissue. According to one embodiment, the at least one viable population of tissuegenic cells derived from fascial tissue is capable of regenerating a synovial tissue. According to one embodiment, the at least one viable population of tissuegenic cells derived from fascial tissue is capable of regenerating a tendon tissue. According to one embodiment, the at least one viable population of tissuegenic cells derived from fascial tissue is capable of regenerating a testes tissue. According to one embodiment, the at least one viable population of tissuegenic cells derived from fascial tissue is capable of regenerating a urological tissue. According to one embodiment, the at least one viable population of tissuegenic cells derived from fascial tissue is capable of regenerating a vascular tissue. According to one embodiment, the at least one viable population of tissuegenic cells derived from fascial tissue is capable of regenerating a vein tissue.

According to one embodiment, the at least one viable population of tissuegenic cells derived from fascial tissue is capable of differentiating into a target tissue cell lineage. According to one embodiment, the target tissue cell lineage is selected from the group consisting of an adipose cell lineage, an amnion cell lineage, an artery cell lineage, a bone cell lineage, a cartilage cell lineage, a dental cell lineage, a dermal cell lineage, a duodenal cell lineage, an endothelial lineage, an epithelial cell lineage, a fascial cell lineage, a gastrointestinal cell lineage, a growth plate cell lineage, an intervertebral disc cell lineage, an intestinal mucosal cell lineage, an intestinal serosal cell lineage, a kidney cell lineage, a ligament cell lineage, a liver cell lineage, a lung cell lineage, a meniscal cell lineage, a muscle cell lineage, a nerve cell lineage, an ovarian cell lineage, a pancreatic cell lineage, a parenchymal organ cell lineage, a pericardial cell lineage, a periosteal cell lineage, a peritoneal cell lineage, a skin cell lineage, a spleen cell lineage, a synovial cell lineage, a tendon cell lineage, a testes cell lineage, a urological cell lineage, a vascular cell lineage, a vein cell lineage, and a combination thereof.

According to one embodiment, the at least one viable population of tissuegenic cells derived from fascial tissue is capable of differentiating into an adipose cell lineage. According to one embodiment, the at least one viable population of tissuegenic cells derived from fascial tissue is capable of differentiating into an amnion cell lineage. According to one embodiment, the at least one viable population of tissuegenic cells derived from fascial tissue is capable of differentiating into an artery cell lineage. According to one embodiment, the at least one viable population of tissuegenic cells derived from fascial tissue is capable of differentiating into a bone cell lineage. According to one embodiment, the at least one viable population of tissuegenic cells derived from fascial tissue is capable of differentiating into a cartilage cell lineage. According to one embodiment, the at least one viable population of tissuegenic cells derived from fascial tissue is capable of differentiating into a chorion cell lineage. According to one embodiment, the at least one viable population of tissuegenic cells derived from fascial tissue is capable of differentiating into a colon cell lineage. According to one embodiment, the at least one viable population of tissuegenic cells derived from fascial tissue is capable of differentiating into a dental cell lineage. According to one embodiment, the at least one viable population of tissuegenic cells derived from fascial tissue is capable of differentiating into a dermal cell lineage. According to one embodiment, the at least one viable population of tissuegenic cells derived from fascial tissue is capable of differentiating into a duodenal cell lineage. According to one embodiment, the at least one viable population of tissuegenic cells derived from fascial tissue is capable of differentiating into an endothelial cell lineage. According to one embodiment, the at least one viable population of tissuegenic cells derived from fascial tissue is capable of differentiating into an epithelial cell lineage. According to one embodiment, the at least one viable population of tissuegenic cells derived from fascial tissue is capable of differentiating into a fascial cell lineage. According to one embodiment, the at least one viable population of tissuegenic cells derived from fascial tissue is capable of differentiating into a gastrointestinal cell lineage. According to one embodiment, the at least one viable population of tissuegenic cells derived from fascial tissue is capable of differentiating into a growth plate cell lineage. According to one embodiment, the at least one viable population of tissuegenic cells derived from fascial tissue is capable of differentiating into an intervertebral disc cell lineage. According to one embodiment, the at least one viable population of tissuegenic cells derived from fascial tissue is capable of differentiating into an intestinal mucosal cell lineage. According to one embodiment, the at least one viable population of tissuegenic cells derived from fascial tissue is capable of differentiating into an intestinal serosal cell lineage. According to one embodiment, the at least one viable population of tissuegenic cells derived from fascial tissue is capable of differentiating into a kidney cell lineage. According to one embodiment, the at least one viable population of tissuegenic cells derived from fascial tissue is capable of differentiating into a ligament cell lineage. According to one embodiment, the at least one viable population of tissuegenic cells derived from fascial tissue is capable of differentiating into a liver cell lineage. According to one embodiment, the at least one viable population of tissuegenic cells derived from fascial tissue is capable of differentiating into a lung cell lineage. According to one embodiment, the at least one viable population of tissuegenic cells derived from fascial tissue is capable of differentiating into a meniscal cell lineage. According to one embodiment, the at least one viable population of tissuegenic cells derived from fascial tissue is capable of differentiating into a muscle cell lineage. According to one embodiment, the at least one viable population of tissuegenic cells derived from fascial tissue is capable of differentiating into a nerve cell lineage. According to one embodiment, the at least one viable population of tissuegenic cells derived from fascial tissue is capable of differentiating into an ovarian cell lineage. According to one embodiment, the at least one viable population of tissuegenic cells derived from fascial tissue is capable of differentiating into a pancreatic cell lineage. According to one embodiment, the at least one viable population of tissuegenic cells derived from fascial tissue is capable of differentiating into a parenchymal organ cell lineage. According to one embodiment, the at least one viable population of tissuegenic cells derived from fascial tissue is capable of differentiating into a pericardial cell lineage. According to one embodiment, the at least one viable population of tissuegenic cells derived from fascial tissue is capable of differentiating into a periosteal cell lineage. According to one embodiment, the at least one viable population of tissuegenic cells is capable of differentiating into a peritoneal cell lineage. According to one embodiment, the at least one viable population of tissuegenic cells derived from fascial tissue is capable of differentiating into a skin cell lineage. According to one embodiment, the at least one viable population of tissuegenic cells derived from fascial tissue is capable of differentiating into a spleen cell lineage. According to one embodiment, the at least one viable population of tissuegenic cells derived from fascial tissue is capable of differentiating into a synovial cell lineage. According to one embodiment, the at least one viable population of tissuegenic cells derived from fascial tissue is capable of differentiating into a tendon cell lineage. According to one embodiment, the at least one viable population of tissuegenic cells derived from fascial tissue is capable of differentiating into a testes cell lineage. According to one embodiment, the at least one viable population of tissuegenic cells derived from fascial tissue is capable of differentiating into a urological cell lineage. According to one embodiment, the at least one viable population of tissuegenic cells derived from fascial tissue is capable of differentiating into a vascular cell lineage. According to one embodiment, the at least one viable population of tissuegenic cells derived from fascial tissue is capable of differentiating into a vein cell lineage.

According to one embodiment, the at least one viable population of tissuegenic cells derived from fascial tissue can be reprogrammed to at least one viable induced pluripotent stem cell (iPSC) population.

According to one embodiment, the at least one viable population of tissuegenic cells derived from fascial tissue differentiates along an osteogenic lineage. According to one embodiment, the at least one viable population of tissuegenic cells derived from fascial tissue differentiates along an adipogenic lineage. According to one embodiment, the at least one viable population of tissuegenic cells derived from fascial tissue differentiates along a chondrogenic lineage. According to one embodiment, the at least one viable population of tissuegenic cells derived from fascial tissue differentiates along a neurogenic lineage.

According to one embodiment, the at least one viable population of tissuegenic cells derived from fascial tissue is capable of migrating from or to the at least one growth-conductive matrix. According to one embodiment, the at least one viable population of tissuegenic cells derived from fascial tissue comprises a viable nonexpanded population of tissuegenic cells. According to one embodiment, the at least one viable population of tissuegenic cells derived from fascial tissue comprises a viable expanded population of tissuegenic cells. According to some embodiments, the at least one viable population of tissuegenic cells derived from fascial tissue adherent to and resident in the endogenous milieu of the growth conductive matrix is immune privileged. The term "immune privileged" as used herein refers to the characteristic of tissuegenic cells by which there is no induction of an immune response upon transplantation of such cells.

Tissuegenic Cells Derived from Ligament Tissue

According to one embodiment, the at least one viable population of tissuegenic cells derived from ligament tissue comprises a viable ligament-derived mesenchymal stem cell population. Exemplary tissuegenic cells derived from ligament tissue are listed in Cheng et al. (2010), Tissue Engg. A, 16(7):2237-2253, the entire contents of which are incorporated herein by reference.

According to one embodiment, the at least one viable population of tissuegenic cells from ligament tissue secretes at least one growth-inductive factor.

According to one embodiment, the at least one viable population of tissuegenic cells derived from ligament tissue is capable of differentiating into cells of at least one embryonic lineage. According to one embodiment, the embryonic lineage is selected from the group consisting of an ectodermal lineage, a mesodermal lineage and an endodermal lineage. According to one embodiment, the at least one viable population of tissuegenic cells derived from ligament tissue is capable of differentiating into cells of an ectodermal lineage. According to one embodiment, the at least one viable population of tissuegenic cells derived from ligament tissue is capable of differentiating into cells of a mesodermal lineage. According to one embodiment, the at least one viable population of tissuegenic cells derived from ligament tissue is capable of differentiating into cells of an endodermal lineage.

According to one embodiment, the at least one viable population of tissuegenic cells derived from ligament tissue is capable of regenerating a target tissue. According to one embodiment, the target tissue is selected from the group consisting of an adipose tissue, an amnion tissue, an artery tissue, a bone tissue, a cartilage tissue, a chorion tissue, a colon tissue, a dental tissue, a dermal tissue, a duodenal tissue, an endothelial tissue, an epithelial tissue, a gastrointestinal tissue, a growth plate tissue, an intervertebral disc tissue, an intestinal mucosal tissue, an intestinal serosal tissue, a kidney tissue, a ligament tissue, a liver tissue, a lung tissue, a meniscal tissue, a muscle tissue, a nerve tissue, an ovarian tissue, a pancreatic tissue, a parenchymal organ tissue, a pericardial tissue, a periosteal tissue, a peritoneal tissue, a skin tissue, a spleen tissue, a synovial tissue, a tendon tissue, a testes tissue, a urological tissue, a vascular tissue, a vein tissue, and a combination thereof.

According to one embodiment, the at least one viable population of tissuegenic cells derived from ligament tissue is capable of regenerating an adipose tissue. According to one embodiment, the at least one viable population of tissuegenic cells derived from ligament tissue is capable of regenerating an amnion tissue. According to one embodiment, the at least one viable population of tissuegenic cells derived from ligament tissue is capable of regenerating an artery tissue. According to one embodiment, the at least one viable population of tissuegenic cells derived from ligament tissue is capable of regenerating a bone tissue. According to one embodiment, the at least one viable population of tissuegenic cells derived from ligament tissue is capable of regenerating a cartilage tissue. According to one embodiment, the at least one viable population of tissuegenic cells derived from ligament tissue is capable of regenerating a chorion tissue. According to one embodiment, the at least one viable population of tissuegenic cells derived from ligament tissue is capable of regenerating a colon tissue. According to one embodiment, the at least one viable population of tissuegenic cells derived from ligament tissue is capable of regenerating a dental tissue. According to one embodiment, the at least one viable population of tissuegenic cells derived from ligament tissue is capable of regenerating a dermal tissue. According to one embodiment, the at least one viable population of tissuegenic cells derived from ligament tissue is capable of regenerating a duodenal tissue. According to one embodiment, the at least one viable population of tissuegenic cells derived from ligament tissue is capable of regenerating an endothelial tissue. According to one embodiment, the at least one viable population of tissuegenic cells derived from ligament tissue is capable of regenerating a gastrointestinal tissue. According to one embodiment, the at least one viable population of tissuegenic cells derived from ligament tissue is capable of regenerating a growth plate tissue. According to one embodiment, the at least one viable population of tissuegenic cells derived from ligament tissue is is capable of regenerating an intervertebral disc tissue. According to one embodiment, the at least one viable population of tissuegenic cells derived from ligament tissue is is capable of regenerating an intestinal mucosal tissue. According to one embodiment, the at least one viable population of tissuegenic cells derived from ligament tissue is is capable of regenerating an intestinal serosal tissue. According to one embodiment, the at least one viable population of tissuegenic cells derived from ligament tissue is is capable of regenerating a kidney tissue. According to one embodiment, the at least one viable population of tissuegenic cells derived from ligament tissue is capable of regenerating a ligament tissue. According to one embodiment, the at least one viable population of tissuegenic cells derived from ligament tissue is capable of regenerating a liver tissue. According to one embodiment, the at least one viable population of tissuegenic cells derived from ligament tissue is capable of regenerating a lung tissue. According to one embodiment, the at least one viable population of tissuegenic cells derived from ligament tissue is capable of regenerating a meniscal tissue. According to one embodiment, the at least one viable population of tissuegenic cells derived from ligament tissue is capable of regenerating a muscle tissue. According to one embodiment, the at least one viable population of tissuegenic cells derived from ligament tissue is capable of regenerating a nerve tissue. According to one embodiment, the at least one viable population of tissuegenic cells derived from ligament tissue is capable of regenerating an ovarian tissue. According to one embodiment, the at least one viable population of tissuegenic cells derived from ligament tissue is capable of regenerating a pancreatic tissue. According to one embodiment, the at least one viable population of tissuegenic cells derived from ligament tissue is capable of regenerating a parenchymal organ tissue. According to one embodiment, the at least one viable population of tissuegenic cells derived from ligament tissue is capable of regenerating a pericardial tissue. According to one embodiment, the at least one viable population of tissuegenic cells derived from ligament tissue is capable of regenerating a periosteal tissue. According to one embodiment, the at least one viable population of tissuegenic cells derived from ligament tissue is capable of regenerating a peritoneal tissue. According to one embodiment, the at least one viable population of tissuegenic cells derived from ligament tissue is capable of regenerating a skin tissue. According to one embodiment, the at least one viable population of tissuegenic cells derived from ligament tissue is capable of regenerating a spleen tissue. According to one embodiment, the at least one viable population of tissuegenic cells derived from ligament tissue is capable of regenerating a synovial tissue. According to one embodiment, the at least one viable population of tissuegenic cells derived from ligament tissue is capable of regenerating a tendon tissue. According to one embodiment, the at least one viable population of tissuegenic cells derived from ligament tissue is capable of regenerating a testes tissue. According to one embodiment, the at least one viable population of tissuegenic cells derived from ligament tissue is capable of regenerating a urological tissue. According to one embodiment, the at least one viable population of tissuegenic cells derived from ligament tissue is capable of regenerating a vascular tissue. According to one embodiment, the at least one viable population of tissuegenic cells derived from ligament tissue is capable of regenerating a vein tissue.

According to one embodiment, the at least one viable population of tissuegenic cells derived from ligament tissue is capable of differentiating into a target tissue cell lineage. According to one embodiment, the target tissue cell lineage is selected from the group consisting of an adipose cell lineage, an amnion cell lineage, an artery cell lineage, a bone cell lineage, a cartilage cell lineage, a dental cell lineage, a dermal cell lineage, a duodenal cell lineage, an endothelial lineage, an epithelial cell lineage, a gastrointestinal cell lineage, a growth plate cell lineage, an intervertebral disc cell lineage, an intestinal mucosal cell lineage, an intestinal serosal cell lineage, a kidney cell lineage, a ligament cell lineage, a liver cell lineage, a lung cell lineage, a meniscal cell lineage, a muscle cell lineage, a nerve cell lineage, an ovarian cell lineage, a pancreatic cell lineage, a parenchymal organ cell lineage, a pericardial cell lineage, a periosteal cell lineage, a peritoneal cell lineage, a skin cell lineage, a spleen cell lineage, a synovial cell lineage, a tendon cell lineage, a testes cell lineage, a urological cell lineage, a vascular cell lineage, a vein cell lineage, and a combination thereof.

According to one embodiment, the at least one viable population of tissuegenic cells derived from ligament tissue is capable of differentiating into an adipose cell lineage. According to one embodiment, the at least one viable population of tissuegenic cells derived from ligament tissue is capable of differentiating into an amnion cell lineage. According to one embodiment, the at least one viable population of tissuegenic cells derived from ligament tissue is capable of differentiating into an artery cell lineage. According to one embodiment, the at least one viable population of tissuegenic cells derived from ligament tissue is capable of differentiating into a bone cell lineage. According to one embodiment, the at least one viable population of tissuegenic cells derived from ligament tissue is capable of differentiating into a cartilage cell lineage. According to one embodiment, the at least one viable population of tissuegenic cells derived from ligament tissue is capable of differentiating into a chorion cell lineage. According to one embodiment, the at least one viable population of tissuegenic cells derived from ligament tissue is capable of differentiating into a colon cell lineage. According to one embodiment, the at least one viable population of tissuegenic cells derived from ligament tissue is capable of differentiating into a dental cell lineage. According to one embodiment, the at least one viable population of tissuegenic cells derived from ligament tissue is capable of differentiating into a dermal cell lineage. According to one embodiment, the at least one viable population of tissuegenic cells derived from ligament tissue is capable of differentiating into a duodenal cell lineage. According to one embodiment, the at least one viable population of tissuegenic cells derived from ligament tissue is capable of differentiating into an endothelial cell lineage. According to one embodiment, the at least one viable population of tissuegenic cells derived from ligament tissue is capable of differentiating into an epithelial cell lineage. According to one embodiment, the at least one viable population of tissuegenic cells derived from ligament tissue is capable of differentiating into a gastrointestinal cell lineage. According to one embodiment, the at least one viable population of tissuegenic cells derived from ligament tissue is capable of differentiating into a growth plate cell lineage. According to one embodiment, the at least one viable population of tissuegenic cells derived from ligament tissue is capable of differentiating into an intervertebral disc cell lineage. According to one embodiment, the at least one viable population of tissuegenic cells derived from ligament tissue is capable of differentiating into an intestinal mucosal cell lineage. According to one embodiment, the at least one viable population of tissuegenic cells derived from ligament tissue is capable of differentiating into an intestinal serosal cell lineage. According to one embodiment, the at least one viable population of tissuegenic cells derived from ligament tissue is capable of differentiating into a kidney cell lineage. According to one embodiment, the at least one viable population of tissuegenic cells derived from ligament tissue is capable of differentiating into a ligament cell lineage. According to one embodiment, the at least one viable population of tissuegenic cells derived from ligament tissue is capable of differentiating into a liver cell lineage. According to one embodiment, the at least one viable population of tissuegenic cells derived from ligament tissue is capable of differentiating into a lung cell lineage. According to one embodiment, the at least one viable population of tissuegenic cells derived from ligament tissue is capable of differentiating into a meniscal cell lineage. According to one embodiment, the at least one viable population of tissuegenic cells derived from ligament tissue is capable of differentiating into a muscle cell lineage. According to one embodiment, the at least one viable population of tissuegenic cells derived from ligament tissue is capable of differentiating into a nerve cell lineage. According to one embodiment, the at least one viable population of tissuegenic cells derived from ligament tissue is capable of differentiating into an ovarian cell lineage. According to one embodiment, the at least one viable population of tissuegenic cells derived from ligament tissue is capable of differentiating into a pancreatic cell lineage. According to one embodiment, the at least one viable population of tissuegenic cells derived from ligament tissue is capable of differentiating into a parenchymal organ cell lineage. According to one embodiment, the at least one viable population of tissuegenic cells derived from ligament tissue is capable of differentiating into a pericardial cell lineage. According to one embodiment, the at least one viable population of tissuegenic cells derived from ligament tissue is capable of differentiating into a periosteal cell lineage. According to one embodiment, the at least one viable population of tissuegenic cells is capable of differentiating into a peritoneal cell lineage. According to one embodiment, the at least one viable population of tissuegenic cells derived from ligament tissue is capable of differentiating into a skin cell lineage. According to one embodiment, the at least one viable population of tissuegenic cells derived from ligament tissue is capable of differentiating into a spleen cell lineage. According to one embodiment, the at least one viable population of tissuegenic cells derived from ligament tissue is capable of differentiating into a synovial cell lineage. According to one embodiment, the at least one viable population of tissuegenic cells derived from ligament tissue is capable of differentiating into a tendon cell lineage. According to one embodiment, the at least one viable population of tissuegenic cells derived from ligament tissue is capable of differentiating into a testes cell lineage. According to one embodiment, the at least one viable population of tissuegenic cells derived from ligament tissue is capable of differentiating into a urological cell lineage. According to one embodiment, the at least one viable population of tissuegenic cells derived from ligament tissue is capable of differentiating into a vascular cell lineage. According to one embodiment, the at least one viable population of tissuegenic cells derived from ligament tissue is capable of differentiating into a vein cell lineage.

According to one embodiment, the at least one viable population of tissuegenic cells derived from ligament tissue can be reprogrammedreprogrammed to at least one viable induced pluripotent stem cell (iPSC) population.

According to one embodiment, the at least one viable population of tissuegenic cells derived from ligament tissue differentiates along an osteogenic lineage. According to one embodiment, the at least one viable population of tissuegenic cells derived from ligament tissue differentiates along an adipogenic lineage. According to one embodiment, the at least one viable population of tissuegenic cells derived from ligament tissue differentiates along a chondrogenic lineage. According to one embodiment, the at least one viable population of tissuegenic cells derived from ligament tissue differentiates along a neurogenic lineage.

According to one embodiment, the at least one viable population of tissuegenic cells derived from ligament tissue is capable of migrating from or to the at least one growth-conductive matrix. According to one embodiment, the at least one viable population of tissuegenic cells derived from ligament tissue comprises a viable nonexpanded population of tissuegenic cells. According to one embodiment, the at least one viable population of tissuegenic cells derived from ligament tissue comprises a viable expanded population of tissuegenic cells. According to some embodiments, the at least one viable population of tissuegenic cells derived from ligament tissue adherent to and resident in the endogenous milieu of the growth conductive matrix is immune privileged. The term "immune privileged" as used herein refers to the characteristic of tissuegenic cells by which there is no induction of an immune response upon transplantation of such cells.

Tissuegenic Cells Derived from Lung Tissue

According to one embodiment, the at least one viable population of tissuegenic cells derived from lung tissue comprises a viable lung-derived stem cell population. Exemplary tissuegenic cells derived from lung tissue are disclosed in Kajstura et al. (2011), N. Engl. J. Med., 364(19):1795-1806, the entire contents of which are incorporated herein by reference.

According to one embodiment, the at least one viable population of tissuegenic cells from lung tissue secretes at least one growth-inductive factor.

According to one embodiment, the at least one viable population of tissuegenic cells derived from lung tissue is capable of differentiating into cells of at least one embryonic lineage. According to one embodiment, the embryonic lineage is selected from the group consisting of an ectodermal lineage, a mesodermal lineage and an endodermal lineage. According to one embodiment, the at least one viable population of tissuegenic cells derived from lung tissue is capable of differentiating into cells of an ectodermal lineage. According to one embodiment, the at least one viable population of tissuegenic cells derived from lung tissue is capable of differentiating into cells of a mesodermal lineage. According to one embodiment, the at least one viable population of tissuegenic cells derived from lung tissue is capable of differentiating into cells of an endodermal lineage.

According to one embodiment, the at least one viable population of tissuegenic cells derived from lung tissue is capable of regenerating a target tissue. According to one embodiment, the target tissue is selected from the group consisting of an adipose tissue, an amnion tissue, an artery tissue, a bone tissue, a cartilage tissue, a chorion tissue, a colon tissue, a dental tissue, a dermal tissue, a duodenal tissue, an endothelial tissue, an epithelial tissue, a gastrointestinal tissue, a growth plate tissue, an intervertebral disc tissue, an intestinal mucosal tissue, an intestinal serosal tissue, a kidney tissue, a ligament tissue, a liver tissue, a lung tissue, a meniscal tissue, a muscle tissue, a nerve tissue, an ovarian tissue, a pancreatic tissue, a parenchymal organ tissue, a pericardial tissue, a periosteal tissue, a peritoneal tissue, a skin tissue, a spleen tissue, a synovial tissue, a tendon tissue, a testes tissue, a urological tissue, a vascular tissue, a vein tissue, and a combination thereof.

According to one embodiment, the at least one viable population of tissuegenic cells derived from lung tissue is capable of regenerating an adipose tissue. According to one embodiment, the at least one viable population of tissuegenic cells derived from lung tissue is capable of regenerating an amnion tissue. According to one embodiment, the at least one viable population of tissuegenic cells derived from lung tissue is capable of regenerating an artery tissue. According to one embodiment, the at least one viable population of tissuegenic cells derived from lung tissue is capable of regenerating a bone tissue. According to one embodiment, the at least one viable population of tissuegenic cells derived from lung tissue is capable of regenerating a cartilage tissue. According to one embodiment, the at least one viable population of tissuegenic cells derived from lung tissue is capable of regenerating a chorion tissue. According to one embodiment, the at least one viable population of tissuegenic cells derived from lung tissue is capable of regenerating a colon tissue. According to one embodiment, the at least one viable population of tissuegenic cells derived from lung tissue is capable of regenerating a dental tissue. According to one embodiment, the at least one viable population of tissuegenic cells derived from lung tissue is capable of regenerating a dermal tissue. According to one embodiment, the at least one viable population of tissuegenic cells derived from lung tissue is capable of regenerating a duodenal tissue. According to one embodiment, the at least one viable population of tissuegenic cells derived from lung tissue is capable of regenerating an endothelial tissue. According to one embodiment, the at least one viable population of tissuegenic cells derived from lung tissue is capable of regenerating a gastrointestinal tissue. According to one embodiment, the at least one viable population of tissuegenic cells derived from lung tissue is capable of regenerating a growth plate tissue. According to one embodiment, the at least one viable population of tissuegenic cells derived from lung tissue is is capable of regenerating an intervertebral disc tissue. According to one embodiment, the at least one viable population of tissuegenic cells derived from lung tissue is is capable of regenerating an intestinal mucosal tissue. According to one embodiment, the at least one viable population of tissuegenic cells derived from lung tissue is is capable of regenerating an intestinal serosal tissue. According to one embodiment, the at least one viable population of tissuegenic cells derived from lung tissue is is capable of regenerating a kidney tissue. According to one embodiment, the at least one viable population of tissuegenic cells derived from lung tissue is capable of regenerating a ligament tissue. According to one embodiment, the at least one viable population of tissuegenic cells derived from lung tissue is capable of regenerating a liver tissue. According to one embodiment, the at least one viable population of tissuegenic cells derived from lung tissue is capable of regenerating a lung tissue. According to one embodiment, the at least one viable population of tissuegenic cells derived from lung tissue is capable of regenerating a meniscal tissue. According to one embodiment, the at least one viable population of tissuegenic cells derived from lung tissue is capable of regenerating a muscle tissue. According to one embodiment, the at least one viable population of tissuegenic cells derived from lung tissue is capable of regenerating a nerve tissue. According to one embodiment, the at least one viable population of tissuegenic cells derived from lung tissue is capable of regenerating an ovarian tissue. According to one embodiment, the at least one viable population of tissuegenic cells derived from lung tissue is capable of regenerating a pancreatic tissue. According to one embodiment, the at least one viable population of tissuegenic cells derived from lung tissue is capable of regenerating a parenchymal organ tissue. According to one embodiment, the at least one viable population of tissuegenic cells derived from lung tissue is capable of regenerating a pericardial tissue. According to one embodiment, the at least one viable population of tissuegenic cells derived from lung tissue is capable of regenerating a periosteal tissue. According to one embodiment, the at least one viable population of tissuegenic cells derived from lung tissue is capable of regenerating a peritoneal tissue. According to one embodiment, the at least one viable population of tissuegenic cells derived from lung tissue is capable of regenerating a skin tissue. According to one embodiment, the at least one viable population of tissuegenic cells derived from lung tissue is capable of regenerating a spleen tissue. According to one embodiment, the at least one viable population of tissuegenic cells derived from lung tissue is capable of regenerating a synovial tissue. According to one embodiment, the at least one viable population of tissuegenic cells derived from lung tissue is capable of regenerating a tendon tissue. According to one embodiment, the at least one viable population of tissuegenic cells derived from lung tissue is capable of regenerating a testes tissue. According to one embodiment, the at least one viable population of tissuegenic cells derived from lung tissue is capable of regenerating a urological tissue. According to one embodiment, the at least one viable population of tissuegenic cells derived from lung tissue is capable of regenerating a vascular tissue. According to one embodiment, the at least one viable population of tissuegenic cells derived from lung tissue is capable of regenerating a vein tissue.

According to one embodiment, the at least one viable population of tissuegenic cells derived from lung tissue is capable of differentiating into a target tissue cell lineage. According to one embodiment, the target tissue cell lineage is selected from the group consisting of an adipose cell lineage, an amnion cell lineage, an artery cell lineage, a bone cell lineage, a cartilage cell lineage, a dental cell lineage, a dermal cell lineage, a duodenal cell lineage, an endothelial lineage, an epithelial cell lineage, a gastrointestinal cell lineage, a growth plate cell lineage, an intervertebral disc cell lineage, an intestinal mucosal cell lineage, an intestinal serosal cell lineage, a kidney cell lineage, a ligament cell lineage, a liver cell lineage, a lung cell lineage, a meniscal cell lineage, a muscle cell lineage, a nerve cell lineage, an ovarian cell lineage, a pancreatic cell lineage, a parenchymal organ cell lineage, a pericardial cell lineage, a periosteal cell lineage, a peritoneal cell lineage, a skin cell lineage, a spleen cell lineage, a synovial cell lineage, a tendon cell lineage, a testes cell lineage, a urological cell lineage, a vascular cell lineage, a vein cell lineage, and a combination thereof.

According to one embodiment, the at least one viable population of tissuegenic cells derived from lung tissue is capable of differentiating into an adipose cell lineage. According to one embodiment, the at least one viable population of tissuegenic cells derived from lung tissue is capable of differentiating into an amnion cell lineage. According to one embodiment, the at least one viable population of tissuegenic cells derived from lung tissue is capable of differentiating into an artery cell lineage. According to one embodiment, the at least one viable population of tissuegenic cells derived from lung tissue is capable of differentiating into a bone cell lineage. According to one embodiment, the at least one viable population of tissuegenic cells derived from lung tissue is capable of differentiating into a cartilage cell lineage. According to one embodiment, the at least one viable population of tissuegenic cells derived from lung tissue is capable of differentiating into a chorion cell lineage. According to one embodiment, the at least one viable population of tissuegenic cells derived from lung tissue is capable of differentiating into a colon cell lineage. According to one embodiment, the at least one viable population of tissuegenic cells derived from lung tissue is capable of differentiating into a dental cell lineage. According to one embodiment, the at least one viable population of tissuegenic cells derived from lung tissue is capable of differentiating into a dermal cell lineage. According to one embodiment, the at least one viable population of tissuegenic cells derived from lung tissue is capable of differentiating into a duodenal cell lineage. According to one embodiment, the at least one viable population of tissuegenic cells derived from lung tissue is capable of differentiating into an endothelial cell lineage. According to one embodiment, the at least one viable population of tissuegenic cells derived from lung tissue is capable of differentiating into an epithelial cell lineage. According to one embodiment, the at least one viable population of tissuegenic cells derived from lung tissue is capable of differentiating into a gastrointestinal cell lineage. According to one embodiment, the at least one viable population of tissuegenic cells derived from lung tissue is capable of differentiating into a growth plate cell lineage. According to one embodiment, the at least one viable population of tissuegenic cells derived from lung tissue is capable of differentiating into an intervertebral disc cell lineage. According to one embodiment, the at least one viable population of tissuegenic cells derived from lung tissue is capable of differentiating into an intestinal mucosal cell lineage. According to one embodiment, the at least one viable population of tissuegenic cells derived from lung tissue is capable of differentiating into an intestinal serosal cell lineage. According to one embodiment, the at least one viable population of tissuegenic cells derived from lung tissue is capable of differentiating into a kidney cell lineage. According to one embodiment, the at least one viable population of tissuegenic cells derived from lung tissue is capable of differentiating into a ligament cell lineage. According to one embodiment, the at least one viable population of tissuegenic cells derived from lung tissue is capable of differentiating into a liver cell lineage. According to one embodiment, the at least one viable population of tissuegenic cells derived from lung tissue is capable of differentiating into a lung cell lineage. According to one embodiment, the at least one viable population of tissuegenic cells derived from lung tissue is capable of differentiating into a meniscal cell lineage. According to one embodiment, the at least one viable population of tissuegenic cells derived from lung tissue is capable of differentiating into a muscle cell lineage. According to one embodiment, the at least one viable population of tissuegenic cells derived from lung tissue is capable of differentiating into a nerve cell lineage. According to one embodiment, the at least one viable population of tissuegenic cells derived from lung tissue is capable of differentiating into an ovarian cell lineage. According to one embodiment, the at least one viable population of tissuegenic cells derived from lung tissue is capable of differentiating into a pancreatic cell lineage. According to one embodiment, the at least one viable population of tissuegenic cells derived from lung tissue is capable of differentiating into a parenchymal organ cell lineage. According to one embodiment, the at least one viable population of tissuegenic cells derived from lung tissue is capable of differentiating into a pericardial cell lineage. According to one embodiment, the at least one viable population of tissuegenic cells derived from lung tissue is capable of differentiating into a periosteal cell lineage. According to one embodiment, the at least one viable population of tissuegenic cells is capable of differentiating into a peritoneal cell lineage. According to one embodiment, the at least one viable population of tissuegenic cells derived from lung tissue is capable of differentiating into a skin cell lineage. According to one embodiment, the at least one viable population of tissuegenic cells derived from lung tissue is capable of differentiating into a spleen cell lineage. According to one embodiment, the at least one viable population of tissuegenic cells derived from lung tissue is capable of differentiating into a synovial cell lineage. According to one embodiment, the at least one viable population of tissuegenic cells derived from lung tissue is capable of differentiating into a tendon cell lineage.

According to one embodiment, the at least one viable population of tissuegenic cells derived from lung tissue is capable of differentiating into a testes cell lineage. According to one embodiment, the at least one viable population of tissuegenic cells derived from lung tissue is capable of differentiating into a urological cell lineage. According to one embodiment, the at least one viable population of tissuegenic cells derived from lung tissue is capable of differentiating into a vascular cell lineage. According to one embodiment, the at least one viable population of tissuegenic cells derived from lung tissue is capable of differentiating into a vein cell lineage.

According to one embodiment, the at least one viable population of tissuegenic cells derived from lung tissue can be reprogrammedreprogrammed to at least one viable induced pluripotent stem cell (iPSC) population.

According to one embodiment, the at least one viable population of tissuegenic cells derived from lung tissue differentiates along an osteogenic lineage. According to one embodiment, the at least one viable population of tissuegenic cells derived from lung tissue differentiates along an adipogenic lineage. According to one embodiment, the at least one viable population of tissuegenic cells derived from lung tissue differentiates along a chondrogenic lineage. According to one embodiment, the at least one viable population of tissuegenic cells derived from lung tissue differentiates along a neurogenic lineage.

According to one embodiment, the at least one viable population of tissuegenic cells derived from lung tissue is capable of migrating from or to the at least one growth-conductive matrix. According to one embodiment, the at least one viable population of tissuegenic cells derived from lung tissue comprises a viable nonexpanded population of tissuegenic cells. According to one embodiment, the at least one viable population of tissuegenic cells derived from lung tissue comprises a viable expanded population of tissuegenic cells. According to some embodiments, the at least one viable population of tissuegenic cells derived from lung tissue adherent to and resident in the endogenous milieu of the growth conductive matrix is immune privileged. The term "immune privileged" as used herein refers to the characteristic of tissuegenic cells by which there is no induction of an immune response upon transplantation of such cells.

Tissuegenic Cells Derived from Mammary Tissue

According to one embodiment, the at least one viable population of tissuegenic cells derived from mammary tissue comprises a viable mammary-derived stem cell population. Exemplary tissuegenic cells derived from mammary tissue are listed in LaBarge, 2007, Stem Cell Rev., 3(2): 137-146, the entire contents of which are incorporated herein by reference.

According to one embodiment, the at least one viable population of tissuegenic cells from mammary tissue secretes at least one growth-inductive factor.

According to one embodiment, the at least one viable population of tissuegenic cells derived from mammary tissue is capable of differentiating into cells of at least one embryonic lineage. According to one embodiment, the embryonic lineage is selected from the group consisting of an ectodermal lineage, a mesodermal lineage and an endodermal lineage. According to one embodiment, the at least one viable population of tissuegenic cells derived from mammary tissue is capable of differentiating into cells of an ectodermal lineage. According to one embodiment, the at least one viable population of tissuegenic cells derived from mammary tissue is capable of differentiating into cells of a mesodermal lineage. According to one embodiment, the at least one viable population of tissuegenic cells derived from mammary tissue is capable of differentiating into cells of an endodermal lineage.

According to one embodiment, the at least one viable population of tissuegenic cells derived from mammary tissue is capable of regenerating a target tissue. According to one embodiment, the target tissue is selected from the group consisting of an adipose tissue, an amnion tissue, an artery tissue, a bone tissue, a cartilage tissue, a chorion tissue, a colon tissue, a dental tissue, a dermal tissue, a duodenal tissue, an endothelial tissue, an epithelial tissue, a gastrointestinal tissue, a growth plate tissue, an intervertebral disc tissue, an intestinal mucosal tissue, an intestinal serosal tissue, a kidney tissue, a ligament tissue, a liver tissue, a lung tissue, a meniscal tissue, a muscle tissue, a nerve tissue, an ovarian tissue, a pancreatic tissue, a parenchymal organ tissue, a pericardial tissue, a periosteal tissue, a peritoneal tissue, a skin tissue, a spleen tissue, a synovial tissue, a tendon tissue, a testes tissue, a urological tissue, a vascular tissue, a vein tissue, and a combination thereof.

According to one embodiment, the at least one viable population of tissuegenic cells derived from mammary tissue is capable of regenerating an adipose tissue. According to one embodiment, the at least one viable population of tissuegenic cells derived from mammary tissue is capable of regenerating an amnion tissue. According to one embodiment, the at least one viable population of tissuegenic cells derived from mammary tissue is capable of regenerating an artery tissue. According to one embodiment, the at least one viable population of tissuegenic cells derived from mammary tissue is capable of regenerating a bone tissue. According to one embodiment, the at least one viable population of tissuegenic cells derived from mammary tissue is capable of regenerating a cartilage tissue. According to one embodiment, the at least one viable population of tissuegenic cells derived from mammary tissue is capable of regenerating a chorion tissue. According to one embodiment, the at least one viable population of tissuegenic cells derived from mammary tissue is capable of regenerating a colon tissue. According to one embodiment, the at least one viable population of tissuegenic cells derived from mammary tissue is capable of regenerating a dental tissue. According to one embodiment, the at least one viable population of tissuegenic cells derived from mammary tissue is capable of regenerating a dermal tissue. According to one embodiment, the at least one viable population of tissuegenic cells derived from mammary tissue is capable of regenerating a duodenal tissue. According to one embodiment, the at least one viable population of tissuegenic cells derived from mammary tissue is capable of regenerating an endothelial tissue. According to one embodiment, the at least one viable population of tissuegenic cells derived from mammary tissue is capable of regenerating a gastrointestinal tissue. According to one embodiment, the at least one viable population of tissuegenic cells derived from mammary tissue is capable of regenerating a growth plate tissue. According to one embodiment, the at least one viable population of tissuegenic cells derived from mammary tissue is is capable of regenerating an intervertebral disc tissue. According to one embodiment, the at least one viable population of tissuegenic cells derived from mammary tissue is is capable of regenerating an intestinal mucosal tissue. According to one embodiment, the at least one viable population of tissuegenic cells derived from mammary tissue is is capable of regenerating an intestinal serosal tissue. According to one embodiment, the at least one viable population of tissuegenic cells derived from mammary tissue is is capable of regenerating a kidney tissue. According to one embodiment, the at least one viable population of tissuegenic cells derived from mammary tissue is capable of regenerating a ligament tissue. According to one embodiment, the at least one viable population of tissuegenic cells derived from mammary tissue is capable of regenerating a liver tissue. According to one embodiment, the at least one viable population of tissuegenic cells derived from mammary tissue is capable of regenerating a lung tissue. According to one embodiment, the at least one viable population of tissuegenic cells derived from mammary tissue is capable of regenerating a meniscal tissue. According to one embodiment, the at least one viable population of tissuegenic cells derived from mammary tissue is capable of regenerating a muscle tissue. According to one embodiment, the at least one viable population of tissuegenic cells derived from mammary tissue is capable of regenerating a nerve tissue. According to one embodiment, the at least one viable population of tissuegenic cells derived from mammary tissue is capable of regenerating an ovarian tissue. According to one embodiment, the at least one viable population of tissuegenic cells derived from mammary tissue is capable of regenerating a pancreatic tissue. According to one embodiment, the at least one viable population of tissuegenic cells derived from mammary tissue is capable of regenerating a parenchymal organ tissue. According to one embodiment, the at least one viable population of tissuegenic cells derived from mammary tissue is capable of regenerating a pericardial tissue. According to one embodiment, the at least one viable population of tissuegenic cells derived from mammary tissue is capable of regenerating a periosteal tissue. According to one embodiment, the at least one viable population of tissuegenic cells derived from mammary tissue is capable of regenerating a peritoneal tissue. According to one embodiment, the at least one viable population of tissuegenic cells derived from mammary tissue is capable of regenerating a skin tissue. According to one embodiment, the at least one viable population of tissuegenic cells derived from mammary tissue is capable of regenerating a spleen tissue. According to one embodiment, the at least one viable population of tissuegenic cells derived from mammary tissue is capable of regenerating a synovial tissue. According to one embodiment, the at least one viable population of tissuegenic cells derived from mammary tissue is capable of regenerating a tendon tissue. According to one embodiment, the at least one viable population of tissuegenic cells derived from mammary tissue is capable of regenerating a testes tissue. According to one embodiment, the at least one viable population of tissuegenic cells derived from mammary tissue is capable of regenerating a urological tissue. According to one embodiment, the at least one viable population of tissuegenic cells derived from mammary tissue is capable of regenerating a vascular tissue. According to one embodiment, the at least one viable population of tissuegenic cells derived from mammary tissue is capable of regenerating a vein tissue.

According to one embodiment, the at least one viable population of tissuegenic cells derived from mammary tissue is capable of differentiating into a target tissue cell lineage. According to one embodiment, the target tissue cell lineage is selected from the group consisting of an adipose cell lineage, an amnion cell lineage, an artery cell lineage, a bone cell lineage, a cartilage cell lineage, a dental cell lineage, a dermal cell lineage, a duodenal cell lineage, an endothelial cell lineage, an epithelial cell lineage, a gastrointestinal cell lineage, a growth plate cell lineage, an intervertebral disc cell lineage, an intestinal mucosal cell lineage, an intestinal serosal cell lineage, a kidney cell lineage, a ligament cell lineage, a liver cell lineage, a lung cell lineage, a meniscal cell lineage, a muscle cell lineage, a nerve cell lineage, an ovarian cell lineage, a pancreatic cell lineage, a parenchymal organ cell lineage, a pericardial cell lineage, a periosteal cell lineage, a peritoneal cell lineage, a skin cell lineage, a spleen cell lineage, a synovial cell lineage, a tendon cell lineage, a testes cell lineage, a urological cell lineage, a vascular cell lineage, a vein cell lineage, and a combination thereof.

According to one embodiment, the at least one viable population of tissuegenic cells derived from mammary tissue is capable of differentiating into an adipose cell lineage. According to one embodiment, the at least one viable population of tissuegenic cells derived from mammary tissue is capable of differentiating into an amnion cell lineage. According to one embodiment, the at least one viable population of tissuegenic cells derived from mammary tissue is capable of differentiating into an artery cell lineage. According to one embodiment, the at least one viable population of tissuegenic cells derived from mammary tissue is capable of differentiating into a bone cell lineage. According to one embodiment, the at least one viable population of tissuegenic cells derived from mammary tissue is capable of differentiating into a cartilage cell lineage. According to one embodiment, the at least one viable population of tissuegenic cells derived from mammary tissue is capable of differentiating into a chorion cell lineage. According to one embodiment, the at least one viable population of tissuegenic cells derived from mammary tissue is capable of differentiating into a colon cell lineage. According to one embodiment, the at least one viable population of tissuegenic cells derived from mammary tissue is capable of differentiating into a dental cell lineage. According to one embodiment, the at least one viable population of tissuegenic cells derived from mammary tissue is capable of differentiating into a dermal cell lineage. According to one embodiment, the at least one viable population of tissuegenic cells derived from mammary tissue is capable of differentiating into a duodenal cell lineage. According to one embodiment, the at least one viable population of tissuegenic cells derived from mammary tissue is capable of differentiating into an endothelial cell lineage. According to one embodiment, the at least one viable population of tissuegenic cells derived from mammary tissue is capable of differentiating into an epithelial cell lineage. According to one embodiment, the at least one viable population of tissuegenic cells derived from mammary tissue is capable of differentiating into a gastrointestinal cell lineage. According to one embodiment, the at least one viable population of tissuegenic cells derived from mammary tissue is capable of differentiating into a growth plate cell lineage. According to one embodiment, the at least one viable population of tissuegenic cells derived from mammary tissue is capable of differentiating into an intervertebral disc cell lineage. According to one embodiment, the at least one viable population of tissuegenic cells derived from mammary tissue is capable of differentiating into an intestinal mucosal cell lineage. According to one embodiment, the at least one viable population of tissuegenic cells derived from mammary tissue is capable of differentiating into an intestinal serosal cell lineage. According to one embodiment, the at least one viable population of tissuegenic cells derived from mammary tissue is capable of differentiating into a kidney cell lineage. According to one embodiment, the at least one viable population of tissuegenic cells derived from mammary tissue is capable of differentiating into a ligament cell lineage. According to one embodiment, the at least one viable population of tissuegenic cells derived from mammary tissue is capable of differentiating into a liver cell lineage. According to one embodiment, the at least one viable population of tissuegenic cells derived from mammary tissue is capable of differentiating into a lung cell lineage. According to one embodiment, the at least one viable population of tissuegenic cells derived from mammary tissue is capable of differentiating into a meniscal cell lineage. According to one embodiment, the at least one viable population of tissuegenic cells derived from mammary tissue is capable of differentiating into a muscle cell lineage. According to one embodiment, the at least one viable population of tissuegenic cells derived from mammary tissue is capable of differentiating into a nerve cell lineage. According to one embodiment, the at least one viable population of tissuegenic cells derived from mammary tissue is capable of differentiating into an ovarian cell lineage. According to one embodiment, the at least one viable population of tissuegenic cells derived from mammary tissue is capable of differentiating into a pancreatic cell lineage. According to one embodiment, the at least one viable population of tissuegenic cells derived from mammary tissue is capable of differentiating into a parenchymal organ cell lineage. According to one embodiment, the at least one viable population of tissuegenic cells derived from mammary tissue is capable of differentiating into a pericardial cell lineage. According to one embodiment, the at least one viable population of tissuegenic cells derived from mammary tissue is capable of differentiating into a periosteal cell lineage. According to one embodiment, the at least one viable population of tissuegenic cells is capable of differentiating into a peritoneal cell lineage. According to one embodiment, the at least one viable population of tissuegenic cells derived from mammary tissue is capable of differentiating into a skin cell lineage. According to one embodiment, the at least one viable population of tissuegenic cells derived from mammary tissue is capable of differentiating into a spleen cell lineage. According to one embodiment, the at least one viable population of tissuegenic cells derived from mammary tissue is capable of differentiating into a synovial cell lineage. According to one embodiment, the at least one viable population of tissuegenic cells derived from mammary tissue is capable of differentiating into a tendon cell lineage. According to one embodiment, the at least one viable population of tissuegenic cells derived from mammary tissue is capable of differentiating into a testes cell lineage. According to one embodiment, the at least one viable population of tissuegenic cells derived from mammary tissue is capable of differentiating into a urological cell lineage. According to one embodiment, the at least one viable population of tissuegenic cells derived from mammary tissue is capable of differentiating into a vascular cell lineage. According to one embodiment, the at least one viable population of tissuegenic cells derived from mammary tissue is capable of differentiating into a vein cell lineage.

According to one embodiment, the at least one viable population of tissuegenic cells derived from mammary tissue can be reprogrammedreprogrammed to at least one viable induced pluripotent stem cell (iPSC) population.

According to one embodiment, the at least one viable population of tissuegenic cells derived from mammary tissue differentiates along an osteogenic lineage. According to one embodiment, the at least one viable population of tissuegenic cells derived from mammary tissue differentiates along an adipogenic lineage. According to one embodiment, the at least one viable population of tissuegenic cells derived from mammary tissue differentiates along a chondrogenic lineage. According to one embodiment, the at least one viable population of tissuegenic cells derived from mammary tissue differentiates along a neurogenic lineage.

According to one embodiment, the at least one viable population of tissuegenic cells derived from mammary tissue is capable of migrating from or to the at least one growth-conductive matrix. According to one embodiment, the at least one viable population of tissuegenic cells derived from mammary tissue comprises a viable nonexpanded population of tissuegenic cells. According to one embodiment, the at least one viable population of tissuegenic cells derived from mammary tissue comprises a viable expanded population of tissuegenic cells. According to some embodiments, the at least one viable population of tissuegenic cells derived from mammary tissue adherent to and resident in the endogenous milieu of the growth conductive matrix is immune privileged. The term "immune privileged" as used herein refers to the characteristic of tissuegenic cells by which there is no induction of an immune response upon transplantation of such cells.

Tissuegenic Cells Derived from Muscle Tissue

According to one embodiment, the at least one viable population of tissuegenic cells derived from muscle tissue is selected from the group consisting of a viable cardiac muscle stem cell population, a viable skeletal muscle stem cell population and a viable smooth muscle stem cell population. According to one embodiment, the at least viable population of tissuegenic cells derived from muscle tissue comprises a viable cardiac muscle stem cell population. According to one embodiment, the at least viable population of tissuegenic cells derived from muscle tissue comprises a viable skeletal muscle stem cell population. According to one embodiment, the at least viable population of tissuegenic cells derived from muscle tissue comprises a viable smooth muscle stem cell population.

According to one embodiment, the at least one viable population of tissuegenic cells from muscle tissue secretes at least one growth-inductive factor.

According to one embodiment, the at least one viable population of tissuegenic cells derived from muscle tissue is capable of differentiating into cells of at least one embryonic lineage. According to one embodiment, the embryonic lineage is selected from the group consisting of an ectodermal lineage, a mesodermal lineage and an endodermal lineage. According to one embodiment, the at least one viable population of tissuegenic cells derived from muscle tissue is capable of differentiating into cells of an ectodermal lineage. According to one embodiment, the at least one viable population of tissuegenic cells derived from muscle tissue is capable of differentiating into cells of a mesodermal lineage. According to one embodiment, the at least one viable population of tissuegenic cells derived from muscle tissue is capable of differentiating into cells of an endodermal lineage. Exemplary target lineages of tissuegenic cells derived from muscle tissue are listed in Xu et al. (2010), Cell Tissue Res., 340: 549-567, the entire contents of which are incorporated herein by reference.

According to one embodiment, the at least one viable population of tissuegenic cells derived from muscle tissue is capable of regenerating a target tissue. According to one embodiment, the target tissue is selected from the group consisting of an adipose tissue, an amnion tissue, an artery tissue, a bone tissue, a cartilage tissue, a chorion tissue, a colon tissue, a dental tissue, a dermal tissue, a duodenal tissue, an endothelial tissue, an epithelial tissue, a gastrointestinal tissue, a growth plate tissue, an intervertebral disc tissue, an intestinal mucosal tissue, an intestinal serosal tissue, a kidney tissue, a ligament tissue, a liver tissue, a lung tissue, a meniscal tissue, a muscle tissue, a nerve tissue, an ovarian tissue, a pancreatic tissue, a parenchymal organ tissue, a pericardial tissue, a periosteal tissue, a peritoneal tissue, a skin tissue, a spleen tissue, a synovial tissue, a tendon tissue, a testes tissue, a urological tissue, a vascular tissue, a vein tissue, and a combination thereof.

According to one embodiment, the at least one viable population of tissuegenic cells derived from muscle tissue is capable of regenerating an adipose tissue. According to one embodiment, the at least one viable population of tissuegenic cells derived from muscle tissue is capable of regenerating an amnion tissue. According to one embodiment, the at least one viable population of tissuegenic cells derived from muscle tissue is capable of regenerating an artery tissue. According to one embodiment, the at least one viable population of tissuegenic cells derived from muscle tissue is capable of regenerating a bone tissue. According to one embodiment, the at least one viable population of tissuegenic cells derived from muscle tissue is capable of regenerating a cartilage tissue. According to one embodiment, the at least one viable population of tissuegenic cells derived from muscle tissue is capable of regenerating a chorion tissue. According to one embodiment, the at least one viable population of tissuegenic cells derived from muscle tissue is capable of regenerating a colon tissue. According to one embodiment, the at least one viable population of tissuegenic cells derived from muscle tissue is capable of regenerating a dental tissue. According to one embodiment, the at least one viable population of tissuegenic cells derived from muscle tissue is capable of regenerating a dermal tissue. According to one embodiment, the at least one viable population of tissuegenic cells derived from muscle tissue is capable of regenerating a duodenal tissue. According to one embodiment, the at least one viable population of tissuegenic cells derived from muscle tissue is capable of regenerating an endothelial tissue. According to one embodiment, the at least one viable population of tissuegenic cells derived from muscle tissue is capable of regenerating a gastrointestinal tissue. According to one embodiment, the at least one viable population of tissuegenic cells derived from muscle tissue is capable of regenerating a growth plate tissue. According to one embodiment, the at least one viable population of tissuegenic cells derived from muscle tissue is is capable of regenerating an intervertebral disc tissue. According to one embodiment, the at least one viable population of tissuegenic cells derived from muscle tissue is is capable of regenerating an intestinal mucosal tissue. According to one embodiment, the at least one viable population of tissuegenic cells derived from muscle tissue is is capable of regenerating an intestinal serosal tissue. According to one embodiment, the at least one viable population of tissuegenic cells derived from muscle tissue is is capable of regenerating a kidney tissue. According to one embodiment, the at least one viable population of tissuegenic cells derived from muscle tissue is capable of regenerating a ligament tissue. According to one embodiment, the at least one viable population of tissuegenic cells derived from muscle tissue is capable of regenerating a liver tissue. According to one embodiment, the at least one viable population of tissuegenic cells derived from muscle tissue is capable of regenerating a lung tissue. According to one embodiment, the at least one viable population of tissuegenic cells derived from muscle tissue is capable of regenerating a meniscal tissue. According to one embodiment, the at least one viable population of tissuegenic cells derived from muscle tissue is capable of regenerating a muscle tissue. According to one embodiment, the at least one viable population of tissuegenic cells derived from muscle tissue is capable of regenerating a nerve tissue. According to one embodiment, the at least one viable population of tissuegenic cells derived from muscle tissue is capable of regenerating an ovarian tissue. According to one embodiment, the at least one viable population of tissuegenic cells derived from muscle tissue is capable of regenerating a pancreatic tissue. According to one embodiment, the at least one viable population of tissuegenic cells derived from muscle tissue is capable of regenerating a parenchymal organ tissue. According to one embodiment, the at least one viable population of tissuegenic cells derived from muscle tissue is capable of regenerating a pericardial tissue. According to one embodiment, the at least one viable population of tissuegenic cells derived from muscle tissue is capable of regenerating a periosteal tissue. According to one embodiment, the at least one viable population of tissuegenic cells derived from muscle tissue is capable of regenerating a peritoneal tissue. According to one embodiment, the at least one viable population of tissuegenic cells derived from muscle tissue is capable of regenerating a skin tissue. According to one embodiment, the at least one viable population of tissuegenic cells derived from muscle tissue is capable of regenerating a spleen tissue. According to one embodiment, the at least one viable population of tissuegenic cells derived from muscle tissue is capable of regenerating a synovial tissue. According to one embodiment, the at least one viable population of tissuegenic cells derived from muscle tissue is capable of regenerating a tendon tissue. According to one embodiment, the at least one viable population of tissuegenic cells derived from muscle tissue is capable of regenerating a testes tissue. According to one embodiment, the at least one viable population of tissuegenic cells derived from muscle tissue is capable of regenerating a urological tissue. According to one embodiment, the at least one viable population of tissuegenic cells derived from muscle tissue is capable of regenerating a vascular tissue. According to one embodiment, the at least one viable population of tissuegenic cells derived from muscle tissue is capable of regenerating a vein tissue.

According to one embodiment, the at least one viable population of tissuegenic cells derived from muscle tissue is capable of differentiating into a target tissue cell lineage. According to one embodiment, the target tissue cell lineage is selected from the group consisting of an adipose cell lineage, an amnion cell lineage, an artery cell lineage, a bone cell lineage, a cartilage cell lineage, a dental cell lineage, a dermal cell lineage, a duodenal cell lineage, an endothelial lineage, an epithelial cell lineage, a gastrointestinal cell lineage, a growth plate cell lineage, an intervertebral disc cell lineage, an intestinal mucosal cell lineage, an intestinal serosal cell lineage, a kidney cell lineage, a ligament cell lineage, a liver cell lineage, a lung cell lineage, a meniscal cell lineage, a muscle cell lineage, a nerve cell lineage, an ovarian cell lineage, a pancreatic cell lineage, a parenchymal organ cell lineage, a pericardial cell lineage, a periosteal cell lineage, a peritoneal cell lineage, a skin cell lineage, a spleen cell lineage, a synovial cell lineage, a tendon cell lineage, a testes cell lineage, a urological cell lineage, a vascular cell lineage, a vein cell lineage, and a combination thereof.

According to one embodiment, the at least one viable population of tissuegenic cells derived from muscle tissue is capable of differentiating into an adipose cell lineage. According to one embodiment, the at least one viable population of tissuegenic cells derived from mammary tissue is capable of differentiating into an amnion cell lineage. According to one embodiment, the at least one viable population of tissuegenic cells derived from muscle tissue is capable of differentiating into an artery cell lineage. According to one embodiment, the at least one viable population of tissuegenic cells derived from muscle tissue is capable of differentiating into a bone cell lineage. According to one embodiment, the at least one viable population of tissuegenic cells derived from muscle tissue is capable of differentiating into a cartilage cell lineage. According to one embodiment, the at least one viable population of tissuegenic cells derived from muscle tissue is capable of differentiating into a chorion cell lineage. According to one embodiment, the at least one viable population of tissuegenic cells derived from muscle tissue is capable of differentiating into a colon cell lineage. According to one embodiment, the at least one viable population of tissuegenic cells derived from muscle tissue is capable of differentiating into a dental cell lineage. According to one embodiment, the at least one viable population of tissuegenic cells derived from muscle tissue is capable of differentiating into a dermal cell lineage. According to one embodiment, the at least one viable population of tissuegenic cells derived from muscle tissue is capable of differentiating into a duodenal cell lineage. According to one embodiment, the at least one viable population of tissuegenic cells derived from muscle tissue is capable of differentiating into an endothelial cell lineage. According to one embodiment, the at least one viable population of tissuegenic cells derived from muscle tissue is capable of differentiating into an epithelial cell lineage. According to one embodiment, the at least one viable population of tissuegenic cells derived from muscle tissue is capable of differentiating into a gastrointestinal cell lineage. According to one embodiment, the at least one viable population of tissuegenic cells derived from muscle tissue is capable of differentiating into a growth plate cell lineage. According to one embodiment, the at least one viable population of tissuegenic cells derived from muscle tissue is capable of differentiating into an intervertebral disc cell lineage. According to one embodiment, the at least one viable population of tissuegenic cells derived from muscle tissue is capable of differentiating into an intestinal mucosal cell lineage. According to one embodiment, the at least one viable population of tissuegenic cells derived from muscle tissue is capable of differentiating into an intestinal serosal cell lineage. According to one embodiment, the at least one viable population of tissuegenic cells derived from muscle tissue is capable of differentiating into a kidney cell lineage. According to one embodiment, the at least one viable population of tissuegenic cells derived from muscle tissue is capable of differentiating into a ligament cell lineage. According to one embodiment, the at least one viable population of tissuegenic cells derived from muscle tissue is capable of differentiating into a liver cell lineage. According to one embodiment, the at least one viable population of tissuegenic cells derived from muscle tissue is capable of differentiating into a lung cell lineage. According to one embodiment, the at least one viable population of tissuegenic cells derived from muscle tissue is capable of differentiating into a meniscal cell lineage. According to one embodiment, the at least one viable population of tissuegenic cells derived from muscle tissue is capable of differentiating into a muscle cell lineage. According to one embodiment, the at least one viable population of tissuegenic cells derived from muscle tissue is capable of differentiating into a nerve cell lineage. According to one embodiment, the at least one viable population of tissuegenic cells derived from muscle tissue is capable of differentiating into an ovarian cell lineage. According to one embodiment, the at least one viable population of tissuegenic cells derived from muscle tissue is capable of differentiating into a pancreatic cell lineage. According to one embodiment, the at least one viable population of tissuegenic cells derived from muscle tissue is capable of differentiating into a parenchymal organ cell lineage. According to one embodiment, the at least one viable population of tissuegenic cells derived from muscle tissue is capable of differentiating into a pericardial cell lineage. According to one embodiment, the at least one viable population of tissuegenic cells derived from muscle tissue is capable of differentiating into a periosteal cell lineage. According to one embodiment, the at least one viable population of tissuegenic cells is capable of differentiating into a peritoneal cell lineage. According to one embodiment, the at least one viable population of tissuegenic cells derived from muscle tissue is capable of differentiating into a skin cell lineage. According to one embodiment, the at least one viable population of tissuegenic cells derived from muscle tissue is capable of differentiating into a spleen cell lineage. According to one embodiment, the at least one viable population of tissuegenic cells derived from muscle tissue is capable of differentiating into a synovial cell lineage. According to one embodiment, the at least one viable population of tissuegenic cells derived from muscle tissue is capable of differentiating into a tendon cell lineage. According to one embodiment, the at least one viable population of tissuegenic cells derived from muscle tissue is capable of differentiating into a testes cell lineage. According to one embodiment, the at least one viable population of tissuegenic cells derived from muscle tissue is capable of differentiating into a urological cell lineage. According to one embodiment, the at least one viable population of tissuegenic cells derived from muscle tissue is capable of differentiating into a vascular cell lineage. According to one embodiment, the at least one viable population of tissuegenic cells derived from muscle tissue is capable of differentiating into a vein cell lineage.

According to one embodiment, the at least one viable population of tissuegenic cells derived from muscle tissue can be reprogrammedreprogrammed to at least one viable induced pluripotent stem cell (iPSC) population.

According to one embodiment, the at least one viable population of tissuegenic cells derived from muscle tissue differentiates along an osteogenic lineage. According to one embodiment, the at least one viable population of tissuegenic cells derived from muscle tissue differentiates along an adipogenic lineage. According to one embodiment, the at least one viable population of tissuegenic cells derived from muscle tissue differentiates along a chondrogenic lineage. According to one embodiment, the at least one viable population of tissuegenic cells derived from muscle tissue differentiates along a neurogenic lineage.

According to one embodiment, the at least one viable population of tissuegenic cells derived from muscle tissue is capable of migrating from or to the at least one growth-conductive matrix. According to one embodiment, the at least one viable population of tissuegenic cells derived from muscle tissue comprises a viable nonexpanded population of tissuegenic cells. According to one embodiment, the at least one viable population of tissuegenic cells derived from muscle tissue comprises a viable expanded population of tissuegenic cells. According to some embodiments, the at least one viable population of tissuegenic cells derived from muscle tissue adherent to and resident in the endogenous milieu of the growth conductive matrix is immune privileged. The term "immune privileged" as used herein refers to the characteristic of tissuegenic cells by which there is no induction of an immune response upon transplantation of such cells.

Tissuegenic Cells Derived from Nerve Tissue

According to one embodiment, the at least one viable population of tissuegenic cells derived from nerve tissue comprises a viable neural stem cell population. Exemplary tissuegenic cells derived from nerve tissue are listed in Alvarez-Buylla and Lim (2004), Neuron, 41: 683-686, the entire contents of which are incorporated herein by reference.

According to one embodiment, the at least one viable population of tissuegenic cells from nerve tissue secretes at least one growth-inductive factor. Exemplary growth factors secreted by tissuegenic cells derived from nerve tissue are listed in Alvarez-Buylla and Lim (2004), Neuron, 41: 683-686, the entire contents of which are incorporated herein by reference.

According to one embodiment, the at least one viable population of tissuegenic cells derived from nerve tissue is capable of differentiating into cells of at least one embryonic lineage. According to one embodiment, the embryonic lineage is selected from the group consisting of an ectodermal lineage, a mesodermal lineage and an endodermal lineage. According to one embodiment, the at least one viable population of tissuegenic cells derived from nerve tissue is capable of differentiating into cells of an ectodermal lineage. According to one embodiment, the at least one viable population of tissuegenic cells derived from nerve tissue is capable of differentiating into cells of a mesodermal lineage. According to one embodiment, the at least one viable population of tissuegenic cells derived from nerve tissue is capable of differentiating into cells of an endodermal lineage. Exemplary target lineages of tissuegenic cells derived from nerve tissue are listed in Xu et al. (2010), Cell Tissue Res., 340: 549-567, the entire contents of which are incorporated herein by reference.

According to one embodiment, the at least one viable population of tissuegenic cells derived from nerve tissue is capable of regenerating a target tissue. According to one embodiment, the target tissue is selected from the group consisting of an adipose tissue, an amnion tissue, an artery tissue, a bone tissue, a cartilage tissue, a chorion tissue, a colon tissue, a dental tissue, a dermal tissue, a duodenal tissue, an endothelial tissue, an epithelial tissue, a gastrointestinal tissue, a growth plate tissue, an intervertebral disc tissue, an intestinal mucosal tissue, an intestinal serosal tissue, a kidney tissue, a ligament tissue, a liver tissue, a lung tissue, a meniscal tissue, a muscle tissue, a nerve tissue, an ovarian tissue, a pancreatic tissue, a parenchymal organ tissue, a pericardial tissue, a periosteal tissue, a peritoneal tissue, a skin tissue, a spleen tissue, a synovial tissue, a tendon tissue, a testes tissue, a urological tissue, a vascular tissue, a vein tissue, and a combination thereof.

According to one embodiment, the at least one viable population of tissuegenic cells derived from nerve tissue is capable of regenerating an adipose tissue. According to one embodiment, the at least one viable population of tissuegenic cells derived from nerve tissue is capable of regenerating an amnion tissue. According to one embodiment, the at least one viable population of tissuegenic cells derived from nerve tissue is capable of regenerating an artery tissue. According to one embodiment, the at least one viable population of tissuegenic cells derived from nerve tissue is capable of regenerating a bone tissue. According to one embodiment, the at least one viable population of tissuegenic cells derived from nerve tissue is capable of regenerating a cartilage tissue. According to one embodiment, the at least one viable population of tissuegenic cells derived from nerve tissue is capable of regenerating a chorion tissue. According to one embodiment, the at least one viable population of tissuegenic cells derived from nerve tissue is capable of regenerating a colon tissue. According to one embodiment, the at least one viable population of tissuegenic cells derived from nerve tissue is capable of regenerating a dental tissue. According to one embodiment, the at least one viable population of tissuegenic cells derived from nerve tissue is capable of regenerating a dermal tissue. According to one embodiment, the at least one viable population of tissuegenic cells derived from nerve tissue is capable of regenerating a duodenal tissue. According to one embodiment, the at least one viable population of tissuegenic cells derived from nerve tissue is capable of regenerating an endothelial tissue. According to one embodiment, the at least one viable population of tissuegenic cells derived from nerve tissue is capable of regenerating a gastrointestinal tissue. According to one embodiment, the at least one viable population of tissuegenic cells derived from nerve tissue is capable of regenerating a growth plate tissue. According to one embodiment, the at least one viable population of tissuegenic cells derived from nerve tissue is is capable of regenerating an intervertebral disc tissue. According to one embodiment, the at least one viable population of tissuegenic cells derived from nerve tissue is is capable of regenerating an intestinal mucosal tissue. According to one embodiment, the at least one viable population of tissuegenic cells derived from nerve tissue is is capable of regenerating an intestinal serosal tissue. According to one embodiment, the at least one viable population of tissuegenic cells derived from nerve tissue is is capable of regenerating a kidney tissue. According to one embodiment, the at least one viable population of tissuegenic cells derived from nerve tissue is capable of regenerating a ligament tissue. According to one embodiment, the at least one viable population of tissuegenic cells derived from nerve tissue is capable of regenerating a liver tissue. According to one embodiment, the at least one viable population of tissuegenic cells derived from nerve tissue is capable of regenerating a lung tissue. According to one embodiment, the at least one viable population of tissuegenic cells derived from nerve tissue is capable of regenerating a meniscal tissue. According to one embodiment, the at least one viable population of tissuegenic cells derived from nerve tissue is capable of regenerating a muscle tissue. According to one embodiment, the at least one viable population of tissuegenic cells derived from nerve tissue is capable of regenerating a nerve tissue. According to one embodiment, the at least one viable population of tissuegenic cells derived from nerve tissue is capable of regenerating an ovarian tissue. According to one embodiment, the at least one viable population of tissuegenic cells derived from nerve tissue is capable of regenerating a pancreatic tissue. According to one embodiment, the at least one viable population of tissuegenic cells derived from nerve tissue is capable of regenerating a parenchymal organ tissue. According to one embodiment, the at least one viable population of tissuegenic cells derived from nerve tissue is capable of regenerating a pericardial tissue. According to one embodiment, the at least one viable population of tissuegenic cells derived from nerve tissue is capable of regenerating a periosteal tissue. According to one embodiment, the at least one viable population of tissuegenic cells derived from nerve tissue is capable of regenerating a peritoneal tissue. According to one embodiment, the at least one viable population of tissuegenic cells derived from nerve tissue is capable of regenerating a skin tissue. According to one embodiment, the at least one viable population of tissuegenic cells derived from nerve tissue is capable of regenerating a spleen tissue. According to one embodiment, the at least one viable population of tissuegenic cells derived from nerve tissue is capable of regenerating a synovial tissue. According to one embodiment, the at least one viable population of tissuegenic cells derived from nerve tissue is capable of regenerating a tendon tissue. According to one embodiment, the at least one viable population of tissuegenic cells derived from nerve tissue is capable of regenerating a testes tissue. According to one embodiment, the at least one viable population of tissuegenic cells derived from nerve tissue is capable of regenerating a urological tissue. According to one embodiment, the at least one viable population of tissuegenic cells derived from nerve tissue is capable of regenerating a vascular tissue. According to one embodiment, the at least one viable population of tissuegenic cells derived from nerve tissue is capable of regenerating a vein tissue.

According to one embodiment, the at least one viable population of tissuegenic cells derived from nerve tissue is capable of differentiating into a target tissue cell lineage. According to one embodiment, the target tissue cell lineage is selected from the group consisting of an adipose cell lineage, an amnion cell lineage, an artery cell lineage, a bone cell lineage, a cartilage cell lineage, a dental cell lineage, a dermal cell lineage, a duodenal cell lineage, an endothelial lineage, an epithelial cell lineage, a gastrointestinal cell lineage, a growth plate cell lineage, an intervertebral disc cell lineage, an intestinal mucosal cell lineage, an intestinal serosal cell lineage, a kidney cell lineage, a ligament cell lineage, a liver cell lineage, a lung cell lineage, a meniscal cell lineage, a muscle cell lineage, a nerve cell lineage, an ovarian cell lineage, a pancreatic cell lineage, a parenchymal organ cell lineage, a pericardial cell lineage, a periosteal cell lineage, a peritoneal cell lineage, a skin cell lineage, a spleen cell lineage, a synovial cell lineage, a tendon cell lineage, a testes cell lineage, a urological cell lineage, a vascular cell lineage, a vein cell lineage, and a combination thereof.

According to one embodiment, the at least one viable population of tissuegenic cells derived from nerve tissue is capable of differentiating into an adipose cell lineage. According to one embodiment, the at least one viable population of tissuegenic cells derived from nerve tissue is capable of differentiating into an amnion cell lineage. According to one embodiment, the at least one viable population of tissuegenic cells derived from nerve tissue is capable of differentiating into an artery cell lineage. According to one embodiment, the at least one viable population of tissuegenic cells derived from nerve tissue is capable of differentiating into a bone cell lineage. According to one embodiment, the at least one viable population of tissuegenic cells derived from nerve tissue is capable of differentiating into a cartilage cell lineage. According to one embodiment, the at least one viable population of tissuegenic cells derived from nerve tissue is capable of differentiating into a chorion cell lineage. According to one embodiment, the at least one viable population of tissuegenic cells derived from nerve tissue is capable of differentiating into a colon cell lineage. According to one embodiment, the at least one viable population of tissuegenic cells derived from nerve tissue is capable of differentiating into a dental cell lineage. According to one embodiment, the at least one viable population of tissuegenic cells derived from nerve tissue is capable of differentiating into a dermal cell lineage. According to one embodiment, the at least one viable population of tissuegenic cells derived from nerve tissue is capable of differentiating into a duodenal cell lineage. According to one embodiment, the at least one viable population of tissuegenic cells derived from nerve tissue is capable of differentiating into an endothelial cell lineage. According to one embodiment, the at least one viable population of tissuegenic cells derived from nerve tissue is capable of differentiating into an epithelial cell lineage. According to one embodiment, the at least one viable population of tissuegenic cells derived from nerve tissue is capable of differentiating into a gastrointestinal cell lineage. According to one embodiment, the at least one viable population of tissuegenic cells derived from nerve tissue is capable of differentiating into a growth plate cell lineage. According to one embodiment, the at least one viable population of tissuegenic cells derived from nerve tissue is capable of differentiating into an intervertebral disc cell lineage. According to one embodiment, the at least one viable population of tissuegenic cells derived from nerve tissue is capable of differentiating into an intestinal mucosal cell lineage. According to one embodiment, the at least one viable population of tissuegenic cells derived from nerve tissue is capable of differentiating into an intestinal serosal cell lineage. According to one embodiment, the at least one viable population of tissuegenic cells derived from nerve tissue is capable of differentiating into a kidney cell lineage. According to one embodiment, the at least one viable population of tissuegenic cells derived from nerve tissue is capable of differentiating into a ligament cell lineage. According to one embodiment, the at least one viable population of tissuegenic cells derived from nerve tissue is capable of differentiating into a liver cell lineage. According to one embodiment, the at least one viable population of tissuegenic cells derived from nerve tissue is capable of differentiating into a lung cell lineage. According to one embodiment, the at least one viable population of tissuegenic cells derived from nerve tissue is capable of differentiating into a meniscal cell lineage. According to one embodiment, the at least one viable population of tissuegenic cells derived from nerve tissue is capable of differentiating into a muscle cell lineage. According to one embodiment, the at least one viable population of tissuegenic cells derived from nerve tissue is capable of differentiating into a nerve cell lineage. According to one embodiment, the at least one viable population of tissuegenic cells derived from nerve tissue is capable of differentiating into an ovarian cell lineage. According to one embodiment, the at least one viable population of tissuegenic cells derived from nerve tissue is capable of differentiating into a pancreatic cell lineage. According to one embodiment, the at least one viable population of tissuegenic cells derived from nerve tissue is capable of differentiating into a parenchymal organ cell lineage. According to one embodiment, the at least one viable population of tissuegenic cells derived from nerve tissue is capable of differentiating into a pericardial cell lineage. According to one embodiment, the at least one viable population of tissuegenic cells derived from nerve tissue is capable of differentiating into a periosteal cell lineage. According to one embodiment, the at least one viable population of tissuegenic cells is capable of differentiating into a peritoneal cell lineage. According to one embodiment, the at least one viable population of tissuegenic cells derived from nerve tissue is capable of differentiating into a skin cell lineage. According to one embodiment, the at least one viable population of tissuegenic cells derived from nerve tissue is capable of differentiating into a spleen cell lineage. According to one embodiment, the at least one viable population of tissuegenic cells derived from nerve tissue is capable of differentiating into a synovial cell lineage. According to one embodiment, the at least one viable population of tissuegenic cells derived from nerve tissue is capable of differentiating into a tendon cell lineage. According to one embodiment, the at least one viable population of tissuegenic cells derived from nerve tissue is capable of differentiating into a testes cell lineage. According to one embodiment, the at least one viable population of tissuegenic cells derived from nerve tissue is capable of differentiating into a urological cell lineage. According to one embodiment, the at least one viable population of tissuegenic cells derived from nerve tissue is capable of differentiating into a vascular cell lineage. According to one embodiment, the at least one viable population of tissuegenic cells derived from nerve tissue is capable of differentiating into a vein cell lineage.

According to one embodiment, the at least one viable population of tissuegenic cells derived from nerve tissue can be reprogrammedreprogrammed to at least one viable induced pluripotent stem cell (iPSC) population.

According to one embodiment, the at least one viable population of tissuegenic cells derived from nerve tissue differentiates along an osteogenic lineage. According to one embodiment, the at least one viable population of tissuegenic cells derived from nerve tissue differentiates along an adipogenic lineage. According to one embodiment, the at least one viable population of tissuegenic cells derived from nerve tissue differentiates along a chondrogenic lineage. According to one embodiment, the at least one viable population of tissuegenic cells derived from nerve tissue differentiates along a neurogenic lineage.

According to one embodiment, the at least one viable population of tissuegenic cells derived from nerve tissue is capable of migrating from or to the at least one growth-conductive matrix. According to one embodiment, the at least one viable population of tissuegenic cells derived from nerve tissue comprises a viable nonexpanded population of tissuegenic cells. According to one embodiment, the at least one viable population of tissuegenic cells derived from nerve tissue comprises a viable expanded population of tissuegenic cells. According to some embodiments, the at least one viable population of tissuegenic cells derived from nerve tissue adherent to and resident in the endogenous milieu of the growth conductive matrix is immune privileged. The term "immune privileged" as used herein refers to the characteristic of tissuegenic cells by which there is no induction of an immune response upon transplantation of such cells.

Tissuegenic Cells Derived from Periosteal Tissue

According to one embodiment, the at least one viable population of tissuegenic cells derived from periosteal tissue comprises a viable periosteum-derived stem cell population. Exemplary tissuegenic cells derived from periosteal tissue are listed in Zhang et al., 2005, J. Musculoskelet. Neuronal. Interact. 5(4): 360-362, the entire contents of which are incorporated herein by reference.

According to one embodiment, the at least one viable population of tissuegenic cells from periosteal tissue secretes at least one growth-inductive factor.

According to one embodiment, the at least one viable population of tissuegenic cells derived from periosteal tissue is capable of differentiating into cells of at least one embryonic lineage. According to one embodiment, the embryonic lineage is selected from the group consisting of an ectodermal lineage, a mesodermal lineage and an endodermal lineage. According to one embodiment, the at least one viable population of tissuegenic cells derived from periosteal tissue is capable of differentiating into cells of an ectodermal lineage. According to one embodiment, the at least one viable population of tissuegenic cells derived from periosteal tissue is capable of differentiating into cells of a mesodermal lineage. According to one embodiment, the at least one viable population of tissuegenic cells derived from periosteal tissue is capable of differentiating into cells of an endodermal lineage.

According to one embodiment, the at least one viable population of tissuegenic cells derived from periosteal tissue is capable of regenerating a target tissue. According to one embodiment, the target tissue is selected from the group consisting of an adipose tissue, an amnion tissue, an artery tissue, a bone tissue, a cartilage tissue, a chorion tissue, a colon tissue, a dental tissue, a dermal tissue, a duodenal tissue, an endothelial tissue, an epithelial tissue, a gastrointestinal tissue, a growth plate tissue, an intervertebral disc tissue, an intestinal mucosal tissue, an intestinal serosal tissue, a kidney tissue, a ligament tissue, a liver tissue, a lung tissue, a meniscal tissue, a muscle tissue, a nerve tissue, an ovarian tissue, a pancreatic tissue, a parenchymal organ tissue, a pericardial tissue, a periosteal tissue, a peritoneal tissue, a skin tissue, a spleen tissue, a synovial tissue, a tendon tissue, a testes tissue, a urological tissue, a vascular tissue, a vein tissue, and a combination thereof.

According to one embodiment, the at least one viable population of tissuegenic cells derived from periosteal tissue is capable of regenerating an adipose tissue. According to one embodiment, the at least one viable population of tissuegenic cells derived from periosteal tissue is capable of regenerating an amnion tissue. According to one embodiment, the at least one viable population of tissuegenic cells derived from periosteal tissue is capable of regenerating an artery tissue. According to one embodiment, the at least one viable population of tissuegenic cells derived from periosteal tissue is capable of regenerating a bone tissue. According to one embodiment, the at least one viable population of tissuegenic cells derived from periosteal tissue is capable of regenerating a cartilage tissue. According to one embodiment, the at least one viable population of tissuegenic cells derived from periosteal tissue is capable of regenerating a chorion tissue. According to one embodiment, the at least one viable population of tissuegenic cells derived from periosteal tissue is capable of regenerating a colon tissue. According to one embodiment, the at least one viable population of tissuegenic cells derived from periosteal tissue is capable of regenerating a dental tissue. According to one embodiment, the at least one viable population of tissuegenic cells derived from periosteal tissue is capable of regenerating a dermal tissue. According to one embodiment, the at least one viable population of tissuegenic cells derived from periosteal tissue is capable of regenerating a duodenal tissue. According to one embodiment, the at least one viable population of tissuegenic cells derived from periosteal tissue is capable of regenerating an endothelial tissue. According to one embodiment, the at least one viable population of tissuegenic cells derived from periosteal tissue is capable of regenerating a gastrointestinal tissue. According to one embodiment, the at least one viable population of tissuegenic cells derived from periosteal tissue is capable of regenerating a growth plate tissue. According to one embodiment, the at least one viable population of tissuegenic cells derived from periosteal tissue is is capable of regenerating an intervertebral disc tissue. According to one embodiment, the at least one viable population of tissuegenic cells derived from periosteal tissue is is capable of regenerating an intestinal mucosal tissue. According to one embodiment, the at least one viable population of tissuegenic cells derived from periosteal tissue is is capable of regenerating an intestinal serosal tissue. According to one embodiment, the at least one viable population of tissuegenic cells derived from periosteal tissue is is capable of regenerating a kidney tissue. According to one embodiment, the at least one viable population of tissuegenic cells derived from periosteal tissue is capable of regenerating a ligament tissue. According to one embodiment, the at least one viable population of tissuegenic cells derived from periosteal tissue is capable of regenerating a liver tissue. According to one embodiment, the at least one viable population of tissuegenic cells derived from periosteal tissue is capable of regenerating a lung tissue. According to one embodiment, the at least one viable population of tissuegenic cells derived from periosteal tissue is capable of regenerating a meniscal tissue. According to one embodiment, the at least one viable population of tissuegenic cells derived from periosteal tissue is capable of regenerating a muscle tissue. According to one embodiment, the at least one viable population of tissuegenic cells derived from periosteal tissue is capable of regenerating a nerve tissue. According to one embodiment, the at least one viable population of tissuegenic cells derived from periosteal tissue is capable of regenerating an ovarian tissue. According to one embodiment, the at least one viable population of tissuegenic cells derived from periosteal tissue is capable of regenerating a pancreatic tissue. According to one embodiment, the at least one viable population of tissuegenic cells derived from periosteal tissue is capable of regenerating a parenchymal organ tissue. According to one embodiment, the at least one viable population of tissuegenic cells derived from periosteal tissue is capable of regenerating a pericardial tissue. According to one embodiment, the at least one viable population of tissuegenic cells derived from periosteal tissue is capable of regenerating a periosteal tissue. According to one embodiment, the at least one viable population of tissuegenic cells derived from periosteal tissue is capable of regenerating a peritoneal tissue. According to one embodiment, the at least one viable population of tissuegenic cells derived from periosteal tissue is capable of regenerating a skin tissue. According to one embodiment, the at least one viable population of tissuegenic cells derived from periosteal tissue is capable of regenerating a spleen tissue. According to one embodiment, the at least one viable population of tissuegenic cells derived from periosteal tissue is capable of regenerating a synovial tissue. According to one embodiment, the at least one viable population of tissuegenic cells derived from periosteal tissue is capable of regenerating a tendon tissue. According to one embodiment, the at least one viable population of tissuegenic cells derived from periosteal tissue is capable of regenerating a testes tissue. According to one embodiment, the at least one viable population of tissuegenic cells derived from periosteal tissue is capable of regenerating a urological tissue. According to one embodiment, the at least one viable population of tissuegenic cells derived from periosteal tissue is capable of regenerating a vascular tissue. According to one embodiment, the at least one viable population of tissuegenic cells derived from periosteal tissue is capable of regenerating a vein tissue.

According to one embodiment, the at least one viable population of tissuegenic cells derived from periosteal tissue is capable of differentiating into a target tissue cell lineage. According to one embodiment, the target tissue cell lineage is selected from the group consisting of an adipose cell lineage, an amnion cell lineage, an artery cell lineage, a bone cell lineage, a cartilage cell lineage, a dental cell lineage, a dermal cell lineage, a duodenal cell lineage, an endothelial lineage, an epithelial cell lineage, a gastrointestinal cell lineage, a growth plate cell lineage, an intervertebral disc cell lineage, an intestinal mucosal cell lineage, an intestinal serosal cell lineage, a kidney cell lineage, a ligament cell lineage, a liver cell lineage, a lung cell lineage, a meniscal cell lineage, a muscle cell lineage, a nerve cell lineage, an ovarian cell lineage, a pancreatic cell lineage, a parenchymal organ cell lineage, a pericardial cell lineage, a periosteal cell lineage, a peritoneal cell lineage, a skin cell lineage, a spleen cell lineage, a synovial cell lineage, a tendon cell lineage, a testes cell lineage, a urological cell lineage, a vascular cell lineage, a vein cell lineage, and a combination thereof.

According to one embodiment, the at least one viable population of tissuegenic cells derived from periosteal tissue is capable of differentiating into an adipose cell lineage. According to one embodiment, the at least one viable population of tissuegenic cells derived from periosteal tissue is capable of differentiating into an amnion cell lineage. According to one embodiment, the at least one viable population of tissuegenic cells derived from periosteal tissue is capable of differentiating into an artery cell lineage. According to one embodiment, the at least one viable population of tissuegenic cells derived from periosteal tissue is capable of differentiating into a bone cell lineage. According to one embodiment, the at least one viable population of tissuegenic cells derived from periosteal tissue is capable of differentiating into a cartilage cell lineage. According to one embodiment, the at least one viable population of tissuegenic cells derived from periosteal tissue is capable of differentiating into a chorion cell lineage. According to one embodiment, the at least one viable population of tissuegenic cells derived from periosteal tissue is capable of differentiating into a colon cell lineage. According to one embodiment, the at least one viable population of tissuegenic cells derived from periosteal tissue is capable of differentiating into a dental cell lineage. According to one embodiment, the at least one viable population of tissuegenic cells derived from periosteal tissue is capable of differentiating into a dermal cell lineage. According to one embodiment, the at least one viable population of tissuegenic cells derived from periosteal tissue is capable of differentiating into a duodenal cell lineage. According to one embodiment, the at least one viable population of tissuegenic cells derived from periosteal tissue is capable of differentiating into an endothelial cell lineage. According to one embodiment, the at least one viable population of tissuegenic cells derived from periosteal tissue is capable of differentiating into an epithelial cell lineage. According to one embodiment, the at least one viable population of tissuegenic cells derived from periosteal tissue is capable of differentiating into a gastrointestinal cell lineage. According to one embodiment, the at least one viable population of tissuegenic cells derived from periosteal tissue is capable of differentiating into a growth plate cell lineage. According to one embodiment, the at least one viable population of tissuegenic cells derived from periosteal tissue is capable of differentiating into an intervertebral disc cell lineage. According to one embodiment, the at least one viable population of tissuegenic cells derived from periosteal tissue is capable of differentiating into an intestinal mucosal cell lineage. According to one embodiment, the at least one viable population of tissuegenic cells derived from periosteal tissue is capable of differentiating into an intestinal serosal cell lineage. According to one embodiment, the at least one viable population of tissuegenic cells derived from periosteal tissue is capable of differentiating into a kidney cell lineage. According to one embodiment, the at least one viable population of tissuegenic cells derived from periosteal tissue is capable of differentiating into a ligament cell lineage. According to one embodiment, the at least one viable population of tissuegenic cells derived from periosteal tissue is capable of differentiating into a liver cell lineage. According to one embodiment, the at least one viable population of tissuegenic cells derived from periosteal tissue is capable of differentiating into a lung cell lineage. According to one embodiment, the at least one viable population of tissuegenic cells derived from periosteal tissue is capable of differentiating into a meniscal cell lineage. According to one embodiment, the at least one viable population of tissuegenic cells derived from periosteal tissue is capable of differentiating into a muscle cell lineage. According to one embodiment, the at least one viable population of tissuegenic cells derived from periosteal tissue is capable of differentiating into a nerve cell lineage. According to one embodiment, the at least one viable population of tissuegenic cells derived from periosteal tissue is capable of differentiating into an ovarian cell lineage. According to one embodiment, the at least one viable population of tissuegenic cells derived from periosteal tissue is capable of differentiating into a pancreatic cell lineage. According to one embodiment, the at least one viable population of tissuegenic cells derived from periosteal tissue is capable of differentiating into a parenchymal organ cell lineage. According to one embodiment, the at least one viable population of tissuegenic cells derived from periosteal tissue is capable of differentiating into a pericardial cell lineage. According to one embodiment, the at least one viable population of tissuegenic cells derived from periosteal tissue is capable of differentiating into a periosteal cell lineage. According to one embodiment, the at least one viable population of tissuegenic cells is capable of differentiating into a peritoneal cell lineage. According to one embodiment, the at least one viable population of tissuegenic cells derived from periosteal tissue is capable of differentiating into a skin cell lineage. According to one embodiment, the at least one viable population of tissuegenic cells derived from periosteal tissue is capable of differentiating into a spleen cell lineage. According to one embodiment, the at least one viable population of tissuegenic cells derived from periosteal tissue is capable of differentiating into a synovial cell lineage. According to one embodiment, the at least one viable population of tissuegenic cells derived from periosteal tissue is capable of differentiating into a tendon cell lineage. According to one embodiment, the at least one viable population of tissuegenic cells derived from periosteal tissue is capable of differentiating into a testes cell lineage. According to one embodiment, the at least one viable population of tissuegenic cells derived from periosteal tissue is capable of differentiating into a urological cell lineage. According to one embodiment, the at least one viable population of tissuegenic cells derived from periosteal tissue is capable of differentiating into a vascular cell lineage. According to one embodiment, the at least one viable population of tissuegenic cells derived from periosteal tissue is capable of differentiating into a vein cell lineage.

According to one embodiment, the at least one viable population of tissuegenic cells derived from periosteal tissue can be reprogrammedreprogrammed to at least one viable induced pluripotent stem cell (iPSC) population.

According to one embodiment, the at least one viable population of tissuegenic cells derived from periosteal tissue differentiates along an osteogenic lineage. According to one embodiment, the at least one viable population of tissuegenic cells derived from periosteal tissue differentiates along an adipogenic lineage. According to one embodiment, the at least one viable population of tissuegenic cells derived from periosteal tissue differentiates along a chondrogenic lineage. According to one embodiment, the at least one viable population of tissuegenic cells derived from periosteal tissue differentiates along a neurogenic lineage.

According to one embodiment, the at least one viable population of tissuegenic cells derived from periosteal tissue is capable of migrating from or to the at least one growth-conductive matrix. According to one embodiment, the at least one viable population of tissuegenic cells derived from periosteal tissue comprises a viable nonexpanded population of tissuegenic cells. According to one embodiment, the at least one viable population of tissuegenic cells derived from periosteal tissue comprises a viable expanded population of tissuegenic cells. According to some embodiments, the at least one viable population of tissuegenic cells derived from periosteal tissue adherent to and resident in the endogenous milieu of the growth conductive matrix is immune privileged. The term "immune privileged" as used herein refers to the characteristic of tissuegenic cells by which there is no induction of an immune response upon transplantation of such cells.

Tissuegenic Cells Derived from Placental Tissue

According to one embodiment, the at least one viable population of tissuegenic cells derived from placental tissue is selected from the group consisting of a viable population of amniotic stem cells, a viable population of pluripotent stem cells, a viable population of amnion-derived mesenchymal stem cells, and a viable population of chorion-derived stem cells. According to one embodiment, the at least one viable population of tissuegenic cells derived from placental tissue is a viable pluripotent stem cell population. According to one embodiment, the at least one viable population of tissuegenic cells derived from placental tissue is a viable amnion-derived mesenchymal stem cell population. According to one embodiment, the at least one viable population of tissuegenic cells derived from placental is a viable chorion-derived mesenchymal stem cell population. Exemplary amnion-derived and chorion-derived stem cells are listed in Wei J. et al., Cell Transplant, 2003, 12: 545-552; Wolbank, S. et al., Tissue Eng, 2007, 13: 1173-1183; Alviano, F. et al., BMC Dev Biol, 2007, 7: 11; Zhao, P. et al, Transplantation, 2005, 79: 528-535, the entire contents of which are incorporated herein by reference.

According to one embodiment, the at least one viable population of tissuegenic cells derived from placental tissue secretes at least one growth-inductive factor.

According to one embodiment, the at least one viable population of tissuegenic cells derived from placental tissue is capable of differentiating into cells of at least one embryonic lineage. According to one embodiment, the embryonic lineage is selected from the group consisting of an ectodermal lineage, a mesodermal lineage and an endodermal lineage. According to one embodiment, the at least one viable population of tissuegenic cells derived from placental tissue is capable of differentiating into cells of an ectodermal lineage. According to one embodiment, the at least one viable population of tissuegenic cells derived from placental tissue is capable of differentiating into cells of a mesodermal lineage. According to one embodiment, the at least one viable population of tissuegenic cells derived from placental tissue is capable of differentiating into cells of an endodermal lineage. Exemplary target lineages generated from tissuegenic cells derived from placental tissue are listed in Int'Anker, P. et al., Stem Cells, 2004, 22: 1338-1345; Portmann-Lanz, C. et al, Am J Obstet Gynecol, 2006, 194: 664-673; Wolbank, S. et al., Tissue Eng, 2007, 13: 1173-1183; Soncini, M. et al., J Tissue Eng Regen Med, 2007, 1:296-305; Alviano, F., BMC Dev Biol, 2007, 7: 11, the entire contents of which are incorporated herein by reference.

According to one embodiment, the at least one viable population of tissuegenic cells derived from placental tissue is capable of regenerating a target tissue. According to one embodiment, the target tissue is selected from the group consisting of an adipose tissue, an amnion tissue, an artery tissue, a bone tissue, a cartilage tissue, a chorion tissue, a colon tissue, a dental tissue, a dermal tissue, a duodenal tissue, an endothelial tissue, an epithelial tissue, a gastrointestinal tissue, a growth plate tissue, an intervertebral disc tissue, an intestinal mucosal tissue, an intestinal serosal tissue, a kidney tissue, a ligament tissue, a liver tissue, a lung tissue, a meniscal tissue, a muscle tissue, a nerve tissue, an ovarian tissue, a pancreatic tissue, a parenchymal organ tissue, a pericardial tissue, a periosteal tissue, a peritoneal tissue, a skin tissue, a spleen tissue, a synovial tissue, a tendon tissue, a testes tissue, a urological tissue, a vascular tissue, a vein tissue, and a combination thereof.

According to one embodiment, the at least one viable population of tissuegenic cells derived from placental tissue is capable of regenerating an adipose tissue. According to one embodiment, the at least one viable population of tissuegenic cells derived from placental tissue is capable of regenerating an amnion tissue. According to one embodiment, the at least one viable population of tissuegenic cells derived from placental tissue is capable of regenerating an artery tissue. According to one embodiment, the at least one viable population of tissuegenic cells derived from placental tissue is capable of regenerating a bone tissue. According to one embodiment, the at least one viable population of tissuegenic cells derived from placental tissue is capable of regenerating a cartilage tissue. According to one embodiment, the at least one viable population of tissuegenic cells derived from placental tissue is capable of regenerating a chorion tissue. According to one embodiment, the at least one viable population of tissuegenic cells derived from placental tissue is capable of regenerating a colon tissue. According to one embodiment, the at least one viable population of tissuegenic cells derived from placental tissue is capable of regenerating a dental tissue. According to one embodiment, the at least one viable population of tissuegenic cells derived from placental tissue is capable of regenerating a dermal tissue. According to one embodiment, the at least one viable population of tissuegenic cells derived from placental tissue is capable of regenerating a duodenal tissue. According to one embodiment, the at least one viable population of tissuegenic cells derived from placental tissue is capable of regenerating an endothelial tissue. According to one embodiment, the at least one viable population of tissuegenic cells derived from placental tissue is capable of regenerating a gastrointestinal tissue. According to one embodiment, the at least one viable population of tissuegenic cells derived from placental tissue is capable of regenerating a growth plate tissue. According to one embodiment, the at least one viable population of tissuegenic cells derived from placental tissue is is capable of regenerating an intervertebral disc tissue. According to one embodiment, the at least one viable population of tissuegenic cells derived from placental tissue is is capable of regenerating an intestinal mucosal tissue. According to one embodiment, the at least one viable population of tissuegenic cells derived from placental tissue is is capable of regenerating an intestinal serosal tissue. According to one embodiment, the at least one viable population of tissuegenic cells derived from placental tissue is is capable of regenerating a kidney tissue. According to one embodiment, the at least one viable population of tissuegenic cells derived from placental tissue is capable of regenerating a ligament tissue. According to one embodiment, the at least one viable population of tissuegenic cells derived from nerve tissue is capable of regenerating a liver tissue. According to one embodiment, the at least one viable population of tissuegenic cells derived from placental tissue is capable of regenerating a lung tissue. According to one embodiment, the at least one viable population of tissuegenic cells derived from placental tissue is capable of regenerating a meniscal tissue. According to one embodiment, the at least one viable population of tissuegenic cells derived from placental tissue is capable of regenerating a muscle tissue. According to one embodiment, the at least one viable population of tissuegenic cells derived from placental tissue is capable of regenerating a nerve tissue. According to one embodiment, the at least one viable population of tissuegenic cells derived from placental tissue is capable of regenerating an ovarian tissue. According to one embodiment, the at least one viable population of tissuegenic cells derived from placental tissue is capable of regenerating a pancreatic tissue. According to one embodiment, the at least one viable population of tissuegenic cells derived from placental tissue is capable of regenerating a parenchymal organ tissue. According to one embodiment, the at least one viable population of tissuegenic cells derived from placental tissue is capable of regenerating a pericardial tissue. According to one embodiment, the at least one viable population of tissuegenic cells derived from placental tissue is capable of regenerating a periosteal tissue. According to one embodiment, the at least one viable population of tissuegenic cells derived from placental tissue is capable of regenerating a peritoneal tissue. According to one embodiment, the at least one viable population of tissuegenic cells derived from placental tissue is capable of regenerating a skin tissue. According to one embodiment, the at least one viable population of tissuegenic cells derived from placental tissue is capable of regenerating a spleen tissue. According to one embodiment, the at least one viable population of tissuegenic cells derived from placental tissue is capable of regenerating a synovial tissue. According to one embodiment, the at least one viable population of tissuegenic cells derived from placental tissue is capable of regenerating a tendon tissue. According to one embodiment, the at least one viable population of tissuegenic cells derived from placental tissue is capable of regenerating a testes tissue. According to one embodiment, the at least one viable population of tissuegenic cells derived from placental tissue is capable of regenerating a urological tissue. According to one embodiment, the at least one viable population of tissuegenic cells derived from placental tissue is capable of regenerating a vascular tissue. According to one embodiment, the at least one viable population of tissuegenic cells derived from placental tissue is capable of regenerating a vein tissue.

According to one embodiment, the at least one viable population of tissuegenic cells derived from placental tissue is capable of differentiating into a target tissue cell lineage. According to one embodiment, the target tissue cell lineage is selected from the group consisting of an adipose cell lineage, an amnion cell lineage, an artery cell lineage, a bone cell lineage, a cartilage cell lineage, a dental cell lineage, a dermal cell lineage, a duodenal cell lineage, an endothelial lineage, an epithelial cell lineage, a gastrointestinal cell lineage, a growth plate cell lineage, an intervertebral disc cell lineage, an intestinal mucosal cell lineage, an intestinal serosal cell lineage, a kidney cell lineage, a ligament cell lineage, a liver cell lineage, a lung cell lineage, a meniscal cell lineage, a muscle cell lineage, a nerve cell lineage, an ovarian cell lineage, a pancreatic cell lineage, a parenchymal organ cell lineage, a pericardial cell lineage, a periosteal cell lineage, a peritoneal cell lineage, a skin cell lineage, a spleen cell lineage, a synovial cell lineage, a tendon cell lineage, a testes cell lineage, a urological cell lineage, a vascular cell lineage, a vein cell lineage, and a combination thereof.

According to one embodiment, the at least one viable population of tissuegenic cells derived from placental tissue is capable of differentiating into an adipose cell lineage. According to one embodiment, the at least one viable population of tissuegenic cells derived from placental tissue is capable of differentiating into an amnion cell lineage. According to one embodiment, the at least one viable population of tissuegenic cells derived from placental tissue is capable of differentiating into an artery cell lineage. According to one embodiment, the at least one viable population of tissuegenic cells derived from placental tissue is capable of differentiating into a bone cell lineage. According to one embodiment, the at least one viable population of tissuegenic cells derived from placental tissue is capable of differentiating into a cartilage cell lineage. According to one embodiment, the at least one viable population of tissuegenic cells derived from placental tissue is capable of differentiating into a chorion cell lineage. According to one embodiment, the at least one viable population of tissuegenic cells derived from placental tissue is capable of differentiating into a colon cell lineage. According to one embodiment, the at least one viable population of tissuegenic cells derived from placental tissue is capable of differentiating into a dental cell lineage. According to one embodiment, the at least one viable population of tissuegenic cells derived from placental tissue is capable of differentiating into a dermal cell lineage. According to one embodiment, the at least one viable population of tissuegenic cells derived from placental tissue is capable of differentiating into a duodenal cell lineage. According to one embodiment, the at least one viable population of tissuegenic cells derived from placental tissue is capable of differentiating into an endothelial cell lineage. According to one embodiment, the at least one viable population of tissuegenic cells derived from placental tissue is capable of differentiating into an epithelial cell lineage. According to one embodiment, the at least one viable population of tissuegenic cells derived from placental tissue is capable of differentiating into a gastrointestinal cell lineage. According to one embodiment, the at least one viable population of tissuegenic cells derived from placental tissue is capable of differentiating into a growth plate cell lineage. According to one embodiment, the at least one viable population of tissuegenic cells derived from placental tissue is capable of differentiating into an intervertebral disc cell lineage. According to one embodiment, the at least one viable population of tissuegenic cells derived from placental tissue is capable of differentiating into an intestinal mucosal cell lineage. According to one embodiment, the at least one viable population of tissuegenic cells derived from placental tissue is capable of differentiating into an intestinal serosal cell lineage. According to one embodiment, the at least one viable population of tissuegenic cells derived from placental tissue is capable of differentiating into a kidney cell lineage.

According to one embodiment, the at least one viable population of tissuegenic cells derived from placental tissue is capable of differentiating into a ligament cell lineage. According to one embodiment, the at least one viable population of tissuegenic cells derived from placental tissue is capable of differentiating into a liver cell lineage. According to one embodiment, the at least one viable population of tissuegenic cells derived from placental tissue is capable of differentiating into a lung cell lineage. According to one embodiment, the at least one viable population of tissuegenic cells derived from placental tissue is capable of differentiating into a meniscal cell lineage. According to one embodiment, the at least one viable population of tissuegenic cells derived from placental tissue is capable of differentiating into a muscle cell lineage. According to one embodiment, the at least one viable population of tissuegenic cells derived from placental tissue is capable of differentiating into a nerve cell lineage. According to one embodiment, the at least one viable population of tissuegenic cells derived from placental tissue is capable of differentiating into an ovarian cell lineage. According to one embodiment, the at least one viable population of tissuegenic cells derived from placental tissue is capable of differentiating into a pancreatic cell lineage. According to one embodiment, the at least one viable population of tissuegenic cells derived from placental tissue is capable of differentiating into a parenchymal organ cell lineage. According to one embodiment, the at least one viable population of tissuegenic cells derived from placental tissue is capable of differentiating into a pericardial cell lineage. According to one embodiment, the at least one viable population of tissuegenic cells derived from placental tissue is capable of differentiating into a periosteal cell lineage. According to one embodiment, the at least one viable population of tissuegenic cells is capable of differentiating into a peritoneal cell lineage. According to one embodiment, the at least one viable population of tissuegenic cells derived from placental tissue is capable of differentiating into a skin cell lineage. According to one embodiment, the at least one viable population of tissuegenic cells derived from placental tissue is capable of differentiating into a spleen cell lineage. According to one embodiment, the at least one viable population of tissuegenic cells derived from placental tissue is capable of differentiating into a synovial cell lineage. According to one embodiment, the at least one viable population of tissuegenic cells derived from placental tissue is capable of differentiating into a tendon cell lineage. According to one embodiment, the at least one viable population of tissuegenic cells derived from placental tissue is capable of differentiating into a testes cell lineage. According to one embodiment, the at least one viable population of tissuegenic cells derived from placental tissue is capable of differentiating into a urological cell lineage. According to one embodiment, the at least one viable population of tissuegenic cells derived from placental tissue is capable of differentiating into a vascular cell lineage. According to one embodiment, the at least one viable population of tissuegenic cells derived from placental tissue is capable of differentiating into a vein cell lineage.

According to one embodiment, the at least one viable population of tissuegenic cells derived from placental tissue can be reprogrammedreprogrammed to at least one viable induced pluripotent stem cell (iPSC) population.

According to one embodiment, the at least one viable population of tissuegenic cells derived from placental tissue differentiates along an osteogenic lineage. According to one embodiment, the at least one viable population of tissuegenic cells derived from placental tissue differentiates along an adipogenic lineage. According to one embodiment, the at least one viable population of tissuegenic cells derived from placental tissue differentiates along a chondrogenic lineage. According to one embodiment, the at least one viable population of tissuegenic cells derived from placental tissue differentiates along a neurogenic lineage.

According to one embodiment, the at least one viable population of tissuegenic cells derived from placental tissue is capable of migrating from or to the at least one growth-conductive matrix. According to one embodiment, the at least one viable population of tissuegenic cells derived from placental tissue comprises a viable nonexpanded population of tissuegenic cells. According to one embodiment, the at least one viable population of tissuegenic cells derived from placental tissue comprises a viable expanded population of tissuegenic cells. According to some embodiments, the at least one viable population of tissuegenic cells derived from placental tissue adherent to and resident in the endogenous milieu of the growth conductive matrix is immune privileged. The term "immune privileged" as used herein refers to the characteristic of tissuegenic cells by which there is no induction of an immune response upon transplantation of such cells.

Tissuegenic Cells Derived from Skin Tissue

According to one embodiment, the at least one viable population of tissuegenic cells derived from skin tissue is selected from the group consisting of a viable population of epidermal stem cells of interfollicular epidermis, a viable population of bulge stem cells, a viable population of epidermal stem cells of a hair follicle, dermis derived muiltipotent cells, dermis derived progenitor cells and dermis derived fibrocytes. According to one embodiment, the at least one viable population of tissuegenic cells derived from skin tissue comprises a viable population of epidermal stem cells of interfollicular epidermis. According to one embodiment, the at least one viable population of tissuegenic cells derived from skin tissue comprises a viable population of bulge stem cells. According to one embodiment, the at least one viable population of tissuegenic cells derived from skin tissue comprises a viable population of epidermal stem cells of a hair follicle. According to one embodiment, the at least one viable population of tissuegenic cells derived from skin tissue comprises a viable population of dermis derived muiltipotent cells. According to one embodiment, the at least one viable population of tissuegenic cells derived from skin tissue comprises a viable population of dermis derived progenitor cells. According to one embodiment, the at least one viable population of tissuegenic cells derived from skin tissue comprises a viable population of dermis derived fibrocytes. Exemplary tissuegenic cells derived from skin tissue are listed in Zouboulis et al., 2008, Exp. Gerontol. 43: 986-997; Blanpain, 2010, Nature, 464: 686-687, the entire contents of which are incorporated herein by reference.

According to one embodiment, the at least one viable population of tissuegenic cells from skin tissue secretes at least one growth-inductive factor. Exemplary growth-inductive factors secreted by tissuegenic cells derived from skin tissue are disclosed in Blanpain and Fuchs, 2009, Nat. Rev. Mol. Cell. Biol., 10(3): 207-217, the entire contents of which are incorporated herein by reference.

According to one embodiment, the at least one viable population of tissuegenic cells derived from skin tissue is capable of differentiating into cells of at least one embryonic lineage. According to one embodiment, the embryonic lineage is selected from the group consisting of an ectodermal lineage, a mesodermal lineage and an endodermal lineage.

According to one embodiment, the at least one viable population of tissuegenic cells derived from skin tissue is capable of differentiating into cells of an ectodermal lineage. According to one embodiment, the at least one viable population of tissuegenic cells derived from skin tissue is capable of differentiating into cells of a mesodermal lineage. According to one embodiment, the at least one viable population of tissuegenic cells derived from skin tissue is capable of differentiating into cells of an endodermal lineage. Exemplary target lineages generated from tissuegenic cells derived from skin tissue are listed in Int'Anker, P. et al., Stem Cells, 2004, 22: 1338-1345; Portmann-Lanz, C. et al, Am J Obstet Gynecol, 2006, 194: 664-673; Wolbank, S. et al., Tissue Eng, 2007, 13: 1173-1183; Soncini, M. et al., J Tissue Eng Regen Med, 2007, 1:296-305; Alviano, F., BMC Dev Biol, 2007, 7: 11, the entire contents of which are incorporated herein by reference.

According to one embodiment, the at least one viable population of tissuegenic cells derived from skin tissue is capable of regenerating a target tissue. According to one embodiment, the target tissue is selected from the group consisting of an adipose tissue, an amnion tissue, an artery tissue, a bone tissue, a cartilage tissue, a chorion tissue, a colon tissue, a dental tissue, a dermal tissue, a duodenal tissue, an endothelial tissue, an epithelial tissue, a gastrointestinal tissue, a growth plate tissue, an intervertebral disc tissue, an intestinal mucosal tissue, an intestinal serosal tissue, a kidney tissue, a ligament tissue, a liver tissue, a lung tissue, a meniscal tissue, a muscle tissue, a nerve tissue, an ovarian tissue, a pancreatic tissue, a parenchymal organ tissue, a pericardial tissue, a periosteal tissue, a peritoneal tissue, a skin tissue, a spleen tissue, a synovial tissue, a tendon tissue, a testes tissue, a urological tissue, a vascular tissue, a vein tissue, and a combination thereof.

According to one embodiment, the at least one viable population of tissuegenic cells derived from skin tissue is capable of regenerating an adipose tissue. According to one embodiment, the at least one viable population of tissuegenic cells derived from skin tissue is capable of regenerating an amnion tissue. According to one embodiment, the at least one viable population of tissuegenic cells derived from skin tissue is capable of regenerating an artery tissue. According to one embodiment, the at least one viable population of tissuegenic cells derived from skin tissue is capable of regenerating a bone tissue. According to one embodiment, the at least one viable population of tissuegenic cells derived from skin tissue is capable of regenerating a cartilage tissue. According to one embodiment, the at least one viable population of tissuegenic cells derived from skin tissue is capable of regenerating a chorion tissue. According to one embodiment, the at least one viable population of tissuegenic cells derived from skin tissue is capable of regenerating a colon tissue. According to one embodiment, the at least one viable population of tissuegenic cells derived from skin tissue is capable of regenerating a dental tissue. According to one embodiment, the at least one viable population of tissuegenic cells derived from skin tissue is capable of regenerating a dermal tissue. According to one embodiment, the at least one viable population of tissuegenic cells derived from skin tissue is capable of regenerating a duodenal tissue. According to one embodiment, the at least one viable population of tissuegenic cells derived from skin tissue is capable of regenerating an endothelial tissue. According to one embodiment, the at least one viable population of tissuegenic cells derived from skin tissue is capable of regenerating a gastrointestinal tissue. According to one embodiment, the at least one viable population of tissuegenic cells derived from skin tissue is capable of regenerating a growth plate tissue. According to one embodiment, the at least one viable population of tissuegenic cells derived from skin tissue is is capable of regenerating an intervertebral disc tissue. According to one embodiment, the at least one viable population of tissuegenic cells derived from skin tissue is is capable of regenerating an intestinal mucosal tissue. According to one embodiment, the at least one viable population of tissuegenic cells derived from skin tissue is is capable of regenerating an intestinal serosal tissue. According to one embodiment, the at least one viable population of tissuegenic cells derived from skin tissue is is capable of regenerating a kidney tissue. According to one embodiment, the at least one viable population of tissuegenic cells derived from skin tissue is capable of regenerating a ligament tissue. According to one embodiment, the at least one viable population of tissuegenic cells derived from skin tissue is capable of regenerating a liver tissue. According to one embodiment, the at least one viable population of tissuegenic cells derived from skin tissue is capable of regenerating a lung tissue. According to one embodiment, the at least one viable population of tissuegenic cells derived from skin tissue is capable of regenerating a meniscal tissue. According to one embodiment, the at least one viable population of tissuegenic cells derived from skin tissue is capable of regenerating a muscle tissue. According to one embodiment, the at least one viable population of tissuegenic cells derived from skin tissue is capable of regenerating a nerve tissue. According to one embodiment, the at least one viable population of tissuegenic cells derived from skin tissue is capable of regenerating an ovarian tissue. According to one embodiment, the at least one viable population of tissuegenic cells derived from skin tissue is capable of regenerating a pancreatic tissue. According to one embodiment, the at least one viable population of tissuegenic cells derived from skin tissue is capable of regenerating a parenchymal organ tissue. According to one embodiment, the at least one viable population of tissuegenic cells derived from skin tissue is capable of regenerating a pericardial tissue. According to one embodiment, the at least one viable population of tissuegenic cells derived from skin tissue is capable of regenerating a periosteal tissue. According to one embodiment, the at least one viable population of tissuegenic cells derived from skin tissue is capable of regenerating a peritoneal tissue. According to one embodiment, the at least one viable population of tissuegenic cells derived from skin tissue is capable of regenerating a skin tissue. According to one embodiment, the at least one viable population of tissuegenic cells derived from skin tissue is capable of regenerating a spleen tissue. According to one embodiment, the at least one viable population of tissuegenic cells derived from skin tissue is capable of regenerating a synovial tissue. According to one embodiment, the at least one viable population of tissuegenic cells derived from skin tissue is capable of regenerating a tendon tissue. According to one embodiment, the at least one viable population of tissuegenic cells derived from skin tissue is capable of regenerating a testes tissue. According to one embodiment, the at least one viable population of tissuegenic cells derived from skin tissue is capable of regenerating a urological tissue. According to one embodiment, the at least one viable population of tissuegenic cells derived from skin tissue is capable of regenerating a vascular tissue. According to one embodiment, the at least one viable population of tissuegenic cells derived from skin tissue is capable of regenerating a vein tissue.

According to one embodiment, the at least one viable population of tissuegenic cells derived from skin tissue is capable of differentiating into a target tissue cell lineage. According to one embodiment, the target tissue cell lineage is selected from the group consisting of an adipose cell lineage, an amnion cell lineage, an artery cell lineage, a bone cell lineage, a cartilage cell lineage, a dental cell lineage, a dermal cell lineage, a duodenal cell lineage, an endothelial lineage, an epithelial cell lineage, a gastrointestinal cell lineage, a growth plate cell lineage, an intervertebral disc cell lineage, an intestinal mucosal cell lineage, an intestinal serosal cell lineage, a kidney cell lineage, a ligament cell lineage, a liver cell lineage, a lung cell lineage, a meniscal cell lineage, a muscle cell lineage, a nerve cell lineage, an ovarian cell lineage, a pancreatic cell lineage, a parenchymal organ cell lineage, a pericardial cell lineage, a periosteal cell lineage, a peritoneal cell lineage, a skin cell lineage, a spleen cell lineage, a synovial cell lineage, a tendon cell lineage, a testes cell lineage, a urological cell lineage, a vascular cell lineage, a vein cell lineage, and a combination thereof.

According to one embodiment, the at least one viable population of tissuegenic cells derived from skin tissue is capable of differentiating into an adipose cell lineage. According to one embodiment, the at least one viable population of tissuegenic cells derived from skin tissue is capable of differentiating into an amnion cell lineage. According to one embodiment, the at least one viable population of tissuegenic cells derived from skin tissue is capable of differentiating into an artery cell lineage. According to one embodiment, the at least one viable population of tissuegenic cells derived from skin tissue is capable of differentiating into a bone cell lineage. According to one embodiment, the at least one viable population of tissuegenic cells derived from skin tissue is capable of differentiating into a cartilage cell lineage. According to one embodiment, the at least one viable population of tissuegenic cells derived from skin tissue is capable of differentiating into a chorion cell lineage. According to one embodiment, the at least one viable population of tissuegenic cells derived from skin tissue is capable of differentiating into a colon cell lineage. According to one embodiment, the at least one viable population of tissuegenic cells derived from skin tissue is capable of differentiating into a dental cell lineage. According to one embodiment, the at least one viable population of tissuegenic cells derived from skin tissue is capable of differentiating into a dermal cell lineage. According to one embodiment, the at least one viable population of tissuegenic cells derived from skin tissue is capable of differentiating into a duodenal cell lineage. According to one embodiment, the at least one viable population of tissuegenic cells derived from skin tissue is capable of differentiating into an endothelial cell lineage. According to one embodiment, the at least one viable population of tissuegenic cells derived from skin tissue is capable of differentiating into an epithelial cell lineage. According to one embodiment, the at least one viable population of tissuegenic cells derived from skin tissue is capable of differentiating into a gastrointestinal cell lineage. According to one embodiment, the at least one viable population of tissuegenic cells derived from skin tissue is capable of differentiating into a growth plate cell lineage. According to one embodiment, the at least one viable population of tissuegenic cells derived from skin tissue is capable of differentiating into an intervertebral disc cell lineage. According to one embodiment, the at least one viable population of tissuegenic cells derived from skin tissue is capable of differentiating into an intestinal mucosal cell lineage. According to one embodiment, the at least one viable population of tissuegenic cells derived from skin tissue is capable of differentiating into an intestinal serosal cell lineage. According to one embodiment, the at least one viable population of tissuegenic cells derived from skin tissue is capable of differentiating into a kidney cell lineage. According to one embodiment, the at least one viable population of tissuegenic cells derived from skin tissue is capable of differentiating into a ligament cell lineage. According to one embodiment, the at least one viable population of tissuegenic cells derived from skin tissue is capable of differentiating into a liver cell lineage. According to one embodiment, the at least one viable population of tissuegenic cells derived from skin tissue is capable of differentiating into a lung cell lineage. According to one embodiment, the at least one viable population of tissuegenic cells derived from skin tissue is capable of differentiating into a meniscal cell lineage. According to one embodiment, the at least one viable population of tissuegenic cells derived from skin tissue is capable of differentiating into a muscle cell lineage. According to one embodiment, the at least one viable population of tissuegenic cells derived from skin tissue is capable of differentiating into a nerve cell lineage. According to one embodiment, the at least one viable population of tissuegenic cells derived from skin tissue is capable of differentiating into an ovarian cell lineage. According to one embodiment, the at least one viable population of tissuegenic cells derived from skin tissue is capable of differentiating into a pancreatic cell lineage. According to one embodiment, the at least one viable population of tissuegenic cells derived from skin tissue is capable of differentiating into a parenchymal organ cell lineage. According to one embodiment, the at least one viable population of tissuegenic cells derived from skin tissue is capable of differentiating into a pericardial cell lineage. According to one embodiment, the at least one viable population of tissuegenic cells derived from skin tissue is capable of differentiating into a periosteal cell lineage. According to one embodiment, the at least one viable population of tissuegenic cells is capable of differentiating into a peritoneal cell lineage. According to one embodiment, the at least one viable population of tissuegenic cells derived from skin tissue is capable of differentiating into a skin cell lineage. According to one embodiment, the at least one viable population of tissuegenic cells derived from skin tissue is capable of differentiating into a spleen cell lineage. According to one embodiment, the at least one viable population of tissuegenic cells derived from skin tissue is capable of differentiating into a synovial cell lineage. According to one embodiment, the at least one viable population of tissuegenic cells derived from skin tissue is capable of differentiating into a tendon cell lineage. According to one embodiment, the at least one viable population of tissuegenic cells derived from skin tissue is capable of differentiating into a testes cell lineage. According to one embodiment, the at least one viable population of tissuegenic cells derived from skin tissue is capable of differentiating into a urological cell lineage. According to one embodiment, the at least one viable population of tissuegenic cells derived from skin tissue is capable of differentiating into a vascular cell lineage. According to one embodiment, the at least one viable population of tissuegenic cells derived from skin tissue is capable of differentiating into a vein cell lineage.

According to one embodiment, the at least one viable population of tissuegenic cells derived from skin tissue can be reprogrammedreprogrammed to at least one viable induced pluripotent stem cell (iPSC) population.

According to one embodiment, the at least one viable population of tissuegenic cells derived from skin tissue differentiates along an osteogenic lineage. According to one embodiment, the at least one viable population of tissuegenic cells derived from skin tissue differentiates along an adipogenic lineage. According to one embodiment, the at least one viable population of tissuegenic cells derived from skin tissue differentiates along a chondrogenic lineage. According to one embodiment, the at least one viable population of tissuegenic cells derived from skin tissue differentiates along a neurogenic lineage.

According to one embodiment, the at least one viable population of tissuegenic cells derived from skin tissue is capable of migrating from or to the at least one growth-conductive matrix. According to one embodiment, the at least one viable population of tissuegenic cells derived from skin tissue comprises a viable nonexpanded population of tissuegenic cells. According to one embodiment, the at least one viable population of tissuegenic cells derived from skin tissue comprises a viable expanded population of tissuegenic cells. According to some embodiments, the at least one viable population of tissuegenic cells derived from skin tissue adherent to and resident in the endogenous milieu of the growth conductive matrix is immune privileged. The term "immune privileged" as used herein refers to the characteristic of tissuegenic cells by which there is no induction of an immune response upon transplantation of such cells.

Tissuegenic Cells Derived from Synovial Tissue

According to one embodiment, the at least one viable population of tissuegenic cells derived from synovial tissue is selected from the group consisting of a viable population of synovial-derived stem cells and synovial-derived progenitor cells. According to one embodiment, the at least one viable population of tissuegenic cells derived from synovial tissue comprises a viable population of synovial-derived stem cells. According to one embodiment, the at least one viable population of tissuegenic cells derived from synovial tissue comprises a viable population of synovial-derived progenitor cells. Exemplary tissuegenic cells derived from synovial tissue are disclosed in Kurth et al., Arthritis Rheum., 2011, 63(5): 1289-1300, the entire contents of which are incorporated herein by reference.

According to one embodiment, the at least one viable population of tissuegenic cells from synovial tissue secretes at least one growth-inductive factor.

According to one embodiment, the at least one viable population of tissuegenic cells derived from synovial tissue is capable of differentiating into cells of at least one embryonic lineage. According to one embodiment, the embryonic lineage is selected from the group consisting of an ectodermal lineage, a mesodermal lineage and an endodermal lineage. According to one embodiment, the at least one viable population of tissuegenic cells derived from synovial tissue is capable of differentiating into cells of an ectodermal lineage. According to one embodiment, the at least one viable population of tissuegenic cells derived from synovial tissue is capable of differentiating into cells of a mesodermal lineage. According to one embodiment, the at least one viable population of tissuegenic cells derived from synovial tissue is capable of differentiating into cells of an endodermal lineage. Exemplary target lineages generated from tissuegenic cells derived from synovial tissue are disclosed in Koga et al., 2008, Cell Tissue Res., 333: 207-215, Miyamoto et al., 2010, Arthritis Res. Ther., 12: R206-218; and Lee et al., 2010, Tissue Engg. A, 16(1): 317-325, the entire contents of which are incorporated herein by reference.

According to one embodiment, the at least one viable population of tissuegenic cells derived from synovial tissue is capable of regenerating a target tissue. According to one embodiment, the target tissue is selected from the group consisting of an adipose tissue, an amnion tissue, an artery tissue, a bone tissue, a cartilage tissue, a chorion tissue, a colon tissue, a dental tissue, a dermal tissue, a duodenal tissue, an endothelial tissue, an epithelial tissue, a gastrointestinal tissue, a growth plate tissue, an intervertebral disc tissue, an intestinal mucosal tissue, an intestinal serosal tissue, a kidney tissue, a ligament tissue, a liver tissue, a lung tissue, a meniscal tissue, a muscle tissue, a nerve tissue, an ovarian tissue, a pancreatic tissue, a parenchymal organ tissue, a pericardial tissue, a periosteal tissue, a peritoneal tissue, a skin tissue, a spleen tissue, a synovial tissue, a tendon tissue, a testes tissue, a urological tissue, a vascular tissue, a vein tissue, and a combination thereof.

According to one embodiment, the at least one viable population of tissuegenic cells derived from synovial tissue is capable of regenerating an adipose tissue. According to one embodiment, the at least one viable population of tissuegenic cells derived from synovial tissue is capable of regenerating an amnion tissue. According to one embodiment, the at least one viable population of tissuegenic cells derived from synovial tissue is capable of regenerating an artery tissue. According to one embodiment, the at least one viable population of tissuegenic cells derived from synovial tissue is capable of regenerating a bone tissue. According to one embodiment, the at least one viable population of tissuegenic cells derived from synovial tissue is capable of regenerating a cartilage tissue. According to one embodiment, the at least one viable population of tissuegenic cells derived from synovial tissue is capable of regenerating a chorion tissue. According to one embodiment, the at least one viable population of tissuegenic cells derived from synovial tissue is capable of regenerating a colon tissue. According to one embodiment, the at least one viable population of tissuegenic cells derived from synovial tissue is capable of regenerating a dental tissue. According to one embodiment, the at least one viable population of tissuegenic cells derived from synovial tissue is capable of regenerating a dermal tissue. According to one embodiment, the at least one viable population of tissuegenic cells derived from synovial tissue is capable of regenerating a duodenal tissue. According to one embodiment, the at least one viable population of tissuegenic cells derived from synovial tissue is capable of regenerating an endothelial tissue. According to one embodiment, the at least one viable population of tissuegenic cells derived from synovial tissue is capable of regenerating a gastrointestinal tissue. According to one embodiment, the at least one viable population of tissuegenic cells derived from synovial tissue is capable of regenerating a growth plate tissue. According to one embodiment, the at least one viable population of tissuegenic cells derived from synovial tissue is is capable of regenerating an intervertebral disc tissue. According to one embodiment, the at least one viable population of tissuegenic cells derived from synovial tissue is is capable of regenerating an intestinal mucosal tissue. According to one embodiment, the at least one viable population of tissuegenic cells derived from synovial tissue is is capable of regenerating an intestinal serosal tissue. According to one embodiment, the at least one viable population of tissuegenic cells derived from synovial tissue is is capable of regenerating a kidney tissue. According to one embodiment, the at least one viable population of tissuegenic cells derived from synovial tissue is capable of regenerating a ligament tissue. According to one embodiment, the at least one viable population of tissuegenic cells derived from synovial tissue is capable of regenerating a liver tissue. According to one embodiment, the at least one viable population of tissuegenic cells derived from synovial tissue is capable of regenerating a lung tissue. According to one embodiment, the at least one viable population of tissuegenic cells derived from synovial tissue is capable of regenerating a meniscal tissue. According to one embodiment, the at least one viable population of tissuegenic cells derived from synovial tissue is capable of regenerating a muscle tissue. According to one embodiment, the at least one viable population of tissuegenic cells derived from synovial tissue is capable of regenerating a nerve tissue. According to one embodiment, the at least one viable population of tissuegenic cells derived from synovial tissue is capable of regenerating an ovarian tissue. According to one embodiment, the at least one viable population of tissuegenic cells derived from synovial tissue is capable of regenerating a pancreatic tissue. According to one embodiment, the at least one viable population of tissuegenic cells derived from synovial tissue is capable of regenerating a parenchymal organ tissue. According to one embodiment, the at least one viable population of tissuegenic cells derived from synovial tissue is capable of regenerating a pericardial tissue. According to one embodiment, the at least one viable population of tissuegenic cells derived from synovial tissue is capable of regenerating a periosteal tissue. According to one embodiment, the at least one viable population of tissuegenic cells derived from synovial tissue is capable of regenerating a peritoneal tissue. According to one embodiment, the at least one viable population of tissuegenic cells derived from synovial tissue is capable of regenerating a skin tissue. According to one embodiment, the at least one viable population of tissuegenic cells derived from synovial tissue is capable of regenerating a spleen tissue. According to one embodiment, the at least one viable population of tissuegenic cells derived from synovial tissue is capable of regenerating a synovial tissue. According to one embodiment, the at least one viable population of tissuegenic cells derived from synovial tissue is capable of regenerating a tendon tissue. According to one embodiment, the at least one viable population of tissuegenic cells derived from synovial tissue is capable of regenerating a testes tissue. According to one embodiment, the at least one viable population of tissuegenic cells derived from synovial tissue is capable of regenerating a urological tissue. According to one embodiment, the at least one viable population of tissuegenic cells derived from synovial tissue is capable of regenerating a vascular tissue. According to one embodiment, the at least one viable population of tissuegenic cells derived from synovial tissue is capable of regenerating a vein tissue.

According to one embodiment, the at least one viable population of tissuegenic cells derived from synovial tissue is capable of differentiating into a target tissue cell lineage. According to one embodiment, the target tissue cell lineage is selected from the group consisting of an adipose cell lineage, an amnion cell lineage, an artery cell lineage, a bone cell lineage, a cartilage cell lineage, a dental cell lineage, a dermal cell lineage, a duodenal cell lineage, an endothelial lineage, an epithelial cell lineage, a gastrointestinal cell lineage, a growth plate cell lineage, an intervertebral disc cell lineage, an intestinal mucosal cell lineage, an intestinal serosal cell lineage, a kidney cell lineage, a ligament cell lineage, a liver cell lineage, a lung cell lineage, a meniscal cell lineage, a muscle cell lineage, a nerve cell lineage, an ovarian cell lineage, a pancreatic cell lineage, a parenchymal organ cell lineage, a pericardial cell lineage, a periosteal cell lineage, a peritoneal cell lineage, a skin cell lineage, a spleen cell lineage, a synovial cell lineage, a tendon cell lineage, a testes cell lineage, a urological cell lineage, a vascular cell lineage, a vein cell lineage, and a combination thereof.

According to one embodiment, the at least one viable population of tissuegenic cells derived from synovial tissue is capable of differentiating into an adipose cell lineage. According to one embodiment, the at least one viable population of tissuegenic cells derived from synovial tissue is capable of differentiating into an amnion cell lineage. According to one embodiment, the at least one viable population of tissuegenic cells derived from synovial tissue is capable of differentiating into an artery cell lineage. According to one embodiment, the at least one viable population of tissuegenic cells derived from synovial tissue is capable of differentiating into a bone cell lineage. According to one embodiment, the at least one viable population of tissuegenic cells derived from synovial tissue is capable of differentiating into a cartilage cell lineage. According to one embodiment, the at least one viable population of tissuegenic cells derived from synovial tissue is capable of differentiating into a chorion cell lineage. According to one embodiment, the at least one viable population of tissuegenic cells derived from synovial tissue is capable of differentiating into a colon cell lineage. According to one embodiment, the at least one viable population of tissuegenic cells derived from synovial tissue is capable of differentiating into a dental cell lineage. According to one embodiment, the at least one viable population of tissuegenic cells derived from synovial tissue is capable of differentiating into a dermal cell lineage. According to one embodiment, the at least one viable population of tissuegenic cells derived from synovial tissue is capable of differentiating into a duodenal cell lineage. According to one embodiment, the at least one viable population of tissuegenic cells derived from synovial tissue is capable of differentiating into an endothelial cell lineage. According to one embodiment, the at least one viable population of tissuegenic cells derived from synovial tissue is capable of differentiating into an epithelial cell lineage. According to one embodiment, the at least one viable population of tissuegenic cells derived from synovial tissue is capable of differentiating into a gastrointestinal cell lineage. According to one embodiment, the at least one viable population of tissuegenic cells derived from synovial tissue is capable of differentiating into a growth plate cell lineage. According to one embodiment, the at least one viable population of tissuegenic cells derived from synovial tissue is capable of differentiating into an intervertebral disc cell lineage. According to one embodiment, the at least one viable population of tissuegenic cells derived from synovial tissue is capable of differentiating into an intestinal mucosal cell lineage. According to one embodiment, the at least one viable population of tissuegenic cells derived from synovial tissue is capable of differentiating into an intestinal serosal cell lineage. According to one embodiment, the at least one viable population of tissuegenic cells derived from synovial tissue is capable of differentiating into a kidney cell lineage. According to one embodiment, the at least one viable population of tissuegenic cells derived from synovial tissue is capable of differentiating into a ligament cell lineage. According to one embodiment, the at least one viable population of tissuegenic cells derived from synovial tissue is capable of differentiating into a liver cell lineage. According to one embodiment, the at least one viable population of tissuegenic cells derived from synovial tissue is capable of differentiating into a lung cell lineage. According to one embodiment, the at least one viable population of tissuegenic cells derived from synovial tissue is capable of differentiating into a meniscal cell lineage. According to one embodiment, the at least one viable population of tissuegenic cells derived from synovial tissue is capable of differentiating into a muscle cell lineage. According to one embodiment, the at least one viable population of tissuegenic cells derived from synovial tissue is capable of differentiating into a nerve cell lineage. According to one embodiment, the at least one viable population of tissuegenic cells derived from synovial tissue is capable of differentiating into an ovarian cell lineage. According to one embodiment, the at least one viable population of tissuegenic cells derived from synovial tissue is capable of differentiating into a pancreatic cell lineage. According to one embodiment, the at least one viable population of tissuegenic cells derived from synovial tissue is capable of differentiating into a parenchymal organ cell lineage. According to one embodiment, the at least one viable population of tissuegenic cells derived from synovial tissue is capable of differentiating into a pericardial cell lineage. According to one embodiment, the at least one viable population of tissuegenic cells derived from synovial tissue is capable of differentiating into a periosteal cell lineage. According to one embodiment, the at least one viable population of tissuegenic cells is capable of differentiating into a peritoneal cell lineage. According to one embodiment, the at least one viable population of tissuegenic cells derived from synovial tissue is capable of differentiating into a skin cell lineage. According to one embodiment, the at least one viable population of tissuegenic cells derived from synovial tissue is capable of differentiating into a spleen cell lineage. According to one embodiment, the at least one viable population of tissuegenic cells derived from synovial tissue is capable of differentiating into a synovial cell lineage. According to one embodiment, the at least one viable population of tissuegenic cells derived from synovial tissue is capable of differentiating into a tendon cell lineage. According to one embodiment, the at least one viable population of tissuegenic cells derived from synovial tissue is capable of differentiating into a testes cell lineage. According to one embodiment, the at least one viable population of tissuegenic cells derived from synovial tissue is capable of differentiating into a urological cell lineage. According to one embodiment, the at least one viable population of tissuegenic cells derived from synovial tissue is capable of differentiating into a vascular cell lineage. According to one embodiment, the at least one viable population of tissuegenic cells derived from synovial tissue is capable of differentiating into a vein cell lineage.

According to one embodiment, the at least one viable population of tissuegenic cells derived from synovial tissue can be reprogrammedreprogrammed to at least one viable induced pluripotent stem cell (iPSC) population.

According to one embodiment, the at least one viable population of tissuegenic cells derived from synovial tissue differentiates along an osteogenic lineage. According to one embodiment, the at least one viable population of tissuegenic cells derived from synovial tissue differentiates along an adipogenic lineage. According to one embodiment, the at least one viable population of tissuegenic cells derived from synovial tissue differentiates along a chondrogenic lineage. According to one embodiment, the at least one viable population of tissuegenic cells derived from synovial tissue differentiates along a neurogenic lineage.

According to one embodiment, the at least one viable population of tissuegenic cells derived from synovial tissue is capable of migrating from or to the at least one growth-conductive matrix. According to one embodiment, the at least one viable population of tissuegenic cells derived from synovial tissue comprises a viable nonexpanded population of tissuegenic cells. According to one embodiment, the at least one viable population of tissuegenic cells derived from synovial tissue comprises a viable expanded population of tissuegenic cells. According to some embodiments, the at least one viable population of tissuegenic cells derived from synovial tissue adherent to and resident in the endogenous milieu of the growth conductive matrix is immune privileged. The term "immune privileged" as used herein refers to the characteristic of tissuegenic cells by which there is no induction of an immune response upon transplantation of such cells.

Tissuegenic Cells Derived from Tendon Tissue

According to one embodiment, the at least one viable population of tissuegenic cells derived from tendon tissue is selected from the group consisting of a viable population of tendon-derived stem cells and tendon derived progenitor cells. According to one embodiment, the at least one viable population of tissuegenic cells derived from tendon tissue comprises a viable population of tendon-derived stem cells. According to one embodiment, the at least one viable population of tissuegenic cells derived from tendon tissue comprises a viable population of tendon-derived progenitor cells. Exemplary tissuegenic cells derived from synovial tissue are disclosed in Bi et al., 2007, Nat. Med., 13(10): 1219-1227, the entire contents of which are incorporated herein by reference.

According to one embodiment, the at least one viable population of tissuegenic cells from tendon tissue secretes at least one growth-inductive factor.

According to one embodiment, the at least one viable population of tissuegenic cells derived from tendon tissue is capable of differentiating into cells of at least one embryonic lineage. According to one embodiment, the embryonic lineage is selected from the group consisting of an ectodermal lineage, a mesodermal lineage and an endodermal lineage. According to one embodiment, the at least one viable population of tissuegenic cells derived from tendon tissue is capable of differentiating into cells of an ectodermal lineage. According to one embodiment, the at least one viable population of tissuegenic cells derived from tendon tissue is capable of differentiating into cells of a mesodermal lineage. According to one embodiment, the at least one viable population of tissuegenic cells derived from tendon tissue is capable of differentiating into cells of an endodermal lineage. Exemplary target lineages generated from tissuegenic cells derived from tendon tissue are disclosed in Koga et al., 2008, Cell Tissue Res., 333: 207-215, Miyamoto et al., 2010, Arthritis Res. Ther., 12: R206-218; and Lee et al., 2010, Tissue Engg. A, 16(1): 317-325, the entire contents of which are incorporated herein by reference.

According to one embodiment, the at least one viable population of tissuegenic cells derived from tendon tissue is capable of regenerating a target tissue. According to one embodiment, the target tissue is selected from the group consisting of an adipose tissue, an amnion tissue, an artery tissue, a bone tissue, a cartilage tissue, a chorion tissue, a colon tissue, a dental tissue, a dermal tissue, a duodenal tissue, an endothelial tissue, an epithelial tissue, a gastrointestinal tissue, a growth plate tissue, an intervertebral disc tissue, an intestinal mucosal tissue, an intestinal serosal tissue, a kidney tissue, a ligament tissue, a liver tissue, a lung tissue, a meniscal tissue, a muscle tissue, a nerve tissue, an ovarian tissue, a pancreatic tissue, a parenchymal organ tissue, a pericardial tissue, a periosteal tissue, a peritoneal tissue, a skin tissue, a spleen tissue, a synovial tissue, a tendon tissue, a testes tissue, a urological tissue, a vascular tissue, a vein tissue, and a combination thereof.

According to one embodiment, the at least one viable population of tissuegenic cells derived from tendon tissue is capable of regenerating an adipose tissue. According to one embodiment, the at least one viable population of tissuegenic cells derived from tendon tissue is capable of regenerating an amnion tissue. According to one embodiment, the at least one viable population of tissuegenic cells derived from tendon tissue is capable of regenerating an artery tissue. According to one embodiment, the at least one viable population of tissuegenic cells derived from tendon tissue is capable of regenerating a bone tissue. According to one embodiment, the at least one viable population of tissuegenic cells derived from tendon tissue is capable of regenerating a cartilage tissue. According to one embodiment, the at least one viable population of tissuegenic cells derived from tendon tissue is capable of regenerating a chorion tissue. According to one embodiment, the at least one viable population of tissuegenic cells derived from tendon tissue is capable of regenerating a colon tissue. According to one embodiment, the at least one viable population of tissuegenic cells derived from tendon tissue is capable of regenerating a dental tissue. According to one embodiment, the at least one viable population of tissuegenic cells derived from tendon tissue is capable of regenerating a dermal tissue. According to one embodiment, the at least one viable population of tissuegenic cells derived from tendon tissue is capable of regenerating a duodenal tissue. According to one embodiment, the at least one viable population of tissuegenic cells derived from tendon tissue is capable of regenerating an endothelial tissue. According to one embodiment, the at least one viable population of tissuegenic cells derived from tendon tissue is capable of regenerating a gastrointestinal tissue. According to one embodiment, the at least one viable population of tissuegenic cells derived from tendon tissue is capable of regenerating a growth plate tissue. According to one embodiment, the at least one viable population of tissuegenic cells derived from tendon tissue is is capable of regenerating an intervertebral disc tissue. According to one embodiment, the at least one viable population of tissuegenic cells derived from tendon tissue is is capable of regenerating an intestinal mucosal tissue. According to one embodiment, the at least one viable population of tissuegenic cells derived from tendon tissue is is capable of regenerating an intestinal serosal tissue. According to one embodiment, the at least one viable population of tissuegenic cells derived from tendon tissue is is capable of regenerating a kidney tissue. According to one embodiment, the at least one viable population of tissuegenic cells derived from tendon tissue is capable of regenerating a ligament tissue. According to one embodiment, the at least one viable population of tissuegenic cells derived from tendon tissue is capable of regenerating a liver tissue. According to one embodiment, the at least one viable population of tissuegenic cells derived from tendon tissue is capable of regenerating a lung tissue. According to one embodiment, the at least one viable population of tissuegenic cells derived from tendon tissue is capable of regenerating a meniscal tissue. According to one embodiment, the at least one viable population of tissuegenic cells derived from tendon tissue is capable of regenerating a muscle tissue. According to one embodiment, the at least one viable population of tissuegenic cells derived from tendon tissue is capable of regenerating a nerve tissue. According to one embodiment, the at least one viable population of tissuegenic cells derived from tendon tissue is capable of regenerating an ovarian tissue. According to one embodiment, the at least one viable population of tissuegenic cells derived from tendon tissue is capable of regenerating a pancreatic tissue. According to one embodiment, the at least one viable population of tissuegenic cells derived from tendon tissue is capable of regenerating a parenchymal organ tissue. According to one embodiment, the at least one viable population of tissuegenic cells derived from tendon tissue is capable of regenerating a pericardial tissue. According to one embodiment, the at least one viable population of tissuegenic cells derived from tendon tissue is capable of regenerating a periosteal tissue. According to one embodiment, the at least one viable population of tissuegenic cells derived from tendon tissue is capable of regenerating a peritoneal tissue. According to one embodiment, the at least one viable population of tissuegenic cells derived from tendon tissue is capable of regenerating a skin tissue. According to one embodiment, the at least one viable population of tissuegenic cells derived from tendon tissue is capable of regenerating a spleen tissue. According to one embodiment, the at least one viable population of tissuegenic cells derived from tendon tissue is capable of regenerating a synovial tissue. According to one embodiment, the at least one viable population of tissuegenic cells derived from tendon tissue is capable of regenerating a tendon tissue. According to one embodiment, the at least one viable population of tissuegenic cells derived from tendon tissue is capable of regenerating a testes tissue. According to one embodiment, the at least one viable population of tissuegenic cells derived from tendon tissue is capable of regenerating a urological tissue. According to one embodiment, the at least one viable population of tissuegenic cells derived from tendon tissue is capable of regenerating a vascular tissue. According to one embodiment, the at least one viable population of tissuegenic cells derived from tendon tissue is capable of regenerating a vein tissue.

According to one embodiment, the at least one viable population of tissuegenic cells derived from tendon tissue is capable of differentiating into a target tissue cell lineage. According to one embodiment, the target tissue cell lineage is selected from the group consisting of an adipose cell lineage, an amnion cell lineage, an artery cell lineage, a bone cell lineage, a cartilage cell lineage, a dental cell lineage, a dermal cell lineage, a duodenal cell lineage, an endothelial lineage, an epithelial cell lineage, a gastrointestinal cell lineage, a growth plate cell lineage, an intervertebral disc cell lineage, an intestinal mucosal cell lineage, an intestinal serosal cell lineage, a kidney cell lineage, a ligament cell lineage, a liver cell lineage, a lung cell lineage, a meniscal cell lineage, a muscle cell lineage, a nerve cell lineage, an ovarian cell lineage, a pancreatic cell lineage, a parenchymal organ cell lineage, a pericardial cell lineage, a periosteal cell lineage, a peritoneal cell lineage, a skin cell lineage, a spleen cell lineage, a synovial cell lineage, a tendon cell lineage, a testes cell lineage, a urological cell lineage, a vascular cell lineage, a vein cell lineage, and a combination thereof.

According to one embodiment, the at least one viable population of tissuegenic cells derived from tendon tissue is capable of differentiating into an adipose cell lineage. According to one embodiment, the at least one viable population of tissuegenic cells derived from tendon tissue is capable of differentiating into an amnion cell lineage. According to one embodiment, the at least one viable population of tissuegenic cells derived from tendon tissue is capable of differentiating into an artery cell lineage. According to one embodiment, the at least one viable population of tissuegenic cells derived from tendon tissue is capable of differentiating into a bone cell lineage. According to one embodiment, the at least one viable population of tissuegenic cells derived from tendon tissue is capable of differentiating into a cartilage cell lineage. According to one embodiment, the at least one viable population of tissuegenic cells derived from tendon tissue is capable of differentiating into a chorion cell lineage. According to one embodiment, the at least one viable population of tissuegenic cells derived from tendon tissue is capable of differentiating into a colon cell lineage. According to one embodiment, the at least one viable population of tissuegenic cells derived from tendon tissue is capable of differentiating into a dental cell lineage. According to one embodiment, the at least one viable population of tissuegenic cells derived from tendon tissue is capable of differentiating into a dermal cell lineage. According to one embodiment, the at least one viable population of tissuegenic cells derived from tendon tissue is capable of differentiating into a duodenal cell lineage. According to one embodiment, the at least one viable population of tissuegenic cells derived from tendon tissue is capable of differentiating into an endothelial cell lineage. According to one embodiment, the at least one viable population of tissuegenic cells derived from tendon tissue is capable of differentiating into an epithelial cell lineage. According to one embodiment, the at least one viable population of tissuegenic cells derived from tendon tissue is capable of differentiating into a gastrointestinal cell lineage. According to one embodiment, the at least one viable population of tissuegenic cells derived from tendon tissue is capable of differentiating into a growth plate cell lineage. According to one embodiment, the at least one viable population of tissuegenic cells derived from tendon tissue is capable of differentiating into an intervertebral disc cell lineage. According to one embodiment, the at least one viable population of tissuegenic cells derived from tendon tissue is capable of differentiating into an intestinal mucosal cell lineage. According to one embodiment, the at least one viable population of tissuegenic cells derived from tendon tissue is capable of differentiating into an intestinal serosal cell lineage. According to one embodiment, the at least one viable population of tissuegenic cells derived from tendon tissue is capable of differentiating into a kidney cell lineage. According to one embodiment, the at least one viable population of tissuegenic cells derived from tendon tissue is capable of differentiating into a ligament cell lineage. According to one embodiment, the at least one viable population of tissuegenic cells derived from tendon tissue is capable of differentiating into a liver cell lineage. According to one embodiment, the at least one viable population of tissuegenic cells derived from tendon tissue is capable of differentiating into a lung cell lineage. According to one embodiment, the at least one viable population of tissuegenic cells derived from tendon tissue is capable of differentiating into a meniscal cell lineage. According to one embodiment, the at least one viable population of tissuegenic cells derived from tendon tissue is capable of differentiating into a muscle cell lineage. According to one embodiment, the at least one viable population of tissuegenic cells derived from tendon tissue is capable of differentiating into a nerve cell lineage. According to one embodiment, the at least one viable population of tissuegenic cells derived from tendon tissue is capable of differentiating into an ovarian cell lineage. According to one embodiment, the at least one viable population of tissuegenic cells derived from tendon tissue is capable of differentiating into a pancreatic cell lineage. According to one embodiment, the at least one viable population of tissuegenic cells derived from tendon tissue is capable of differentiating into a parenchymal organ cell lineage. According to one embodiment, the at least one viable population of tissuegenic cells derived from tendon tissue is capable of differentiating into a pericardial cell lineage. According to one embodiment, the at least one viable population of tissuegenic cells derived from tendon tissue is capable of differentiating into a periosteal cell lineage. According to one embodiment, the at least one viable population of tissuegenic cells is capable of differentiating into a peritoneal cell lineage. According to one embodiment, the at least one viable population of tissuegenic cells derived from tendon tissue is capable of differentiating into a skin cell lineage. According to one embodiment, the at least one viable population of tissuegenic cells derived from tendon tissue is capable of differentiating into a spleen cell lineage. According to one embodiment, the at least one viable population of tissuegenic cells derived from tendon tissue is capable of differentiating into a synovial cell lineage. According to one embodiment, the at least one viable population of tissuegenic cells derived from tendon tissue is capable of differentiating into a tendon cell lineage. According to one embodiment, the at least one viable population of tissuegenic cells derived from tendon tissue is capable of differentiating into a testes cell lineage. According to one embodiment, the at least one viable population of tissuegenic cells derived from tendon tissue is capable of differentiating into a urological cell lineage. According to one embodiment, the at least one viable population of tissuegenic cells derived from tendon tissue is capable of differentiating into a vascular cell lineage. According to one embodiment, the at least one viable population of tissuegenic cells derived from tendon tissue is capable of differentiating into a vein cell lineage.

According to one embodiment, the at least one viable population of tissuegenic cells derived from tendon tissue can be reprogrammedreprogrammed to at least one viable induced pluripotent stem cell (iPSC) population.

According to one embodiment, the at least one viable population of tissuegenic cells derived from tendon tissue differentiates along an osteogenic lineage. According to one embodiment, the at least one viable population of tissuegenic cells derived from tendon tissue differentiates along an adipogenic lineage. According to one embodiment, the at least one viable population of tissuegenic cells derived from tendon tissue differentiates along a chondrogenic lineage. According to one embodiment, the at least one viable population of tissuegenic cells derived from tendon tissue differentiates along a neurogenic lineage.

According to one embodiment, the at least one viable population of tissuegenic cells derived from tendon tissue is capable of migrating from or to the at least one growth-conductive matrix. According to one embodiment, the at least one viable population of tissuegenic cells derived from tendon tissue comprises a viable nonexpanded population of tissuegenic cells. According to one embodiment, the at least one viable population of tissuegenic cells derived from tendon tissue comprises a viable expanded population of tissuegenic cells. According to some embodiments, the at least one viable population of tissuegenic cells derived from tendon tissue adherent to and resident in the endogenous milieu of the growth conductive matrix is immune privileged. The term "immune privileged" as used herein refers to the characteristic of tissuegenic cells by which there is no induction of an immune response upon transplantation of such cells.

Tissuegenic Cells Derived from Umbilical Cord Tissue

According to one embodiment, the at least one viable population of tissuegenic cells derived from umbilical cord tissue is selected from the group consisting of a viable population of umbilical cord-derived hematopoietic stem cells (UC-HS), a viable population of umbilical cord-derived mesenchyma stem cells (UC-MS), and a viable population of umbilical cord-derived Wharton's Jelly stem cells (UC-MM). According to one embodiment, the at least one viable population of tissuegenic cells derived from umbilical cordtissue comprises a viable population of umbilical cord-derived hematopoietic stem cells (UC-HS). According to one embodiment, the at least one viable population of tissuegenic cells derived from umbilical cordtissue comprises a viable population of umbilical cord-derived mesenchyma stem cells (UC-MS). According to one embodiment, the at least one viable population of tissuegenic cells derived from umbilical cordtissue comprises a viable population of umbilical cord-derived Wharton's Jelly stem cells (UC-MM). Exemplary tissuegenic cells derived from umbilical cord tissue are disclosed in Munn, D. et al., Science, 1998, 281: 1191-1193; Munn, D. et al., J Exp Med, 1999, 189: 1363-1372, the entire contents of which are incorporated herein by reference.

According to one embodiment, the at least one viable population of tissuegenic cells from umbilical cord tissue secretes at least one growth-inductive factor. Exemplary growth-inductive factors secreted by tissuegenic cells derived from umbilical cord tissue are disclosed in Zhang, X et al., Biochem Biophys Res Commun, 2006, 351: 853-859, the entire contents of which are incorporated herein by reference.

According to one embodiment, the at least one viable population of tissuegenic cells derived from umbilical cord tissue is capable of differentiating into cells of at least one embryonic lineage. According to one embodiment, the embryonic lineage is selected from the group consisting of an ectodermal lineage, a mesodermal lineage and an endodermal lineage. According to one embodiment, the at least one viable population of tissuegenic cells derived from umbilical cord tissue is capable of differentiating into cells of an ectodermal lineage. According to one embodiment, the at least one viable population of tissuegenic cells derived from umbilical cord tissue is capable of differentiating into cells of a mesodermal lineage. According to one embodiment, the at least one viable population of tissuegenic cells derived from umbilical cord tissue is capable of differentiating into cells of an endodermal lineage. Exemplary target lineages generated from tissuegenic cells derived from umbilical cord tissue are disclosed in Koga et al., 2008, Cell Tissue Res., 333: 207-215, Miyamoto et al., 2010, Arthritis Res. Ther., 12: R206-218; and Lee et al., 2010, Tissue Engg. A, 16(1): 317-325, the entire contents of which are incorporated herein by reference.

According to one embodiment, the at least one viable population of tissuegenic cells derived from umbilical cord tissue is capable of regenerating a target tissue. According to one embodiment, the target tissue is selected from the group consisting of an adipose tissue, an amnion tissue, an artery tissue, a bone tissue, a cartilage tissue, a chorion tissue, a colon tissue, a dental tissue, a dermal tissue, a duodenal tissue, an endothelial tissue, an epithelial tissue, a gastrointestinal tissue, a growth plate tissue, an intervertebral disc tissue, an intestinal mucosal tissue, an intestinal serosal tissue, a kidney tissue, a ligament tissue, a liver tissue, a lung tissue, a meniscal tissue, a muscle tissue, a nerve tissue, an ovarian tissue, a pancreatic tissue, a parenchymal organ tissue, a pericardial tissue, a periosteal tissue, a peritoneal tissue, a skin tissue, a spleen tissue, a synovial tissue, a tendon tissue, a testes tissue, a urological tissue, a vascular tissue, a vein tissue, and a combination thereof.

According to one embodiment, the at least one viable population of tissuegenic cells derived from umbilical cord tissue is capable of regenerating an adipose tissue. According to one embodiment, the at least one viable population of tissuegenic cells derived from umbilical cord tissue is capable of regenerating an amnion tissue. According to one embodiment, the at least one viable population of tissuegenic cells derived from umbilical cord tissue is capable of regenerating an artery tissue. According to one embodiment, the at least one viable population of tissuegenic cells derived from umbilical cord tissue is capable of regenerating a bone tissue. According to one embodiment, the at least one viable population of tissuegenic cells derived from umbilical cord tissue is capable of regenerating a cartilage tissue. According to one embodiment, the at least one viable population of tissuegenic cells derived from umbilical cord tissue is capable of regenerating a chorion tissue. According to one embodiment, the at least one viable population of tissuegenic cells derived from umbilical cord tissue is capable of regenerating a colon tissue. According to one embodiment, the at least one viable population of tissuegenic cells derived from umbilical cord tissue is capable of regenerating a dental tissue. According to one embodiment, the at least one viable population of tissuegenic cells derived from umbilical cord tissue is capable of regenerating a dermal tissue. According to one embodiment, the at least one viable population of tissuegenic cells derived from umbilical cord tissue is capable of regenerating a duodenal tissue. According to one embodiment, the at least one viable population of tissuegenic cells derived from umbilical cord tissue is capable of regenerating an endothelial tissue. According to one embodiment, the at least one viable population of tissuegenic cells derived from umbilical cord tissue is capable of regenerating a gastrointestinal tissue. According to one embodiment, the at least one viable population of tissuegenic cells derived from umbilical cord tissue is capable of regenerating a growth plate tissue. According to one embodiment, the at least one viable population of tissuegenic cells derived from umbilical cord tissue is is capable of regenerating an intervertebral disc tissue. According to one embodiment, the at least one viable population of tissuegenic cells derived from umbilical cord tissue is is capable of regenerating an intestinal mucosal tissue. According to one embodiment, the at least one viable population of tissuegenic cells derived from umbilical cord tissue is is capable of regenerating an intestinal serosal tissue. According to one embodiment, the at least one viable population of tissuegenic cells derived from umbilical cord tissue is is capable of regenerating a kidney tissue. According to one embodiment, the at least one viable population of tissuegenic cells derived from umbilical cord tissue is capable of regenerating a ligament tissue. According to one embodiment, the at least one viable population of tissuegenic cells derived from umbilical cord tissue is capable of regenerating a liver tissue. According to one embodiment, the at least one viable population of tissuegenic cells derived from umbilical cord tissue is capable of regenerating a lung tissue. According to one embodiment, the at least one viable population of tissuegenic cells derived from umbilical cord tissue is capable of regenerating a meniscal tissue. According to one embodiment, the at least one viable population of tissuegenic cells derived from umbilical cord tissue is capable of regenerating a muscle tissue. According to one embodiment, the at least one viable population of tissuegenic cells derived from umbilical cord tissue is capable of regenerating a nerve tissue. According to one embodiment, the at least one viable population of tissuegenic cells derived from umbilical cord tissue is capable of regenerating an ovarian tissue. According to one embodiment, the at least one viable population of tissuegenic cells derived from umbilical cord tissue is capable of regenerating a pancreatic tissue. According to one embodiment, the at least one viable population of tissuegenic cells derived from umbilical cord tissue is capable of regenerating a parenchymal organ tissue. According to one embodiment, the at least one viable population of tissuegenic cells derived from umbilical cord tissue is capable of regenerating a pericardial tissue. According to one embodiment, the at least one viable population of tissuegenic cells derived from umbilical cord tissue is capable of regenerating a periosteal tissue. According to one embodiment, the at least one viable population of tissuegenic cells derived from umbilical cord tissue is capable of regenerating a peritoneal tissue. According to one embodiment, the at least one viable population of tissuegenic cells derived from umbilical cord tissue is capable of regenerating a skin tissue. According to one embodiment, the at least one viable population of tissuegenic cells derived from umbilical cord tissue is capable of regenerating a spleen tissue. According to one embodiment, the at least one viable population of tissuegenic cells derived from umbilical cord tissue is capable of regenerating a synovial tissue. According to one embodiment, the at least one viable population of tissuegenic cells derived from umbilical cord tissue is capable of regenerating a tendon tissue. According to one embodiment, the at least one viable population of tissuegenic cells derived from umbilical cord tissue is capable of regenerating a testes tissue. According to one embodiment, the at least one viable population of tissuegenic cells derived from umbilical cord tissue is capable of regenerating a urological tissue. According to one embodiment, the at least one viable population of tissuegenic cells derived from umbilical cord tissue is capable of regenerating a vascular tissue. According to one embodiment, the at least one viable population of tissuegenic cells derived from umbilical cord tissue is capable of regenerating a vein tissue.

According to one embodiment, the at least one viable population of tissuegenic cells derived from umbilical cord tissue is capable of differentiating into a target tissue cell lineage. According to one embodiment, the target tissue cell lineage is selected from the group consisting of an adipose cell lineage, an amnion cell lineage, an artery cell lineage, a bone cell lineage, a cartilage cell lineage, a dental cell lineage, a dermal cell lineage, a duodenal cell lineage, an endothelial lineage, an epithelial cell lineage, a gastrointestinal cell lineage, a growth plate cell lineage, an intervertebral disc cell lineage, an intestinal mucosal cell lineage, an intestinal serosal cell lineage, a kidney cell lineage, a ligament cell lineage, a liver cell lineage, a lung cell lineage, a meniscal cell lineage, a muscle cell lineage, a nerve cell lineage, an ovarian cell lineage, a pancreatic cell lineage, a parenchymal organ cell lineage, a pericardial cell lineage, a periosteal cell lineage, a peritoneal cell lineage, a skin cell lineage, a spleen cell lineage, a synovial cell lineage, a tendon cell lineage, a testes cell lineage, a urological cell lineage, a vascular cell lineage, a vein cell lineage, and a combination thereof.

According to one embodiment, the at least one viable population of tissuegenic cells derived from umbilical cord tissue is capable of differentiating into an adipose cell lineage. According to one embodiment, the at least one viable population of tissuegenic cells derived from umbilical cord tissue is capable of differentiating into an amnion cell lineage. According to one embodiment, the at least one viable population of tissuegenic cells derived from umbilical cord tissue is capable of differentiating into an artery cell lineage. According to one embodiment, the at least one viable population of tissuegenic cells derived from umbilical cord tissue is capable of differentiating into a bone cell lineage. According to one embodiment, the at least one viable population of tissuegenic cells derived from umbilical cord tissue is capable of differentiating into a cartilage cell lineage. According to one embodiment, the at least one viable population of tissuegenic cells derived from umbilical cord tissue is capable of differentiating into a chorion cell lineage. According to one embodiment, the at least one viable population of tissuegenic cells derived from umbilical cord tissue is capable of differentiating into a colon cell lineage. According to one embodiment, the at least one viable population of tissuegenic cells derived from umbilical cord tissue is capable of differentiating into a dental cell lineage. According to one embodiment, the at least one viable population of tissuegenic cells derived from umbilical cord tissue is capable of differentiating into a dermal cell lineage. According to one embodiment, the at least one viable population of tissuegenic cells derived from umbilical cord tissue is capable of differentiating into a duodenal cell lineage. According to one embodiment, the at least one viable population of tissuegenic cells derived from umbilical cord tissue is capable of differentiating into an endothelial cell lineage. According to one embodiment, the at least one viable population of tissuegenic cells derived from umbilical cord tissue is capable of differentiating into an epithelial cell lineage. According to one embodiment, the at least one viable population of tissuegenic cells derived from umbilical cord tissue is capable of differentiating into a gastrointestinal cell lineage. According to one embodiment, the at least one viable population of tissuegenic cells derived from umbilical cord tissue is capable of differentiating into a growth plate cell lineage. According to one embodiment, the at least one viable population of tissuegenic cells derived from umbilical cord tissue is capable of differentiating into an intervertebral disc cell lineage. According to one embodiment, the at least one viable population of tissuegenic cells derived from umbilical cord tissue is capable of differentiating into an intestinal mucosal cell lineage. According to one embodiment, the at least one viable population of tissuegenic cells derived from umbilical cord tissue is capable of differentiating into an intestinal serosal cell lineage. According to one embodiment, the at least one viable population of tissuegenic cells derived from umbilical cord tissue is capable of differentiating into a kidney cell lineage. According to one embodiment, the at least one viable population of tissuegenic cells derived from umbilical cord tissue is capable of differentiating into a ligament cell lineage. According to one embodiment, the at least one viable population of tissuegenic cells derived from umbilical cord tissue is capable of differentiating into a liver cell lineage. According to one embodiment, the at least one viable population of tissuegenic cells derived from umbilical cord tissue is capable of differentiating into a lung cell lineage. According to one embodiment, the at least one viable population of tissuegenic cells derived from umbilical cord tissue is capable of differentiating into a meniscal cell lineage. According to one embodiment, the at least one viable population of tissuegenic cells derived from umbilical cord tissue is capable of differentiating into a muscle cell lineage. According to one embodiment, the at least one viable population of tissuegenic cells derived from umbilical cord tissue is capable of differentiating into a nerve cell lineage. According to one embodiment, the at least one viable population of tissuegenic cells derived from umbilical cord tissue is capable of differentiating into an ovarian cell lineage. According to one embodiment, the at least one viable population of tissuegenic cells derived from umbilical cord tissue is capable of differentiating into a pancreatic cell lineage. According to one embodiment, the at least one viable population of tissuegenic cells derived from umbilical cord tissue is capable of differentiating into a parenchymal organ cell lineage. According to one embodiment, the at least one viable population of tissuegenic cells derived from umbilical cord tissue is capable of differentiating into a pericardial cell lineage. According to one embodiment, the at least one viable population of tissuegenic cells derived from umbilical cord tissue is capable of differentiating into a periosteal cell lineage. According to one embodiment, the at least one viable population of tissuegenic cells is capable of differentiating into a peritoneal cell lineage. According to one embodiment, the at least one viable population of tissuegenic cells derived from umbilical cord tissue is capable of differentiating into a skin cell lineage. According to one embodiment, the at least one viable population of tissuegenic cells derived from umbilical cord tissue is capable of differentiating into a spleen cell lineage. According to one embodiment, the at least one viable population of tissuegenic cells derived from umbilical cord tissue is capable of differentiating into a synovial cell lineage. According to one embodiment, the at least one viable population of tissuegenic cells derived from umbilical cord tissue is capable of differentiating into a tendon cell lineage. According to one embodiment, the at least one viable population of tissuegenic cells derived from umbilical cord tissue is capable of differentiating into a testes cell lineage. According to one embodiment, the at least one viable population of tissuegenic cells derived from umbilical cord tissue is capable of differentiating into a urological cell lineage. According to one embodiment, the at least one viable population of tissuegenic cells derived from umbilical cord tissue is capable of differentiating into a vascular cell lineage. According to one embodiment, the at least one viable population of tissuegenic cells derived from umbilical cord tissue is capable of differentiating into a vein cell lineage.

According to one embodiment, the at least one viable population of tissuegenic cells derived from umbilical cord tissue can be reprogrammedreprogrammed to at least one viable induced pluripotent stem cell (iPSC) population.

According to one embodiment, the at least one viable population of tissuegenic cells derived from umbilical cord tissue differentiates along an osteogenic lineage. According to one embodiment, the at least one viable population of tissuegenic cells derived from umbilical cord tissue differentiates along an adipogenic lineage. According to one embodiment, the at least one viable population of tissuegenic cells derived from umbilical cord tissue differentiates along a chondrogenic lineage. According to one embodiment, the at least one viable population of tissuegenic cells derived from umbilical cord tissue differentiates along a neurogenic lineage.

According to one embodiment, the at least one viable population of tissuegenic cells derived from umbilical cord tissue is capable of migrating from or to the at least one growth-conductive matrix. According to one embodiment, the at least one viable population of tissuegenic cells derived from umbilical cord tissue comprises a viable nonexpanded population of tissuegenic cells. According to one embodiment, the at least one viable population of tissuegenic cells derived from umbilical cord tissue comprises a viable expanded population of tissuegenic cells. According to some embodiments, the at least one viable population of tissuegenic cells derived from umbilical cord tissue adherent to and resident in the endogenous milieu of the growth conductive matrix is immune privileged. The term "immune privileged" as used herein refers to the characteristic of tissuegenic cells by which there is no induction of an immune response upon transplantation of such cells.

Tissuegenic Cells Derived from Vascular Tissue

According to one embodiment, the at least one viable population of tissuegenic cells derived from vascular tissue is selected from the group consisting of a viable population of progenitor cells and a viable population of stem cells. According to one embodiment, the at least one viable population of tissuegenic cells derived from vascular tissue comprises a viable population of progenitor cells. According to one embodiment, the at least one viable population of tissuegenic cells derived from vascular tissue comprises a viable population of stem cells. Exemplary tissuegenic cells derived from vascular tissue are disclosed in Tilki et al., 2009, Trends Mol. Med. 15(11): 501-509, the entire contents of which are incorporated herein by reference.

According to one embodiment, the at least one viable population of tissuegenic cells from vascular tissue secretes at least one growth-inductive factor. Exemplary growth-inductive factors secreted by tissuegenic cells derived from vascular tissue are disclosed in Tilki et al., 2009, Trends Mol. Med. 15(11): 501-509, the entire contents of which are incorporated herein by reference.

According to one embodiment, the at least one viable population of tissuegenic cells derived from vascular tissue is capable of differentiating into cells of at least one embryonic lineage. According to one embodiment, the embryonic lineage is selected from the group consisting of an ectodermal lineage, a mesodermal lineage and an endodermal lineage. According to one embodiment, the at least one viable population of tissuegenic cells derived from vascular tissue is capable of differentiating into cells of an ectodermal lineage. According to one embodiment, the at least one viable population of tissuegenic cells derived from vascular tissue is capable of differentiating into cells of a mesodermal lineage. According to one embodiment, the at least one viable population of tissuegenic cells derived from vascular tissue is capable of differentiating into cells of an endodermal lineage. Exemplary target lineages generated from tissuegenic cells derived from vascular tissue are disclosed in Koga et al., 2008, Cell Tissue Res., 333: 207-215, Miyamoto et al., 2010, Arthritis Res. Ther., 12: R206-218; and Lee et al., 2010, Tissue Engg. A, 16(1): 317-325, the entire contents of which are incorporated herein by reference.

According to one embodiment, the at least one viable population of tissuegenic cells derived from vascular tissue is capable of regenerating a target tissue. According to one embodiment, the target tissue is selected from the group consisting of an adipose tissue, an amnion tissue, an artery tissue, a bone tissue, a cartilage tissue, a chorion tissue, a colon tissue, a dental tissue, a dermal tissue, a duodenal tissue, an endothelial tissue, an epithelial tissue, a gastrointestinal tissue, a growth plate tissue, an intervertebral disc tissue, an intestinal mucosal tissue, an intestinal serosal tissue, a kidney tissue, a ligament tissue, a liver tissue, a lung tissue, a meniscal tissue, a muscle tissue, a nerve tissue, an ovarian tissue, a pancreatic tissue, a parenchymal organ tissue, a pericardial tissue, a periosteal tissue, a peritoneal tissue, a skin tissue, a spleen tissue, a synovial tissue, a tendon tissue, a testes tissue, a urological tissue, a vascular tissue, a vein tissue, and a combination thereof.

According to one embodiment, the at least one viable population of tissuegenic cells derived from vascular tissue is capable of regenerating an adipose tissue. According to one embodiment, the at least one viable population of tissuegenic cells derived from vascular tissue is capable of regenerating an amnion tissue. According to one embodiment, the at least one viable population of tissuegenic cells derived from vascular tissue is capable of regenerating an artery tissue. According to one embodiment, the at least one viable population of tissuegenic cells derived from vascular tissue is capable of regenerating a bone tissue. According to one embodiment, the at least one viable population of tissuegenic cells derived from vascular tissue is capable of regenerating a cartilage tissue. According to one embodiment, the at least one viable population of tissuegenic cells derived from vascular tissue is capable of regenerating a chorion tissue. According to one embodiment, the at least one viable population of tissuegenic cells derived from vascular tissue is capable of regenerating a colon tissue. According to one embodiment, the at least one viable population of tissuegenic cells derived from vascular tissue is capable of regenerating a dental tissue. According to one embodiment, the at least one viable population of tissuegenic cells derived from vascular tissue is capable of regenerating a dermal tissue. According to one embodiment, the at least one viable population of tissuegenic cells derived from vascular tissue is capable of regenerating a duodenal tissue. According to one embodiment, the at least one viable population of tissuegenic cells derived from vascular tissue is capable of regenerating an endothelial tissue. According to one embodiment, the at least one viable population of tissuegenic cells derived from vascular tissue is capable of regenerating a gastrointestinal tissue. According to one embodiment, the at least one viable population of tissuegenic cells derived from vascular tissue is capable of regenerating a growth plate tissue. According to one embodiment, the at least one viable population of tissuegenic cells derived from vascular tissue is is capable of regenerating an intervertebral disc tissue. According to one embodiment, the at least one viable population of tissuegenic cells derived from vascular tissue is is capable of regenerating an intestinal mucosal tissue. According to one embodiment, the at least one viable population of tissuegenic cells derived from vascular tissue is is capable of regenerating an intestinal serosal tissue. According to one embodiment, the at least one viable population of tissuegenic cells derived from vascular tissue is is capable of regenerating a kidney tissue. According to one embodiment, the at least one viable population of tissuegenic cells derived from vascular tissue is capable of regenerating a ligament tissue. According to one embodiment, the at least one viable population of tissuegenic cells derived from vascular tissue is capable of regenerating a liver tissue. According to one embodiment, the at least one viable population of tissuegenic cells derived from vascular tissue is capable of regenerating a lung tissue. According to one embodiment, the at least one viable population of tissuegenic cells derived from vascular tissue is capable of regenerating a meniscal tissue. According to one embodiment, the at least one viable population of tissuegenic cells derived from vascular tissue is capable of regenerating a muscle tissue. According to one embodiment, the at least one viable population of tissuegenic cells derived from vascular tissue is capable of regenerating a nerve tissue. According to one embodiment, the at least one viable population of tissuegenic cells derived from vascular tissue is capable of regenerating an ovarian tissue. According to one embodiment, the at least one viable population of tissuegenic cells derived from vascular tissue is capable of regenerating a pancreatic tissue. According to one embodiment, the at least one viable population of tissuegenic cells derived from vascular tissue is capable of regenerating a parenchymal organ tissue. According to one embodiment, the at least one viable population of tissuegenic cells derived from vascular tissue is capable of regenerating a pericardial tissue. According to one embodiment, the at least one viable population of tissuegenic cells derived from vascular tissue is capable of regenerating a periosteal tissue. According to one embodiment, the at least one viable population of tissuegenic cells derived from vascular tissue is capable of regenerating a peritoneal tissue. According to one embodiment, the at least one viable population of tissuegenic cells derived from vascular tissue is capable of regenerating a skin tissue. According to one embodiment, the at least one viable population of tissuegenic cells derived from vascular tissue is capable of regenerating a spleen tissue. According to one embodiment, the at least one viable population of tissuegenic cells derived from vascular tissue is capable of regenerating a synovial tissue. According to one embodiment, the at least one viable population of tissuegenic cells derived from vascular tissue is capable of regenerating a tendon tissue. According to one embodiment, the at least one viable population of tissuegenic cells derived from vascular tissue is capable of regenerating a testes tissue. According to one embodiment, the at least one viable population of tissuegenic cells derived from vascular tissue is capable of regenerating a urological tissue. According to one embodiment, the at least one viable population of tissuegenic cells derived from vascular tissue is capable of regenerating a vascular tissue. According to one embodiment, the at least one viable population of tissuegenic cells derived from vascular tissue is capable of regenerating a vein tissue.

According to one embodiment, the at least one viable population of tissuegenic cells derived from vascular tissue is capable of differentiating into a target tissue cell lineage. According to one embodiment, the target tissue cell lineage is selected from the group consisting of an adipose cell lineage, an amnion cell lineage, an artery cell lineage, a bone cell lineage, a cartilage cell lineage, a dental cell lineage, a dermal cell lineage, a duodenal cell lineage, an endothelial lineage, an epithelial cell lineage, a gastrointestinal cell lineage, a growth plate cell lineage, an intervertebral disc cell lineage, an intestinal mucosal cell lineage, an intestinal serosal cell lineage, a kidney cell lineage, a ligament cell lineage, a liver cell lineage, a lung cell lineage, a meniscal cell lineage, a muscle cell lineage, a nerve cell lineage, an ovarian cell lineage, a pancreatic cell lineage, a parenchymal organ cell lineage, a pericardial cell lineage, a periosteal cell lineage, a peritoneal cell lineage, a skin cell lineage, a spleen cell lineage, a synovial cell lineage, a tendon cell lineage, a testes cell lineage, a urological cell lineage, a vascular cell lineage, a vein cell lineage, and a combination thereof.

According to one embodiment, the at least one viable population of tissuegenic cells derived from vascular tissue is capable of differentiating into an adipose cell lineage. According to one embodiment, the at least one viable population of tissuegenic cells derived from vascular tissue is capable of differentiating into an amnion cell lineage. According to one embodiment, the at least one viable population of tissuegenic cells derived from vascular tissue is capable of differentiating into an artery cell lineage. According to one embodiment, the at least one viable population of tissuegenic cells derived from vascular tissue is capable of differentiating into a bone cell lineage. According to one embodiment, the at least one viable population of tissuegenic cells derived from vascular tissue is capable of differentiating into a cartilage cell lineage. According to one embodiment, the at least one viable population of tissuegenic cells derived from vascular tissue is capable of differentiating into a chorion cell lineage. According to one embodiment, the at least one viable population of tissuegenic cells derived from vascular tissue is capable of differentiating into a colon cell lineage. According to one embodiment, the at least one viable population of tissuegenic cells derived from vascular tissue is capable of differentiating into a dental cell lineage. According to one embodiment, the at least one viable population of tissuegenic cells derived from vascular tissue is capable of differentiating into a dermal cell lineage. According to one embodiment, the at least one viable population of tissuegenic cells derived from vascular tissue is capable of differentiating into a duodenal cell lineage. According to one embodiment, the at least one viable population of tissuegenic cells derived from vascular tissue is capable of differentiating into an endothelial cell lineage. According to one embodiment, the at least one viable population of tissuegenic cells derived from vascular tissue is capable of differentiating into an epithelial cell lineage. According to one embodiment, the at least one viable population of tissuegenic cells derived from vascular tissue is capable of differentiating into a gastrointestinal cell lineage. According to one embodiment, the at least one viable population of tissuegenic cells derived from vascular tissue is capable of differentiating into a growth plate cell lineage. According to one embodiment, the at least one viable population of tissuegenic cells derived from vascular tissue is capable of differentiating into an intervertebral disc cell lineage. According to one embodiment, the at least one viable population of tissuegenic cells derived from vascular tissue is capable of differentiating into an intestinal mucosal cell lineage. According to one embodiment, the at least one viable population of tissuegenic cells derived from vascular tissue is capable of differentiating into an intestinal serosal cell lineage. According to one embodiment, the at least one viable population of tissuegenic cells derived from vascular tissue is capable of differentiating into a kidney cell lineage. According to one embodiment, the at least one viable population of tissuegenic cells derived from vascular tissue is capable of differentiating into a ligament cell lineage. According to one embodiment, the at least one viable population of tissuegenic cells derived from vascular tissue is capable of differentiating into a liver cell lineage. According to one embodiment, the at least one viable population of tissuegenic cells derived from vascular tissue is capable of differentiating into a lung cell lineage. According to one embodiment, the at least one viable population of tissuegenic cells derived from vascular tissue is capable of differentiating into a meniscal cell lineage. According to one embodiment, the at least one viable population of tissuegenic cells derived from vascular tissue is capable of differentiating into a muscle cell lineage. According to one embodiment, the at least one viable population of tissuegenic cells derived from vascular tissue is capable of differentiating into a nerve cell lineage. According to one embodiment, the at least one viable population of tissuegenic cells derived from vascular tissue is capable of differentiating into an ovarian cell lineage. According to one embodiment, the at least one viable population of tissuegenic cells derived from vascular tissue is capable of differentiating into a pancreatic cell lineage. According to one embodiment, the at least one viable population of tissuegenic cells derived from vascular tissue is capable of differentiating into a parenchymal organ cell lineage. According to one embodiment, the at least one viable population of tissuegenic cells derived from vascular tissue is capable of differentiating into a pericardial cell lineage. According to one embodiment, the at least one viable population of tissuegenic cells derived from vascular tissue is capable of differentiating into a periosteal cell lineage. According to one embodiment, the at least one viable population of tissuegenic cells is capable of differentiating into a peritoneal cell lineage. According to one embodiment, the at least one viable population of tissuegenic cells derived from vascular tissue is capable of differentiating into a skin cell lineage. According to one embodiment, the at least one viable population of tissuegenic cells derived from vascular tissue is capable of differentiating into a spleen cell lineage. According to one embodiment, the at least one viable population of tissuegenic cells derived from vascular tissue is capable of differentiating into a synovial cell lineage. According to one embodiment, the at least one viable population of tissuegenic cells derived from vascular tissue is capable of differentiating into a tendon cell lineage. According to one embodiment, the at least one viable population of tissuegenic cells derived from vascular tissue is capable of differentiating into a testes cell lineage. According to one embodiment, the at least one viable population of tissuegenic cells derived from vascular tissue is capable of differentiating into a urological cell lineage. According to one embodiment, the at least one viable population of tissuegenic cells derived from vascular tissue is capable of differentiating into a vascular cell lineage. According to one embodiment, the at least one viable population of tissuegenic cells derived from vascular tissue is capable of differentiating into a vein cell lineage.

According to one embodiment, the at least one viable population of tissuegenic cells derived from vascular tissue can be reprogrammedreprogrammed to at least one viable induced pluripotent stem cell (iPSC) population.

According to one embodiment, the at least one viable population of tissuegenic cells derived from vascular tissue differentiates along an osteogenic lineage. According to one embodiment, the at least one viable population of tissuegenic cells derived from vascular tissue differentiates along an adipogenic lineage. According to one embodiment, the at least one viable population of tissuegenic cells derived from vascular tissue differentiates along a chondrogenic lineage. According to one embodiment, the at least one viable population of tissuegenic cells derived from vascular tissue differentiates along a neurogenic lineage.

According to one embodiment, the at least one viable population of tissuegenic cells derived from vascular tissue is capable of migrating from or to the at least one growth-conductive matrix. According to one embodiment, the at least one viable population of tissuegenic cells derived from vascular tissue comprises a viable nonexpanded population of tissuegenic cells. According to one embodiment, the at least one viable population of tissuegenic cells derived from vascular tissue comprises a viable expanded population of tissuegenic cells. According to some embodiments, the at least one viable population of tissuegenic cells derived from vascular tissue adherent to and resident in the endogenous milieu of the growth conductive matrix is immune privileged. The term "immune privileged" as used herein refers to the characteristic of tissuegenic cells by which there is no induction of an immune response upon transplantation of such cells.

Frequency of Tissuegenic Cells

According to some embodiments, the at least one viable population of tissuegenic cells comprise a relative frequency substantially similar to the total cell population of the growth-conductive matrix. According to some embodiments, the at least one viable population of tissuegenic cells comprise a relative frequency substantially higher than the total cell population of the growth-conductive matrix.

According to some embodiments, the at least one viable population of tissuegenic cells comprise at least about 10% to at least about 95% of the total cell population of the growth-conductive matrix. According to some embodiments, the at least one viable population of tissuegenic cells comprise at least about 10% of the total cell population of the growth-conductive matrix. According to some embodiments, the viable population of tissuegenic cells comprise at least about 15% of the total cell population of the growth-conductive matrix. According to some embodiments, the at least one viable population of tissuegenic cells comprise at least about 20% of the total cell population of the growth-conductive matrix. According to some embodiments, the at least one viable population of tissuegenic cells comprise at least about 25% of the total cell population of the growth-conductive matrix. According to some embodiments, the viable population of tissuegenic cells comprise at least about 30% of the total cell population of the growth-conductive matrix. According to some embodiments, the viable population of tissuegenic cells comprise at least about 35% of the total cell population of the growth-conductive matrix. According to some embodiments, the at least one viable population of tissuegenic cells comprise at least about 40% of the total cell population of the growth-conductive matrix. According to some embodiments, the at least one viable population of tissuegenic cells comprise at least about 45% of the total cell population of the growth-conductive matrix. According to some embodiments, the at least one viable population of tissuegenic cells comprise at least about 50% of the total cell population of the growth-conductive matrix. According to some embodiments, the at least one viable population of tissuegenic cells comprise at least about 55% of the total cell population of the growth-conductive matrix. According to some embodiments, the at least one viable population of tissuegenic cells comprise at least about 60% of the total cell population of the growth-conductive matrix. According to some embodiments, the at least one viable population of tissuegenic cells comprise at least about 65% of the total cell population of the growth-conductive matrix. According to some embodiments, the at least one viable population of tissuegenic cells comprise at least about 70% of the total cell population of the growth-conductive matrix. According to some embodiments, the at least one viable population of tissuegenic cells comprise at least about 75% of the total cell population of the growth-conductive matrix. According to some embodiments, the at least one viable population of tissuegenic cells comprise at least about 80% of the total cell population of the growth-conductive matrix. According to some embodiments, the at least one viable population of tissuegenic cells comprise at least about 85% of the total cell population of the growth-conductive matrix. According to some embodiments, the at least one viable population of tissuegenic cells comprise at least about 90% of the total cell population of the growth-conductive matrix. According to some embodiments, the at least one viable population of tissuegenic cells comprise at least about 95% of the total cell population of the growth-conductive matrix.

According to some embodiments, the at least one viable population of tissuegenic cells comprise at least about at least about 10,000 tissuegenic cells per cc of implant. According to some embodiments, the at least one viable population of tissuegenic cells comprise at least about at least about 20,000 tissuegenic cells per cc of implant. According to some embodiments, the at least one viable population of tissuegenic cells comprise at least about at least about 30,000 tissuegenic cells per cc of implant. According to some embodiments, the at least one viable population of tissuegenic cells comprise at least about at least about 40,000 tissuegenic cells per cc of implant. According to some embodiments, the at least one viable population of tissuegenic cells comprise at least about at least about 50,000 tissuegenic cells per cc of implant.

Growth-Inductive Component

According to some embodiments, the implant further comprises at least one growth-inductive component. According to some such embodiments, the growth-inductive component is at least one cytokine. According to some such embodiments, the at least one growth-inductive component comprises at least one growth factor. According to some such embodiments, the at least one growth factor is fibroblast growth factor-2 (FGF-2). According to some such embodiments, the at least one growth factor is fibroblast growth factor-5 (FGF-5). According to some such embodiments, the at least one growth factor is insulin-like growth factor-1 (IGF-1). According to some such embodiments, the at least one growth factor is transdermal growth factor-beta (TGF-β). According to some such embodiments, the at least one growth factor is bone morphogenic protein-2 (BMP-2). According to some such embodiments, the at least one growth factor is bone morphogenic protein-7 (BMP-7). According to some such embodiments, the at least one growth factor is platelet derived growth factor (PDGF). According to some such embodiments, the at least one growth factor is vascular endothelial growth factor (VEGF). According to some such embodiments, the at least one growth factor is neural epidermal growth-factor-like 1 (NELL-1).

According to some such embodiments, the at least one growth-inductive component is a demineralized bone matrix (DBM). According to some such embodiments, the DCB is demineralized autologous bone. According to some such embodiments, the DBM is demineralized allogeneic bone. According to some such embodiments, the DBM is demineralized xenogeneic bone. According to some such embodiments, the DBM is derived by demineralization of cancellous bone. According to some such embodiments the DBM is derived by demineralization of cortical bone (i.e., demineralized cortical bone or DCB). According to some such embodiments, DBM has a residual mineral content of 8% or less (w/w). According to some such embodiments, DBM has a residual mineral content of 5% or less (w/w). According to some such embodiments, DBM has a residual mineral content of 2% or less (w/w). According to some such embodiments, DBM has a residual mineral content of 1% or less (w/w). According to some such embodiments, DBM has a residual mineral content of 0.5% or less (w/w). According to some such embodiments, DBM consists essentially of collagen, non-collagen proteins such as growth factors, and other nonmineral substances found in the original bone, although not necessarily in the original quantities.

According to some such embodiments, the at least one growth-inductive component comprises at least one carrier. According to some such embodiments, the carrier comprises an isotonic solution. According to some such embodiments, the carrier comprises a sodium chloride solution. According to some such embodiments, the sodium chloride solution is at a concentration of about 0.1% to about 1%. According to some such embodiments, the sodium chloride solution is at a concentration of about 0.9%. According to some such embodiments, the carrier comprises a lactated Ringer's solution. According to some such embodiments, the carrier comprises PBS. According to some such embodiments, the carrier comprises platelet rich plasma (PRP). According to some such embodiments, the carrier comprises hyaluronic acid (HA). According to some such embodiments, the carrier comprises a derivative of HA. According to some such embodiments, the carrier comprises sodium hyaluronate. Non-limiting examples of HA derivatives include salt derivatives, such as sodium hyaluronate, ester derivatives, such as, ethyl, bezyl, octadecyl ester derivatives. According to some such embodiments, the carrier comprises thrombin. According to some such embodiments, the carrier comprises fibrin. According to some such embodiments, the carrier comprises thrombin and fibrin. According to some such embodiments, the carrier comprises glycerin. According to some such embodiments, the carrier comprises collagen. According to some such embodiments, the carrier comprises lecithin.

According to some embodiments, the growth-conductive component further comprises a growth-inductive component, such as, for example, without limitation, DCB, such that the growth-inductive component represents about 30%, about 31%, about 32%, about 33%, about 34%, about 35%, about 36%, about 37%, about 38%, about 39% or about 40% of the implant. According to some embodiments, at least about 60%, 65%, 70%, 75%, 80%, 85%, 90%, 95%, 96%, 97%, 98%, 99% of the implant is growth conductive. According to some embodiments, the growth-inductive component of the implant according to the described invention is at least about 5000 pg of at least one growth-inductive factor, such as, but not limited to, a growth factor, a cytokine, and a BMP, such as, but not limited to, BMP-2, per gram of a growth-inductive component. The growth-inductive component generally averages about 25000 pg of growth-inductive factor per gram of a growth-inductive component. However, dosage levels are based on a variety of factors, including the type of injury, the age, weight, sex, medical condition of the patient, the severity of the condition, the route of administration, and the particular active agent employed. Thus the dosage regimen may vary widely, but can be determined routinely by a physician using standard methods. In prophylactic or preventative applications of the described invention, pharmaceutical compositions or medicaments are administered to a patient susceptible to, or otherwise at risk of, a disease, disorder or condition in an amount sufficient to eliminate or reduce the risk, lessen the severity, or delay the onset of the disease, disorder or condition, including biochemical, histologic and/or behavioral symptoms of the disease, disorder or condition, its complications, and intermediate pathological phenotypes presenting during development of the disease, disorder or condition.

According to some embodiments, the implant further comprises at least one cryopreservative. According to some such embodiments, the at least one cryopreservative is a solution. According to some such embodiments, the cryopreservative is dimethylsulfoxide (DMSO). According to some such embodiments, the cryopreservative is basal media solution comprising about 5% DMSO. According to some such embodiments, the cryopreservative is basal media solution comprising about 10% DMSO. According to some such embodiments, the cryopreservative is basal media solution comprising about 15% DMSO. According to some such embodiments, the cryopreservative is fetal bovine serum comprising about 5% DMSO. According to some such embodiments, the cryopreservative is fetal bovine serum comprising about 10% DMSO. According to some such embodiments, the cryopreservative is a human serum comprising about 15% DMSO. According to some such embodiments, the cryopreservative is human serum comprising about 5% DMSO. According to some such embodiments, the cryopreservative is human serum comprising about 10% DMSO. According to some such embodiments, the cryopreservative is ethylene glycol. According to some such embodiments, the cryopreservative is propylene glycol. According to some such embodiments, the cryopreservative is glycerol.

Orthopedic Implant

According to another embodiment, the described invention provides an orthopedic implant comprising a plurality of particles comprising at least one growth-conductive matrix or at least one fragment thereof; and a viable population of tissuegenic cells adherent to and resident in the growth-conductive matrix.

According to one embodiment, the plurality of particles or pieces comprising at least one growth-conductive matrix can be of any form. According to some embodiments, the plurality of particles or pieces comprises a plurality of sheets. According to some embodiments, the plurality of particles or pieces comprises a slurry form. According to some embodiments, the plurality of particles or pieces comprises a paste form. According to some embodiments, the plurality of particles or pieces comprises a three-dimensional form. According to some embodiments, the three-dimensional form is selected from the group consisting of a block, a dowel, a sheet, and a combination thereof. According to some such embodiments, the three-dimensional form comprises a block. According to some such embodiments, the three-dimensional form comprises a dowel. According to some such embodiments, the three-dimensional form comprises a sheet.

According to another embodiment, the implant is an implantable composition comprising a growth-conductive matrix (e.g., an osteoconductive matrix including bone), a viable population of tissuegenic cells (e.g., osteogenic cells), and a growth-inductive matrix (e.g., demineralized bone matrix). In an embodiment, a second growth-inductive matrix (e.g., a second demineralized bone matrix) is provided separately from the aforesaid implantable composition for addition to the implantable composition at a later time.

2. Method of Fabricating an Implant Using a Tissue-Derived Matrix Containing Endogenous Tissuegenic Cells According to another aspect, the described invention provides a method of fabricating an implant, the method comprising steps:

(a) providing at least one growth-conductive matrix wherein the growth-conductive matrix comprises at least one viable population of tissuegenic cells endogenous to the tissue, wherein the tissuegenic cells are adherent to and resident in an endogenous milieu of the growth-conductive matrix;

(b) separating the at least one growth-conductive matrix of (a) to generate a plurality of separated matrix pieces comprising the at least one viable population of tissuegenic cells adherent to and resident in the endogenous milieu of the growth-conductive matrix, wherein a relative frequency of a stem cell subtype in the at least one viable tissuegenic cell population of step (b) is of a relative frequency substantially similar to that found in the growth-conductive matrix of step (a);

(c) rinsing the plurality of separated matrix pieces of (b) comprising the at least one viable population of tissuegenic cells adherent to and resident in the endogenous milieu of the growth-conductive matrix of (b) to form a plurality of rinsed separated matrix pieces comprising the at least one viable population of tissuegenic cells adherent to and resident in the the endogenous milieu of the growth-conductive matrix of (b), wherein a relative frequency of a stem cell subtype in the at least one viable tissuegenic cell population of step (c) is of a relative frequency substantially similar to that found in the growth-conductive matrix of step (a);

(d) collecting the plurality of rinsed separated matrix pieces of (c) comprising the at least one viable population of tissuegenic cells adherent to and resident in the endogenous milieu of the growth-conductive matrix of (c) wherein the at least one viable tissuegenic cell population is of a relative frequency substantially similar to that found in the growth-conductive matrix of step (a);

(e) packaging the plurality of collected rinsed separated matrix pieces of (d) comprising at least one viable population of tissuegenic cells adherent to and resident in the endogenous milieu of the growth-conductive matrix of (c) wherein the at least one viable tissuegenic cell population is of a relative frequency substantially similar to that found in the growth-conductive matrix of step (a) to form the implant. Providing step (a): providing at least one growth-conductive matrix wherein the growth-conductive matrix comprises at least one viable population of tissuegenic cells endogenous to the tissue, wherein the tissuegenic cells are adherent to and resident in an endogenous milieu of the growth-conductive matrix According to some embodiments, providing step (a) comprises excising the tissue from its source. According to some embodiments, providing step (a) comprises removing the tissue from its source. According to some embodiments, providing step (a) comprises isolating the tissue from its source. According to some embodiments, providing step (a) comprises recovering the tissue from its source.

According to some embodiments, providing step (a) is at a temperature of about 25° C. According to some embodiments, providing step (a) is at a temperature of about 4° C. to about 10° C. According to some embodiments, providing step (a) is at an ambient temperature.

According to some embodiments, the tissue is rinsed with a liquid prior to being separated into pieces to reduce bioburden levels on the surface of the tissue. According to some embodiments, the liquid comprises phosphate buffered saline (PBS). According to some embodiments, the liquid comprises acetic acid. According to some embodiments, the liquid comprises peracetic acid.

According to another embodiment, the method of fabricating an implant, further comprises step (f) supplementing the growth-conductive matrix of step (a) with at least one growth-inductivecomponent. According to some such embodiments, the at least one growth-inductive component comprises at least one growth-inductive factor. According to some such embodiments, the at least one growth-inductive factor comprises at least one growth factor. According to some such embodiments, the at least one growth factor is fibroblast growth factor-2 (FGF-2). According to some such embodiments, the at least one growth factor is fibroblast growth factor-5 (FGF-5). According to some such embodiments, the at least one growth factor is insulin-like growth factor 1 (IGF-1). According to some such embodiments, the at least one growth factor is transforming growth factor beta (TGF-β). According to some such embodiments, the at least one growth factor is bone morphogenic protein-2 (BMP-2). According to some such embodiments, the at least one growth factor is bone morphogenic protein-7 (BMP-7). According to some such embodiments, the at least one growth factor is platelet-derived growth factor (PDGF). According to some such embodiments, the at least one growth factor is vascular endothelial growth factor (VEGF). According to some such embodiments, the at least one growth factor is neural epidermal growth-factor-like 1 (NELL-1). According to another embodiment, the rinsed osteoconductive matrix particles are supplemented with at least one cytokine.

According to one embodiment, the at least one growth-inductive component is tissue-derived. According to one embodiment, the at least one growth-inductive component comprises inducible pluripotent stem cells (iPSCs). According to one embodiment, the at least one growth-inductive component originates from a component of the tissue-derived growth-inductive component other than cells. According to one embodiment, the at least one growth-inductive component is endogenous to the at least one growth-conductive matrix. According to one embodiment, the tissuegenic cells adherent to and resident in the endogenous milieu of the growth conductive matrix secrete the at least one growth-inductive component. According to one embodiment, the at least one growth-inductive component is exogenous to the at least one growth-conductive matrix. According to one embodiment, the growth-inductive component comprises a growth medium derived from expanded tissuegenic cells. According to one embodiment, the at least one growth-inductive component comprises demineralized cortical bone.

Separating step (b): separating the at least one growth-conductive matrix of (a) to generate a plurality of separated matrix pieces comprising the at least one viable population of tissuegenic cells adherent to and resident in the endogenous milieu of the growth-conductive matrix, wherein a relative frequency of a stem cell subtype in the at least one viable tissuegenic cell population of step (b) is of a relative frequency substantially similar to that found in the growth-conductive matrix of step (a)

According to some embodiments, separating step (b) comprises mincing the tissue. According to some embodiments, separating step (b) comprises cutting the tissue. According to some embodiments, separating step (b) comprises a slicing step. According to some embodiments, separating step (b) comprises milling the tissue. According to some embodiments, separating step (b) comprises homogenizing the tissue.

According to some embodiments, separating step (b) is at a temperature of about 25° C. According to some embodiments, separating step (b) is at a temperature of about 4° C. to about 10° C. According to some embodiments, separating step (b) is at an ambient temperature.

According to some embodiments, the plurality of separated growth-conductive matrix pieces of step (b) comprises a plurality of matrix particles.

According to some embodiments, the plurality of growth-conductive matrix pieces can be of virtually any shape. According to some embodiments, the plurality of growth-conductive matrix pieces are of a similar shape. According to some embodiments, the plurality of growth-conductive matrix pieces are of a circular shape. According to some embodiments, the plurality of growth-conductive matrix pieces are of a square shape. According to some embodiments, the plurality of growth-conductive matrix pieces are of a polygonal shape. According to some embodiments, the plurality of growth-conductive matrix pieces are of a rectangular shape. According to some embodiments, the plurality of growth-conductive matrix pieces are of a triangular shape. According to some embodiments, the plurality of growth-conductive matrix pieces are of a octagonal shape. According to some embodiments, the plurality of growth-conductive matrix pieces are of irregular shapes. According to some embodiments, the plurality of growth-conductive pieces are of an elongated shape (e.g., as a fiber). According to some embodiments, the plurality of growth-conductive matrix pieces are of an amorphous shape.

According to some embodiments, the plurality of growth-conductive matrix pieces comprises at least one growth-conductive matrix piece whose longest dimension (which is used herein as an equivalent term to "maximum dimension") is of about 10 μm to about 20 cm. According to some such embodiments, the at least one growth-conductive matrix piece is a growth-conductive matrix piece whose longest dimension is of about 10 μm. According to some such embodiments, the at least one growth-conductive matrix piece is a growth-conductive matrix piece whose longest dimension is of about 20 μm. According to some such embodiments, the at least one growth-conductive matrix piece is a growth-conductive matrix piece whose longest dimension is of about 30 μm. According to some such embodiments, the at least one growth-conductive matrix piece is a growth-conductive matrix piece whose longest dimension is of about 40 μm. According to some such embodiments, the at least one growth-conductive matrix piece is a growth-conductive matrix piece whose longest dimension is of about 50 μm. According to some such embodiments, the at least one growth-conductive matrix piece is a growth-conductive matrix piece whose longest dimension is of about 100 μm. According to some such embodiments, the at least one growth-conductive matrix piece is a growth-conductive matrix piece whose longest dimension is of about 150 μm. According to some such embodiments, the at least one growth-conductive matrix piece is a growth-conductive matrix piece whose longest dimension is of about 200 μm. According to some such embodiments, the at least one growth-conductive matrix piece is a growth-conductive matrix piece whose longest dimension is of about 250 μm. According to some such embodiments, the at least one growth-conductive matrix piece is a growth-conductive matrix piece whose longest dimension is of about 300 μm. According to some such embodiments, the at least one growth-conductive matrix piece is a growth-conductive matrix piece whose longest dimension is of about 350 μm. According to some such embodiments, the at least growth-conductive matrix piece is a growth-conductive matrix piece whose longest dimension is of about 400 μm. According to some such embodiments, the at least one growth-conductive matrix piece is a growth-conductive matrix piece whose longest dimension is of about 450 μm. According to some such embodiments, the at least one growth-conductive matrix piece is a growth-conductive matrix piece whose longest dimension is of about 500 μm. According to some such embodiments, the at least one growth-conductive matrix piece is a growth-conductive matrix piece whose longest dimension is of about 550 μm. According to some such embodiments, the at least one growth-conductive matrix piece is a growth-conductive matrix piece whose longest dimension is of about 600 μm. According to some such embodiments, the at least one growth-conductive matrix piece is a growth-conductive matrix piece whose longest dimension is of about 650 μm. According to some such embodiments, the at least one growth-conductive matrix piece is a growth-conductive matrix piece whose longest dimension is of about 700 μm. According to some such embodiments, the at least one growth-conductive matrix piece is a growth-conductive matrix piece whose longest dimension is of about 750 μm. According to some such embodiments, the at least one growth-conductive matrix piece is a growth-conductive matrix piece whose longest dimension is of about 800 μm. According to some such embodiments, the at least one growth-conductive matrix piece is a growth-conductive matrix piece whose longest dimension is of about 850 μm. According to some such embodiments, the at least one growth-conductive matrix piece is a growth-conductive matrix piece whose longest dimension is of about 900 μm. According to some such embodiments, the at least one growth-conductive matrix piece is a growth-conductive matrix piece whose longest dimension is of about 950 μm. According to some embodiments, the at least one growth-conductive matrix piece is a growth-conductive matrix piece whose longest dimension is in the range of about 100 μm to about 1000 μm.

According to some such embodiments, the at least one growth-conductive matrix piece is a growth-conductive matrix piece whose longest dimension is of about 1 mm. According to some such embodiments, the at least one growth-conductive matrix piece is a growth-conductive matrix piece whose longest dimension is of about 2 mm. According to some such embodiments, the at least one growth-conductive matrix piece is a growth-conductive matrix piece whose longest dimension is of about 3 mm. According to some such embodiments, the at least one growth-conductive matrix piece is a growth-conductive matrix piece whose longest dimension is of about 4 mm. According to some such embodiments, the at least one osteocogrowth-conductive matrix piece is a growth-conductive matrix piece whose longest dimension is of about 5 mm. According to some such embodiments, the at least one growth-conductive matrix piece is a growth-conductive matrix piece whose longest dimension is of about 6 mm. According to some such embodiments, the at least one growth-conductive matrix piece is a growth-conductive matrix piece whose longest dimension is of about 7 mm. According to some such embodiments, the at least one growth-conductive matrix piece is a growth-conductive matrix piece whose longest dimension is of about 8 mm. According to some such embodiments, the at least one growth-conductive matrix piece is a growth-conductive matrix piece whose longest dimension is of about 9 mm. According to some such embodiments, the at least one growth-conductive matrix piece is a growth-conductive matrix piece whose longest dimension is of about 10 mm. According to some such embodiments, the at least one growth-conductive matrix piece is a growth-conductive matrix piece whose longest dimension is of about 12 mm. According to some such embodiments, the at least one growth-conductive matrix piece is a growth-conductive matrix piece whose longest dimension is of about 14 mm. According to some such embodiments, the at least one growth-conductive matrix piece is a growth-conductive matrix piece whose longest dimension is of about 16 mm. According to some such embodiments, the at least one growth-conductive matrix piece is a growth-conductive matrix piece whose longest dimension is of about 18 mm. According to some such embodiments, the at least one growth-conductive matrix piece is a growth-conductive matrix piece whose longest dimension is of about 20 mm. According to some such embodiments, the at least one growth-conductive matrix piece is a growth-conductive matrix piece whose longest dimension is of about 22 mm. According to some such embodiments, the at least one growth-conductive matrix piece is a growth-conductive matrix piece whose longest dimension is of about 24 mm. According to some such embodiments, the at least one growth-conductive matrix piece is a growth-conductive matrix piece whose longest dimension is of about 26 mm. According to some such embodiments, the at least one growth-conductive matrix piece is a growth-conductive matrix piece whose longest dimension is of about 28 mm. According to some such embodiments, the at least one growth-conductive matrix piece is a growth-conductive matrix piece whose longest dimension is of about 30 mm. According to some such embodiments, the at least one growth-conductive matrix piece is a growth-conductive matrix piece whose longest dimension is of about 35 mm. According to some such embodiments, the at least one growth-conductive matrix piece is a growth-conductive matrix piece whose longest dimension is of about 40 mm. According to some such embodiments, the at least one growth-conductive matrix piece is a growth-conductive matrix piece whose longest dimension is of about 45 mm. According to some such embodiments, the at least one growth-conductive matrix piece is a growth-conductive matrix piece whose longest dimension is of about 50 mm. According to some such embodiments, the at least one growth-conductive matrix piece is a growth-conductive matrix piece whose longest dimension is of about 100 mm. According to some such embodiments, the at least one growth-conductive matrix piece is a growth-conductive matrix piece whose longest dimension is of about 200 mm. According to some such embodiments, the at least one growth-conductive matrix piece is a osteocongrowth-conductive matrix piece whose longest dimension is of about 300 mm. According to some such embodiments, the at least one growth-conductive matrix piece is a growth-conductive matrix piece whose longest dimension is of about 400 mm. According to some such embodiments, the at least one growth-conductive matrix piece is a growth-conductive matrix piece whose longest dimension is of about 500 mm. According to some such embodiments, the at least one growth-conductive matrix piece is a growth-conductive matrix piece whose longest dimension is of about 600 mm. According to some such embodiments, the at least one growth-conductive matrix piece is a growth-conductive matrix piece whose longest dimension is of about 700 mm. According to some such embodiments, the at least one growth-conductive matrix piece is a growth-conductive matrix piece whose longest dimension is of about 800 mm. According to some such embodiments, the at least one growth-conductive matrix piece is a growth-conductive matrix piece whose longest dimension is of about 900 mm. According to some such embodiments, the at least one growth-conductive matrix piece is a growth-conductive matrix piece whose longest dimension is of about 1000 mm.

According to some such embodiments, the at least one growth-conductive matrix piece is a growth-conductive matrix piece whose longest dimension is in the range of about 1 mm to about 10 mm. According to some such embodiments, the at least one growth-conductive matrix piece is a growth-conductive matrix piece whose longest dimension is in the range of about 5 mm to about 15 mm. According to some such embodiments, the at least one growth-conductive matrix piece is a growth-conductive matrix piece whose longest dimension is in the range of about 10 mm to about 20 mm. According to some such embodiments, the at least one growth-conductive matrix piece is a growth-conductive matrix piece whose longest dimension is in the range of about 15 mm to about 25 mm. According to some such embodiments, the at least one growth-conductive matrix piece is a growth-conductive matrix piece whose longest dimension is in the range of about 20 mm to about 30 mm. According to some such embodiments, the at least one growth-conductive matrix piece is a growth-conductive matrix piece whose longest dimension is in the range of about 25 mm to about 35 mm. According to some such embodiments, the at least one growth-conductive matrix piece is a growth-conductive matrix piece whose longest dimension is in the range of about 30 mm to about 40 mm. According to some such embodiments, the at least one growth-conductive matrix piece is a growth-conductive matrix piece whose longest dimension is in the range of about 40 mm to about 50 mm. According to some such embodiments, the at least one growth-conductive matrix piece is a growth-conductive matrix piece whose longest dimension is in the range of about 10 mm to about 15 mm. According to some such embodiments, the at least one growth-conductive matrix piece is a growth-conductive matrix piece whose longest dimension is in the range of about 15 mm to about 20 mm. According to some such embodiments, the at least one growth-conductive matrix piece is a growth-conductive matrix piece whose longest dimension is in the range of about 25 mm to about 30 mm. According to some such embodiments, the at least one growth-conductive matrix piece is a growth-conductive matrix piece whose longest dimension is in the range of about 30 mm to about 35 mm. According to some such embodiments, the at least one growth-conductive matrix piece is a growth-conductive matrix piece whose longest dimension is in the range of about 35 mm to about 40 mm. According to some such embodiments, the at least one growth-conductive matrix piece is a growth-conductive matrix piece whose longest dimension is in the range of about 40 mm to about 45 mm. According to some such embodiments the at least one growth-conductive matrix piece is a growth-conductive matrix piece whose longest dimension is in the range of about 45 mm to about 50 mm.

According to some such embodiments, the at least one growth-conductive matrix piece is a growth-conductive matrix piece whose longest dimension is at least 1 mm. According to some such embodiments, the at least one growth-conductive matrix piece is a growth-conductive matrix piece whose longest dimension is at least 10 mm. According to some such embodiments, the at least one growth-conductive matrix piece is a growth-conductive matrix piece whose longest dimension is at least 15 mm. According to some such embodiments, the at least one growth-conductive matrix piece is a growth-conductive matrix piece whose longest dimension is at least 20 mm. According to some such embodiments, the at least one growth-conductive matrix piece is a growth-conductive matrix piece whose longest dimension is at least 25 mm. According to some such embodiments, the at least one growth-conductive matrix piece is a growth-conductive matrix piece whose longest dimension is at least 30 mm. According to some such embodiments, the at least one growth-conductive matrix piece is a growth-conductive matrix piece whose longest dimension is at least 35 mm. According to some such embodiments, the at least one growth-conductive matrix piece is a growth-conductive matrix piece whose longest dimension is at least 40 mm. According to some such embodiments, the at least one growth-conductive matrix piece is a growth-conductive matrix piece whose longest dimension is at least 45 mm. According to some such embodiments, the at least one growth-conductive matrix piece is a growth-conductive matrix piece whose longest dimension is at least 50 mm.

According to some such embodiments, the at least one growth-conductive matrix piece is a growth-conductive matrix piece whose longest dimension is of about 1 cm. According to some such embodiments, the at least one growth-conductive matrix piece is a growth-conductive matrix piece whose longest dimension is of about 2 cm. According to some such embodiments, the at least one growth-conductive matrix piece is a growth-conductive matrix piece whose longest dimension is of about 3 cm. According to some such embodiments, the at least one growth-conductive matrix piece is a growth-conductive matrix piece whose longest dimension is of about 4 cm. According to some such embodiments, the at least one growth-conductive matrix piece is a growth-conductive matrix piece whose longest dimension is of about 5 cm. According to some such embodiments, the at least one growth-conductive matrix piece is a growth-conductive matrix piece whose longest dimension is of about 6 cm. According to some such embodiments, the at least one growth-conductive matrix piece is a growth-conductive matrix piece whose longest dimension is of about 7 cm. According to some such embodiments, the at least one growth-conductive matrix piece is a growth-conductive matrix piece whose longest dimension is of about 8 cm. According to some such embodiments, the at least one growth-conductive matrix piece is a growth-conductive matrix piece whose longest dimension is of about 9 cm. According to some such embodiments, the at least one growth-conductive matrix piece is a growth-conductive matrix piece whose longest dimension is of about 10 cm. According to some such embodiments, the at least one growth-conductive matrix piece is a growth-conductive matrix piece whose longest dimension is of about 11 cm. According to some such embodiments, the at least one growth-conductive matrix piece is a growth-conductive matrix piece whose longest dimension is of about 12 cm. According to some such embodiments, the at least one growth-conductive matrix piece is a growth-conductive matrix piece whose longest dimension is of about 13 cm. According to some such embodiments, the at least one growth-conductive matrix piece is a growth-conductive matrix piece whose longest dimension is of about 14 cm. According to some such embodiments, the at least one growth-conductive matrix piece is a growth-conductive matrix piece whose longest dimension is of about 15 cm. According to some such embodiments, the at least one growth-conductive matrix piece is a growth-conductive matrix piece whose longest dimension is of about 16 cm. According to some such embodiments, the at least one growth-conductive matrix piece is a growth-conductive matrix piece whose longest dimension is of about 17 cm. According to some such embodiments, the at least one growth-conductive matrix piece is a growth-conductive matrix piece whose longest dimension is of about 18 cm. According to some such embodiments, the at least one growth-conductive matrix piece is a growth-conductive matrix piece whose longest dimension is of about 19 cm. According to some such embodiments, the at least one growth-conductive matrix piece is a growth-conductive matrix piece whose longest dimension is of about 20 cm.

According to some embodiments, the plurality of separated growth-conductive matrix pieces can be of any form. According to some embodiments, the plurality of separated growth-conductive matrix pieces comprises a plurality of sheets. According to some embodiments, the plurality of separated growth-conductive matrix pieces comprises a powder form. According to some embodiments, the plurality of separated growth-conductive matrix pieces comprises a slurry form. According to some embodiments, the plurality of separated growth-conductive matrix pieces comprises a three-dimensional form. According to some embodiments, the three-dimensional form is selected from the group consisting of a block, a dowel, a sheet, and a combination thereof. According to some such embodiments, the three-dimensional form comprises a block. According to some such embodiments, the three-dimensional form comprises a dowel. According to some such embodiments, the three-dimensional form comprises a sheet.

According to another embodiment, the method of fabricating an implant further comprises step (f) supplementing the plurality of separated growth-conductive matrix pieces of step (b) with at least one growth-inductive component. According to some such embodiments, the at least one growth-inductive component comprises at least one growth-inductive factor. According to some such embodiments, the at least one growth-inductive factor comprises at least one growth factor. According to some such embodiments, the at least one growth factor is fibroblast growth factor-2 (FGF-2). According to some such embodiments, the at least one growth factor is fibroblast growth factor-5 (FGF-5). According to some such embodiments, the at least one growth factor is insulin-like growth factor 1 (IGF-1). According to some such embodiments, the at least one growth factor is transforming growth factor beta (TGF-β). According to some such embodiments, the at least one growth factor is bone morphogenic protein-2 (BMP-2). According to some such embodiments, the at least one growth factor is bone morphogenic protein-7 (BMP-7). According to some such embodiments, the at least one growth factor is platelet-derived growth factor (PDGF). According to some such embodiments, the at least one growth factor is vascular endothelial growth factor (VEGF). According to some such embodiments, the at least one growth factor is neural epidermal growth-factor-like 1 (NELL-1). According to another embodiment, the rinsed growth conductive matrix particles are supplemented with at least one cytokine.

According to one embodiment, the at least one growth-inductive component is tissue-derived. According to one embodiment, the at least one growth-inductive component comprises inducible pluripotent stem cells (iPSCs). According to one embodiment, the at least one growth-inductive component originates from a component of the tissue-derived growth-inductive component other than cells. According to one embodiment, the at least one growth-inductive component is endogenous to the at least one growth-conductive matrix. According to one embodiment, the tissuegenic cells adherent to and resident in the endogenous milieu of the growth conductive matrix secrete the at least one growth-inductive component. According to one embodiment, the at least one growth-inductive component is exogenous to the at least one growth-conductive matrix. According to one embodiment, the growth-inductive component comprises a growth medium derived from expanded tissuegenic cells.

According to one embodiment, the at least one growth-inductive component comprises demineralized bone matrix, which may be demineralized cortical bone. According to some embodiments, the demineralized bone matrix is provided as a plurality of pieces of demineralized bone matrix derived from a single piece of demineralized bone matrix.

According to some embodiments, the demineralized bone matrix is provided as a plurality of pieces of demineralized bone matrix derived from a plurality of pieces of bone tissue.

According to some embodiments, the pieces of bone tissue that are to be demineralized have a longest dimension (which is used herein as an equivalent term to "maximum dimension") that is measurable prior to demineralization of the pieces of bone. All such longest dimensions related in this paragraph are the longest dimension of a piece of bone tissue prior to demineralization. According to some embodiments, the plurality of pieces of bone tissue includes at least one piece of bone tissue whose longest dimension is of about 10 µm to about 20 cm. According to some such embodiments, the plurality of pieces of bone tissue includes a piece of bone tissue whose longest dimension is of about 10 µm. According to some such embodiments, the plurality of pieces of bone tissue includes a piece of bone tissue whose longest dimension is of about 20 µm. According to some such embodiments, the plurality of pieces of bone tissue includes at least one piece of bone tissue whose longest dimension is of about 30 µm. According to some such embodiments, the plurality of pieces of bone tissue includes at least one piece of bone tissue whose longest dimension is of about 40 µm. According to some such embodiments, the plurality of pieces of bone tissue includes at least one piece of bone tissue whose longest dimension is of about 50 µm. According to some such embodiments, the plurality of pieces of bone tissue includes at least one piece of bone tissue whose longest dimension is of about 100 µm. According to some such embodiments, the plurality of pieces of bone tissue includes at least one piece of bone tissue whose longest dimension is of about 150 µm. According to some such embodiments, the plurality of pieces of bone tissue includes at least one piece of bone tissue whose longest dimension is of about 200 µm. According to some such embodiments, the plurality of pieces of bone tissue includes at least one piece of bone tissue whose longest dimension is of about 250 µm. According to some such embodiments, the plurality of pieces of bone tissue includes at least one piece of bone tissue whose longest dimension is of about 300 µm. According to some such embodiments, the plurality of pieces of bone tissue includes at least one piece of bone tissue whose longest dimension is of about 350 µm. According to some such embodiments, the plurality of pieces of bone tissue includes at least one piece of bone tissue whose longest dimension is of about 400 µm. According to some such embodiments, the plurality of pieces of bone tissue includes at least one piece of bone tissue whose longest dimension is of about 450 µm. According to some such embodiments, the plurality of pieces of bone tissue includes at least one piece of bone tissue whose longest dimension is of about 500 µm. According to some such embodiments, the plurality of pieces of bone tissue includes at least one piece of bone tissue whose longest dimension is of about 550 µm. According to some such embodiments, the plurality of pieces of bone tissue includes at least one piece of bone tissue whose longest dimension is of about 600 µm. According to some such embodiments, the plurality of pieces of bone tissue includes at least one piece of bone tissue whose longest dimension is of about 650 µm. According to some such embodiments, the plurality of pieces of bone tissue includes at least one piece of bone tissue whose longest dimension is of about 700 µm. According to some such embodiments, the plurality of pieces of bone tissue includes at least one piece of bone tissue whose longest dimension is of about 750 µm. According to some such embodiments, the plurality of pieces of bone tissue includes at least one piece of bone tissue whose longest dimension is of about 800 µm. According to some such embodiments, the plurality of pieces of bone tissue includes at least one piece of bone tissue whose longest dimension is of about 850 µm. According to some such embodiments, the plurality of pieces of bone tissue includes at least one piece of bone tissue whose longest dimension is of about 900 µm. According to some such embodiments, the plurality of pieces of bone tissue includes at least one piece of bone tissue whose longest dimension is of about 950 µm. According to some such embodiments, the plurality of pieces of bone tissue includes at least one piece of bone tissue whose longest dimension is in the range of about 100 µm to about 1000 µm.

According to some such embodiments, the plurality of pieces of bone tissue includes at least one piece of bone tissue whose longest dimension is of about 1 mm. According to some such embodiments, the plurality of pieces of bone tissue includes at least one piece of bone tissue whose longest dimension is of about 2 mm. According to some such embodiments, the plurality of pieces of bone tissue includes at least one piece of bone tissue whose longest dimension is of about 3 mm. According to some such embodiments, the plurality of pieces of bone tissue includes at least one piece of bone tissue whose longest dimension is of about 4 mm. According to some such embodiments, the plurality of pieces of bone tissue includes at least one piece of bone tissue whose longest dimension is of about 5 mm. According to some such embodiments, the plurality of pieces of bone tissue includes at least one piece of bone tissue whose longest dimension is of about 6 mm. According to some such embodiments, the plurality of pieces of bone tissue includes at least one piece of bone tissue whose longest dimension is of about 7 mm. According to some such embodiments, the plurality of pieces of bone tissue includes at least one piece of bone tissue whose longest dimension is of about 8 mm. According to some such embodiments, the plurality of pieces of bone tissue includes at least one piece of bone tissue whose longest dimension is of about 9 mm. According to some such embodiments, the plurality of pieces of bone tissue includes at least one piece of bone tissue whose longest dimension is of about 10 mm. According to some such embodiments, the plurality of pieces of bone tissue includes at least one piece of bone tissue whose longest dimension is of about 12 mm. According to some such embodiments the plurality of pieces of bone tissue includes at least one piece of bone tissue whose longest dimension is of about 14 mm. According to some such embodiments, the plurality of pieces of bone tissue includes at least one piece of bone tissue whose longest dimension is of about 16 mm. According to some such embodiments, the plurality of pieces of bone tissue includes at least one piece of bone tissue whose longest dimension is of about 18 mm. According to some such embodiments, the plurality of pieces of bone tissue includes at least one piece of bone tissue whose longest dimension is of about 20 mm. According to some such embodiments, the plurality of pieces of bone tissue includes at least one piece of bone tissue whose longest dimension is of about 22 mm. According to some such embodiments, the plurality of pieces of bone tissue includes at least one piece of bone tissue whose longest dimension is of about 24 mm. According to some such embodiments, the plurality of pieces of bone tissue includes at least one piece of bone tissue whose longest dimension is of about 26 mm. According to some such embodiments, the plurality of pieces of bone tissue includes at least one piece of bone tissue whose longest dimension is of about 28 mm. According to some such embodiments, the plurality of pieces of bone tissue includes at least one piece of bone tissue whose longest dimension is of about 30 mm. According to some such embodiments, the plurality of pieces of bone tissue includes at least one piece of bone tissue whose longest dimension is of about 35 mm. According to some such embodiments, the plurality of pieces of bone tissue includes at least one piece of bone tissue whose longest dimension is of about 40 mm. According to some such embodiments, the plurality of pieces of bone tissue includes at least one piece of bone tissue whose longest dimension is of about 45 mm. According to some such embodiments, the plurality of pieces of bone tissue includes at least one piece of bone tissue whose longest dimension is of about 50 mm. According to some such embodiments, the plurality of pieces of bone tissue includes at least one piece of bone tissue whose longest dimension is of about 100 mm. According to some such embodiments, the plurality of pieces of bone tissue includes at least one piece of bone tissue whose longest dimension is of about 200 mm. According to some such embodiments, the plurality of pieces of bone tissue includes at least one piece of bone tissue whose longest dimension is of about 300 mm. According to some such embodiments, the plurality of pieces of bone tissue includes at least one piece of bone tissue whose longest dimension is of about 400 mm. According to some such embodiments, the plurality of pieces of bone tissue includes at least one piece of bone tissue whose longest dimension is of about 500 mm. According to some such embodiments, the plurality of pieces of bone tissue includes at least one piece of bone tissue whose longest dimension is of about 600 mm. According to some such embodiments, the plurality of pieces of bone tissue includes at least one piece of bone tissue whose longest dimension is of about 700 mm. According to some such embodiments, the plurality of pieces of bone tissue includes at least one piece of bone tissue whose longest dimension is of about 800 mm. According to some such embodiments, the plurality of pieces of bone tissue includes at least one piece of bone tissue whose longest dimension is of about 900 mm. According to some such embodiments, the plurality of pieces of bone tissue includes at least one piece of bone tissue whose longest dimension is of about 1000 mm.

According to some such embodiments, the plurality of pieces of bone tissue includes at least one piece of bone tissue whose longest dimension is in the range of about 1 mm to about 10 mm. According to some such embodiments, the plurality of pieces of bone tissue includes at least one piece of bone tissue whose longest dimension is in the range of about 5 mm to about 15 mm. According to some such embodiments, the plurality of pieces of bone tissue includes at least one piece of bone tissue whose longest dimension is in the range of about 10 mm to about 20 mm. According to some such embodiments, the plurality of pieces of bone tissue includes at least one piece of bone tissue whose longest dimension is in the range of about 15 mm to about 25 mm. According to some such embodiments, the plurality of pieces of bone tissue includes at least one piece of bone tissue whose longest dimension is in the range of about 20 mm to about 30 mm. According to some such embodiments, the plurality of pieces of bone tissue includes at least one piece of bone tissue whose longest dimension is in the range of about 25 mm to about 35 mm. According to some such embodiments, the plurality of pieces of bone tissue includes at least one piece of bone tissue whose longest dimension is in the range of about 30 mm to about 40 mm. According to some such embodiments, the plurality of pieces of bone tissue includes at least one piece of bone tissue whose longest dimension is in the range of about 40 mm to about 50 mm. According to some such embodiments, the plurality of pieces of bone tissue includes at least one piece of bone tissue whose longest dimension is in the range of about 10 mm to about 15 mm. According to some such embodiments, the plurality of pieces of bone tissue includes at least one piece of bone tissue whose longest dimension is in the range of about 15 mm to about 20 mm. According to some such embodiments, the plurality of pieces of bone tissue includes at least one piece of bone tissue whose longest dimension is in the range of about 25 mm to about 30 mm. According to some such embodiments, the plurality of pieces of bone tissue includes at least one piece of bone tissue whose longest dimension is in the range of about 30 mm to about 35 mm. According to some such embodiments, the plurality of pieces of bone tissue includes at least one piece of bone tissue whose longest dimension is in the range of about 35 mm to about 40 mm. According to some such embodiments, the plurality of pieces of bone tissue includes at least one piece of bone tissue whose longest dimension is in the range of about 40 mm to about 45 mm. According to some such embodiments the plurality of pieces of bone tissue includes at least one piece of bone tissue whose longest dimension is in the range of about 45 mm to about 50 mm.

According to some such embodiments, the plurality of pieces of bone tissue includes at least one piece of bone tissue whose longest dimension is at least 1 mm. According to some such embodiments, the plurality of pieces of bone tissue includes at least one piece of bone tissue whose longest dimension is at least 10 mm. According to some such embodiments, the plurality of pieces of bone tissue includes at least one piece of bone tissue whose longest dimension is at least 15 mm. According to some such embodiments, the plurality of pieces of bone tissue includes at least one piece of bone tissue whose longest dimension is at least 20 mm. According to some such embodiments, the plurality of pieces of bone tissue includes at least one piece of bone tissue whose longest dimension is at least 25 mm. According to some such embodiments, the plurality of pieces of bone tissue includes at least one piece of bone tissue whose longest dimension is at least 30 mm. According to some such embodiments, the plurality of pieces of bone tissue includes at least one piece of bone tissue whose longest dimension is at least 35 mm. According to some such embodiments, the plurality of pieces of bone tissue includes at least one piece of bone tissue whose longest dimension is at least 40 mm. According to some such embodiments, the plurality of pieces of bone tissue includes at least one piece of bone tissue whose longest dimension is at least 45 mm. According to some such embodiments, the plurality of pieces of bone tissue includes at least one piece of bone tissue whose longest dimension is at least 50 mm.

According to some such embodiments, the plurality of pieces of bone tissue includes at least one piece of bone tissue whose longest dimension is of about 1 cm. According to some such embodiments, the plurality of pieces of bone tissue includes at least one piece of bone tissue whose longest dimension is of about 2 cm. According to some such embodiments, the plurality of pieces of bone tissue includes at least one piece of bone tissue whose longest dimension is of about 3 cm. According to some such embodiments, the plurality of pieces of bone tissue includes at least one piece of bone tissue whose longest dimension is of about 4 cm. According to some such embodiments, the plurality of pieces of bone tissue includes at least one piece of bone tissue whose longest dimension is of about 5 cm. According to some such embodiments, the plurality of pieces of bone tissue includes at least one piece of bone tissue whose longest dimension is of about 6 cm. According to some such embodiments, the plurality of pieces of bone tissue includes at least one piece of bone tissue whose longest dimension is of about 7 cm. According to some such embodiments, the plurality of pieces of bone tissue includes at least one piece of bone tissue whose longest dimension is of about 8 cm. According to some such embodiments, the plurality of pieces of bone tissue includes at least one piece of bone tissue whose longest dimension is of about 9 cm. According to some such embodiments, the plurality of pieces of bone tissue includes at least one piece of bone tissue whose longest dimension is of about 10 cm. According to some such embodiments, the plurality of pieces of bone tissue includes at least one piece of bone tissue whose longest dimension is of about 11 cm. According to some such embodiments, the plurality of pieces of bone tissue includes at least one piece of bone tissue whose longest dimension is of about 12 cm. According to some such embodiments, the plurality of pieces of bone tissue includes at least one piece of bone tissue whose longest dimension is of about 13 cm. According to some such embodiments, the plurality of pieces of bone tissue includes at least one piece of bone tissue whose longest dimension is of about 14 cm. According to some such embodiments, the plurality of pieces of bone tissue includes at least one piece of bone tissue whose longest dimension is of about 15 cm. According to some such embodiments, the plurality of pieces of bone tissue includes at least one piece of bone tissue whose longest dimension is of about 16 cm. According to some such embodiments, the plurality of pieces of bone tissue includes at least one piece of bone tissue whose longest dimension is of about 17 cm. According to some such embodiments, the plurality of pieces of bone tissue includes at least one piece of bone tissue whose longest dimension is of about 18 cm. According to some such embodiments, the plurality of pieces of bone tissue includes at least one piece of bone tissue whose longest dimension is of about 19 cm. According to some such embodiments, the plurality of pieces of bone tissue includes at least one piece of bone tissue whose longest dimension is of about 20 cm.

According to some embodiments, the pieces of bone tissue that are to be demineralized have a shortest dimension (which is used herein as an equivalent term to "minimum dimension") that is measurable prior to demineralization of the pieces of bone. All such shortest dimensions related in this paragraph are the shortest dimension of a piece of bone tissue prior to demineralization. According to some embodiments, the plurality of pieces of bone tissue includes at least one piece of bone tissue whose shortest dimension is of about 10 μm to about 20 cm. According to some such embodiments, the plurality of pieces of bone tissue includes a piece of bone tissue whose shortest dimension is of about 10 μm. According to some such embodiments, the plurality of pieces of bone tissue includes a piece of bone tissue whose shortest dimension is of about 20 μm. According to some such embodiments, the plurality of pieces of bone tissue includes at least one piece of bone tissue whose shortest dimension is of about 30 μm. According to some such embodiments, the plurality of pieces of bone tissue includes at least one piece of bone tissue whose shortest dimension is of about 40 μm. According to some such embodiments, the plurality of pieces of bone tissue includes at least one piece of bone tissue whose shortest dimension is of about 50 μm. According to some such embodiments, the plurality of pieces of bone tissue includes at least one piece of bone tissue whose shortest dimension is of about 100 μm. According to some such embodiments, the plurality of pieces of bone tissue includes at least one piece of bone tissue whose shortest dimension is of about 150 μm. According to some such embodiments, the plurality of pieces of bone tissue includes at least one piece of bone tissue whose shortest dimension is of about 200 μm. According to some such embodiments, the plurality of pieces of bone tissue includes at least one piece of bone tissue whose shortest dimension is of about 250 μm. According to some such embodiments, the plurality of pieces of bone tissue includes at least one piece of bone tissue whose shortest dimension is of about 300 μm. According to some embodiments, the plurality of pieces of bone tissue includes at least one piece of bone tissue having a shortest dimension in the range of about 5 μm to about 300 μm. According to some such embodiments, the plurality of pieces of bone tissue includes at least one piece of bone tissue whose shortest dimension is of about 350 μm. According to some such embodiments, the plurality of pieces of bone tissue includes at least one piece of bone tissue whose shortest dimension is of about 400 μm. According to some such embodiments, the plurality of pieces of bone tissue includes at least one piece of bone tissue whose shortest dimension is of about 450 μm. According to some such embodiments, the plurality of pieces of bone tissue includes at least one piece of bone tissue whose shortest dimension is of about 500 μm. According to some such embodiments, the plurality of pieces of bone tissue includes at least one piece of bone tissue whose shortest dimension is of about 550 μm. According to some such embodiments, the plurality of pieces of bone tissue includes at least one piece of bone tissue whose shortest dimension is of about 600 μm. According to some such embodiments, the plurality of pieces of bone tissue includes at least one piece of bone tissue whose shortest dimension is of about 650 μm. According to some such embodiments, the plurality of pieces of bone tissue includes at least one piece of bone tissue whose shortest dimension is of about 700 μm. According to some such embodiments, the plurality of pieces of bone tissue includes at least one piece of bone tissue whose shortest dimension is of about 750 μm. According to some such embodiments, the plurality of pieces of bone tissue includes at least one piece of bone tissue whose shortest dimension is of about 800 μm. According to some such embodiments, the plurality of pieces of bone tissue includes at least one piece of bone tissue whose shortest dimension is of about 850 μm. According to some such embodiments, the plurality of pieces of bone tissue includes at least one piece of bone tissue whose shortest dimension is of about 900 μm. According to some such embodiments, the plurality of pieces of bone tissue includes at least one piece of bone tissue whose shortest dimension is of about 950 μm. According to some such embodiments, the plurality of pieces of bone tissue includes at least one piece of bone tissue whose shortest dimension is in the range of about 100 μm to about 1000 μm. According to some such embodiments, the plurality of pieces of bone tissue includes at least one piece of bone tissue whose shortest dimension is of about 1 mm. According to some such embodiments, the plurality of pieces of bone tissue includes at least one piece of bone tissue whose shortest dimension is of about 2 mm. According to some such embodiments, the plurality of pieces of bone tissue includes at least one piece of bone tissue whose shortest dimension is of about 3 mm. According to some such embodiments, the plurality of pieces of bone tissue includes at least one piece of bone tissue whose shortest dimension is of about 4 mm. According to some such embodiments, the plurality of pieces of bone tissue includes at least one piece of bone tissue whose shortest dimension is of about 5 mm. According to some such embodiments, the plurality of pieces of bone tissue includes at least one piece of bone tissue whose shortest dimension is of about 6 mm. According to some such embodiments, the plurality of pieces of bone tissue includes at least one piece of bone tissue whose shortest dimension is of about 7 mm. According to some such embodiments, the plurality of pieces of bone tissue includes at least one piece of bone tissue whose shortest dimension is of about 8 mm. According to some such embodiments, the plurality of pieces of bone tissue includes at least one piece of bone tissue whose shortest dimension is of about 9 mm. According to some such embodiments, the plurality of pieces of bone tissue includes at least one piece of bone tissue whose shortest dimension is of about 10 mm. According to some such embodiments, the plurality of pieces of bone tissue includes at least one piece of bone tissue whose shortest dimension is in the range of about 1 mm to about 10 mm. According to some such embodiments, the plurality of pieces of bone tissue includes at least one piece of bone tissue whose shortest dimension is of about 50 mm. According to some such embodiments, the plurality of pieces of bone tissue includes at least one piece of bone tissue whose shortest dimension is of about 100 mm. According to some such embodiments, the plurality of pieces of bone tissue includes at least one piece of bone tissue whose shortest dimension is of about 200 mm. According to some such embodiments, the plurality of pieces of bone tissue includes at least one piece of bone tissue whose shortest dimension is of about 300 mm. According to some such embodiments, the plurality of pieces of bone tissue includes at least one piece of bone tissue whose shortest dimension is of about 400 mm. According to some such embodiments, the plurality of pieces of bone tissue includes at least one piece of bone tissue whose shortest dimension is of about 500 mm. According to some such embodiments, the plurality of pieces of bone tissue includes at least one piece of bone tissue whose shortest dimension is of about 600 mm. According to some such embodiments, the plurality of pieces of bone tissue includes at least one piece of bone tissue whose shortest dimension is of about 700 mm. According to some such embodiments, the plurality of pieces of bone tissue includes at least one piece of bone tissue whose shortest dimension is of about 800 mm. According to some such embodiments, the plurality of pieces of bone tissue includes at least one piece of bone tissue whose shortest dimension is of about 900 mm. According to some such embodiments, the plurality of pieces of bone tissue includes at least one piece of bone tissue whose shortest dimension is of about 1 cm. According to some such embodiments, the plurality of pieces of bone tissue includes at least one piece of bone tissue whose shortest dimension is of about 2 cm. According to some such embodiments, the plurality of pieces of bone tissue includes at least one piece of bone tissue whose shortest dimension is of about 3 cm. According to some such embodiments, the plurality of pieces of bone tissue includes at least one piece of bone tissue whose shortest dimension is of about 4 cm. According to some such embodiments, the plurality of pieces of bone tissue includes at least one piece of bone tissue whose shortest dimension is of about 5 cm. According to some such embodiments, the plurality of pieces of bone tissue includes at least one piece of bone tissue whose shortest dimension is of about 6 cm. According to some such embodiments, the plurality of pieces of bone tissue includes at least one piece of bone tissue whose shortest dimension is of about 7 cm. According to some such embodiments, the plurality of pieces of bone tissue includes at least one piece of bone tissue whose shortest dimension is of about 8 cm. According to some such embodiments, the plurality of pieces of bone tissue includes at least one piece of bone tissue whose shortest dimension is of about 9 cm. According to some such embodiments, the plurality of pieces of bone tissue includes at least one piece of bone tissue whose shortest dimension is of about 10 cm. According to some such embodiments, the plurality of pieces of bone tissue includes at least one piece of bone tissue whose shortest dimension is of about 11 cm. According to some such embodiments, the plurality of pieces of bone tissue includes at least one piece of bone tissue whose shortest dimension is of about 12 cm. According to some such embodiments, the plurality of pieces of bone tissue includes at least one piece of bone tissue whose shortest dimension is of about 13 cm. According to some such embodiments, the plurality of pieces of bone tissue includes at least one piece of bone tissue whose shortest dimension is of about 14 cm. According to some such embodiments, the plurality of pieces of bone tissue includes at least one piece of bone tissue whose shortest dimension is of about 15 cm. According to some such embodiments, the plurality of pieces of bone tissue includes at least one piece of bone tissue whose shortest dimension is of about 16 cm. According to some such embodiments, the plurality of pieces of bone tissue includes at least one piece of bone tissue whose shortest dimension is of about 17 cm. According to some such embodiments, the plurality of pieces of bone tissue includes at least one piece of bone tissue whose shortest dimension is of about 18 cm. According to some such embodiments, the plurality of pieces of bone tissue includes at least one piece of bone tissue whose shortest dimension is of about 19 cm. According to some such embodiments, the plurality of pieces of bone tissue includes at least one piece of bone tissue whose shortest dimension is of about 20 cm.

Rinsing step (c): rinsing the plurality of separated matrix pieces of (b) comprising the at least one viable population of tissuegenic cells adherent to and resident in the endogenous milieu of the growth-conductive matrix of (b) to form a plurality of rinsed separated matrix pieces comprising the at least one viable population of tissuegenic cells adherent to and resident in the the endogenous milieu of the growth-conductive matrix of (b), wherein a relative frequency of a stem cell subtype in the at least one viable tissuegenic cell population of step (c) is of a relative frequency substantially similar to that found in the growth-conductive matrix of step (a)

According to another embodiment, rinsing step (c) comprises admixing the plurality of separated growth-conductive matrix pieces of (b) comprising the at least one viable population of tissuegenic cells adherent to and resident in the endogenous milieu of the growth-conductive matrix with a liquid, wherein the liquid is a buffer. According to some embodiments, the liquid comprises a physiological saline solution. According to some embodiments, the liquid comprises a buffered isotonic solution. According to some embodiments, the physiological saline solution is a phosphate buffered saline (PBS) solution. According to some embodiments, the liquid comprises an acetic acid solution. According to some embodiments, the liquid comprises an ammonium chloride solution. According to some embodiments, the ammonium chloride solution further comprises ethylenediaminetetraacetic acid (EDTA). According to some such embodiments, the EDTA is at a concentration from about 0.1 mM to about 0.5 mM.

According to some embodiments, rinsing step (c) comprises admixing the plurality of separated growth-conductive matrix pieces of (b) with a liquid at a temperature of about 4° C. to about 10° C. According to some embodiments, rinsing step (c) comprises admixing the plurality of separated growth-conductive matrix pieces of (b) with a liquid at a temperature of about 25° C. According to some embodiments, rinsing step (c) comprises admixing the plurality of separated growth-conductive matrix pieces of (b) with a liquid at an ambient temperature.

According to one embodiment, rinsing step (c) comprises admixing the plurality of separated growth-conductive matrix pieces of (b) with a liquid such that unwanted cells are removed. According to one embodiment, the plurality of growth-conductive matrix pieces comprises a plurality of growth conductive matrix pieces from which unwanted cells have been removed. According to some embodiments, the at least one viable population of tissuegenic cells adherent to and resident in the endogenous milieu of the growth conductive matrix is immune privileged. The term "immune privileged" as used herein refers to the characteristic of tissuegenic cells by which there is no induction of an immune response upon transplantation of such cells.

According to another embodiment, the method of fabricating an implant further comprises step (f) supplementing the plurality of rinsed growth-conductive matrix pieces of step (c) with at least one growth-inductivecomponent. According to some such embodiments, the at least one growth-inductivecomponent comprises at least one growth-inductivefactor. According to some such embodiments, the at least one growth-inductivefactor comprises at least one growth factor. According to some such embodiments, the at least one growth factor is fibroblast growth factor-2 (FGF-2). According to some such embodiments, the at least one growth factor is fibroblast growth factor-5 (FGF-5). According to some such embodiments, the at least one growth factor is insulin-like growth factor 1 (IGF-1). According to some such embodiments, the at least one growth factor is transforming growth factor beta (TGF-β). According to some such embodiments, the at least one growth factor is bone morphogenic protein-2 (BMP-2). According to some such embodiments, the at least one growth factor is bone morphogenic protein-7 (BMP-7). According to some such embodiments, the at least one growth factor is platelet-derived growth factor (PDGF). According to some such embodiments, the at least one growth factor is vascular endothelial growth factor (VEGF). According to some such embodiments, the at least one growth factor is neural epidermal growth-factor-like 1 (NELL-1). According to another embodiment, the rinsed growth conductive matrix pieces are supplemented with at least one cytokine.

According to one embodiment, the at least one growth-inductive component is tissue-derived. According to one embodiment, the at least one growth-inductive component comprises inducible pluripotent stem cells (iPSCs). According to one embodiment, the at least one growth-inductive component originates from a component of the tissue-derived growth-inductive component other than cells. According to one embodiment, the at least one growth-inductive component is endogenous to the at least one growth-conductive matrix. According to one embodiment, the tissuegenic cells adherent to and resident in the endogenous milieu of the growth conductive matrix secrete the at least one growth-inductive component. According to one embodiment, the at least one growth-inductivecomponent is exogenous to the at least one growth-conductive matrix. According to one embodiment, the growth-inductive component comprises a growth medium derived from expanded tissuegenic cells. According to one embodiment, the at least one growth-inductive component comprises demineralized bone matrix, which may be demineralized cortical bone.

Packaging Step (e): packaging the plurality of collected rinsed separated matrix pieces of (d) comprising at least one viable population of tissuegenic cells adherent to and resident in the endogenous milieu of the growth-conductive matrix of (c) wherein the at least one viable tissuegenic cell population is of a similar relative frequency as found in the growth-conductive matrix of step (a) to form the implant.

Cryopreservation is used for the long-term preservation of various tissues and cells. According to some embodiments, tissuegenic cells derived from a tissue can be cryopreserved, reconstituted, and seeded onto an isolated matrix. According to some embodiments, tissuegenic cells derived from a tissue can be cryopreserved, reconstituted, and seeded onto an isolated matrix to promote tissuegenesis in vitro and in vivo. According to some such embodiments, the isolated matrix is a demineralized bone matrix, which may be demineralized cortical bone.

Water is the major component of all living cells and must be available for the chemical processes of life to occur; cellular metabolism stops when all water in the system is converted to ice. For reconstitution, most cells are warmed quickly until complete thawing is achieved (e.g., a 37° C. water bath) in order to prevent recrystallization of ice.

The detrimental effects of ice crystal formation and increased solute concentration can be reduced by using cryoprotective additives or chemicals that protect cells during freezing. Commonly used cryoprotective agents include, but are not limited to, dimethylsulfoxide (DMSO), ethylene glycol, propylene glycol, 2-Methyl-2.4-pentanediol (MPD), sucrose, and glycerol. Examples of cryopreservation solutions that can be used in preserving a tissue or a matrix include, but are not limited to, a commercially available basal media solution such as, Mesencult (Stem Cell Technologies), or Hyclone AdvanceStem, Fetal Bovine Serum with 5-15% DMSO, Bovine Serum Albumin with 5-15% DMSO, Human Serum Albumin with 5-15% DMSO, Aedesta (Cell Preservation Solutions), LiforCell (Lifeblood Medical), ethylene glycol, propylene glycol, and glycerol.

According to one embodiment, the growth-conductive matrix of step (a), step (b), step (c) or step (d) comprises a frozen growth-conductive matrix. According to one embodiment, the growth-conductive matrix of step (a), step (b), step (c) or step (d) comprises a fresh growth-conductive matrix.

According to some embodiments, packaging step (e) comprises admixing the plurality of collected rinsed separated matrix pieces of (d) with at least one cryopreservative. According to some such embodiments, packaging step (e) comprises admixing the plurality of collected rinsed separated matrix pieces of (d) with at least one cryopreservative, wherein the cryopreservative is a solution. According to some such embodiments, packaging step (e) comprises admixing the plurality of collected rinsed separated matrix pieces of (d) with at least one cryopreservative, wherein the cryopreservative is dimethylsulfoxide (DMSO). According to some such embodiments, packaging step (e) comprises admixing the plurality of collected rinsed separated matrix pieces of (d) with at least one cryopreservative, wherein the cryopreservative is a basal media solution comprising about 5% DMSO. According to some such embodiments, packaging step (e) comprises admixing the plurality of collected rinsed separated matrix pieces of (d) with at least one cryopreservative, wherein the cryopreservative is a basal media solution comprising about 10% DMSO. According to some such embodiments, packaging step (e) comprises admixing the plurality of collected rinsed separated matrix pieces of (d) with at least one cryopreservative, wherein the cryopreservative is a basal media solution comprising about 15% DMSO. According to some such embodiments, packaging step (e) comprises admixing the plurality of collected rinsed separated matrix pieces of (d) with at least one cryopreservative, wherein the cryopreservative comprises fetal bovine serum comprising about 5% DMSO. According to some such embodiments, packaging step (e) comprises admixing the plurality of collected rinsed separated matrix pieces of (d) with at least one cryopreservative, wherein the cryopreservative comprises fetal bovine serum comprising about 10% DMSO. According to some such embodiments, packaging step (e) comprises admixing the plurality of collected rinsed separated matrix pieces of (d) with at least one cryopreservative, wherein the cryopreservative comprises fetal bovine serum comprising about 15% DMSO. According to some such embodiments, packaging step (e) comprises admixing the plurality of collected rinsed separated matrix pieces of (d) with at least one cryopreservative, wherein the cryopreservative comprises bovine serum albumin (BSA) comprising about 5% DMSO. According to some such embodiments, packaging step (e) comprises admixing the plurality of collected rinsed separated matrix pieces of (d) with at least one cryopreservative, wherein the cryopreservative comprises BSA comprising about 10% DMSO. According to some such embodiments, packaging step (e) comprises admixing the plurality of collected rinsed separated matrix pieces of (d) with at least one cryopreservative, wherein the cryopreservative comprises BSA comprising about 15% DMSO. According to some such embodiments, packaging step (e) comprises admixing the plurality of collected rinsed separated matrix pieces of (d) with at least one cryopreservative, wherein the cryopreservative comprises human serum comprising about 5% DMSO. According to some such embodiments, packaging step (e) comprises admixing the plurality of collected rinsed separated matrix pieces of (d) with at least one cryopreservative, wherein the cryopreservative comprises human serum comprising about 10% DMSO. According to some such embodiments, packaging step (e) comprises admixing the plurality of collected rinsed separated matrix pieces of (d) with at least one cryopreservative, wherein the cryopreservative comprises human serum comprising about 15% DMSO. According to some such embodiments, packaging step (e) comprises admixing the plurality of collected rinsed separated matrix pieces of (d) with at least one cryopreservative, wherein the cryopreservative comprises human serum albumin comprising about 5% DMSO. According to some such embodiments, packaging step (e) comprises admixing the plurality of collected rinsed separated matrix pieces of (d) with at least one cryopreservative, wherein the cryopreservative comprises human serum albumin comprising about 10% DMSO. According to some such embodiments, packaging step (e) comprises admixing the plurality of collected rinsed separated matrix pieces of (d) with at least one cryopreservative, wherein the cryopreservative comprises human serum albumin comprising about 15% DMSO. According to some such embodiments, packaging step (e) comprises admixing the plurality of collected rinsed separated matrix pieces of (d) with at least one cryopreservative, wherein the cryopreservative comprises ethylene glycol. According to some such embodiments, packaging step (e) comprises admixing the plurality of collected rinsed separated matrix pieces of (d) with at least one cryopreservative, wherein the cryopreservative comprises propylene glycol. According to some such embodiments, packaging step (e) comprises admixing the plurality of collected rinsed separated matrix pieces of (d) with at least one cryopreservative, wherein the cryopreservative comprises glycerol.

According to some embodiments of the described invention, the packaged implant can be preserved for an extended period of time by slowly cooling the packaged implant in the presence of a cryoprotective agent and by storing at ultra low temperatures. According to some such embodiments, packaging step (e) comprises freezing the the plurality of growth-conductive matrix pieces to at least a temperature of −80° C. According to some such embodiments, packaging step (e) comprises freezing the plurality of collected growth-conductive matrix pieces at a controlled freezing rate. According to some such embodiments, the controlled freezing rate is a controlled freezing rate of about 0.5° C. per minute to about 10° C. per minute. According to some such embodiments, the controlled freezing rate is a controlled freezing rate of about 1° C. per minute until about −100° C.

According to some such embodiments, the method of fabricating an implant further comprises (f) thawing the plurality of rinsed growth-conductive matrix pieces of step (e) to form a plurality of thawed rinsed growth-conductive matrix pieces. According to some such embodiments, the plurality of growth-conductive matrix pieces comprises the implant.

According to another embodiment, the packaged implant comprising the plurality of packaged growth-conductive matrix pieces of (e) comprises at least one viable population of tissuegenic cells adherent to and resident in the endogenous milieu of the growth-conductive matrix. According to some such embodiments, the at least one viable population of tissuegenic cells adherent to and resident in the endogenous milieu of the growth-conductive matrix is derived from an adipose tissue. According to some such embodiments, the at least one viable population of tissuegenic cells adherent to and resident in the endogenous milieu of the growth-conductive matrix is derived from an amnion tissue. According to some such embodiments, the at least one viable population of tissuegenic cells adherent to and resident in the endogenous milieu of the growth-conductive matrix is derived from an artery tissue. According to some such embodiments, the at least one viable population of tissuegenic cells adherent to and resident in the endogenous milieu of the growth-conductive matrix is derived from a bone tissue. According to some such embodiments, the at least one viable population of tissuegenic cells adherent to and resident in the endogenous milieu of the growth-conductive matrix is derived from a cartilage tissue. According to some such embodiments, the at least one viable population of tissuegenic cells adherent to and resident in the endogenous milieu of the growth-conductive matrix is derived from a chorion tissue. According to some such embodiments, the at least one viable population of tissuegenic cells adherent to and resident in the endogenous milieu of the growth-conductive matrix is derived from a colon tissue. According to some such embodiments, the at least one viable population of tissuegenic cells adherent to and resident in the endogenous milieu of the growth-conductive matrix is derived from a dental tissue. According to some such embodiments, the at least one viable population of tissuegenic cells adherent to and resident in the endogenous milieu of the growth-conductive matrix is derived from a dermal tissue. According to some such embodiments, the at least one viable population of tissuegenic cells adherent to and resident in the endogenous milieu of the growth-conductive matrix is derived from a duodenal tissue. According to some such embodiments, the at least one viable population of tissuegenic cells adherent to and resident in the endogenous milieu of the growth-conductive matrix is derived from an epithelial tissue. According to some such embodiments, the at least one viable population of tissuegenic cells adherent to and resident in the endogenous milieu of the growth-conductive matrix is derived from a fascial tissue. According to some such embodiments, the at least one viable population of tissuegenic cells adherent to and resident in the endogenous milieu of the growth-conductive matrix is derived from a gastrointestinal tissue. According to some such embodiments, the at least one viable population of tissuegenic cells adherent to and resident in the endogenous milieu of the growth-conductive matrix is derived from a growth plate tissue. According to some such embodiments, the at least one viable population of tissuegenic cells adherent to and resident in the endogenous milieu of the growth-conductive matrix is derived from an intervertebral disc tissue. According to some such embodiments, the at least one viable population of tissuegenic cells adherent to and resident in the endogenous milieu of the growth-conductive matrix is derived from an intestinal mucosal tissue. According to some such embodiments, the at least one viable population of tissuegenic cells adherent to and resident in the endogenous milieu of the growth-conductive matrix is derived from an intestinal serosal tissue. According to some such embodiments, the at least one viable population of tissuegenic cells adherent to and resident in the endogenous milieu of the growth-conductive matrix is derived from a kidney tissue. According to some such embodiments, the at least one viable population of tissuegenic cells adherent to and resident in the endogenous milieu of the growth-conductive matrix is derived from a ligament tissue. According to some such embodiments, the at least one viable population of tissuegenic cells adherent to and resident in the endogenous milieu of the growth-conductive matrix is derived from a liver tissue. According to some such embodiments, the at least one viable population of tissuegenic cells adherent to and resident in the endogenous milieu of the growth-conductive matrix is derived from a lung tissue. According to some such embodiments, the at least one viable population of tissuegenic cells adherent to and resident in the endogenous milieu of the growth-conductive matrix is derived from a mammary tissue. According to some such embodiments, the at least one viable population of tissuegenic cells adherent to and resident in the endogenous milieu of the growth-conductive matrix is derived from a meniscal tissue. According to some such embodiments, the at least one viable population of tissuegenic cells adherent to and resident in the endogenous milieu of the growth-conductive matrix is derived from a muscle tissue. According to some such embodiments, the at least one viable population of tissuegenic cells adherent to and resident in the endogenous milieu of the growth-conductive matrix is derived from a nerve tissue. According to some such embodiments, the at least one viable population of tissuegenic cells adherent to and resident in the endogenous milieu of the growth-conductive matrix is derived from an ovarian tissue. According to some such embodiments, the at least one viable population of tissuegenic cells adherent to and resident in the endogenous milieu of the growth-conductive matrix is derived from a pancreatic tissue. According to some such embodiments, the at least one viable population of tissuegenic cells adherent to and resident in the endogenous milieu of the growth-conductive matrix is derived from a parenchymal organ tissue. According to some such embodiments, the at least one viable population of tissuegenic cells adherent to and resident in the endogenous milieu of the growth-conductive matrix is derived from a pericardial tissue. According to some such embodiments, the at least one viable population of tissuegenic cells adherent to and resident in the endogenous milieu of the growth-conductive matrix is derived from a periosteal tissue. According to some such embodiments, the at least one viable population of tissuegenic cells adherent to and resident in the endogenous milieu of the growth-conductive matrix is derived from a peritoneal tissue. According to some such embodiments, the at least one viable population of tissuegenic cells adherent to and resident in the endogenous milieu of the growth-conductive matrix is derived from a placental tissue. According to some such embodiments, the at least one viable population of tissuegenic cells adherent to and resident in the endogenous milieu of the growth-conductive matrix is derived from a skin tissue. According to some such embodiments, the at least one viable population of tissuegenic cells adherent to and resident in the endogenous milieu of the growth-conductive matrix is derived from a spleen tissue. According to some such embodiments, the at least one viable population of tissuegenic cells adherent to and resident in the endogenous milieu of the growth-conductive matrix is derived from a stomach tissue. According to some such embodiments, the at least one viable population of tissuegenic cells adherent to and resident in the endogenous milieu of the growth-conductive matrix is derived from a tendon tissue. According to some such embodiments, the at least one viable population of tissuegenic cells adherent to and resident in the endogenous milieu of the growth-conductive matrix is derived from a synovial tissue. According to some such embodiments, the at least one viable population of tissuegenic cells adherent to and resident in the endogenous milieu of the growth-conductive matrix is derived from a tendon tissue. According to some such embodiments, the at least one viable population of tissuegenic cells adherent to and resident in the endogenous milieu of the growth-conductive matrix is derived from a testes tissue. According to some such embodiments, the at least one viable population of tissuegenic cells adherent to and resident in the endogenous milieu of the growth-conductive matrix is derived from an umbilical cord tissue. According to some such embodiments, the at least one viable population of tissuegenic cells adherent to and resident in the endogenous milieu of the growth-conductive matrix is derived from a urological tissue. According to some such embodiments, the at least one viable population of tissuegenic cells adherent to and resident in the endogenous milieu of the growth-conductive matrix is derived from a vascular tissue. According to some such embodiments, the at least one viable population of tissuegenic cells adherent to and resident in the endogenous milieu of the growth-conductive matrix is derived from a vein tissue.

According to another embodiment, the method of fabricating an implant further comprises step (f) supplementing the plurality of rinsed growth-conductive matrix pieces of step (c) with at least one growth-inductive component. According to some such embodiments, the at least one growth-inductive component comprises at least one growth-inductive factor. According to some such embodiments, the at least one growth-inductive factor comprises at least one growth factor. According to some such embodiments, the at least one growth-inductive component comprises a demineralized cortical bone. According to some such embodiments, the at least one growth factor is fibroblast growth factor-2 (FGF-2). According to some such embodiments, the at least one growth factor is fibroblast growth factor-5

(FGF-5). According to some such embodiments, the at least one growth factor is insulin-like growth factor 1 (IGF-1). According to some such embodiments, the at least one growth factor is transforming growth factor beta (TGF-β). According to some such embodiments, the at least one growth factor is bone morphogenic protein-2 (BMP-2). According to some such embodiments, the at least one growth factor is bone morphogenic protein-7 (BMP-7). According to some such embodiments, the at least one growth factor is platelet-derived growth factor (PDGF). According to some such embodiments, the at least one growth factor is vascular endothelial growth factor (VEGF). According to some such embodiments, the at least one growth factor is neural epidermal growth-factor-like 1 (NELL-1). According to another embodiment, the rinsed osteoconductive matrix particles are supplemented with at least one cytokine.

According to one embodiment, the at least one growth-inductive component is tissue-derived. According to one embodiment, the at least one growth-inductive component comprises inducible pluripotent stem cells (iPSCs). According to one embodiment, the at least one growth-inductive component originates from a component of the tissue-derived growth-inductivecomponent other than cells. According to one embodiment, the at least one growth-inductive component is endogenous to the at least one growth-conductive matrix. According to one embodiment, the tissuegenic cells adherent to and resident in the endogenous milieu of the growth conductive matrix secrete the at least one growth-inductive component. According to one embodiment, the at least one growth-inductive component is exogenous to the at least one growth-conductive matrix. According to one embodiment, the growth-inductive component comprises a growth medium derived from expanded tissuegenic cells.

3. Method of Fabricating an Implant Using a Tissue-Derived Matrix Containing Reseeded Tissuegenic Cells Caused to be in Contact with the Matrix According to another aspect, the described invention provides a method of fabricating an implant, the method comprising steps:

(i) providing at least one first growth-conductive matrix or a fragment thereof derived from human tissue, wherein the growth-conductive matrix comprises at least one viable population of tissuegenic cells endogenous to the tissue, wherein the tissuegenic cells are adherent to and resident in the endogenous milieu of the first growth-conductive matrix;

(ii) isolating from the at least one growth-conductive matrix of (i) a plurality of the at least one viable isolated population of tissuegenic cells;

(iii) processing a second growth-conductive matrix comprising a decellularized growth-conductive matrix to generate a plurality of pieces;

(iv) seeding the decellularized growth-conductive matrix pieces of (iii) with the plurality of at least one viable isolated population of tissuegenic cells of (ii) to form a plurality of reseeded growth-conductive matrix pieces, wherein the at least one viable population of tissuegenic cells is caused to be in contact with the growth-conductive matrix;

(v) collecting the plurality of reseeded growth-conductive matrix pieces of (iv) comprising the at least one viable population of tissuegenic cells caused to be in contact with the growth-conductive matrix of (iv), wherein the at least one viable tissuegenic cell population is of a relative frequency substantially similar to that found in the growth-conductive matrix of step (i);

(vi) packaging the plurality of collected reseeded growth-conductive matrix pieces of (v) comprising the at least one viable population of tissuegenic cells caused to be in contact with the growth-conductive matrix of (iv), wherein the at least one viable tissuegenic cell population is of a relative frequency substantially similar to that found in the growth-conductive matrix of step (i) to form an implant.

Isolating step (ii): isolating from the at least one growth-conductive matrix of (i) a plurality of the at least one viable isolated population of tissuegenic cells According to some embodiments, isolating step (ii) comprises isolating from the at least one growth-conductive matrix of (i) a plurality of the at least one viable isolated population of tissuegenic cells.

According to some such embodiments, isolating step (ii) comprises the steps: (1) washing of the tissue of (i); (2) optionally digesting the washed tissue of (1); (3) fractionating the tissue of (1) or the digested tissue of (2) into an isolated fraction comprising at least one viable population of tissuegenic cells; (4) washing the isolated fraction comprising at least one viable population of tissuegenic cells; and (5) filtering the washed fraction comprising at least one viable population of tissuegenic cells to generate a plurality of the at least one viable isolated population of tissuegenic cells.

According to some embodiments, isolating step (ii) is at a temperature of about 25° C. According to some embodiments, isolating step (ii) is at a temperature of about 4° C. to about 10° C. According to some embodiments, isolating step (ii) is at an ambient temperature. According to some embodiments, washing step (1) is at a temperature of about 25° C. According to some embodiments, washing step (1) is at a temperature of about 4° C. to about 10° C. According to some embodiments, washing step (1) is at an ambient temperature. According to some embodiments, digesting step (2) is at a temperature of about 25° C. According to some embodiments, digesting step (2) is at a temperature of about 4° C. to about 10° C. According to some embodiments, digesting step (2) is at an ambient temperature. According to some embodiments, fractionating step (3) is at a temperature of about 25° C. According to some embodiments, fractionating step (3) is at a temperature of about 4° C. to about 10° C. According to some embodiments, fractionating step (3) is at an ambient temperature. According to some embodiments, washing step (4) is at a temperature of about 25° C. According to some embodiments, washing step (4) is at a temperature of about 4° C. to about 10° C. According to some embodiments, washing step (4) is at an ambient temperature. According to some embodiments, filtering step (5) is at a temperature of about 25° C. According to some embodiments, filtering step (5) is at a temperature of about 4° C. to about 10° C. According to some embodiments, filtering step (5) is at an ambient temperature.

According to some embodiments, washing step (1) comprise washing of the tissue of (i) with a liquid. According to some embodiments, washing step (1) comprises washing of the tissue of (i) with a liquid wherein the liquid is a buffer. According to some embodiments, washing step (1) comprises washing of the tissue of (i) with a buffer, wherein the buffer is a physiological saline solution. According to some embodiments, washing step (1) comprises washing of the tissue of (i) with a buffer, wherein the buffer is a buffered isotonic solution. According to some embodiments, washing step (1) comprises washing of the tissue of (i) with a buffer, wherein the buffer is a buffered salt solution. According to some embodiments, the buffered salt solution is a Hank's buffered salt solution (HBSS). According to some embodiments, the buffered salt solution is a phosphate buffered saline (PBS) solution.

According to some embodiments, optional digesting step (2) comprises digesting the washed tissue of (1) with an enzyme to yield a crude extract. According to some embodiments, digesting step (2) comprises digesting the washed tissue of (1) with an enzyme, wherein the enzyme is collagenase. According to some embodiments, digesting step (2) comprises digesting the washed tissue of (1) with an enzyme, wherein the enzyme is trypsin. According to some such embodiments, isolating step (ii) optionally comprises a step comprising admixing the crude extract of step (2) with a neutralizing solution. According to some such embodiments, neutralizing solution is a basal media solution. According to some embodiments, the neutralizing solution comprises serum. According to some embodiments, the serum comprises a human serum. According to some such embodiments, fractionating step (3) comprises isolating from the optionally neutralized crude extract of step (2) to yield a fraction comprising at least one viable population of tissuegenic cells. According to some such embodiments, fractionating step (3) comprises a centrifugation step. According to some such embodiments, centrifugation step generates a pellet fraction comprising at least one viable population of tissuegenic cells. According to some such embodiments, fractionating step (3) further comprises resuspending the pellet in a liquid. According to some embodiments, the liquid is a basal media solution. According to some embodiments, the resuspended pellet fraction comprising at least one viable population of tissuegenic cells is further digested with an enzyme to yield a double-digested extract comprising at least one viable population of tissuegenic cells. According to some embodiments, the double-digested extract comprising the at least one viable population of tissuegenic cells is fractionated to yield an isolated fraction comprising the at least one viable population of tissuegenic cells.

According to some embodiments, fractionating step (3) comprises isolating a fraction comprising the at least one viable population of tissuegenic cells from the tissue of step (1), using an immunoseparation step. The immunoseparation step can be any cell based immunoseparation methods well known in the art, including but not limited to immunoprecipitation using magnetic beads, affinity chromatography, fluorescence activated cell sorting (FACS) or flow cytometry.

According to some embodiments, the isolated fraction comprising the at least one viable population of tissuegenic cells comprises a nonexpanded population of tissuegenic cells. According to some embodiments, the isolated fraction comprising the at least one viable population of tissuegenic cells is further expanded to generate an expanded population of tissuegenic cells. Any method of clonal expansion well known in the art can be used.

According to some embodiments, isolating step (ii) further comprises a washing step, wherein the isolated fraction of the at least one viable population of tissuegenic cells is further washed with a liquid. According to some embodiments, the liquid comprises a buffered isotonic solution. According to some embodiments, the liquid comprises a buffered salt solution. According to some embodiments, the buffered salt solution comprises a PBS solution. According to some embodiments, isolating step (ii) further comprises a filtering step, wherein the isolated fraction of the at least one viable population of tissuegenic cells is filtered.

According to another embodiment, the method of fabricating an implant further comprises step (vii) supplementing the plurality of the at least one viable isolated population of tissuegenic cells. According to some such embodiments, the at least one growth-inductive component comprises at least one growth-inductive factor. According to some such embodiments, the at least one growth-inductive factor comprises at least one growth factor. According to some such embodiments, the at least one growth-inductive component comprises a demineralized bone matrix, which may be demineralized cortical bone. According to some such embodiments, the at least one growth factor is fibroblast growth factor-2 (FGF-2). According to some such embodiments, the at least one growth factor is fibroblast growth factor-5 (FGF-5). According to some such embodiments, the at least one growth factor is insulin-like growth factor 1 (IGF-1). According to some such embodiments, the at least one growth factor is transforming growth factor beta (TGF-β). According to some such embodiments, the at least one growth factor is bone morphogenic protein-2 (BMP-2). According to some such embodiments, the at least one growth factor is bone morphogenic protein-7 (BMP-7). According to some such embodiments, the at least one growth factor is platelet-derived growth factor (PDGF). According to some such embodiments, the at least one growth factor is vascular endothelial growth factor (VEGF). According to some such embodiments, the at least one growth factor is neural epidermal growth-factor-like 1 (NELL-1). According to another embodiment, the rinsed osteoconductive matrix particles are supplemented with at least one cytokine.

According to one embodiment, the at least one growth-inductive component is tissue-derived. According to one embodiment, the at least one growth-inductive component comprises inducible pluripotent stem cells (iPSCs). According to one embodiment, the at least one growth-inductive component originates from a component of the tissue-derived growth-inductive component other than cells. According to one embodiment, the at least one growth-inductive component is endogenous to the at least one growth-conductive matrix. According to one embodiment, the tissuegenic cells adherent to and resident in the endogenous milieu of the growth conductive matrix secrete the at least one growth-inductive component. According to one embodiment, the at least one growth-inductive component is exogenous to the at least one growth-conductive matrix. According to one embodiment, the growth-inductive component comprises a growth medium derived from expanded tissuegenic cells. According to one embodiment, the at least one growth-inductive component comprises a demineralized bone matrix, which may be demineralized cortical bone.

Processing Step (iii): processing a second growth-conductive matrix comprising a decellularized growth-conductive matrix to generate a plurality of pieces According to some embodiments, processing step (iii) comprises steps: (1) preparing the at least one growth-conductive matrix derived from a tissue so as to yield a plurality of growth-conductive matrix pieces; (2) soaking the plurality of growth-conductive matrix pieces of (1); and (3) decellularizing the plurality of growth-conductive matrix pieces of (2) to generate a plurality of decellularized growth-conductive matrix pieces.

According to some embodiments, preparing step (1) comprises mincing the tissue. According to some embodiments, preparing step (1) comprises cutting the tissue. According to some embodiments, preparing step (1) comprises slicing the tissue. According to some embodiments, preparing step (1)

comprises milling the tisse. According to some embodiments, procuring step (1) comprises homogenizing the tissue.

According to some embodiments, processing step (iii) is at a temperature of about 25° C. According to some embodiments, processing step (iii) is at a temperature of about 4° C. to about 10° C. According to some embodiments, processing step (iii) is at an ambient temperature. According to some embodiments, preparing step (1) is at a temperature of about 25° C. According to some embodiments, preparing step (1) is at a temperature of about 4° C. to about 10° C. According to some embodiments, preparing step (1) is at an ambient temperature. According to some embodiments, soaking step (2) is at a temperature of about 25° C. According to some embodiments, soaking step (2) is at a temperature of about 4° C. to about 10° C. According to some embodiments, soaking step (2) is at an ambient temperature. According to some embodiments, decellularizing step (3) is at a temperature of about 25° C. According to some embodiments, decellularizing step (3) is at a temperature of about 4° C. to about 10° C. According to some embodiments, decellularizing step (3) is at an ambient temperature.

According to some embodiments, the plurality of growth-conductive matrix pieces of step (1) comprises a plurality of matrix particles. According to some embodiments, the plurality of growth-conductive matrix pieces of step (1) comprises a plurality of matrix slices. According to some embodiments, the plurality of growth-conductive matrix pieces of step (1) comprises a plurality of matrix sheets.

According to some embodiments, the plurality of growth-conductive matrix pieces can be of virtually any shape. According to some embodiments, the plurality of growth-conductive matrix pieces are of a similar shape. According to some embodiments, the plurality of growth-conductive matrix pieces are of a circular shape. According to some embodiments, the plurality of growth-conductive matrix pieces are of a square shape. According to some embodiments, the plurality of growth-conductive matrix pieces are of a polygonal shape. According to some embodiments, the plurality of growth-conductive matrix pieces are of a rectangular shape. According to some embodiments, the plurality of growth-conductive matrix pieces are of a triangular shape. According to some embodiments, the plurality of growth-conductive matrix pieces are of a octagonal shape. According to some embodiments, the plurality of growth-conductive matrix are of an irregular shape. According to some embodiments, the plurality of growth-conductive matrix pieces are of an elongated shape (e.g., as a fiber). According to some embodiments, the plurality of growth-conductive matrix pieces are of an amorphous shape.

According to some embodiments, the plurality of growth-conductive matrix pieces comprises at least one growth-conductive matrix piece whose longest dimension is of about 10 μm to about 20 cm. According to some such embodiments, the at least one growth-conductive matrix piece is a growth-conductive matrix piece whose longest dimension is of about 10 μm. According to some such embodiments, the at least one growth-conductive matrix piece is a growth-conductive matrix piece whose longest dimension is of about 20 μm. According to some such embodiments, the at least one growth-conductive matrix piece is a growth-conductive matrix piece whose longest dimension is of about 30 μm. According to some such embodiments, the at least one growth-conductive matrix piece is a growth-conductive matrix piece whose longest dimension is of about 40 μm. According to some such embodiments, the at least one growth-conductive matrix piece is a growth-conductive matrix piece whose longest dimension is of about 50 μm. According to some such embodiments, the at least one growth-conductive matrix piece is a growth-conductive matrix piece whose longest dimension is of about 100 μm. According to some such embodiments, the at least one growth-conductive matrix piece is a growth-conductive matrix piece whose longest dimension is of about 150 μm. According to some such embodiments, the at least one growth-conductive matrix piece is a osteocondgrowth-conductive matrix piece whose longest dimension is of about 200 μm. According to some such embodiments, the at least one growth-conductive matrix piece is a growth-conductive matrix piece whose longest dimension is of about 250 μm. According to some such embodiments, the at least one growth-conductive matrix piece is a growth-conductive matrix piece whose longest dimension is of about 300 μm. According to some such embodiments, the at least one growth-conductive matrix piece is a growth-conductive matrix piece whose longest dimension is of about 350 μm. According to some such embodiments, the at least growth-conductive matrix piece is a growth-conductive matrix piece whose longest dimension is of about 400 μm. According to some such embodiments, the at least one growth-conductive matrix piece is a growth-conductive matrix piece whose longest dimension is of about 450 μm. According to some such embodiments, the at least one growth-conductive matrix piece is a growth-conductive matrix piece whose longest dimension is of about 500 μm. According to some such embodiments, the at least one growth-conductive matrix piece is a growth-conductive matrix piece whose longest dimension is of about 550 μm. According to some such embodiments, the at least one growth-conductive matrix piece is a growth-conductive matrix piece whose longest dimension is of about 600 μm. According to some such embodiments, the at least one growth-conductive matrix piece is a growth-conductive matrix piece whose longest dimension is of about 650 μm. According to some such embodiments, the at least one growth-conductive matrix piece is a growth-conductive matrix piece whose longest dimension is of about 700 μm. According to some such embodiments, the at least one growth-conductive matrix piece is a growth-conductive matrix piece whose longest dimension is of about 750 μm. According to some such embodiments, the at least one growth-conductive matrix piece is a growth-conductive matrix piece whose longest dimension is of about 800 μm. According to some such embodiments, the at least one growth-conductive matrix piece is a growth-conductive matrix piece whose longest dimension is of about 850 μm. According to some such embodiments, the at least one growth-conductive matrix piece is a growth-conductive matrix piece whose longest dimension is of about 900 μm. According to some such embodiments, the at least one growth-conductive matrix piece is a growth-conductive matrix piece whose longest dimension is of about 950 μm. According to some such embodiments, the at least one growth-conductive matrix piece is a growth-conductive matrix piece whose longest dimension is in the range of about 100 μm to about 1000 μm.

According to some such embodiments, the at least one growth-conductive matrix piece is a growth-conductive matrix piece whose longest dimension is of about 1 mm. According to some such embodiments, the at least one growth-conductive matrix piece is a growth-conductive matrix piece whose longest dimension is of about 2 mm. According to some such embodiments, the at least one growth-conductive matrix piece is a growth-conductive matrix piece whose longest dimension is of about 3 mm. According to some such embodiments, the at least one growth-conductive matrix piece is a growth-conductive matrix piece whose longest dimension is of about 4 mm. According to some such embodiments, the at least one growth-conductive matrix piece is a growth-conductive matrix piece whose longest dimension is of about 5 mm. According to some such embodiments, the at least one growth-conductive matrix piece is a growth-conductive matrix piece whose longest dimension is of about 6 mm. According to some such embodiments, the at least one growth-conductive matrix piece is a growth-conductive matrix piece whose longest dimension is of about 7 mm. According to some such embodiments, the at least one growth-conductive matrix piece is a growth-conductive matrix piece whose longest dimension is of about 8 mm. According to some such embodiments, the at least one growth-conductive matrix piece is a growth-conductive matrix piece whose longest dimension is of about 9 mm. According to some such embodiments, the at least one growth-conductive matrix piece is a growth-conductive matrix piece whose longest dimension is of about 10 mm. According to some such embodiments, the at least one growth-conductive matrix piece is a growth-conductive matrix piece whose longest dimension is of about 12 mm. According to some such embodiments, the at least one growth-conductive matrix piece is a growth-conductive matrix piece whose longest dimension is of about 14 mm. According to some such embodiments, the at least one growth-conductive matrix piece is a growth-conductive matrix piece whose longest dimension is of about 16 mm. According to some such embodiments, the at least one growth-conductive matrix piece is a growth-conductive matrix piece whose longest dimension is of about 18 mm. According to some such embodiments, the at least one growth-conductive matrix piece is a growth-conductive matrix piece whose longest dimension is of about 20 mm. According to some such embodiments, the at least one growth-conductive matrix piece is a growth-conductive matrix piece whose longest dimension is of about 22 mm. According to some such embodiments, the at least one growth-conductive matrix piece is a growth-conductive matrix piece whose longest dimension is of about 24 mm. According to some such embodiments, the at least one growth-conductive matrix piece is a growth-conductive matrix piece whose longest dimension is of about 26 mm. According to some such embodiments, the at least one growth-conductive matrix piece is a growth-conductive matrix piece whose longest dimension is of about 28 mm. According to some such embodiments, the at least one growth-conductive matrix piece is a growth-conductive matrix piece whose longest dimension is of about 30 mm. According to some such embodiments, the at least one growth-conductive matrix piece is a growth-conductive matrix piece whose longest dimension is of about 35 mm. According to some such embodiments, the at least one growth-conductive matrix piece is a growth-conductive matrix piece whose longest dimension is of about 40 mm. According to some such embodiments, the at least one growth-conductive matrix piece is a growth-conductive matrix piece whose longest dimension is of about 45 mm. According to some such embodiments, the at least one growth-conductive matrix piece is a growth-conductive matrix piece whose longest dimension is of about 50 mm. According to some such embodiments, the at least one growth-conductive matrix piece is a growth-conductive matrix piece whose longest dimension is of about 100 mm. According to some such embodiments, the at least one growth-conductive matrix piece is a growth-conductive matrix piece whose longest dimension is of about 200 mm. According to some such embodiments, the at least one growth-conductive matrix piece is a growth-conductive matrix piece whose longest dimension is of about 300 mm. According to some such embodiments, the at least one growth-conductive matrix piece is a growth-conductive matrix piece whose longest dimension is of about 400 mm. According to some such embodiments, the at least one growth-conductive matrix piece is a growth-conductive matrix piece whose longest dimension is of about 500 mm. According to some such embodiments, the at least one growth-conductive matrix piece is a growth-conductive matrix piece whose longest dimension is of about 600 mm. According to some such embodiments, the at least one growth-conductive matrix piece is a growth-conductive matrix piece whose longest dimension is of about 700 mm. According to some such embodiments, the at least one growth-conductive matrix piece is a growth-conductive matrix piece whose longest dimension is of about 800 mm. According to some such embodiments, the at least one growth-conductive matrix piece is a growth-conductive matrix piece whose longest dimension is of about 900 mm. According to some such embodiments, the at least one growth-conductive matrix piece is a growth-conductive matrix piece whose longest dimension is of about 1000 mm.

According to some such embodiments, the at least one growth-conductive matrix piece is a growth-conductive matrix piece whose longest dimension is of about 1 cm. According to some such embodiments, the at least one growth-conductive matrix piece is a growth-conductive matrix piece whose longest dimension is of about 2 cm. According to some such embodiments, the at least one growth-conductive matrix piece is a growth-conductive matrix piece whose longest dimension is of about 3 cm. According to some such embodiments, the at least one growth-conductive matrix piece is a growth-conductive matrix piece whose longest dimension is of about 4 cm. According to some such embodiments, the at least one growth-conductive matrix piece is a growth-conductive matrix piece whose longest dimension is of about 5 cm. According to some such embodiments, the at least one growth-conductive matrix piece is a growth-conductive matrix piece whose longest dimension is of about 6 cm. According to some such embodiments, the at least one growth-conductive matrix piece is a growth-conductive matrix piece whose longest dimension is of about 7 cm. According to some such embodiments, the at least one growth-conductive matrix piece is a growth-conductive matrix piece whose longest dimension is of about 8 cm. According to some such embodiments, the at least one growth-conductive matrix piece is a growth-conductive matrix piece whose longest dimension is of about 9 cm. According to some such embodiments, the at least one growth-conductive matrix piece is a growth-conductive matrix piece whose longest dimension is of about 10 cm. According to some such embodiments, the at least one growth-conductive matrix piece is a growth-conductive matrix piece whose longest dimension is of about 11 cm. According to some such embodiments, the at least one growth-conductive matrix piece is a growth-conductive matrix piece whose longest dimension is of about 12 cm. According to some such embodiments, the at least one growth-conductive matrix piece is a growth-conductive matrix piece whose longest dimension is of about 13 cm. According to some such embodiments, the at least one growth-conductive matrix piece is a growth-conductive matrix piece whose longest dimension is of about 14 cm. According to some such embodiments, the at least one growth-conductive matrix piece is a growth-conductive matrix piece whose longest dimension is of about 15 cm. According to some such embodiments, the at least one growth-conductive matrix piece is a growth-conductive matrix piece whose longest dimension is of about 16 cm. According to some such embodiments, the at least one growth-conductive matrix piece is a growth-conductive matrix piece whose longest dimension is of about 17 cm. According to some such embodiments, the at least one growth-conductive matrix piece is a growth-conductive matrix piece whose longest dimension is of about 18 cm. According to some such embodiments, the at least one growth-conductive matrix piece is a growth-conductive matrix piece whose longest dimension is of about 19 cm. According to some such embodiments, the at least one growth-conductive matrix piece is a growth-conductive matrix piece whose longest dimension is of about 20 cm.

According to some embodiments, the plurality of separated growth-conductive matrix pieces can be of any form. According to some embodiments, the plurality of separated growth-conductive matrix pieces comprises a plurality of sheets. According to some embodiments, the plurality of separated growth-conductive matrix pieces comprises a powder form. According to some embodiments, the plurality of separated growth-conductive matrix pieces comprises a slurry form. According to some embodiments, the plurality of separated growth-conductive matrix pieces comprises a three-dimensional form. According to some embodiments, the three-dimensional form is selected from the group consisting of a block, a dowel, a sheet, and a combination thereof. According to some such embodiments, the three-dimensional form comprises a block. According to some such embodiments, the three-dimensional form comprises a dowel. According to some such embodiments, the three-dimensional form comprises a sheet.

According to some embodiments, soaking step (2) comprises soaking the plurality of growth-conductive matrix pieces of (1) with a liquid. According to some embodiments, soaking step (2) comprises soaking the plurality of growth-conductive matrix pieces of (1) with a liquid, wherein the liquid is a buffer. According to some embodiments, soaking step (2) comprises soaking the plurality of growth-conductive matrix pieces of (1) with a buffered isotonic solution. According to some embodiments, soaking step (2) comprises soaking of the plurality of growth-conductive matrix pieces of (1) with phosphate buffered saline (PBS). According to some embodiments, soaking step (2) comprises soaking the plurality of growth-conductive matrix pieces of (1) with tris buffered saline (TBS). According to some embodiments, soaking step (2) comprises soaking the plurality of growth-conductive matrix pieces of (1) with deionized water.

According to some embodiments, decellularizing step (3) comprises steps: (1) delipidating the plurality of growth-conductive matrix pieces; and (2) disinfecting the plurality of growth-conductive matrix pieces; to generate a plurality of pieces comprising a decellularized tissue derived growth-conductive matrix.

According to some embodiments, decellularizing step (3) further comprises step (4) lyophilizing the decellularized tissue derived growth-conductive matrix and exposing it to a freezer mill to generate a particularized tissue derived matrix powder. According to some embodiments, decellularizing step (3) further comprises step (4) homogenizing the decellularized tissue derived growth-conductive matrix to generate a decellularized tissue derived matrix paste. According to some embodiments, decellularizing step (3) further comprises step (4) homogenizing the decellularized tissue derived growth-conductive matrix to generate a decellularized tissue derived matrix slurry. According to some embodiments, decellularizing step (3) further comprises step (4) homogenizing the decellularized tissue derived growth-conductive matrix and a further step (5) lyophilizing the decellularized tissue derived growth-conductive matrix to generate a three dimensional decellularized tissue derived matrix. According to some embodiments, decellularizing step (3) further comprises a step (4) lyophilizing the decellularized tissue derived growth-conductive matrix to generate a decellularized tissue derived matrix sheet.

According to another embodiment, the method of fabricating an implant further comprises step (vii) supplementing the plurality of growth-conductive matrix pieces. According to some such embodiments, the at least one growth-inductive component comprises at least one growth-inductive factor. According to some such embodiments, the at least one growth-inductive factor comprises at least one growth factor. According to some such embodiments, the at least one growth factor is fibroblast growth factor-2 (FGF-2). According to some such embodiments, the at least one growth factor is fibroblast growth factor-5 (FGF-5). According to some such embodiments, the at least one growth factor is insulin-like growth factor 1 (IGF-1). According to some such embodiments, the at least one growth factor is transforming growth factor beta (TGF-β). According to some such embodiments, the at least one growth factor is bone morphogenic protein-2 (BMP-2). According to some such embodiments, the at least one growth factor is bone morphogenic protein-7 (BMP-7). According to some such embodiments, the at least one growth factor is platelet-derived growth factor (PDGF). According to some such embodiments, the at least one growth factor is vascular endothelial growth factor (VEGF). According to some such embodiments, the at least one growth factor is neural epidermal growth-factor-like 1 (NELL-1). According to another embodiment, the rinsed osteoconductive matrix particles are supplemented with at least one cytokine.

According to some such embodiments, the at least one growth-inductive component comprises a demineralized bone matrix, which may be demineralized cortical bone. According to some embodiments, the demineralized bone matrix is provided as a plurality of pieces of demineralized bone matrix derived from a single piece of demineralized bone. According to some embodiments, the demineralized bone matrix is provided as a plurality of pieces of demineralized bone matrix derived from a plurality of pieces of bone tissue.

According to some embodiments, the pieces of bone tissue that are to be demineralized have a longest dimension (which is used herein as an equivalent term to "maximum dimension") that is measurable prior to demineralization of the pieces of bone. All such longest dimensions related in this paragraph are the longest dimension of a piece of bone tissue prior to demineralization. According to some embodiments, the plurality of pieces of bone tissue includes at least one piece of bone tissue whose longest dimension is of about 10 µm to about 20 cm. According to some such embodiments, the plurality of pieces of bone tissue includes a piece of bone tissue whose longest dimension is of about 10 µm. According to some such embodiments, the plurality of pieces of bone tissue includes a piece of bone tissue whose longest dimension is of about 20 µm. According to some such embodiments, the plurality of pieces of bone tissue includes at least one piece of bone tissue whose longest dimension is of about 30 µm. According to some such embodiments, the plurality of pieces of bone tissue includes at least one piece of bone tissue whose longest dimension is of about 40 µm. According to some such embodiments, the plurality of pieces of bone tissue includes at least one piece of bone tissue whose longest dimension is of about 50 µm. According to some such embodiments, the plurality of pieces of bone tissue includes at least one piece of bone tissue whose longest dimension is of about 100 µm. According to some such embodiments, the plurality of pieces of bone tissue includes at least one piece of bone tissue whose longest dimension is of about 150 µm. According to some such embodiments, the plurality of pieces of bone tissue includes at least one piece of bone tissue whose longest dimension is of about 200 µm. According to some such embodiments, the plurality of pieces of bone tissue includes at least one piece of bone tissue whose longest dimension is of about 250 µm. According to some such embodiments, the plurality of pieces of bone tissue includes at least one piece of bone tissue whose longest dimension is of about 300 µm. According to some such embodiments, the plurality of pieces of bone tissue includes at least one piece of bone tissue whose longest dimension is of about 350 µm. According to some such embodiments, the plurality of pieces of bone tissue includes at least one piece of bone tissue whose longest dimension is of about 400 µm. According to some such embodiments, the plurality of pieces of bone tissue includes at least one piece of bone tissue whose longest dimension is of about 450 µm. According to some such embodiments, the plurality of pieces of bone tissue includes at least one piece of bone tissue whose longest dimension is of about 500 µm. According to some such embodiments, the plurality of pieces of bone tissue includes at least one piece of bone tissue whose longest dimension is of about 550 µm. According to some such embodiments, the plurality of pieces of bone tissue includes at least one piece of bone tissue whose longest dimension is of about 600 µm. According to some such embodiments, the plurality of pieces of bone tissue includes at least one piece of bone tissue whose longest dimension is of about 650 µm. According to some such embodiments, the plurality of pieces of bone tissue includes at least one piece of bone tissue whose longest dimension is of about 700 µm. According to some such embodiments, the plurality of pieces of bone tissue includes at least one piece of bone tissue whose longest dimension is of about 750 µm. According to some such embodiments, the plurality of pieces of bone tissue includes at least one piece of bone tissue whose longest dimension is of about 800 µm. According to some such embodiments, the plurality of pieces of bone tissue includes at least one piece of bone tissue whose longest dimension is of about 850 µm. According to some such embodiments, the plurality of pieces of bone tissue includes at least one piece of bone tissue whose longest dimension is of about 900 µm. According to some such embodiments, the plurality of pieces of bone tissue includes at least one piece of bone tissue whose longest dimension is of about 950 µm. According to some such embodiments, the plurality of pieces of bone tissue includes at least one piece of bone tissue whose longest dimension is in the range of about 100 µm to about 1000 µm.

According to some such embodiments, the plurality of pieces of bone tissue includes at least one piece of bone tissue whose longest dimension is of about 1 mm. According to some such embodiments, the plurality of pieces of bone tissue includes at least one piece of bone tissue whose longest dimension is of about 2 mm. According to some such embodiments, the plurality of pieces of bone tissue includes at least one piece of bone tissue whose longest dimension is of about 3 mm. According to some such embodiments, the plurality of pieces of bone tissue includes at least one piece of bone tissue whose longest dimension is of about 4 mm. According to some such embodiments, the plurality of pieces of bone tissue includes at least one piece of bone tissue whose longest dimension is of about 5 mm. According to some such embodiments, the plurality of pieces of bone tissue includes at least one piece of bone tissue whose longest dimension is of about 6 mm. According to some such embodiments, the plurality of pieces of bone tissue includes at least one piece of bone tissue whose longest dimension is of about 7 mm. According to some such embodiments, the plurality of pieces of bone tissue includes at least one piece of bone tissue whose longest dimension is of about 8 mm. According to some such embodiments, the plurality of pieces of bone tissue includes at least one piece of bone tissue whose longest dimension is of about 9 mm. According to some such embodiments, the plurality of pieces of bone tissue includes at least one piece of bone tissue whose longest dimension is of about 10 mm. According to some such embodiments, the plurality of pieces of bone tissue includes at least one piece of bone tissue whose longest dimension is of about 12 mm. According to some such embodiments the plurality of pieces of bone tissue includes at least one piece of bone tissue whose longest dimension is of about 14 mm. According to some such embodiments, the plurality of pieces of bone tissue includes at least one piece of bone tissue whose longest dimension is of about 16 mm. According to some such embodiments, the plurality of pieces of bone tissue includes at least one piece of bone tissue whose longest dimension is of about 18 mm. According to some such embodiments, the plurality of pieces of bone tissue includes at least one piece of bone tissue whose longest dimension is of about 20 mm. According to some such embodiments, the plurality of pieces of bone tissue includes at least one piece of bone tissue whose longest dimension is of about 22 mm. According to some such embodiments, the plurality of pieces of bone tissue includes at least one piece of bone tissue whose longest dimension is of about 24 mm. According to some such embodiments, the plurality of pieces of bone tissue includes at least one piece of bone tissue whose longest dimension is of about 26 mm. According to some such embodiments, the plurality of pieces of bone tissue includes at least one piece of bone tissue whose longest dimension is of about 28 mm. According to some such embodiments, the plurality of pieces of bone tissue includes at least one piece of bone tissue whose longest dimension is of about 30 mm. According to some such embodiments, the plurality of pieces of bone tissue includes at least one piece of bone tissue whose longest dimension is of about 35 mm. According to some such embodiments, the plurality of pieces of bone tissue includes at least one piece of bone tissue whose longest dimension is of about 40 mm. According to some such embodiments, the plurality of pieces of bone tissue includes at least one piece of bone tissue whose longest dimension is of about 45 mm. According to some such embodiments, the plurality of pieces of bone tissue includes at least one piece of bone tissue whose longest dimension is of about 50 mm. According to some such embodiments, the plurality of pieces of bone tissue includes at least one piece of bone tissue whose longest dimension is of about 100 mm. According to some such embodiments, the plurality of pieces of bone tissue includes at least one piece of bone tissue whose longest dimension is of about 200 mm. According to some such embodiments, the plurality of pieces of bone tissue includes at least one piece of bone tissue whose longest dimension is of about 300 mm. According to some such embodiments, the plurality of pieces of bone tissue includes at least one piece of bone tissue whose longest dimension is of about 400 mm. According to some such embodiments, the plurality of pieces of bone tissue includes at least one piece of bone tissue whose longest dimension is of about 500 mm. According to some such embodiments, the plurality of pieces of bone tissue includes at least one piece of bone tissue whose longest dimension is of about 600 mm. According to some such embodiments, the plurality of pieces of bone tissue includes at least one piece of bone tissue whose longest dimension is of about 700 mm. According to some such embodiments, the plurality of pieces of bone tissue includes at least one piece of bone tissue whose longest dimension is of about 800 mm. According to some such embodiments, the plurality of pieces of bone tissue includes at least one piece of bone tissue whose longest dimension is of about 900 mm. According to some such embodiments, the plurality of pieces of bone tissue includes at least one piece of bone tissue whose longest dimension is of about 1000 mm.

According to some such embodiments, the plurality of pieces of bone tissue includes at least one piece of bone tissue whose longest dimension is in the range of about 1 mm to about 10 mm. According to some such embodiments, the plurality of pieces of bone tissue includes at least one piece of bone tissue whose longest dimension is in the range of about 5 mm to about 15 mm. According to some such embodiments, the plurality of pieces of bone tissue includes at least one piece of bone tissue whose longest dimension is in the range of about 10 mm to about 20 mm. According to some such embodiments, the plurality of pieces of bone tissue includes at least one piece of bone tissue whose longest dimension is in the range of about 15 mm to about 25 mm. According to some such embodiments, the plurality of pieces of bone tissue includes at least one piece of bone tissue whose longest dimension is in the range of about 20 mm to about 30 mm. According to some such embodiments, the plurality of pieces of bone tissue includes at least one piece of bone tissue whose longest dimension is in the range of about 25 mm to about 35 mm. According to some such embodiments, the plurality of pieces of bone tissue includes at least one piece of bone tissue whose longest dimension is in the range of about 30 mm to about 40 mm. According to some such embodiments, the plurality of pieces of bone tissue includes at least one piece of bone tissue whose longest dimension is in the range of about 40 mm to about 50 mm. According to some such embodiments, the plurality of pieces of bone tissue includes at least one piece of bone tissue whose longest dimension is in the range of about 10 mm to about 15 mm. According to some such embodiments, the plurality of pieces of bone tissue includes at least one piece of bone tissue whose longest dimension is in the range of about 15 mm to about 20 mm. According to some such embodiments, the plurality of pieces of bone tissue includes at least one piece of bone tissue whose longest dimension is in the range of about 25 mm to about 30 mm. According to some such embodiments, the plurality of pieces of bone tissue includes at least one piece of bone tissue whose longest dimension is in the range of about 30 mm to about 35 mm. According to some such embodiments, the plurality of pieces of bone tissue includes at least one piece of bone tissue whose longest dimension is in the range of about 35 mm to about 40 mm. According to some such embodiments, the plurality of pieces of bone tissue includes at least one piece of bone tissue whose longest dimension is in the range of about 40 mm to about 45 mm. According to some such embodiments the plurality of pieces of bone tissue includes at least one piece of bone tissue whose longest dimension is in the range of about 45 mm to about 50 mm.

According to some such embodiments, the plurality of pieces of bone tissue includes at least one piece of bone tissue whose longest dimension is at least 1 mm. According to some such embodiments, the plurality of pieces of bone tissue includes at least one piece of bone tissue whose longest dimension is at least 10 mm. According to some such embodiments, the plurality of pieces of bone tissue includes at least one piece of bone tissue whose longest dimension is at least 15 mm. According to some such embodiments, the plurality of pieces of bone tissue includes at least one piece of bone tissue whose longest dimension is at least 20 mm. According to some such embodiments, the plurality of pieces of bone tissue includes at least one piece of bone tissue whose longest dimension is at least 25 mm. According to some such embodiments, the plurality of pieces of bone tissue includes at least one piece of bone tissue whose longest dimension is at least 30 mm. According to some such embodiments, the plurality of pieces of bone tissue includes at least one piece of bone tissue whose longest dimension is at least 35 mm. According to some such embodiments, the plurality of pieces of bone tissue includes at least one piece of bone tissue whose longest dimension is at least 40 mm. According to some such embodiments, the plurality of pieces of bone tissue includes at least one piece of bone tissue whose longest dimension is at least 45 mm. According to some such embodiments, the plurality of pieces of bone tissue includes at least one piece of bone tissue whose longest dimension is at least 50 mm.

According to some such embodiments, the plurality of pieces of bone tissue includes at least one piece of bone tissue whose longest dimension is of about 1 cm. According to some such embodiments, the plurality of pieces of bone tissue includes at least one piece of bone tissue whose longest dimension is of about 2 cm. According to some such embodiments, the plurality of pieces of bone tissue includes at least one piece of bone tissue whose longest dimension is of about 3 cm. According to some such embodiments, the plurality of pieces of bone tissue includes at least one piece of bone tissue whose longest dimension is of about 4 cm. According to some such embodiments, the plurality of pieces of bone tissue includes at least one piece of bone tissue whose longest dimension is of about 5 cm. According to some such embodiments, the plurality of pieces of bone tissue includes at least one piece of bone tissue whose longest dimension is of about 6 cm. According to some such embodiments, the plurality of pieces of bone tissue includes at least one piece of bone tissue whose longest dimension is of about 7 cm. According to some such embodiments, the plurality of pieces of bone tissue includes at least one piece of bone tissue whose longest dimension is of about 8 cm. According to some such embodiments, the plurality of pieces of bone tissue includes at least one piece of bone tissue whose longest dimension is of about 9 cm. According to some such embodiments, the plurality of pieces of bone tissue includes at least one piece of bone tissue whose longest dimension is of about 10 cm. According to some such embodiments, the plurality of pieces of bone tissue includes at least one piece of bone tissue whose longest dimension is of about 11 cm. According to some such embodiments, the plurality of pieces of bone tissue includes at least one piece of bone tissue whose longest dimension is of about 12 cm. According to some such embodiments, the plurality of pieces of bone tissue includes at least one piece of bone tissue whose longest dimension is of about 13 cm. According to some such embodiments, the plurality of pieces of bone tissue includes at least one piece of bone tissue whose longest dimension is of about 14 cm. According to some such embodiments, the plurality of pieces of bone tissue includes at least one piece of bone tissue whose longest dimension is of about 15 cm. According to some such embodiments, the plurality of pieces of bone tissue includes at least one piece of bone tissue whose longest dimension is of about 16 cm. According to some such embodiments, the plurality of pieces of bone tissue includes at least one piece of bone tissue whose longest dimension is of about 17 cm. According to some such embodiments, the plurality of pieces of bone tissue includes at least one piece of bone tissue whose longest dimension is of about 18 cm. According to some such embodiments, the plurality of pieces of bone tissue includes at least one piece of bone tissue whose longest dimension is of about 19 cm. According to some such embodiments, the plurality of pieces of bone tissue includes at least one piece of bone tissue whose longest dimension is of about 20 cm.

According to some embodiments, the pieces of bone tissue that are to be demineralized have a shortest dimension (which is used herein as an equivalent term to "minimum dimension") that is measurable prior to demineralization of the pieces of bone. All such shortest dimensions related in this paragraph are the shortest dimension of a piece of bone tissue prior to demineralization. According to some embodiments, the plurality of pieces of bone tissue includes at least one piece of bone tissue whose shortest dimension is of about 10 µm to about 20 cm. According to some such embodiments, the plurality of pieces of bone tissue includes a piece of bone tissue whose shortest dimension is of about 10 µm. According to some such embodiments, the plurality of pieces of bone tissue includes a piece of bone tissue whose shortest dimension is of about 20 µm. According to some such embodiments, the plurality of pieces of bone tissue includes at least one piece of bone tissue whose shortest dimension is of about 30 µm. According to some such embodiments, the plurality of pieces of bone tissue includes at least one piece of bone tissue whose shortest dimension is of about 40 µm. According to some such embodiments, the plurality of pieces of bone tissue includes at least one piece of bone tissue whose shortest dimension is of about 50 µm. According to some such embodiments, the plurality of pieces of bone tissue includes at least one piece of bone tissue whose shortest dimension is of about 100 µm. According to some such embodiments, the plurality of pieces of bone tissue includes at least one piece of bone tissue whose shortest dimension is of about 150 µm. According to some such embodiments, the plurality of pieces of bone tissue includes at least one piece of bone tissue whose shortest dimension is of about 200 µm. According to some such embodiments, the plurality of pieces of bone tissue includes at least one piece of bone tissue whose shortest dimension is of about 250 µm. According to some such embodiments, the plurality of pieces of bone tissue includes at least one piece of bone tissue whose shortest dimension is of about 300 µm. According to some embodiments, the plurality of pieces of bone tissue includes at least one piece of bone tissue whose shortest dimension is in the range of about 5 µm to about 300 µm. According to some such embodiments, the plurality of pieces of bone tissue includes at least one piece of bone tissue whose shortest dimension is of about 350 µm. According to some such embodiments, the plurality of pieces of bone tissue includes at least one piece of bone tissue whose shortest dimension is of about 400 µm. According to some such embodiments, the plurality of pieces of bone tissue includes at least one piece of bone tissue whose shortest dimension is of about 450 µm. According to some such embodiments, the plurality of pieces of bone tissue includes at least one piece of bone tissue whose shortest dimension is of about 500 µm. According to some such embodiments, the plurality of pieces of bone tissue includes at least one piece of bone tissue whose shortest dimension is of about 550 µm. According to some such embodiments, the plurality of pieces of bone tissue includes at least one piece of bone tissue whose shortest dimension is of about 600 µm. According to some such embodiments, the plurality of pieces of bone tissue includes at least one piece of bone tissue whose shortest dimension is of about 650 µm. According to some such embodiments, the plurality of pieces of bone tissue includes at least one piece of bone tissue whose shortest dimension is of about 700 µm. According to some such embodiments, the plurality of pieces of bone tissue includes at least one piece of bone tissue whose shortest dimension is of about 750 µm. According to some such embodiments, the plurality of pieces of bone tissue includes at least one piece of bone tissue whose shortest dimension is of about 800 µm. According to some such embodiments, the plurality of pieces of bone tissue includes at least one piece of bone tissue whose shortest dimension is of about 850 µm. According to some such embodiments, the plurality of pieces of bone tissue includes at least one piece of bone tissue whose shortest dimension is of about 900 µm. According to some such embodiments, the plurality of pieces of bone tissue includes at least one piece of bone tissue whose shortest dimension is of about 950 µm. According to some such embodiments, the plurality of pieces of bone tissue includes at least one piece of bone tissue whose shortest dimension is in the range of about 100 µm to about 1000 µm. According to some such embodiments, the plurality of pieces of bone tissue includes at least one piece of bone tissue whose shortest dimension is of about 1 mm. According to some such embodiments, the plurality of pieces of bone tissue includes at least one piece of bone tissue whose shortest dimension is of about 2 mm. According to some such embodiments, the plurality of pieces of bone tissue includes at least one piece of bone tissue whose shortest dimension is of about 3 mm. According to some such embodiments, the plurality of pieces of bone tissue includes at least one piece of bone tissue whose shortest dimension is of about 4 mm. According to some such embodiments, the plurality of pieces of bone tissue includes at least one piece of bone tissue whose shortest dimension is of about 5 mm. According to some such embodiments, the plurality of pieces of bone tissue includes at least one piece of bone tissue whose shortest dimension is of about 6 mm. According to some such embodiments, the plurality of pieces of bone tissue includes at least one piece of bone tissue whose shortest dimension is of about 7 mm. According to some such embodiments, the plurality of pieces of bone tissue includes at least one piece of bone tissue whose shortest dimension is of about 8 mm. According to some such embodiments, the plurality of pieces of bone tissue includes at least one piece of bone tissue whose shortest dimension is of about 9 mm. According to some such embodiments, the plurality of pieces of bone tissue includes at least one piece of bone tissue whose shortest dimension is of about 10 mm. According to some such embodiments, the plurality of pieces of bone tissue includes at least one piece of bone tissue whose shortest dimension is in the range of about 1 mm to about 10 mm. According to some such embodiments, the plurality of pieces of bone tissue includes at least one piece of bone tissue whose shortest dimension is of about 50 mm. According to some such embodiments, the plurality of pieces of bone tissue includes at least one piece of bone tissue whose shortest dimension is of about 100 mm. According to some such embodiments, the plurality of pieces of bone tissue includes at least one piece of bone tissue whose shortest dimension is of about 200 mm. According to some such embodiments, the plurality of pieces of bone tissue includes at least one piece of bone tissue whose shortest dimension is of about 300 mm. According to some such embodiments, the plurality of pieces of bone tissue includes at least one piece of bone tissue whose shortest dimension is of about 400 mm. According to some such embodiments, the plurality of pieces of bone tissue includes at least one piece of bone tissue whose shortest dimension is of about 500 mm. According to some such embodiments, the plurality of pieces of bone tissue includes at least one piece of bone tissue whose shortest dimension is of about 600 mm. According to some such embodiments, the plurality of pieces of bone tissue includes at least one piece of bone tissue whose shortest dimension is of about 700 mm. According to some such embodiments, the plurality of pieces of bone tissue includes at least one piece of bone tissue whose shortest dimension is of about 800 mm. According to some such embodiments, the plurality of pieces of bone tissue includes at least one piece of bone tissue whose shortest dimension is of about 900 mm. According to some such embodiments, the plurality of pieces of bone tissue includes at least one piece of bone tissue whose shortest dimension is of about 1 cm. According to some such embodiments, the plurality of pieces of bone tissue includes at least one piece of bone tissue whose shortest dimension is of about 2 cm. According to some such embodiments, the plurality of pieces of bone tissue includes at least one piece of bone tissue whose shortest dimension is of about 3 cm. According to some such embodiments, the plurality of pieces of bone tissue includes at least one piece of bone tissue whose shortest dimension is of about 4 cm. According to some such embodiments, the plurality of pieces of bone tissue includes at least one piece of bone tissue whose shortest dimension is of about 5 cm. According to some such embodiments, the plurality of pieces of bone tissue includes at least one piece of bone tissue whose shortest dimension is of about 6 cm. According to some such embodiments, the plurality of pieces of bone tissue includes at least one piece of bone tissue whose shortest dimension is of about 7 cm. According to some such embodiments, the plurality of pieces of bone tissue includes at least one piece of bone tissue whose shortest dimension is of about 8 cm. According to some such embodiments, the plurality of pieces of bone tissue includes at least one piece of bone tissue whose shortest dimension is of about 9 cm. According to some such embodiments, the plurality of pieces of bone tissue includes at least one piece of bone tissue whose shortest dimension is of about 10 cm. According to some such embodiments, the plurality of pieces of bone tissue includes at least one piece of bone tissue whose shortest dimension is of about 11 cm. According to some such embodiments, the plurality of pieces of bone tissue includes at least one piece of bone tissue whose shortest dimension is of about 12 cm. According to some such embodiments, the plurality of pieces of bone tissue includes at least one piece of bone tissue whose shortest dimension is of about 13 cm. According to some such embodiments, the plurality of pieces of bone tissue includes at least one piece of bone tissue whose shortest dimension is of about 14 cm. According to some such embodiments, the plurality of pieces of bone tissue includes at least one piece of bone tissue whose shortest dimension is of about 15 cm. According to some such embodiments, the plurality of pieces of bone tissue includes at least one piece of bone tissue whose shortest dimension is of about 16 cm. According to some such embodiments, the plurality of pieces of bone tissue includes at least one piece of bone tissue whose shortest dimension is of about 17 cm. According to some such embodiments, the plurality of pieces of bone tissue includes at least one piece of bone tissue whose shortest dimension is of about 18 cm. According to some such embodiments, the plurality of pieces of bone tissue includes at least one piece of bone tissue whose shortest dimension is of about 19 cm. According to some such embodiments, the plurality of pieces of bone tissue includes at least one piece of bone tissue whose shortest dimension is of about 20 cm.

According to one embodiment, the at least one growth-inductive component is tissue-derived. According to one embodiment, the at least one growth-inductive component comprises inducible pluripotent stem cells (iPSCs). According to one embodiment, the at least one growth-inductive component originates from a component of the tissue-derived growth-inductive component other than cells. According to one embodiment, the at least one growth-inductive component is endogenous to the at least one growth-conductive matrix. According to one embodiment, the tissuegenic cells adherent to and resident in the endogenous milieu of the growth conductive matrix secrete the at least one growth-inductive component. According to one embodiment, the at least one growth-inductivecomponent is exogenous to the at least one growth-conductive matrix. According to one embodiment, the growth-inductive component comprises a growth medium derived from expanded tissuegenic cells. According to one embodiment, the at least one growth-inductive component comprises a demineralized bone matrix, which may be demineralized cortical bone.

Seeding Step (iv): seeding the decellularized growth-conductive matrix pieces of (iii) with the plurality of at least one viable isolated population of tissuegenic cells of (ii) to form a plurality of reseeded growth-conductive matrix pieces, where the at least one viable population of tissuegenic cells is caused to be in contact with the growth-conductive matrix According to some embodiments, seeding step (iv) comprises the steps: (1) providing a suspension comprising a plurality of the at least one viable isolated population of tissuegenic cells; (2) admixing a portion of the suspension comprising a plurality of the at least one viable isolated population of tissuegenic cells with a plurality of pieces comprising a decellularized tissue derived growth-conductive matrix; (3) bringing the at least one viable isolated population of tissuegenic cells into contact with the matrix; (4) rinsing the at least one viable population of tissuegenic cells caused to be in contact with a plurality of pieces comprising the decellularized tissue derived matrix; to yield the implant.

According to one embodiment, the incubating step comprises placing the plurality of pieces comprising a decellularized tissue derived matrix at a temperature of 37° C. for 24 hours. According to one embodiment, the incubating step comprises placing the plurality of pieces comprising a decellularized tissue derived matrix at a temperature of 37° C. for 24 hours under static seeding conditions. According to one embodiment, the incubating step comprises placing the plurality of pieces comprising a decellularized tissue derived matrix at a temperature of 37° C. for 24 hours under dynamic seeding condition with gentle agitation.

According to one embodiment, the rinsing step comprises washing with a liquid to remove non-adhering cells. According to some embodiments, the liquid comprises a buffered isotonic solution. According to some embodiments, the liquid comprises a buffered salt solution. According to some embodiments, the buffered salt solution comprises a PBS solution. According to some embodiments, the buffered salt solution comprises a TBS solution.

According to another embodiment, the method of fabricating an implant further comprises step (vii) supplementing the implant of step (iv). According to some such embodiments, the at least one growth-inductive component comprises at least one growth-inductive factor. According to some such embodiments, the at least one growth-inductive factor comprises at least one growth factor. According to some such embodiments, the at least one growth-inductive component comprises a demineralized bone matrix, which may be demineralized cortical bone. According to some such embodiments, the at least one growth factor is fibroblast growth factor-2 (FGF-2). According to some such embodiments, the at least one growth factor is fibroblast growth factor-5 (FGF-5). According to some such embodiments, the at least one growth factor is insulin-like growth factor 1 (IGF-1). According to some such embodiments, the at least one growth factor is transforming growth factor beta (TGF-β). According to some such embodiments, the at least one growth factor is bone morphogenic protein-2 (BMP-2). According to some such embodiments, the at least one growth factor is bone morphogenic protein-7 (BMP-7). According to some such embodiments, the at least one growth factor is platelet-derived growth factor (PDGF). According to some such embodiments, the at least one growth factor is vascular endothelial growth factor (VEGF). According to some such embodiments, the at least one growth factor is neural epidermal growth-factor-like 1 (NELL-1). According to another embodiment, the rinsed osteoconductive matrix particles are supplemented with at least one cytokine.

According to one embodiment, the at least one growth-inductive component is tissue-derived. According to one embodiment, the at least one growth-inductive component comprises inducible pluripotent stem cells (iPSCs). According to one embodiment, the at least one growth-inductive component originates from a component of the tissue-derived growth-inductive component other than cells. According to one embodiment, the at least one growth-inductive component is endogenous to the at least one growth-conductive matrix. According to one embodiment, the tissuegenic cells adherent to and resident in the endogenous milieu of the growth conductive matrix secrete the at least one growth-inductive component. According to one embodiment, the at least one growth-inductivecomponent is exogenous to the at least one growth-conductive matrix. According to one embodiment, the growth-inductive component comprises a growth medium derived from expanded tissuegenic cells. According to one embodiment, the at least one growth-inductive component comprises a demineralized bone matrix, which may be demineralized cortical bone.

3. An Implant Fabricated by the Methods Described

According to another aspect, the described invention provides an implant fabricated by a method comprising steps:

(a) providing at least one growth-conductive matrix or at least one fragment thereof, wherein the growth-conductive matrix comprises at least one viable population of tissuegenic cells endogenous to the tissue, wherein the tissuegenic cells are adherent to and resident in the endogenous milieu of the growth-conductive matrix;

(b) separating the at least one growth-conductive matrix of (a) to generate a plurality of separated matrix pieces comprising the at least one viable population of tissuegenic cells caused to be in contact with and resident in the endogenous milieu of the growth-conductive matrix wherein the relative frequency of a stem cell subtype in the at least one viable tissuegenic cell population of step (b) is of a similar relative frequency as found in the growth-conductive matrix of step (a);

(c) rinsing the plurality of separated matrix pieces of (b) comprising the at least one viable population of tissuegenic cells caused to be in contact with and resident in the endogenous milieu of the growth-conductive matrix of (b) to form a plurality of rinsed separated matrix pieces comprising the at least one viable population of tissuegenic cells caused to be in contact with and resident in the the endogenous milieu of the growth-conductive matrix of (b), wherein a relative frequency of a stem cell subtype in the at least one viable tissuegenic cell population of step (c) is of a similar relative frequency to that found in the growth-conductive matrix of step (a);

(d) collecting the plurality of rinsed separated matrix pieces of (c) comprising the at least one viable population of tissuegenic cells caused to be in contact with and resident in the endogenous milieu of the growth-conductive matrix of (c) wherein the at least one viable tissuegenic cell population is of a similar relative frequency to that found in the growth-conductive matrix of step (a);

(e) packaging the plurality of collected rinsed separated matrix pieces of (d) comprising at least one viable population of tissuegenic cells caused to be in contact with and resident in the endogenous milieu of the growth-conductive matrix of (c) wherein the at least one viable tissuegenic cell population is of a similar relative frequency as found in the growth-conductive matrix of step (a) to form the implant.

According to another embodiment, the described invention provides an implant fabricated by a method comprising steps:

(i) providing at least one first growth-conductive matrix or at least one fragment thereof, derived from human tissue, wherein the growth-conductive matrix comprises at least one viable population of tissuegenic cells endogenous to the tissue, wherein the tissuegenic cells are adherent to and resident in the endogenous milieu of the growth-conductive matrix;

(ii) isolating from the at least one growth-conductive matrix of (i) a plurality of the at least one viable isolated population of tissuegenic cells;

(iii) processing a second growth-conductive matrix comprising a decellularized growth-conductive matrix to generate a plurality of pieces;

(iv) seeding the decellularized growth-conductive matrix pieces of (iii) with the plurality of at least one viable isolated population of tissuegenic cells of (ii) to form a plurality of reseeded growth-conductive matrix pieces, where the at least one viable population of tissuegenic cells is caused to be in contact with the growth-conductive matrix;

(v) collecting the plurality of reseeded growth-conductive matrix pieces of (iv) comprising the at least one viable population of tissuegenic cells caused to be in contact with or in contact with the growth-conductive matrix of (iv), wherein the at least one viable tissuegenic cell population is of a relative frequency substantially similar to that found in the growth-conductive matrix of step (i);

(vi) packaging the plurality of collected reseeded growth-conductive matrix pieces of (v) comprising the at least one viable population of tissuegenic cells caused to be in contact with or in contact with the growth-conductive matrix of (iv), wherein the at least one viable tissuegenic cell population is of a relative frequency substantially similar to that found in the growth-conductive matrix of step (i) to form the implant.

A Fabricated Orthopedic Implant

According to one embodiment, the described invention provides an orthopedic implant fabricated by a method comprising steps:

(a) providing at least one growth-conductive matrix or at least one fragment thereof, wherein the growth-conductive matrix comprises at least one viable population of tissuegenic cells caused to be in contact with and resident in the growth-conductive matrix;

(b) milling the growth-conductive matrix of (a) to generate a plurality of milled matrix particles comprising the at least one viable population of tissuegenic cells caused to be in contact with and resident in the growth-conductive matrix, wherein a relative frequency of a cell subtype in the at least one viable tissuegenic cell population of step (b) is of a relative frequency substantially similar to that found in the growth-conductive matrix of step (a);

(c) rinsing the plurality of milled matrix particles of (b) comprising the at least one viable population of tissuegenic cells caused to be in contact with and resident in the growth-conductive matrix of (b) to form a plurality of rinsed milled matrix particles comprising the at least one viable population of tissuegenic cells caused to be in contact with and resident in the growth-conductive matrix of (b), wherein a relative frequency of a cell subtype in the at least one viable tissuegenic cell population of step (c) is of a relative frequency substantially similar to that found in the growth-conductive matrix of step (a);

(d) collecting the plurality of rinsed matrix particles comprising at least one viable population of tissuegenic cells caused to be in contact with and resident in the growth-conductive matrix of (c) wherein the at least one viable tissuegenic cell population is of a relative frequency substantially similar to that found in the growth-conductive matrix of step (a), step (b) or step (c); to form the orthopedic implant.

The method of fabricating an implant may include the addition of a demineralized bone matrix, which may be demineralized cortical bone. According to some embodiments, the implant is an implantable composition comprising a growth-conductive matrix (e.g., an osteoconductive matrix derived from a bone tissue), a viable population of tissuegenic cells (e.g., osteogenic cells), and an osteoinductive matrix (e.g., a demineralized bone matrix). In an embodiment, a osteoinductive matrix (e.g., a second demineralized bone matrix) is provided separately from the aforesaid implantable composition for addition to the implantable composition at a later time.

4. Uses of the Implants of the Described Invention for Tissue Repair

According to another aspect, the implant of the described invention can be used for a tissue engineering application. Tissue engineering is the application of principles and methods of engineering and life sciences toward a fundamental understanding and development of biological substitutes to restore, maintain and improve human tissue functions. According to one embodiment, the tissue engineering application is a surgical application. According to one embodiment, the tissue engineering application is a nonsurgical application.

According to one embodiment, the implant can be used for tissue repair. According to one such embodiment, the implant is an orthopedic implant. According to one embodiment, a method for treating a bony defect at a defect site in a subject in need thereof comprises the steps:

(a) providing an orthopedic implant comprising
   (i) a plurality of pieces comprising at least one tissue-derived growth-conductive matrix; and
   (ii) at least one viable population of tissuegenic cells adherent to and resident in an endogenous milieu of the growth-conductive matrix;
(b) implanting the orthopedic implant at the defect site; and
(c) filling the bony defect.

According to another embodiment, the implant is an implantable composition comprising a growth-conductive matrix (e.g., an osteoconductive matrix derived from bone), a viable population of tissuegenic cells (e.g., osteogenic cells), and an osteoinductive matrix (e.g., demineralized bone matrix). In some such embodiments, the composition is applied to the bone defect so as to fill the bone defect. In some such embodiments, the composition is applied with a spatula. In some such embodiments, the composition is injected into the bony defect. In another embodiment, a second osteoinductive matrix (e.g., a second demineralized bone matrix) is provided separately from the aforesaid implantable composition, and is mixed with the implantable composition at the surgical location, before application to the bone defect.

According to one embodiment of the method, the bony defect resulted from tumor surgery. According to another embodiment, the bony defect resulted from a traumatic injury. According to another embodiment, the bony defect resulted from a congenital skeletal abnormality. According to another embodiment, the bony defect resulted from a fracture. According to another embodiment, the bony defect resulted from a spinal arthrodesis. According to another embodiment, the bony defect resulted from a joint replacement.

According to one embodiment, the tissue to be repaired using the implant is selected from the group consisting of an adipose tissue, an amnion tissue, an artery tissue, a bone tissue, a cartilage tissue, a chorion tissue, a colon tissue, a dental tissue, a dermal tissue, a duodenal tissue, an endodermal tissue, an epithelial tissue, a fascial tissue, a gastrointestinal tissue, a growth plate tissue, an intervertebral disc tissue, an intestinal mucosal tissue, an intestinal serosal tissue, a kidney tissue, a ligament tissue, a liver tissue, a lung tissue, a mammary tissue, a meniscal tissue, a muscle tissue, a nerve tissue, an ovarian tissue, a pancreatic tissue, a parenchymal organ tissue, a pericardial tissue, a periosteal tissue, a peritoneal tissue, a placental tissue, a reproductive epithelial tissue, a respiratory epithelial tissue, a skin tissue, a spleen tissue, a stomach tissue, a synovial tissue, a tendon tissue, a testes tissue, an umbilical cord tissue, a urological tissue, a vascular tissue, a vein tissue, and a combination thereof.

According to one embodiment, the implant can be used in repairing adipose tissue. According to one embodiment, the implant can be used in repairing amnion tissue. According to one embodiment, the implant can be used in repairing artery tissue. According to one embodiment, the implant can be used in repairing bone tissue. According to one embodiment, the implant can be used in repairing cartilage tissue. According to one embodiment, the implant can be used in repairing chorion tissue. According to one embodiment, the implant can be used in repairing colon tissue. According to one embodiment, the implant can be used in repairing dental tissue. According to one embodiment, the implant can be used in repairing dermal tissue. According to one embodiment, the implant can be used in repairing duodenal tissue. According to one embodiment, the implant can be used in repairing endothelial tissue. According to one embodiment, the implant can be used in repairing epithelial tissue. According to one embodiment, the implant can be used in repairing fascial tissue. According to one embodiment, the implant can be used in repairing gastrointestinal tissue. According to one embodiment, the implant can be used in repairing growth plate tissue. According to one embodiment, the implant can be used in repairing intervertebral disc tissue. According to one embodiment, the implant can be used in repairing intestinal mucosal tissue. According to one embodiment, the implant can be used in repairing intestinal sclerosal tissue. According to one embodiment, the implant can be used in repairing kidney tissue. According to one embodiment, the implant can be used in repairing ligament tissue. According to one embodiment, the implant can be used in repairing liver tissue. According to one embodiment, the implant can be used in repairing lung tissue. According to one embodiment, the implant can be used in repairing mammary tissue. According to one embodiment, the implant can be used in repairing meniscal tissue. According to one embodiment, the implant can be used in repairing muscle tissue. According to one embodiment, the implant can be used in repairing nerve tissue. According to one embodiment, the implant can be used in repairing ovarian tissue. According to one embodiment, the implant can be used in repairing pancreatic tissue. According to one embodiment, the implant can be used in repairing parenchymal organ tissue. According to one embodiment, the implant can be used in repairing pericardial tissue. According to one embodiment, the implant can be used in repairing periosteal tissue. According to one embodiment, the implant can be used in repairing peritoneal tissue. According to one embodiment, the implant can be used in repairing placental tissue. According to one embodiment, the implant can be used in repairing reproductive epithelial tissue. According to one embodiment, the implant can be used in repairing respiratory epithelial tissue. According to one embodiment, the implant can be used in repairing skin tissue. According to one embodiment, the implant can be used in repairing spleen tissue. According to one embodiment, the implant can be used in repairing stomach tissue. According to one embodiment, the implant can be used in repairing synovial tissue. According to one embodiment, the implant can be used in repairing tendon tissue. According to one embodiment, the implant can be used in repairing testes tissue. According to one embodiment, the implant can be used in repairing umbilical cord tissue. According to one embodiment, the implant can be used in repairing urological tissue. According to one embodiment, the implant can be used in repairing vascular tissue. According to one embodiment, the implant can be used in repairing vein tissue.

EXAMPLES

The following examples are put forth so as to provide those of ordinary skill in the art with a complete disclosure and description of how to make and use the described invention, and are not intended to limit the scope of what the inventors regard as their invention nor are they intended to represent that the experiments below are all or the only experiments performed. Efforts have been made to ensure accuracy with respect to numbers used (e.g., amounts, temperatures, etc.) but some experimental errors and deviations should be accounted for. Unless indicated otherwise, parts are parts by weight, molecular weight is weight average molecular weight, temperature is in degrees centigrade, and pressure is at or near atmospheric.

I. Source Tissue: Bone

Example 1: Orthopedic Implant Fabrication

Human ilium is recovered aseptically from deceased donors between the ages of 18 and 45 years of age within 24 hours post-mortem to yield ilium tissue. The ilium tissue is stored at 4° C. until ready for processing. Generally, tissue processing commences within 72 hours post-mortem. The ilium tissue is exposed to a bioburden reducer to generate preprocessed ilium tissue. The preprocessed ilium tissue is subjected to three to four 5 minute soaks with agitation in a buffered isotonic solution (e.g., PBS (0.01 M, pH 7.4)). The preprocessed agitated ilium tissue then is debrided of all soft tissue and cut into strips of approximately 3×3 cm. The crest is cut off and used for other grafts, and the acetabulum is discarded. The strips are milled into particles approximately 2 mm in diameter or less using a mill. All components of the mill that come in contact with the tissue are chilled at 4° C. until use. In some embodiments, the preprocessed ilium tissue is crushed to form fragments or a powder.

The particles then are subjected to a series of rinses with cold PBS, followed by a rinse in acetic acid solution for 5 minutes and then followed again by a series of rinses with cold PBS. The pH of the rinseate is at or near physiological pH at the end of the rinses.

Prior to packaging, demineralized bone matrix or another osteoinductive matrix may be added to the tissue to enhance the osteoinductive nature of the tissue form. The demineralized bone matrix may be provided as particles, which may be prepared from particles of bone, or as elongated particles (e.g., as in fibers), or in some other form.

The tissue is placed in a cryopreservation solution and cryopreserved using a controlled rate freezer.

In another embodiment, a second demineralized bone matrix, which may be elongated particles (e.g., as in fibers) of demineralized bone matrix is supplied separately from the implant composition that includes bone-derived particles and demineralized bone matrix, to be mixed with the implant composition at the surgical location. In an example of such an embodiment, a first container of the implant compositions and a second container of the second demineralized bone matrix are provided together as a kit. Implements for mixing the contents of the first and second containers, and for implanting the resulting mixture in a bone defect may be included in the kit.

It should be understood by those skilled in the art that many modifications may be made to adapt a particular situation, material, composition of matter, process, process step or steps, to improve, for example, but not limited to, efficiency, and yield.

Example 2. Identification of Osteogenic Cells

Putative osteogenic cells are assayed in vitro to confirm their identity as MSCs or as osteoprogenitor cells, by using techniques, well-known in the art, including but not limited to oil red O staining assay, Von Kossa staining assay, colony forming unit fibroblast assay, alkaline phosphatase assay, etc.

Example 2.1. Identification of Mesenchymal Stem Cells

Mesenchymal stem cells initially are identified by phase microscopy. Explanted putative MSCs then are assayed in vitro to determine their ability to differentiate into 1) an osteogenic lineage, 2) an adipogenic lineage, and 3) a chondrogenic lineage.

Example 2.1.1: Lipid Accumulation

Preparation of Solutions

5% Oil Red O (Sigma) stock solutions in isopropanol are prepared. 6 ml of stock is added to 4 ml double distilled $H_2O$, mixed well and filtered. Generally, 500 µl to 1 ml are required per well of a 24 well plate.

Oil Red Assay

Lipid accumulation in fully differentiated cells is analyzed. First, medium is aspirated carefully from each well so as not to aspirate the cells. Second, plates are rinsed with PBS (1×), cells are fixed by covering with buffered formalin, and then plates are allowed to sit for at least 15 minutes at room temperature. Third, fixative agent is removed, the plates are rinsed 3 times with PBS (1×), and Oil Red is then added. The plates are allowed to sit at room temperature (approximately 25° C.) for at least 1 hour, and then are rinsed 3 times with double distilled $H_2O$ (1 ml) to remove excess stain and any precipitate that forms. Cell nuclei are stained with Hematoxylin solution (0.5 ml) for 5 to 15 minutes, then rinsed 3 times with double distilled $H_2O$, and allowed to air dry.

The Oil Red O solution stains adipocytes containing lipid droplets red; hematoxylin stains the cell nucleus black/blue.

Example 2.1.2: Determination of Mineralization

Von Kossa Staining

Mesenchymal stem cells that have been induced to follow an osteogenic lineage are stained to determine whether the cultures have mineralized. A 2% solution of silver nitrate (w/v) is prepared, avoiding light exposure. Cultures are rinsed twice with cold Tyrode's balanced salt solution (or Hank's balanced salt solution (HBSS)), fixed with 10% buffered formalin phosphate for 30 minutes (if the cultures were previously stained with fast violet, the plates are kept covered in foil). The culture is rinsed with distilled water, 2% silver nitrate (volume similar to normal volume used for cell culture media for the flask/wells being stained) is added, and allowed to incubate for 10 minutes while covered in foil. The staining solution is removed and cultures are rinsed 3 times with distilled water, leaving the water from the final rinse on the cultures. The cultures are placed on a bright, white background and exposed to bright light for 15 minutes, the water covering the cells is removed and the cultures are rinsed twice with water. The cultures are dehydrated with 100% ethanol for 1 minute, and allowed to air dry. Areas that are stained brown or black indicate mineralization. The cultures can be examined under the microscope to observe any diffuse staining.

Example 2.1.3: Mesenchymal Stem Cell Identification

Colony Forming Unit-Fibroblast Assay

Mesenchymal stem cells (MSCs) are identified using a colony forming unit-fibroblast (CFU-F) assay following the manufacturer's instructions (Stem Cell Technologies).

Culture Set-Up

Briefly, the CFU-F assay culture set-up is as follows: 1) Mesenchymal Stem Cell Stimulatory Supplements are thawed at room temperature or 4° C. overnight. The entire contents of the Mesenchymal Stimulatory Supplements are added to MesenCult Basal Medium for Human Mesenchymal Stem Cells and mixed thoroughly. This is now referred to as complete medium; 2) the normal bone marrow samples of red blood cells are lysed (i.e., using an ammonium chloride solution) or a mononuclear cell fraction is prepared by Ficoll-Paque density gradient separation; 3) cells are washed by adding 10 ml of PBS containing 2% FBS to the cell pellet. The cells are centrifuged at 1200 rpm for 10 minutes at 20° C., the supernatant is removed and the cells resuspended in MesenCult complete medium; 4) 1.0 ml, 0.5 ml and 0.25 ml of the cell stock solution is added to separate 100 mm tissue culture treated dishes (or T-25 cm² tissue culture flasks) to yield final cell concentrations of $2 \times 10^6$ cells, $1 \times 10^6$ cells, and $0.5 \times 10^6$ cells respectively in a total volume of 10 ml of MesenCult medium. These concentrations will ensure that the resulting numbers of colonies can be scored, as there are differences in the proliferative potential of CFU-F from various bone marrow samples; 6) the 100 mm dishes (or T-25 cm² tissue culture flasks) are placed into a 37° C. humidified incubator with 5% $CO_2$ in air and >95% humidity for 14 days. Maximum colony size and numbers typically are observed at this time.

Staining the CFU-F (Stromal Stem Cells) Colonies

The CFU-F colonies are stained as follows. Briefly, the media from the tissue culture dishes is removed to T-25 cm² tissue culture flasks and discarded. The culture dishes or flasks are washed twice using PBS (to remove any remaining medium) and the PBS from the two washes is discarded. Next, 5 ml of methanol is added and the culture dishes or flasks are allowed to air dry at room temperature. The methanol is discarded and 5 ml of Giemsa staining solution is added to each culture dish or flask for five minutes. The Giemsa staining solution is removed and the culture dishes or flasks rinsed with distilled water. The distilled water is discarded and the tissue culture dishes or flasks are allowed to dry at room temperature.

Scoring Procedure

Typically, the CFU-F colonies are between 1 mm and 8 mm in diameter and may be scored macroscopically. By confirming that there are as many colonies when cells are plated at $2 \times 10^6$/flask as compared to $1.0 \times 10^6$/flask and that there should be twice as many colonies when cells are plated at $1.0 \times 10^6$/flask as compared to the $0.5 \times 10^6$/flask, it is possible to ensure that there is a linear relationship between the cell numbers that are plated and the resulting colony numbers.

Example 2.1.4: Osteogenic Stem Cell Identification

Cells are assayed for their ability to differentiate into osteogenic progenitors using commercially available kits from, for example, Stem Cell Technologies, Inc.

Medium

Fresh "complete medium" is prepared weekly for the maintenance of cultures along the osteogenic lineage. MesenCult Basal Medium is stored at 4° C. in 10×45 ml aliquots; Osteogenic Stimulatory Supplements is used at a final 15% volume and stored at −20° C. in 10×8 ml aliquots; β-glycerophosphate is used at a final concentration of 3.5 mM in human assays (5.0 mM in rat assays) and is stored at −20° C. in 10×1 ml aliquots; and dexamethasone is used at a final concentration of $10^{-8}$ M. Briefly, the powder is dissolved in a small volume of absolute ethanol and made up with ethanol to a final volume of 25.5 ml, then stored at −20° C. in 500 µl aliquots; ascorbic acid is used at a final concentration of 50 µg/ml. The powder is dissolved in 10 ml of MesenCult Basal Medium thereby generating a stock solution of 10 mg/ml, and stored at −20° C. in 10×1 ml aliquots.

Complete Medium

MesenCult Basal Medium (42.5 ml) is pipetted into a 50 ml conical tube and the following: osteogenic supplements are added (7.5 ml); dexamethasone (10-4 M stock solution, 5 µl); ascorbic acid (10 mg/ml stock solution; 250 µl); β-glycerophosphate (1 M stock solution; 175 µl) if needed. Typically, β-glycerophosphate is added only after there is evidence, by phase microscopy, of cell multilayering.

There are many protocols in the literature for the development of osteogenic cells from various tissue sources including, but not limited to, bone marrow, cultured mesenchymal cells, adipose-derived stem cells, and aminiotic epithelial or stromal cells. The protocol below is just one example of a method that supports the growth of osteogenic cells from human bone marrow. The described complete medium supports the proliferation of rat osteogenic cells. The optimal concentration of β-glycerophosphate used in these studies is 5 mM.

Protocol

The assay is performed as follows: 1) cancellous bone fragments are prepared by mincing the bone into very small pieces (1-3 mm in size); 2) fragments are flushed with 20-30 ml of PBS and the fragments then vortexed with another 20-30 ml PBS; 3) the cell suspension is passed through a sieve to remove bone fragments; 4) cells are spun down at 400 g for 15 minutes; 5) the supernatant is discarded and the cells are resuspended in PBS; 6) cells are placed on Ficoll-Paque and spin at 400 g for 25 minutes; 7) the cells at the interface are removed and resuspended in complete medium (without β-glycerophosphate); 8) cells are seeded in tissue culture treated flasks or plates at a concentration of 100-200,000 cells per $cm^2$; 9) the cultures are re-fed for the first time after 5 days by removing the medium (and non-adherent cells). These can be discarded. The cultures are replenished with fresh complete medium (again without β-glycerophosphate unless cell multi-layering has been noted); and 10) cultures are re-fed every 2-3 days for a minimum of three weeks (for rat cultures) or 5 weeks (for human cultures). Detection of osteogenic cells may be determined by tetracycline labeling or von Kossa staining at this time. If unprocessed bone marrow cells are available, the bone marrow is diluted 1:3 with PBS/2% FBS and the process started at point 6 above.

Example 2.1.5: Determination of Alkaline Phosphatase Activity (Qualitative)

Cultures induced along the osteogenic lineage are stained to visualize any production of alkaline phosphatase (AP).

Preparation of Solutions

Fast Violet Stock is prepared by i) adding one capsule of Fast Violet to 48 ml water; ii) allowing the capsule to soften, then mixing the container occasionally until all the Fast Violet is dissolved; iii) aliquoting into 12 ml units and storing the stocks at 4° C. until ready to use.

Citrate Working Solution is prepared by adding 2 ml citrate concentrated solution to 98 ml Millipore water.

Citrate Buffered Acetone is prepared by combining Citrate Working Solution with acetone to give a solution that is 60% Citrate Working Solution and 40% acetone by volume.

Staining Cultures

Cultures are stained as follows: i) growth media is removed from the culture to be stained; ii) the culture is rinsed 2 times with Tyrode's salt solution (or equivalent); iii) citrate buffered acetone is added and allowed to sit for 30 seconds (to fix the cells); iv) cultures are rinsed twice with water (the water from the second rinse is left on the culture until ready to proceed to the next step); v) 0.5 ml Naphthol AS-MX (Sigma) is added to 12 ml of Fast Violet solution (this solution is light sensitive); vi) the water is removed from cultures and an appropriate volume of Fast Violet/Naphthol solution added to each dish or well (volume will vary with the size of the culture dish or well; generally, the same volume of stain is used as the volume of culture medium used on the plate); vii) the dish is incubated at room temperature (about 25° C.) for 45 minutes (avoid light exposure); and viii) the stain solution is removed and the culture rinsed twice with Millipore water. Areas with purple coloration indicate AP production. The cultures may be stored with water on the growth surface in the dark and stained later with Von Kossa.

Example 3: Characterization of Orthopedic Implant

The orthopedic implant is characterized to determine 1) the cell number (quantification of cells within the bone matrix), 2) cell type (identification of cell populations present in the tissue), 3) cell viability (percentage of viable cells after cryopreservation and thaw), and 4) osteoconductivity of the demineralized component (verification of BMP-2 content).

Example 3.1: Cell Count and Identification

Histological slides are prepared to quantitate cell numbers and cell types of the bone matrix. Briefly, tissue sections (5 µm) are cut, then stained with hematoxylin and eosin (H&E), the MSC marker CD166+, the osteoprogenitor cell marker osteocalcin, and hematopoietic cell markers CD34+ and CD45+. Slides then are quantitated. Quantification can be performed via microscopic image analysis with commercially available systems such as, but not limited to, Image Pro Plus and Aperio (Vista, Calif.).

Stereological methods are used to quantify total cell number and the number of MSC and osteoprogenitor cells. Stereology is an interdisciplinary field that allows for extraction of quantitative information about a three-dimensional material from measurements made on two-dimensional planar sections of the material. Stereology utilizes random, systematic sampling to provide unbiased and quantitative data. Briefly, conversion of cell number per $cm^3$ of tissue is based on scanned serial tissue sections where slides are overlaid to identify an area of interest. A controlled estimation of cell numbers is determined using an Optical Disector. This is an extension of the basic Disector method, which is applied to a thick section using a series, or stack, of Disectors. Rather than using pairs of physical sections (the basic Disector method), optical sectioning is used by creating focal planes with a thin depth-of-field through the section. The Optical Disector begins with a lookup section at the top of the optical disector and ends with a reference section at the bottom of the optical disector. The focal plane is the current reference section. The lookup section is immediately above the focal plane. A particle in focus at the top of the optical disector therefore is seen in the lookup section and not counted. A particle in focus at the bottom of the optical disector, which is in the reference section and therefore not in the lookup section, is counted. Counting frame rules are applied when the particle first comes into focus. The total volume of the sample then can be calculated by determining the maximum pellet size, section thickness, total sections per sample, sample volume and the paraffin mold base. Additionally, computerized image processing utilizing filters (such as, but not limited to, area, aspect, perimeter, and radius ratio) applied on the extracted data and counts allow for determination of cells/volume of each section.

Example 3.2: Cell Viability after Cryopreservation

The viability of cells collected from the finished osteoconductive matrices is analyzed after cryopreservation and post-thaw. According to some embodiments, at least 70% of the viable cells that were present on the sample (i.e., rinsed osteoconductive matrix particles) prior to cryopreservation are present on the osteoconductive matrix. The viability of these cells can be determined using commercially available methods, including but not limited to, for example, metabolic assays, such as involving luciferase, tetrazolium salts, for e.g., 3-(4, 5-dimethyl-2-thiazolyl)-2, 5-diphenyl-2H-tetrazolium bromide (MTT), 3-(4,5-dimethylthiazol-2-yl)-5-(3-carboxymethoxyphenyl)-2-(4-sulfophenyl)-2H-tetrazolium (MTS), 2,3-bis-(2-methoxy-4-nitro-5-sulfophenyl)-2H-tetrazolium-5-carboxanilide (XTT), and other water soluble tetrazolium salts (e.g., WST-1, -3, -4, -5, -8, -9, -10, and -11) and dye exclusion assays such as Tryptan Blue.

Example 3.3: BMP-2 Content of Demineralized Cortical Bone

Studies to determine the stability of DCB supplemented with BMP-2 are performed to confirm retention of osteoinductive potential after cryopreservation. Briefly, osteoinductivity of DCB supplemented with BMP-2 is measured utilizing an ELISA assay. These measured amounts of BMP-2 are compared to an in vitro animal model utilizing an athymic mouse where certain levels of BMP-2 are known to correlate to bone formation.

FIG. 1 shows a plot of BMP-2 (pg/g DCB) versus time (weeks). The levels of BMP-2 remain about or above 10,000 pg/g DCB after 12 weeks post-thaw.

Example 3.4: Immunogenicity

The orthopedic implant is analyzed for immunogenicity.
Mixed Lymphocyte Reaction (MLR)
Generally, the MLR is carried out by co-incubating lymphocytes from two strains that differ in histocompatibility genes for several days. $^3$H-thymidine then is added; the extent of its incorporation into DNA measures the proliferative response of T cells of one lymphocyte population to histocompatibility antigens of the other.

In order to examine the immunogencity of the orthopedic implant, up to 14 samples were analyzed for their stimulatory effects in the MLR. The samples were tested against blood cells from three normal human donors.

To this end, cryopreserved tissue samples were thawed in a 37° C. water bath until crystals were gone (about 20 min). Cryoprotectant solution then was removed; warm 5% dextrose in lactated ringers solution was added to the tissue samples and incubated for 5 minutes. Mitomycin C (30 μg/ml) in culture medium (RPMI (Roswell Park Memorial Institute) supplemented with 2 mM L-glutamine and penicillin (10/mL)) then was added to the samples and incubated at 37° C. for 30 minutes. Test samples were treated with Mitomycin C so that they would not give a signal alone. The samples were cut into small pieces, washed four times in culture medium, and similar amounts of culture medium were added to wells.

Cell samples were warmed in a 37° C. water bath. Following incubation, the cell samples were centrifuged at 1000 rpm for 5 min and the supernatant (cryoprotectant solution) was removed. The pelleted cells were resuspended in culture medium containing 30 μg/mL of Mitomycin-C and incubated for 30 min at 37° C. The cell samples were centrifuged again at 1000 rpm for 5 min, washed four times with RPMI medium, and resuspended in 4 mL of RPMI. For testing, cell numbers were adjusted to $1\times10^6$/mL.

For MLR assay, 30-50 mL blood in a heparinized syringe from each of three healthy volunteers was obtained. Two aliquots of D-PBS (phosphate-buffered saline) in sterile 50 ml screw cap and three tubes of Ficoll-Hupaque were prepared. 25 mL of blood was added to the same amount of PBS in two tubes per donor, and 15 mL of blood was layered to 33 mL of Ficoll-Hypaque. The tubes then were centrifuged at approximately 1400 rpm for 30 min at room temperature, and 10 mL of culture medium was aliquoted to three tubes. The plasma/platelet layer was discarded from each Ficoll-Hypaque gradient, and the cells at the interface from each of the tree tubes per donor were collected. 10 mL of culture medium then was added to the tubes and centrifuged at 1400 rpm for 15 min at room temperature. The red blood cell layer was treated with dispatch or bleach and discarded. The supernatant from each tube was decanted and the cell pellets were resuspended in approximately 10 mL of culture medium (combining three tubes into one). The tubes were centrifuged at approximately 1200 rpm for 10 min at room temperature. The pelleted cells were resuspended in RPMI-10 and cell numbers were adjusted to $1\times10^6$ cells/ml. 3 mL of the cell suspension was kept and treated with 30 μg/mL Mitomycin-C. The prepared cells then were added to 0.1 ml of cells/well or to 0.1 ml of sample/well for MRL assay. For tissue samples, 0.1 mL of RPMI-10 medium was added to each tissue sample and the tissue sample (without liquid) was added to cells.

After five days treatment, cells were labeled overnight with approximately 0.5 μCi/well [$^3$H] thymidine, harvested, and counted in a scintillation counter. All conditions were performed in replicate. Results were reported as incorporation of [$^3$H] thymidine as a measure of lymphocyte proliferation. Proliferation was expressed as a Stimulation Index (SI), where SI=cpm (blood cells+test sample)/[cpm (blood cells alone)+cpm (test sample alone)], which is what is represented on the Y-axis in FIG. 2. Positive controls were normal blood donor cells mixed with mitomycin-treated different normal blood cell donor cells to demonstrate a strong MLR. Negative controls were normal donor cells alone and test samples alone (sample (11)-(14)).

TABLE 12

MLR assay results

| Sample | Stimulation Index | | |
|---|---|---|---|
| | Donor A | Donor B | Donor C |
| (1) #023-93615: Cancellous tissue w/out DCB (cryopreserved product) | 0.9 | 1.1 | 0.4 |
| (2) #005-93647: Cancellous tissue pre-washed sample (cryopreserved) | 0.7 | 0.9 | 0.2 |

TABLE 12-continued

MLR assay results

| Sample | Stimulation Index | | |
|---|---|---|---|
| | Donor A | Donor B | Donor C |
| (3) #005-93647: Cancellous tissue w/out DCB (Cryopreserved product) | 0.6 | 0.8 | 0.3 |
| (4) #005-93647: Cancellous tissue w/DCB (cryopreserved product) | 0.5 | 1.0 | 0.3 |
| (5) #005-93647: Cancellous tissue w/DCB another sample (cryopreserved product) | 0.5 | 1.1 | 0.3 |
| (6) #023-93615: Heat-inactivated Cancellous tissue with DCB | 0.4 | 1.0 | 0.4 |
| (7) #023-93615: Digested Cancellous tissue (sent refrigerated) | 0.3 | 0.6 | 0.3 |
| (8) #005-93647: Digested Tissue (sent refrigerated) | 0.3 | 0.6 | 0.5 |
| (9) #023-93615: Digested cells from Cancellous tissue (sent refrigerated) | 1.6 | 0.8 | 0.7 |
| (10) #005-93647: Digested Cells (sent refrigerated) | 0.6 | 0.5 | 0.1 |
| (11) Control: Trinity ® 1 cc Same Sample as 11 (normal thaw, vial 1) | 0.2 | 0.3 | 0.2 |
| (12) Control Trinity ® 1 cc Same Sample as 10 (thaw, centrifuged, add cells to MLR with tissue for testing, vial 2) | 0.2 | 0.4 | 0.1 |
| (13) Control DCB | 0.4 | 0.3 | 0.3 |
| (14) Control DCB (second sample) Stimulation Index | 0.4 | 0.4 | 0.4 |
| Positive Control (PC) Cells from Donor with Cells from a Different Donor treated with Mitomycin C | 4.4 | 2.5 | 4.1 |

As shown in Table 12, none of the samples significantly stimulated a MLR as measured by the Stimulation Index when compared to the positive controls across blood donors. Some of the tissue/solid samples had a rather high content of $^3$H-thymidine alone that may be due to passive trapping.

Figure 2:
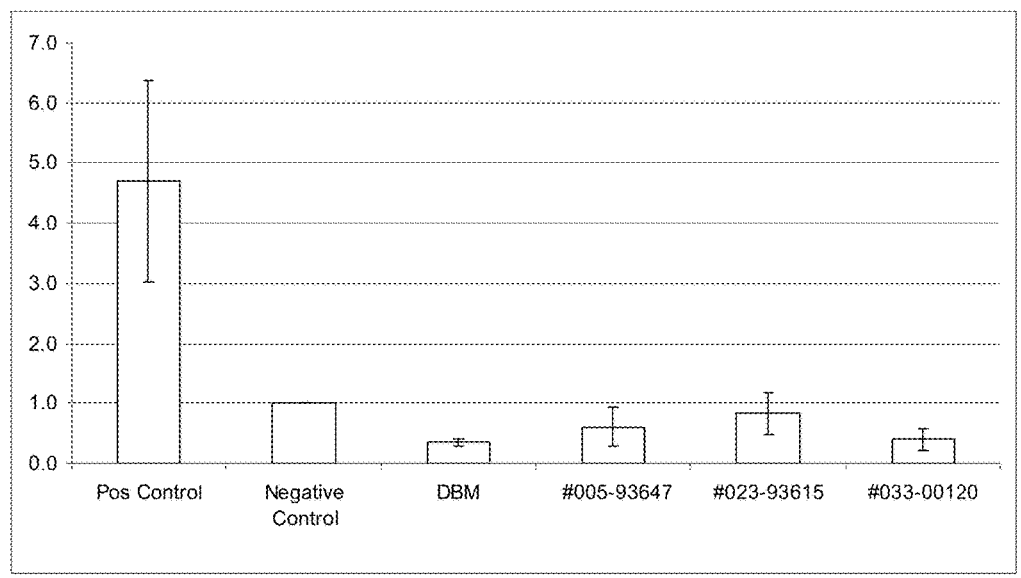
FIG. 2 shows a plot of the MLR response of a positive control (latex glove), a negative control, DCB, and 3 sample orthopedic implants.

FIG. 2 shows a plot of the MLR response of a negative control, DCB, and 3 sample orthopedic implants prepared as described herein. The DCB, 3 sample orthopedic implants, and negative control each demonstrated a lower MLR response than the positive control.

Complement Activation: c3a Protein

The complement system is a complex system of proteolytic enzymes, regulatory and inflammatory proteins and peptides, cells surface receptors, and proteins capable of causing the lysis of cells (see, for example, *Fundamentals Immunology*, 4th Ed., 1999. Paul, W. E. (Eds.), Lippincott-Raven Publishers, New York, N.Y.). The system can be thought of as consisting of three arrays of proteins. Two of these sets of proteins, when engaged, lead to the activation of the third component of complement (C3). The activation of C3 releases proteins that are critical for opsonization (preparation for phagocytosis) of bacteria and other particles and engages the third set of proteins that insert into biologic membranes and produce cell death through osmotic lysis. In addition, fragments generated from some of the complement components (for example, C3a and C5a) have potent inflammatory activities.

The two activation systems for C3 are referred to as the classical pathway and alternative pathway. The classical pathway is initiated by the formation of complexes of antigen with IgM and IgG antibody. This leads to the binding of the first component of complement, C1, and its activation, creating the C1 esterase that can cleave the next two components of the complement system, C4 and C2.

C4 is a trimeric molecule, consisting of α, β, and γ chains. C1 esterase cleaves the α chain, releasing the C4b, which binds to surfaces in the immediate vicinity of the antigen/antibody/C1 esterase complex. A single C1 esterase molecule will cause the deposition of multiple C4b molecules.

C2 is a single polypeptide chain that binds to C4b and is then proteolytically cleaved by C1 esterase, releasing C2b. The resulting complex of the residual portion of C2 (C2a) with C4b (C4b2a) is a serine protease whose substrate is C3. Cleavage of C3 by C4b2a (also referred to as the classical pathway C3 convertase) results in the release of C3a and C3b. The amplification nature of this system is implicit in the capacity of a single antigen/antibody complex and its associated C1 esterase to produce a large number of C3 convertases (i.e., C4b2a complexes) and thus to cleave a large number of C3 molecules.

The components of the classical pathway can be activated by a distinct, non-antibody-dependent mechanism. The mannose-binding lectin (MBLectin) is activated by binding to (and being crosslinked by) repetitive sugar residues such as N-acetylglucosamine or mannose. The activation of MBLectin recruits the MBL-associated serine proteases MASP-1 and MASP-2, which are homologues of two of the constituent chains of C1 (C1r and C1s). This results in the activation of C4 and C2 and the formation of the classical pathway C3 convertase. Because the capsules of several pathogenic microbes can be bound by MBLectin, this provides an antibody-independent pathway through which the complement system can be activated by foreign microorganisms.

The alternative pathway can be activated by a variety of agents such as insoluble yeast cell wall preparations and bacterial lipopolysaccharide. Antigen/antibody complexes also can activate the alternative pathway. The C3 convertase of the alternative pathway consists of a complex of C3b (itself a product of cleavage of C3) bound to the b fragment of the molecule factor B. C3bBb is produced by the action of the hydrolytic enzyme, factor D, that cleaves the factor B; this cleavage only occurs when factor B has been bound by C3b.

The alternative pathway also can act to amplify the classical pathway because the C3 convertase of the classical system (C4b2a) provides a source of C3b that can strikingly enhance formation of the alternative pathway convertase (C3bBb) in the presence of factor D.

C3b, formed from C3 by the action of the C3 convertases, possesses an internal thioester bond that can by cleaved to form a free sulfhydryl group. The latter can form a covalent bond with a variety of surface structures. C3b is recognized by receptors on various types of cells, including macrophages and B cells. The binding of C3b to antibody-coated bacteria is often an essential step for the phagocytosis of these microbes by macrophages.

C3b also is essential to the engagement of the terminal components of the complement system (C5 through C9) to form the membrane attack complex that causes cellular lysis. This process is initiated by the cleavage of C5. The C5 convertases that catalyze this reaction are C4b2a3b (the classical pathway C5 convertase) or a complex of C3bBb with a protein designated properdin (the alternative pathway C5 convertase). Cleaved C5, C5b, forms a complex with C6 and then C7, C8, and C9. This C5b/C9 complex behaves as an integral membrane protein that is responsible for the formation of complement-induced lesions in cell membranes. Such lesions have a donut-like appearance, with C9 molecules forming the ring of the donut.

In addition to the role of the complement system in opsonization and in cell lysis, several of the fragments of complement components formed during activation are potent mediators of inflammation. C3a, a fragment released by the action of C3 convertases, binds to receptors on mast cells and basophils, resulting in the release of histamine and other mediators of anaphylaxis. C3a and C5a (a fragment released by the action of C5 convertases) are termed an anaphylotoxins. C5a also is a chemoattractant for neutrophils and monocytes.

The process of activation of the complement cascade is highly regulated. Several regulatory proteins (for example, C1 esterase inhibitor, decay accelerator factor, membrane cofactor protein) exist that function to prevent uncontrolled complement activation.

Complement activation from two proteins, C3a and SC5b can be assayed. Commercially available assays are available to measure C3a and SC5b, such as, but not limited to, BD OptEIA™ Human C3a ELISA (BD Biosciences) and Micro-Vue SC5b 9 Plus Enzyme Immunoassay (Quidel, San Diego, Calif.). Briefly, the BD OptEIA™ Human C3a ELISA is a solid phase sandwich ELISA that utilizes a monoclonal antibody specific for human C3a-desArg coated on a 96-well plate. Standards and samples are added to the wells, and any C3a-desArg present binds to the immobilized antibody. The wells are washed and a mixture of biotinylated polyclonal anti-human C3a antibody and streptavidin-horseradish peroxidase is added, producing an antibody-antigen-antibody sandwich. The wells are again washed and a substrate solution is added, which produces a blue color in direct proportion to the amount of C3a-desArg present in the initial sample. The Stop Solution changes the color from blue to yellow, and the wells are read at 450 nm. Commercially available assays also are available to measure SC5b9 such as, but not limited to, MicroVue SC5b 9 Plus Enzyme Immunoassay (Quidel, San Diego, Calif.). Briefly, the assay measures the amount of the SC5b 9 complex present in human plasma or serum specimens. The Terminal Complement Complex (TCC, SC5b-9) is generated by the assembly of C5 through C9 as a consequence of activation of the complement system by either the classical, lectin or alternative pathway. The membrane attack complex (MAC), a form of TCC, is a stable complex that mediates the irreversible target cell membrane damage associated with complement activation. Complexes formed in the absence of a target membrane bind to naturally occurring regulatory serum proteins, e.g. the S protein, 5-7 at the C5b 7 stage of assembly forming, soluble, non-lytic TCC. The assay measures the concentration of TCC thereby giving an indication of the status of the terminal complement pathway in the specimen. It uses a monoclonal antibody to the C9 ring of TCC to capture the complex. The trapped TCC is subsequently detected with HRP-conjugated antibodies that bind to antigens of the SC5b 9 complex.

Figure 3A:
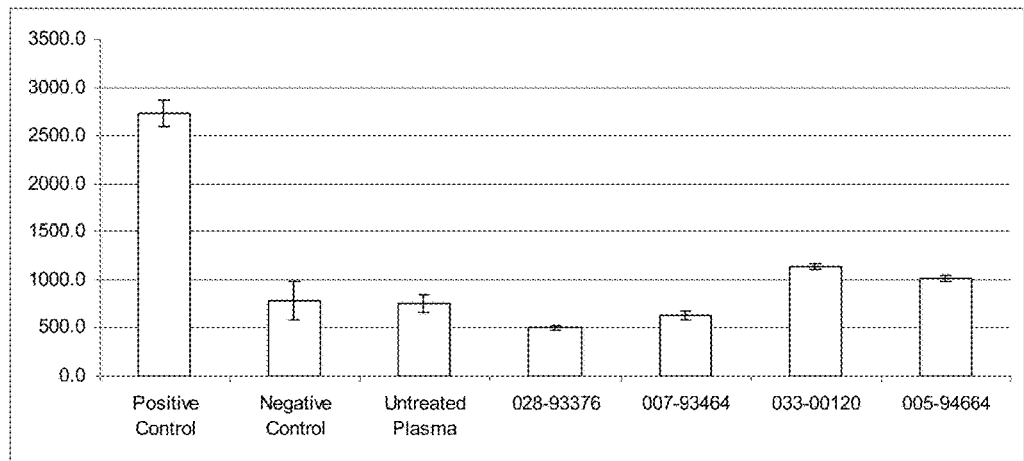
FIG. 3A shows a plot of the complement activation response of c3a protein (ng/ml) of a positive control, negative control, untreated plasma, and 4 sample orthopedic implants.
Figure 3B:
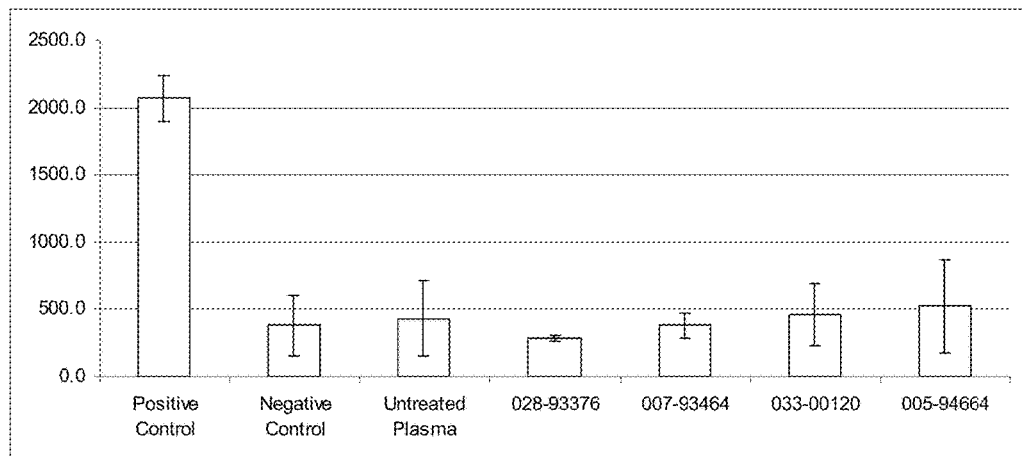
FIG. 3B shows a plot of the complement activation response of SC5b (ng/ml) protein of a positive control, negative control, untreated plasma, and 4 sample orthopedic implants.

FIG. 3A shows a plot of the complement activation response of c3a protein of a positive control, negative control, untreated plasma, and 4 sample orthopedic implants. FIG. 3B shows a plot of the complement activation response of SC5b protein of a positive control, negative control, untreated plasma, and 4 sample orthopedic implants. The plots indicate that the implants provoke no response in either the c3a (FIG. 3A) or SC5b (FIG. 3b) assay.

Example 3.5: Biocompatibility Testing (ISO10993)

The ISO10993 criteria are a series of standards for evaluating the biocompatibility of a medical device. Table 13 shows several of these tests and conclusions drawn therefrom for orthopedic implants prepared from a bone tissue.

TABLE 13

Biocompatibility Testing (ISO10993)

| Test | Conclusion |
| --- | --- |
| Cytotoxicity, ISO Agar diffusion (n = 4) | Not cytotoxic |
| Acute Systemic Toxicity in Mouse, systemic injection (n = 3) | No systemic toxicity |
| Acute intracutaneous injection (n = 2) | No irritation |
| Rabbit pyrogen test (material mediated) (n = 2) | Not pyrogenic |
| Genotoxicity: AMES reverse mutation study (n = 2) | Not mutagenic |
| Hemolysis-Human Blood, direct contact (n = 1) | Not hemolytic |
| Hemolysis-Human Blood, indirect contact (n = 2) | Not hemolytic |

Example 3.6: Rat Intramuscular Study

The three components of the orthopedic implant (osteoinductive component, osteoconductive component, and osteogenic cell component) from a bone tissue were measured at 28 days (the end point for atopic bone formation in a muscle pouch) in vivo using a well-established athymic rat muscle pouch model. Briefly, two test groups were established: (1) $N_1=8$ per test group, randomized, bilateral implantation, and (2) $N_2=10$ sections/implant. The best of 5 slides were scored for each test group on a grade of 0-4. Table 14 shows results from the intramuscular study where scores greater than or equal to 1.0 pass the U.S. Food and Drug Administration osteoinductive test.

TABLE 14

| Athymic rat muscle pouch model assessment of differentiation | |
| --- | --- |
| Sample | Score |
| Day 14 IM | |
| orthopedic implant 1 | 1.25 |
| orthopedic implant 1 with freeze/thaw | 0.86 |
| orthopedic implant 2 | 1.86 |
| Day 28 IM | |
| orthopedic implant 1 | 1.65 |
| orthopedic implant 1 with freeze/thaw | 0.88 |
| orthopedic implant 2 | 1.57 |

Figure 4A:
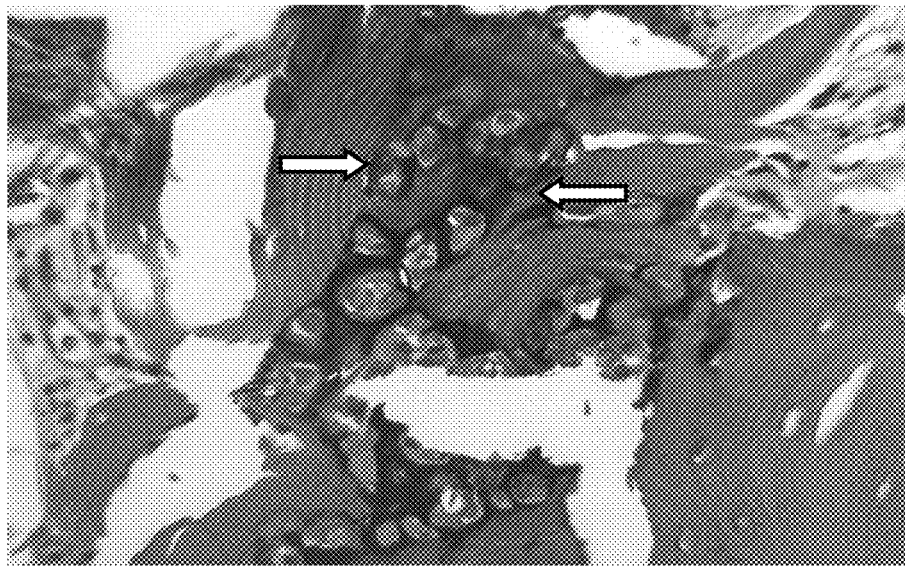
FIG. 4A shows that at day 14 hypotrophic chondrocytes are beginning to form.
Figure 4B:
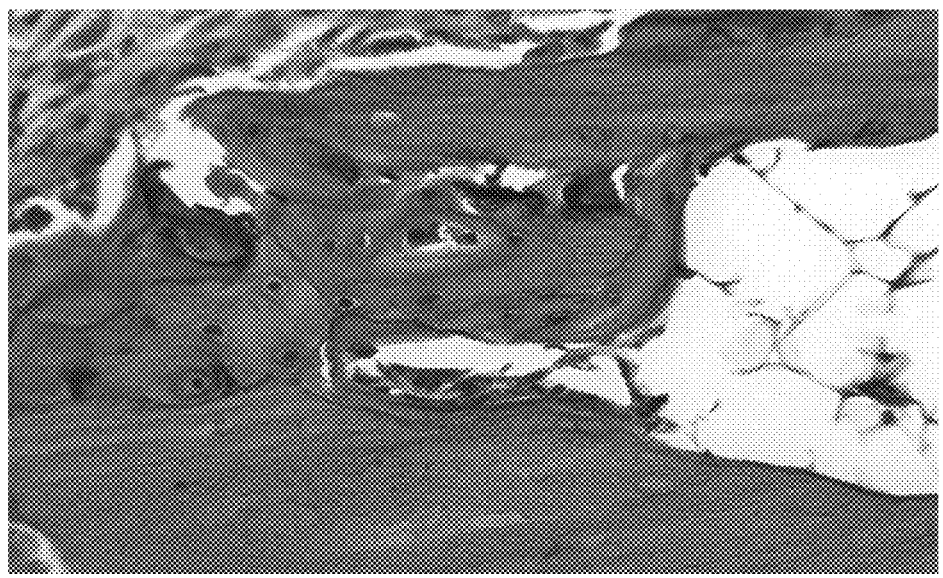
FIG. 4B shows that at day 28, new bone formation is evident.

FIG. 4A shows that at day 14, hypotrophic chondrocytes are beginning to form; FIG. 4B shows that at day 28, new bone formation is evident.

Example 3.7: Rat Posterolateral Spinal Fusion

Orthopedic implants from a bone tissue were implanted into a spinal fusion model. An incision of approximately 4 cm is made on the posterior midline over the distal lumbar spine. The transverse processes of the L4 and L5 are exposed and decorticated to allow blood flow. The bone graft is then placed over the decorticated surfaces in the space between posterolateral vertebral processes of an athymic rat. If the implant is osteogenic, bone will grow and the spine will fuse. The spine is excised and rigidity of the spine tested 8 weeks post-implantation utilizing the manual bend test.

TABLE 15

Results at 8 weeks post-implantation by the manual bend test:

| Sample | Fusion |
| --- | --- |
| orthopedic implant 1 (30% DCB) | 2/7 (29%) |
| orthopedic implant 1 with freeze/thaw | 2/8 (25%) |
| orthopedic implant 2 | 1/6 (17%) |

Table 15 shows results obtained at 8 weeks post-implantation by the manual bend test. Less subjective radiographic data was obtained by CT. Radiographs were scored based on a 6-point grading system: 1) 0 points (no bone formation); 2) 1 point (bone filling less than 25% of area); 3) 2 points (bone filling 25-50% of area; 4) 3 points (bone filling 50-75% of area); 5) 4 points (bone filling 75-99% of area); and 6) 5 points (clear evidence of fusion with the bone filling all gaps between L4 and L5).

Table 16 shows that some explants scored a grade 5 (fusion) by radiographic analysis that were not considered fused using the manual bend test. It was concluded that fusion had occurred because of the conductive effect of the matrix and because the inductive effect of BMP was still present. Radiographic results were graded on a scale of 0-5, with N=3 observers (Grade ≥4 (75-99%; 100%): Fusion in the manual bend test is equivalent to a grade 5 radiograph score.

TABLE 16

Results obtained Post-mplantation Radiographically by CT

| Sample | Radiographic Grade |
| --- | --- |
| orthopedic implant 1 (30% DCB) | 5.7/7 (81%) |
| orthopedic implant 1 with freeze/thaw | 4.7/8 (59%) |
| orthopedic implant 2 | 4.7/6 (78%) |

Because there is a 20% increase in fusion when cells are present, these results suggest that the osteogenic cells together with the osteoinductive components affect bone formation. The presence of osteoconductive, osteoinductive and osteogenic components in the implants of the described invention provided bone formation earlier in time, when compared to controls.

Example 4: Fabrication of Fresh Cancellous Bone Particles from Human Ilium with Acetic Acid Rinse One left ilium from Donor 007-63609 was processed to obtain fresh cancellous bone particles.

Cutting the Tissue

The bulk of the soft tissue was removed from the ilium. The acetabulum was removed and release notches were cut along the iliac crest. The iliac crest was then removed with cutting following its contour. The area of the iliac spine was cut until there was no more growth plate visible via cross section. Any areas of heavy cortical bone and any remaining portions of periosteum were trimmed off. The ilium was then cut into approximately 3 cm by 3 cm cubes.

Milling and Rinsing of Tissue

Prior to placing tissue in the mill, all grinding parts of the mill were wet down with 4° C. phosphate buffered saline solution (PBS). The tissue was placed into the mill. Ground cancellous bone was generated, sized <2 mm in diameter. The tissue was then transferred to a room temperature Nalgene container. The tissue was subjected to a series of rinses with cold PBS, followed by a rinse in acetic acid solution for 5 minutes and then followed again by a series of rinses with cold PBS.

Between each rinse, the rinsing solution was decanted off using a sieve to catch the tissue. After the acetic acid rinse, a new Nalgene container as well as a new sieve were used in order to minimize the tissue's exposure to residual acetic acid. After the last rinsing step, the tissue was then prepared for cryopreservation. A sample was set aside in order to evaluate the cell metabolic activity of the tissue using commercially available methods, including but not limited to, for example, metabolic assays, such as involving luciferase, tetrazolium salts, for e.g., 3-(4, 5-dimethyl-2-thiazolyl)-2, 5-diphenyl-2H-tetrazolium bromide (MTT), 3-(4,5-dimethylthiazol-2-yl)-5-(3-carboxymethoxyphenyl)-2-(4-sulfophenyl)-2H-tetrazolium (MTS), 2,3-bis-(2-methoxy-4-nitro-5-sulfophenyl)-2H-tetrazolium-5-carboxanilide (XTT), and other water soluble tetrazolium salts (e.g., WST-1, -3, -4, -5, -8, -9, -10, and -11) and dye exclusion assays such as Tryptan Blue. The assay confirmed that the tissue contained metabolically active cells within its matrix.

Cryopreservation of Tissue

Mesencult basal media was prepared and sterile filtered. Cryoprotectant (10 ml) was added in order to assure full coverage of the tissue. The samples were packaged in one layer of Teflon pouches (CryoSystems). One sample as a probe sample was cryopreserved in a laboratory cryopreservation unit. Once the program cycle was complete, the tissue was placed in liquid nitrogen.

It should be understood by those skilled in the art that many modifications may be made to adapt a particular situation, material, composition of matter, process, process step or steps, to improve, for example, but not limited to, efficiency, and yield.

Plating of Tissue for Mesenchymal Stem Cell Characterization (Donor 035-59660)

After the last rinsing step, two 6-well tissue culture plates were seeded with approximately 1-2 cc of tissue per well in 4 ml of MSC complete media (Mesencult Basal Media with MSC supplements and 1× pen/strep). The media were changed on the tissue every 2-3 days as needed using aseptic cell culture techniques. The tissue was removed carefully from the culture using sterile forceps after approximately two weeks. While the larger sized pellets were removed, some very small pieces remained on the plate. After two weeks of incubation several cells appeared in each well. The cells were allowed to continue to grow for use in various cell characterization assays described below. The cultured cells were able to differentiate into the osteogenic and adipogenic lineages as demonstrated by the presence of alkaline phosphatase, mineralization of the cell layer, and the presence of lipid containing vesicles within the cells.

Osteogenic Differentiation Assay: Alkaline Phosphatase & Von Kossa Staining

After cell proliferation was observed, the cells were transferred to 25 ml t-flasks. After adherence of the MSC's after sub-culturing, the cells were exposed to osteogenic complete medium (Stem Cell Technologies). After five days of incubation, the old medium and non-adherent cells were removed and the medium replaced with fresh complete medium. The media were exchanged every 2-3 days as needed using aseptic cell culture techniques for 6 weeks. Once the multi-layering of the cells was observed, β-Glycerophosphate was added to the medium. After 6 weeks in culture the cells were fixed and stained using alkaline phosphatase and von kossa.

Adipogenic Differentiation Assay: Oil Red O Staining

After subculturing and adherence of the MSC's, the cells were exposed to adipogenic complete medium (Stem Cell Technologies). The media was exchanged every 2-3 days as needed using aseptic cell culture techniques for 3 weeks. As the cells divided and started forming a multi-layer state, the formation of fat vacuoles was observed. After 3 weeks in culture the cells were fixed and stained using Oil Red O.

Flow Cytometry of Tissue Derived MSC's, Donors 035-59660 & Donor 002-57470:

The cells from Donor 035-59660 and Donor 002-57470 used for the differentiation assays were expanded and used for flow cytometry analysis. The cells were compared to an established MSC line (human Mesenchymal Stem Cells, Catalog No. MSC-001F, Stem Cell Technologies, Vancouver, BC, CN) as well as to KG1A cells (which served as a negative control for MSC markers and a positive control for hematopoietic markers CD34 and CD45). Isotype controls were measured as well as unstained, single and triple stain controls. The isotype controls are used to confirm that the primary antibody binding is specific and not due to other protein interactions or non-specific binding. The stain controls are used in order to determine background autofluorescence of the cells, as well as the spectral overlap of the fluorochromes in the cytometer alignment.

The cells were reacted with CD 34, 44, 45, 90, 105 and 166 antibodies. MSC's were expected to be positive for CD44, 90, 105 and 166 and negative for CD34 and 45. The KG1a cells were expected to be positive for CD34 and 45 and were used as negative control markers for the MSC's. The following antibody and conjugate pairs were used:

TABLE 17

Flow Cytometry Cell Surface Marker Antibodies

| Antibody and conjugate | Volume to use per 500,000 cells |
| --- | --- |
| CD34 APC | 10 µL |
| CD44 FITC | 20 µL |
| CD166 PE | 20 µL |
| CD45 APC | 10 µL |
| CD90 FITC | 20 µL |
| CD105 PE | 20 µL |
| IgG1 APC | 10 µL |
| IgG1 FITC | 20 µL |
| IgG1 PE | 20 µL |
| IgG3 PE | 5 µL |

The following experimental setup was used to characterize cells by flow cytometry:

TABLE 18

Experimental setup used to characterize cells by flow cytometry

| | CD 34 | CD 44 | CD 166 | CD 45 | CD 90 | CD 105 |
| --- | --- | --- | --- | --- | --- | --- |
| Single Stain compensation controls | (500 µl KG-1a) | (500 µL MSCs) | (500 µL MSCs) | (500 µl KG-1a) | (500 µL MSCs) | (500 µL MSCs) |
| Triple Stain Compensation Controls | CD 34 CD 44 CD 166 (250 µl KG-1a and 250 µL MSCs) | | | CD 45 CD 90 CD 105 (250 µl KG-1a and 250 µL MSCs) | | |
| Isotype Controls | IgG1 APC IgG1 | IgG1 | | IgG1 APC IgG1 | IgG1 | |

TABLE 18-continued

Experimental setup used to characterize cells by flow cytometry

| | CD 34 | CD 44 | CD 166 | CD 45 | CD 90 | CD 105 |
| --- | --- | --- | --- | --- | --- | --- |
| Single Stain compensation controls | (500 µl KG-1a) | (500 µL MSCs) | (500 µL MSCs) | (500 µl KG-1a) | (500 µL MSCs) | (500 µL MSCs) |
| | | Fitc IgG1 PE (500 µL MSCs) | Fitc IgG3 PE (500 µL MSCs) | | Fitc IgG1 PE (500 µl KG-1a) | Fitc IgG3 PE (500 µl) KG-1a |
| Unstained Controls | KG-1a 500 µL | | 500 µL MSC line | | | |
| Test Articles | 035-59660 CD 34 CD 44 CD 166 | 002-57470 CD 34 CD 44 CD 166 | | 035-59660 CD 45 CD90 CD 105 | 002-57470 CD 45 CD 90 CD 105 | |
| Test Articles Isotype controls | 035-59660 IgG1 APC IgG1 Fitc IgG1 PE 002-57470 IgG1 APC IgG1 Fitc IgG1 PE | 035-59660 IgG1 APC IgG1 Fitc IgG3 PE 002-57470 IgG1 APC IgG1 Fitc IgG3 PE | | 035-59660 IgG1 APC IgG1 Fitc IgG1 PE 002-57470 IgG1 APC IgG1 Fitc IgG1 PE | 035-59660 IgG1 APC IgG1 Fitc IgG3 PE 002-57470 IgG1 APC IgG1 Fitc IgG3 PE | |

As shown in Table 19, flow cytometry analysis confirmed that the osteogenic cells obtained from the fresh cancellous bone were positive for CD44, 90, 105 and 166 and negative for CD34 and 45, indicating that the osteogenic cells comprise MSC's. In contrast, the KG1a cells were positive for CD34 and 45 and negative for CD44, 90, 105 and 166. The following percentages were representative of the surface markers for the MSC cell line, tissue derived MSC's and the KG1A cells:

TABLE 19

Flow Cytometry Results Obtained for Osteoconductive Matrices obtained from Two Donors

| | MSC cell line | Tissue derived from MSC's from MTF035-59660 [Donor 1] | Tissue derived fromMSC's from MTF002-57470 [Donor 2] | KG1a cell line |
| --- | --- | --- | --- | --- |
| CD44 | 94.07% | 89.69% | 83.11% | 0.20% |
| CD90 | 92.84% | 92.55% | 80.95% | 0.24% |
| CD105 | 98.27% | 92.82% | 82.07% | 0.05% |
| CD166 | 97.06% | 89.56% | 82.96% | 0.66% |
| CD34 | 0.62% | 1.99% | 1.12% | 98.54% |
| CD45 | 0.19% | 1.46% | 3.09% | 98.82% |

Example 5: Fabrication of Fresh Cancellous Bone Particles from Human Ilium with NH$_4$Cl Rinse One left ilium was processed from Donor 041-59941 to obtain cancellous bone particles to compare the rinsing process with acetic acid and the rinsing process with ammonium chloride.

Cutting the Tissue

The bulk of the soft tissue was removed from the ilium. The acetabulum was removed and release notches were cut along the iliac crest. The iliac crest was then removed with cutting following its contour. The area of the iliac spine was cut until there was no more growth plate visible via cross section. Any areas of heavy cortical bone and any remaining portions of periosteum were trimmed off using the band saw. The ilium was then cut into approximately 3 cm by 3 cm cubes.

Milling & Rinsing of Tissue

Prior to placing tissue in the mill, all grinding parts of the mill were wet down with 4° C. phosphate buffered saline solution (PBS). The tissue was placed into the mill. Ground cancellous bone was generated, sized <2 mm in diameter. The tissue was then divided in half and transferred to two room temperature Nalgene containers. The tissue was subjected to a series of rinses with cold PBS, followed by a rinse in acetic acid solution for 5 minutes and then followed again by a series of rinses with cold PBS.

Between each rinse, the rinsing solution was decanted off using a sieve to catch the tissue. After the acetic acid rinse, a new Nalgene container as well as a new sieve was used in order to minimize the tissue's exposure to residual acetic acid.

Between each rinse, the rinsing solution was decanted off using a sieve to catch the tissue. After the ammonium chloride rinse, a new Nalgene container as well a new sieve was used in order to minimize the tissue's exposure to residual ammonium chloride.

At the end of the rinsing steps, a sample was set aside from each rinsing process in order to evaluate the cell metabolic activity of the tissue via methyl tetrazolium (MTS) assay.

The assay confirmed that the metabolic activity of the cells after the acetic acid rinse was unchanged. The assay for the ammonium chloride showed interaction between the chemical and the assay which made it unable to give us accurate metabolic results. Through visual inspection of the tissue, the tissue rinsed using acetic acid appeared to contain less blood products than the tissue rinsed using the ammonium chloride.

Example 6: Fabrication of Demineralized Cortical Bone Particles

Human long bone is recovered aseptically from a deceased donor under the age of 65 years, and stored at 4° C. until ready for processing. The bone is debrided and the shaft of the bone is cut into bulk pieces. An initial cleaning is performed during which the pieces of bone are soaked in a surfactant solution, and then soaked in a disinfectant solution, followed by a water rinse. The bone pieces are then allowed to soak in ethanol, and dried.

To create demineralized bone particles, the bone sections are milled to powder and sieved to capture particles having sizes in the range of about 212 μm to about 850 μm. The particles are cleaned with hydrogen peroxide solution, then rinsed in water, and soaked in about 70% ethanol, and finally air dried in a sieve connected to a vacuum.

The air-dried bone particles are demineralized by agitating them in 0.6 N HCl, followed by one or more soaks in fresh 0.6 N HCl for a sufficient period of time to remove the endogenous calcium salts. The bone particles are then rinsed in water, soaked in 0.1 M sodium phosphate dibasic, then rinsed in water several more times. The bone particles are then air dried in a sieve connected to a vacuum to a residual moisture content in the range of about 15-25%.

Example 7: Fabrication of Demineralized Cortical Bone Fibers

Human long bone is recovered aseptically from a deceased donor under the age of 65 years and stored at 4° C. until ready for processing. The bone is debrided and the shaft of the bone is cut into cross-sections. An initial cleaning is performed during which the cross-sections of bone are soaked in a surfactant solution, and then soaked in a disinfectant solution, followed by a water rinse. The bone sections are then allowed to soak in ethanol, and dried.

To create demineralized bone fibers, the bone sections are first shaved across the shaft of the bone using a controlled advancement rate of a lathe bit having a width approximately equal to the desired length of the bone fibers. The shaft segment is secured in a vice with a sufficient portion of the shaft protruding such that the protruding portion may be shaved. On a milling machine, a straight flute end-mill is set up such that its axis is parallel with the axis of the shaft. Utilizing the required length of the of the broad edge of the lathe bit, fibers are shaved off of the shaft by running the end-mill back and forth along the shaft until substantially all of the bone has been shaved from the shaft. The resulting bone fibers are collected for demineralization.

The bone fibers are demineralized by agitating them in 0.6 N HCl for a sufficient period of time to remove the endogenous calcium salts, after which the fibers are agitated, successively, with water, 0.1 M sodium phosphate dibasic, water again, then PBS. The bone fibers are then air dried in a sieve connected to a vacuum to a residual moisture content in the range of about 60-80%.

Example 8: Selection of the Length of Demineralized Bone Fibers

The length of the demineralized bone fibers in a graft mass affects the graft's cohesiveness and malleability. Longer fibers entangle with each other to a higher degree than shorter fibers, increasing the cohesiveness of the graft mass. When being handled and molded, a graft mass with longer demineralized bone fibers remains intact to a higher degree than a graft mass with shorter demineralized bone fibers, and for a longer period of time. This improved cohesion also enhances the graft's resistance to dispersion caused by compression and to separation due to tensile force. The improved cohesion also decreases the tendency of the graft mass to disperse when it is placed under a stream of pressurized fluid.

In an exemplary embodiment of the present invention, fibers of 150 μm thickness were milled into two separate batches. Fibers in one batch were milled to a length of 8 mm, and in the second batch to a length of 16 mm. Both batches were taken separately through the demineralization process and lyophilized. Four (4) grams of dry weight from each batch were weighed out and a 32% bone hydrated mixture was produced. The two fiber length formulations were tested side by side for overall handling and irrigation. The 16 mm fibers were noted as being more cohesive when handled. Furthermore, when the mass was rolled into an oblong sphere, the 16 mm fibers provided significantly higher resistance to being pulled apart. Each formulation was then placed into a bone model defect and subjected to a compressive force. The 16 mm fibers provided significantly higher resistance to deformation and could not be forced out of the defect, compared to the 8 mm fibers which extruded out with little force. An irrigation procedure was then conducted on both fiber types by applying a water jet to the defect site. Initially, both fiber types withstood the irrigation and swelling and absorbing a portion of the water. With continuing irrigation, the 16 mm fibers withstood washout for a longer time and to a higher degree.

Example 9: Fabrication of Fresh Cancellous Bone Particles from Human Ilium with Demineralized Cortical Bone Particles Added Human ilium is processed from a donor to obtain cancellous bone particles, prepared as in Example 4, to which demineralized cortical bone (DCB) particles, prepared as in Example 6, are added. The freshly-milled cancellous bone particles are mixed with the DCB particles in a ratio of about one-third DCB particles to about two-thirds cancellous bone particles (w/w) in such a manner as to ensure a homogenous mixture.

The mixture of DCB particles and cancellous bone particles is scooped into a suitable container, which is then filled with a basal cell culture media containing 10% dimethyl sulfoxide (DMSO) as a cryoprotectant to maintain the viability of the cells in the cancellous bone particles during freezing and thawing. The mixture is agitated to suspend the DCB particles and cancellous bone particles in the cryoprotective media, and then frozen at a controlled rate to about −100° C. and stored in liquid nitrogen vapor phase at −185° C. for long-term storage.

Example 10: Fabrication of Fresh Cancellous Bone Particles from Human Ilium with Demineralized Cortical Bone Fibers Added Human ilium is processed from a donor to obtain cancellous bone particles, prepared as in Example 4, to which demineralized cortical bone (DCB) fibers, prepared as in Example 7, are added. The freshly milled cancellous bone particles are mixed with the DCB fibers in a ratio of about 60% DCB fibers to about 40% cancellous bone particles (w/w) in such a manner as to ensure a homogenous mixture.

The mixture of DCB fibers and cancellous bone particles is scooped into a suitable container, which is then filled with a basal cell culture media containing 10% dimethyl sulfoxide (DMSO) as a cryoprotectant to maintain the viability of the cells in the cancellous bone particles during freezing and thawing. The mixture is agitated to suspend the DCB fibers and cancellous bone particles in the cryoprotective media, and then frozen at a controlled rate to about −100° C. and stored in liquid nitrogen vapor phase at −185° C. for long-term storage.

Example 11: Fabrication of Fresh Cancellous Bone Particles from Human Ilium with Crushed Demineralized Cancellous Bone Particles Added Human ilium is processed from a Donor to obtain cancellous bone particles as in Example 4 to which crushed demineralized cancellous bone matrix is added.

Example 12: Fabrication of Fresh Cancellous Bone Particles from Human Ilium with Autologous Bone Marrow or Other Autologous Cells Added Human ilium is processed from a Donor to obtain cancellous bone particles as in Example 4 to which autologous bone marrow or other autologous cells is added. Generally, autologous bone marrow or other autologous cells can be added to the cancellous bone particles obtained as in Example 4 to increase the amount or volume of the orthopedic implant thereby increasing the possibility of fusion.

Example 13: Fabrication of Fresh Cancellous Bone Particles from Human Ilium with Growth Factor or Factors Added Human ilium is processed from a Donor to obtain cancellous bone particles as in Example 4 to which at least one growth factor is added.

Example 14: Fabrication of Fresh Cancellous Bone Particles from Human Ilium with Growth Factors and Demineralized Bone Matrix Added Human ilium is processed from a Donor to obtain cancellous bone particles as in Example 4 to which at least one growth factor and demineralized bone matrix are added.

Example 15: Fabrication of Fresh Cancellous Bone Particles from Human Ilium with Growth Factors and DCB Added Human ilium is processed from a Donor to obtain cancellous bone particles as in Example 4 to which at least one growth factor and DCB are added.

Example 16: Fabrication of Fresh Cancellous Bone Particles from Human Ilium with Growth Factors and Crushed Cancellous Bone Matrix Added Human ilium is processed from a Donor to obtain cancellous particles as in Example 4 to which at least one growth factor and crushed cancellous bone matrix are added.

Example 17: Fabrication of Fresh Cancellous Bone Particles from Human Ilium with Growth Factors and Autologous Bone Marrow Cells or Other Autologous Cells Added Human ilium is processed from a Donor to obtain cancellous bone particles as in Example 4 to which at least one growth factor and autologous bone marrow cells or other autologous cells are added. Generally, autologous bone marrow or other autologous cells can be added to the cancellous bone particles obtained as in Example 4 to increase the amount or volume of the orthopedic implant thereby increasing the possibility of fusion.

Example 18: Fabrication of Fresh Cancellous Bone Particles from Human Ilium with Demineralized Bone Matrix and Autologous Bone Marrow Cells or Other Autologous Cells Added Human ilium is processed from a Donor to obtain cancellous bone particles as in Example 4 to which demineralized bone matrix and autologous bone marrow cells or other autologous cells was added. Generally, autologous bone marrow or other autologous cells can be added to the cancellous bone particles obtained as in Example 4 to increase the amount or volume of the orthopedic implant thereby increasing the possibility of fusion.

Example 19: Fabrication of Fresh Cancellous Bone Particles from Human Ilium with Crushed Demineralized Cancellous Bone Matrix and Autologous Bone Marrow Cells or Other Autologous Cells Added Human ilium is processed from a Donor to obtain cancellous bone particles as in Example 4 to which crushed demineralized autologous cortical bone and autologous bone marrow cells or other autologous cells was added. Generally, autologous bone marrow or other autologous cells can be added to the cancellous bone particles obtained as in Example 4 to increase the amount or volume of the orthopedic implant thereby increasing the possibility of fusion.

Example 20: Fabrication of Fresh Cancellous Bone Particles from Human Ilium with Biological Components Added Human ilium is processed from a Donor to obtain cancellous bone particles as in Example 4 to which biological components was added. Biological components include, but are not limited to, DNA, RNA, short hairpin RNA (shRNA), small interfering RNA (siRNA), micro RNA (miRNA), polysaccharides, peptides, matrix proteins, glycosaminoglycans such as, but not limited to, hyaluronic acid, viral vectors, and liposomes.

Example 21: Size Characterization of Demineralized Bone Fibers

A solution of surfactant in deionized ultrafiltered water is added to a portion of a sample of dehydrated demineralized bone fibers and ultrasonically agitated to hydrate and disperse the bone fibers. A dye is added to the mixture (e.g., a fluorescamine dye solution) and, set for a sufficient time to allow the dye to react with the bone fibers. The bone fibers are then dispersed in the mixture, and collected on a polycarbonate filter membrane by vacuum filtration. Multiple portions of the sample may be collected for analysis as described below.

To determine the lengths and widths of the collected bone fibers, each filter membrane is placed under lighting conditions appropriate for the dye used (e.g., under UV light for fluorescamine dye), and each quadrant of the filter is separately imaged for visual examination. A length and width chord is indicated on the image of each fiber as estimates of the length and width of the fiber. The indication and measurement of each chord may be made by a trained technician or an algorithm using calibrated imaging software. Clumps of fibers are excluded from the analysis. A statistical analysis of the measured lengths and widths is performed to determine length and width characteristics of the population of bone fibers in the samples.

Example 22: Thawing Osteogenic Implants

In some embodiments, prior to implantation, a cryopreserved orthopedic implant with or without DCB is thawed. The DCB may be in the form of particles as in Example 6 or fibers as in Example 7. The thaw procedure warms the tissue preparing it for surgical implantation. The vial containing cryopreservation solution and tissue is thawed in saline warmed to 37° C. to expedite the thawing process. Once the cryopreservation solution is free flowing, the cryopreservation solution is decanted from the vial. Then the tissue is rinsed with a wash solution well known in the art, including but not limited to saline, 5% dextrose in lactated ringers solution, phosphate buffered saline, and any additional isotonic solution. Prior to implantation, decant the wash solution. In some embodiments, DCB fibers may be mixed into the orthopedic implant after the orthopedic implant is thawed, mixing the implant and DCB fibers so as to ensure a homogenous mixture.

The wash solution, prior to application to the tissue, is warmed to a temperature, not exceeding 35-39° C. in order to minimize any damage to the cells contained in the tissue. The wash solution is exchanged throughout the rinse. Any remaining tissue from the surgery is not re-frozen for future use. All remaining tissue is disposed of appropriately after surgery.

A strainer is optionally used to contain the tissue during the decanting process. This allows the cryopreservation solution and rinsate to be removed from the tissue while minimizing any possible contamination of tissue during preparation from human contact. Optionally, gauze also is used to contain the tissue during the decant/thaw procedure.

Example 23: Comparison of Frozen and Thawed Cancellous Bone Orthopedic Implant Comprising an Osteoconductive Matrix According to the Described Invention to a Commercially Available Frozen Orthopedic Implant (Commercial Matrix)

The impact of the thaw procedures for both orthopedic implants of the present invention and a commercially available frozen orthopedic implant are compared for loss of viable cells during the thaw and rinsing process prior to implantation. The cryopreservation solution from each implant is analyzed for the presence of viable cells using commercially available methods, including but not limited to, for example, metabolic assays, such as involving luciferase, tetrazolium salts, for e.g., 3-(4, 5-dimethyl-2-thiazolyl)-2, 5-diphenyl-2H-tetrazolium bromide (MTT), 3-(4,5-dimethylthiazol-2-yl)-5-(3-carboxymethoxyphenyl)-2-(4-sulfophenyl)-2H-tetrazolium (MTS), 2,3-bis-(2-methoxy-4-nitro-5-sulfophenyl)-2H-tetrazolium-5-carboxanilide (XTT), and other water soluble tetrazolium salts (e.g., WST-1, -3, -4, -5, -8, -9, -10, and -11), and dye exclusion assays such as Tryptan Blue.

Example 24: Comparison of Fresh Cancellous Bone Allograft with DCB of the Described Invention Versus Commercial Matrix: Rat Spinal Fusion Study The following specimens were implanted into a spinal fusion model: a) donor 1 orthopedic implant; b) donor 2 orthopedic implant; c) Donor freeze/thawed orthopedic implant; d) Commercial Matrix implant; and f) Freeze/Thaw Commercial Matrix implant. An incision of approximately 4 cm is made on the posterior midline over the distal lumbar spine. The transverse processes of the L4 and L5 are exposed and decorticated to allow blood flow. Each specimen then is placed over the decorticated surfaces in the space between posterolateral vertebral processes of an athymic rat.

At the 8 week end point, the spine was removed and fusion was determined by a manual bend method. Using the manual bend test as a measure the following fusion results were defined: 1) 2/7 fused from Donor 1; 2) 2/8 fused from Freeze/Thaw Donor 1; 3) 1/6 fused from Donor 2; 4) 0/8 fused from Commercial Matrix; and 5) 0/8 fused from Commercial Matrix Freeze/Thaw.

Radiographs also were taken at 2, 4, 6 and 8 weeks. Spines are selected for microCATscan. Histology is prepared for all samples after imaging is complete.

The radiographs were scored based on a 6-point grading system: 1) 0 points (no bone formation); 2) 1 point (bone filling less than 25% of area); 3) 2 points (bone filling 25-50% of area; 4) 3 points (bone filling 50-75% of area); 5) 4 points (bone filling 75-99% of area); and 6) 5 points (clear evidence of fusion with the bone filling all gaps between L4 and L5).

Based on analysis of the 8 week results, the following percent radiographs scored a grade of 4 or better (75-100% bone filling of area): a) 81% Donor 1; b) 78% Donor 2; c) 59% Freeze/Thaw Donor 1; d) 9% Commercial Matrix; and e) 41% Freeze/Thaw Commercial Matrix.

II. Source Tissue: Adipose Tissue

Example 25: Fabrication of an Implant

Adipose tissue comprising an endogenous stem cell niche is recovered aseptically from a cadaveric donor within 24 hours post mortem or from a living donor undergoing elective liposuction surgery. For example, Visceral fat can be excised from cadaveric donors or obtained with consent from living donors undergoing elective procedures, such as liposuction, from body regions rich in adipose, for example, hip, thigh and abdomen. Subcutaneous adipose can be procured from the hypodermis by dissection from full thickness skin excised from a cadaveric donor. Adipose tissue from infrapatellar fat pads can be dissected out during recovery of knee-en-bloc from a cadaveric donor. The adipose tissue is stored at 4° C. until ready for processing. Generally, tissue processing commences within 72 hours post-mortem. The adipose tissue is exposed to a bioburden reducer to generate preprocessed adipose tissue. The preprocessed adipose tissue is subjected to a series of PBS soaks with agitation. The preprocessed agitated adipose tissue then is minced and subjected to a series of rinses with cold PBS, followed by a rinse in acetic acid solution and then followed again by a series of rinses with cold PBS. The pH of the rinseate is at or near physiological pH at the end of the rinses.

Additionally, after the last rinsing step, the tissue is prepared for cryopreservation.

Additionally, a sample is set aside in order to evaluate the metabolic activity of the tissue using commercially available methods, including but not limited to, for example, metabolic assays, such as involving luciferase, tetrazolium salts, for e.g., 3-(4, 5-dimethyl-2-thiazolyl)-2, 5-diphenyl-2H-tetrazolium bromide (MTT), 3-(4,5-dimethylthiazol-2-yl)-5-(3-carboxymethoxyphenyl)-2-(4-sulfophenyl)-2H-tetrazolium (MTS), 2,3-bis-(2-methoxy-4-nitro-5-sulfophenyl)-2H-tetrazolium-5-carboxanilide (XTT), and other water soluble tetrazolium salts (e.g., WST-1, -3, -4, -5, -8, -9, -10, and -11) and dye exclusion assays such as Tryptan Blue.

Additionally, prior to cryopreservation, one or more growth-inductive components are optionally added. Examples of the growth-inductive components that can be added include, but are not limited to, BMP-2 and 4, VEGF, bFGF, TGF-β, NELL-1, PDGF, and/or a combination thereof. For cryopreservation, for example, Mesencult basal media is prepared and sterile filtered. Cryoprotectant (10 ml) is added in order to assure full coverage of the tissue. Exemplary cryoprotectant include but are not limited to dimethyl sulfoxide (DMSO), glycerol, ethylene glycol, propylene glycol, 2-Methyl-2.4-pentanediol (MPD), and sucrose. The samples are packaged in cryoresistant containers. The packaged tissue then is subjected to slow controlled rate freezing to at least −80° C. and placed in liquid nitrogen.

It should be understood by those skilled in the art that many modifications may be made to adapt a particular situation, material, composition of matter, process, process step or steps, to improve, for example, but not limited to, efficiency, and yield.

Example 26: Fabrication of an Implant by Reseeding Adipose-Derived Stem Cells on a Decellularized Matrix Adipose tissue with its endogenous stem cell niche is recovered aseptically from a cadaveric donor within 24 hours post mortem or from living donors undergoing elective liposuction surgery. For example, visceral fat can be excised from cadaveric donors or obtained with consent from living donors undergoing elective procedures, such as liposuction, from body regions rich in adipose, for example, hip, thigh and abdomen. Subcutaneous adipose can be procured from the hypodermis by dissecting it out from full thickness skin excised from cadaveric donor. Adipose tissue from infrapatellar fat pads can be dissected out during recovery of knee-en-bloc from cadaveric donor. The adipose tissue is stored at 4° C. until ready for processing. Generally, tissue processing commences within 72 hours post-mortem. The adipose tissue is exposed to a bioburden reducer to generate preprocessed adipose tissue. The preprocessed adipose tissue is subjected to a series of PBS soaks with agitation. The preprocessed agitated adipose tissue is then chopped into small pieces approximately 0.5×0.5×0.5 cm. The chopped adipose pieces are then subjected to a series of rinses with cold PBS. The pH of the rinseate is at or near physiological pH at the end of the rinse. The rinseate is divided into two batches for stem cell isolation and decellularized matrix preparation.

Isolation of ASCs

Viable Adipose-derived stem cells (ASCs) are isolated according to established protocols (Young et al., 2011, Acta Biomaterialia, 7: 1040-1049). Briefly, following rinses with a buffered saline solution (e.g., 0.01M PBS, pH 7.4), one batch of the rinsed tissue is digested with a dissociation agent (e.g., collagenase) in order to disperse the tissue while maintaining cell viability. The digest is subjected to centrifugation to separate the stromal vascular fraction (SVF) rich in adipose-derived stem cells from the supernatant rich in lipid filled adipocytes and matrix. The supernatant is aspirated and the aspirate is frozen at −80° C. until further use. The SVF pellet is resuspended in PBS washing solution and is subjected to a series of cold PBS washes with alternating steps of centrifugation. Following the final wash and resuspension in PBS, the resuspended solution is subjected to filtration to remove undigested tissue and to obtain isolated SVF enriched with ASCs for seeding. Alternatively, ASCs can be isolated from the other cells present in digested adipose tissue on the basis of cell size or immunohistochemically, for example, by using magnetic beads, affinity chromatography, fluorescence-activated cell sorting (FACS), flow cytometry, or with a suitable device.

Additionally, the isolated ASCs express antigens, including, but not limited to, CD73, CD90, CD29, CD44, CD105, and/or a combination thereof. Additionally or alternatively, the isolated ASCs do not express antigens, including, but not limited to CD33, CD34, CD45, CD4, CD31, CD62p CD14, HLA-DR, and/or combination thereof.

Additionally, a sample is set aside in order to evaluate the biological activity of the tissue using commercially available methods, including, but not limited to, for example, metabolic assays, such as involving luciferase, tetrazolium salts, for e.g., 3-(4, 5-dimethyl-2-thiazolyl)-2, 5-diphenyl-2H-tetrazolium bromide (MTT), 3-(4,5-dimethylthiazol-2-yl)-5-(3-carboxymethoxyphenyl)-2-(4-sulfophenyl)-2H-tetrazolium (MTS), 2,3-bis-(2-methoxy-4-nitro-5-sulfophenyl)-2H-tetrazolium-5-carboxanilide (XTT), and other water soluble tetrazolium salts (e.g., WST-1, -3, -4, -5, -8, -9, -10, and -11), and dye exclusion assays such as Tryptan Blue.

Alternatively, isolated ASCs can be cultured without differentiation using standard culture media typically supplemented with 5%-20% serum. For example, the ASCs are passaged at least 5 times in such medium without differentiating, while still retaining their multiplicity. Adipose-derived stem cells can be maintained in control medium until 80% confluent. Cells are harvested at confluence and population doubling calculated using the formula log $N_1$/log $N_2$, where $N_1$ is the number of cells at confluence prior to passaging and $N_2$ is the number of cells seeded after passaging. Cumulative population doubling is determined in cultures maintained until passage 13 (approximately 165 days). The mean cumulative population doubling obtained from 3 donors is expressed as a function of passage number. Confirmation of Multi-Lineage Differentiation of Adipose-Derived Stem Cells Adipose-derived stem cells at passage 1 can be analyzed for their capacity to differentiate toward the adipogenic, osteogenic, chondrogenic, and myogenic lineages. To induce differentiation, the stem cells are cultured with specific induction media as detailed in Table 20.

TABLE 20

Lineage-specific differentiation induced by media supplementation

| Medium | Media | Serum | Supplementation |
|---|---|---|---|
| Control | DMEM | 10% FBS | none |
| Adipogenic (AM) | DMEM | 10% FBS | 0.5 mM isobutyl-methylxanthine (IBMX), 1 μM dexamethasone, 10 vM insulin, 200 μM indomethacin, 1% antibiotic/antimycotic |
| Osteogenic (OM) | DMEM | 10% FBS | 0.1 μM dexamethasone, 50 μM ascorbate-2-phosphat, 10 mM β-glycerophosphate, 1% antibiotic/antimycotic |
| Chondrogenic (CM) | DMEM | 1% FBS | 6.25 μg/ml insulin, 10 ng/ml TGFβ1, 50 nM ascorbate-2-phosphate, 1% antibiotic/antimycotic |
| Myogenic (MM) | DMEM | 10% FBS, 5% HS | 0.1 μM dexamethasone, 50 μM hydrocortisone, 1% antibiotic/antimycotic |

Each media has been previously described and shown to induce multi-lineage differentiation of MSCs (Pittenger, M. et al, 1999, Science 284: 143-147; Grigoradis, A. et al., 1988, J. Cell. Biol., 106: 2139-2151; Cheng, S-L. et al., 1994, Endo, 134: 277-286; Loffler, G. et al., 1987, Klin. Wochenschr., 65: 812-817; Hauner, H. et al., 1987, J. Clin. Endocrinol. Metabol. 64: 832-835). Differentiation is confirmed using the histological and immunohistological assays outlined in Table 21 and compared to a commercial source of bone marrow-derived MSCs, lineage-specific precursors (positive controls), and human foreskin fibroblasts (HFFs) (negative controls)). The adipose-derived stem cells are maintained in Control Medium.

TABLE 21

Differentiation Markers And Assays Of Lineage-Specific Differentiation.

| Lineage | Lineage-specific Determinant | Histologic/Immuno-histochemical Assay |
|---|---|---|
| Adipogenic | 1. Lipid Accumulation | 1. Oil Red O stain |
| Osteogenic | 1. Alkaline phosphatase activity | 1. Alkaline phosphatase stain |
| | 2. Calcified matrix production | 2. Von Kossa stain |
| Chondrogenic | 1. Sulfated proteoglycan-rich matrix | 1. Alcian Blue (pH 1.0) stain |
| | 2. Collagen II synthesis | 2. Safranin O stain |
| | | 3. Collagen II-specific monoclonal antibody |
| Myogenic | 1. Multi-nucleation | 1. Phase contrast microscopy |
| | 2. Skeletal muscle myosin heavy chain and MyoD1 expression | 2. Myosing and MyoD1 specific monoclonal antibodies |

Adipogenesis

Adipogenic differentiation can be induced by culturing the stem cells for 2 weeks in Adipogenic Medium (AM) and assessed using an Oil Red O stain as an indicator of intracellular lipid accumulation (Preece, A. 1972 A Manual for Histologic Technicians, Boston, Mass.: Little, Brown, and Co.). Prior to staining, the cells are fixed for 60 minutes at room temperature in 4% formaldehyde/1% calcium and washed with 70% ethanol. The cells are incubated in 2% (w/v) Oil Red O reagent for 5 minutes at room temperature. Excess stain is removed by washing with 70% ethanol, followed by several changes of distilled water. The cells are counter-stained for 2 minutes with hematoxylin.

Osteogenesis

Osteogenic differentiation can be induced by culturing the stem cells for a minimum of 2 weeks in Osteogenic Medium (OM) and assessed by measuring Alkaline Phosphatase (AP) activity and ECM calcification by von Kossa staining. To detect AP activity, cells are incubated in OM for 2 weeks, rinsed with PBS and stained with a 1% AP solution (1% napthol ABSI phosphate, 1 mg/ml Fast Red TR) at 37° C. for 30 minutes. For von Kossa staining, the cells are incubated in OM for 4 weeks and fixed with 4% paraformaldehyde for 60 minutes at room temperature. The cells are rinsed with distilled water and then overlaid with a 1% (w/v) silver nitrate solution in the absence of light for 30 minutes. The cells are washed several times with distilled water and developed under UV light for 60 minutes. Finally, the cells are counter-stained with 0.1% eosin in ethanol.

Chondrogenesis

Chondrogenic differentiation can be induced using the micromass culture technique (Ahrens, P B, et al., 1977 Develop. Biol. 60:69-82; Reddi, A H 1982 Prog. Clin. Biol. Res. 110 (part B):261-268; Denker, A E., et al., 1995 Differentiation 59:25-34). Briefly, 10 ml of a concentrated adipose-derived stem cell suspension ($8 \times 10^6$ cells/ml) is plated into the center of each well and allowed to attach at 37° C. for two hours. Chondrogenic medium (CM) is gently overlaid so as not to detach the cell nodules and cultures are maintained in CM for 2 weeks prior to analysis. Chondrogenesis is confirmed using the histologic stain Alcian Blue at acidic pH. The stem cell nodules are fixed with 4% paraformaldehyde for 15 minutes at room temperature and washed with several changes of PBS. Studies have shown specific staining of sulfated proteoglycans, present in cartilagenous matrices, at pH levels of 1 and below (Lev, R. and S. Spicer 1964 J. Histochem. Cytochem. 12:309-312). Therefore, the cells are incubated for 30 minutes with 1% (w/v) Alcian Blue (Sigma A-3157) in 0.1N HCl (pH 1.0) and washed with 0.1N HCl for 5 minutes to remove excess stain. In addition to Alcian Blue staining, expression of the cartilage-specific collagen type II isoform also can be determined. The stem cells are fixed in 4% paraformaldehyde for 15 minutes at room temperature. Cells are incubated in 0.2 U/ml chondroitinase ABC for 40 min at 37° C. to facilitate antibody access to collagen II. The cells are rinsed in PBS and endogenous peroxidase activity quenched by incubating for 10 minutes in 3% hydrogen peroxide in methanol. Following a wash in PBS, non-specific sites are blocked by incubating cells for 1 hour in Blocking Buffer (PBS, containing 10% Horse Serum). The cells are subsequently incubated for 1 hour in Blocking Buffer containing a monoclonal antibody specific to human collagen type II (ICN Biomedical, Costa Mesa, Calif.). The cells are washed extensively in Blocking Buffer and collagen type II visualized using a commercially available kit for the detection of monoclonal antibodies according to the manufacturer (VectaStain ABC kit, Vector Labs Inc., Burlingame, Calif.).

Myogenesis

Myogenic differentiation can be induced by culturing the adipose-derived stem cells in Myogenic Medium (MM) for 6 weeks, and can be confirmed by immunohistochemical staining for the muscle-specific transcription factor, MyoD1 and the myosin heavy chain. Specifically, cells are rinsed twice with PBS, fixed for 20 minutes with 4% paraformaldehyde and washed several times with PBS. The cells are incubated with 3% hydrogen peroxide in PBS for 10 minutes to quench endogenous peroxidase enzyme activity and non-specific sites are blocked by incubation in Blocking Buffer (PBS, 10% Horse Serum, 0.1% Triton X-100) for an additional 60 minutes. The cells are washed 3 times for 5 minutes each in Blocking Buffer and incubated for 1 hour in Blocking Buffer containing a monoclonal antibody either specific to skeletal muscle myosin heavy chain (Biomeda, Foster City, Calif.) or to MyoD1 (Dako Corp, Carpenteria, Calif.). The cells are washed extensively in Blocking Buffer and the monoclonal antibodies visualized using the VectaStain ABC kit according to manufacturer's specifications. The cells are counterstained with hematoxylin for 3 minutes.

Preparation of Decellularized Adipose Matrix

Decellularized adipose matrix is obtained either using the original rinseate or the thawed and filtered aspirate obtained during the ASC isolation procedure. Following a series of thorough washes with cold PBS, the washed tissue is soaked in lysis buffer with continuous mechanical agitation. The soaked tissue then is subjected to cell lysis to yield a decellularized tissue.

The sterile decellularized tissue can be subjected to alternate procedures. For example, (1) it can be lyophilized and milled using a freezer mill to yield a decellularized adipose-derived matrix powder; (2) it can be homogenized to obtain a decellularized adipose-derived matrix paste or slurry; (3) it can be homogenized and lyophilized to obtain a three-dimensional adipose-derived matrix; or (4) it can be lyophilized to obtain an adipose decellularized tissue matrix sheet.

Recellularization

Adipose-derived decellularized matrices in powder, paste/slurry, three-dimensional or sheet form may be used to reseed isolated ASCs. Following the filtration step for isolating ASCs, the isolated stromal-vascular fraction (SVF) enriched with ASCs or otherwise purified ASCs are resuspended in basal or nutrient enriched medium. A portion of the resuspended SVF fraction or otherwise purified ASCs are then added to a sample of an adipose-derived decellularized matrix produced in any form (powder, paste/slurry, three dimension or sheet). The decellularized adipose matrix containing the ASCs is incubated at 37° C.]. The incubation step is followed by static or dynamic seeding conditions for 24 hours, which are well known in the art. The re-cellularized adipose matrix is then subjected to a series of cold PBS rinses to wash away unwanted non-adherent cells.

Cryopreservation and Thawing

Additionally, prior to cryopreservation, one or more growth-inductive components optionally can be added. These include, but are not limited to, bone morphogenic proteins (BMPs), vascular endothelial growth factor (VEGF), basic fibroblast growth factor (bFGF), transforming growth factor beta (TGFβ), platelet-derived growth factor (PDGF), neural epidermal growth-factor-like 1 (NELL-1), and a combination thereof. For cryopreservation, for example, mesencult basal media is prepared and sterile filtered. A cryoprotectant solution in basal or nutrient rich medium is added in order to assure full coverage of the tissue. Exemplary cryoprotectant include, but are not limited to, dimethyl sulfoxide (DMSO), glycerol, ethylene glycol, propylene glycol, 2-Methyl-2.4-pentanediol (MPD), and sucrose. The samples are packaged in cryoresistant containers. One sample as a probe sample is cryopreserved in a laboratory cryopreservation unit. The packaged tissue is then subjected to slow controlled rate freezing to at least −80° C. Once the program cycle is complete, the tissue is placed in liquid nitrogen.

Prior to implantation, a cryopreserved adipose implant is thawed. The thaw procedure warms the tissue preparing it for implantation. The vial containing cryopreservation solution and tissue is thawed at room temperature or alternatively warmed to 37° C. to expedite the thawing process. Alternatively, the thawing temperature can be at a temperature in the range of about 4° C. through 50° C. Alternatively, the freeze-thawing process can be repeated. Once the cryopreservation solution is free flowing, the cryopreservation solution is decanted from the vial and the tissue is implanted immediately, without any rinse. Prior to implantation, the tissue is optionally rinsed for 0-15 minutes with the other wash solutions including but not limited to saline, 5% dextrose in lactated ringers solution, phosphate buffered saline, and any additional isotonic solution.

The wash solution is added at room temperature or alternatively, prior to application to the tissue, the wash solution is warmed to a temperature not exceeding 37° C.-39° C. in order to minimize any damage to the cells contained in the tissue. The wash solution is exchanged throughout the rinse or alternatively the tissue is stored in the wash solution at 4° C. until ready for implantation. Any remaining tissue from the surgery is not be re-frozen for future use. All remaining tissue is disposed off appropriately after surgery.

A strainer is used to contain the tissue during the decanting process. This allows the cryopreservation solution and rinseate to be removed from the tissue while minimizing any possible contamination of tissue during preparation (minimizes human contact). Gauze is optionally used to contain the tissue during the decant/thaw procedure.

As described in detail above, adipose-derived stem cells possess a potential to differentiate into a wide variety of cell types, including, but not limited to, nerve cells, astrocytes, fat cells, chondrogenic cells, osteogenic cells, or insulin-releasing pancreatic cells.

III. Source Tissue: Placental Tissue

Example 27: Fabrication of Amnion Implant Sheet

Human placentas are recovered from consenting healthy donor mothers at the time of caesarean section. The amniotic membrane then can be separated or stripped gently from the underlying chorion layer with minimal damage to the basal membrane. The chorion is optionally used for fabrication of a chorion implant or discarded. A sample of the amniotic membrane is cut for bioburden assessment. The separated amnion optionally then is subjected to a series of washes with chilled buffered isotonic solution to remove unwanted blood debris. This may include a series of three 5 minute-soaks in a buffered isotonic solution followed by a soak in an antibiotic solution, such as an antibiotic solution containing 1% Penicillin and 1% Streptomycin. The washed amniotic membrane may then be exposed to a bioburden reducer such as, for example, surfactants and other cleaning agents to generate preprocessed amnion. The preprocessed amnion may then be subjected to a series of rinses with cold PBS. The pH of the rinseate is at or near physiological pH at the end of the rinse. The preprocessed amnion is then cut into strips of desired geometry.

Additionally, prior to packaging, amnion sheets may be supplemented with one or more autoinductive components. Examples of autoinductive components include, but are not limited to, growth factors such as BMP-2 and 4, VEGF, bFGF, TGF-β, NELL-1, PDGF, and/or a combination thereof.

Additionally, the amnion sheets with or without autoinductive component(s) are placed in a cryopreservation solution. Exemplary cryoprotectants include, but are not limited to, dimethyl sulfoxide (DMSO), glycerol, ethylene glycol, propylene glycol, 2-Methyl-2.4-pentanediol (MPD), and sucrose. The samples are packaged in cryoresistant containers or packages and cryopreserved using a controlled rate freezer. Once the program cycle is complete, the containers or packages are placed in liquid nitrogen vapor.

Prior to implantation, cryopreserved amnion implant sheets are thawed. The thaw procedure warms the amnion sheets preparing them for implantation. The package containing cryopreservation solution and amnion sheets is thawed at room temperature or alternatively warmed to 37° C. to expedite the thawing process. Once the cryopreservation solution is free flowing, the cryopreservation solution is decanted from the package. Prior to implantation, the amnion sheets are optionally rinsed for 0-15 minutes with the other wash solutions including, but not limited to, saline, 5% dextrose in lactated ringers solution, phosphate buffered saline, and any additional isotonic solution.

The wash solution is added at room temperature or alternatively, prior to application to the tissue, and warmed to a temperature not exceeding 37° C.-39° C. in order to minimize any damage to the cells contained in the amnion sheets. The wash solution is exchanged throughout the rinses or alternatively the amnion sheets are stored in the wash solution until ready for implantation. Any remaining amnion sheets are not re-frozen for future use. All remaining unused thawed amnion sheets are disposed off appropriately after surgery.

A strainer may be used to contain the amnion sheets during the decanting process. This allows the cryopreservation solution and rinseate to be removed from the amnion sheets while minimizing any possible contamination of tissue during preparation (minimizes human contact). Gauze is optionally used to contain the tissue during the decant/thaw procedure.

Example 28: Fabrication of Amnion Implant Slurry

Human placentas are recovered from consenting healthy donor mothers at the time of caesarean section. The amniotic membrane then can be separated or stripped gently from the underlying chorion layer with minimal damage to the basal membrane. The chorion optionally is used for fabrication of a chorion implant, a combined amnion-chorion implant or discarded. A sample of the amniotic membrane is cut for bioburden assessment. The separated amnion optionally is then subjected to a series of washes with chilled buffered isotonic solution to remove unwanted blood debris. This may include a series of three 5 minute-soaks in a buffered isotonic solution followed by a soak in an antibiotic solution, such as an antibiotic solution containing 1% Penicillin and 1% Streptomycin. The washed amniotic membrane may then be exposed to a bioburden reducer such as, for example, surfactants and other cleaning agents to generate preprocessed amnion. The preprocessed amnion may then be subjected to a series of rinses with cold PBS. The pH of the rinseate is at or near physiological pH at the end of the rinse. The preprocessed amnion is then cut into strips of desired geometry.

Alternatively, prior to packaging, the amnion slurry may be supplemented with one or more autoinductive components. Examples of autoinductive components that can be supplemented to the amnion slurry include, but are not limited to, growth factors such as BMP-2 and 4, VEGF, bFGF, TGF-β, NELL-1, PDGF, and/or a combination thereof.

The amnion slurry with or without autoinductive component(s) is placed in a cryopreservation solution. Exemplary cryoprotectants include, but are not limited to, dimethyl sulfoxide (DMSO), glycerol, ethylene glycol, propylene glycol, 2-Methyl-2.4-pentanediol (MPD), and sucrose. The samples are packaged in cryoresistant containers and cryopreserved using a controlled rate freezer. Once the program cycle is complete, the containers are placed in liquid nitrogen vapor.

It should be understood by those skilled in the art that many modifications may be made to adapt a particular situation, material, composition of matter, process, process step or steps, to improve, for example, but not limited to, efficiency, and yield.

Prior to implantation, the packages containing cryopreserved amnion implant slurry are thawed. The thaw procedure warms the amnion slurry preparing it for implantation. The package containing cryopreservation solution and amnion slurry is thawed at room temperature or alternatively warmed to 37° C. to expedite the thawing process. Alternatively, the thawing temperature can be at a temperature in the range of about 4° C. through 50° C. Once the cryopreservation solution is free flowing, the cryopreservation solution is decanted from the package. Prior to implantation, the amnion slurry is optionally rinsed for 0-15 minutes with the other wash solutions including but not limited to saline, 5% dextrose in lactated ringers solution, phosphate buffered saline, and any additional isotonic solution.

The wash solution is added at room temperature or alternatively, prior to application to the slurry, the wash solution is warmed to a temperature not exceeding 37° C.-39° C. in order to minimize any damage to the cells contained in the amnion slurry. The wash solution is exchanged throughout the rinse or alternatively the amnion slurry is stored in the wash solution until ready for implantation. Any remaining amnion slurry is not re-frozen for future use. All remaining unused thawed portions of amnion slurry are disposed off appropriately after surgery.

A strainer may be used to contain the amnion slurry during the decanting process. This allows the cryopreservation solution and rinseate to be removed from the amnion sheets while minimizing any possible contamination of tissue during preparation (minimizes human contact). A gauze is optionally used to contain the tissue during the decant/thaw procedure.

Example 29: Fabrication of Amniotic Implant by Reseeding Amniotic Stem Cells on Decellularized Amniotic Matrix Human placentas are recovered from consenting healthy donor mothers at the time of caesarean section. To avoid any potential blood-transmittable diseases, the pregnant female is prescreened for HIV-1, HIV-2, HTLV-1, hepatitis B and C viruses and syphilis, using conventional serological tests. Only those placentas for which the maternal blood reveals negative serological results are used to produce the amniotic implant.

When the tissue is ready to be processed further, the sterile supplies necessary for processing the placenta tissue further are assembled in a staging area in a controlled environment and are prepared for introduction into the controlled environment. If the controlled environment is a manufacturing hood, the sterile supplies are opened and placed into the hood using conventional sterile technique. If the controlled environment is a clean room, the sterile supplies are opened and placed on a cart covered by a sterile drape. All the work surfaces are covered by a piece of sterile drape using conventional sterile techniques, and the sterile supplies and the processing equipments are placed on to the sterile drape, again using conventional sterile techniques.

The amniotic membrane can then be separated or stripped gently from the underlying chorion layer with minimal damage to the basal membrane. The chorion is optionally used for fabrication of a chorion implant, a combined amnion and chorion implant, or discarded. A sample of the amniotic membrane is cut for bioburden assessment. Optionally, the separated amnion is then subjected to a series of washes with chilled buffered isotonic solution to remove unwanted blood debris. This may include a series of three 5 minute-soaks in buffered isotonic solution followed by a soak in an antiobotic solution such as an antibiotic solution containing 1% Penicilin and 1% Streptomycin. The washed amniotic membrane may be then exposed to a bioburden reducer such as, for example, surfactants and other cleaning agents to generate preprocessed amnion. The amnion sheets may subsequently be subjected to a series of rinses with cold PBS. The pH of the rinseate is at or near physiological pH at the end of the rinse. The preprocessed amnion is then minced using a scalpel or alternatively using scissors to form an amnion slurry. The amnion slurry is then subjected to a series of rinses with cold PBS. The pH of the rinseate is at or near physiological pH at the end of the rinse.

Additionally, the processed amnion can be disaggregated mechanically and/or treated with digestive enzymes and/or chelating agents that weaken the connections between neighboring cells, making it possible to disperse the tissue suspension of individual cells.

Isolation of Amniotic Stem Cells

One batch of the rinsed tissue is subjected to a pre-digestion soak for 10 minutes in a solution containing trypsin and ethylenediamine tetracetic acid (EDTA). An exemplary trypsin-EDTA solution may contain 0.05% Trypsin and 0.5 mM EDTA. The predigestion soak solution is decanted off and discarded. The presoaked amniotic tissue is subjected to digestion with 0.05% Trypsin for 40 minutes at 37° C. to yield a crude digest solution. A first portion of the crude digest solution is then transferred to a sterile tube, neutralized with a small amount of basal medium and 10% serum. The resulting neutral digest then is centrifuged, the supernatant is aspirated and discarded, and the pellet is resuspended in 5 mL of basal medium. The digested tissue of the first portion is subjected to a subsequent digestion with 0.05% Trypsin for 40 minutes at 37° C. to yield a double-digested tissue. This double-digested tissue is not subjected to neutralization. A second portion of the crude digest solution is then transferred to a sterile tube, neutralized with a small amount of basal medium and [10% serum. The resulting neutral digest is then centrifuged, the supernatant aspirated and discarded and the pellet resuspended in 5 mL of basal medium to yield a single digested portion. The first neutral digest and the second neutral digest portions are combined and subjected to centrifugation. The supernatant is aspirated and the pellet is resuspended in 5 mL basal media to yield a resuspended solution containing amniotic stem cells.

Additionally, the amniotic epithelial and/or stromal cells may be grown on feeder layers. The use of feeder cells, or an extracellular matrix derived from undifferentiated feeder cells is believed to provide one or more substances necessary to promote the growth of the stem cells and/or inhibits the rate of differentiation of such cells. Such substances are believed to include membrane-bound and/or soluble cell products that are secreted into the surrounding medium by the cells. For example, amniotic epithelial and/or stromal cells can be grown on a substrate, including, but not limited to, mouse embryo fibroblast cells, STO cells human fibroblasts, or human epithelium cells and/or combination thereof. Alternatively, additional cell lines can be used with the cell culture medium to equivalent effect; such additional cell lines can be identified using standard methods and materials. Alternatively or additionally, one or more substances produced by the feeder cells, or contained in the extracellular matrix, can be identified and added to the cell culture medium of the invention to obviate the need for such feeder cells and/or such extracellular matrix.

A sample can be set aside in order to evaluate cell count and cell viability/biological activity of the tissue using commercially available methods, including but not limited to, for example, metabolic assays, such as involving luciferase, tetrazolium salts (e.g., 3-(4, 5-dimethyl-2-thiazolyl)-2, 5-diphenyl-2H-tetrazolium bromide (MTT), 3-(4,5-dimethylthiazol-2-yl)-5-(3-carboxymethoxyphenyl)-2-(4-sulfophenyl)-2H-tetrazolium (MTS), 2,3-bis-(2-methoxy-4-nitro-5-sulfophenyl)-2H-tetrazolium-5-carboxanilide (XTT), and other water soluble tetrazolium salts (e.g., WST-1, -3, -4, -5, -8, -9, -10, and -11) and dye exclusion assays such as Tryptan Blue.

In addition, the resuspended solution containing amniotic epithelial and/or stromal cells is placed in a cryopreservation solution. Exemplary cryoprotectants include, but are not limited to, dimethyl sulfoxide (DMSO), glycerol, ethylene glycol, propylene glycol, 2-Methyl-2.4-pentanediol (MPD), and sucrose. The samples are packaged in cryoresistant containers and cryopreserved using a controlled rate freezer. Once the program cycle is complete, the containers are placed in liquid nitrogen vapor.

In addition, the isolated aminiotic epithelial and/or stromal cells express antigens, including, but not limited to, CD105+, CD90+, CD73+, CD44+, CD29+, HLA-A, B, C+, CD13+, CD10+, CD166+, CD49d−, CD49e+, CD117 (+/− very weak signal), CD14−, CD34−, CD45−, HLA-DR−, and/or a combination thereof.

Alternatively, the isolated amniotic epithelial and/or stromal cells express antigens, including, but not limited to, SSEA-3, SSEA-4+, TRA 1-60+, TRA 1-81+, SSEA-1−, and/or a combination thereof.

Alternatively, the isolated aminiotic epithelial and/or stromal express antigens, including, but not limited to, CD324 (E-cadherin)+, POU5F1+, SOX2+, CFC1+, NANOG+, DPPA3+, PROM1+, PAX6+, FOXD3−, GDF3−, CD140b+, CD349−, GCTM2+, and/or a combination thereof.

Alternatively, the isolated amniotic epithelial and/or stromal cells express antigens, including, but not limited to, Thy-1, OCT-4, SOX2, SSEA3, SSEA4, TRA1-60, TRA1-81, Lefty A, FGF-4, Rex-1 and TDGF-1, and/or a combination thereof.

Studies have shown that amniotic epithelial and/or stromal cells can be differentiated into a wide variety of cell types in vitro (Parolini et al, 2008, Stem Cells, 26:300-311). The specific culture conditions for differentiation of amniotic stem cells are shown in Table 22:

TABLE 22

Culture conditions for differentiation of amniotic stem cells

| Differentiation | Culture Conditions |
|---|---|
| Adipogenic | DMEM high glucose (or DMEM/Ham's F-12 medium), 10% FBS, 0.5 mM isobutylmethylxanthine, 1 µM dexamethasone, 10 µM insulin, 200 µM indomethacin |
| Chondrogenic | DMEM high glucose, 1% FBS, 6.25 µg/ml insulin, 10 ng/ml TGF-β1, 50 ng/ml fresh ascorbic acid |
| Osteogenic | DMEM high glucose (or DMEM/Ham's F-12 medium), 10% FBS, 10 µM dexamethasone, 10 nM 1-α, 25-dehydroxyvitamin D3, 50 µg/ml ascorbic acid, 10 mM β-glycerophosphate MesenCult Human Osteogenic Stimulatory Kit (StemCell Technologies) |
| Skeletal myogenic | DMEM/Ham's F-12 medium (or DMEM high glucose), 10% FBS, 5% human serum (or horse serum), 50 µM hydrocortisone (0.1 µM dexamethasone) |
| Cardiomyogenic | DMEM, 10% FBS, 55 µM 2-mercaptoethanol, 1 mM sodium pyruvate, 1 mM ascorbic acid 2-phosphate DMEM/Ham's F-12 medium, 10% FBS, 1 mM ascorbic acid |
| Neurogenic | DMEM high glucose, 10% FBS, 30 µM all-trans retinoic acid DMEM, 10% FBS, 55 µM 2-mercaptoethanol, 1 mM sodium pyruvate, $5 \times 10^{-5}$ M all-trans retinoic acid, 10 ng/ml FGF-4 DMEM/Ham's F-12 medium, 10% FCS, $5 \times 10^{-5}$ M all-trans retinoic acid, 10 ng/ml FGF4, N-2 supplement (Gibco), B-27 supplement (Gibco) |
| Pancreatic | DMEM, 10% FBS, 55 µM 2-mercaptoethanol, 1 mM sodium pyruvate, 10 mM nicotinamide on collagen I-coated plate DMEM (or DMEM/Ham's F-12 medium) containing N2 supplement (Gibco), 10 mM nicotinamide |

TABLE 22-continued

Culture conditions for differentiation of amniotic stem cells

| Differentiation | Culture Conditions |
|---|---|
| Hepatic | DMEM, 10% FBS, 55 µM 2-mercaptoethanol, 1 mM sodium pyruvate, dexamethansone $10^{-7}$ M, 0.1 µM insulin for 3 weeks, addition of 1 mM phenobarbital for the final 3 days, on collagen I-coated plate DMEM, 10% FBS, 20 ng/ml HGF, 10 ng/ml FGF-2, 10 ng/ml oncostatin M, 100 mM dexamethasone, 10 U/ml heparin sodium salt DMEM/Ham's F-12 medium, 10% FCS + 0.1 µM insulin, $1 \times 10^{-7}$ M dexamethasone |

Abbreviations:
DMEM (Dulbecco's modified Eagle's medium);
FBS (fetal bovine serum);
FCS (fetal calf serum)

Prior to recellularization, the cryovials containing cryopreserved suspension of amniotic epithelial and/or stromal cells are thawed. The cells retain their biological function and viability when thawed. The thaw procedure warms the cells preparing them for recellularization. The vial containing cryopreservation solution and amniotic stem cell suspension is thawed at room temperature or alternatively warmed to 37° C. to expedite the thawing process. Once the cryopreservation solution is free flowing, an equal volume of a saline solution or alternatively a washing solution is added to the cryopreservation solution to yield an amniotic stem cell suspension. The resulting amniotic stem cell suspension may be used immediately for recellularization. The thawing procedure is as described above for Example 25.

Alternatively, following preparation of a single cell suspension, the amniotic epithelial and/or stromal cells can be cultured in basal medium, supplemented with serum, hormones, growth factors, cytokines, antibiotics, trace elements, and other additives. Growth factors that can be added include, but are not limited to, fibroblast growth factors (FGFs), epidermal growth factor (EGF), transforming growth factor-β (TGF-β), hepatocyte growth factor (HGF), neural epidermal growth-factor-like 1 (NELL-1), or oncostatin M. Additives to the medium may include insulin, transferrin, selenium, glucose, interleukin-6, and histone deacetylase inhibitor such as sodium butyrate or tricostatin A.

For example, amniotic epithelial and/or stromal cells are plated onto dishes with DMEM, 10% FBS, 2 mM L-glutamine, EGF (10 ng/ml), insulin (10 µg/ml), transferrin (5.5 µg/ml), selenium (6.7 ng/ml) and ethanolamine (2 µg/ml). In addition, sodium pyruvate and non-essential amino acids (1%) may be added to the culture medium. In order to induce demethylation or dedifferentiation, 5-azacytidine and/or BMP inhibitors can be added to the medium.

Decellularization

The epithelium layer present on the amnion is substantially removed in order to expose the basement layer of the amnion. By removing the epithelium, the reduction of an antigenic potential can be expected. Furthermore, since unnecessary cells are removed in advance, target cell layers can be formed. The term "substantially removed" with respect to the amount of epithelium removed is defined herein as removing greater than 90%, greater than 95%, or greater than 99% of the epithelial cells from the amnion. The presence or absence of epithelial cells remaining on the amnion layer can be evaluated using techniques known in the art. For example, after removal of the epithelial cell layer, a representative tissue sample from the processing lot is placed onto a standard microscope examination slide. The tissue sample is then stained using Eosin Y Stain and evaluated as described below. The sample then is covered and allowed to stand. Once an adequate amount of time has passed to allow for staining, visual observation is done under magnification.

The epithelium layer can be removed by techniques known in the art. For example, the epithelium layer can be scraped off of the amnion using a cell scraper, the membrane may be frozen, or the epithelial cells may be exposed to nonionic detergents, anionic detergents, and nucleases. The de-epithelialized tissue then is evaluated to confirm that the basement membrane has not been compromised and remains intact. For example, a representative sample graft is removed for microscopic analysis. The tissue sample is place onto a standard slide and 100 µl of Eosin Y stain is applied to the sample and allowed to set. The tissue sample then is examined under magnification. Cellular material will stain dark indicating the presence of cells. If no stained cells are present, de-epithelization has been achieved.

Recellularization

Additionally, amniotic epithelial and/or stromal cells, which are (1) freshly isolated from placenta, (2) thawed from cryopreservation, or (3) cultured in vitro, can be seeded back onto or into decellularized amniotic tissue matrix by adding a desired number of aminiotic stem cells onto or into decellularized aminiotic matrix and placing the decellularized aminiotic matrix with the cells into an incubator at 37° C. The cells are allowed to attach to the matrix for up to 24 hours under static or dynamic seeding conditions and unwanted, non-adherent cells are rinsed away, if necessary.

Cryopreservation and Thawing

Cryopreservation, storage and thawing procedures for recellularized amniotic matrix are identical to such procedures described above in Example 25.

As described in detail above, amniotic epithelial and/or stromal cells possess the potential to differentiate into various cell types, including, but not limited to, adipogenic cells, chondrogenic cells, osteogenic cells, cardiomyogenic cells, neurogenic cells, pancreatic cells, and hepatic cells.

While the described invention has been described with reference to the specific embodiments thereof, it should be understood by those skilled in the art that various changes may be made and equivalents may be substituted without departing from the true spirit and scope of the invention. In addition, many modifications may be made to adapt a particular situation, material, composition of matter, process, process step or steps, to the objective, spirit and scope of the described invention. All such modifications are intended to be within the scope of the claims appended hereto.

What is claimed is:

1. A composition for implantation in a patient, consisting essentially of:
   cancellous bone particles, wherein the cancellous bone particles have osteoconductive properties;
   wherein the cancellous bone particles have viable endogenous osteogenic cells; and
   demineralized cortical bone fibers, wherein the demineralized cortical bone fibers have osteoinductive properties;
   wherein a sufficient amount of the demineralized cortical bone fibers results in the composition having improved cohesion compared to a composition consisting of less than a sufficient amount of demineralized cortical bone fibers and no other carrier.

2. The composition according to claim 1, wherein the demineralized bone fibers have elongated shapes.

3. The composition according to claim 2, wherein the demineralized bone fibers have a maximum dimension in a range of about 1 mm to about 10 mm before demineralization.

4. The composition according to claim 3, wherein the maximum dimension of the demineralized bone fibers is about 6 mm, about 7 mm, about 8 mm or about 9 mm before demineralization.

5. The composition according to claim 3, wherein the demineralized bone fibers have a minimum dimension in a range of about 5 µm to about 300 µm before demineralization.

6. The composition according to claim 1, wherein the demineralized bone fibers are mixed with the cancellous bone particles in a ratio of about 60% demineralized bone fibers to about 40% cancellous bone particles.

7. The composition according to claim 1, wherein the demineralized bone fibers are allogeneic to the patient.

8. The composition according to claim 1, wherein the cancellous bone particles and the demineralized bone fibers are allogeneic to the patient.

9. The composition according to claim 1, wherein the composition is osteogenic and is not immunologically reactive after implantation in the patient.

10. The composition according to claim 1, wherein the endogenous osteogenic cells include a population of viable osteoprogenitor cells.

11. The composition according to claim 1, wherein the endogenous osteogenic cells are immune privileged.

\* \* \* \* \*